(12) United States Patent
Li et al.

(10) Patent No.: US 9,947,881 B2
(45) Date of Patent: Apr. 17, 2018

(54) PLATINUM COMPLEXES AND DEVICES

(71) Applicants: Arizona Board of Regents on behalf of Arizona State University, Scottsdale, AZ (US); UNIVERSAL DISPLAY CORPORATION, Ewing, NJ (US)

(72) Inventors: Jian Li, Tempe, AZ (US); Guijie Li, Tempe, AZ (US); Jason Brooks, Philadelphia, PA (US)

(73) Assignees: Arizona Board of Regents on behalf of Arizona State University, Scottsdale, AZ (US); Universal Display Corporation, Ewing, NJ (US)

( * ) Notice: Subject to any disclaimer, the term of this patent is extended or adjusted under 35 U.S.C. 154(b) by 0 days.

(21) Appl. No.: 15/202,111

(22) Filed: Jul. 5, 2016

(65) Prior Publication Data

US 2017/0012224 A1    Jan. 12, 2017

Related U.S. Application Data

(63) Continuation of application No. 14/513,506, filed on Oct. 14, 2014, now Pat. No. 9,385,329.
(Continued)

(51) Int. Cl.
*H01L 51/00* (2006.01)
*C09K 11/06* (2006.01)
(Continued)

(52) U.S. Cl.
CPC ...... *H01L 51/0087* (2013.01); *C07F 15/0086* (2013.01); *C09K 11/06* (2013.01);
(Continued)

(58) Field of Classification Search
CPC .. H01L 51/0087; C07F 15/0086; C09K 11/06
(Continued)

(56) References Cited

U.S. PATENT DOCUMENTS

| 4,769,292 A | 9/1988 | Tang et al. |
| 5,707,745 A | 1/1998 | Forrest et al. |

(Continued)

FOREIGN PATENT DOCUMENTS

| CN | 1777663 | 5/2006 |
| CN | 1894269 | 1/2007 |

(Continued)

OTHER PUBLICATIONS

Wong; Challenges in organometallic research—Great opportunity for solar cells and OLEDs, Journal of Organometallic Chemistry, 2009, 694, 2644-2647.
(Continued)

*Primary Examiner* — Daniel R Carcanague
(74) *Attorney, Agent, or Firm* — Fish & Richardson P.C.

(57) ABSTRACT

Platinum compounds of Formulas I and II useful in a variety of devices, such as, for example organic-light emitting diodes (OLEDs).

(Continued)

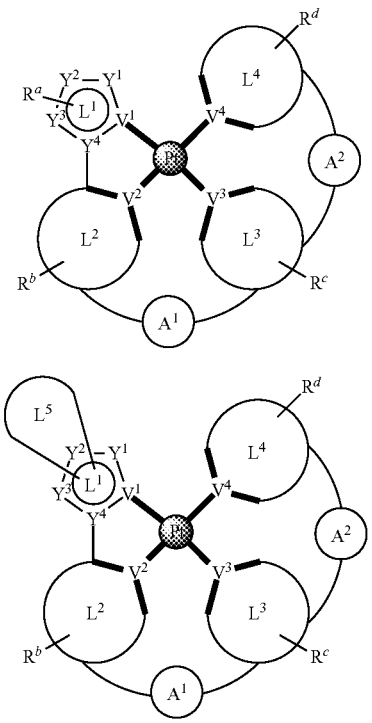

Formula I

Formula II

17 Claims, 4 Drawing Sheets

Related U.S. Application Data

(60) Provisional application No. 61/890,545, filed on Oct. 14, 2013, provisional application No. 61/890,580, filed on Oct. 14, 2013.

(51) Int. Cl.
  *H01L 51/50* (2006.01)
  *C07F 15/00* (2006.01)
  *H01L 51/42* (2006.01)

(52) U.S. Cl.
  CPC ............... *C09K 2211/1007* (2013.01); *C09K 2211/1022* (2013.01); *C09K 2211/1044* (2013.01); *C09K 2211/185* (2013.01); *H01L 51/42* (2013.01); *H01L 51/5012* (2013.01); *H01L 51/5016* (2013.01); *Y02E 10/549* (2013.01)

(58) Field of Classification Search
  USPC .......................................................... 546/4
  See application file for complete search history.

(56) References Cited

U.S. PATENT DOCUMENTS

| | | |
|---|---|---|
| 5,844,363 A | 12/1998 | Gu et al. |
| 6,200,695 B1 | 3/2001 | Arai et al. |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,947,383 B2 | 5/2011 | Ise et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Li et al. |
| 9,059,412 B2 | 6/2015 | Zeng et al. |
| 9,224,963 B2 | 12/2015 | Li et al. |
| 9,238,668 B2 | 1/2016 | Li et al. |
| 9,312,505 B2 | 4/2016 | Brooks et al. |
| 9,324,957 B2 | 4/2016 | Li et al. |
| 9,382,273 B2 | 7/2016 | Li |
| 9,385,329 B2 | 7/2016 | Li et al. |
| 9,425,415 B2 | 8/2016 | Li et al. |
| 9,461,254 B2 | 10/2016 | Tsai et al. |
| 9,550,801 B2 | 1/2017 | Li et al. |
| 9,617,291 B2 | 4/2017 | Li et al. |
| 9,673,409 B2 | 6/2017 | Li et al. |
| 9,698,359 B2 | 7/2017 | Li et al. |
| 9,711,739 B2 | 7/2017 | Li |
| 9,711,742 B2 | 7/2017 | Li et al. |
| 9,755,163 B2 | 9/2017 | Li et al. |
| 2002/0068190 A1 | 6/2002 | Tsuboyama et al. |
| 2003/0062519 A1 | 4/2003 | Yamazaki et al. |
| 2003/0186077 A1 | 10/2003 | Chen |
| 2005/0170207 A1 | 8/2005 | Ma et al. |
| 2005/0260446 A1 | 11/2005 | Mackenzie et al. |
| 2006/0073359 A1 | 4/2006 | Ise et al. |
| 2006/0094875 A1 | 5/2006 | Itoh et al. |
| 2006/0202197 A1 | 9/2006 | Nakayama et al. |
| 2006/0210831 A1 | 9/2006 | Sano et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0171111 A1 | 7/2010 | Takada et al. |
| 2012/0095232 A1 | 4/2012 | Li et al. |
| 2012/0181528 A1 | 7/2012 | Takada et al. |
| 2012/0215001 A1 | 8/2012 | Li et al. |
| 2012/0223634 A1 | 9/2012 | Xia et al. |
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0191206 A1 | 7/2014 | Cho |
| 2014/0203248 A1 | 7/2014 | Zhou et al. |
| 2014/0326960 A1 | 11/2014 | Kim et al. |
| 2014/0330019 A1 | 11/2014 | Li et al. |
| 2014/0364605 A1 | 12/2014 | Li et al. |

(56) References Cited

U.S. PATENT DOCUMENTS

| | | |
|---|---|---|
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0228914 A1 | 8/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133862 A1 | 5/2016 | Li et al. |
| 2016/0197291 A1 | 7/2016 | Li |
| 2016/0285015 A1 | 9/2016 | Li et al. |
| 2016/0359120 A1 | 12/2016 | Li |
| 2016/0359125 A1 | 12/2016 | Li et al. |
| 2017/0005278 A1 | 1/2017 | Li et al. |
| 2017/0040555 A1 | 2/2017 | Li et al. |
| 2017/0047533 A1 | 2/2017 | Li et al. |
| 2017/0066792 A1 | 3/2017 | Li et al. |
| 2017/0069855 A1 | 3/2017 | Li |
| 2017/0267923 A1 | 9/2017 | Li |

FOREIGN PATENT DOCUMENTS

| | | |
|---|---|---|
| CN | 2007053132 | 3/2007 |
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 104232076 | 12/2014 |
| CN | 104693243 | 6/2015 |
| CN | 105367605 | 3/2016 |
| CN | 105418591 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007042875 | 2/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007099765 A1 | 4/2007 |
| JP | 2007110067 | 4/2007 |
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| TW | 201710277 A1 | 3/2017 |
| WO | WO2000070655 | 11/2000 |
| WO | WO2004003108 A1 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 A1 | 1/2014 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 | 9/2015 |
| WO | WO2016025921 | 2/2016 |
| WO | WO2016029186 | 2/2016 |

OTHER PUBLICATIONS

JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Dorwald; Side Reactions in Organic Synthesis: A Guide to Successful Synthesis Design, 2005, Wiley-VCH.
Satake et al., "Interconvertible Cationic and Neutral Pyridinylimidazole η3-Allylpalladium Complexes. Structural

(56) References Cited

OTHER PUBLICATIONS

Assignment by 1H, 13C, and 15N NMR and X-ray Diffraction", Organometallics, vol. 18, No. 24, 1999, pp. 5108-5111.

Baldo et al., "Highly Efficient Phosphorescent Emission from Organic Electroluminescent Devices," Nature, vol. 395, Sep. 10, 1998, pp. 151-154.

Baldo et al., "Very high-efficiency green organic light-emitting devices based on electrophosphorescence," Applied Physics Letters, vol. 75, No. 1, Jul. 5, 1999, pp. 4-6.

Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.

Ayan Maity et al., "Room-temperature synthesis of cyclometalated iridium(III) complexes; kinetic isomers and reactive functionalities" Chem. Sci., vol. 4, pp. 1175-1181 (2013).

Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).

Ji Hyun Seo et al., "Efficient blue-green organic light-emitting diodes based on heteroleptic tris-cyclometalated iridium (III) complexes". Thin Solid Films, vol. 517, pp. 1807-1810 (2009).

Barry O'Brien et al.: White organic light emitting diodes using Pt-based red, green and blue phosphorescent dopants. Proc. SPIE, vol. 8829, pp. 1-6, Aug. 25, 2013.

Vanessa Wood et al., "Colloidal quantum dot light-emitting devices," Nano Reviews, vol. 1, 2010, 8 pages.

Glauco Ponterini et al., "Comparison of Radiationless Decay Processes in Osmium and Platinum Porphyrins," J. Am. Chem. Soc., vol. 105, No. 14, 1983, pp. 4639-4645.

Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.

Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.

Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.

Evan L. Williams et al., "Excimer-Based White Phosphorescent Organic Light Emitting Diodes with Nearly 100% Internal Quantum Efficiency," Adv. Mater., vol. 19, 2007, pp. 197-202.

Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.

Jan Kalinowski et al., "Light-emitting devices based on organometallic platinum complexes as emitters," Coordination Chemistry Reviews, vol. 255, 2011, pp. 2401-2425.

Ke Feng et al., "Norbornene-Based Copolymers Containing Platinum Complexes and Bis(carbazolyl)benzene Groups in Their Side-Chains," Macromolecules, vol. 42, 2009, pp. 6855-6864.

Chi-Ming Che et al., "Photophysical Properties and OLED Applications of Phosphorescent Platinum(II) Schiff Base Complexes," Chem. Eur. J., vol. 16, 2010, pp. 233-247.

Stephen R. Forrest, "The path to ubiquitous and low-cost organic electronic appliances on plastic," Nature, vol. 428, Apr. 29, 2004, pp. 911-918.

Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.

Xiaofan Ren et al., "Ultrahigh Energy Gap Hosts in Deep Blue Organic Electrophosphorescent Devices," Chem. Mater., vol. 16, 2004, pp. 4743-4747.

Dorwald; "Side Reactions in Organic Synthesis: A Guide to Successful Synthesis Design," Chapter 1, 2005 Wiley-VCH Verlag GmbH & Co. KGaA, Wienheim, 32 pages.

Murakami; JP 2007258550, English machine translation from EPO, Oct. 4, 2007. 80 pages.

Murakami; JP 2007324309, English machine translation from EPO, Dec. 13, 2007, 89 pages.

Marc Lepeltier et al., "Efficient blue green organic light-emitting devices based on a monofluorinated heteroleptic Iridium(III) complex," Synthetic Metals, vol. 199, 2015, pp. 139-146.

Stefan Bernhard, "The First Six Years: A Report," Department of Chemistry, Princeton University, May 2008, 11 pages.

Ivaylo Ivanov et al., "Comparison of the INDO band structures of polyacetylene, polythiophene, polyfuran, and polypyrrole," Synthetic Metals, vol. 116, Issues 1-3, Jan. 1, 2001, pp. 111-114.

PLATINUM COMPLEXES AND DEVICES

CROSS-REFERENCE TO RELATED APPLICATIONS

This application is a continuation of U.S. Ser. No. 14/513,506, filed Oct. 14, 2014, now U.S. Pat. No. 9,385,329, entitled "PLATINUM COMPLEXES AND DEVICES", which claims priority to U.S. Ser. No. 61/890,545 entitled "PLATINUM COMPLEXES, DEVICES, AND USES THEREOF" and U.S. Ser. No. 61/890,580 entitled "PLATINUM COMPLEXES, DEVICES, AND USES THEREOF", both filed on Oct. 14, 2013, and each is incorporated by reference herein in their entirety.

TECHNICAL FIELD

This invention is related to platinum complexes and devices including the platinum complexes.

BACKGROUND

Compounds capable of absorbing and/or emitting light can be ideally suited for use in a wide variety of optical and electroluminescent devices, including, for example, photoabsorbing devices such as solar- and photo-sensitive devices, organic light emitting diodes (OLEDs), photoemitting devices, or devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency, as well as improvements in processing ability.

Despite significant advances in research devoted to optical and electro-optical materials, many currently available materials exhibit a number of disadvantages, including poor processing ability, inefficient emission or absorption, and less than ideal stability, among others.

Thus, a need exists for new materials which exhibit improved performance in optical emitting and absorbing applications. Accordingly, such compounds, compositions, and devices comprising the same are disclosed herein

SUMMARY

The present disclosure relates to platinum compounds that can be useful as emitters in display and lighting applications.

Disclosed herein are compounds of Formulas I and II:

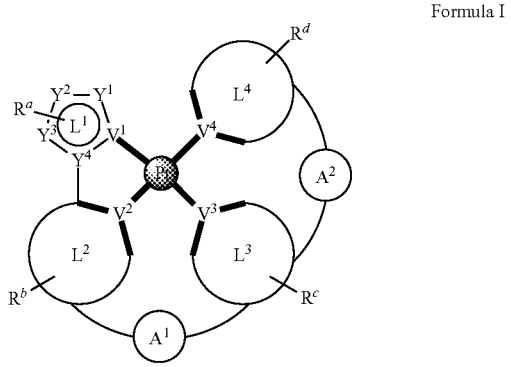

Formula I

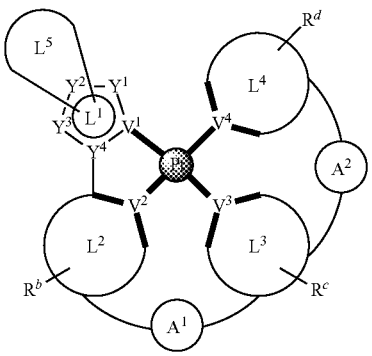

Formula II wherein $L^1$ is a five-membered heterocyclyl, heteroaryl, carbene, or N-heterocyclic carbene, wherein each of $L^2$, $L^3$, and $L^4$ is independently a substituted or an unsubstituted aryl, cycloalkyl, cycloalkenyl, heteroaryl, heterocyclyl, carbene, or N-heterocyclic carbene, wherein $L^5$ is a substituted or unsubstituted aryl cycloalkyl, cycloalkenyl, heterocyclyl, or heteroaryl, wherein each of $A^1$ and $A^2$ is independently present or absent and if present is each independently O, S, S=O, $SO_2$, Se, $NR^3$, $PR^3$, RP=O, $CR^1R^2$, C=O, $SiR^1R^2$, $GeR^1R^2$, or $BR^3$, wherein each of $V^1$, $V^2$, $V^3$, and $V^4$ is coordinated with the Pt and is independently N, C, P, B, or Si, wherein each of $Y^1$, $Y^2$, $Y^3$, and $Y^4$ is independently C, N, O, or S, wherein $R^a$ is present or absent and if present represents mono-, di-, or tri-substitutions, wherein each $R^a$ is independently a substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof wherein two or more of $R^a$ are optionally linked together, wherein $R^b$ is present or absent and if present represents mono-, di-, or tri-substitutions, wherein each $R^b$ is independently a substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^b$ are optionally linked together, wherein $R^c$ is present or absent and if present represents mono-, di-, or tri-substitutions, wherein each $R^c$ is independently substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^c$ are optionally linked together, wherein $R^d$ is present or absent and if present represents mono-, di-, or tri-substitutions, wherein each $R^d$ is independently substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^d$ are optionally linked together, and wherein each of $R^1$, $R^2$, and $R^3$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof.

In one aspect, Formula I includes Formula IA:

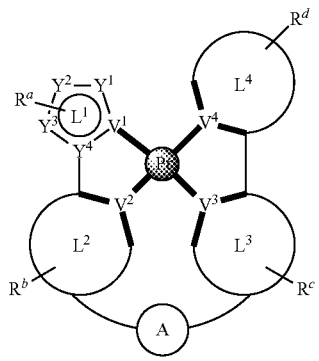

Formula IA wherein A is $A^1$ in Formula I.

In other aspects, Formula II includes Formula IIA and Formula IIB:

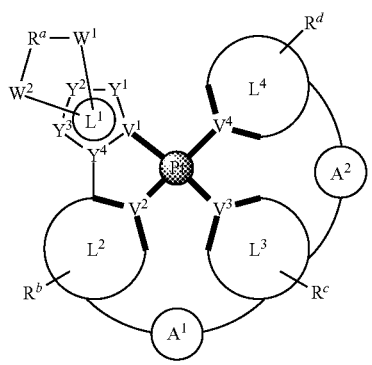

Formula IIA

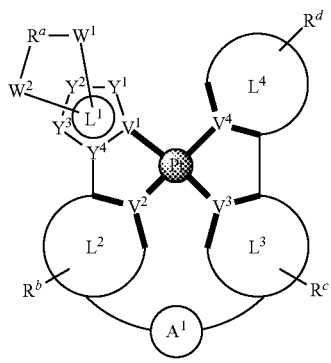

Formula IIB wherein A is $A^1$ in Formula II, wherein each of

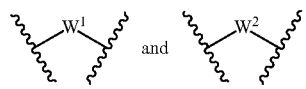

and is independently:

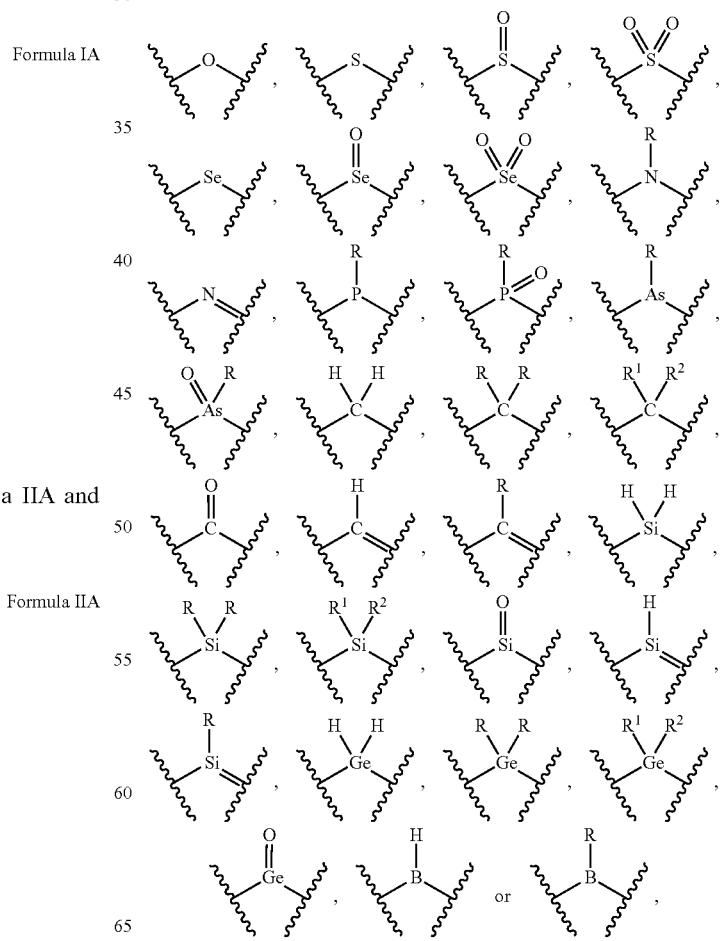

wherein

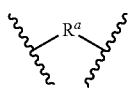

is

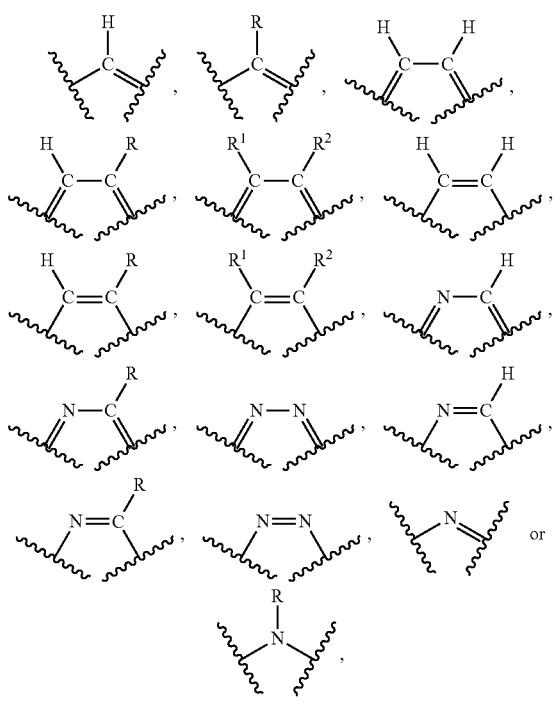

wherein each of R, $R^1$, $R^2$, and $R^3$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of R, $R^1$, $R^2$, and $R^3$ are optionally linked together.

Also disclosed herein are compositions including one or more compounds disclosed herein.

Also disclosed herein are devices, such as OLEDs, including one or more compounds or compositions disclosed herein.

BRIEF DESCRIPTION OF THE FIGURES

The accompanying figures, which are incorporated in and constitute a part of this specification, illustrate several non-limiting aspects and together with the description serve to explain the principles of the invention.

Figure 1:
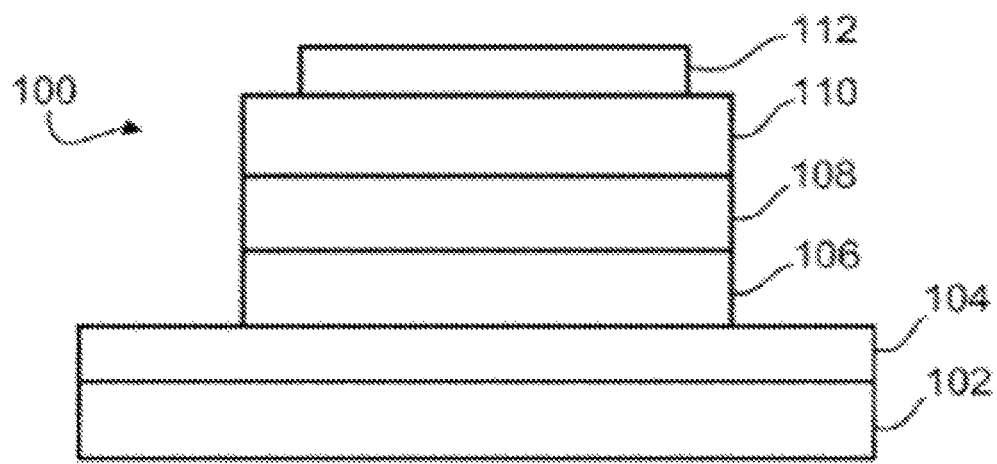
FIG. 1 depicts a device including a platinum complex.

Additional aspects will be set forth in part in the description which follows, and in part will be obvious from the description, or can be learned by practice of the disclosure. Advantages will be realized and attained by means of the elements and combinations particularly pointed out in the appended claims. It is to be understood that both the foregoing general description and the following detailed description are exemplary and explanatory only and are not restrictive.

DETAILED DESCRIPTION

The present disclosure can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As referred to herein, a linking atom can connect two groups such as, for example, an N and C group. A linking group is in one aspect disclosed as A, $A^1$, and/or $A^3$ herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties includes, but are not limited to, hydrogen, hydroxyl, alkyl, alkoxy, =O, halogen, nitro, amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, and heterocyclyl.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bond, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The term "heterocyclyl" includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ is hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ is hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "$R^1$," "$R^2$," "$R^3$," "$R^n$," where n is an integer, as used herein can, independently, include hydrogen or one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within a second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. It is also contemplated that, in certain aspects, unless expressly indicated to the contrary, individual substituents can be further optionally substituted (i.e., further substituted or unsubstituted).

In some aspects, a structure of a compound can be represented by a formula:

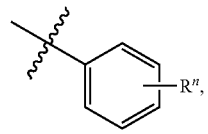

which is understood to be equivalent to a formula:

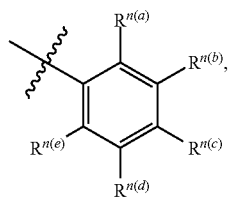

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

1. Compounds

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Generally, a chemical structural change will affect the electronic structure of the compounds, which thereby affects the optical properties of the compounds, for example, emission and absorption spectra. Thus, the compounds of this disclosure can be tailored or tuned to a specific application that desires a particular emission or absorption characteristic. The optical properties of the metal compounds in this disclosure can be tuned by varying the structure of the ligand surrounding the metal center. For example, the metal compounds having a ligand with electron donating substituents or electron withdrawing substituents can be generally exhibit different optical properties, including emission and absorption spectra.

Owing to the potential of phosphorescent tetradentate platinum complexes for harvesting both electro-generated singlet and triplet excitions to achieve 100% internal quantum efficiency, these complexes are good candidate for the emitting materials of OLEDs. In some cases, there is an "emitting portion" and an "ancillary portion" in a ligand of platinum complex (e.g., a tetradentate platinum complex). If stabilizing substitution(s), such as conjugated group(s), aryl or heteroaromatic substitution(s) and so on, were introduced into the emitting portion, the "Highest Occupied Molecular Orbital" (HOMO) energy level, the "Lowest Unoccupied Molecular Orbital" (LUMO) energy level, or both may be changed. So the energy gap between the HOMO and LUMO can be tuned. Thus, the emission spectra of phosphorescent tetradentate platinum complexes can be modified to lesser or greater extents, such that the emission spectra can become narrower or broader, such that the emission spectra can exhibit a blue shift or a red shift, or a combination thereof.

The emission of such disclosed complexes can be tuned, for example, from the ultraviolet to near-infrared, by, for example, modifying the ligand structure. In another aspect, the disclosed complexes can provide emission over a majority of the visible spectrum. In a specific example, the disclosed complexes can emit light over a range of from about 400 nm to about 700 nm. In another aspect, the disclosed complexes have improved stability and efficiency over traditional emission complexes. In yet another aspect, the disclosed complexes can be useful as luminescent labels in, for example, bio-applications, anti-cancer agents, emitters in organic light emitting diodes (OLED), or a combination thereof. In another aspect, the disclosed complexes can be useful in light emitting devices, such as, for example, compact fluorescent lamps (CFL), light emitting diodes (LED), incandescent lamps, and combinations thereof.

The compounds can also have other known emission mechanisms which are useful in devices.

Disclosed herein are compounds or compound complexes comprising platinum. The terms compound or compound complex are used interchangeably herein. In one aspect, the compounds disclosed herein have a neutral charge.

The compounds disclosed herein can exhibit desirable properties and have emission spectra, absorption spectra, or both that can be tuned via the selection of appropriate ligands. In another aspect, the present disclosure can exclude any one or more of the compounds, structures, or portions thereof, specifically recited herein.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are platinum complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLEDs), luminescent devices and displays, and other light emitting devices.

In another aspect, the compounds can provide improved efficiency, improved operational lifetimes, or both in lighting devices, such as, for example, organic light emitting devices, as compared to conventional materials.

The compounds of the disclosure can be made using a variety of methods, including, but not limited to those recited in the examples provided herein.

Disclosed herein are compounds of Formulas I and II:

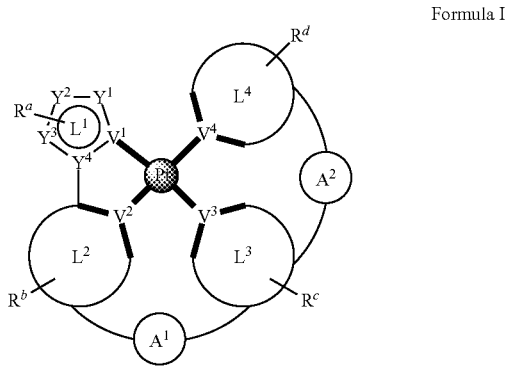

Formula I

Formula II wherein $L^1$ is a five-membered heterocyclyl, heteroaryl, carbene, or N-heterocyclic carbene, wherein each of $L^2$, $L^3$, and $L^4$ is independently a substituted or an unsubstituted aryl, cycloalkyl, cycloalkenyl, heteroaryl, heterocyclyl, carbene, or N-heterocyclic carbene, wherein each of $A^1$ and $A^2$ is independently present or absent, and if present is independently O, S, S=O, $SO_2$, Se, $NR^3$, $PR^3$, RP=O, $CR^1R^2$, C=O, $SiR^1R^2$, $GeR^1R^2$, or $BR^3$, wherein each of $V^1$, $V^2$, $V^3$, and $V^4$ is coordinated with the Pt and is independently N, C, P, B, or Si, wherein each of $Y^1$, $Y^2$, $Y^3$, and $Y^4$ is independently C, N, O, or S, wherein $R^a$ is present or absent and if present represents mono-, di-, or tri-substitutions, wherein each $R^a$ is independently a substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^a$ are optionally linked together, wherein $R^b$ is present or absent and if present represents mono-, di-, or tri-substitutions, wherein each $R^b$ is independently a substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^b$ are optionally linked together, wherein $R^c$ is present or absent and if present represents mono-, di-, or tri-substitutions, wherein each $R^c$ is independently substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^c$ are optionally linked together, wherein $R^d$ is present or absent and if present represents mono-, di-, or tri-substitutions, wherein each $R^d$ independently is substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^d$ are optionally linked together, and wherein each of $R^1$, $R^2$, and $R^3$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof.

In one aspect, Formula I includes Formula IA:

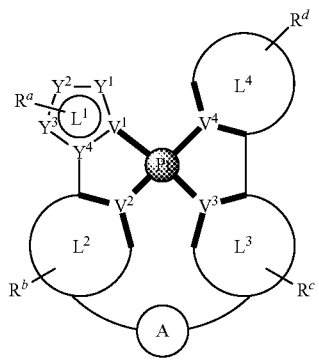

Formula IA wherein A is $A^1$ in Formula I.

In one aspect, Formula II has the structure of Formula IIA or Formula IIB:

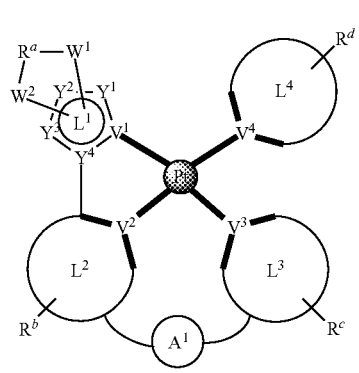

Formula IIA

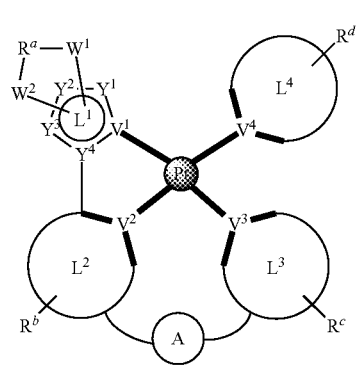

Formula IIB wherein A is $A^1$ in Formula II, wherein each of

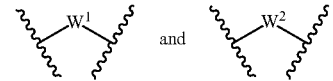

independently includes:

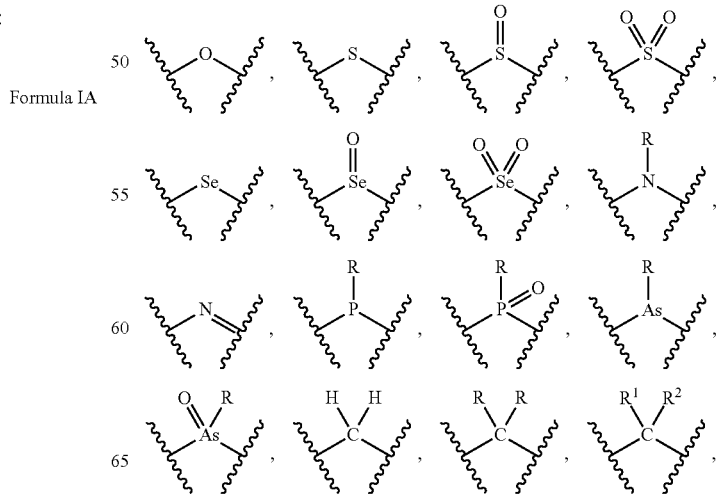

-continued

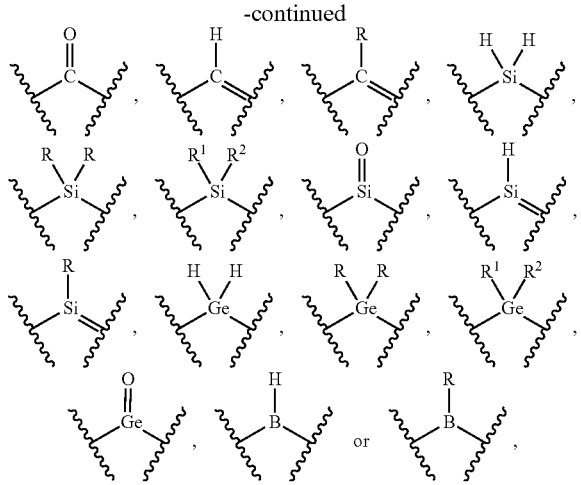

wherein

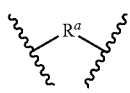

includes:

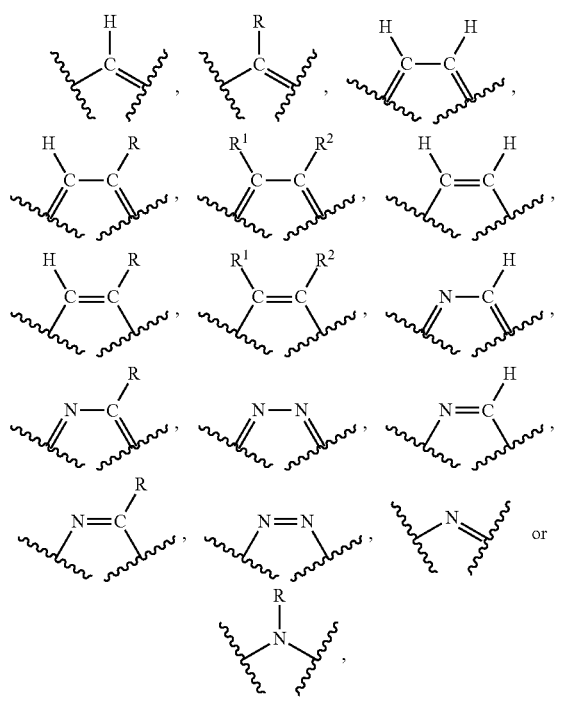

wherein each of R, R¹, R², and R³ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of R, R¹, R², and R³ are optionally linked together.

In one aspect, Formula I includes Formulas I1-I15:

Formula I1-I15:

1

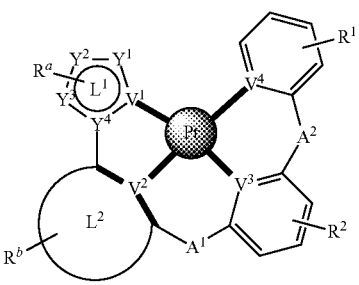

2

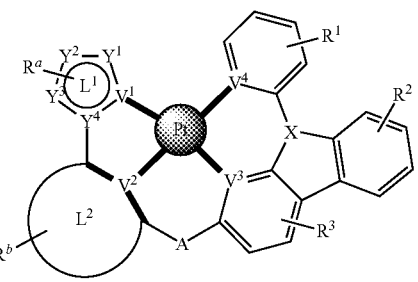

3

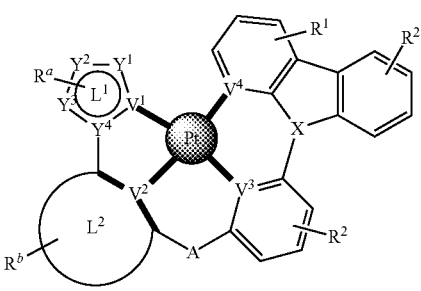

4

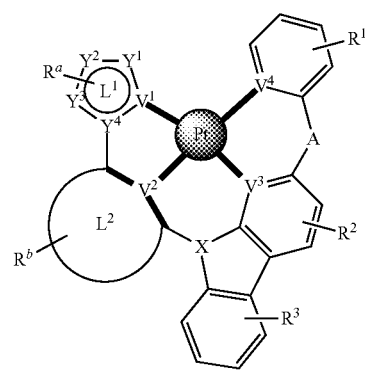

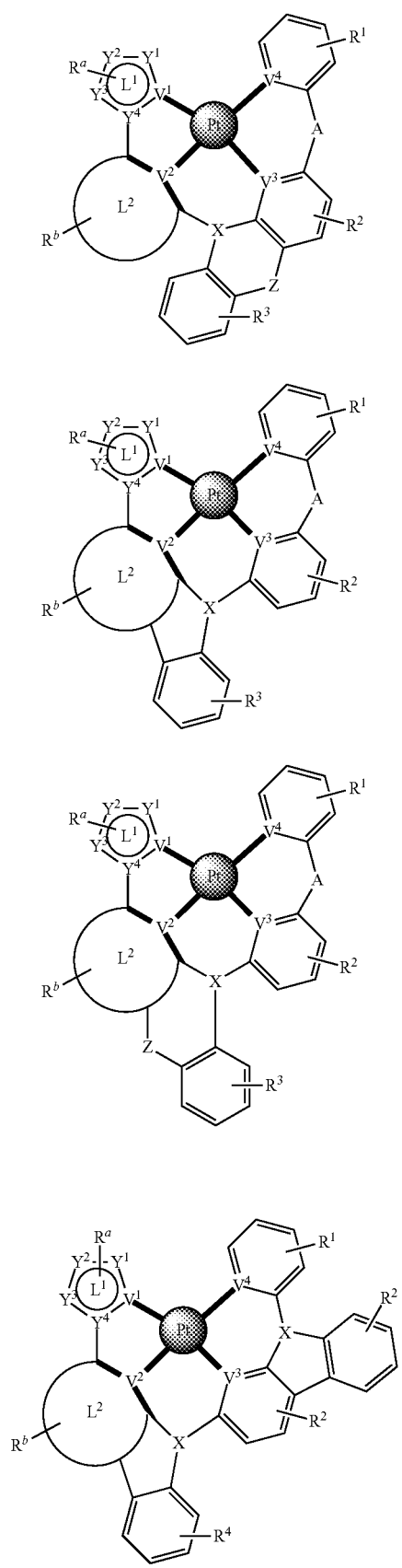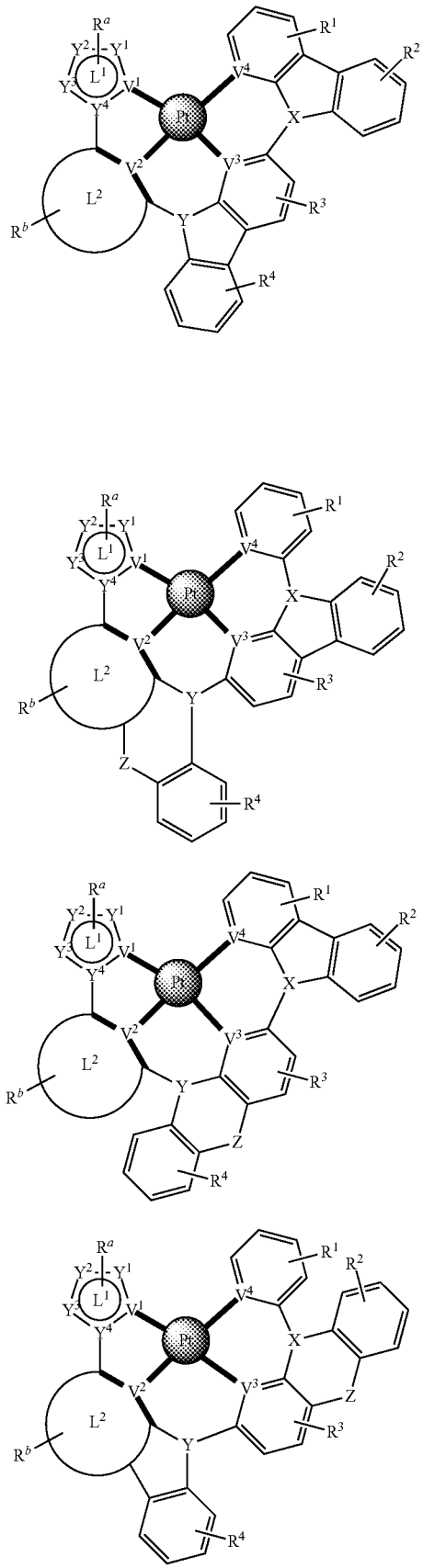

-continued
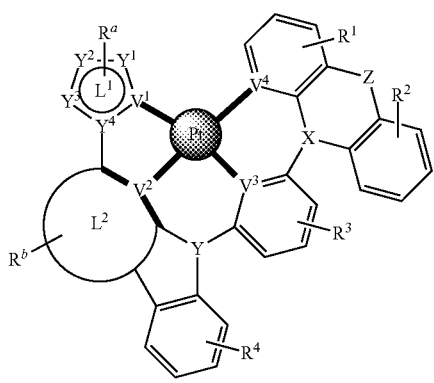
13
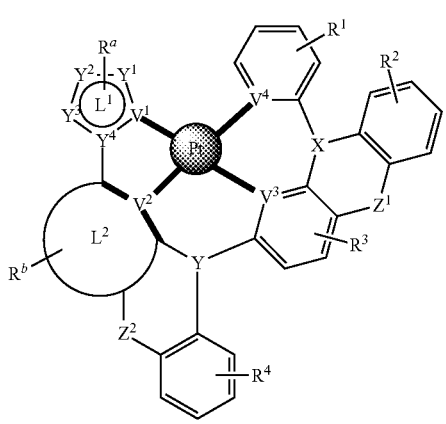
14
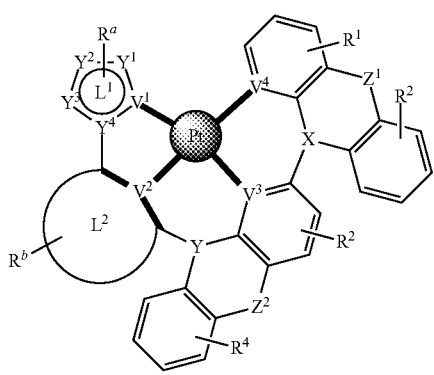
15
In one aspect, Formula II includes Formulas II1-II15:
Formula II1-II15:
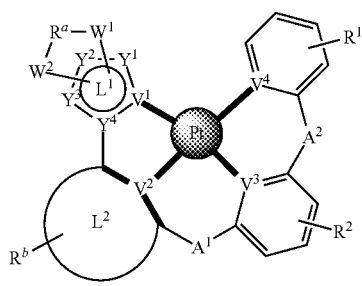
1
-continued
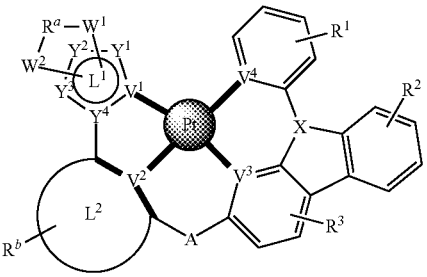
2
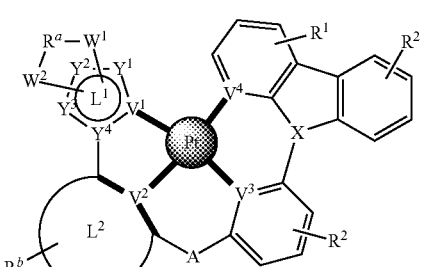
3
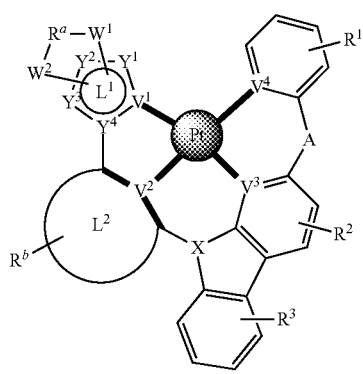
4
5

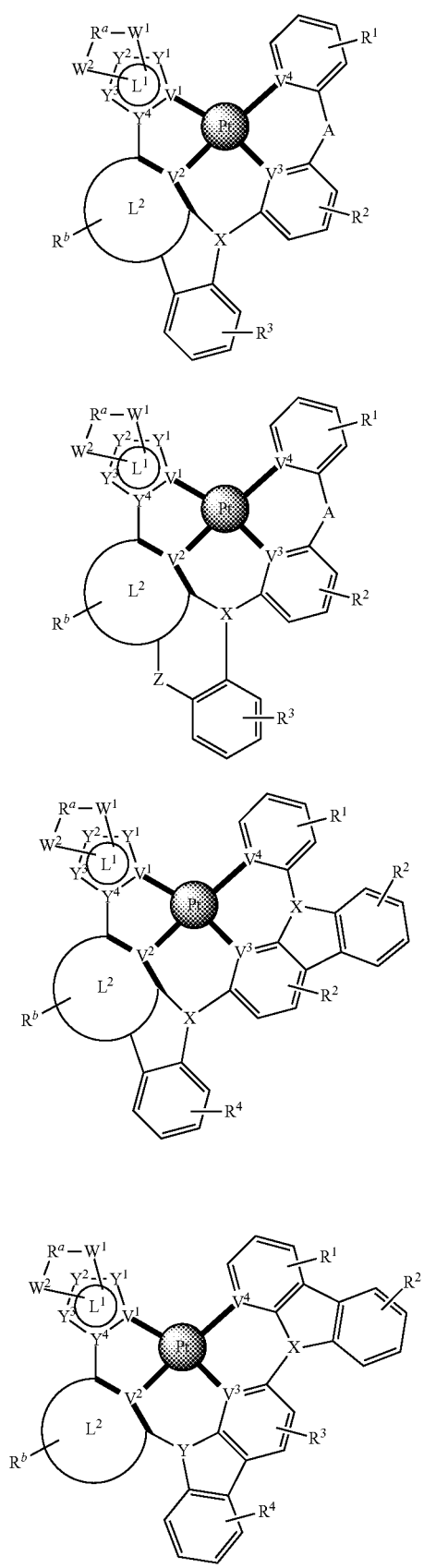
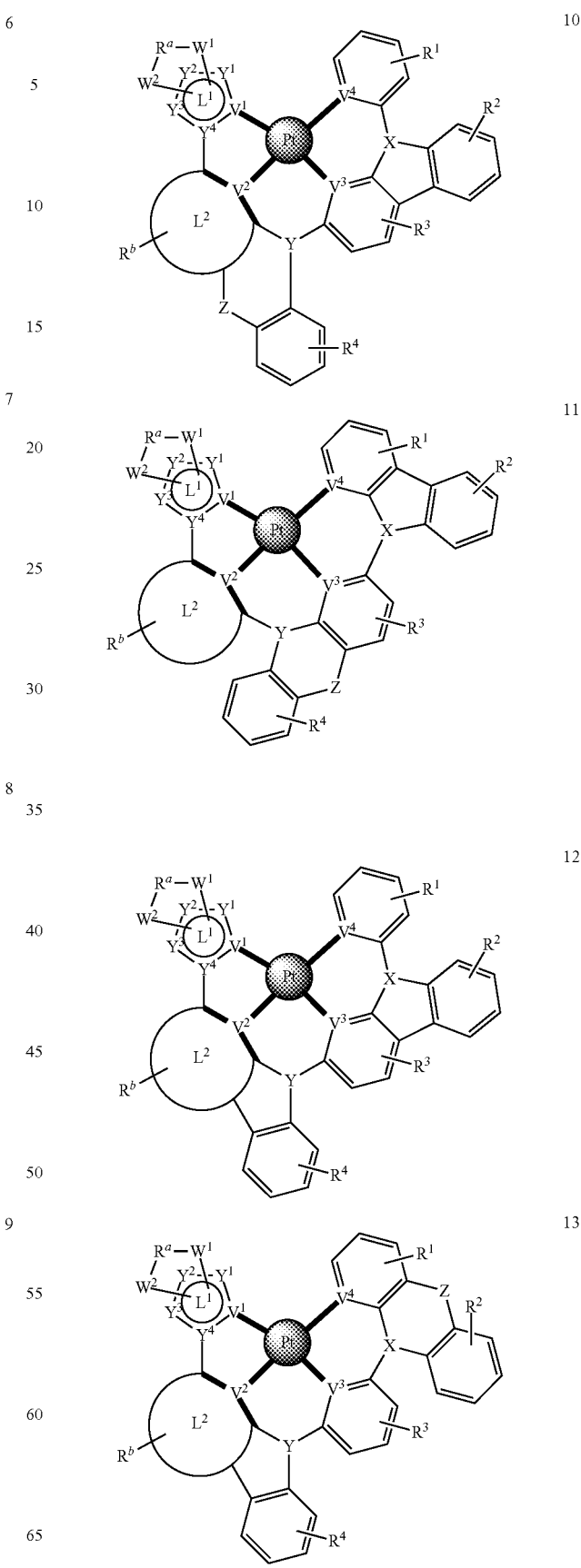

-continued

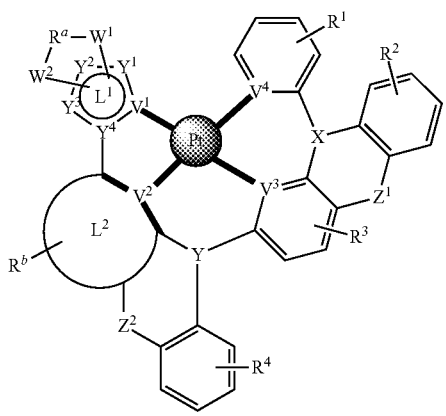

14

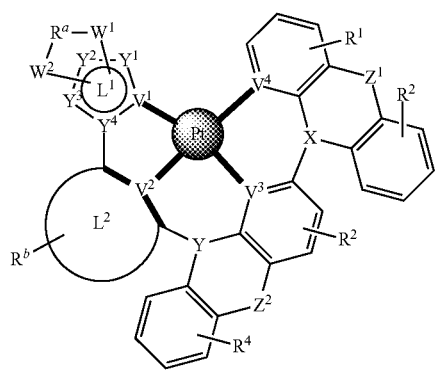

15

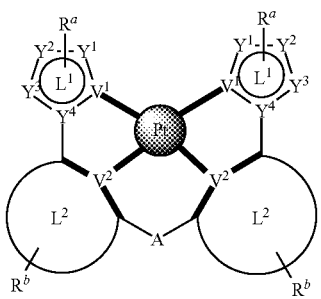

16

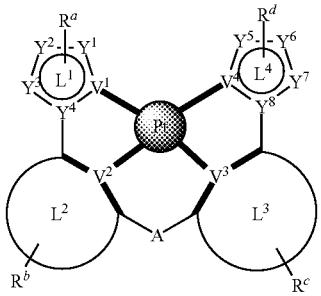

17

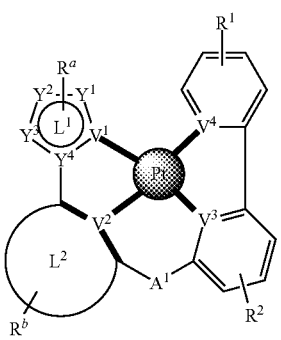

18

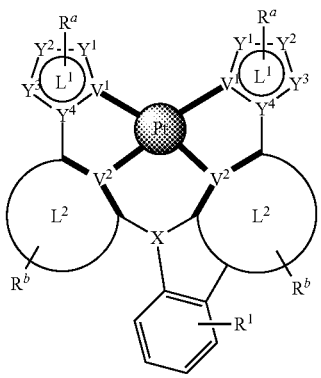

19

In Formulas I1-I15 and II1-II15,

X and Y is each independently N, P, P=O, $CR^1$, CH, $SiR^1$, SiH, $GeR^1$, GeH, Z, $Z^1$, or $Z^2$, wherein each of Z, $Z^1$, and $Z^2$ is independently a linking group, each $R^1$, $R^2$, $R^3$, and $R^4$ is independently mono-, di-, tri, or tetra-substitutions, wherein each $R^1$, $R^2$, $R^3$, and $R^4$ is independently substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^1$, two or more of $R^2$, two or more of $R^3$, two or more of $R^4$, or any combination thereof are optionally linked together.

In one aspect, Formula I disclosed herein includes symmetrical Formula I16 and asymmetrical Formulas I17-I28:

20
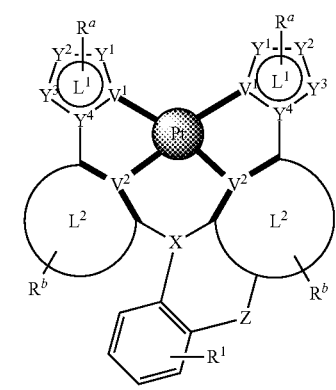
21
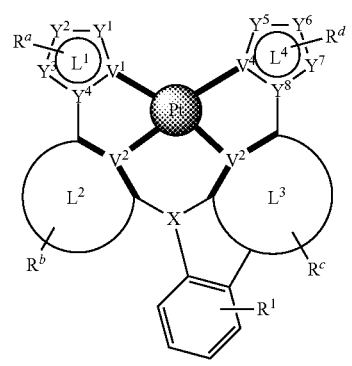
22
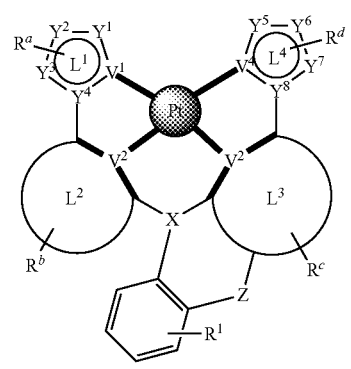
23
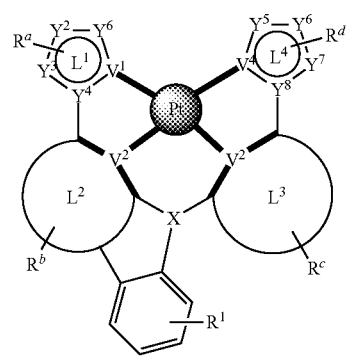
24
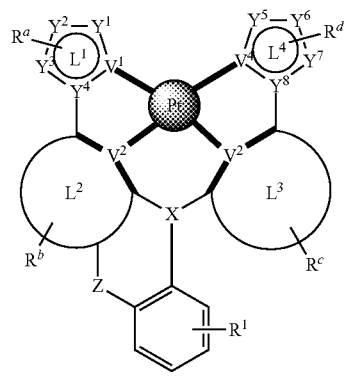
25
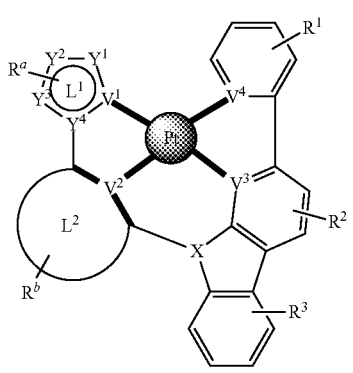
26
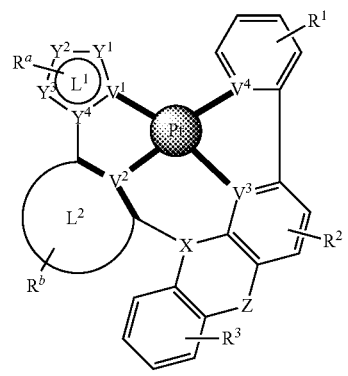
27
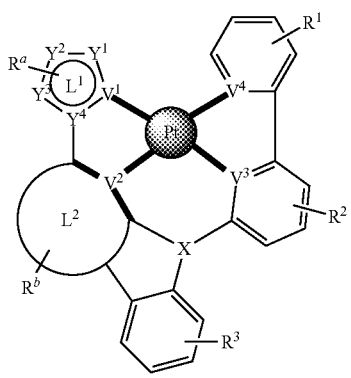

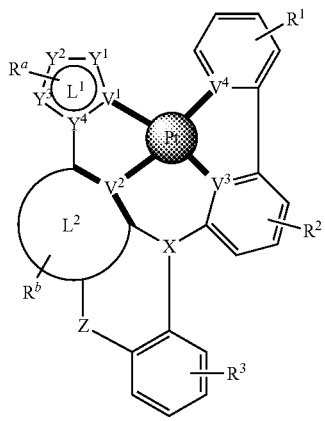
28
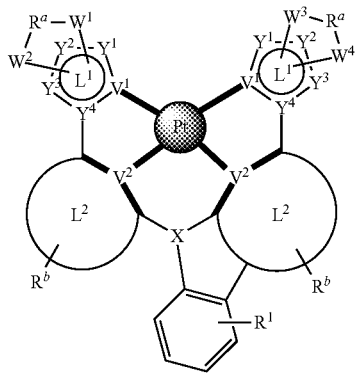
19
In one aspect, Formula II disclosed herein includes symmetrical Formula II16 and asymmetrical Formulas II17-II28:
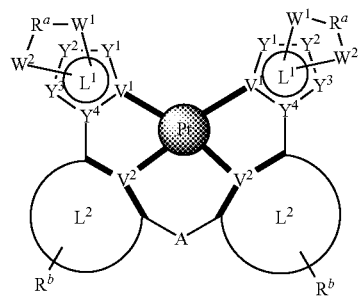
16
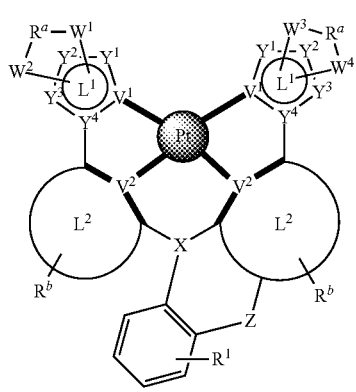
20
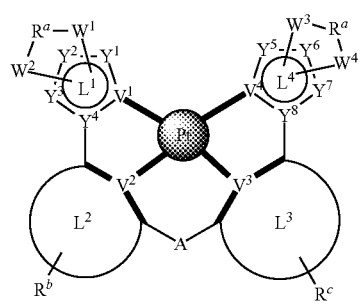
17
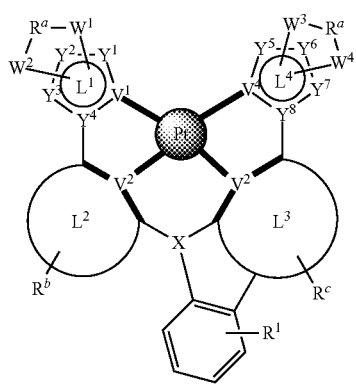
21
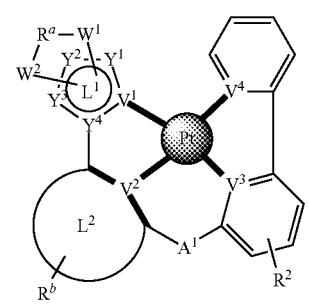
18
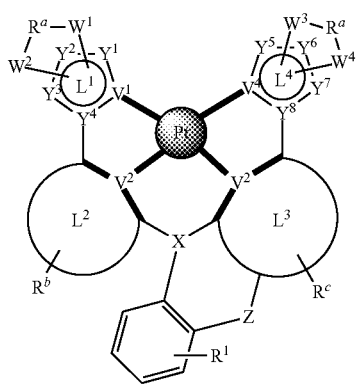
22

23
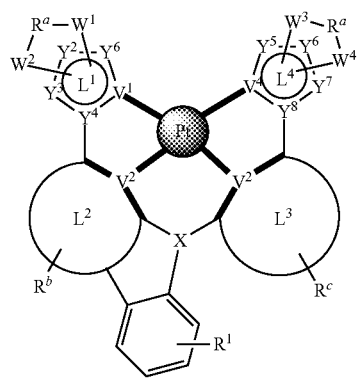
24
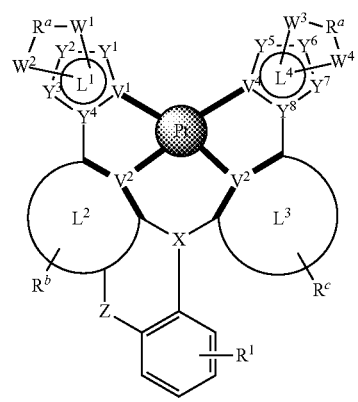
25
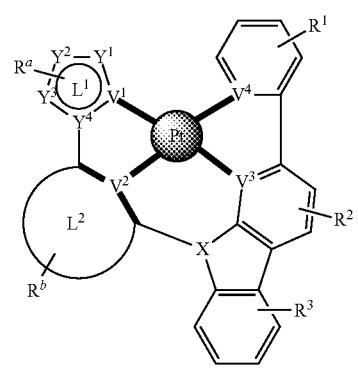
26
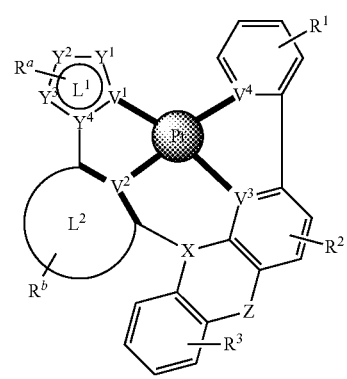
27
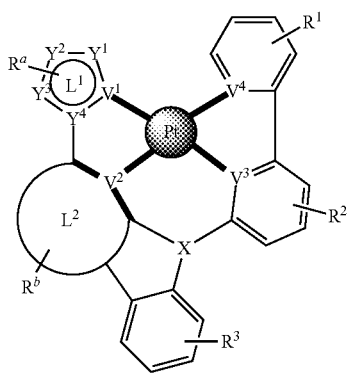
28
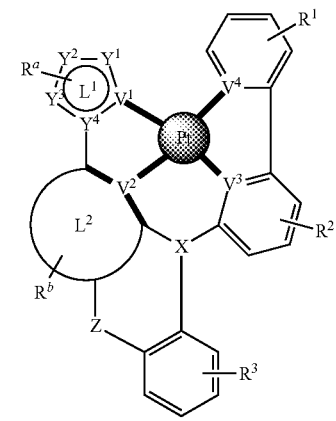
In Formulas I16-I28 and Formulas II16-II28:
each of $Y^5$, $Y^6$, $Y^7$, and $Y^8$ is independently C, N, O, or S,
each of X and Y is independently N, P, P=O, $CR^1$, CH, $SiR^1$, SiH, $GeR^1$, or GeH,
each of Z, $Z^1$, and $Z^2$ is independently a linking group, each of
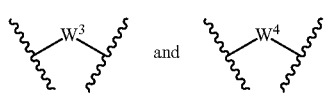 and 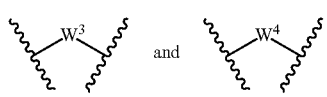
is independently:
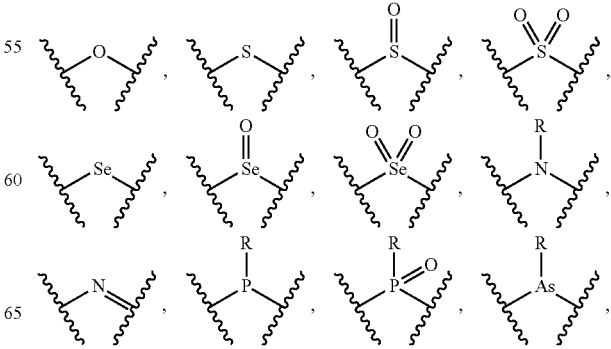

-continued

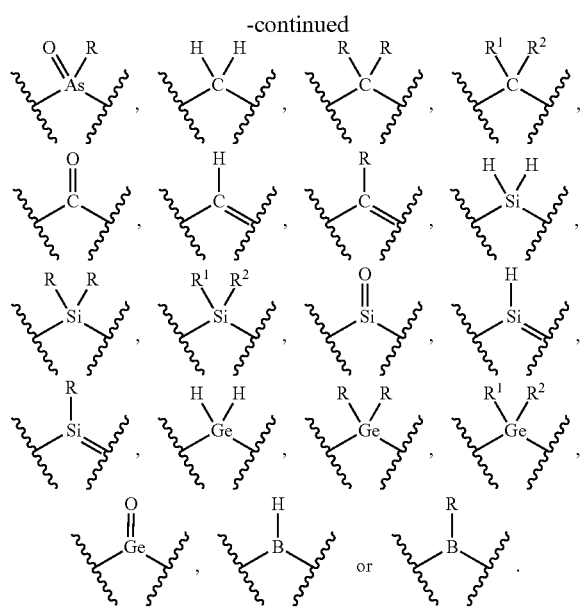

is

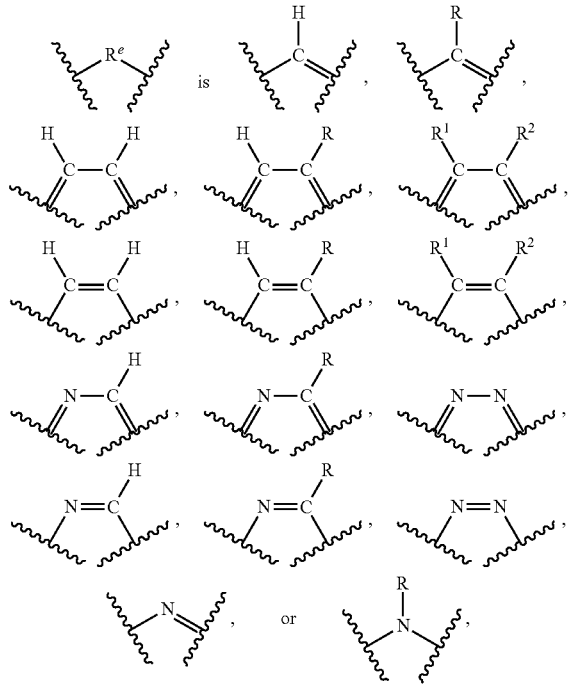

each R, R¹, R², and R³ is independently a mono-, di-, tri-, or tetra-substitution, wherein each R, R¹, R², and R³ independently are substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of R, two or more of R¹, two or more of R², two or more of R³, or any combination thereof, are optionally linked together.

In one aspect, for any of the formulas illustrated in this disclosure,

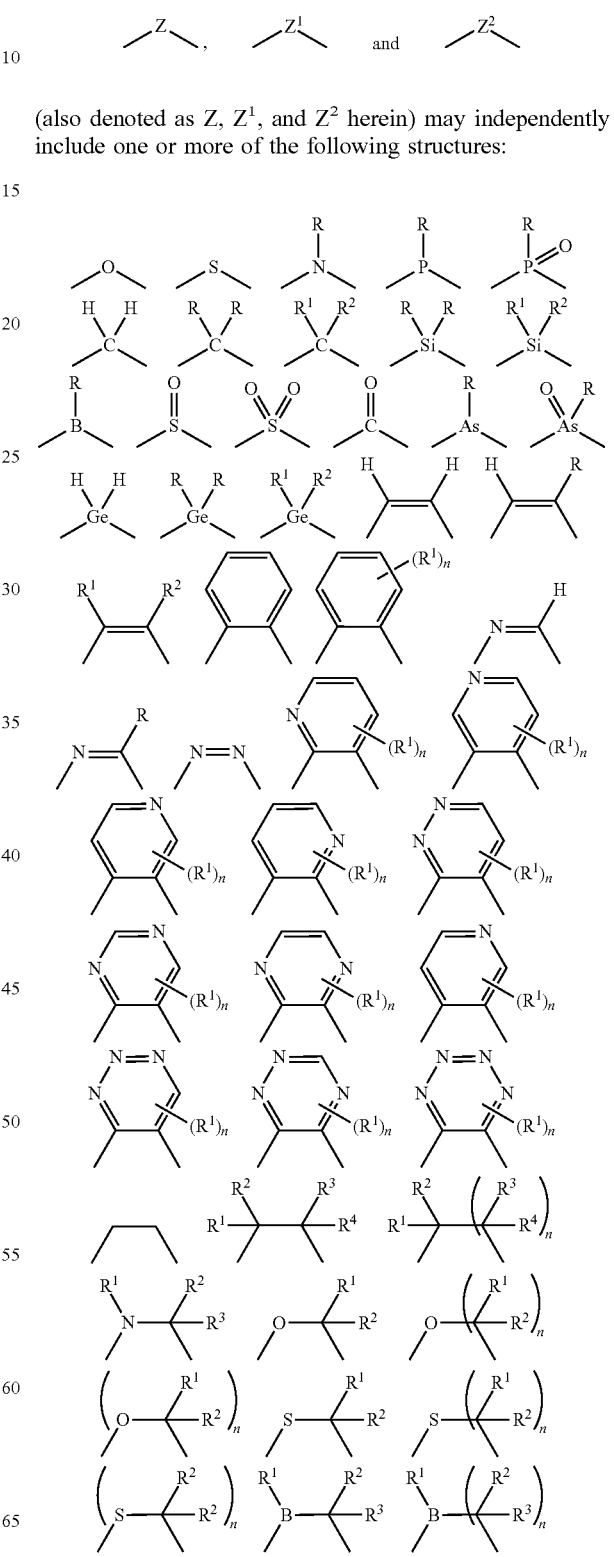

(also denoted as Z, $Z^1$, and $Z^2$ herein) may independently include one or more of the following structures:

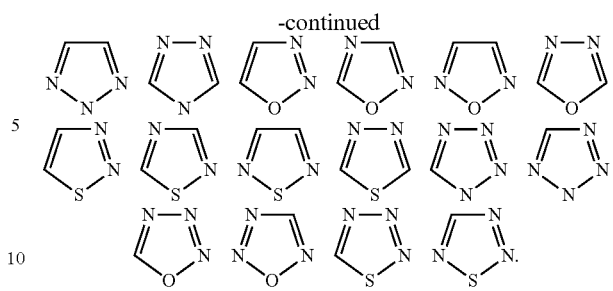

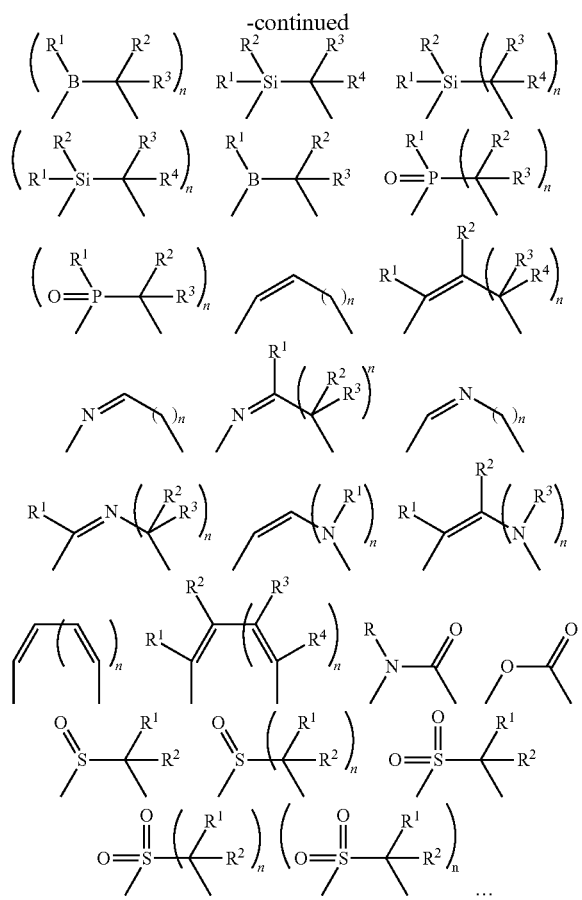

wherein n is from 0 to 3.

In one aspect, n is 0. In another aspect, n is 1. In yet another aspect, n is 2. In yet another aspect, n is 3.

In one aspect, $L^5$ is a mono-, bi-, or tri-cyclic structure of substituted or unsubstituted aryl cycloalkyl, cycloalkenyl, heterocyclyl, or heteroaryl. In one aspect, $L^5$ is a mono-, bi-, or tri-cyclic structure of substituted aryl cycloalkyl, cycloalkenyl, heterocyclyl, or heteroaryl. In another aspect, $L^5$ is a mono-, bi-, or tri-cyclic structure of unsubstituted aryl, cycloalkyl, cycloalkenyl, heterocyclyl, or heteroaryl.

In one aspect, any of the formulas disclosed herein including five-membered heterocylyl

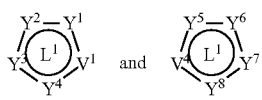

(i.e., a portion of the disclosed compound) can include one or more of the following structures:

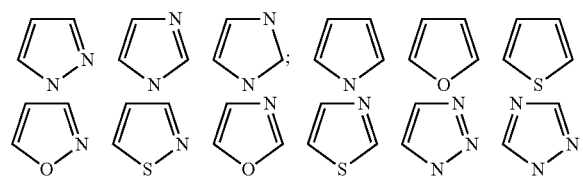

It is understood that one or more of $R^a$ and $R^d$ as described herein can be bonded to

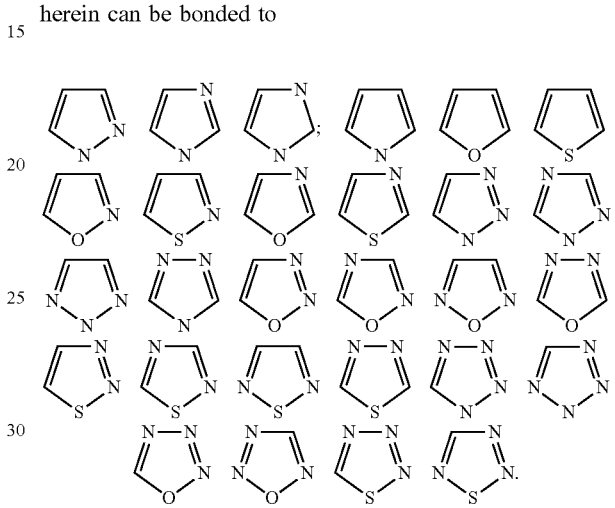

In one aspect, R can, where appropriate, represent mono-, di-, tri, or tetra-substitution, wherein each R is substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of R, where appropriate, are optionally linked together. For example, R is substituted or unsubstituted aryl, cycloalkyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, substituted silyl, or polymerizable group, or any conjugate or combination thereof, wherein two or more of R, where appropriate, are optionally linked together. In another example, R is substituted or unsubstituted aryl, alkyl, alkenyl, alkynyl, or any conjugate or combination thereof, wherein two or more of R, where appropriate, are optionally linked together. In another example, R is substituted or unsubstituted aryl, cycloalkyl, cycloalkenyl, heterocyclyl, or heteroaryl. In another aspect, R is hydrogen.

In one aspect, $R^1$ can, where appropriate, represent mono-, di-, tri, or tetra-substitution, wherein each $R^1$ is substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^1$, where appropriate, are optionally linked together. For example, $R^1$ is substituted or unsubstituted aryl, cycloalkyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, substituted silyl, or polymerizable group, or any conjugate or combination thereof, wherein two or more of $R^1$, where appropriate, are optionally linked together. In another example, $R^1$ is substituted or unsubstituted aryl, alkyl, alkenyl, alkynyl, or any conjugate or combination thereof, wherein two or more of $R^1$, where appropriate, are optionally linked together. In another example, $R^1$ is substituted or unsubstituted aryl, cycloalkyl, cycloalkenyl, heterocyclyl, or heteroaryl. In another aspect, $R^1$ is hydrogen.

In one aspect, $R^2$ can, where appropriate, represent mono-, di-, tri, or tetra-substitution, wherein $R^2$ is substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^2$, where appropriate, are optionally linked together. For example, $R^2$ is substituted or unsubstituted aryl, cycloalkyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, substituted silyl, or polymerizable group, or any conjugate or combination thereof, wherein two or more of $R^2$, where appropriate, are optionally linked together. In another example, $R^2$ is substituted or unsubstituted aryl, alkyl, alkenyl, alkynyl, or any conjugate or combination thereof, wherein two or more of $R^2$, where appropriate, are optionally linked together. In another aspect, $R^2$ is hydrogen.

In one aspect, $R^3$ can, where appropriate, represent mono-, di-, tri, or tetra-substitution, wherein $R^3$ is substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^3$, where appropriate, are optionally linked together. For example, $R^3$ is substituted or unsubstituted aryl, cycloalkyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, substituted silyl, or polymerizable group, or any conjugate or combination thereof, wherein two or more of $R^3$, where appropriate, are optionally linked together. In another example, $R^3$ is substituted or unsubstituted aryl, alkyl, alkenyl, alkynyl, or any conjugate or combination thereof, wherein two or more of $R^3$, where appropriate, are optionally linked together. In another aspect, $R^3$ is hydrogen.

In one aspect, $R^4$ can, where appropriate, represent mono-, di-, tri, or tetra-substitution, wherein $R^4$ is substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^4$, where appropriate, are optionally linked together. For example, $R^4$ is substituted or unsubstituted aryl, cycloalkyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, substituted silyl, or polymerizable group, or any conjugate or combination thereof, wherein two or more of $R^4$, where appropriate, are optionally linked together. In another example, $R^4$ is substituted or unsubstituted aryl, alkyl, alkenyl, alkynyl, or any conjugate or combination thereof, wherein two or more of $R^4$, where appropriate, are optionally linked together. In another aspect, $R^4$ is hydrogen.

In one aspect, $R^5$ can, where appropriate, represent mono-, di-, tri, or tetra-substitution, wherein $R^5$ is substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^5$, where appropriate, are optionally linked together. For example, $R^5$ is substituted or unsubstituted aryl, cycloalkyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, substituted silyl, or polymerizable group, or any conjugate or combination thereof, wherein two or more of $R^5$, where appropriate, are optionally linked together. In another example, $R^5$ is substituted or unsubstituted aryl, alkyl, alkenyl, alkynyl, or any conjugate or combination thereof, wherein two or more of $R^5$, where appropriate, are optionally linked together. In another aspect, $R^5$ is hydrogen.

In one aspect, at least two of R, $R^1$, $R^2$, $R^3$, $R^4$, $R^5$ are linked together. In one aspect, at least two of R, $R^1$, $R^2$, $R^3$, and $R^4$ or at least two of R, $R^1$, $R^2$, and $R^3$ are linked together. In another aspect, two R are linked together. In yet another aspect, two $R^1$ are linked together. In yet another aspect, two $R^2$ are linked together. In yet another aspect, two $R^3$ are linked together. In yet another aspect, two $R^4$ are linked together. In yet another aspect, two $R^5$ are linked together. In yet another aspect, R and W are linked together. In yet another aspect, W and $R^2$ are linked together. In yet another aspect, R and $R^2$ are linked together. In yet another aspect, R and $R^3$ are linked together. In yet another aspect, W and $R^3$ are linked together. In yet another aspect, $R^2$ and $R^3$ are linked together. All other permutations of linkages between R, $R^1$, $R^2$, $R^3$, $R^4$, and $R^5$ are also possible.

In one aspect, at least one $R^a$ is present. In another aspect, $R^a$ is absent.

In one aspect, $R^a$ is a mono-substitution. In another aspect, W is a di-substitution. In yet another aspect, $R^a$ is a tri-substitution.

In one aspect, $R^a$ is connected to at least $Y^1$. In another aspect, $R^a$ is connected to at least $Y^2$. In yet another aspect, $R^a$ is connected to at least $Y^3$. In one aspect, $R^a$ is connected to at least $Y^1$ and $Y^2$. In one aspect, $R^a$ is connected to at least $Y^1$ and $Y^3$. In one aspect, $R^a$ is connected to at least $Y^2$ and $Y^3$. In one aspect, $R^a$ is connected to $Y^1$, $Y^2$, and $Y^3$.

In one aspect, $R^a$ is a di-substitution and the $R^a$'s are linked together. When the $R^a$'s are linked together the resulting structure can be a cyclic structure which includes a portion of the five-membered cyclic structure as described herein. For example, a cyclic structure can be formed when the di-substitution is of and $Y^2$ and the $R^a$'s are linked together. A cyclic structure can also be formed when the di-substitution is of $Y^2$ and $Y^3$ and the $R^a$'s are linked together. A cyclic structure can also be formed when the di-substitution is of $Y^3$ and $Y^4$ and the $R^a$'s are linked together.

In one aspect, each $R^a$ is independently a substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof wherein two or more of $R^a$ are optionally linked together. In one aspect, at least one $R^a$ is substituted or unsubstituted aryl, cycloalkyl, cycloalkenyl, heterocyclyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, or any conjugate or combination thereof wherein two or more of $R^a$ are optionally linked together.

In one aspect, at least one $R^b$ is present. In another aspect, $R^b$ is absent.

In one aspect, $R^b$ is a mono-substitution. In another aspect, $R^b$ is a di-substitution. In yet another aspect, $R^b$ is a tri-substitution.

In one aspect, each $R^b$ is independently a substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof wherein two or more of $R^b$ are optionally linked together. In one aspect, at least one $R^b$ is substituted or unsubstituted aryl, cycloalkyl, cycloalkenyl, heterocyclyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, or any conjugate or combination thereof wherein two or more of $R^b$ are optionally linked together.

In one aspect, at least one $R^c$ is present. In another aspect, $R^c$ is absent.

In one aspect, $R^c$ is a mono-substitution. In another aspect, $R^c$ is a di-substitution. In yet another aspect, $R^c$ is a tri-substitution.

In one aspect, each $R^c$ independently is substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^c$ are optionally linked together. In one aspect, at least one $R^c$ is substituted or unsubstituted aryl, cycloalkyl, cycloalkenyl, heterocyclyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, or any conjugate or combination thereof wherein two or more of $R^c$ are optionally linked together.

In one aspect, at least one $R^d$ is present. In another aspect, $R^d$ is absent.

In one aspect, $R^d$ is a mono-substitution. In another aspect, $R^d$ is a di-substitution. In yet another aspect, $R^d$ is a tri-substitution.

In one aspect, each $R^d$ is independently a substituted or unsubstituted aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof wherein two or more of $R^c$ are optionally linked together. In one aspect, at least one $R^c$ is substituted or unsubstituted aryl, cycloalkyl, cycloalkenyl, heterocyclyl, heteroaryl, alkyl, alkenyl, alkynyl, halogen, hydroxyl, amino, a mono- or di-alkylamino, a mono- or diaryl amino, alkoxy, aryloxy, haloalkyl, aralkyl, or any conjugate or combination thereof wherein two or more of $R^c$ are optionally linked together.

In one aspect, $R^d$ is connected to at least $Y^5$. In another aspect, $R^d$ is connected to at least $Y^6$. In yet another aspect, $R^d$ is connected to at least $Y^7$. In one aspect, $R^d$ is connected to at least $Y^5$ and $Y^6$. In one aspect, $R^d$ is connected to at least $Y^5$ and $Y^7$. In one aspect, $R^d$ is connected to at least $Y^6$ and $Y^7$. In one aspect, $R^d$ is connected to $Y^5$, $Y^6$, and $Y^7$.

In one aspect, $R^d$ is a di-substitution and the $R^d$'s are linked together. When the $R^d$'s are linked together the resulting structure can be a cyclic structure which includes a portion of the five-membered cyclic structure as described herein. For example, a cyclic structure can be formed when the di-substitution is of $Y^5$ and $Y^6$ and the $R^d$'s are linked together. A cyclic structure can also be formed when the di-substitution is of $Y^6$ and $Y^7$ and the $R^d$'s are linked together. Cyclic structure can also be formed when the di-substitution is of $Y^7$ and $Y^8$ and the $R^a$'s are linked together.

In one aspect, each of

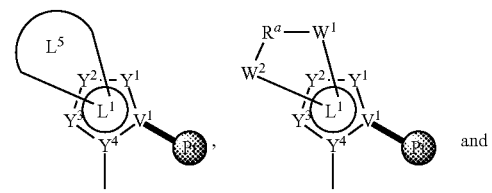

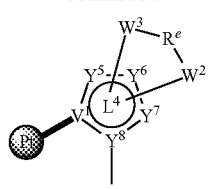
independently has the structure:
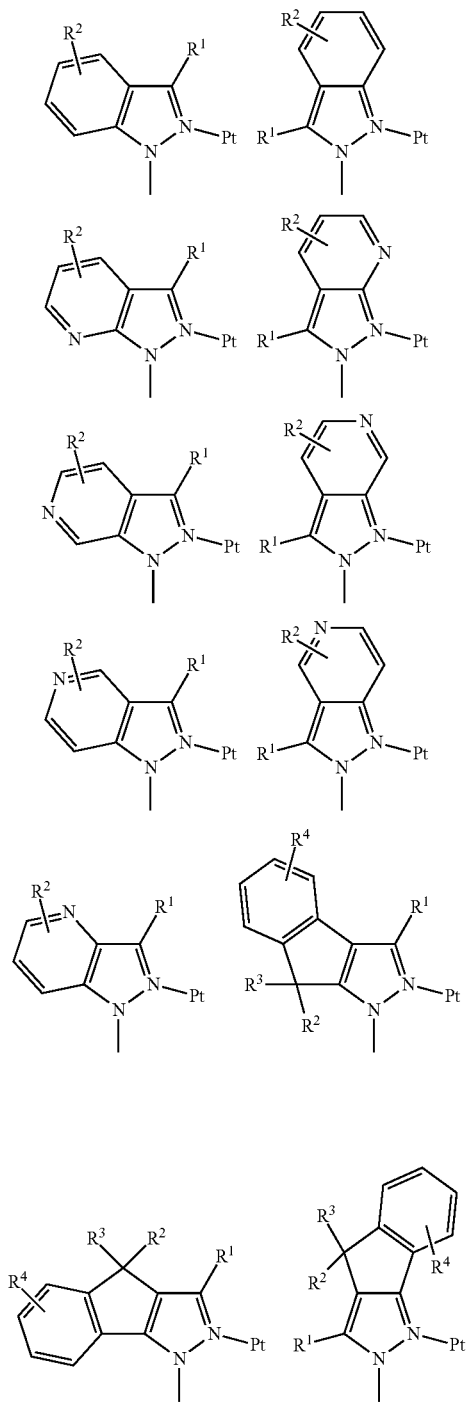
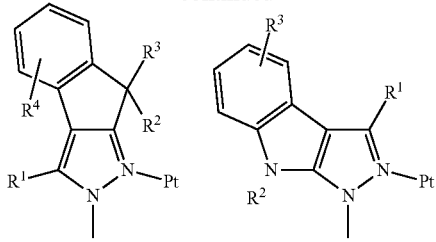
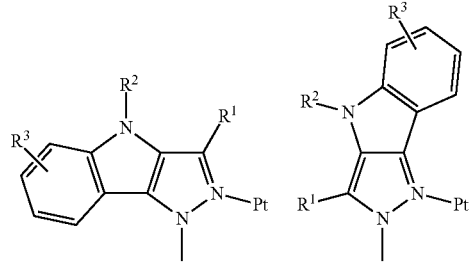
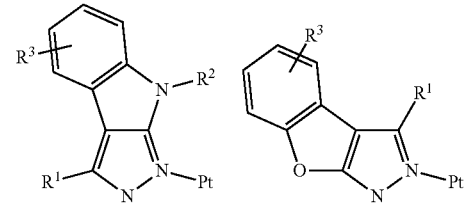
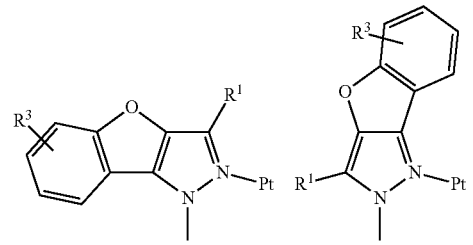
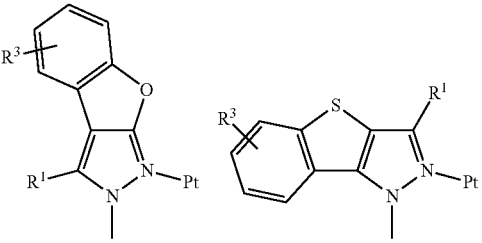
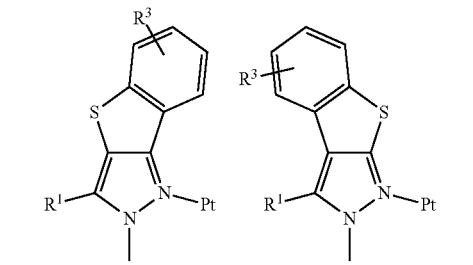
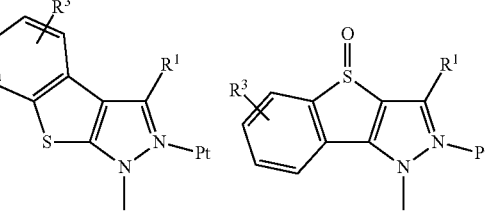

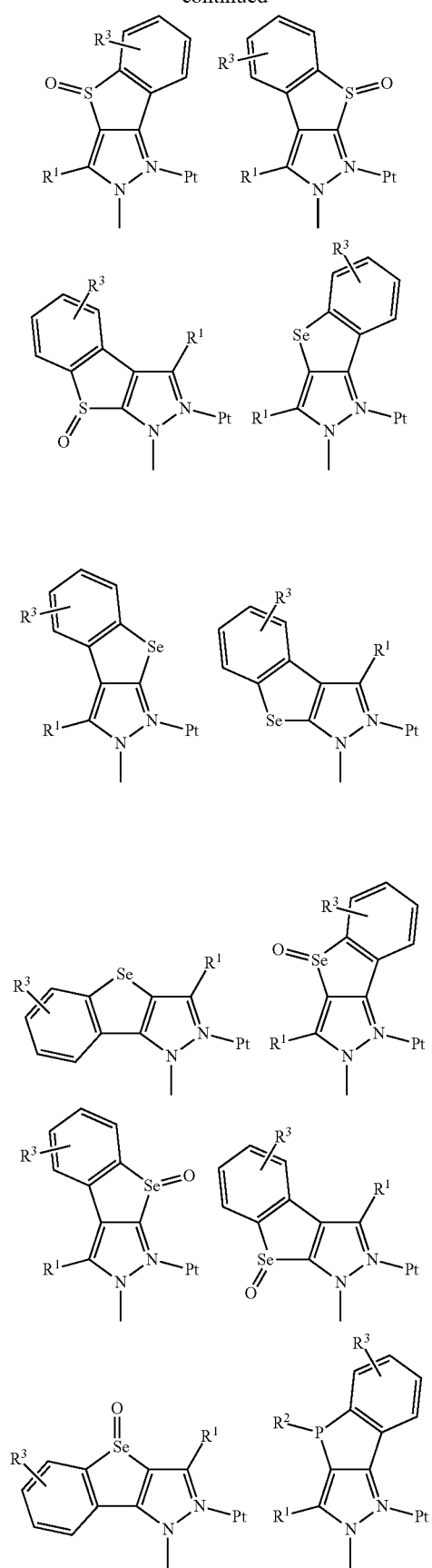
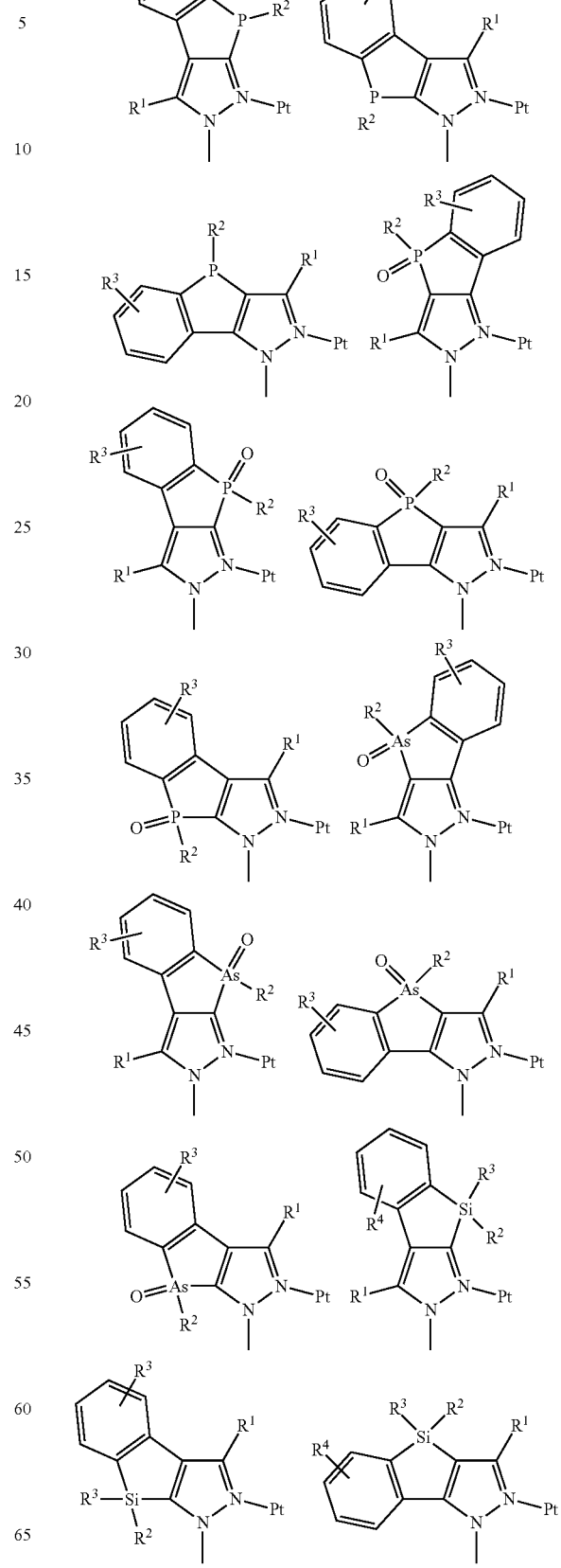

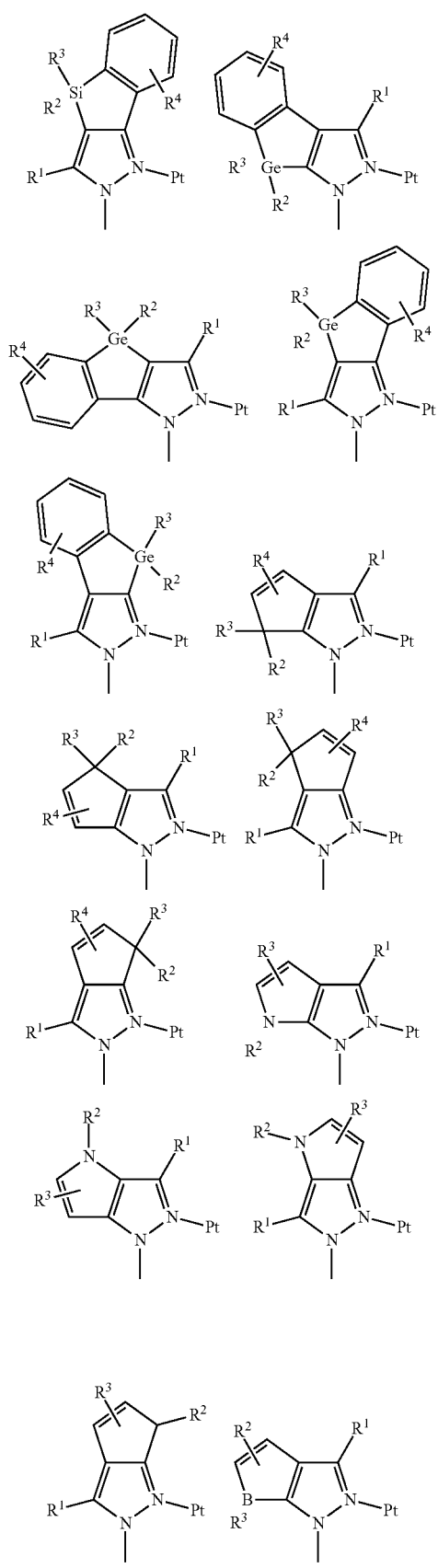
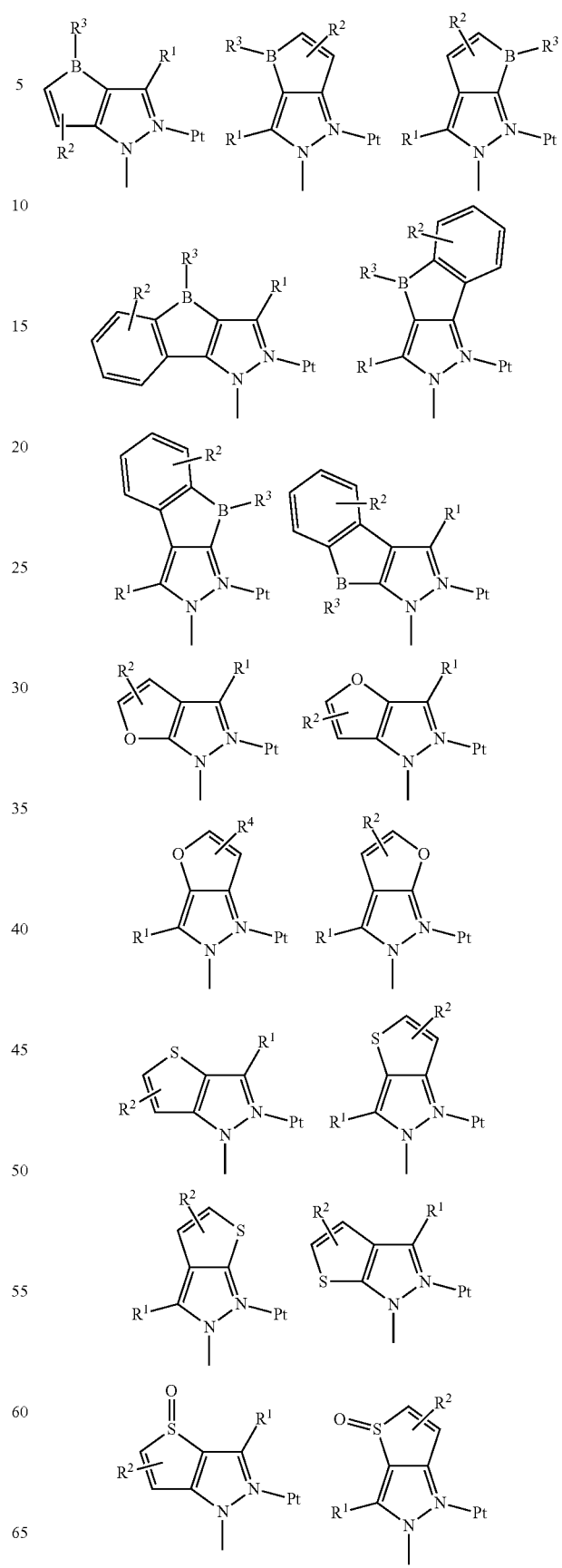

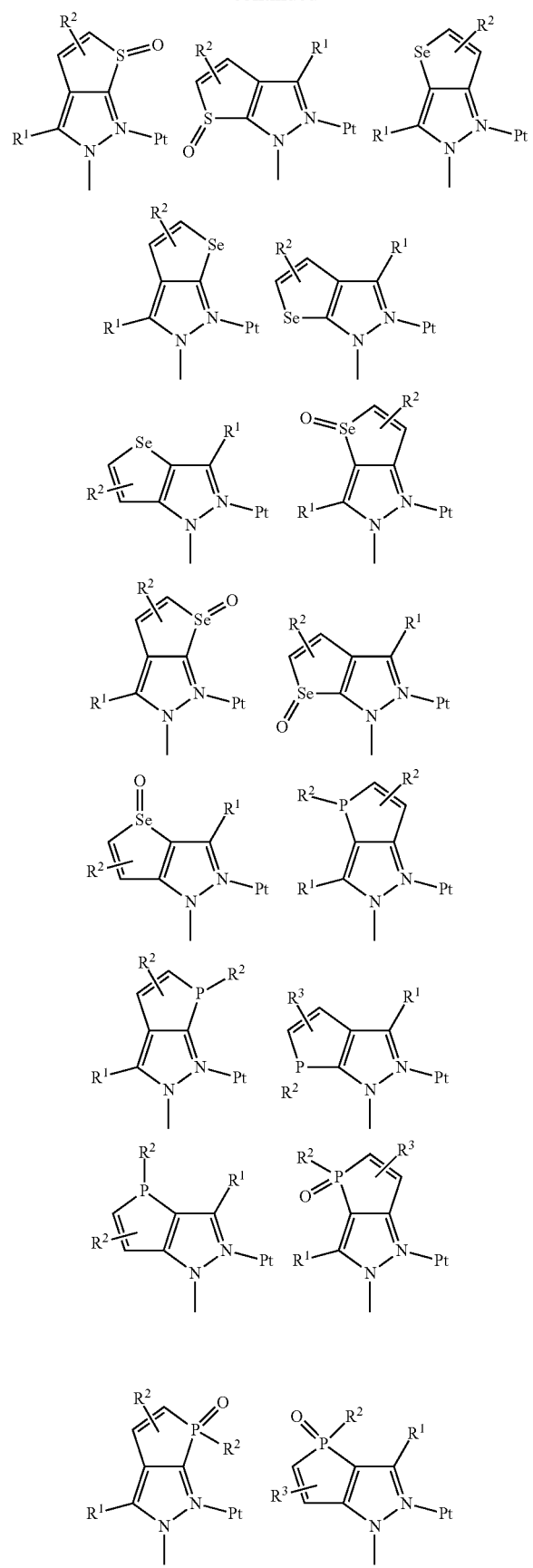
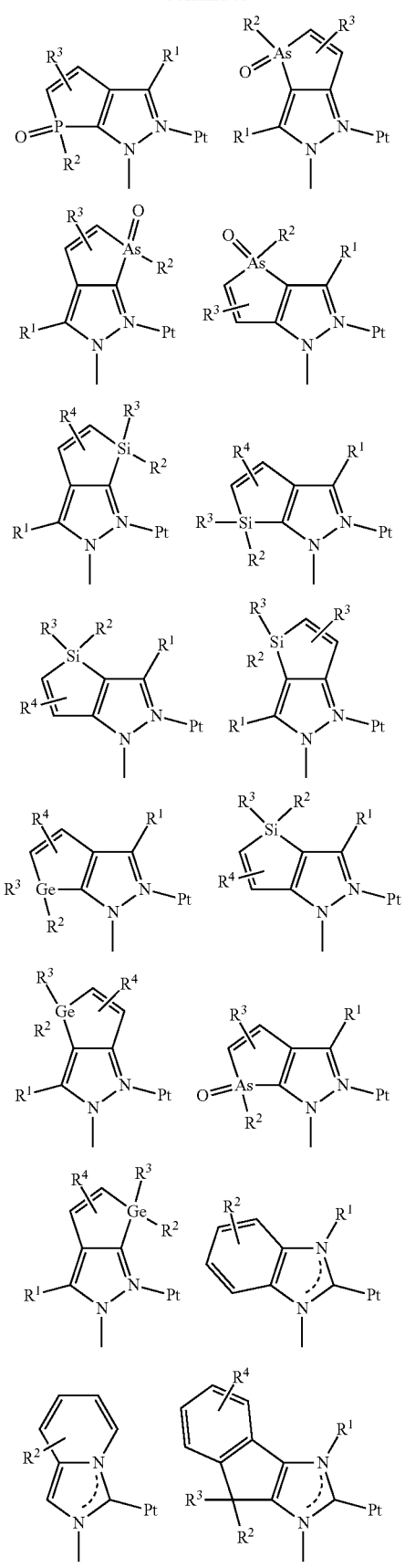

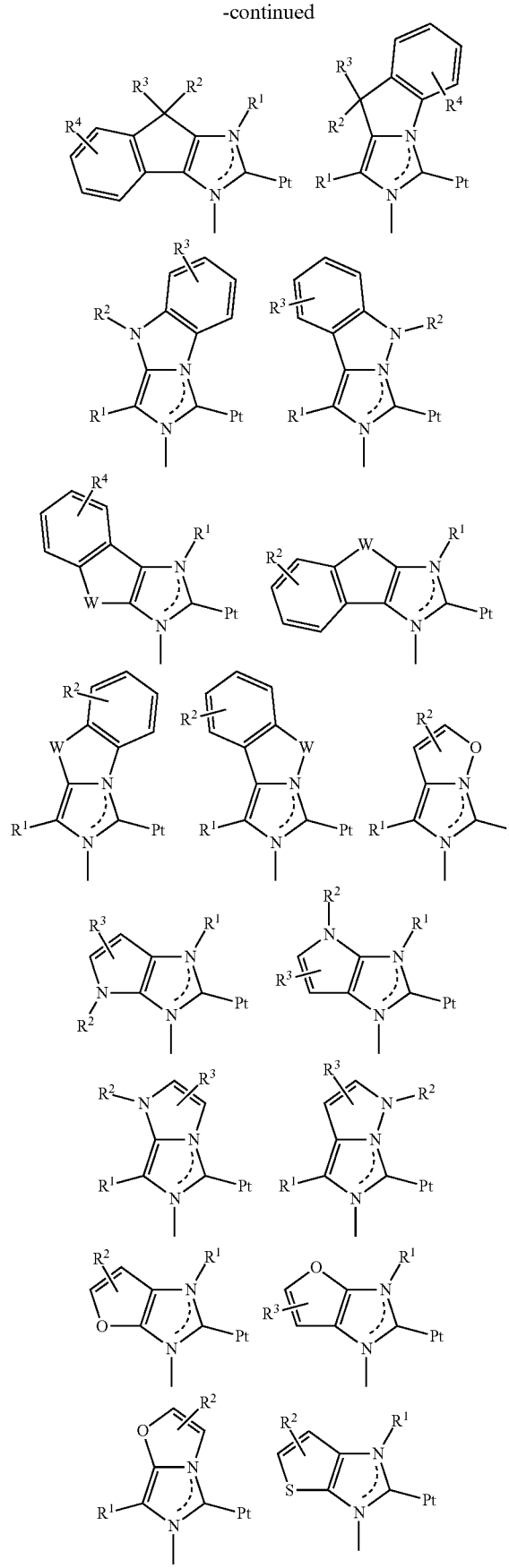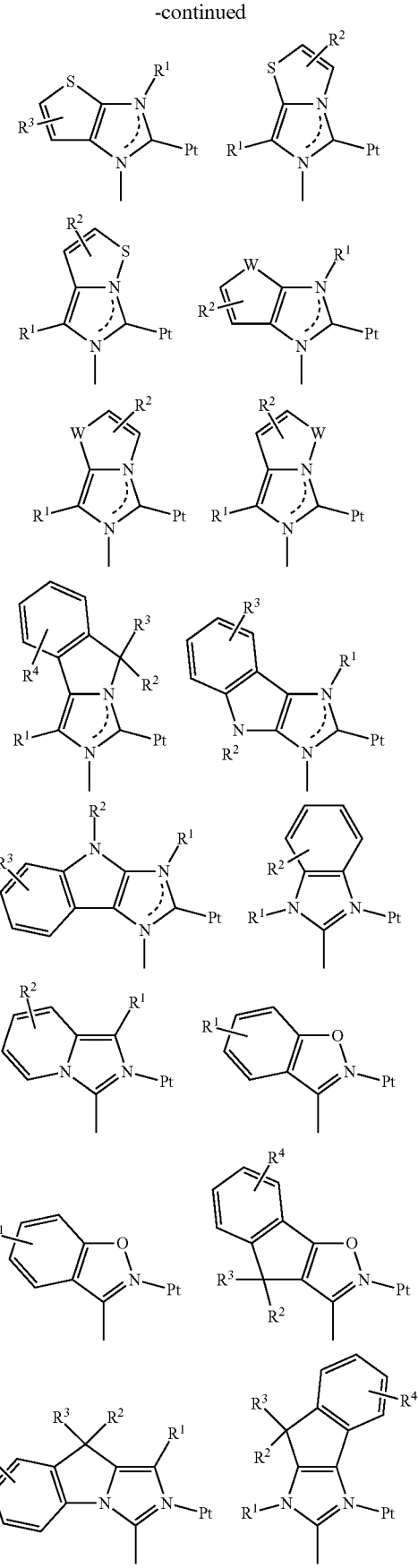

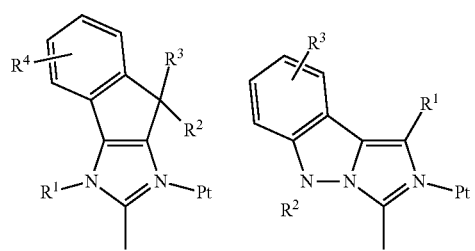
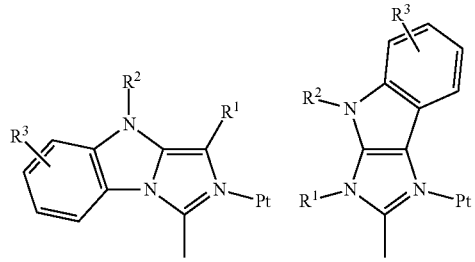
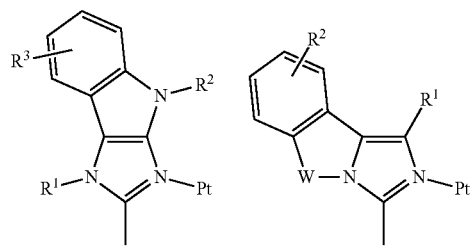
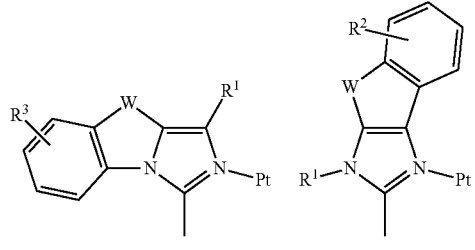
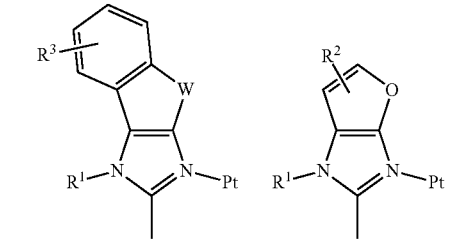
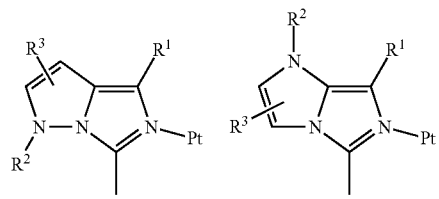
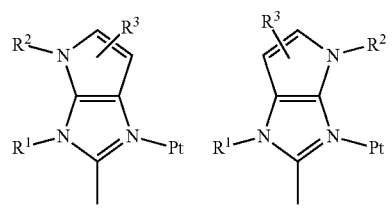
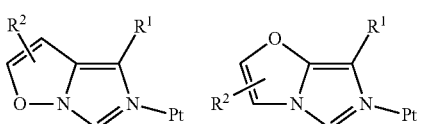
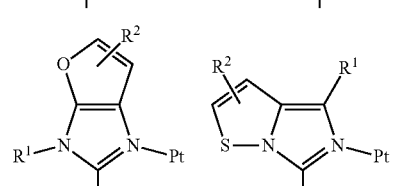
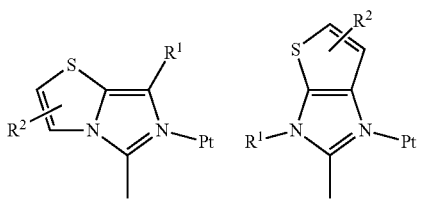
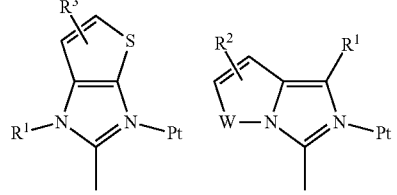
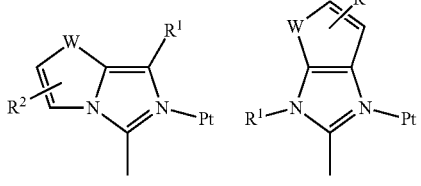
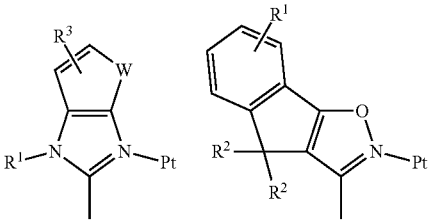
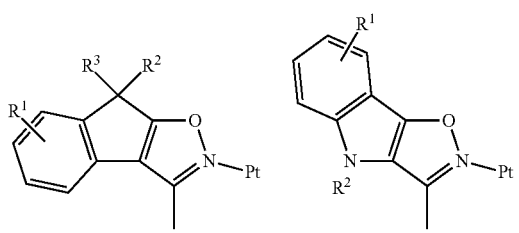
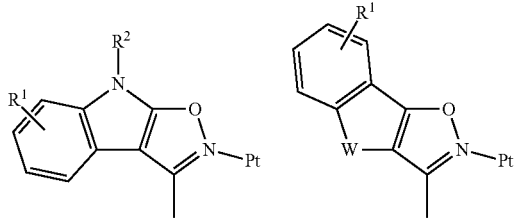

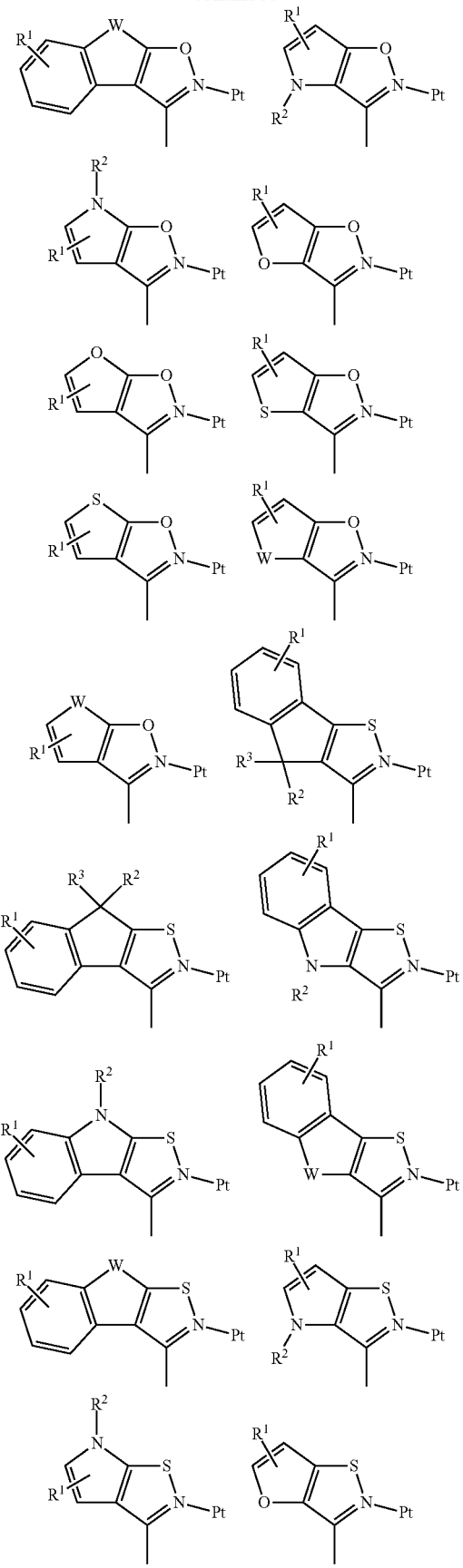
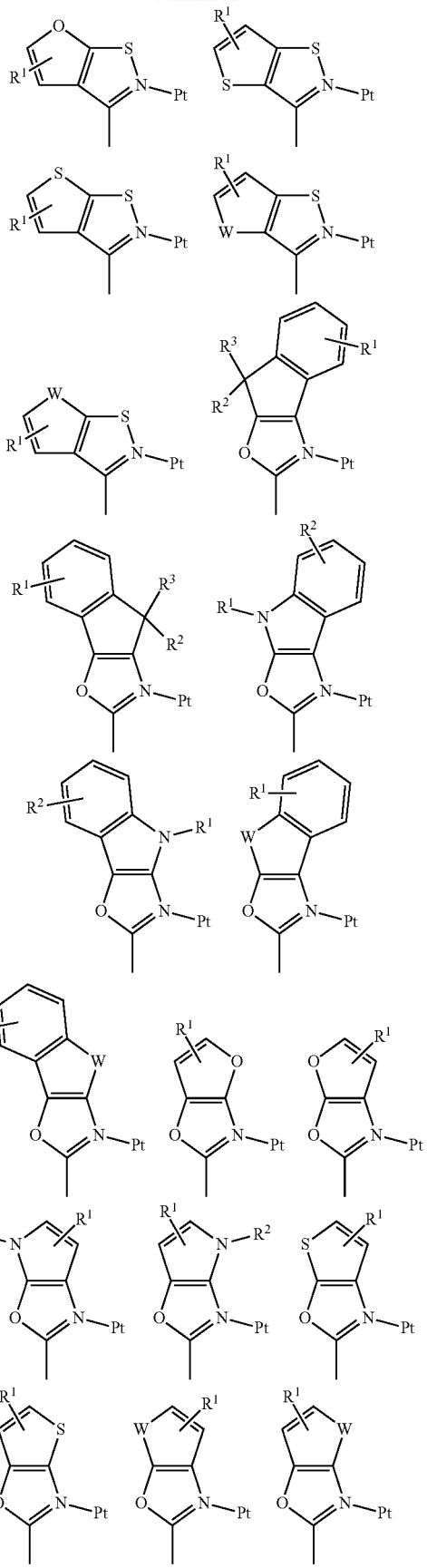

-continued
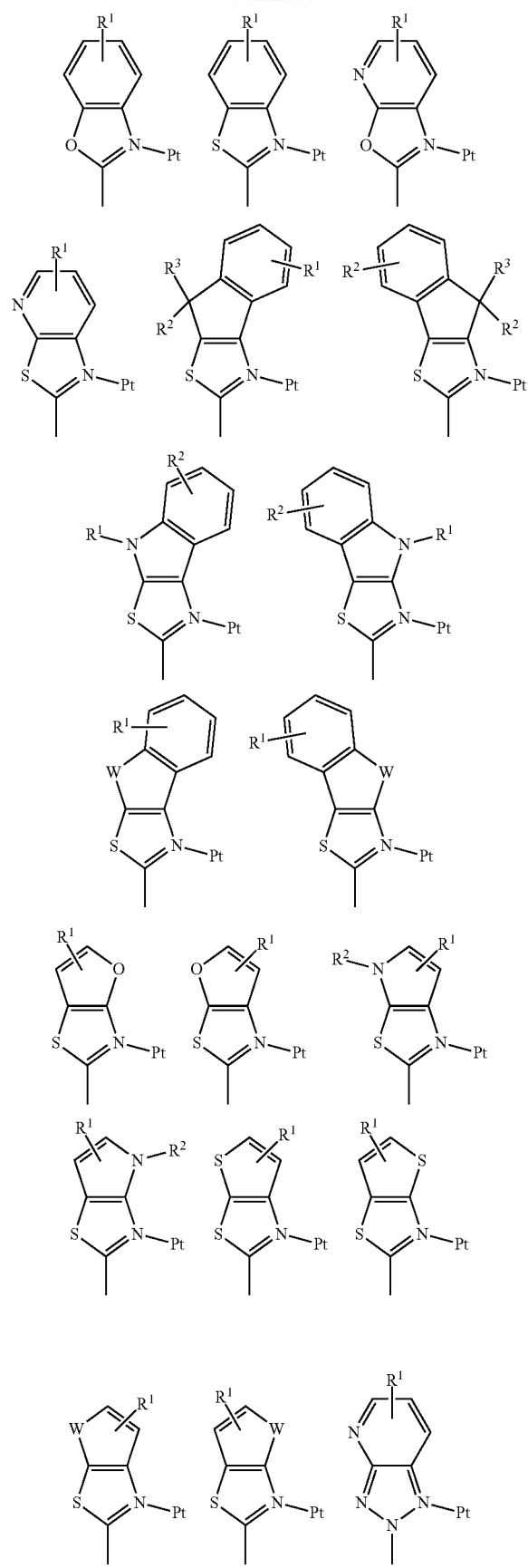
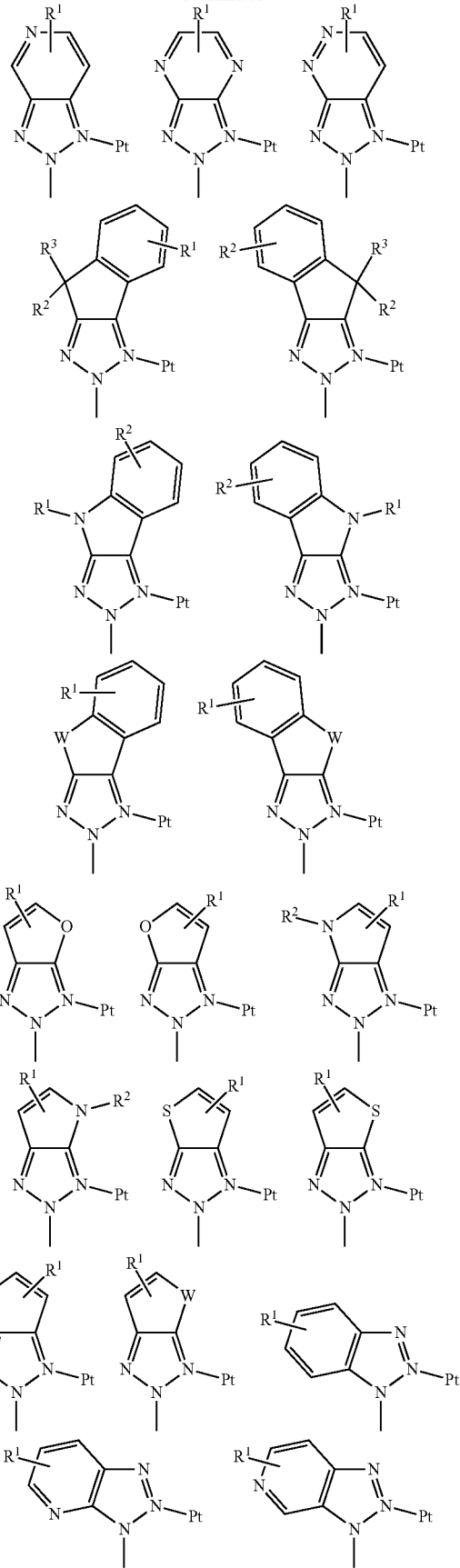

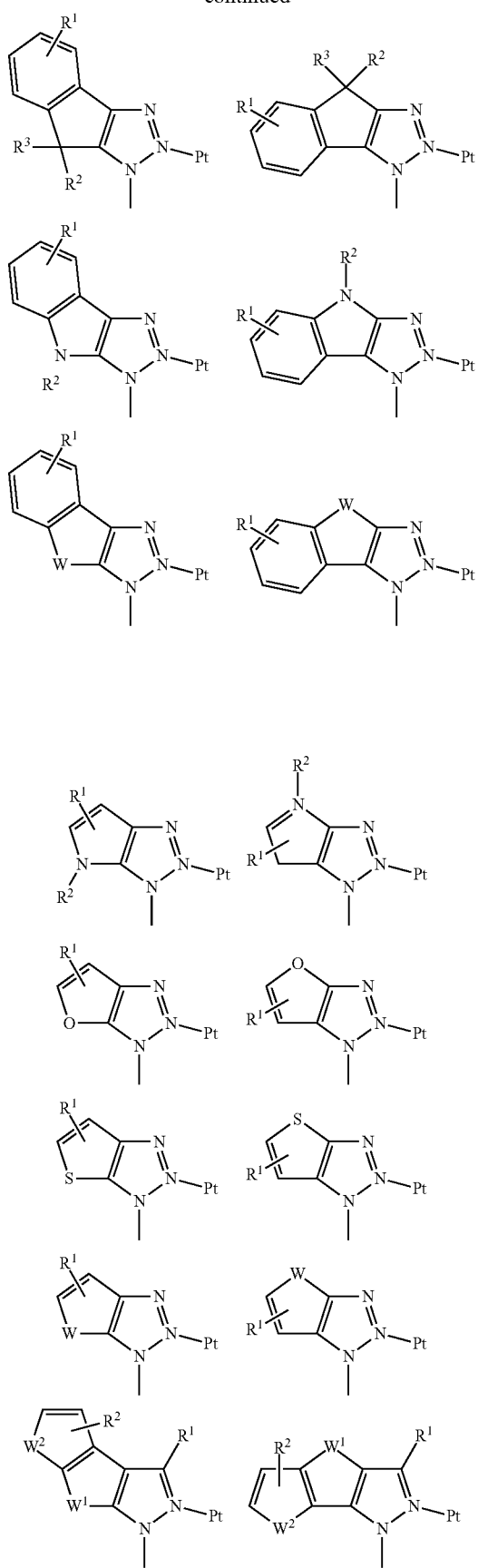
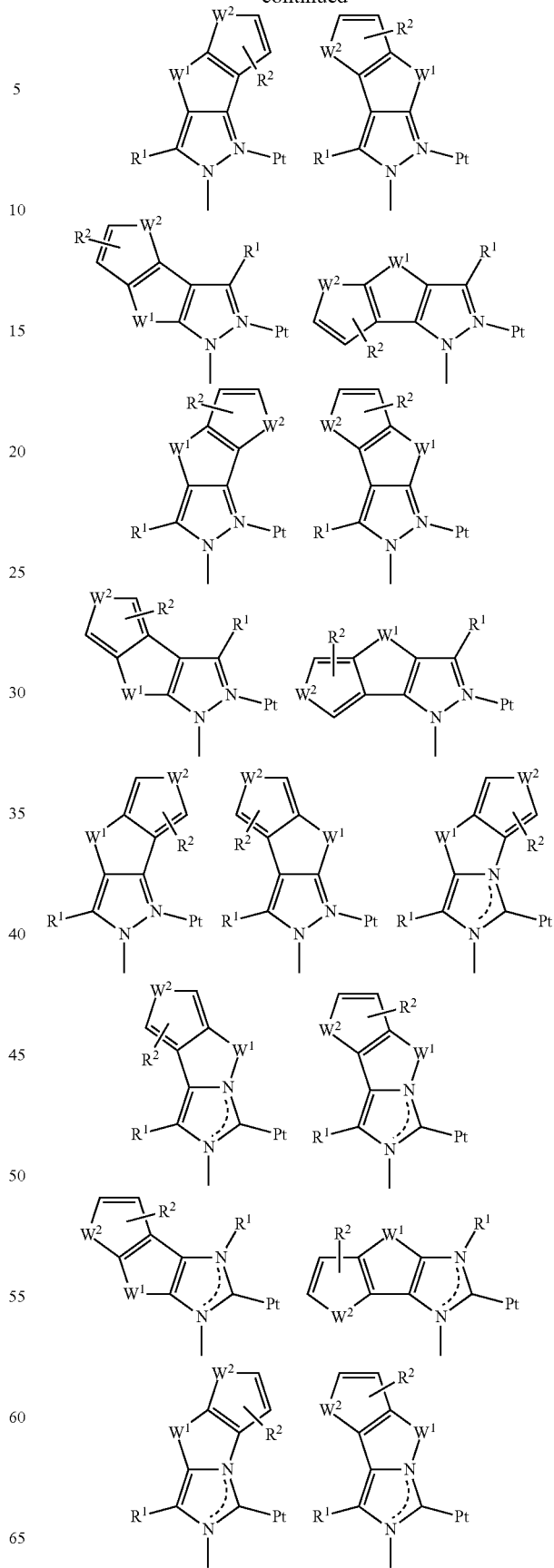

-continued
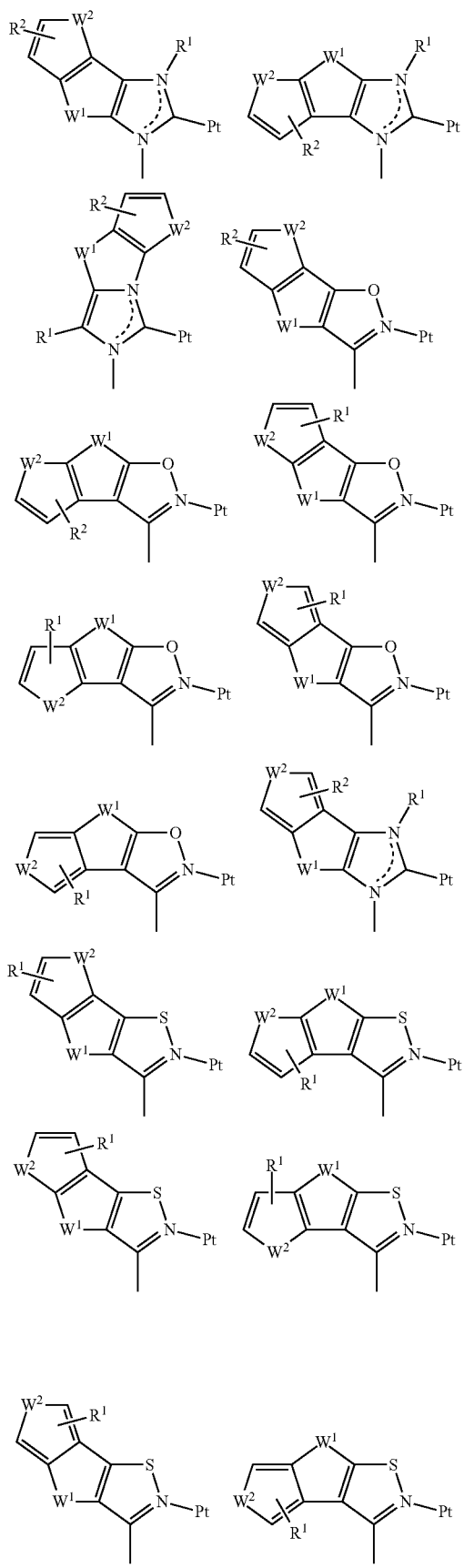
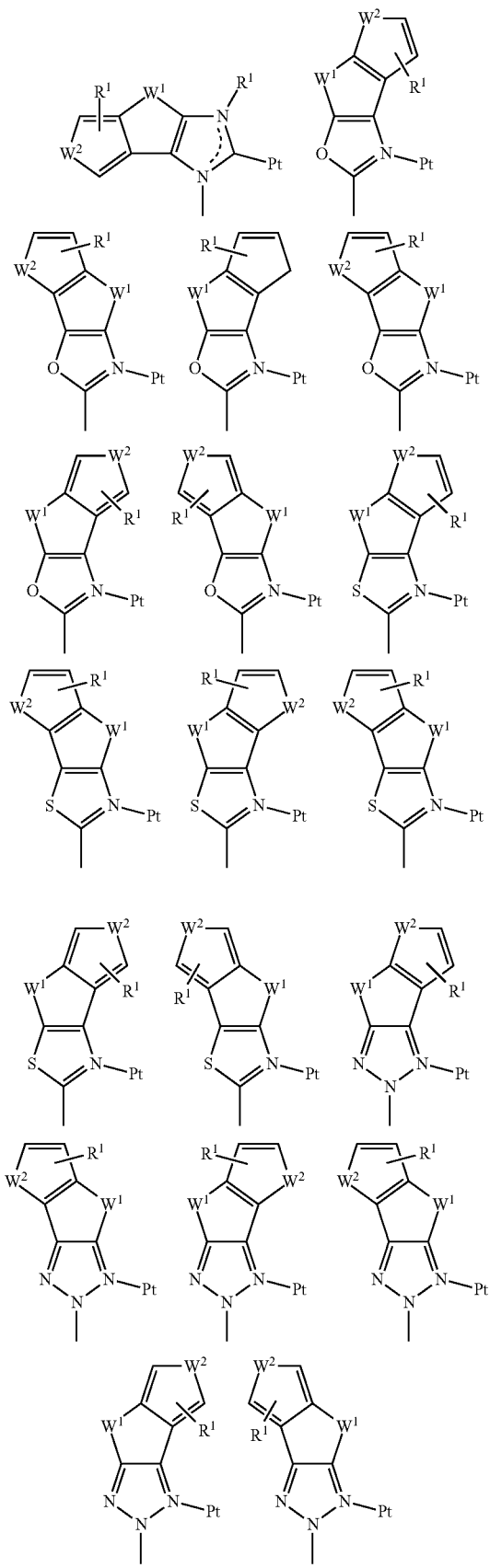

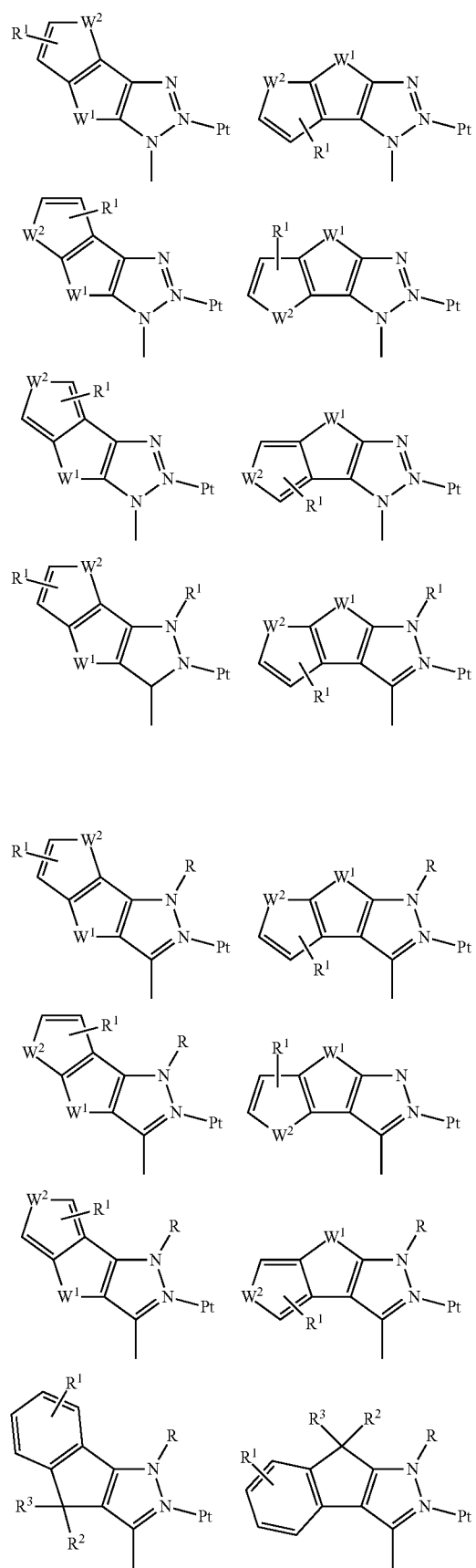
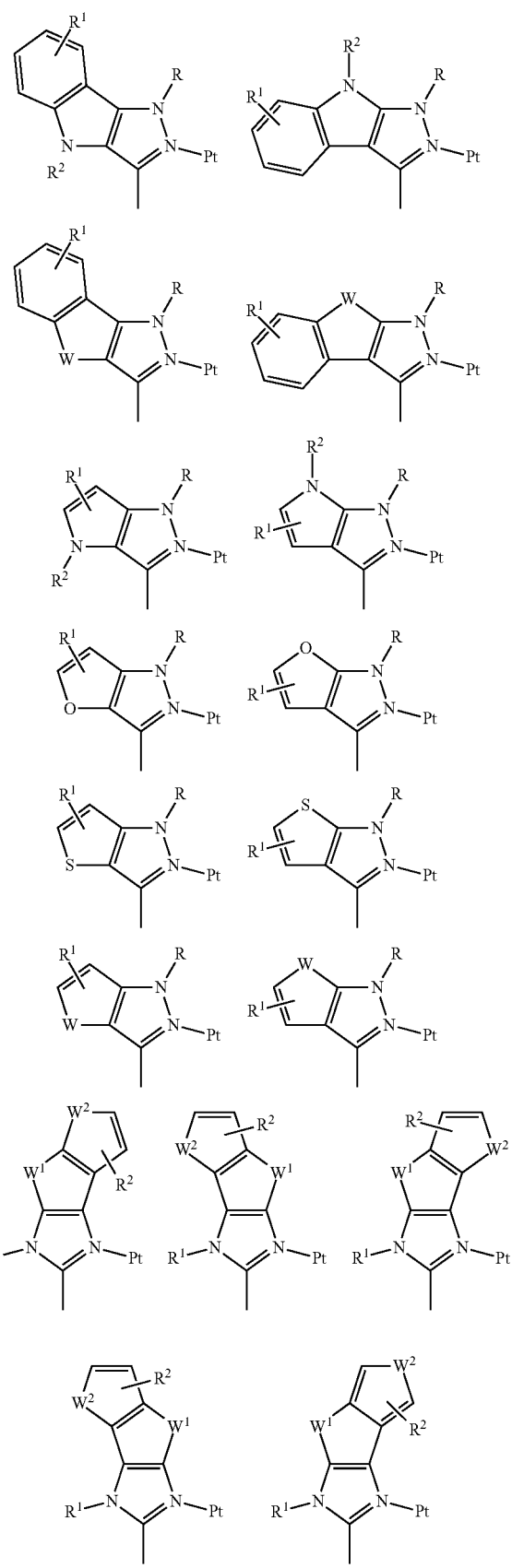

-continued

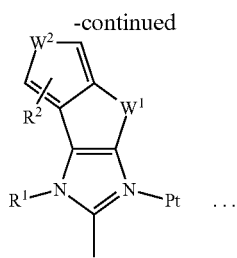

wherein each of

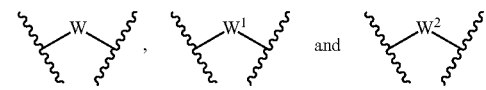

is independently

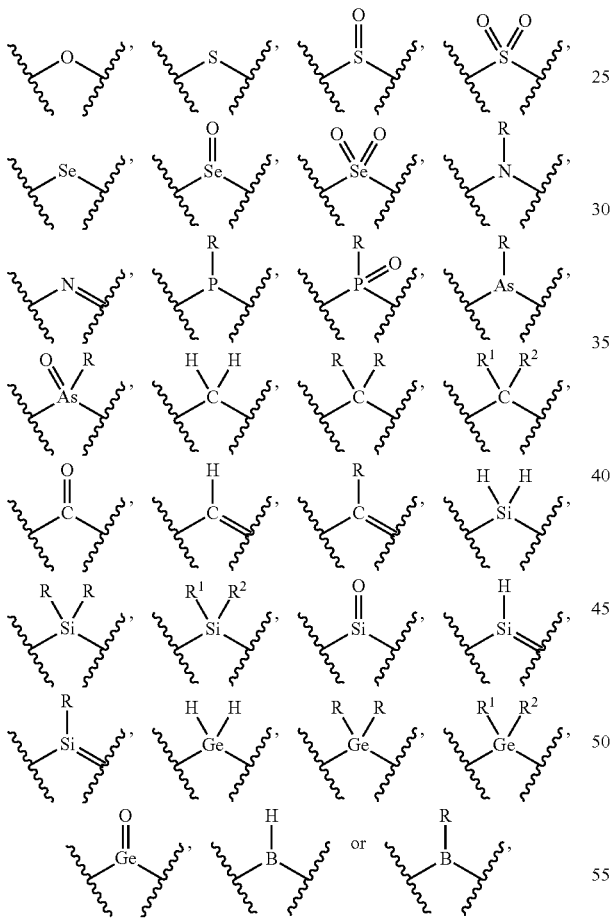

wherein each of R, $R^1$, $R^2$, $R^3$ and $R^4$ is independently a mono-, di-, tri, or tetra-substitution, wherein each of R, $R^1$, $R^2$, $R^3$, and $R^4$ is independently a substituted or unsubstituted hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of R, $R^1$, $R^2$, $R^3$, and $R^4$ are optionally linked together.

In one aspect, each of

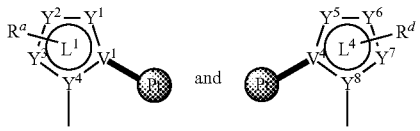

independently has the structure:

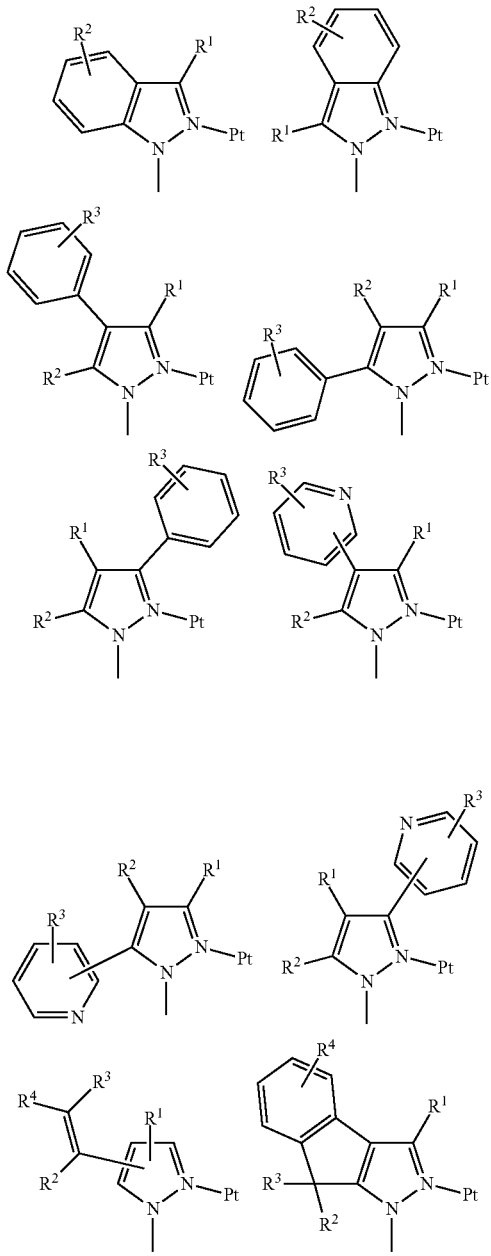

-continued
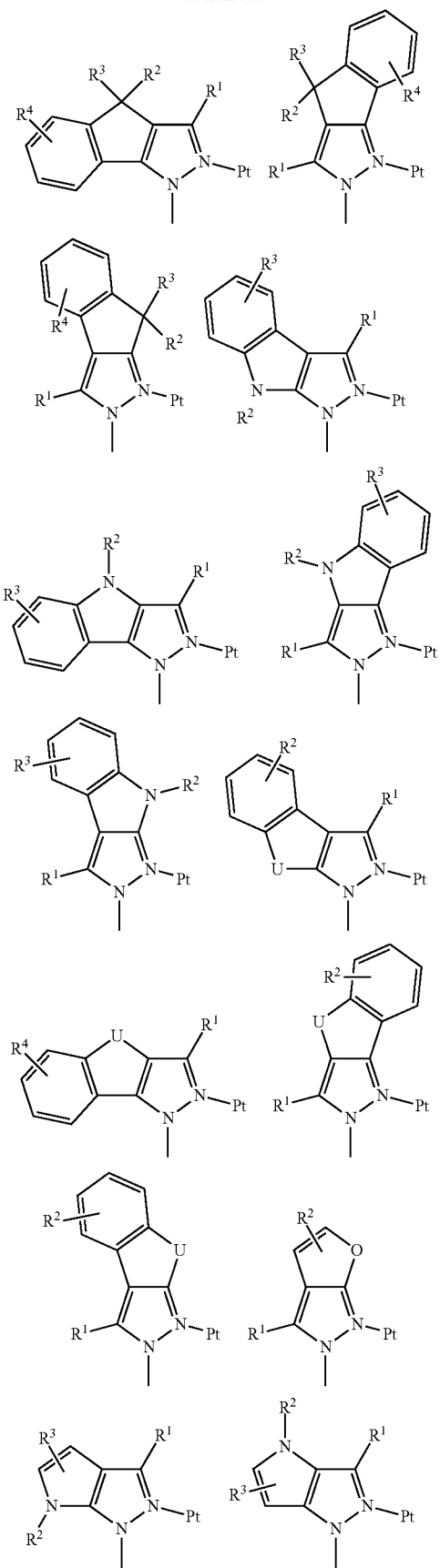
-continued
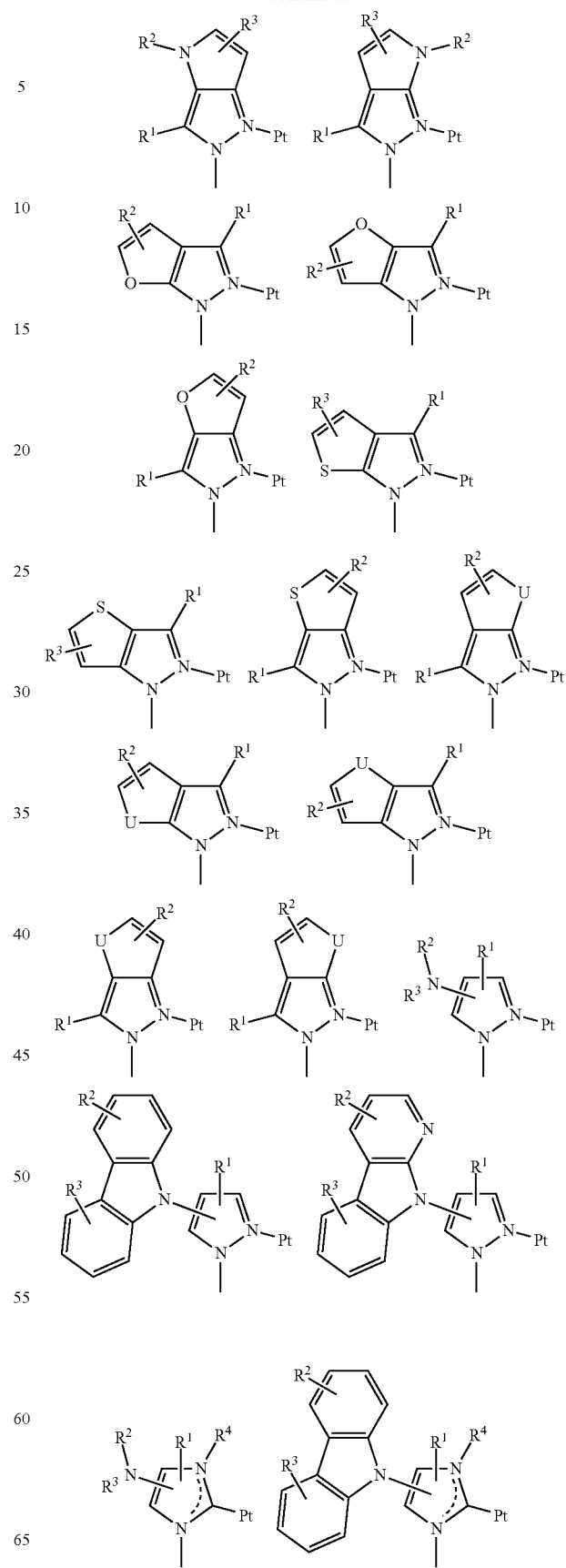

-continued
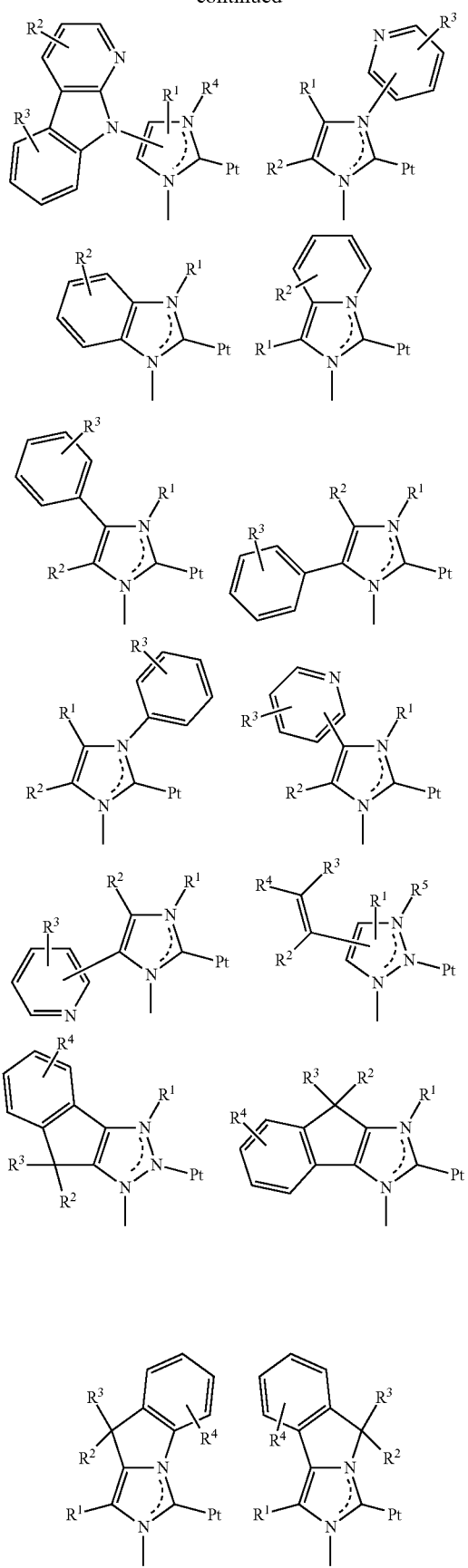
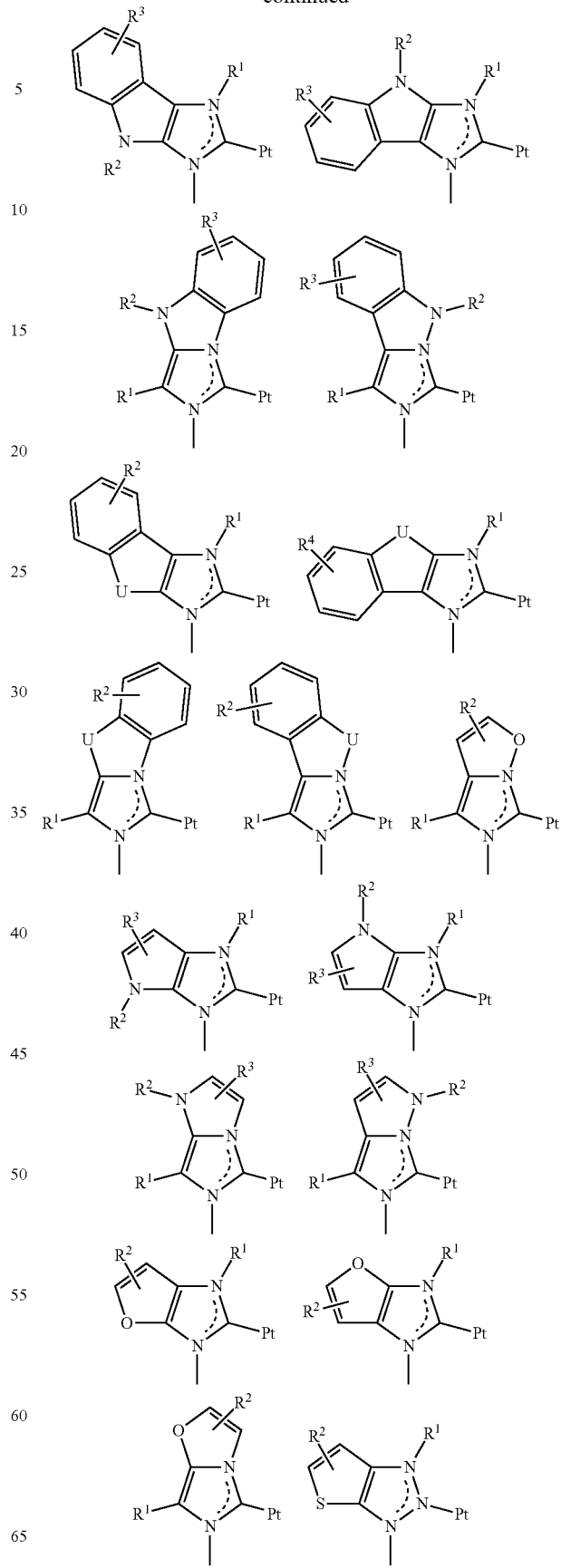

-continued
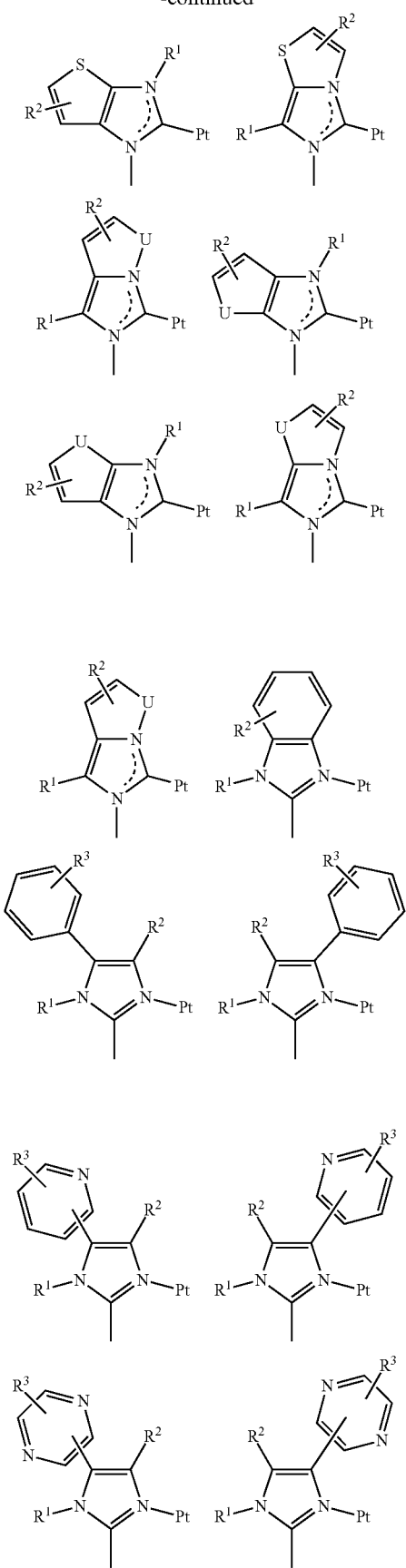
-continued
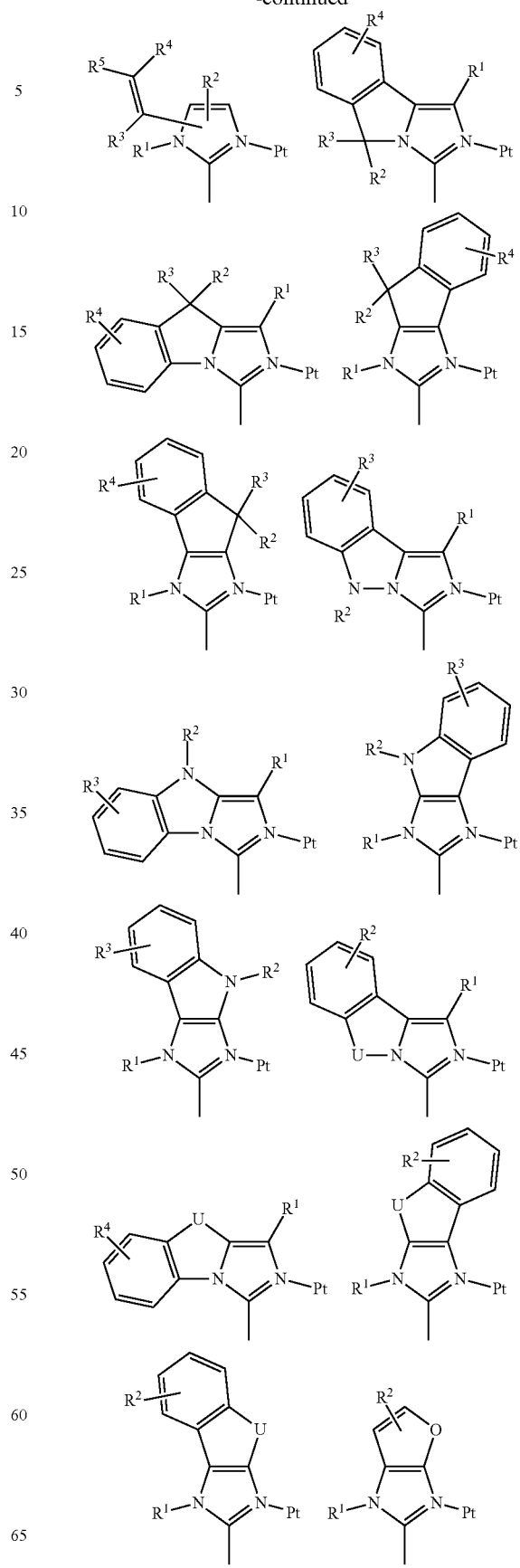

-continued
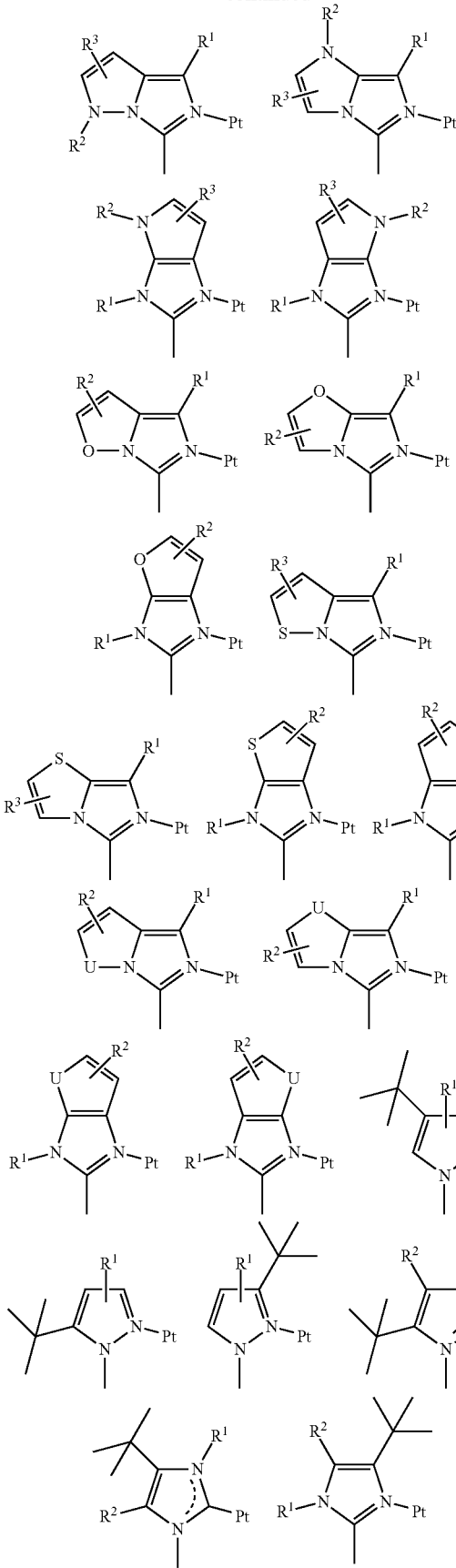
-continued
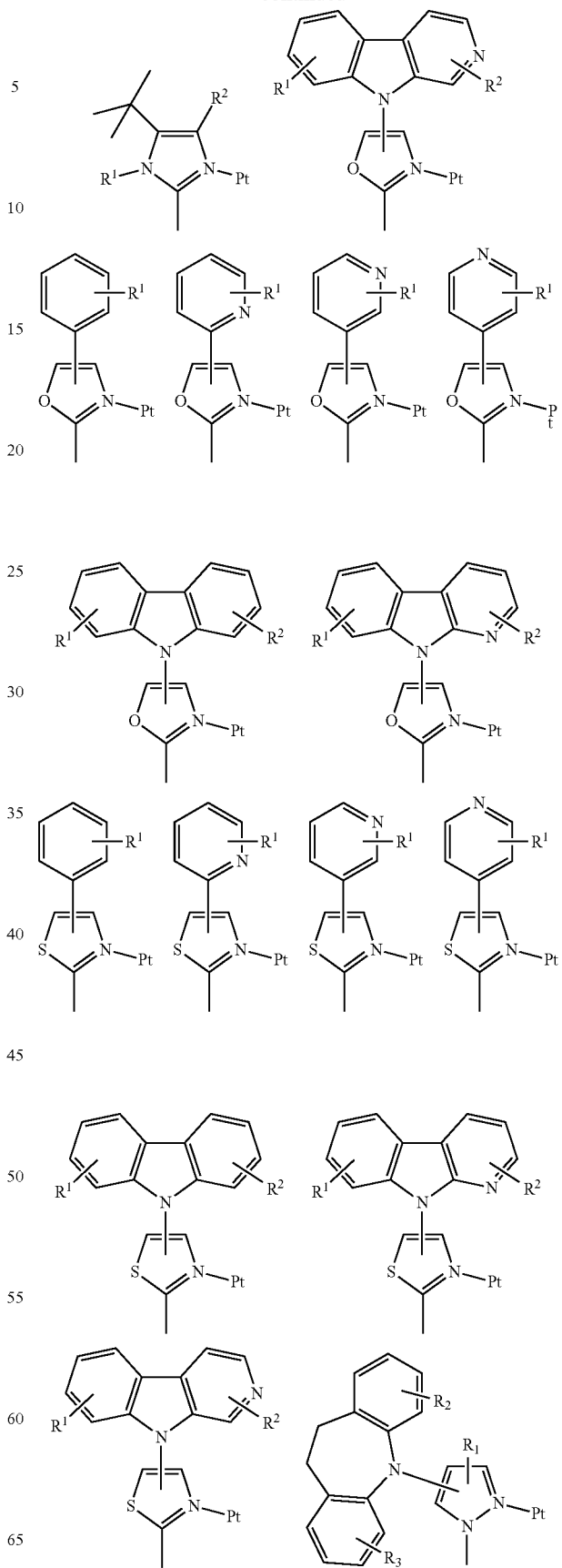

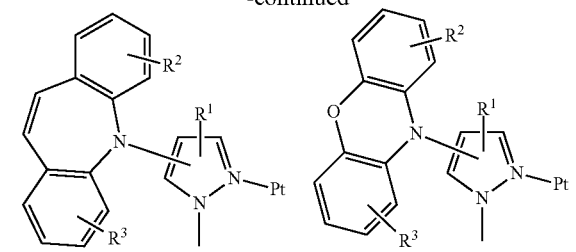
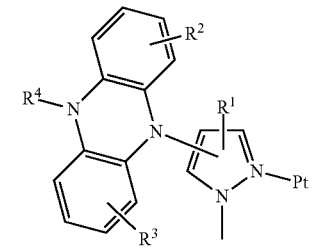
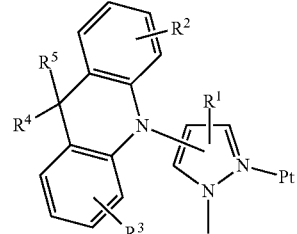

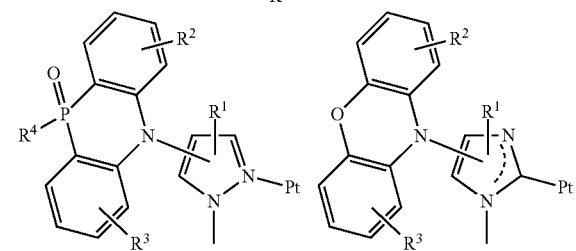
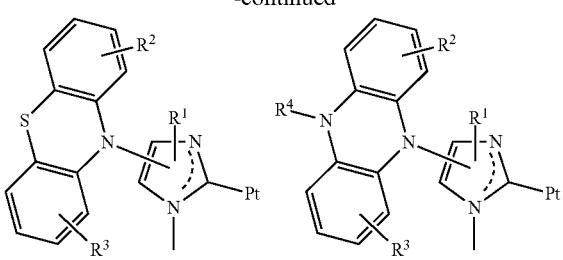
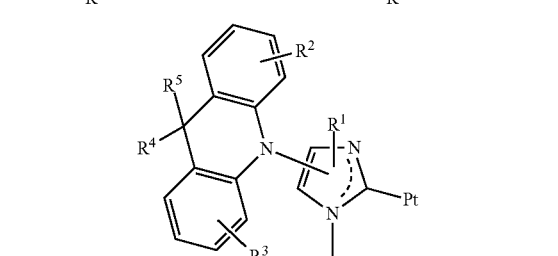
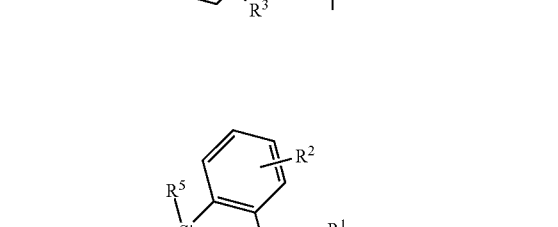
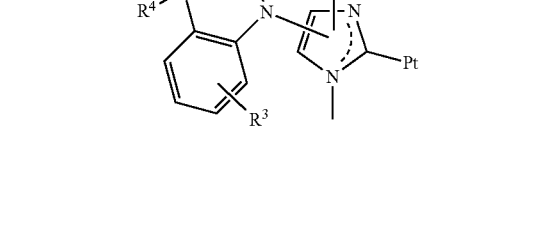
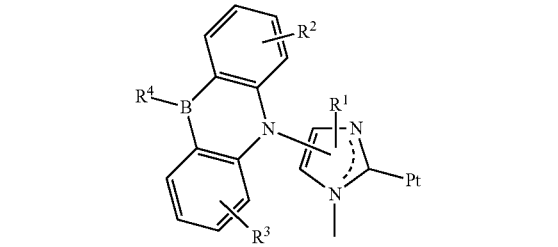
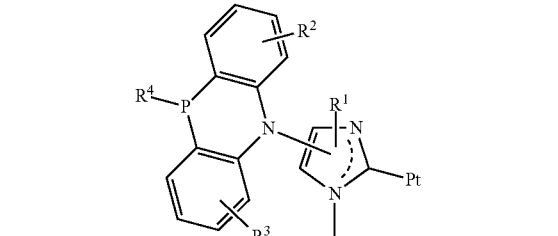
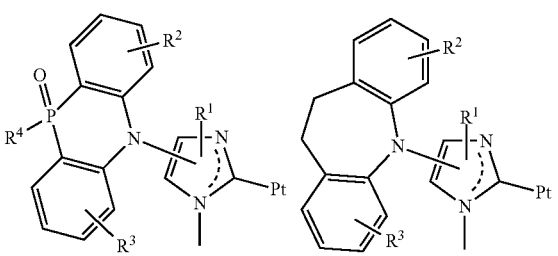

-continued

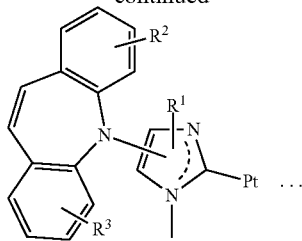

wherein each of $Y^1$, $Y^2$, $Y^3$, $Y^4$, $Y^5$, $Y^6$, $Y^7$, and $Y^8$ is independently C, N, O, or S, wherein U is O, S, S=O, $SO_2$, Se, $NR^3$, $PR^3$, $R^3P$=O, $CR^1R^2$, C=O, $SiR^1R^2$, $GeR^1R^2$, $BR^3$, NH, PH, HP=O, $CH_2$, $CHR^1$, $SiH_2$, $GeH_2$, $SiHR^1$, $GeHR^1$ or BH, wherein each of $R^1$, $R^2$, $R^3$, $R^4$, and $R^5$ is independently a mono-, di-, tri, or tetra-substitution, wherein each of $R^1$, $R^2$, $R^3$, $R^4$, and $R^5$ is independently substituted or unsubstituted hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, substituted silyl, or polymerizable group, or any conjugate or combination thereof, wherein two or more of $R^1$, two or more of $R^2$, two or more of $R^3$, two or more of $R^4$, two or more of $R^5$, or any combination thereof, are optionally linked together, and wherein $R^4$ and $R^5$ are optionally linked to form =O or a cyclic structure.

In one aspect, $R^1$ and $R^2$ are linked to form the cyclic structure:

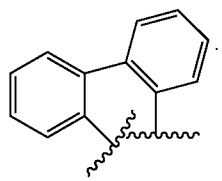 [SMILES: *c1ccccc1-c1ccccc1*]

In another aspect, each $R^a$ is independently one or more of the following structures. In another aspect, each $R^a$ can also comprise other structures or portions thereof not specifically recited herein, and the present invention is not intended to be limited to those structures or portions thereof specifically recited:

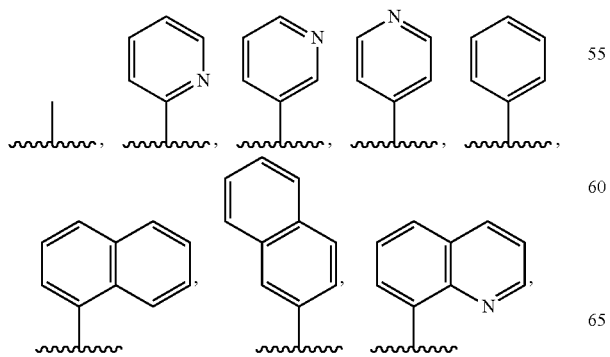

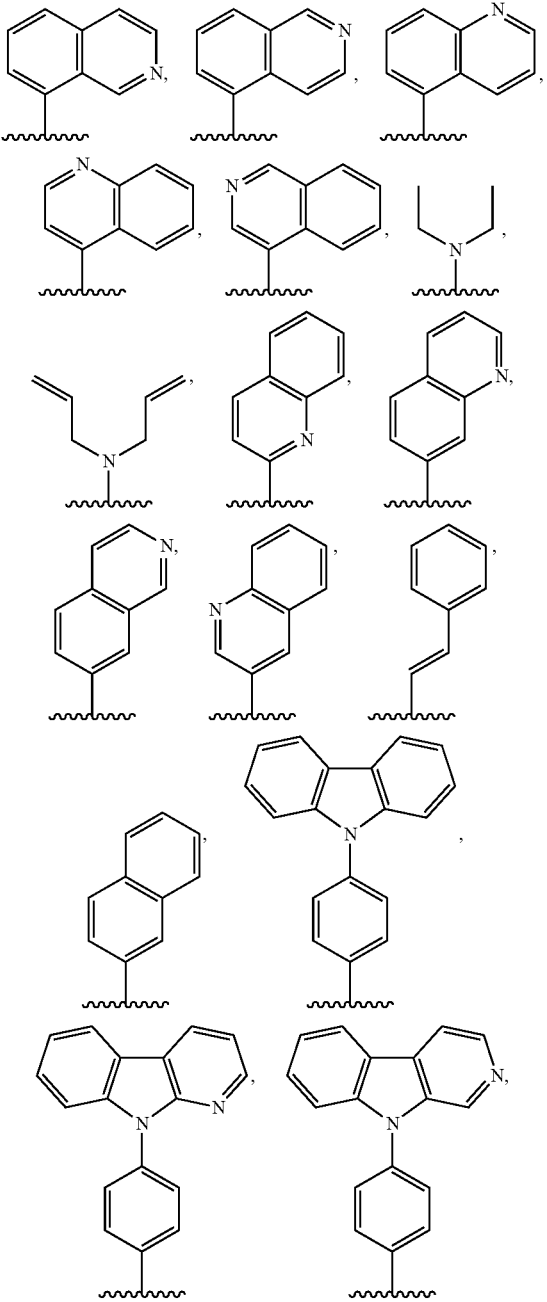

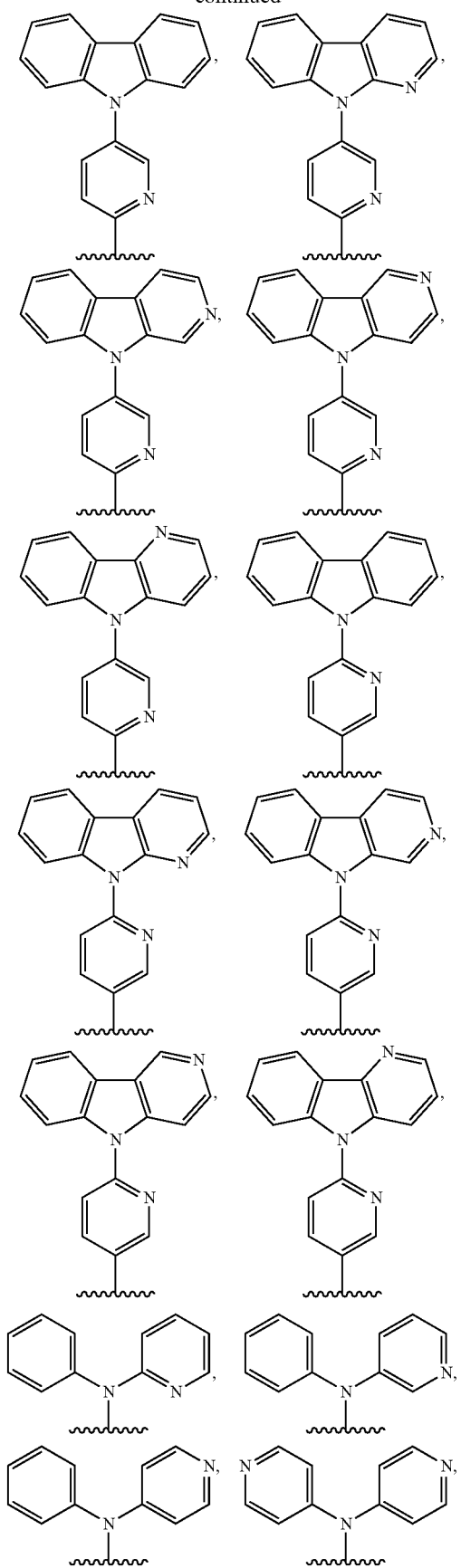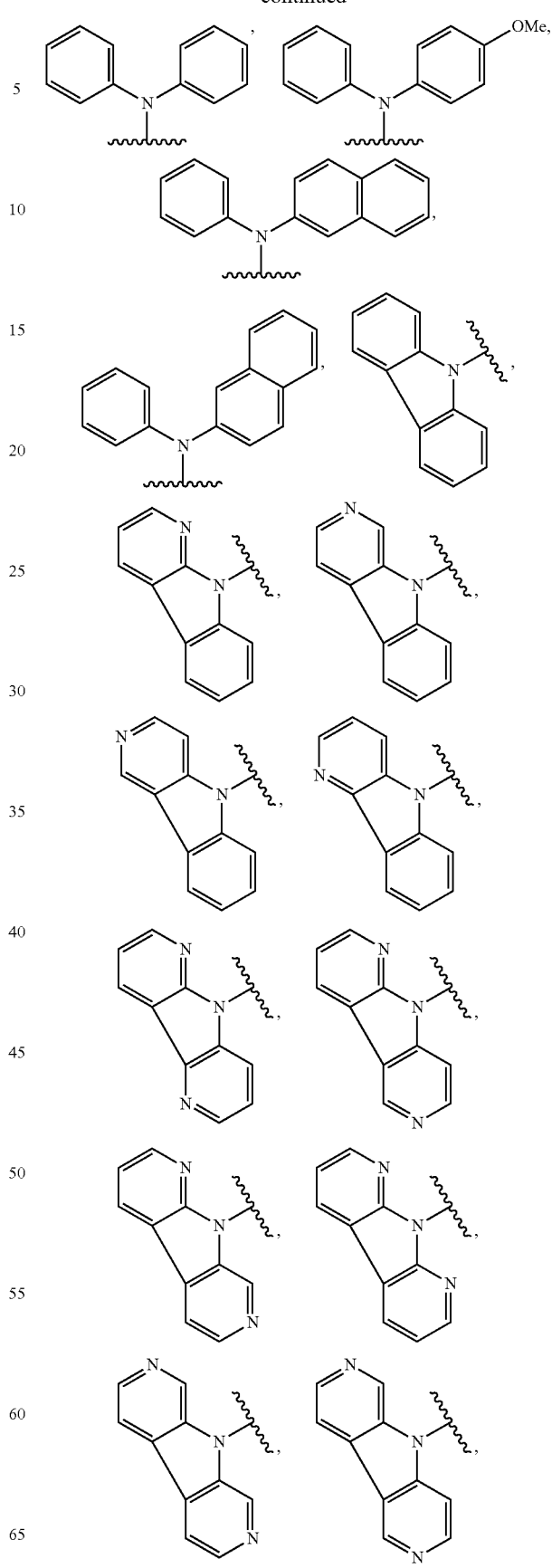

-continued

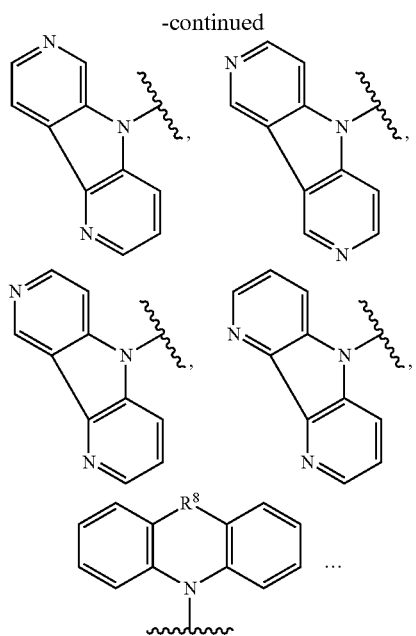

wherein $Q^1$ is S, N, or $CR^6R^7$, wherein $R^6$ and $R^7$ are independently substituted or unsubstituted hydrogen, alkyl, alkenyl, alkynyl, aryl, cycloalkyl, cycloalkenyl, heteroaryl, heterocyclyl, hydroxy, thiol, amino, halogen, or alkoxy, wherein $R^8$ is O, S, $P(O)R^1$, $PR^1$, $NR^1$, $CR^1R^2$, $SiR^1R^2$, BH, P(O)H, PH, NH, $CR^1H$, $CH_2$, $SiH_2$, $SiHR^1$, BH, C(O), C2 alkyl, or C2 alkenyl, and wherein $R^9$ is substituted or unsubstituted hydrogen, alkyl, alkenyl, alkynyl, aryl, cycloalkyl, cycloalkenyl, heteroaryl, or heterocyclyl. It is understood that each $R^a$ can independently be substituted with $R^1$, $R^2$, $R^3$, $R^4$, and $R^5$ as described elsewhere herein.

In another aspect, $R^a$ can also include one or more of the following structures. In another aspect, $R^a$ can also include other structures or portions thereof not specifically recited herein, and the present disclosure is not intended to be limited to those structures or portions thereof specifically recited.

In one aspect, $R^a$ is

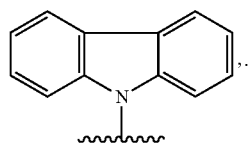 [SMILES: *n1c2ccccc2c2ccccc21]

In one aspect, $R^d$ can have the structure of $R^a$ as described herein. Thus, the structures described above relating to $R^a$ can also be used for the description of $R^d$.

In another aspect, $R^d$ and $R^a$ are identical.

In one aspect, A is $A^1$. In one aspect, $A^1$ is present. For example, when $A^1$ is present, $A^1$ can be O, S, S=O, $SO_2$, Se, $NR^3$, $PR^3$, RP=O, $CR^1R^2$, C=O, $SiR^1R^2$, $GeR^1R^2$BH, P(O)H, PH, NH, $CR^1H$, $CH_2$, $SiH_2$, $SiHR^1$, BH, or $BR^3$. For example, $A^1$ can be O or S, such as O. In another aspect, $A^1$ is absent.

In one aspect, $A^2$ is present. For example, when $A^2$ is present, $A^2$ can be O, S, S=O, $SO_2$, Se, $NR^3$, $PR^3$, RP=O, $CR^1R^2$, C=O, $SiR^1R^2$, $GeR^1R^2$BH, P(O)H, PH, NH, $CR^1H$, $CH_2$, $SiH_2$, $SiHR^1$, BH, or $BR^3$. For example, $A^2$ can be O or S. In another aspect, $A^2$ is absent.

In one aspect, X is N, P, P=O, $CR^1$, CH, $SiR^1$, SiH, $GeR^1$, or GeH. For example, X can be N or P. In another example, X can be $CR^1$, CH, $SiR^1$, SiH, $GeR^1$ or GeH. In another aspect, X can be Z, $Z^1$, or $Z^2$.

In one aspect, Y is N, P, P=O, $CR^1$, CH, $SiR^1$, SiH, $GeR^1$, or GeH. For example, Y can be N or P. In another example, Y can be $CR^1$, CH, $SiR^1$, SiH, $GeR^1$, or GeH. In another aspect, Y can be Z, $Z^1$, or $Z^2$.

In one aspect, $L^2$ can be aryl, cycloalkyl, cycloalkenyl, heteroaryl, heterocyclyl, carbene, or N-heterocyclic carbene. For example, $L^2$ can be aryl, cycloalkyl, cycloalkenyl, heteroaryl, or heterocyclyl. In another example, $L^2$ can be aryl or heteroaryl. In yet another example, $L^2$ can be aryl. In one aspect, $L^2$ can have the structure

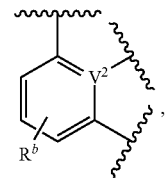

for example,

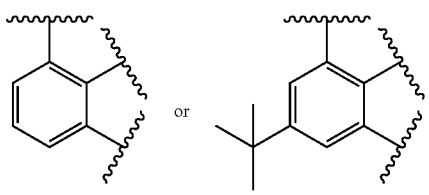

In another aspect, $L^2$ can have the structure

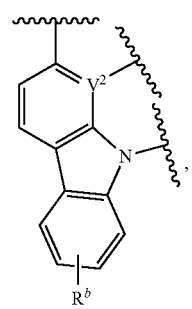

for example,

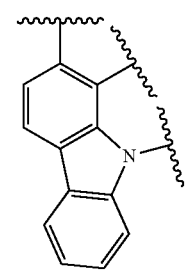 [SMILES: *c1ccc2c3ccccc3n(*)c2c1*]

In another aspect, $L^2$ can have the structure

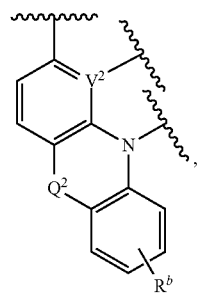

wherein $Q^2$ is O or S, for example,

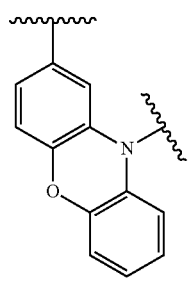

In another aspect, $L^2$ can have the structure

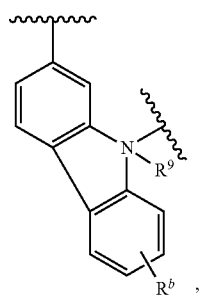

wherein $R^9$ is hydrogen, alkyl, alkenyl, alkynyl, aryl, cycloalkyl, cycloalkenyl, heteroaryl, heterocyclyl, halogen, hydroxyl, amino, or thiol. In one aspect, $V^2$ can be N, C, P, B, or Si. For example, $V^2$ can be N or C, such as C.

In one aspect, $L^3$ can be aryl, cycloalkyl, cycloalkenyl, heteroaryl, heterocyclyl, carbene, or N-heterocyclic carbene. For example, $L^3$ can be aryl, cycloalkyl, cycloalkenyl, heteroaryl, or heterocyclyl. In another example, $L^3$ can be aryl or heteroaryl. In yet another example, $L^3$ can be aryl. In one aspect, $L^3$ can have the structure

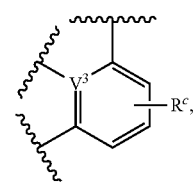

for example,

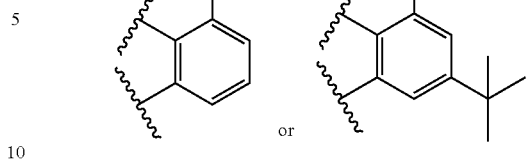

In another aspect, $L^3$ can have the structure

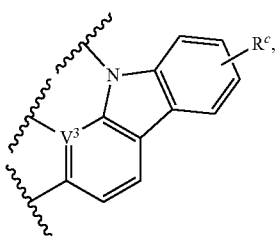

for example,

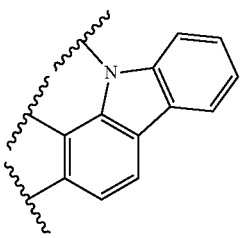

In another aspect, $L^3$ can have the structure

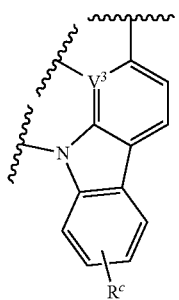

for example,

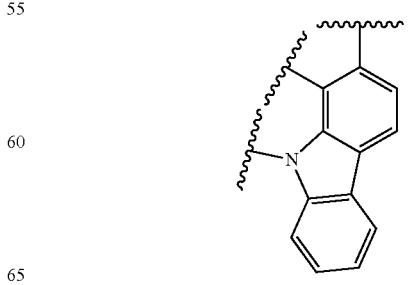

In another aspect, $L^3$ can have the structure

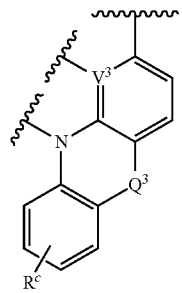

wherein $Q^3$ is O or S, for example,

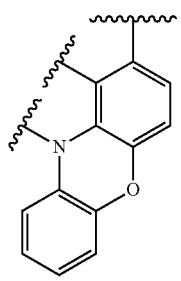

In another aspect, $L^3$ can have the structure

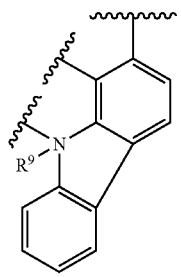

wherein $R^9$ is hydrogen, alkyl, alkenyl, alkynyl, aryl, cycloalkyl, cycloalkenyl, heteroaryl, heterocyclyl, halogen, hydroxyl, amino, or thiol. In one aspect, $V^3$ can be N, C, P, B, or Si. For example, $V^3$ can be N or C, such as C.

In one aspect, $L^4$ can be aryl, cycloalkyl, cycloalkenyl, heteroaryl, heterocyclyl, carbene, or N-heterocyclic carbene. For example, $L^4$ can be aryl, cycloalkyl, cycloalkenyl, heteroaryl, or heterocyclyl. In another example, $L^4$ can be aryl or heteroaryl. In yet another example, $L^4$ can be heteroaryl. In yet another example, $L^4$ can be heterocyclyl. It is understood that, $V^4$ can be a part of $L^4$ and is intended to be included the description of $L^4$ above. In one aspect, $L^4$ can have the structure

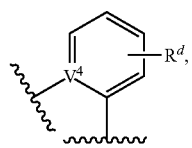

for example,

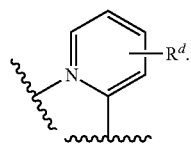

In yet another aspect, $L^4$ can have the structure

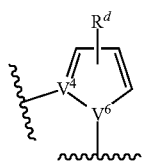

for example,

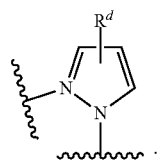

In yet another aspect, $L^4$ can have the structure

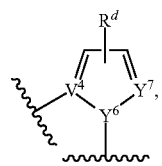

for example,

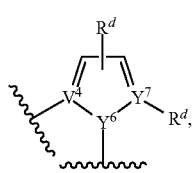

for example

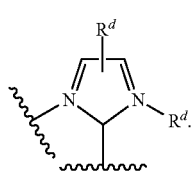

In yet another aspect, L⁴ can have the structure

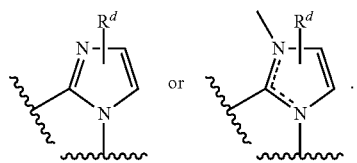

In yet another aspect, L⁴ can have the structure

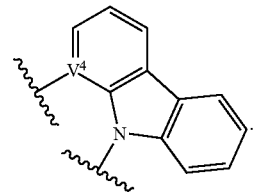

In yet another aspect, L⁴ can have the structure

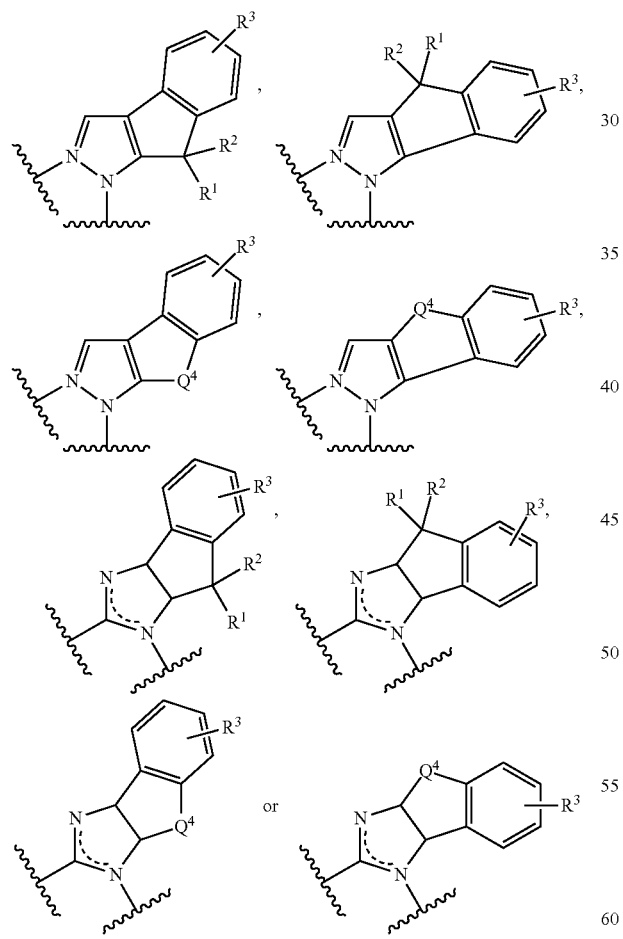

wherein Q⁴ is O, S, S=O, SO₂, Se, NR³, PR³, RP=O, CR¹R², C=O, SiR¹R², GeR¹R², BH, P(O)H, PH, NH, CR¹H, CH₂, SiH₂, SiHR¹, BH, or BR³. In one aspect, V⁴ can be N, C, P, B, or Si. For example, V⁴ can be N or C, such as N.

In one aspect, for any of the platinum complexes illustrated in this disclosure, Formula I can include one or more of the following structures depicted collectively below as Structures 1-32. In another aspect, structures of Formula I can also include other structures or portions thereof not specifically recited herein, and the present disclosure is not intended to be limited to those structures or portions thereof specifically recited.

Structures 1

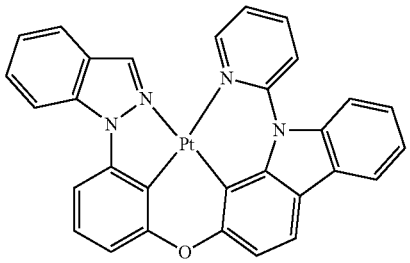

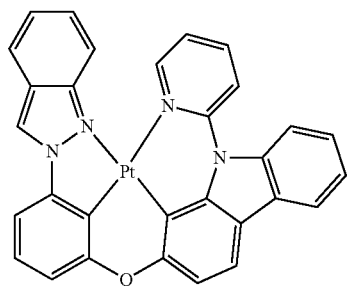

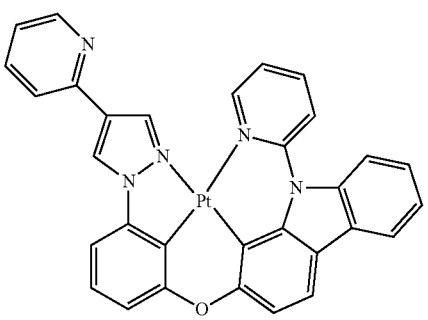

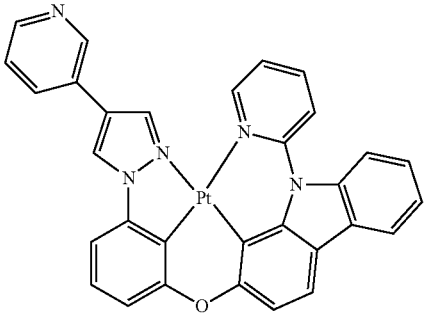

87
-continued
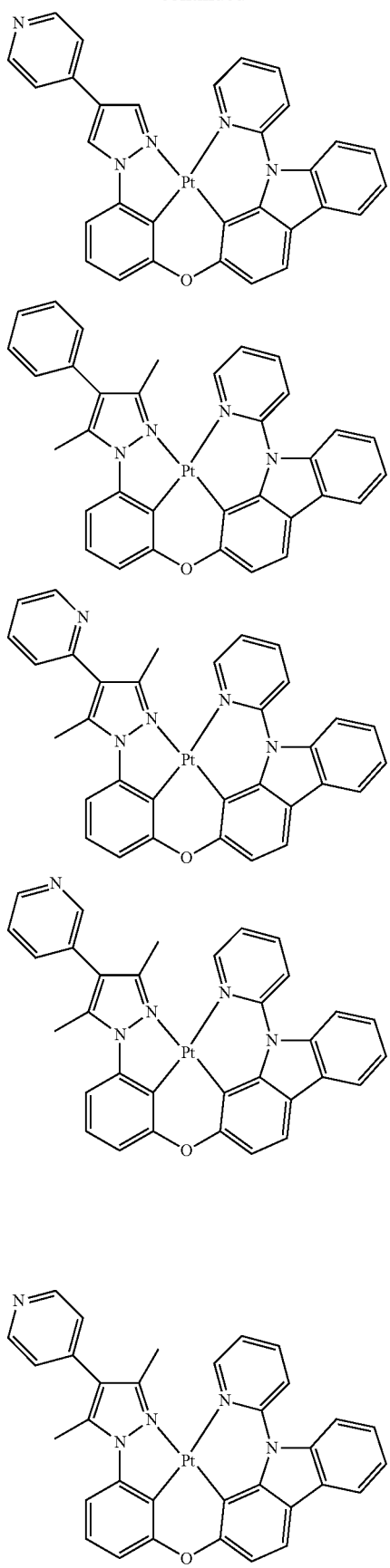
88
-continued
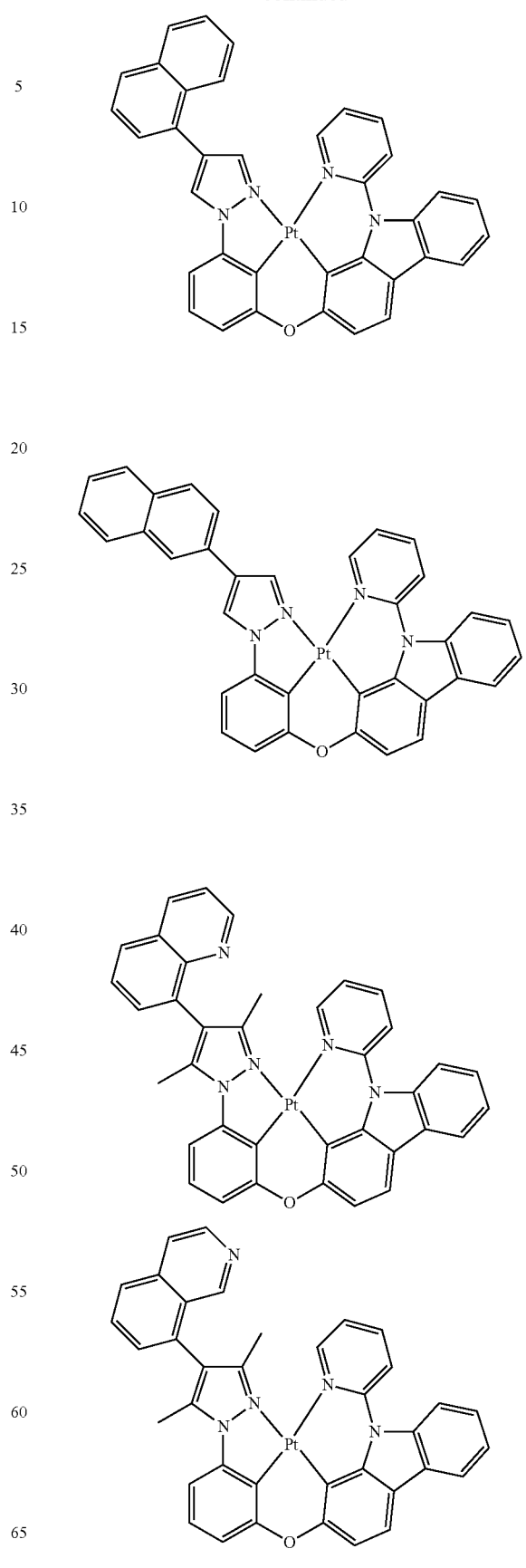

89
-continued
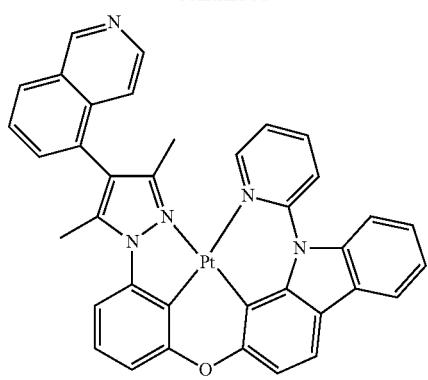
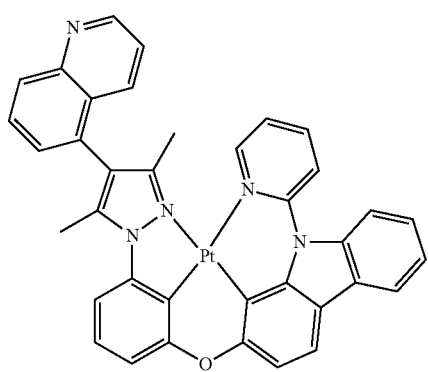
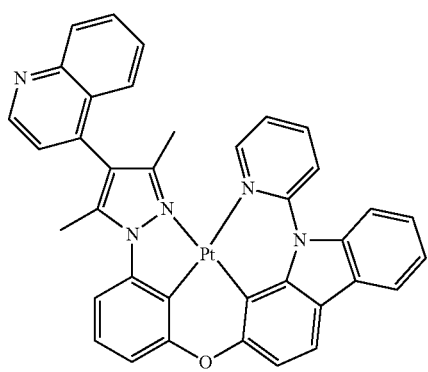
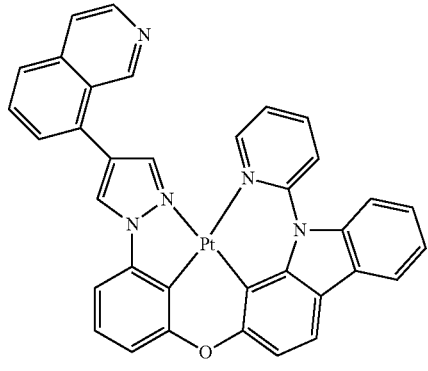
90
-continued
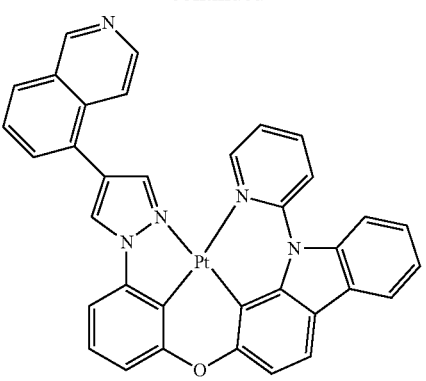
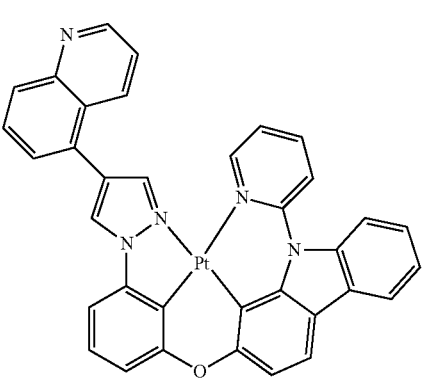
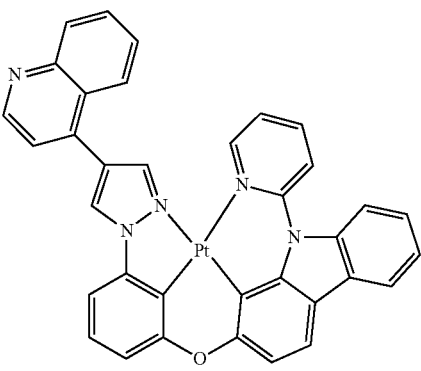
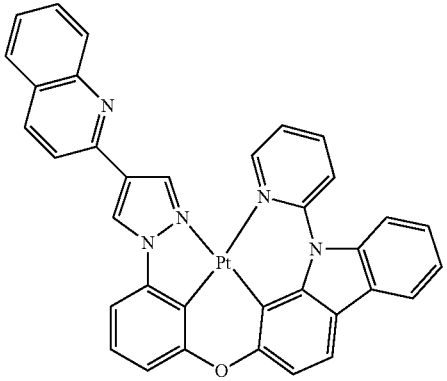

91
-continued
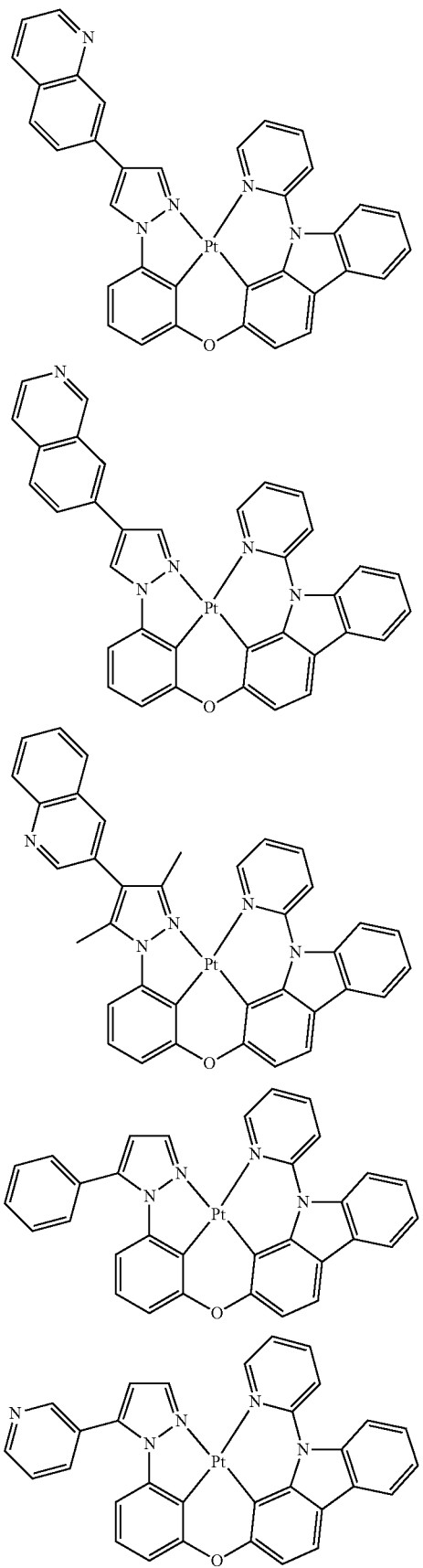
92
-continued
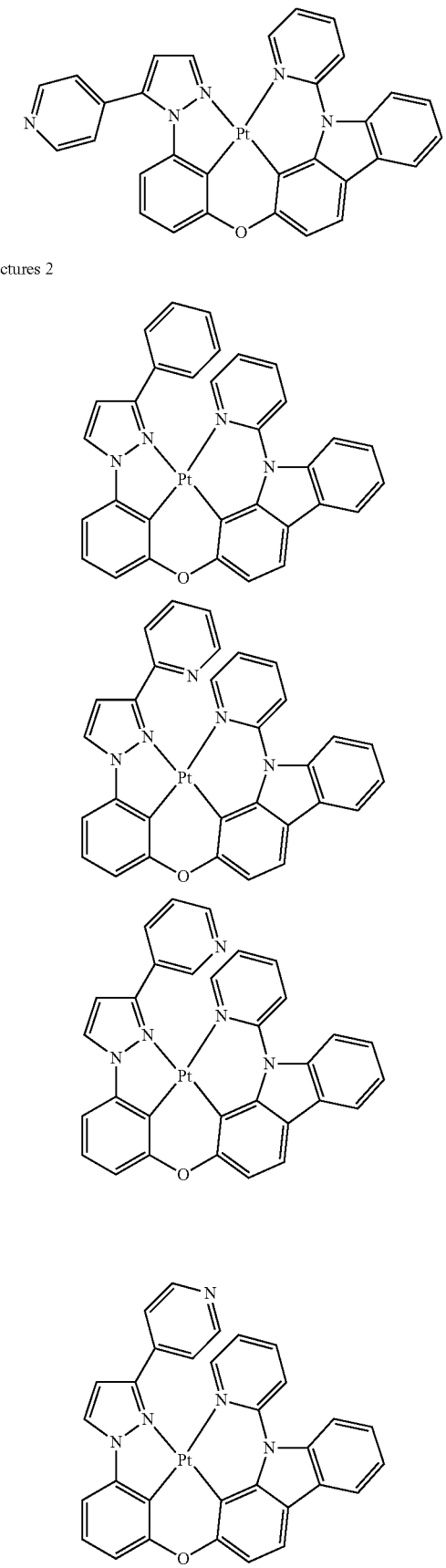
Structures 2

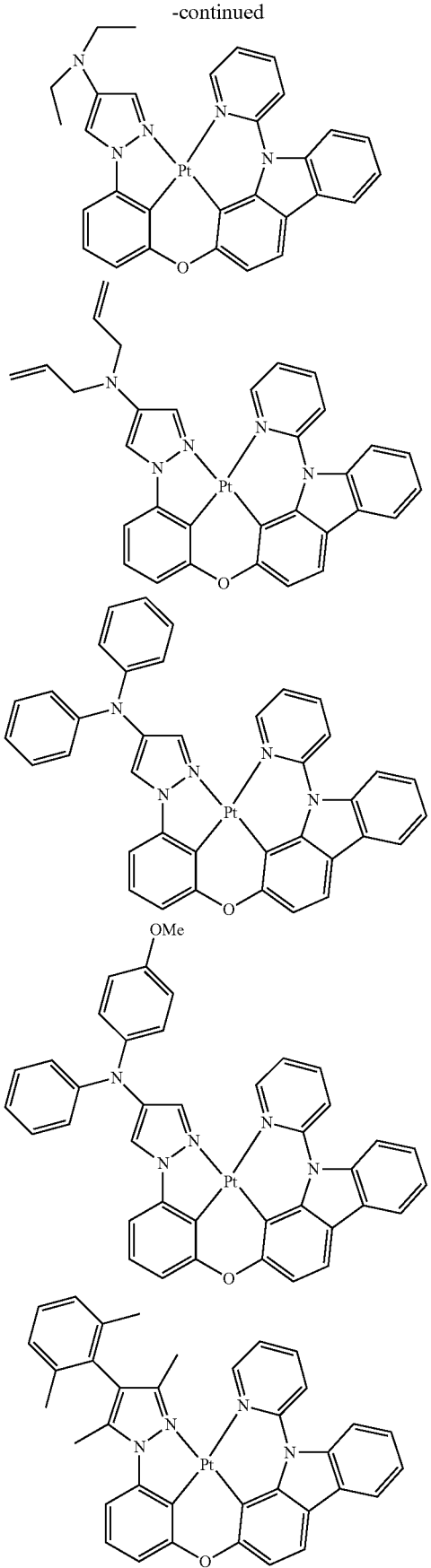
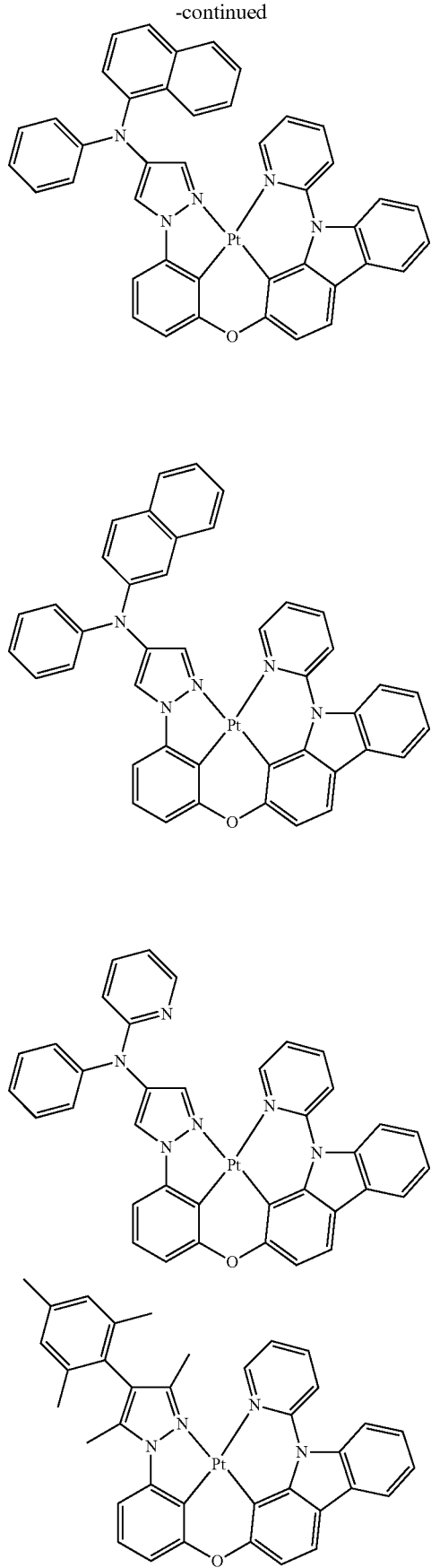

95
-continued
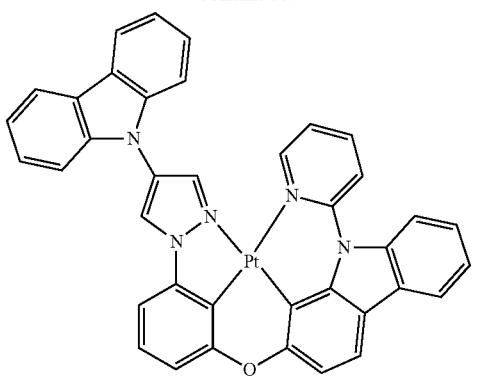
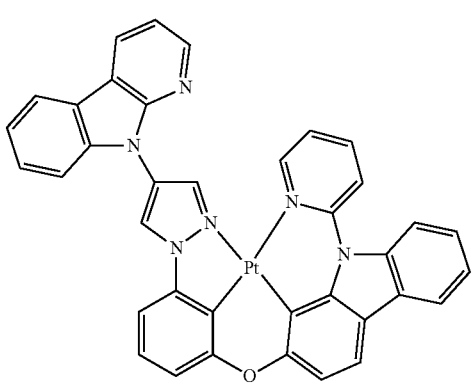
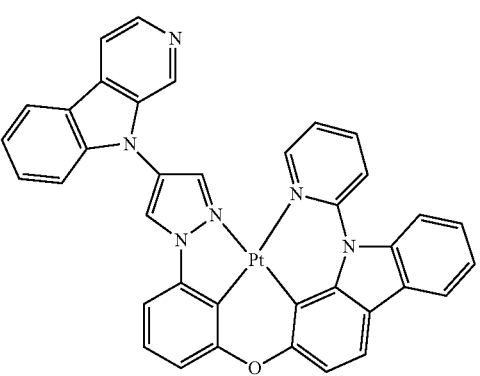
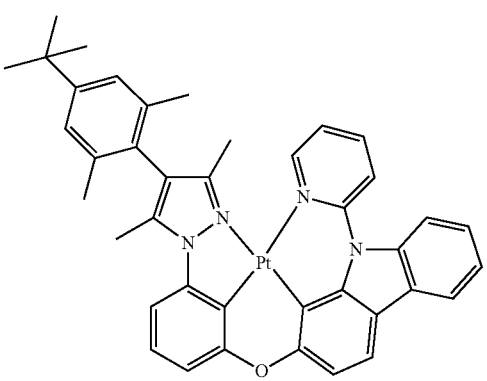
96
-continued
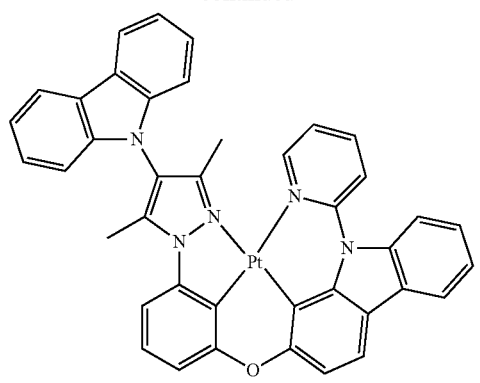
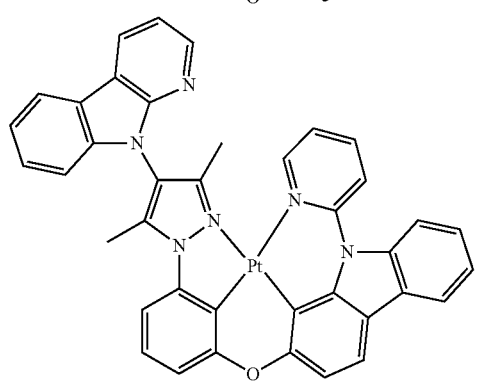
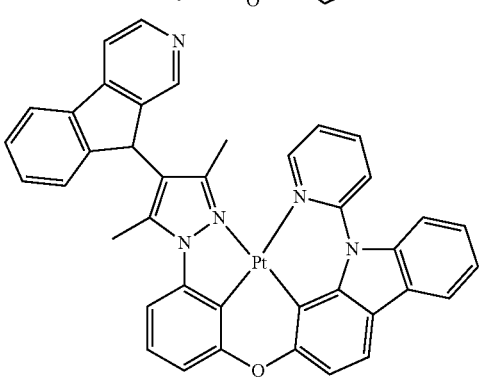
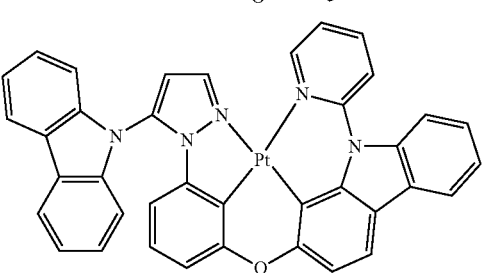

97
-continued
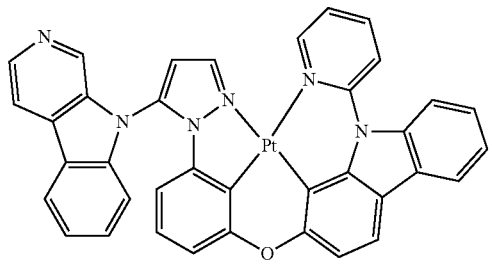
Structures 3
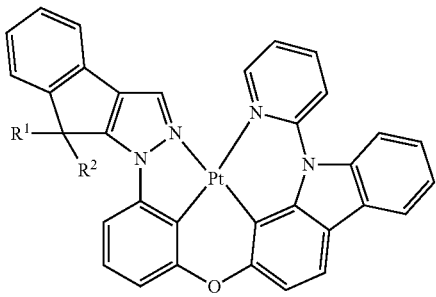
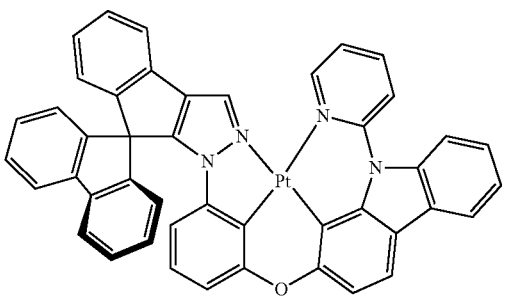
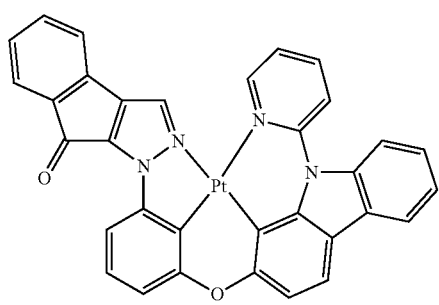
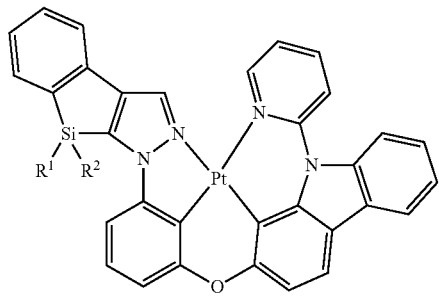
98
-continued
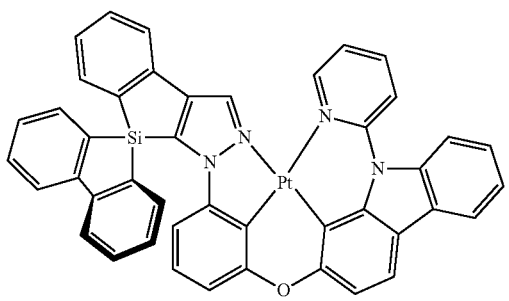
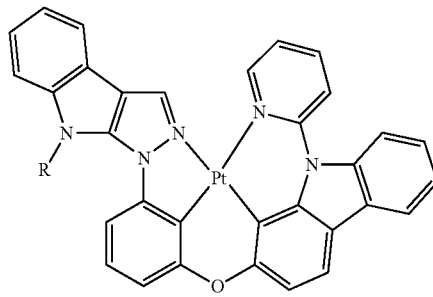
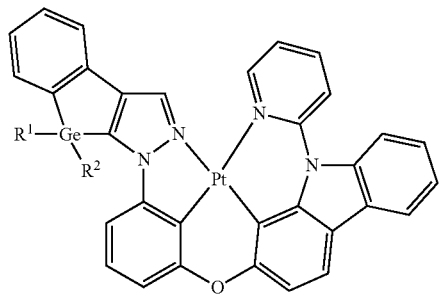
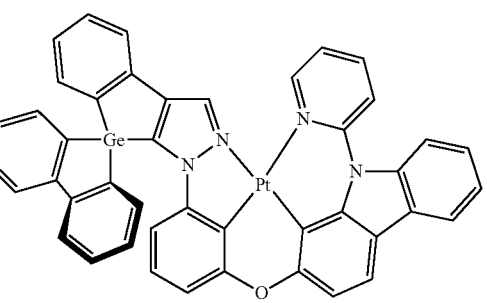
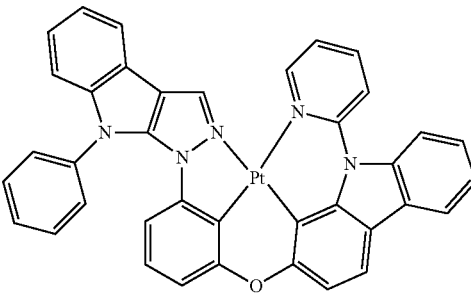

99
-continued
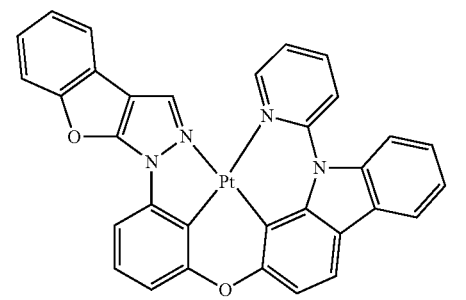
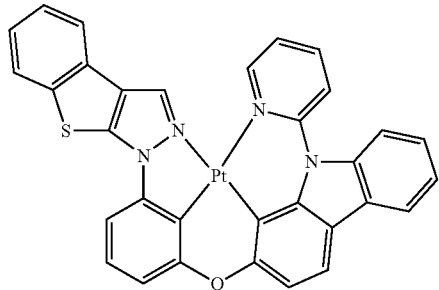
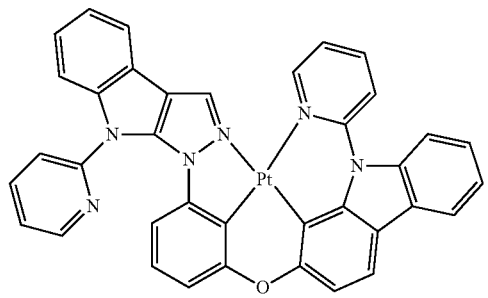
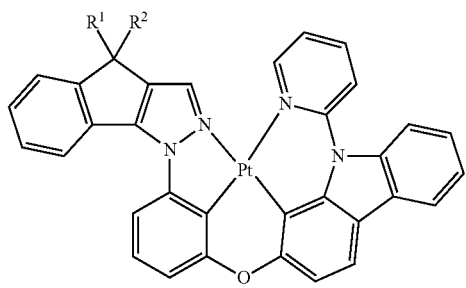
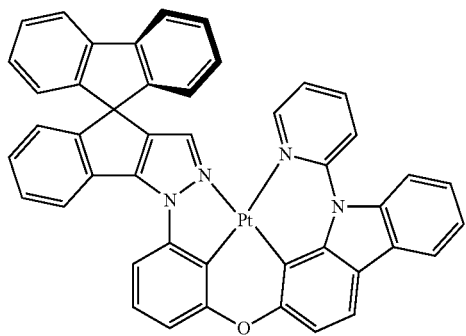
100
-continued
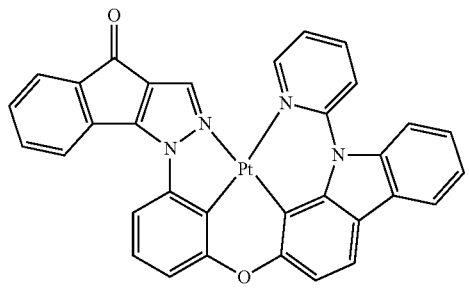
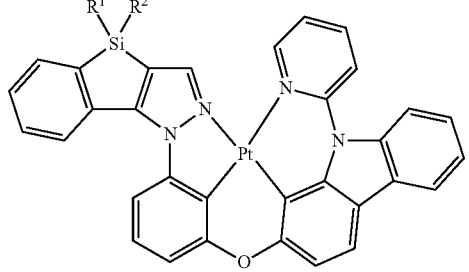
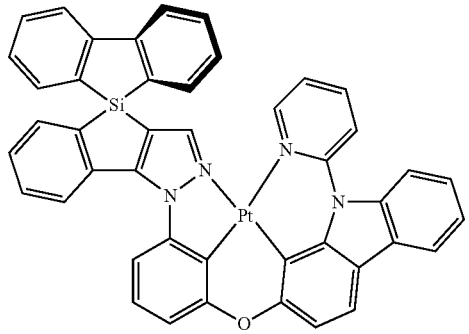
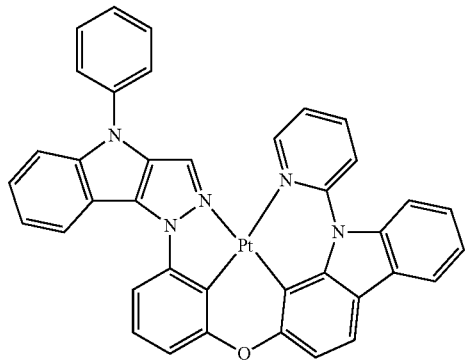
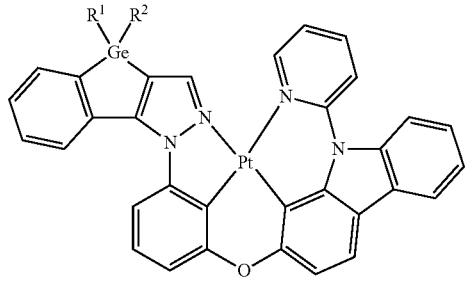

101
-continued
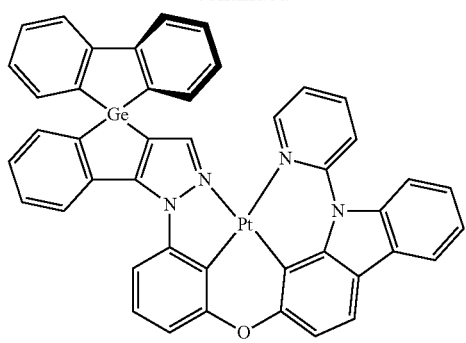
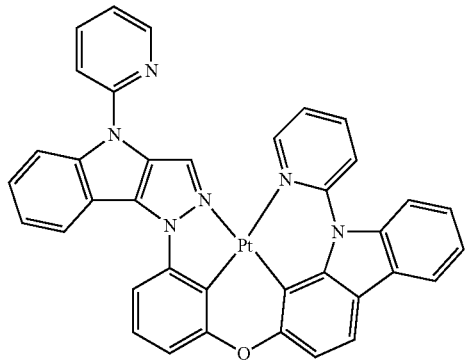
Structures 4
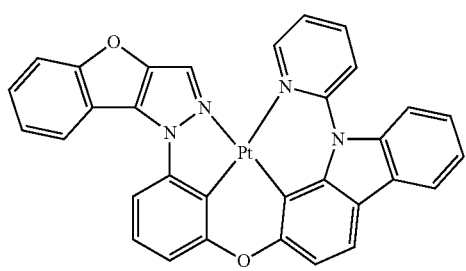
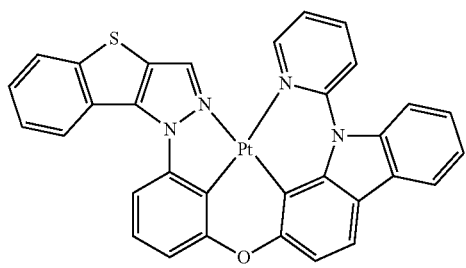
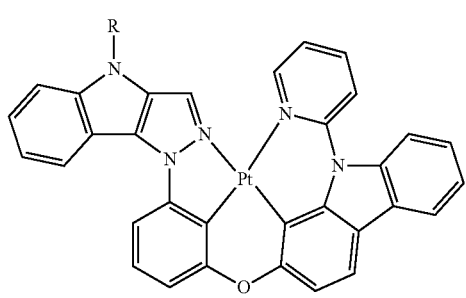
102
-continued
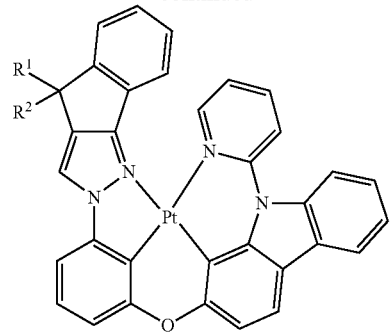
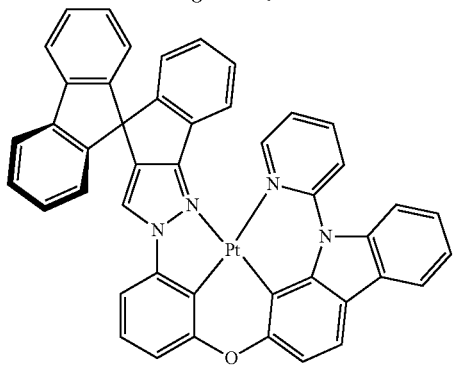
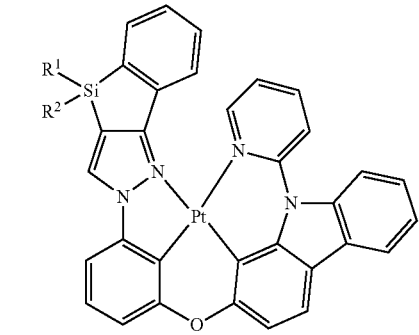
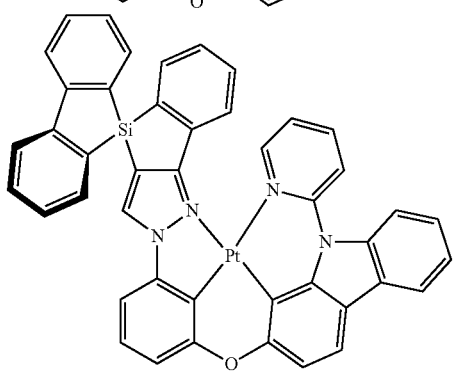
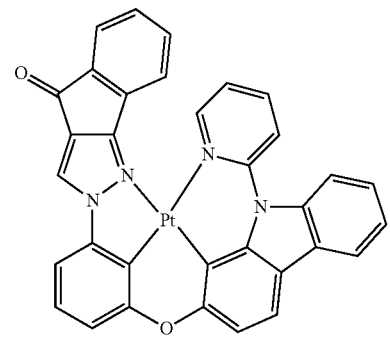

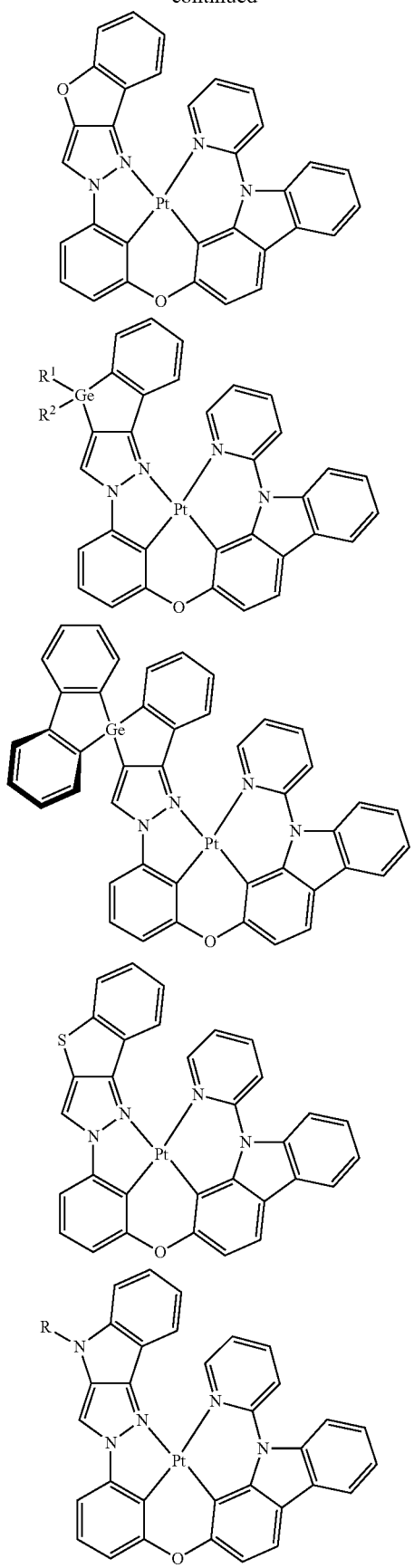
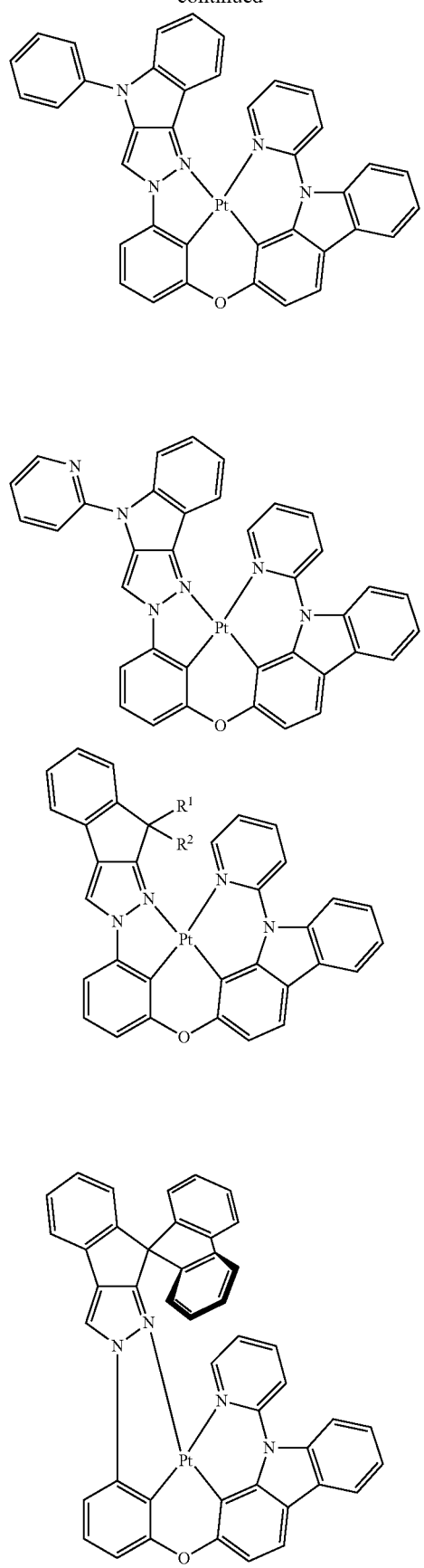

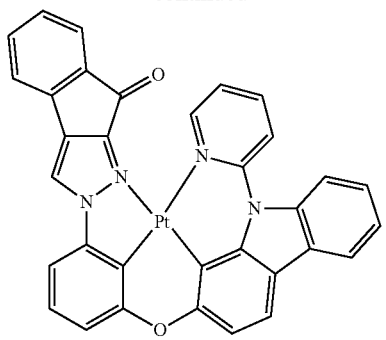
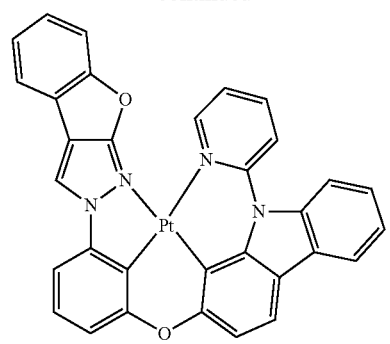
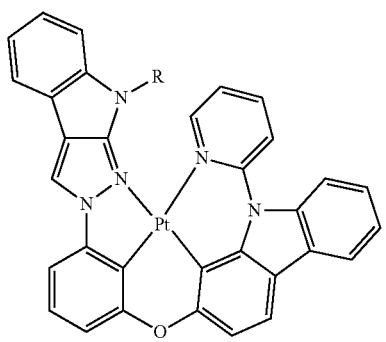
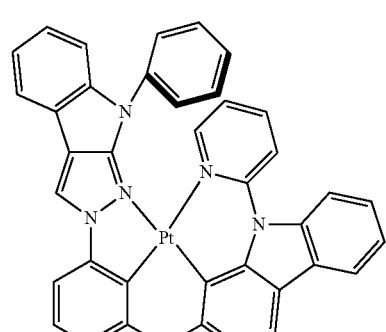
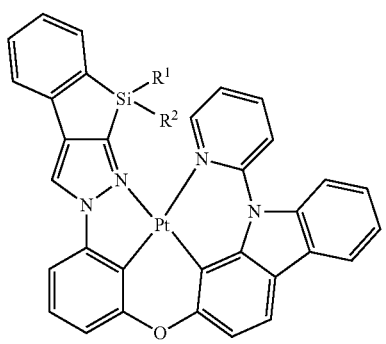
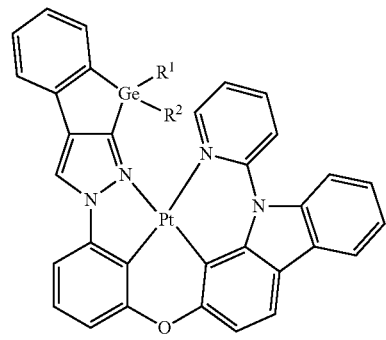
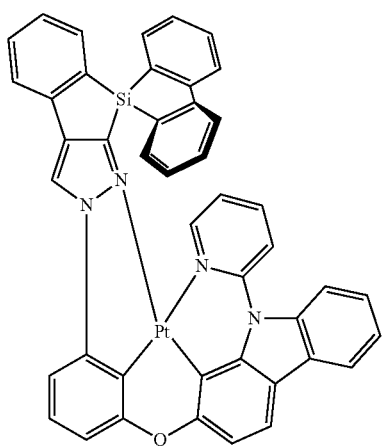
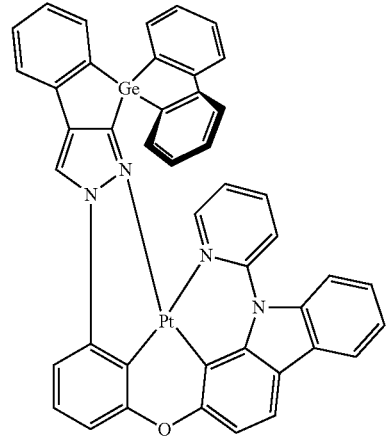

107
-continued
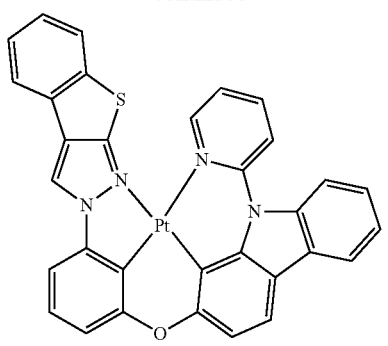
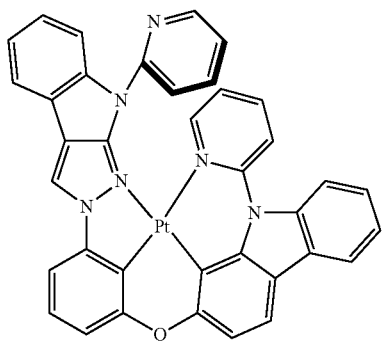
Structures 5
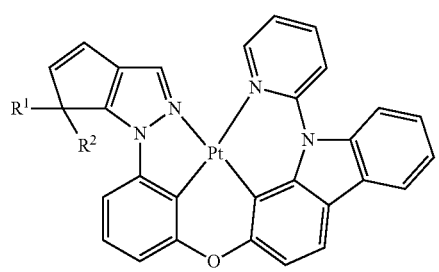
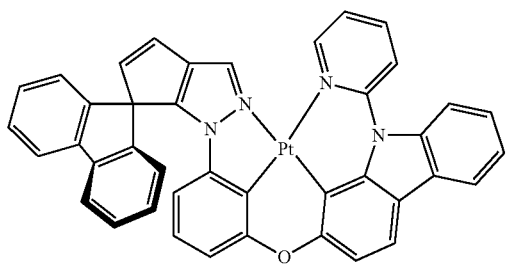
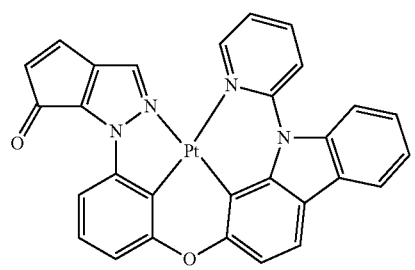
108
-continued
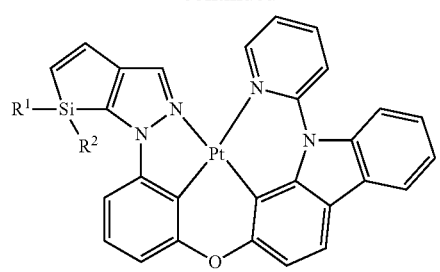
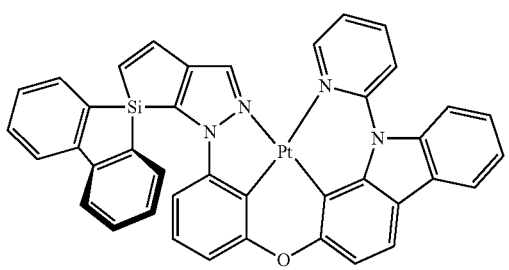
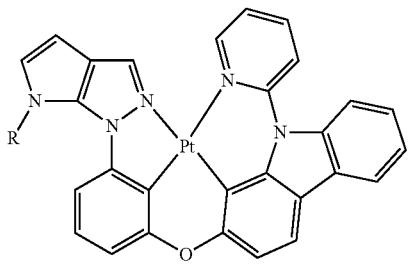
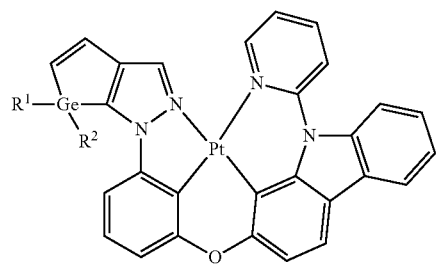
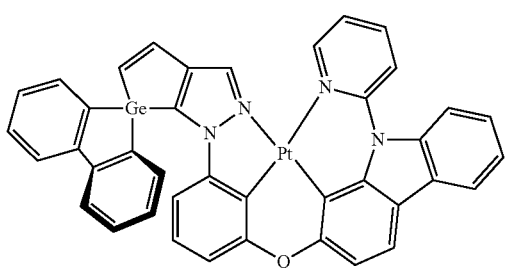
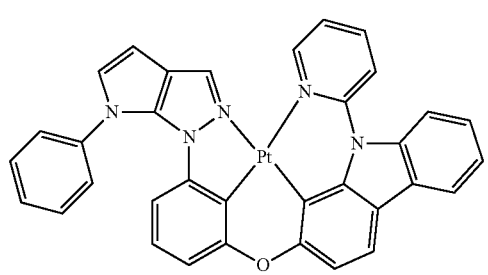

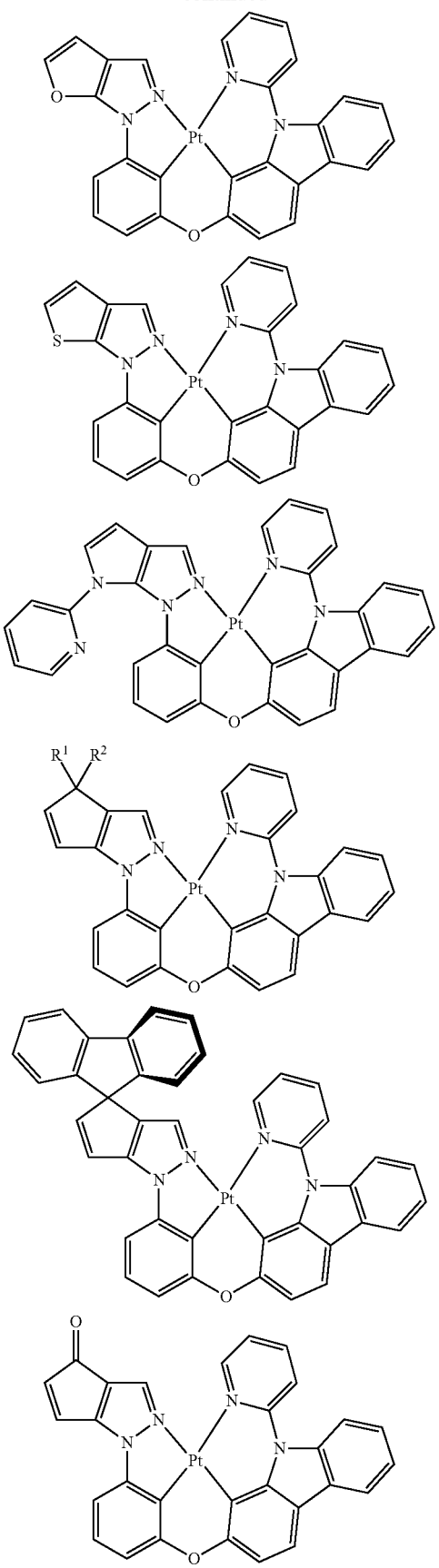
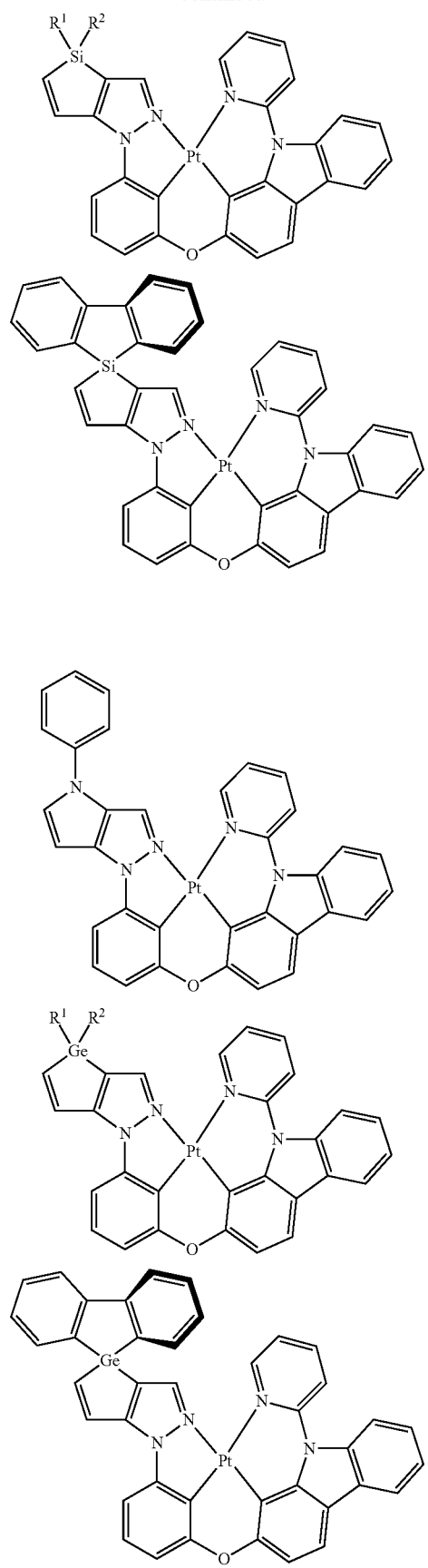

111
-continued
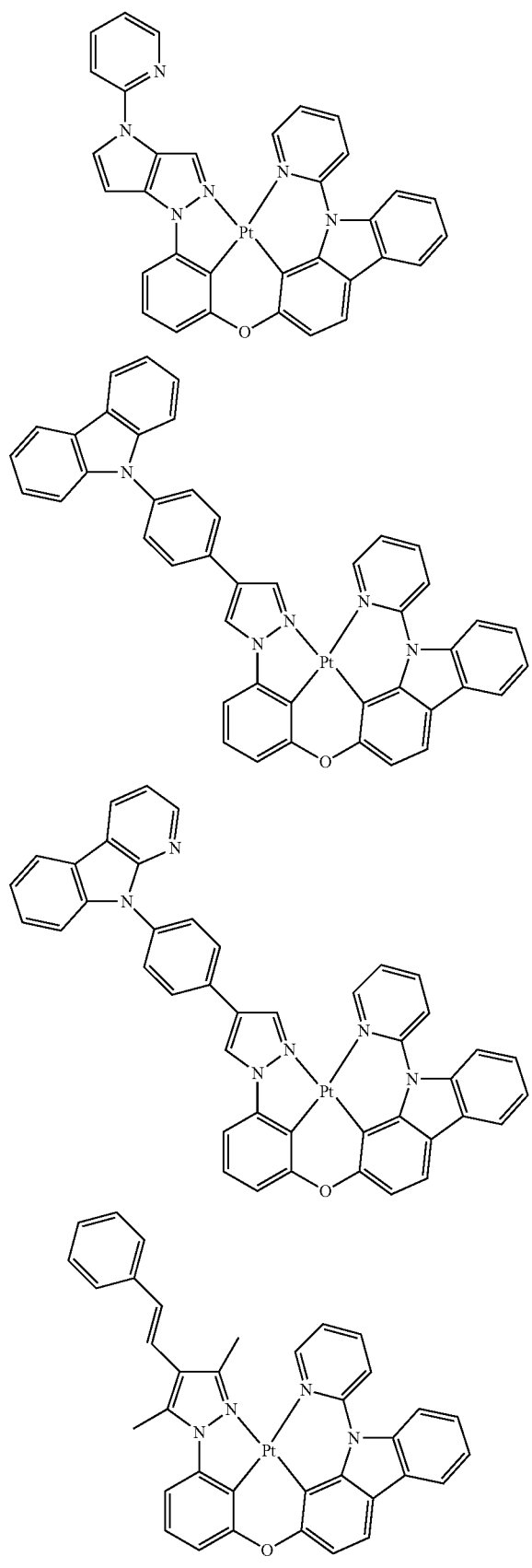
112
Structures 6
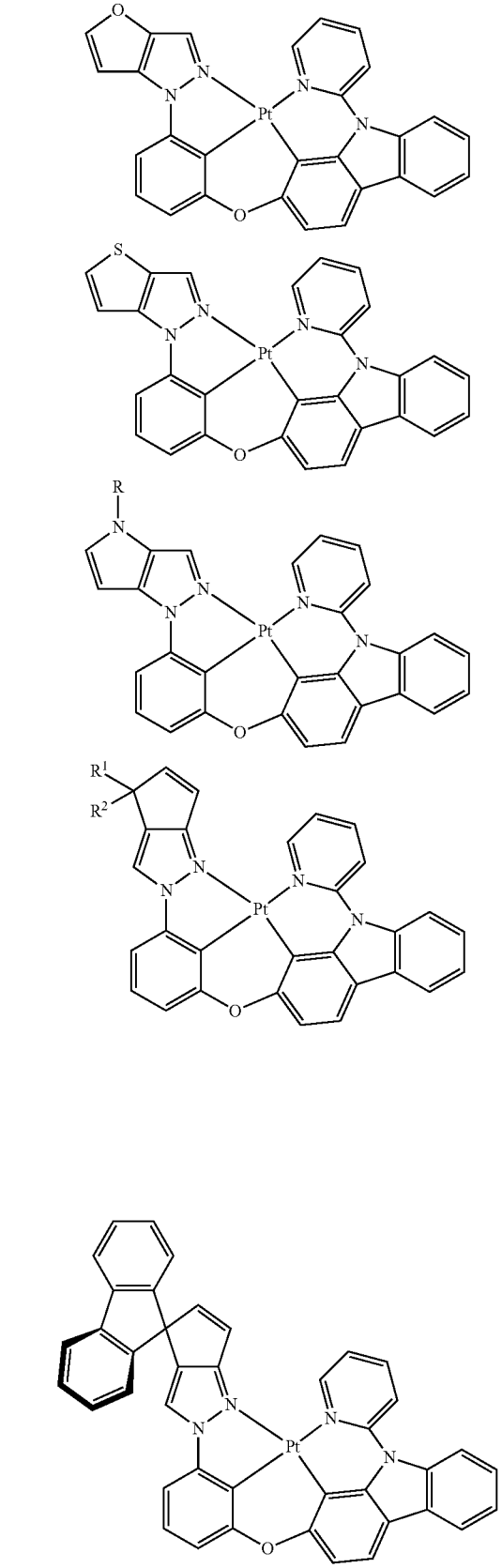

113
-continued
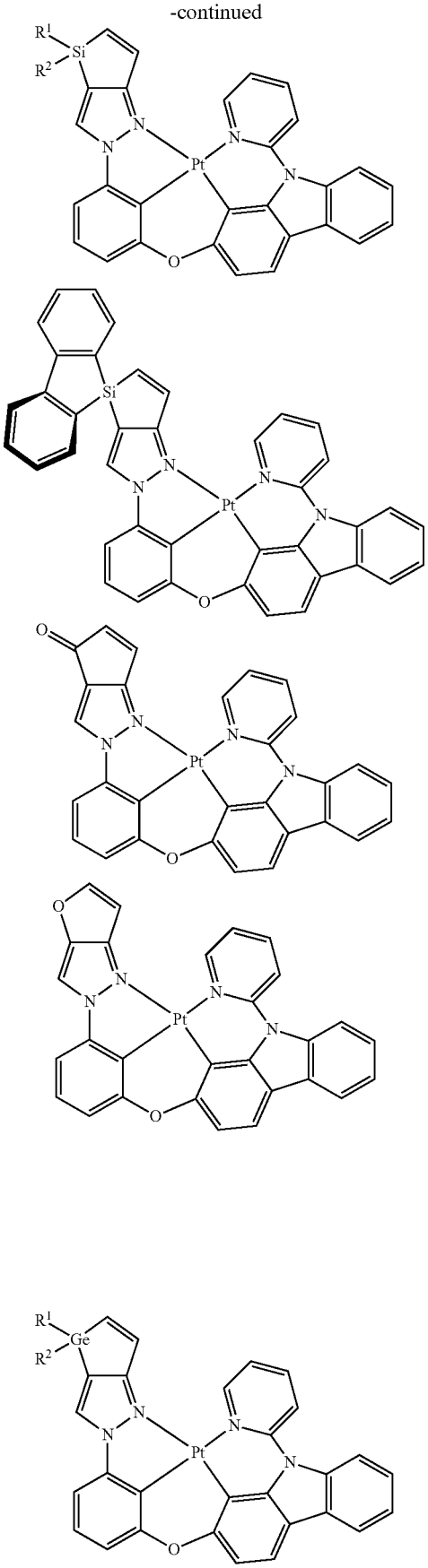
114
-continued
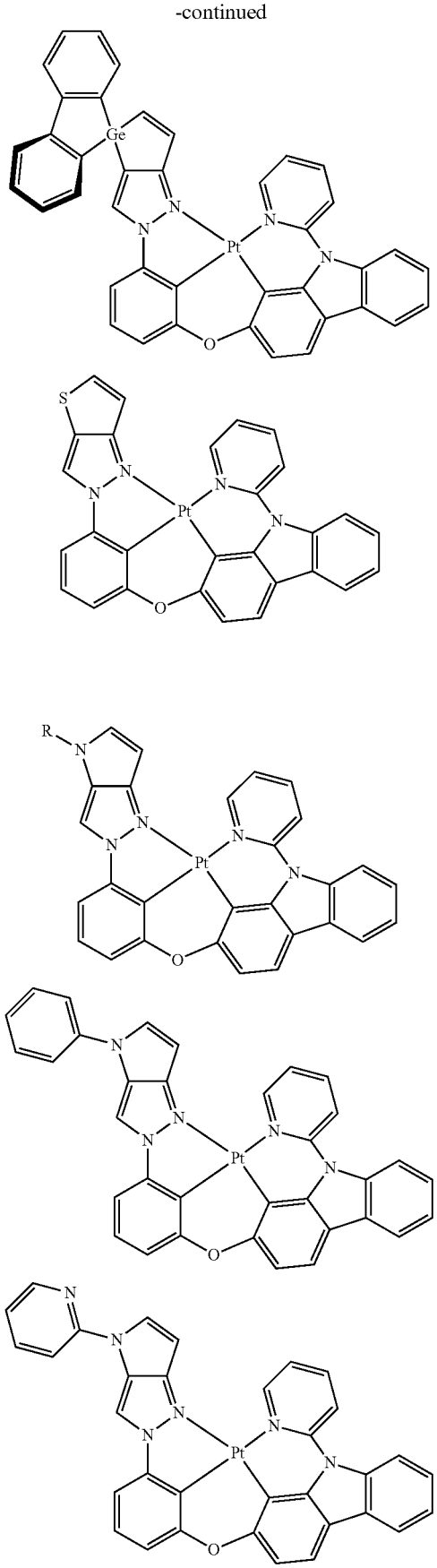

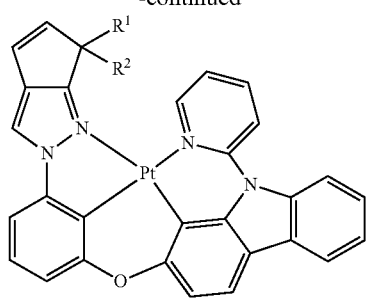
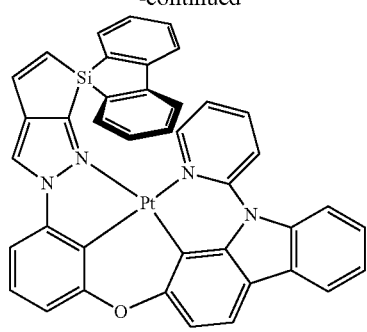
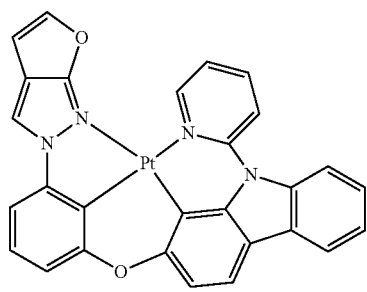
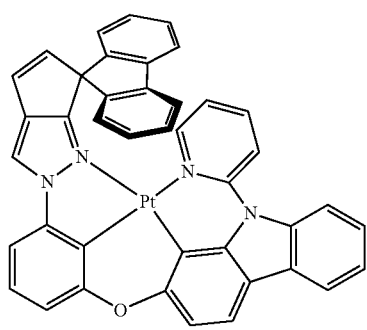
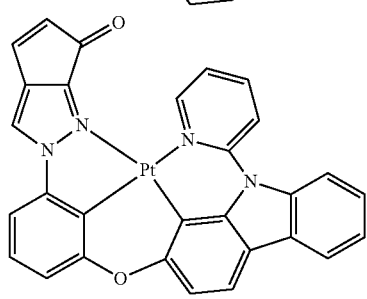
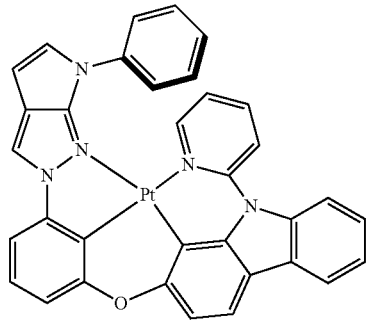
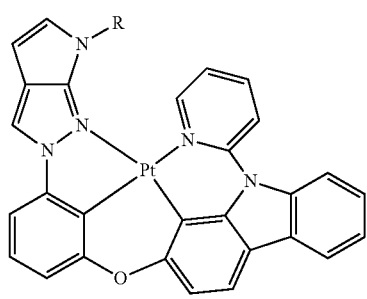
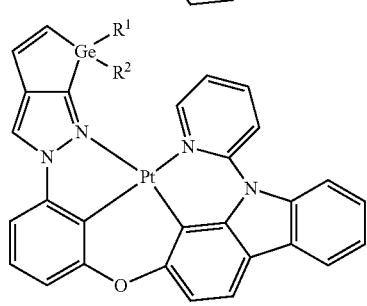
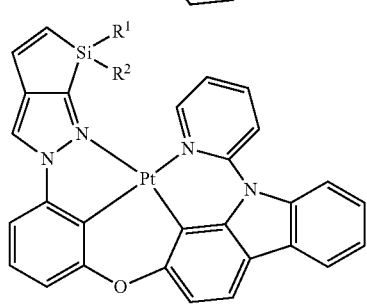

117
-continued
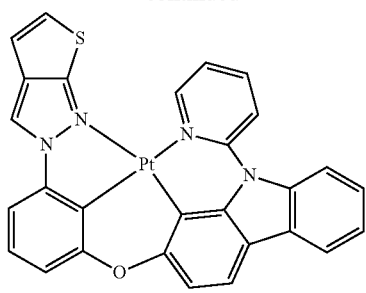
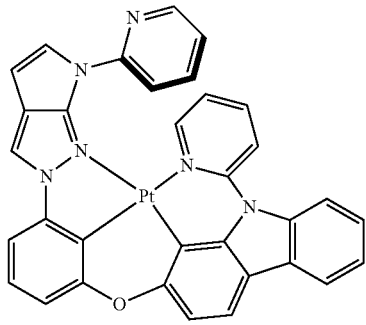
Structures 7
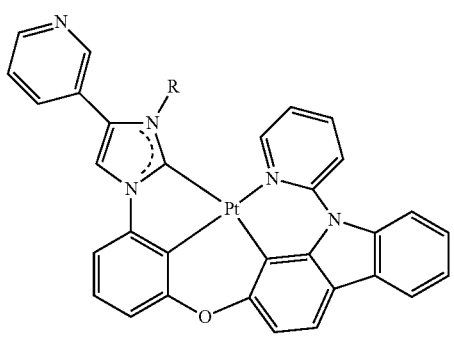
118
-continued
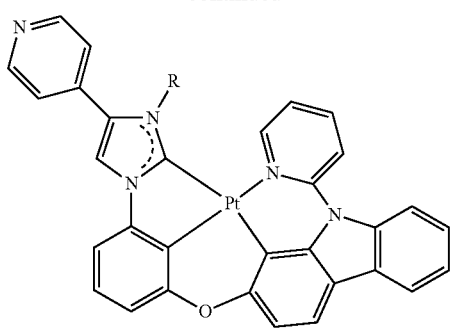
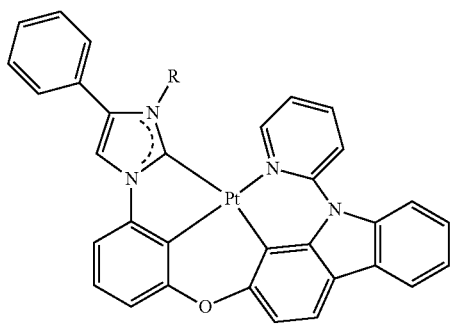
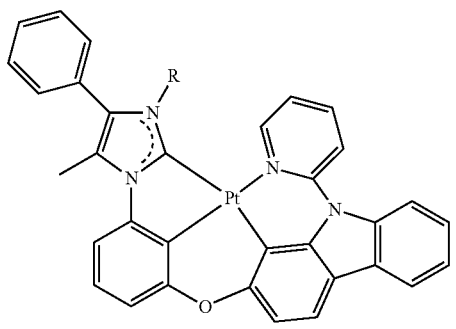
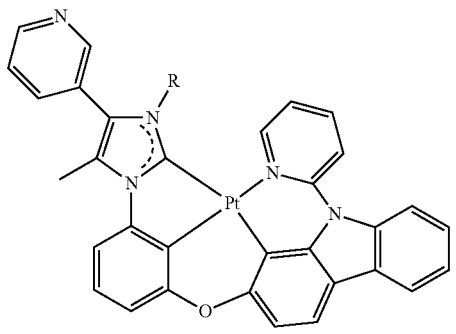

119
-continued
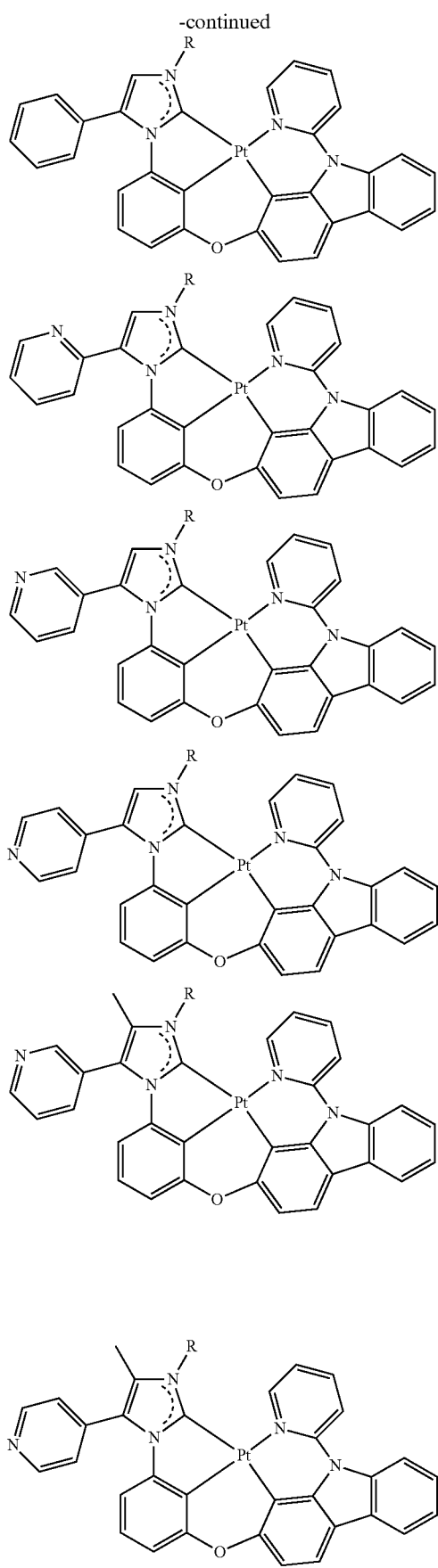
120
-continued
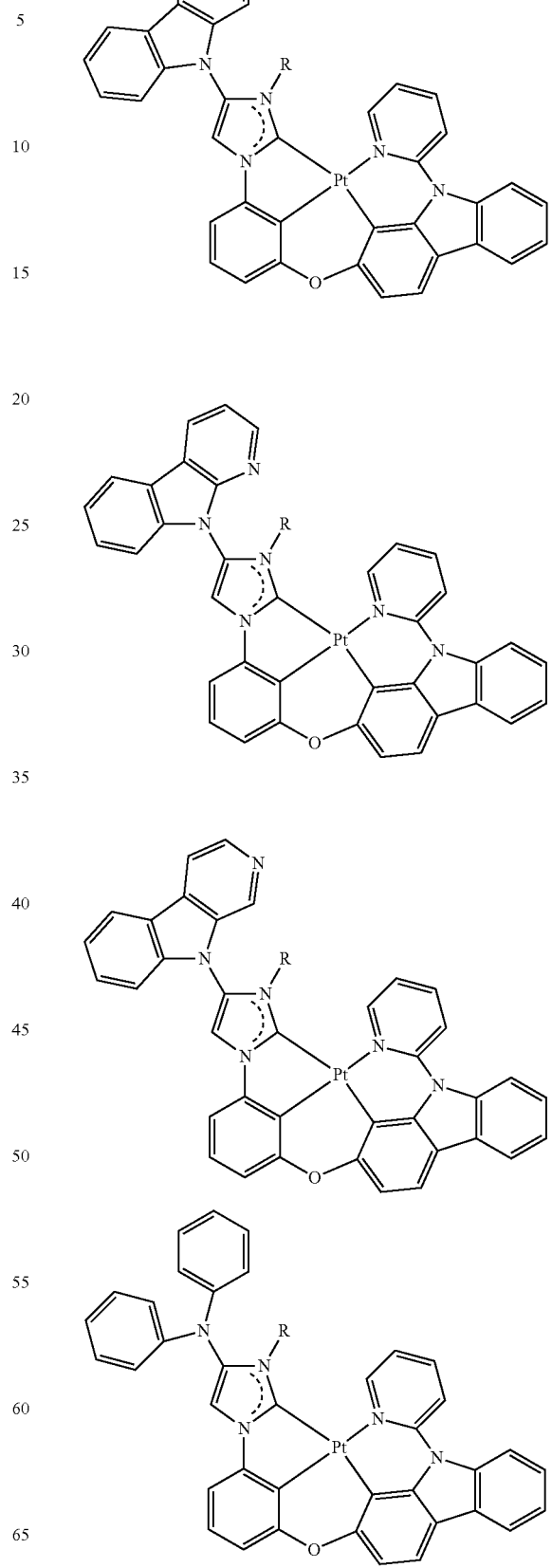

121
-continued
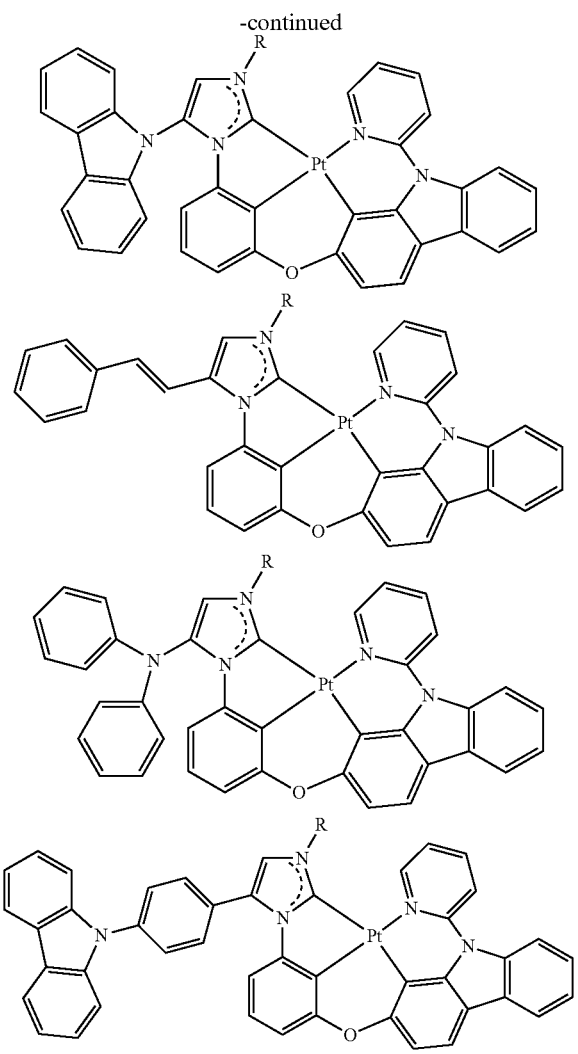
122
-continued
Structures 8
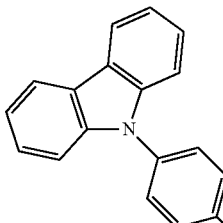
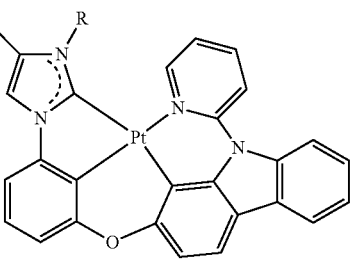
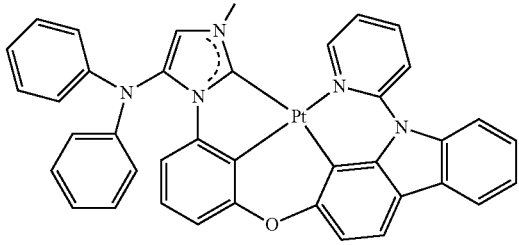
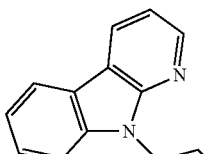
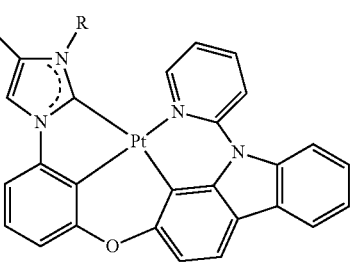
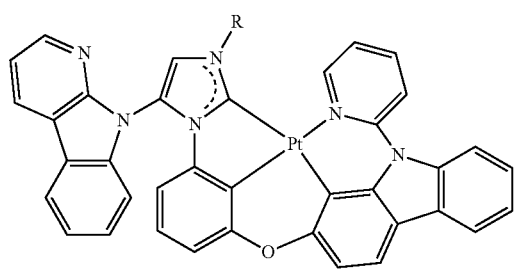
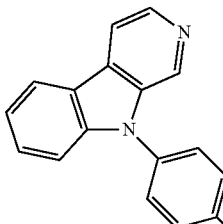
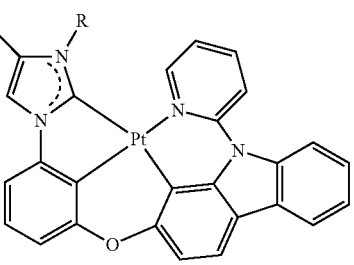
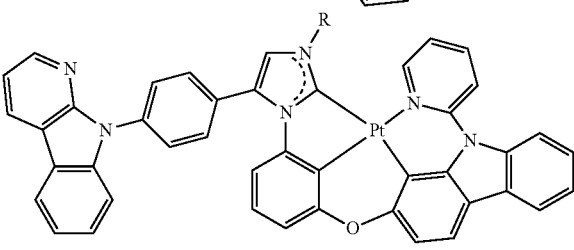

123
-continued
124
-continued
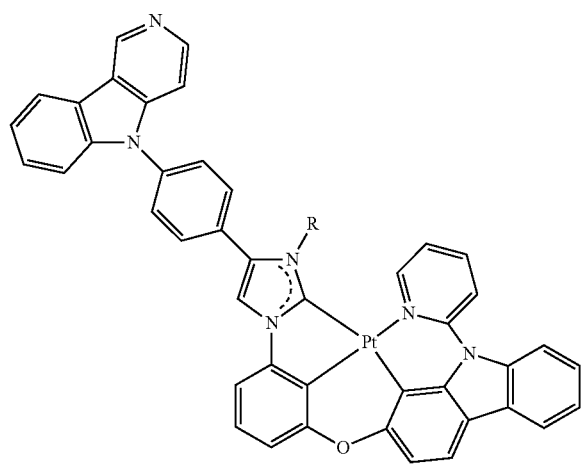
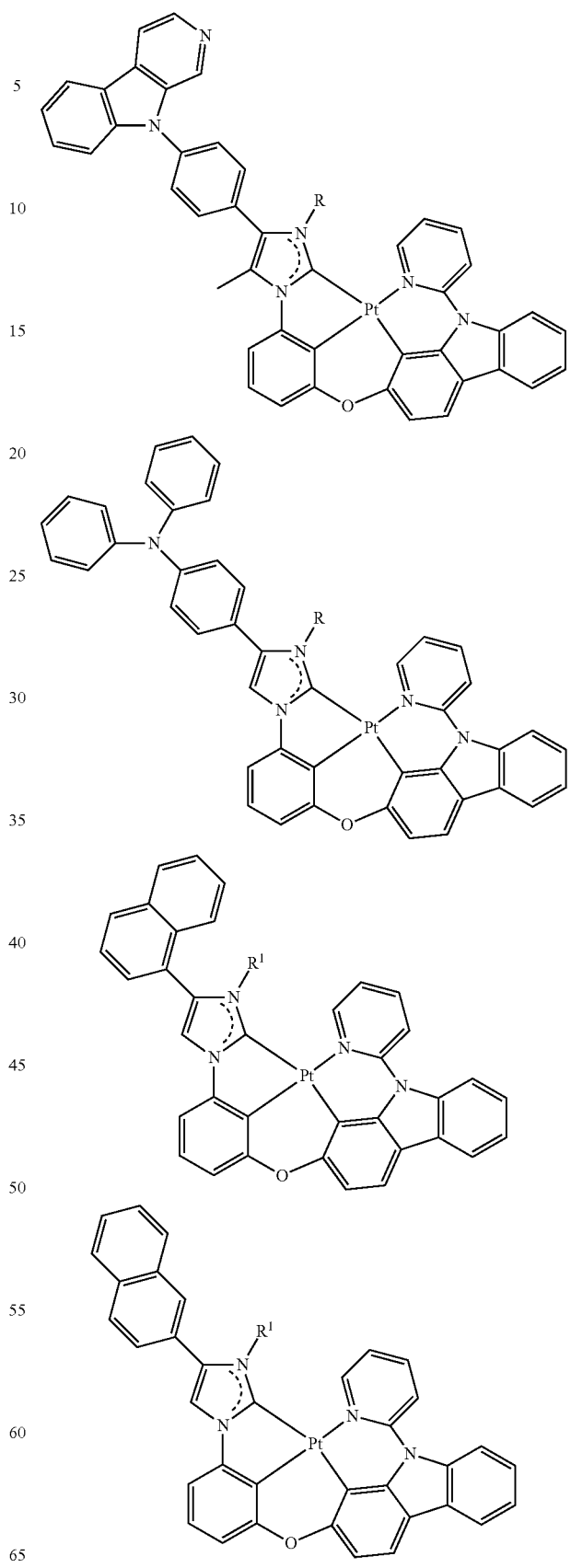

125
-continued
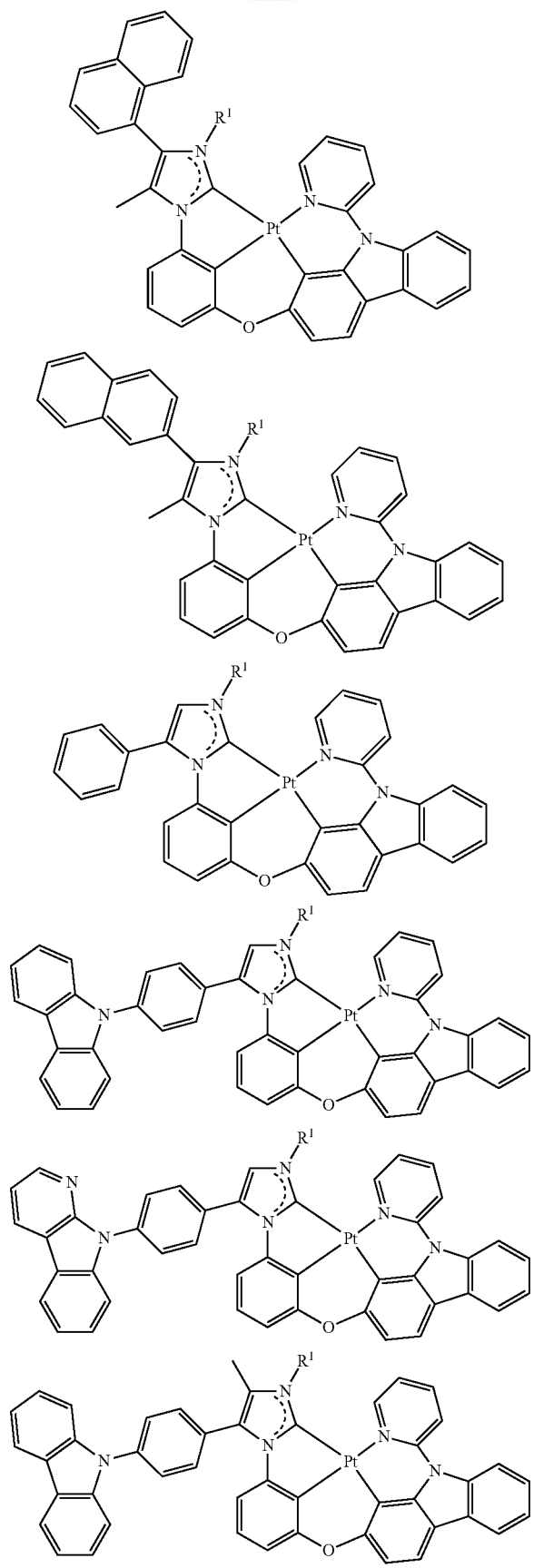
126
-continued
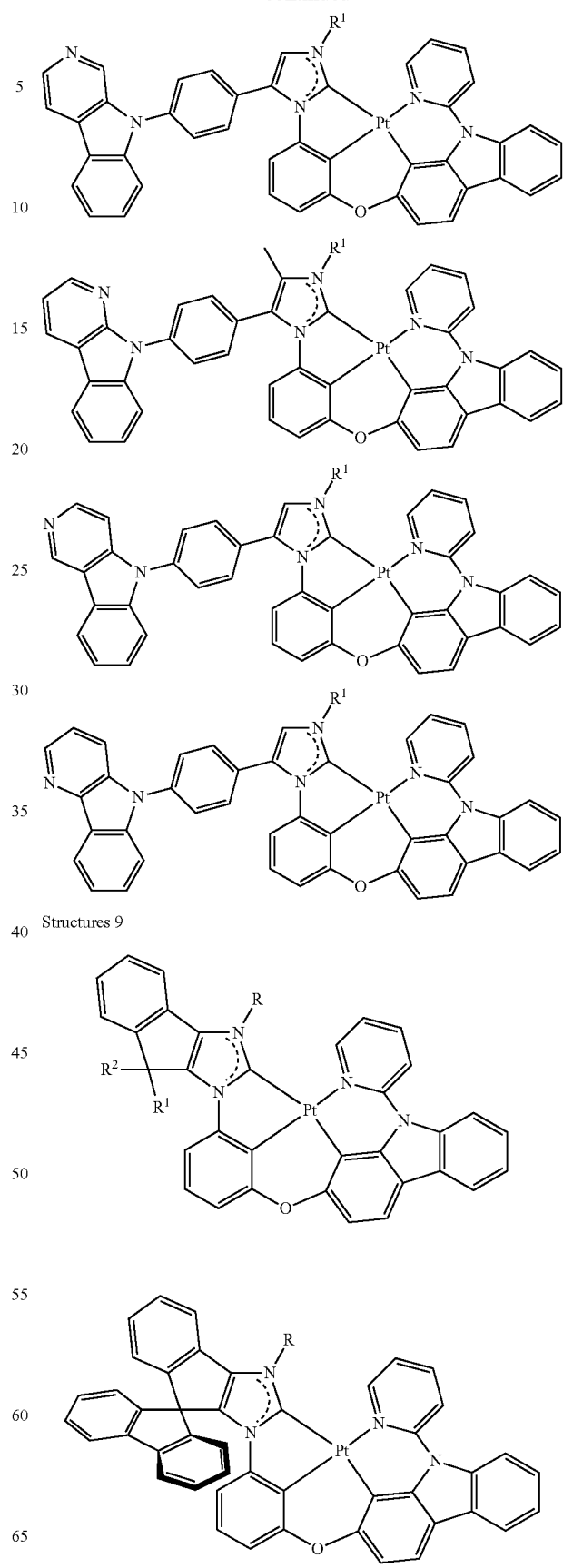
Structures 9

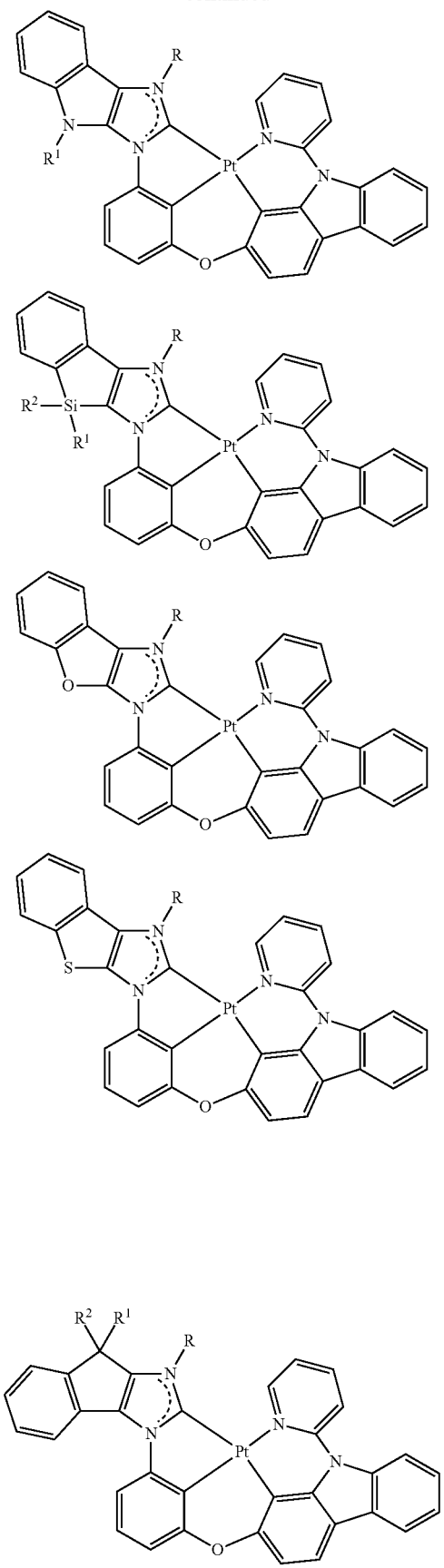
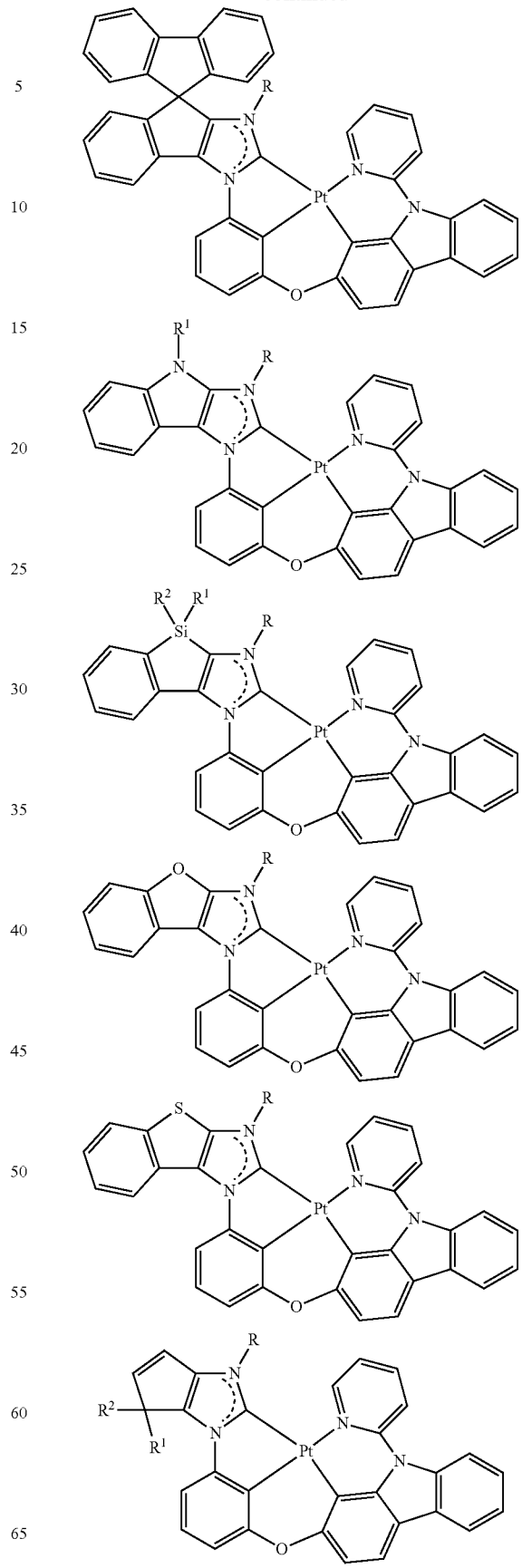

-continued
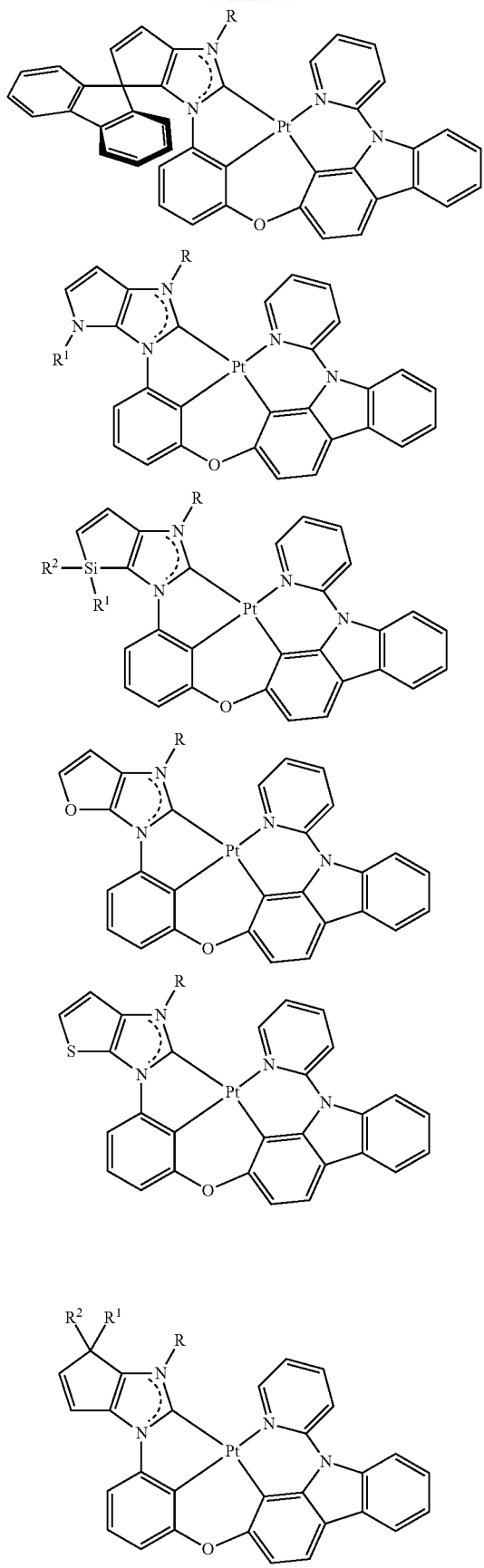
-continued
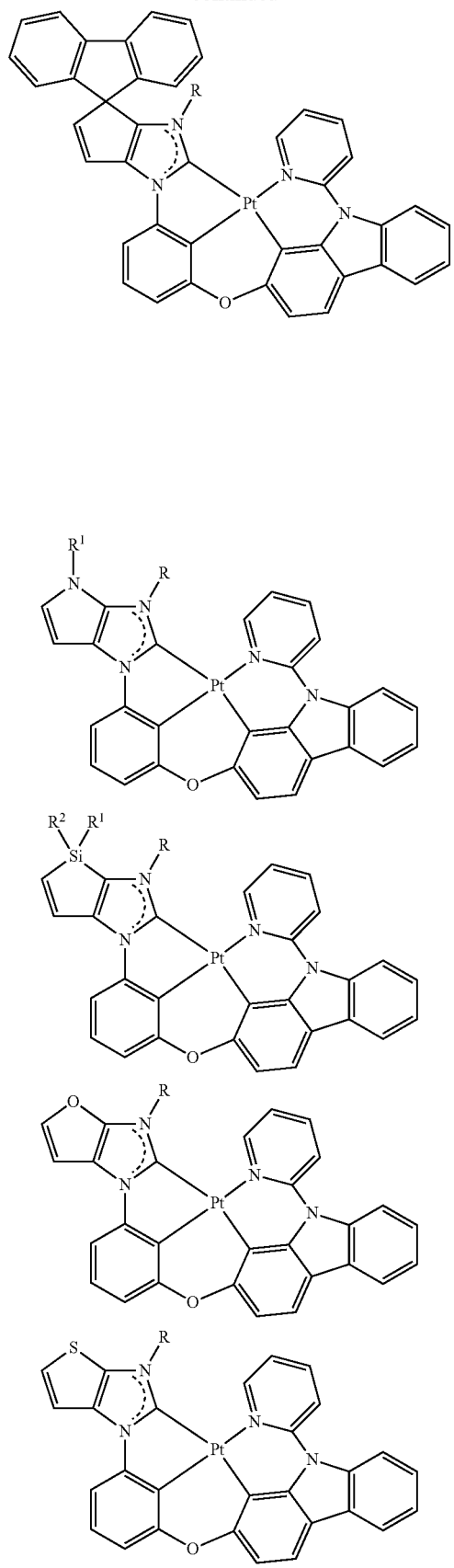

Structures 10
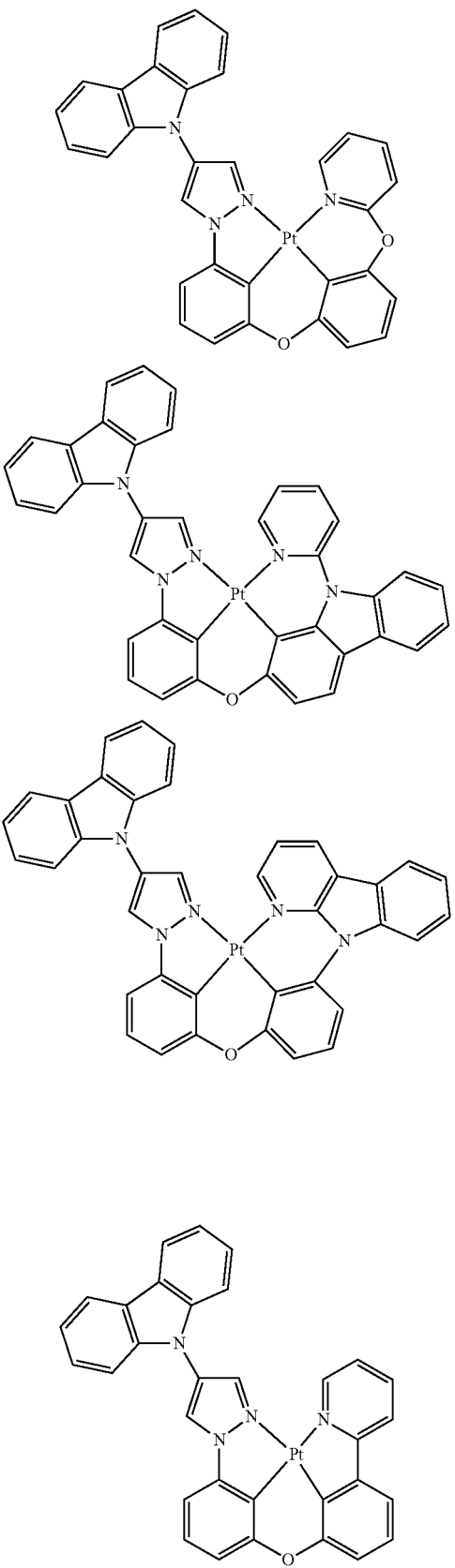
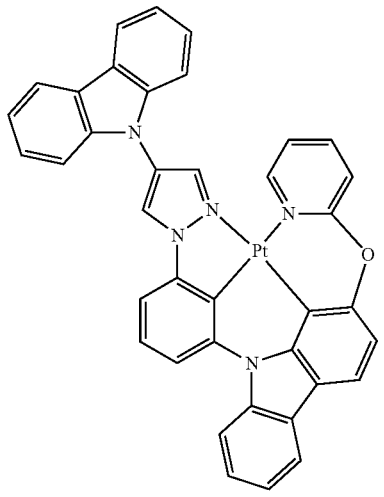
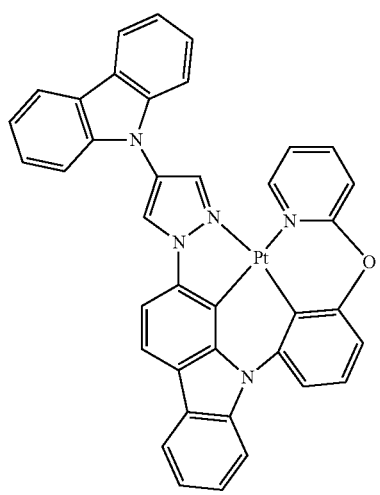
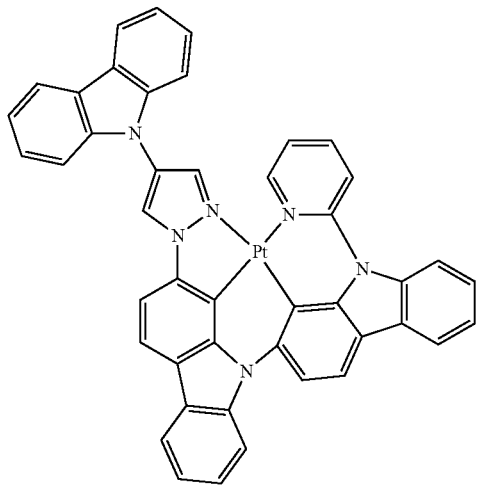

133
-continued
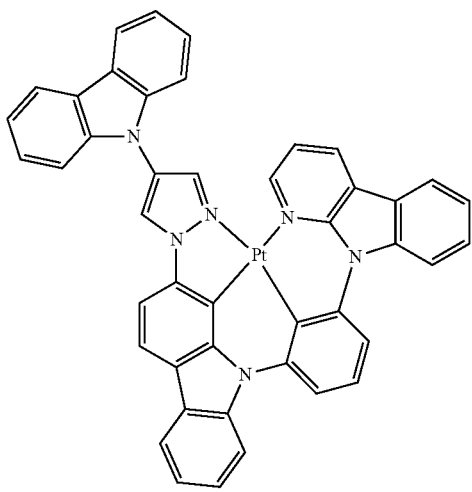
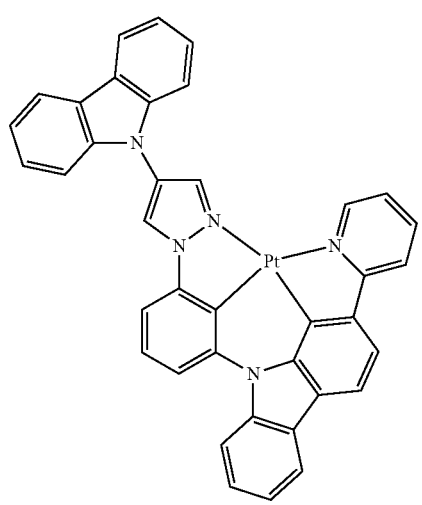
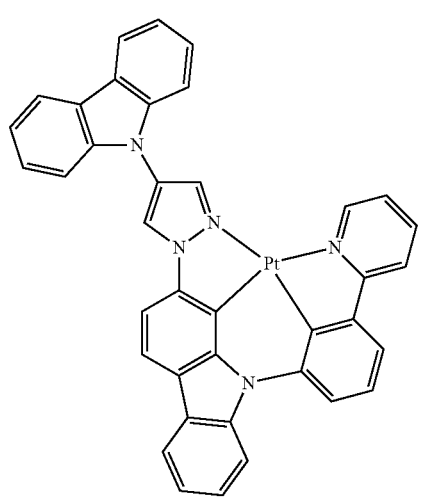
134
-continued
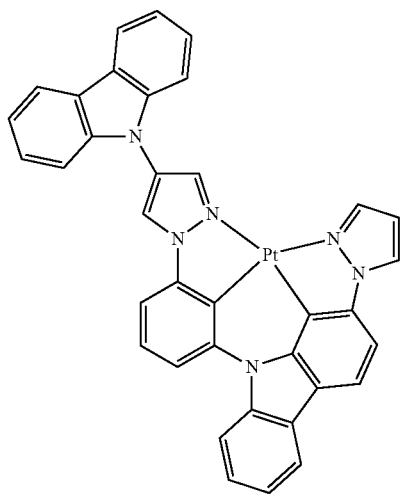
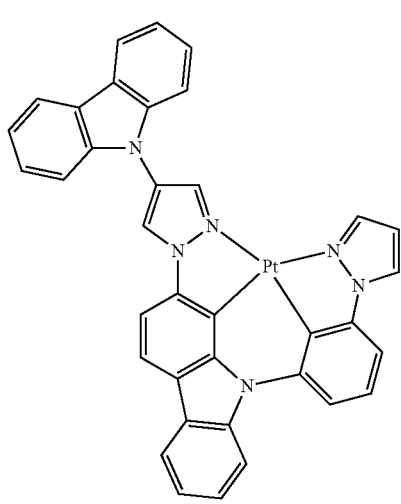
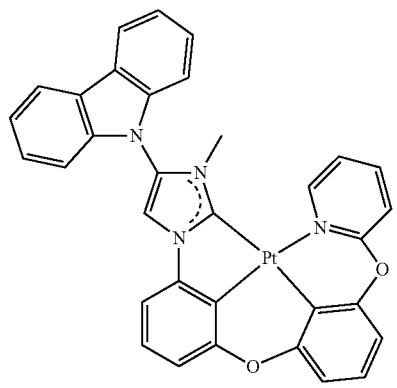

135
-continued
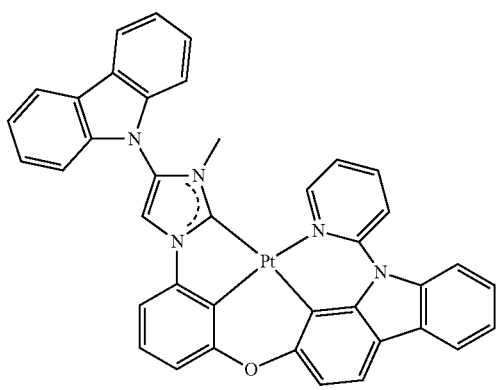
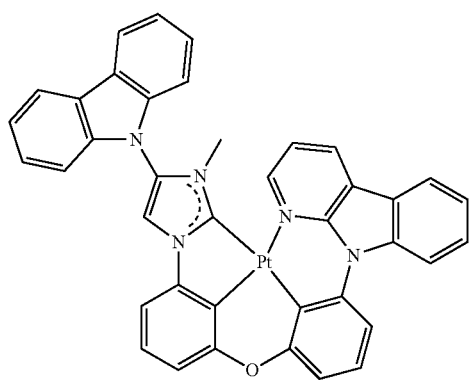
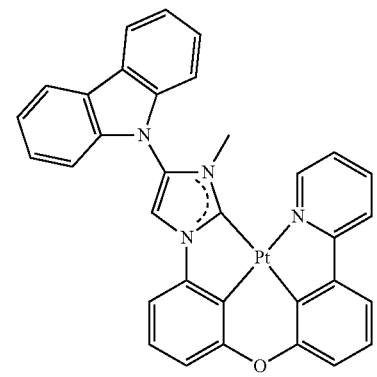
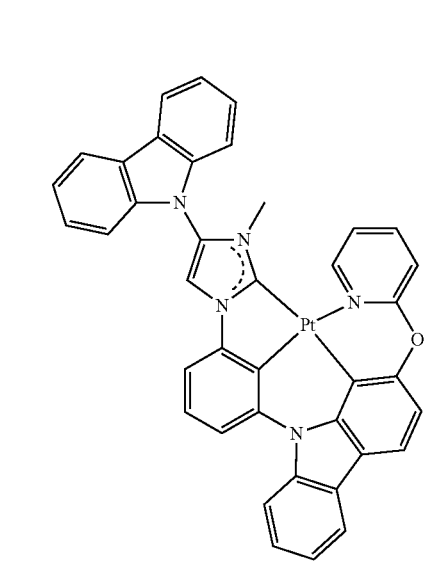
136
-continued
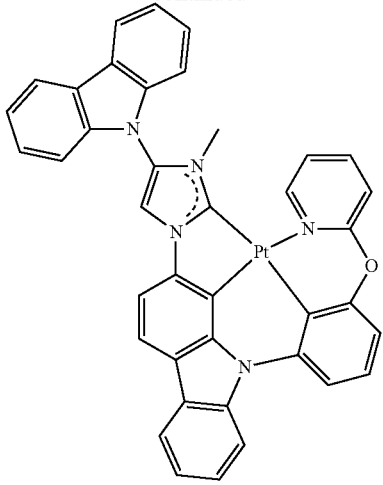
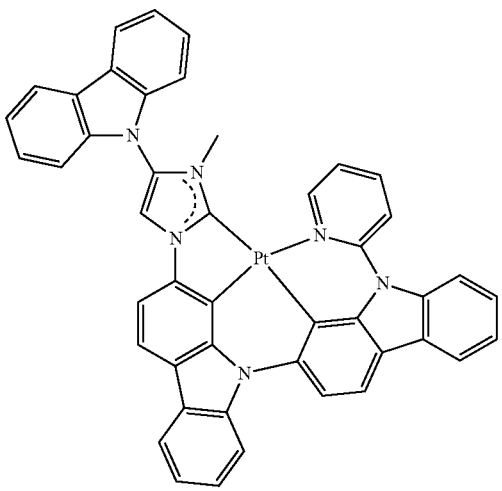
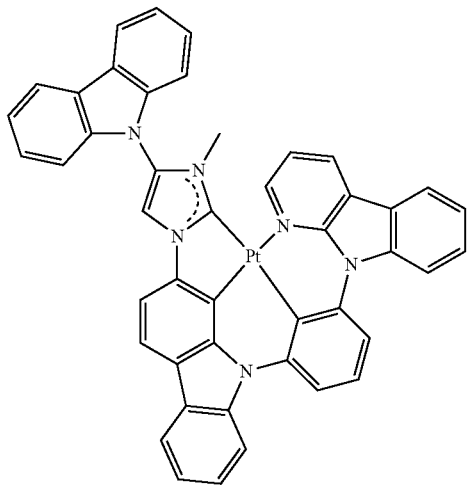

137
-continued
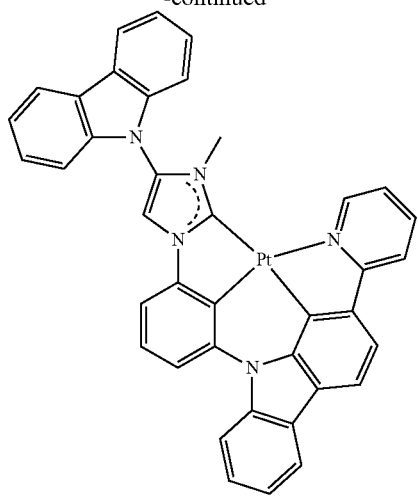
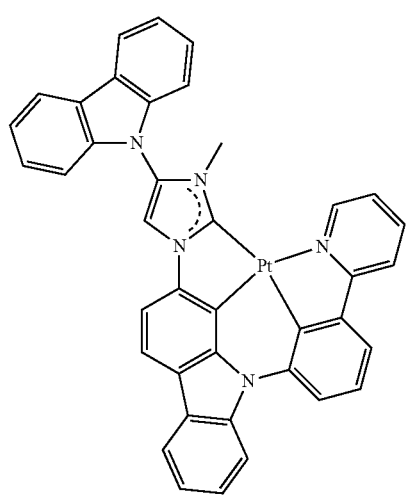
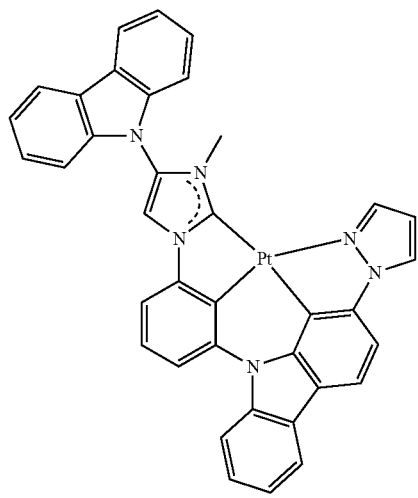
138
-continued
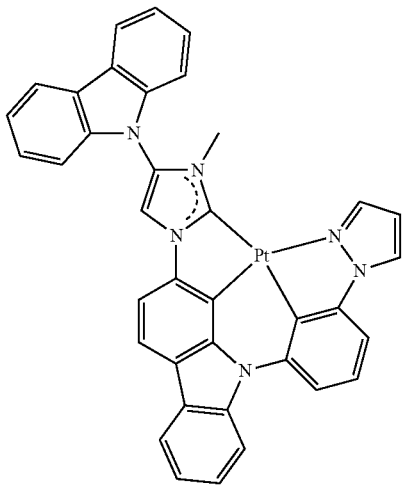
Structures 11
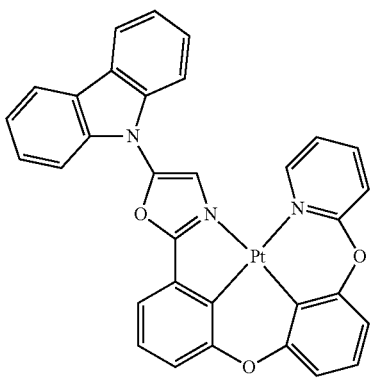
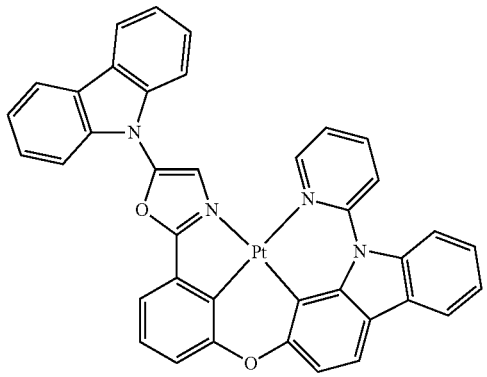

139
-continued
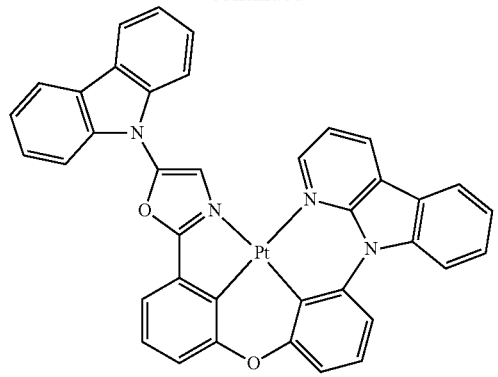
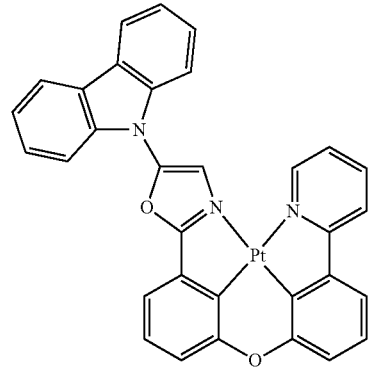
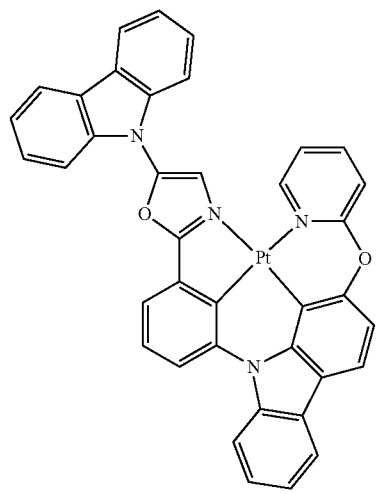
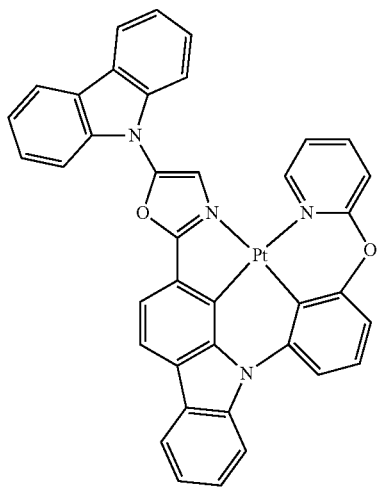
140
-continued
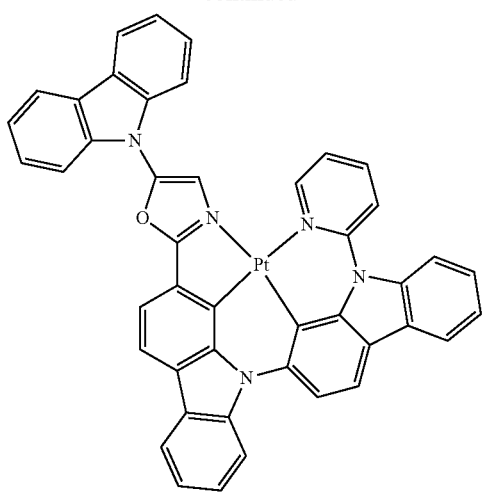
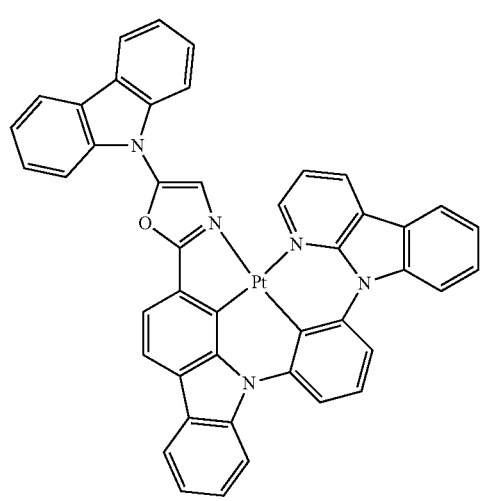
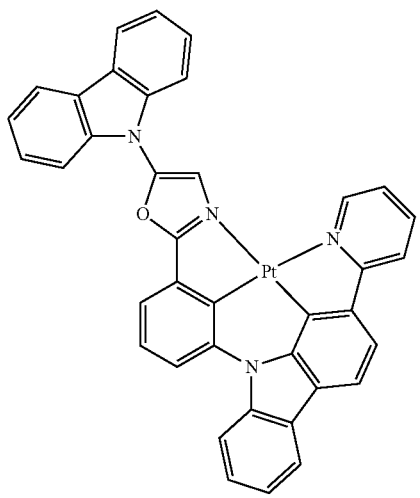

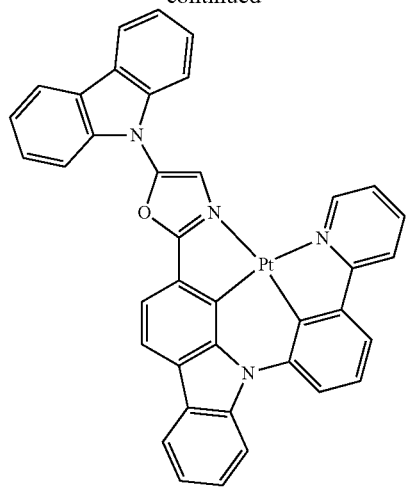
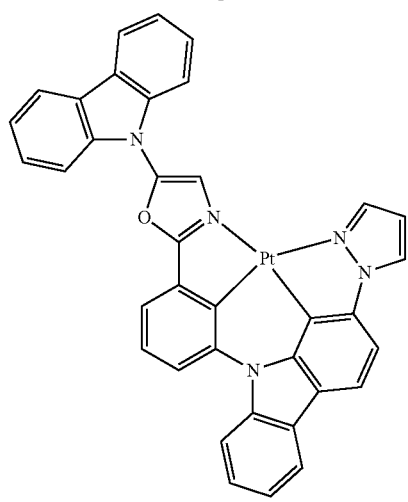
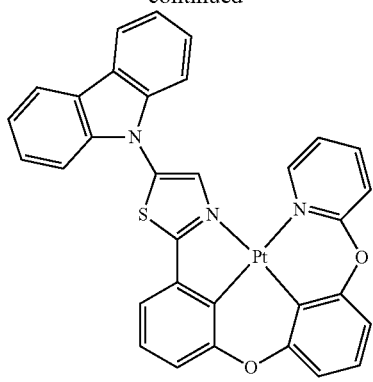
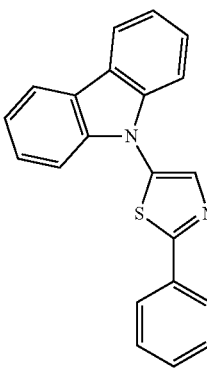
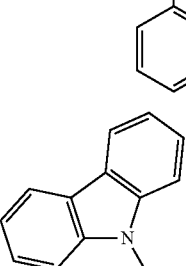
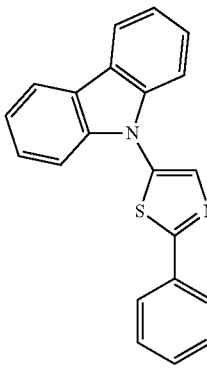
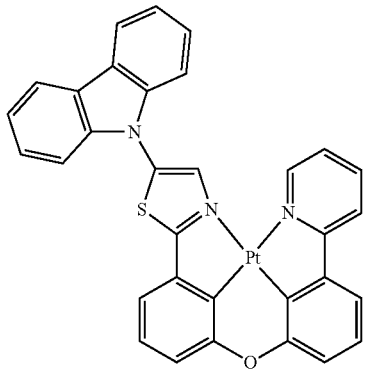

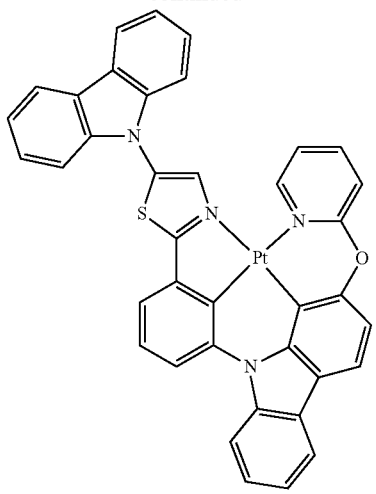
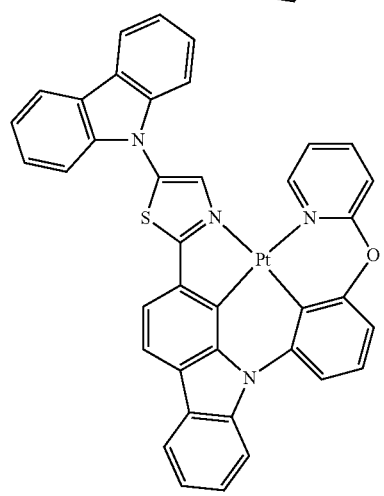
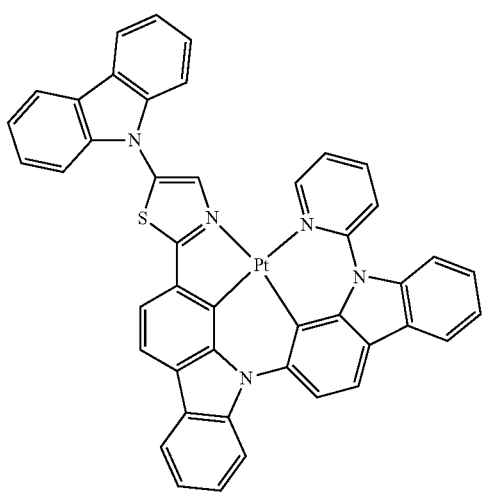
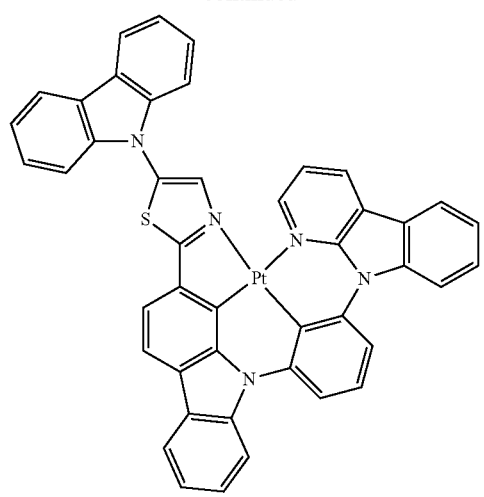
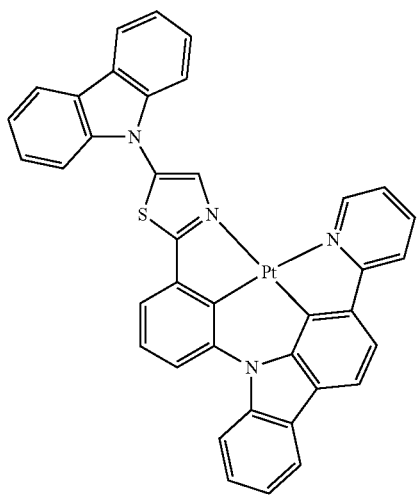
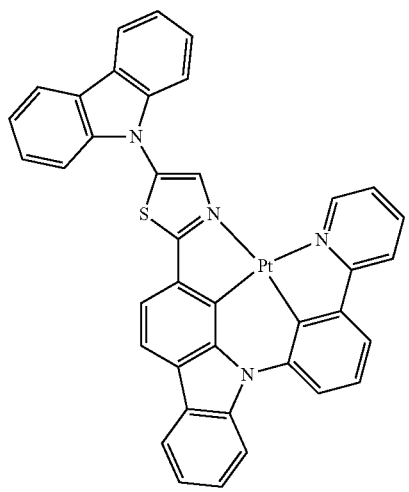

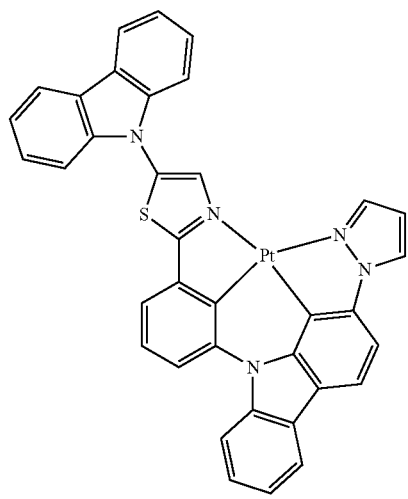
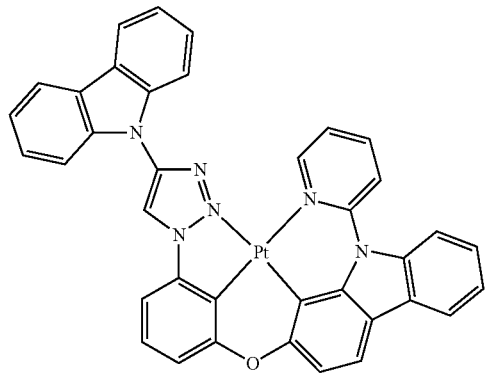
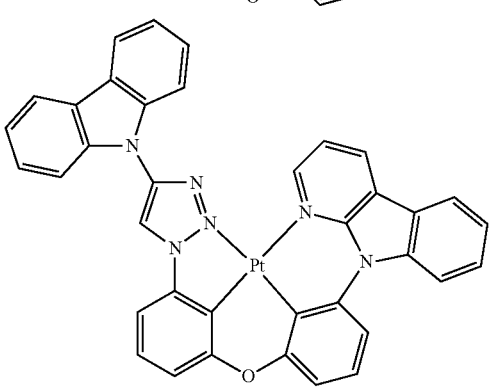
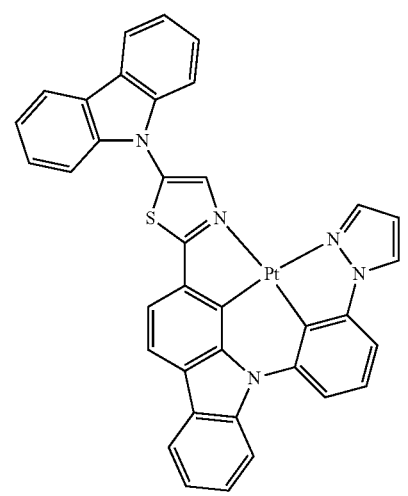
Structures 12
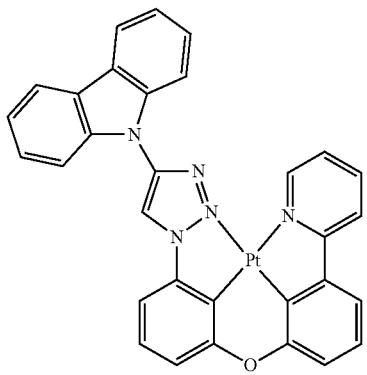
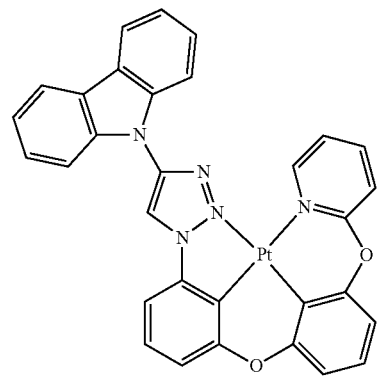
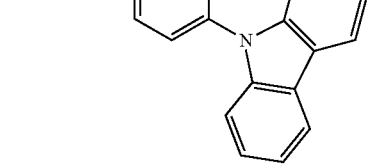

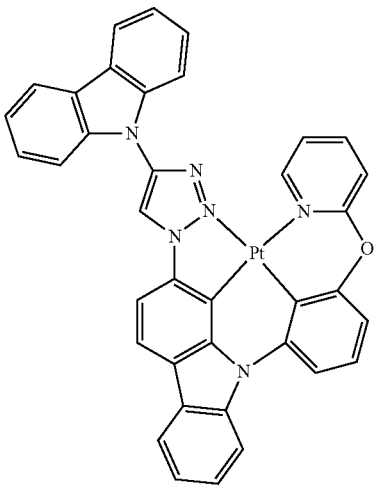
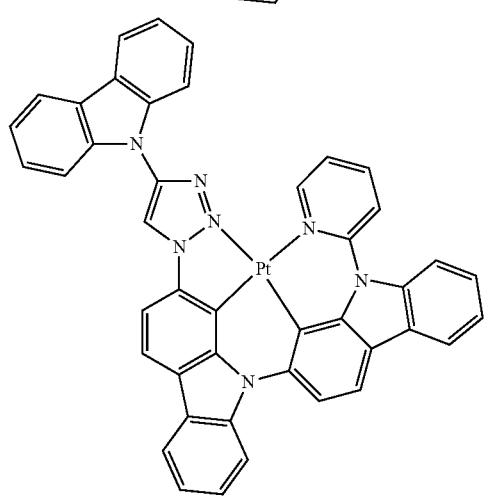
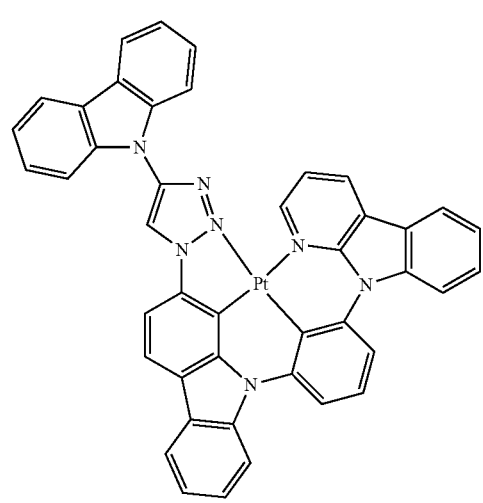
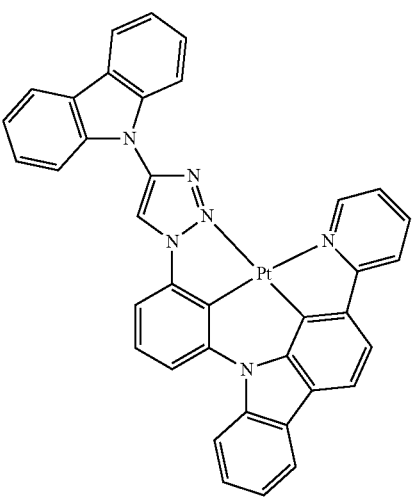
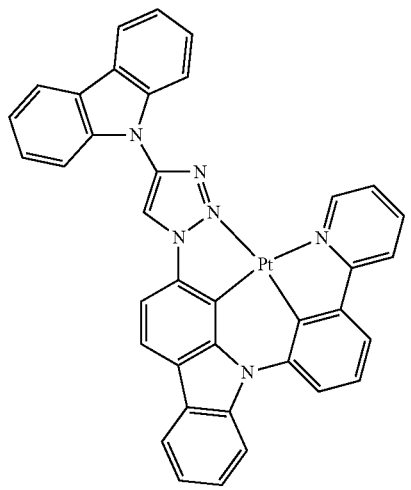
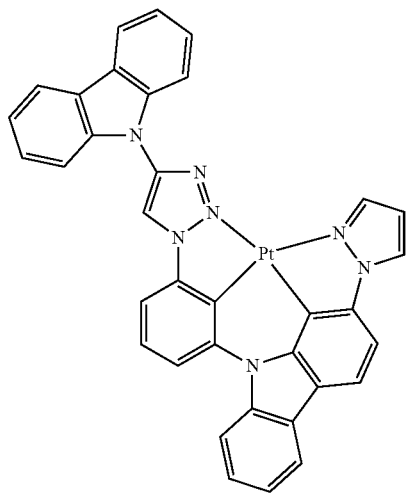

149
-continued
150
-continued
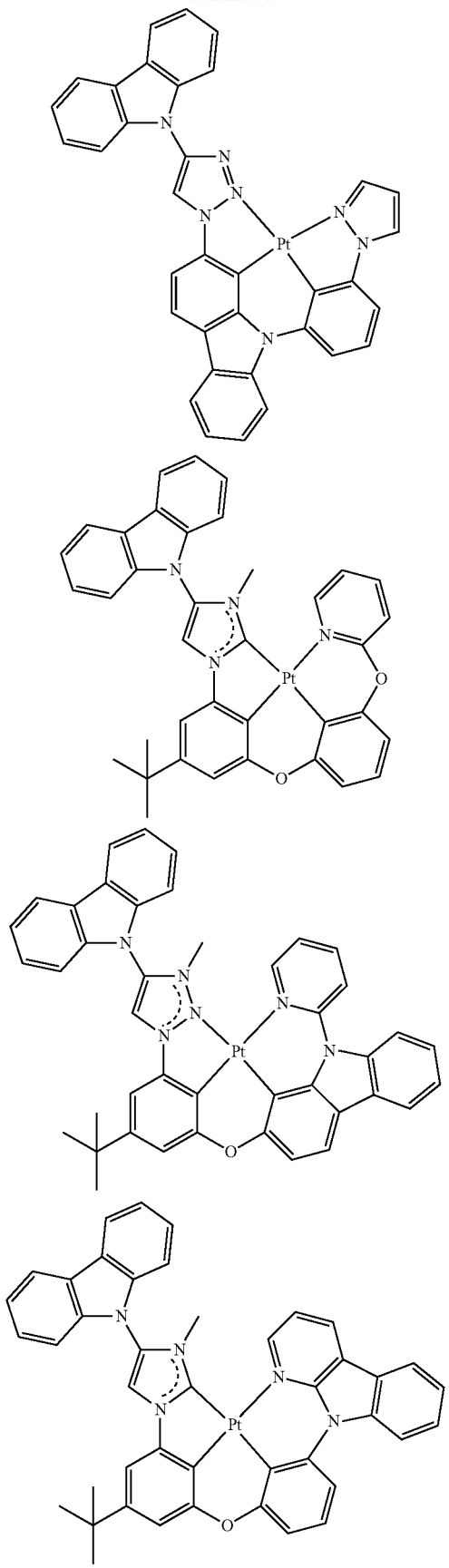
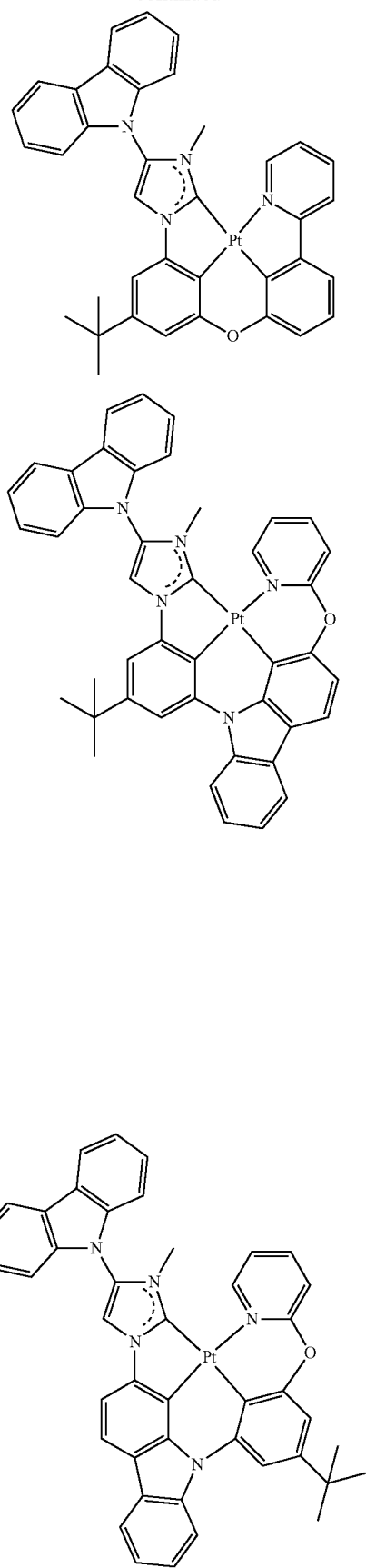

151
-continued
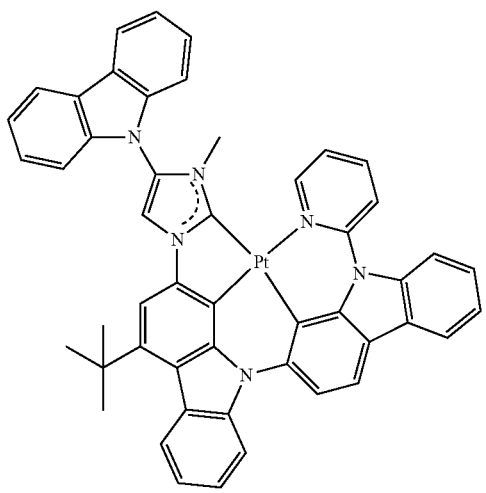
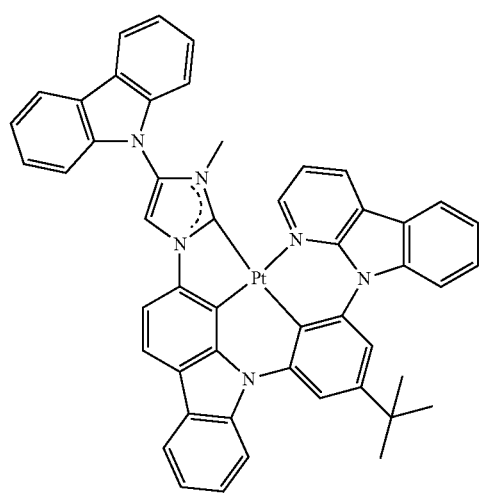
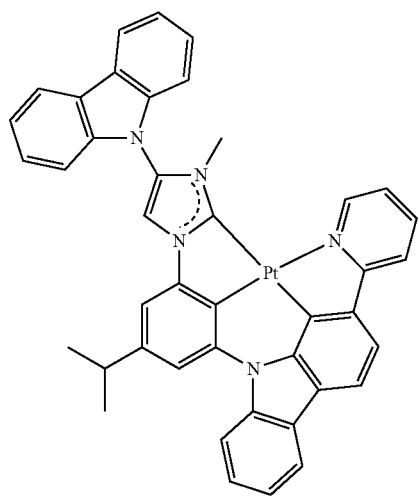
152
-continued
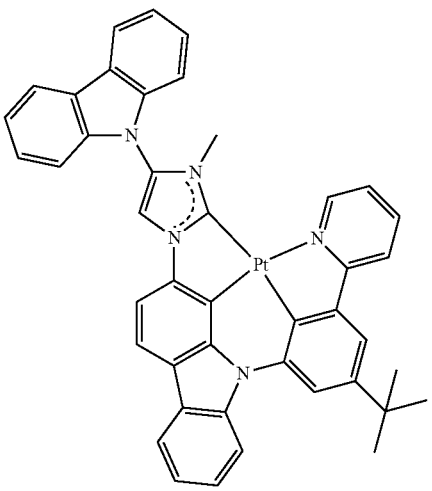
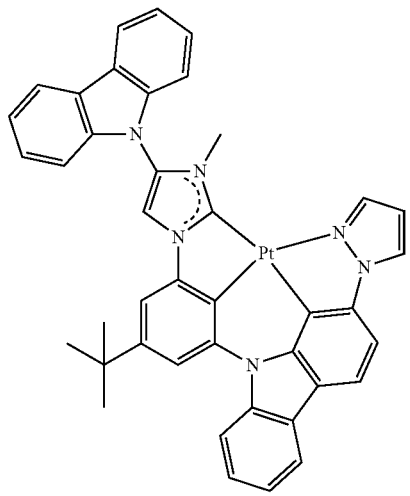
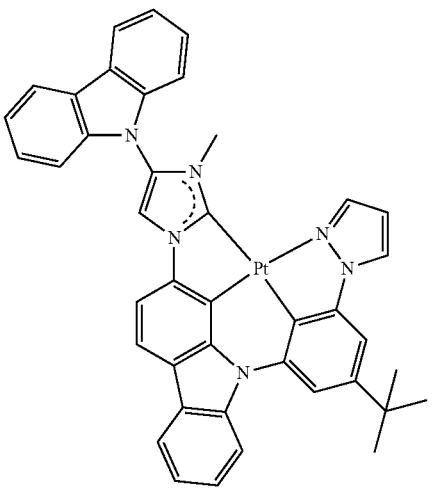

Structures 13 -continued
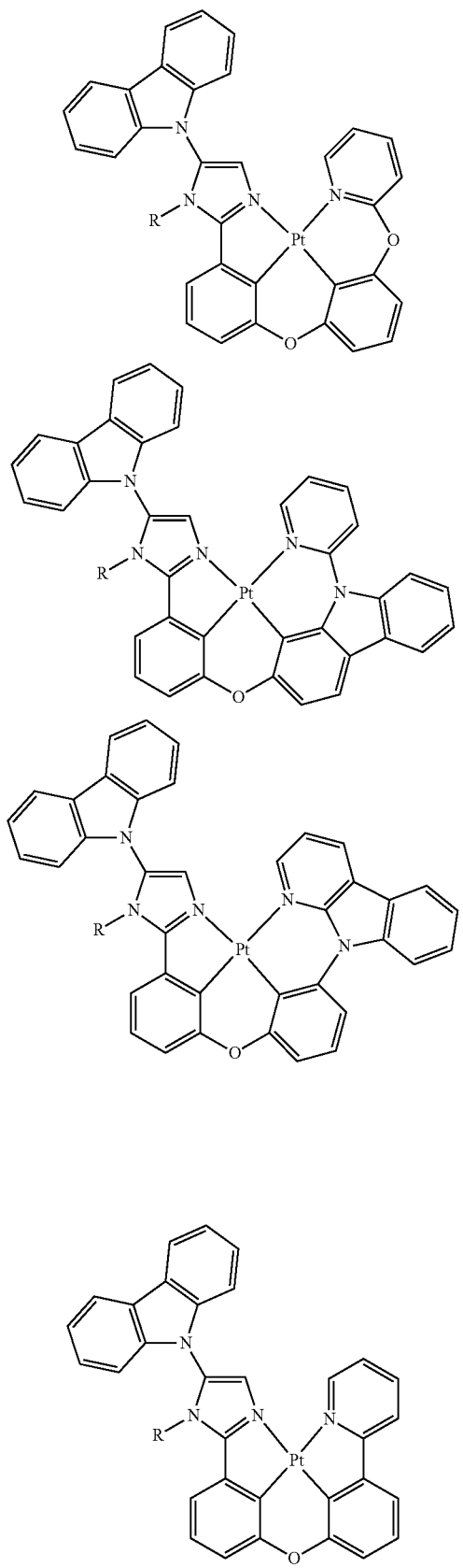
-continued
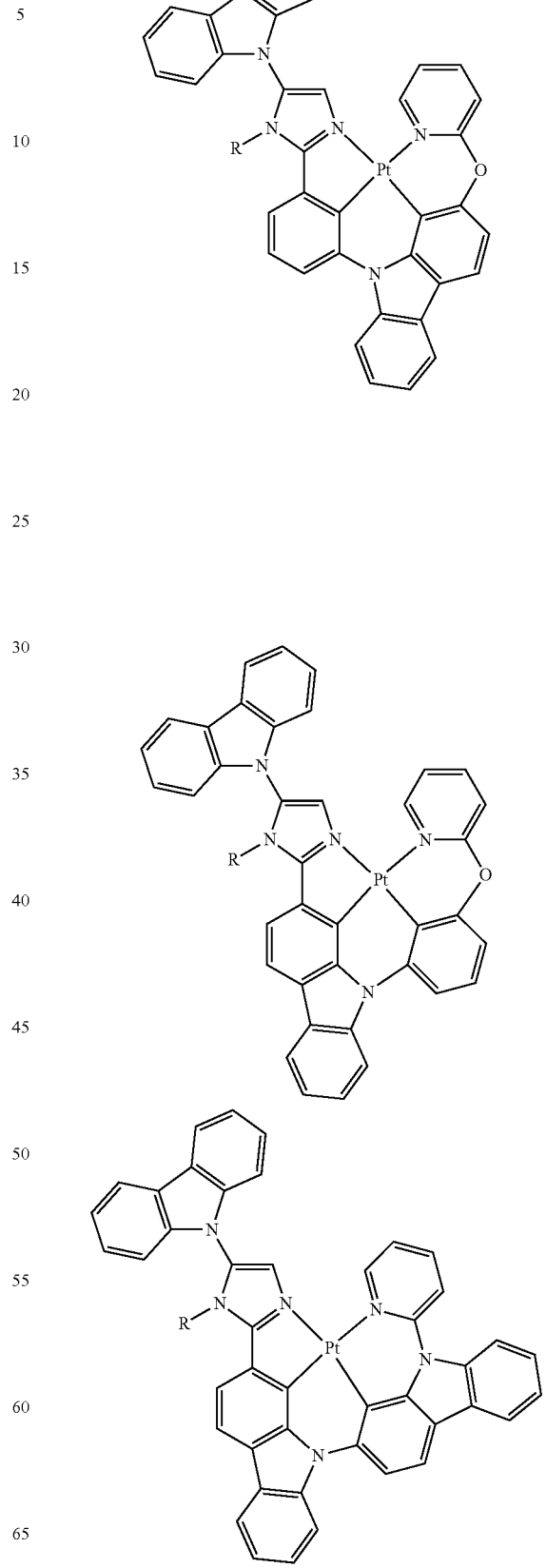

155
-continued
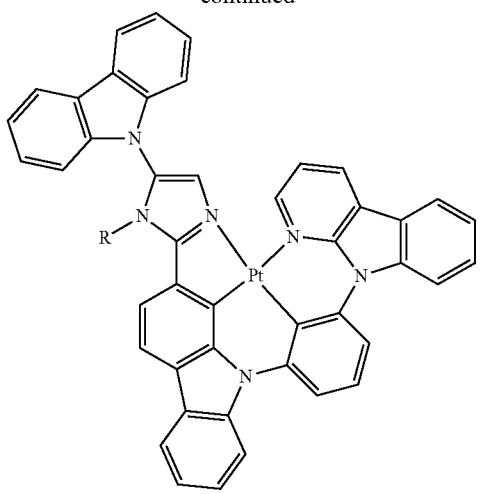
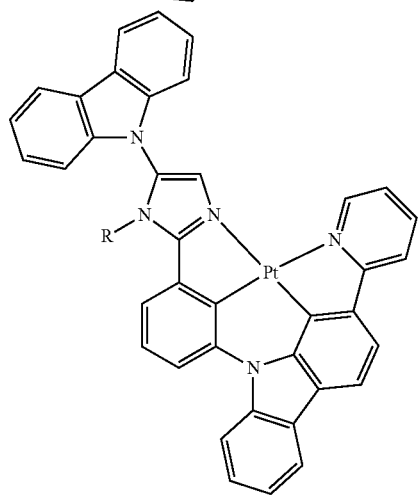
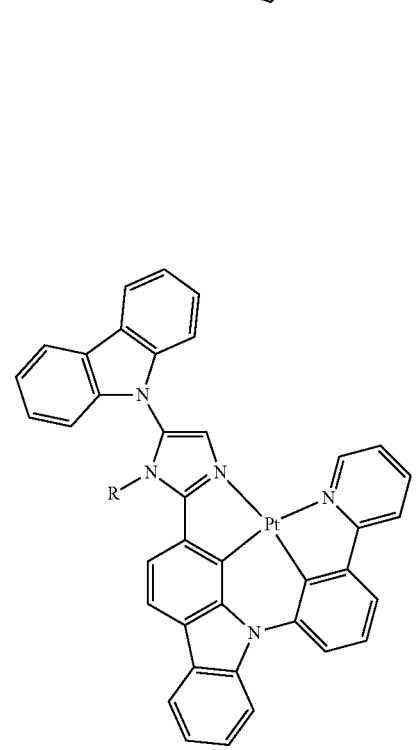
156
-continued
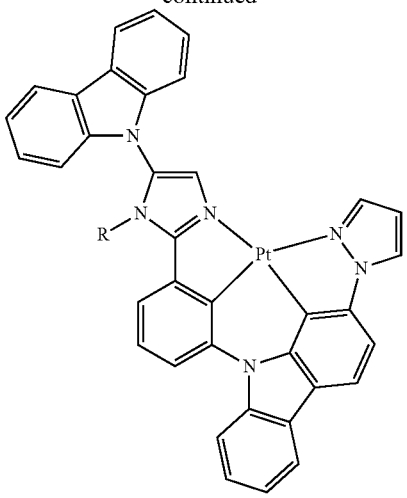
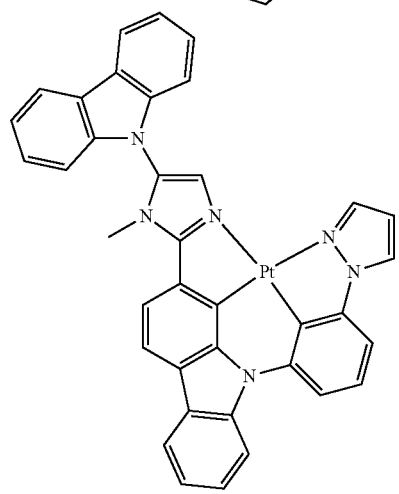
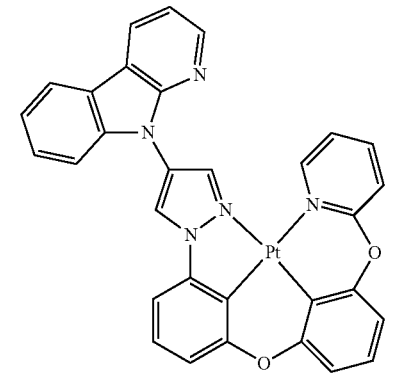
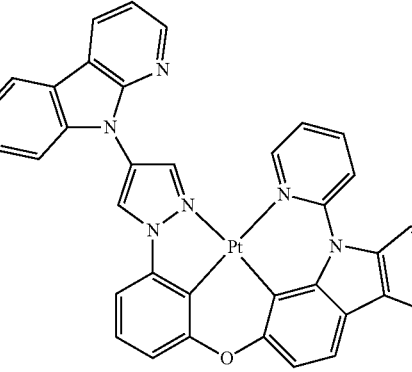

157
-continued
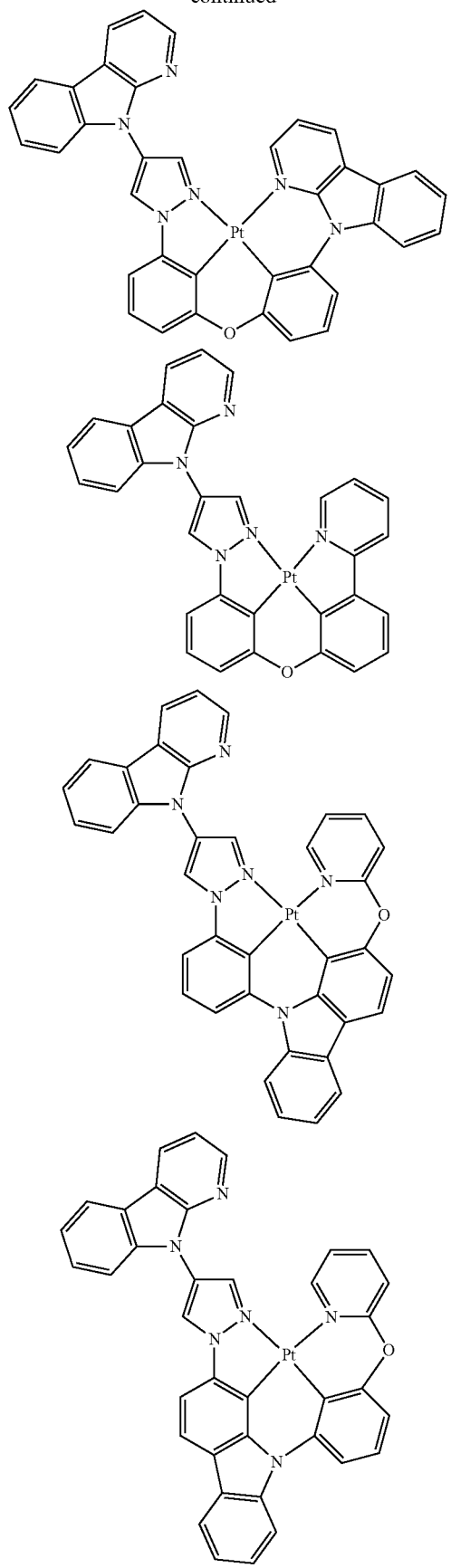
158
-continued
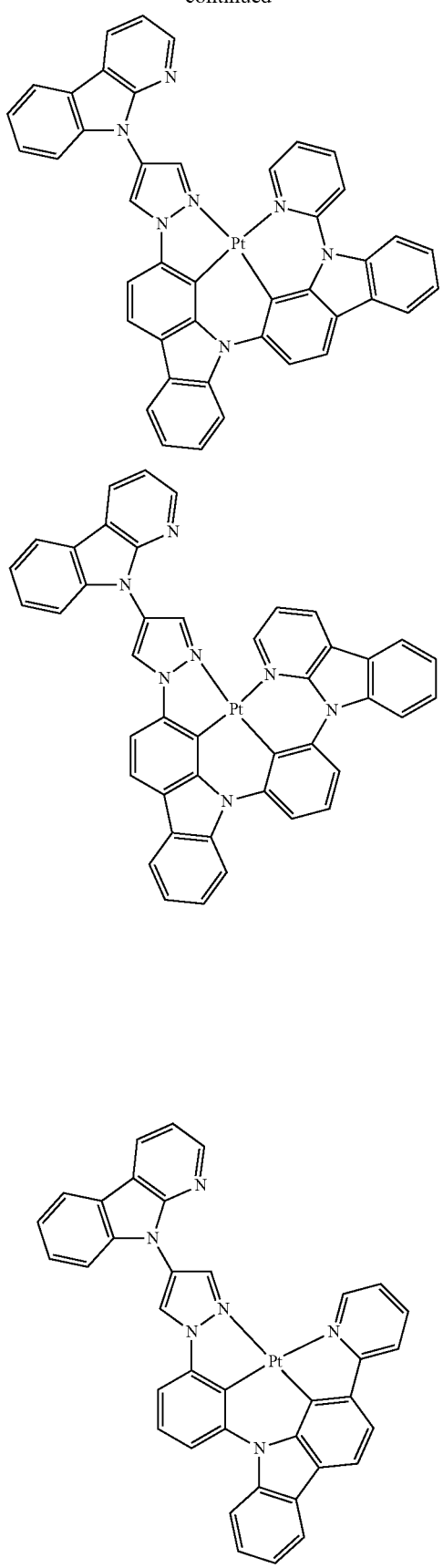

Structures 14
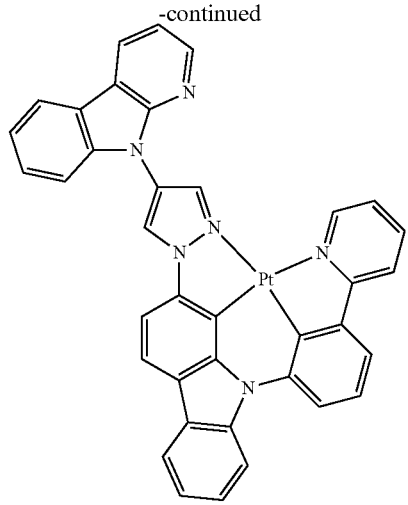
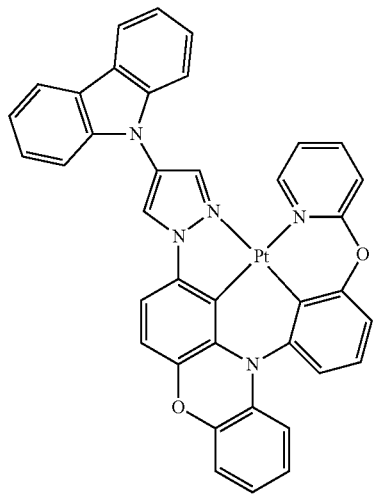
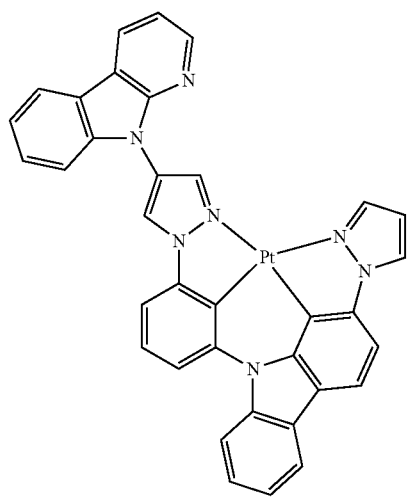
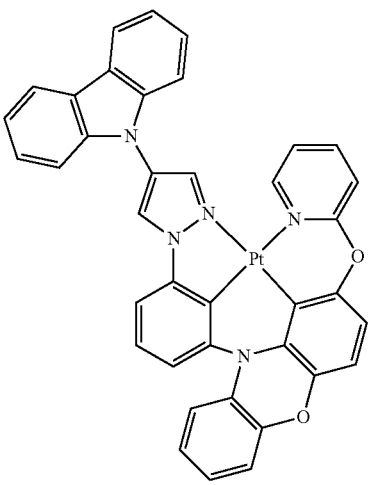
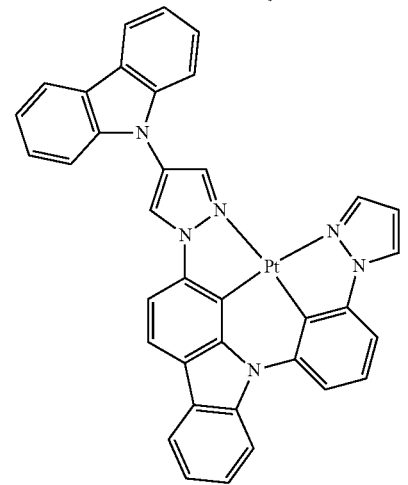
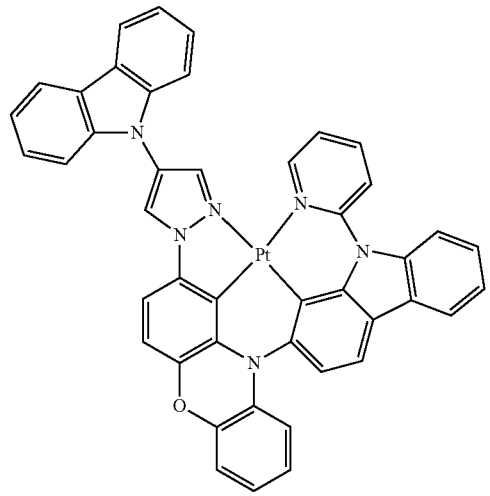

161
-continued
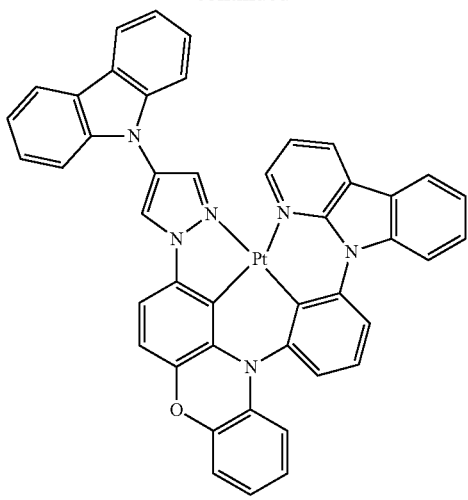
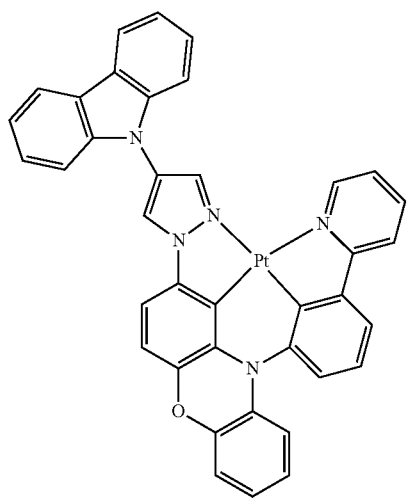
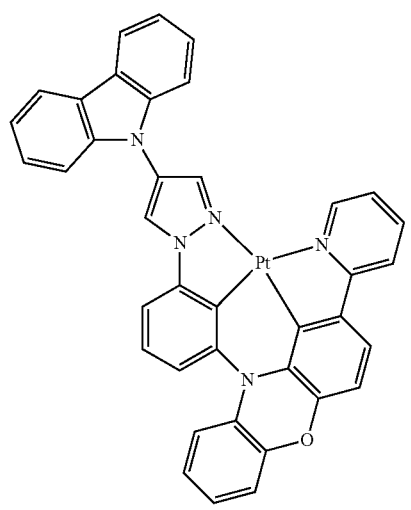
162
-continued
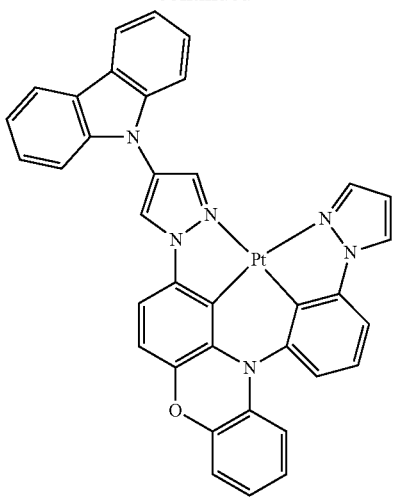
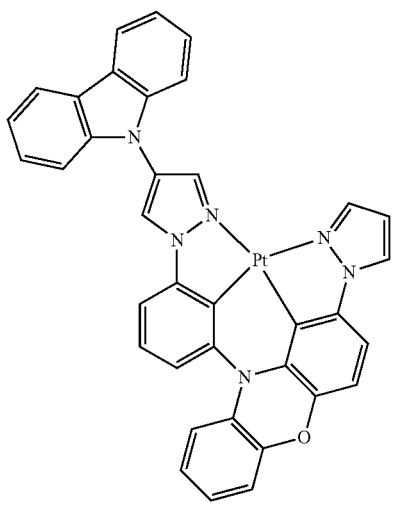
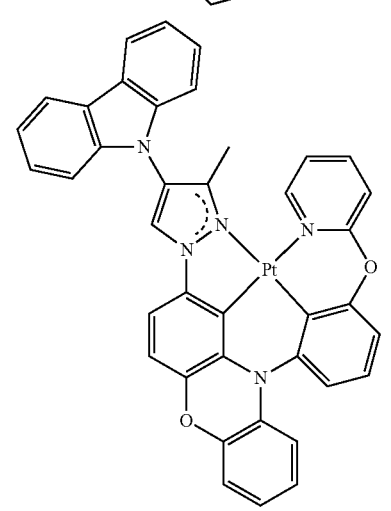

163
-continued
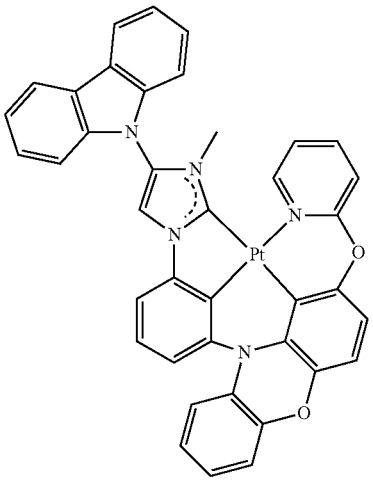
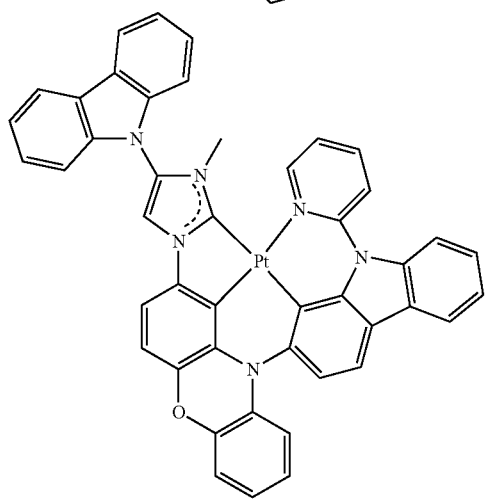
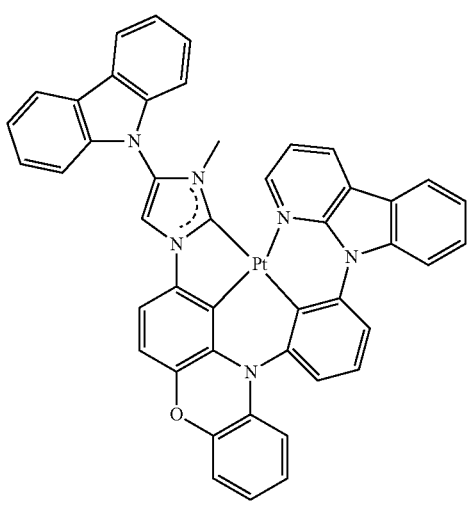
164
-continued
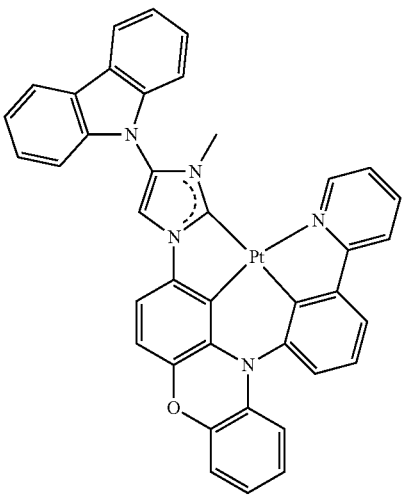
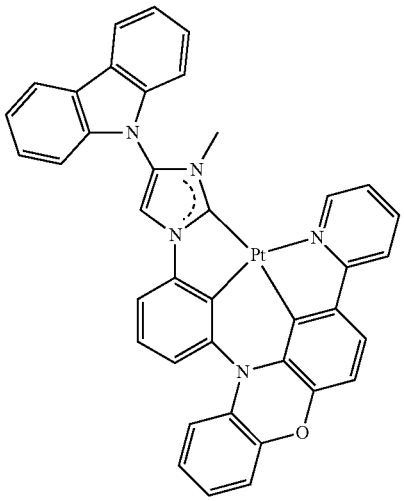
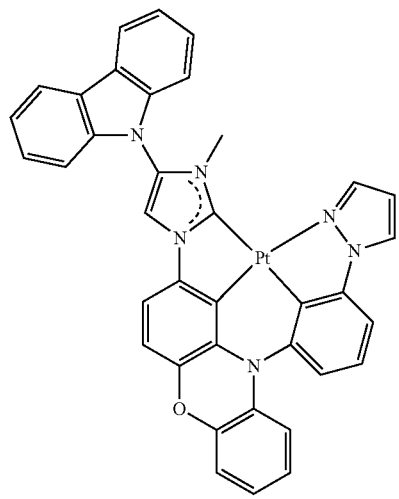

-continued
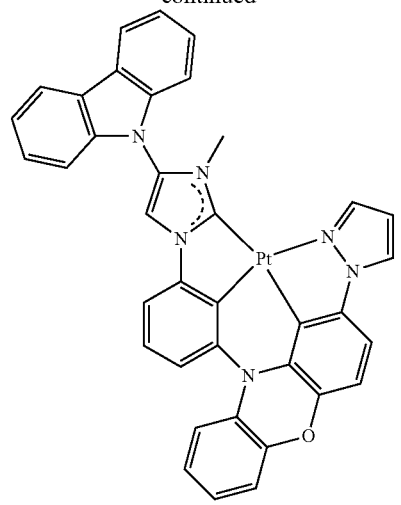
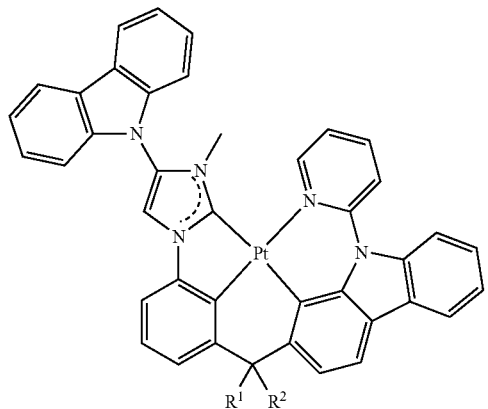
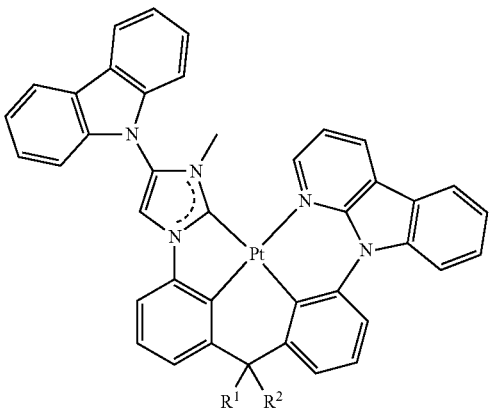
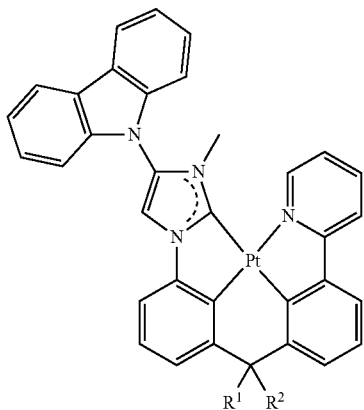
Structures 15
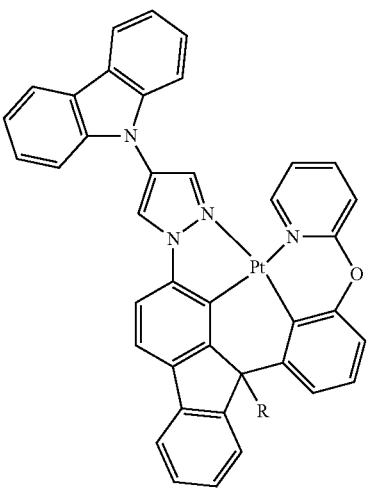
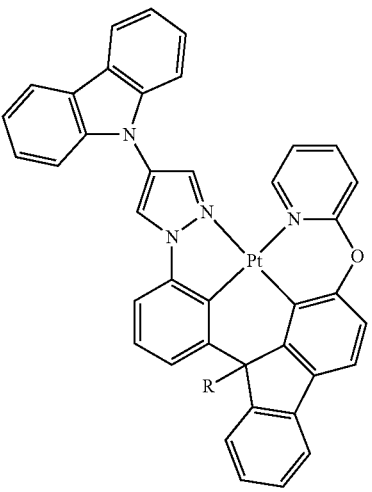

167
-continued
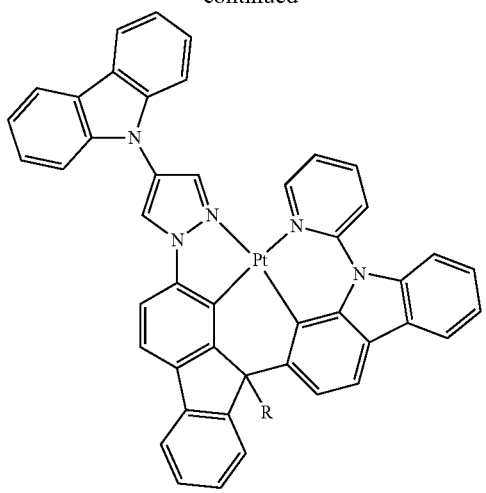
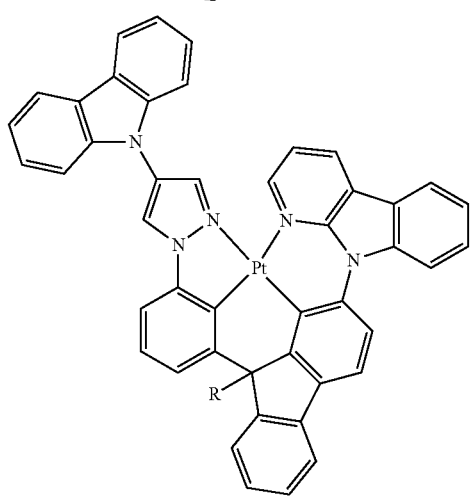
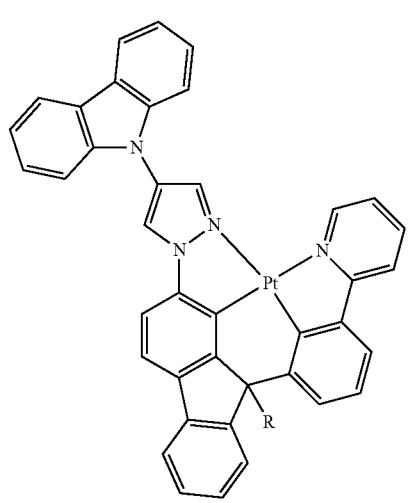
168
-continued
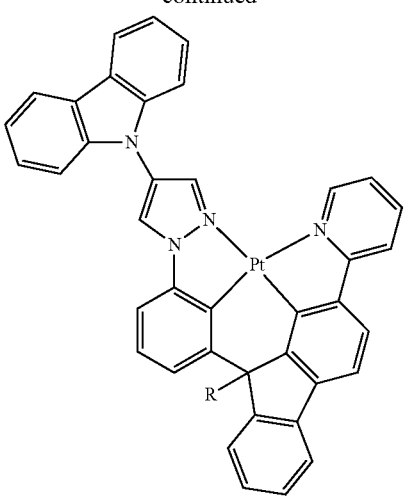
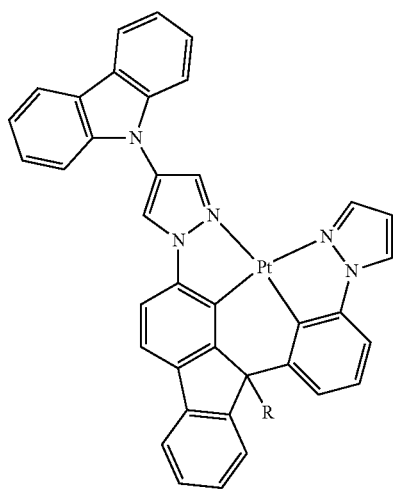
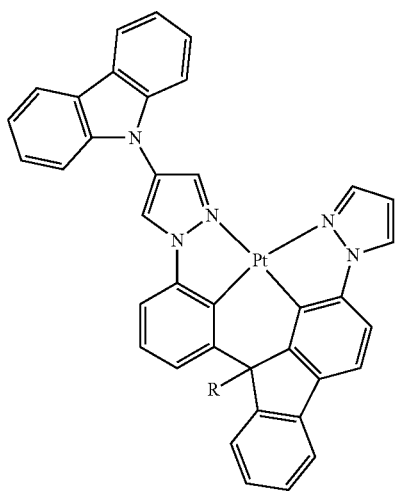

169
-continued
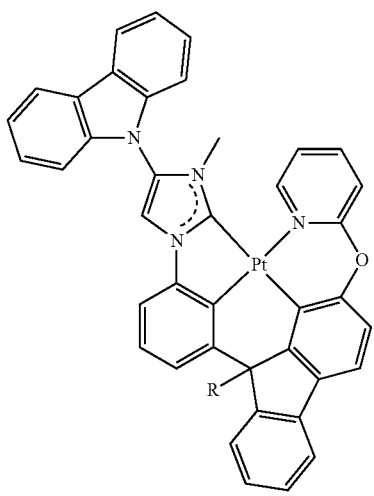
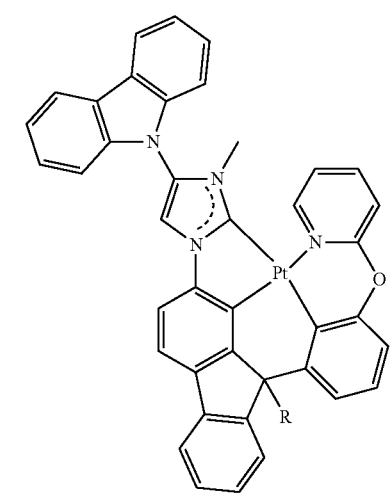
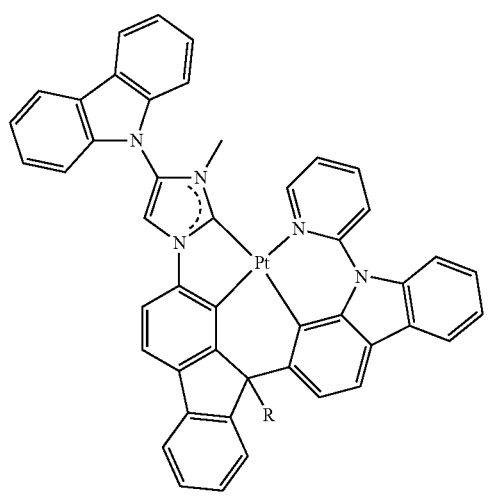
170
-continued
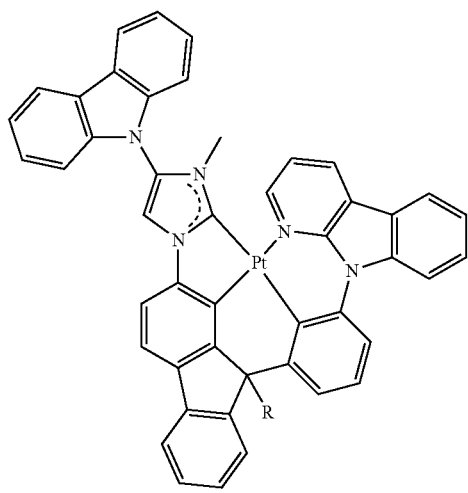
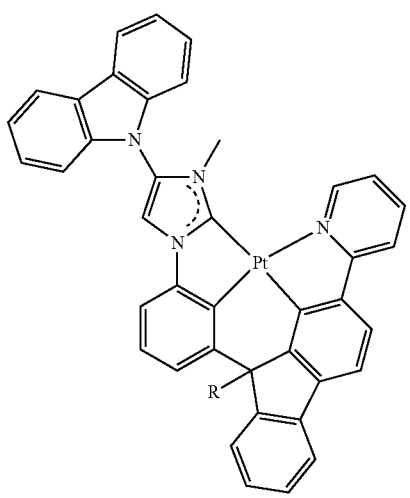
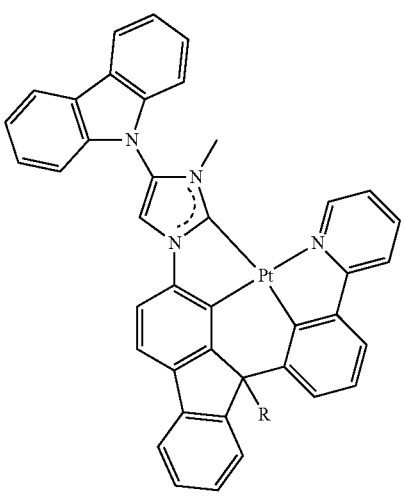

171
-continued
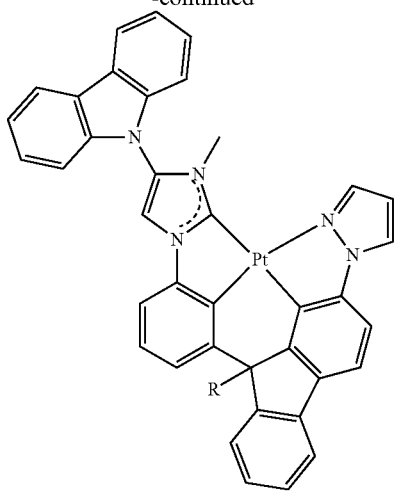
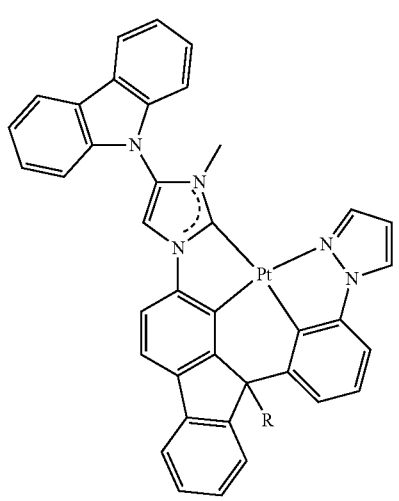
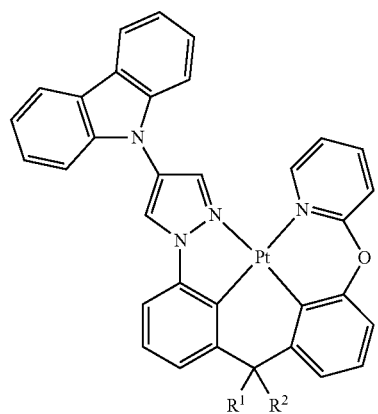
172
-continued
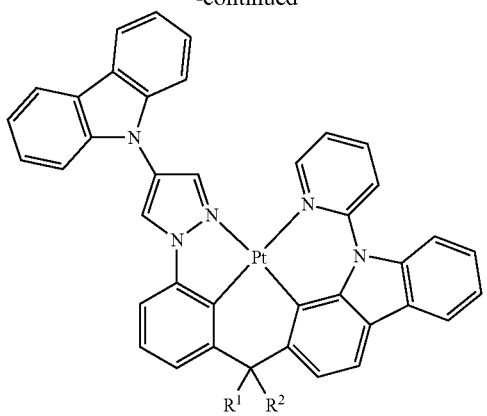
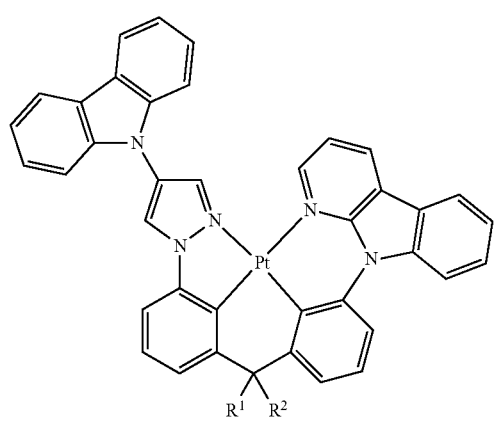
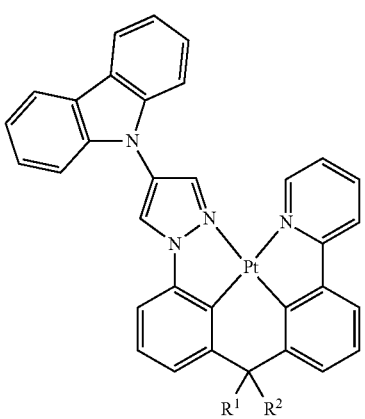

Structures 16
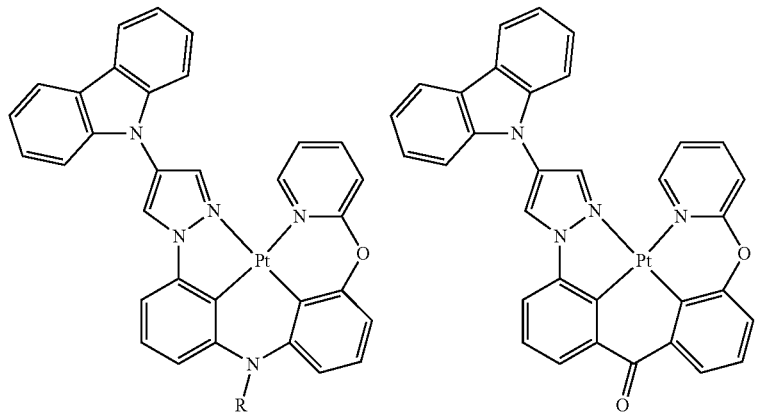
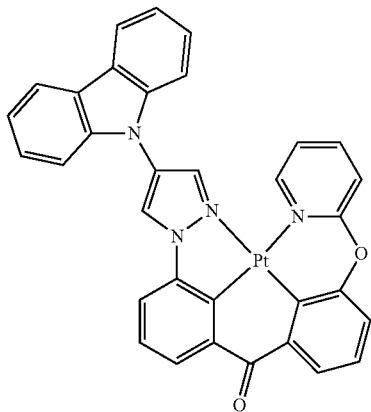
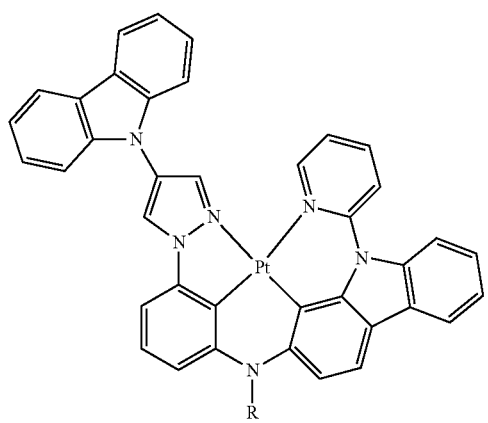
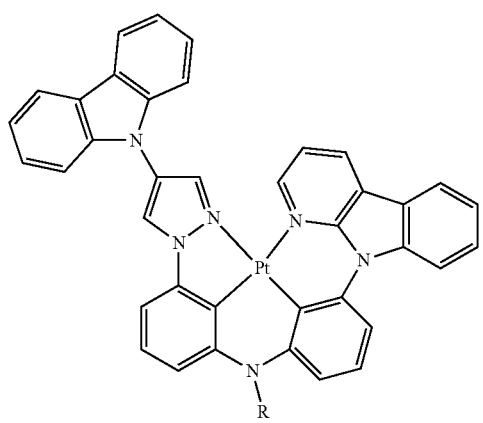
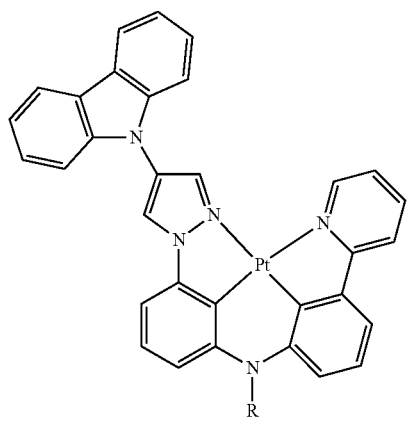
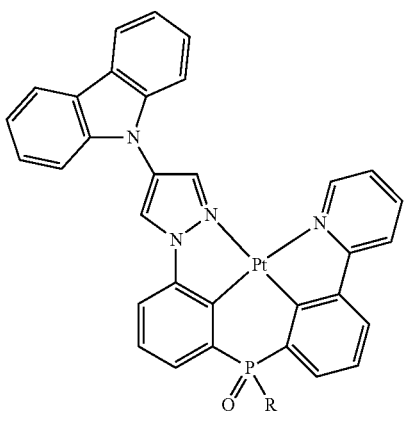
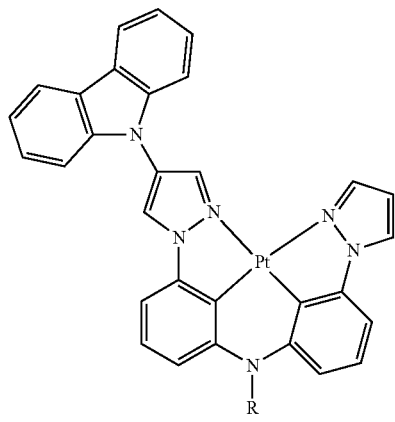
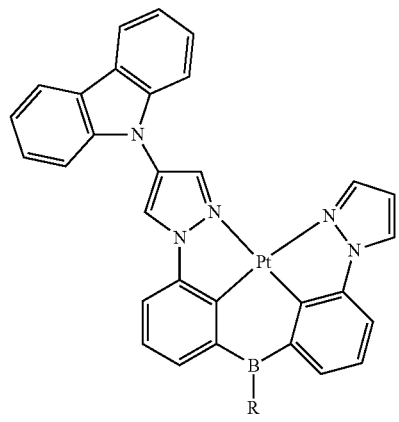

-continued
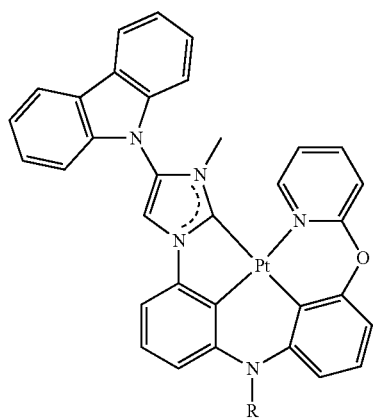
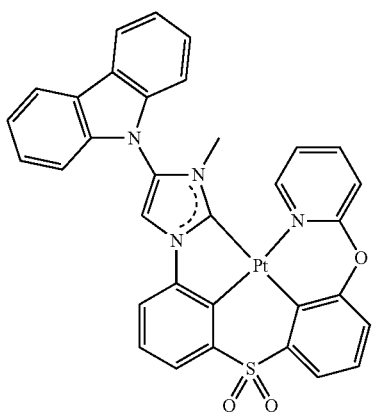
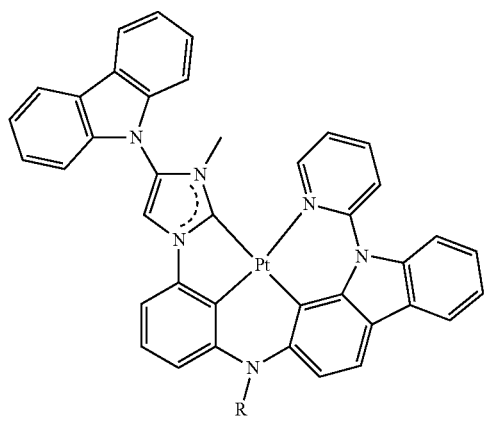
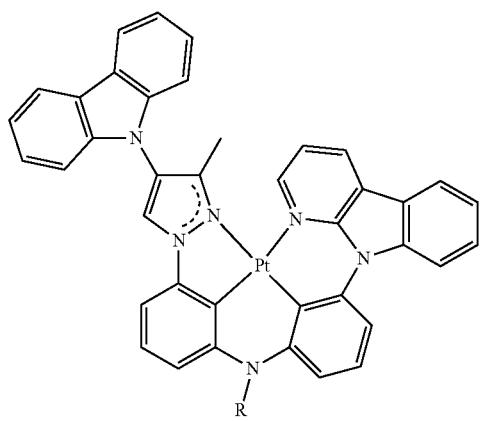
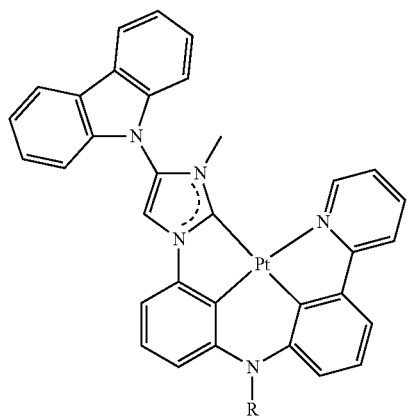
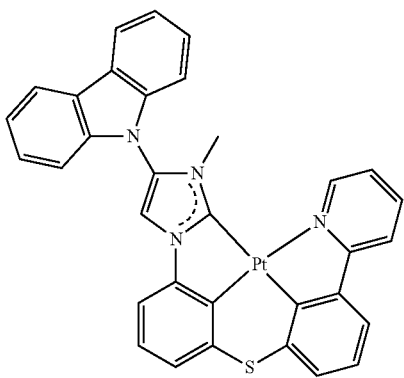
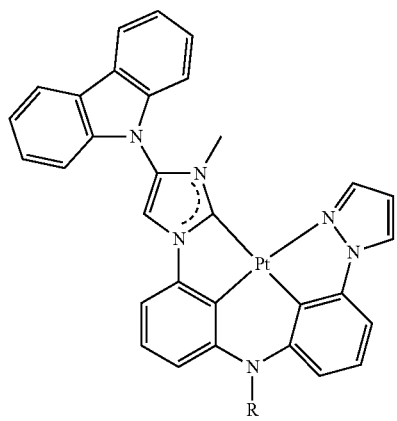
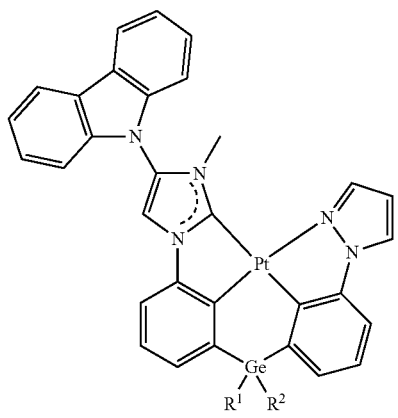

-continued
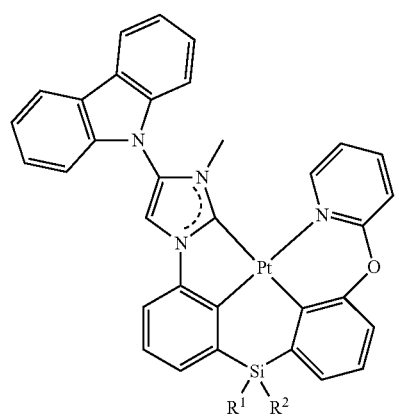
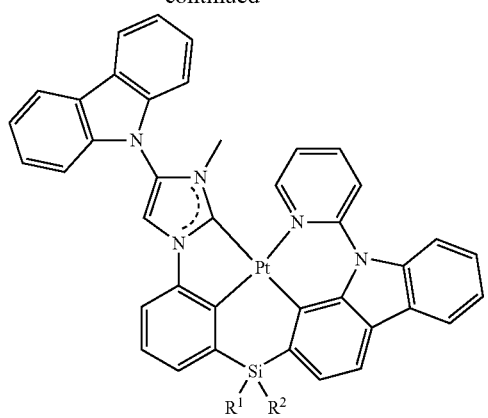
Structures 17
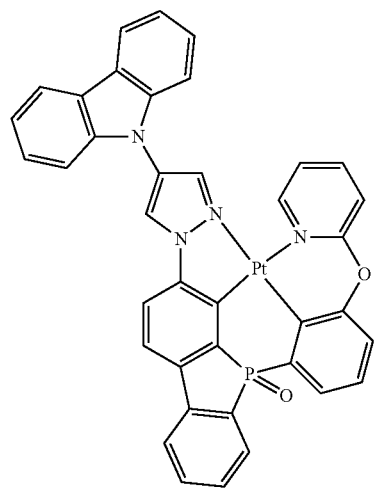
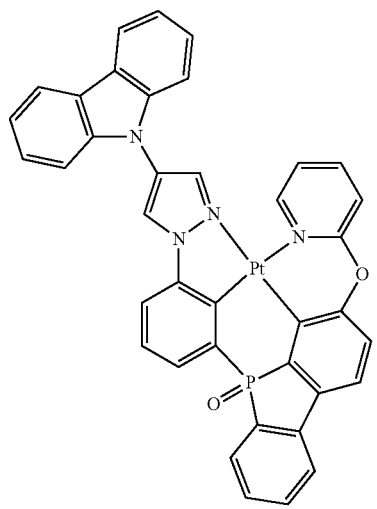

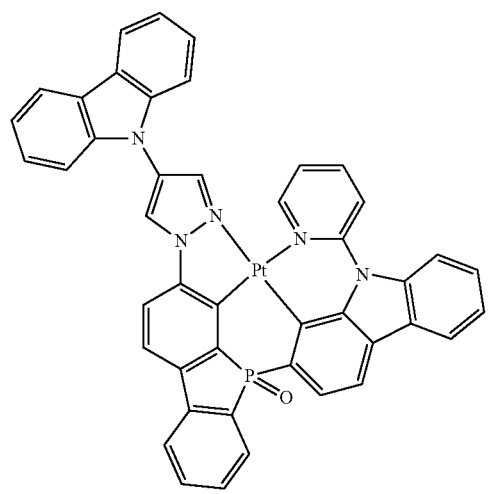
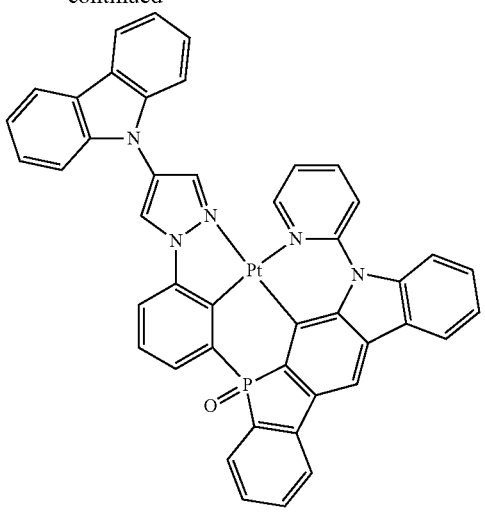
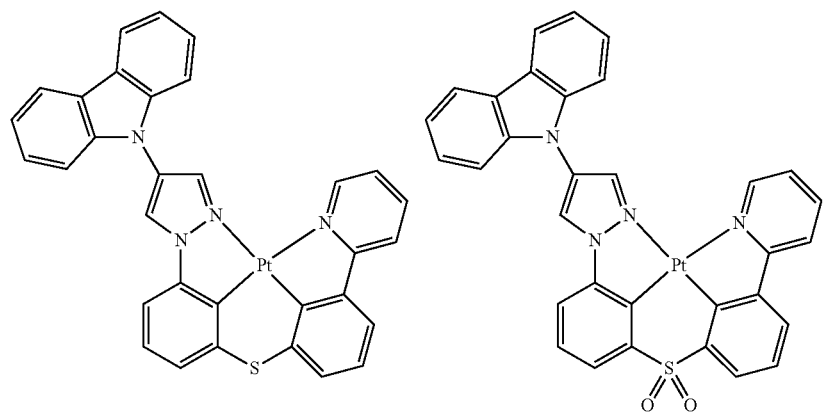
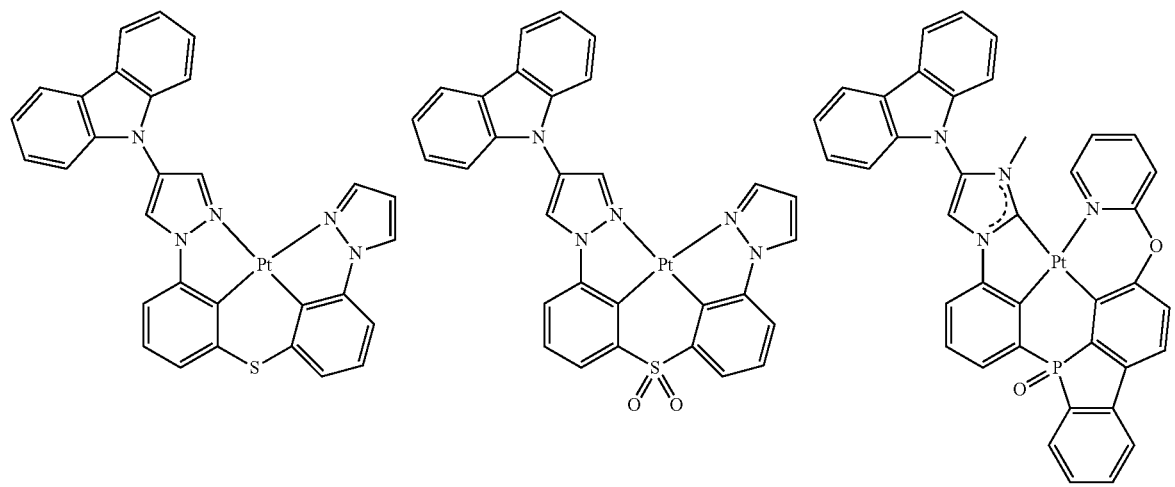

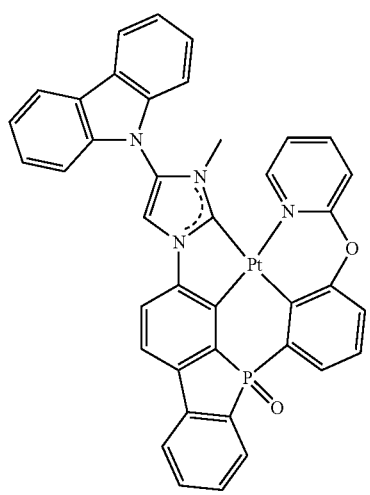
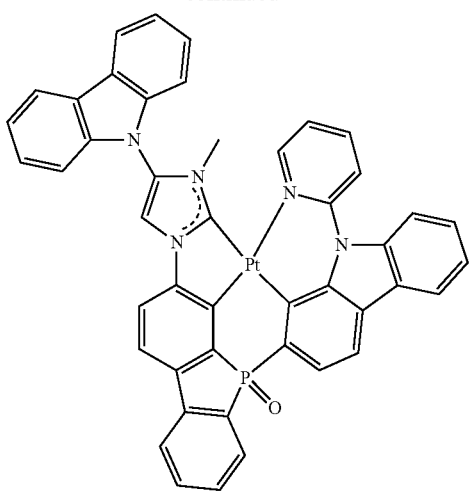
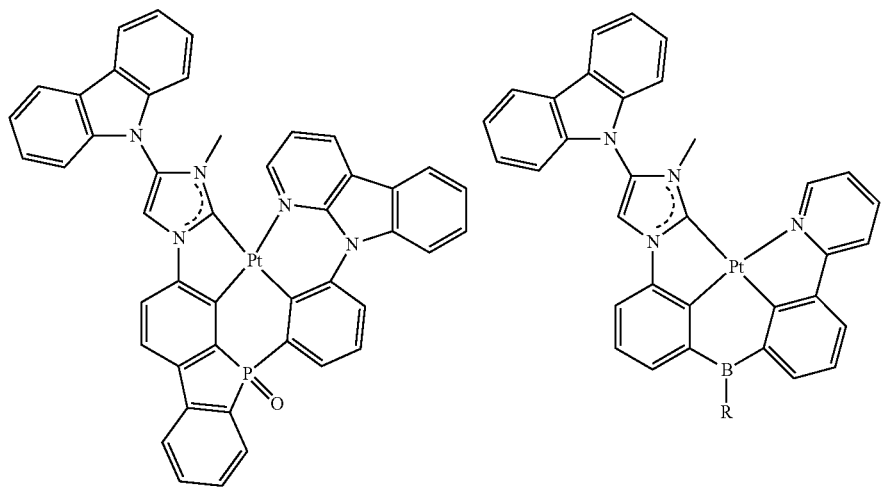
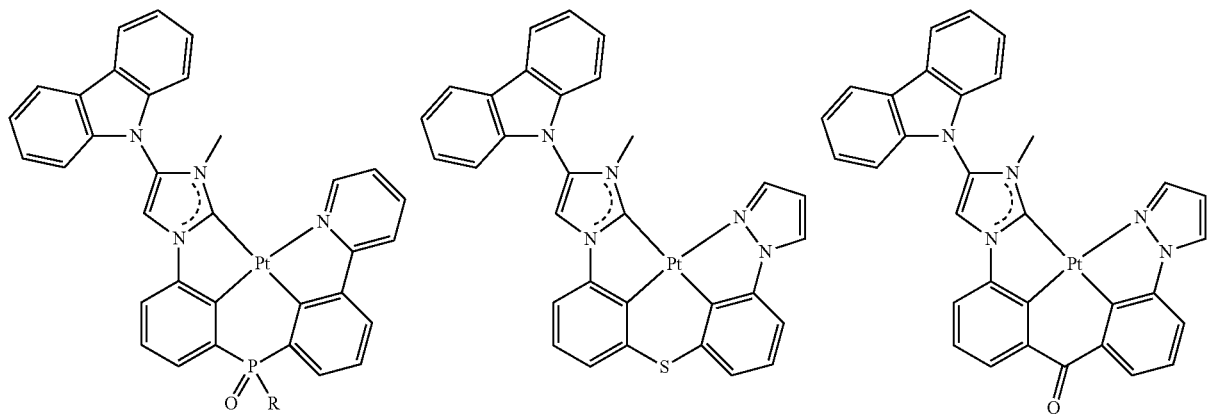

-continued
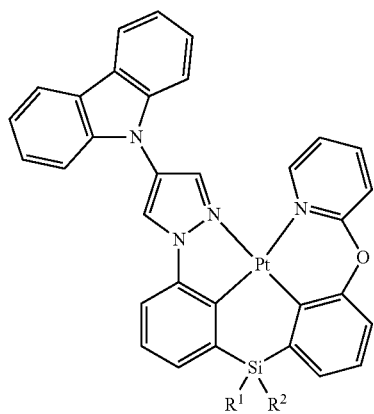
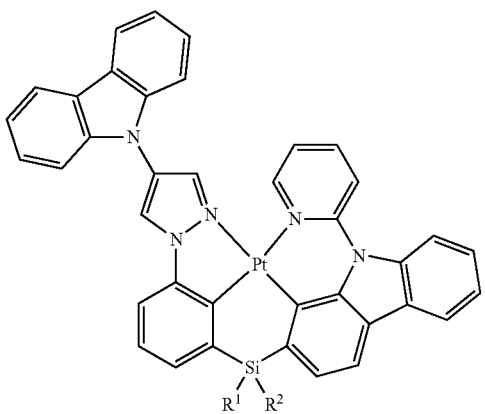
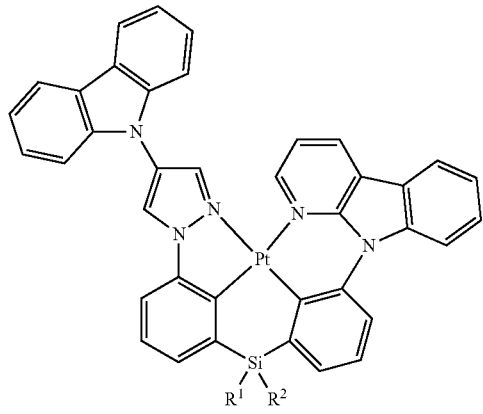
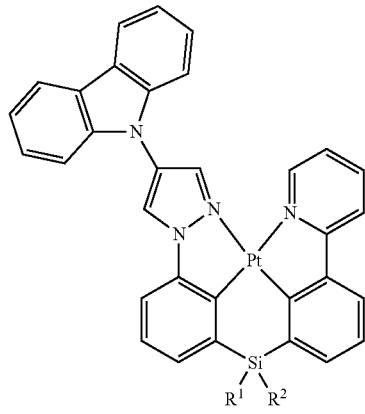
Structures 18
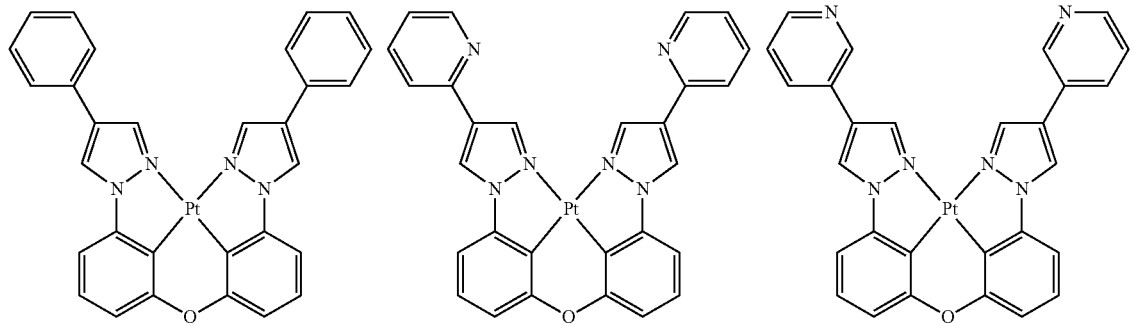
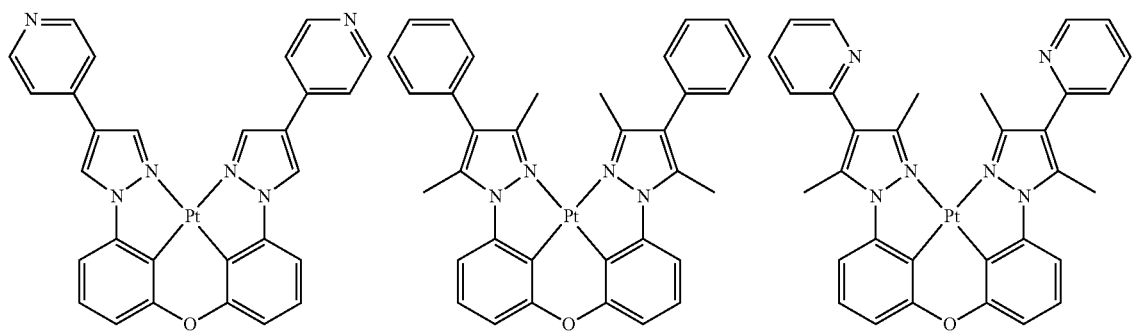

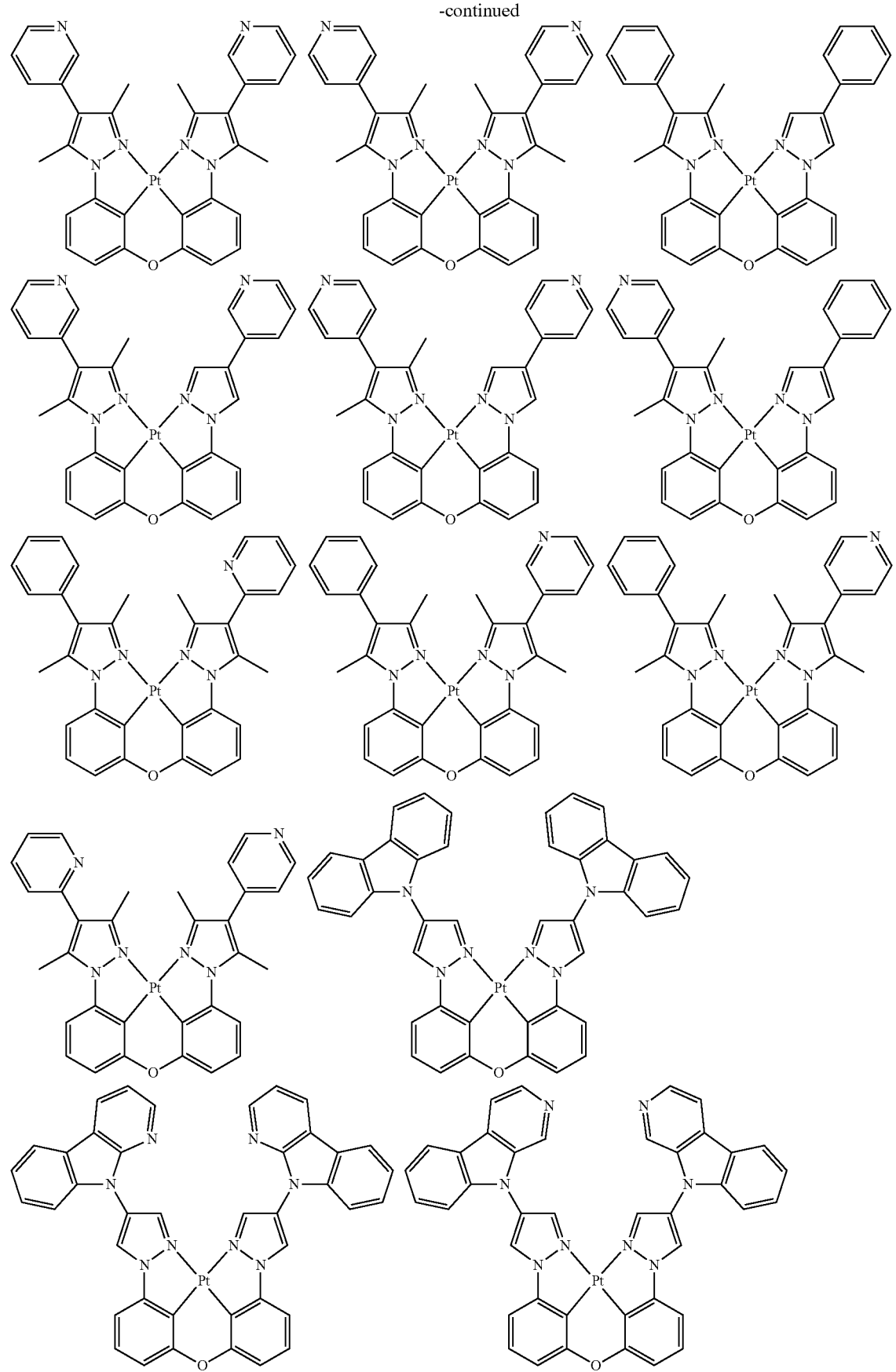

-continued
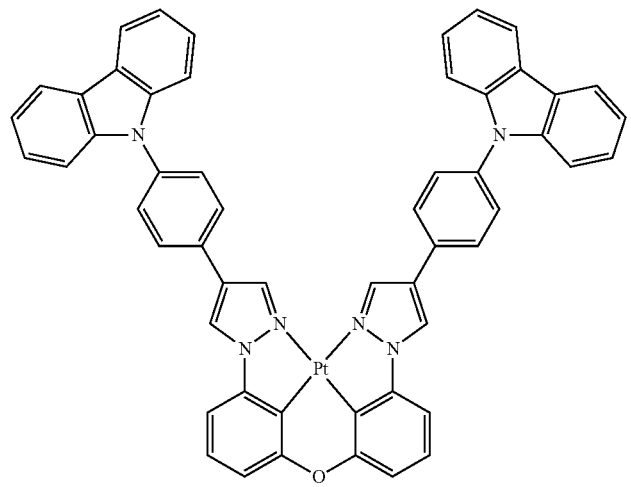
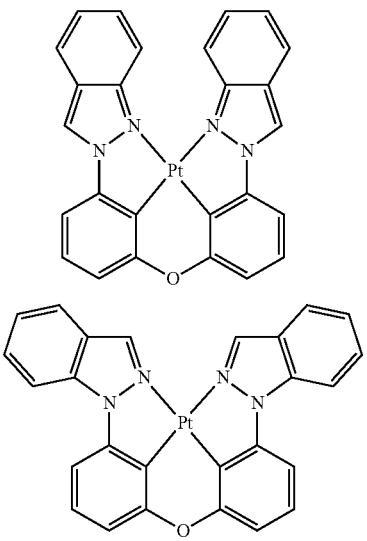
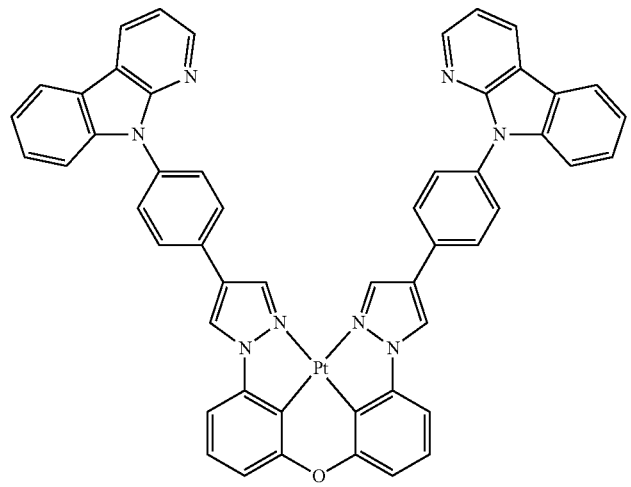
Structure 19
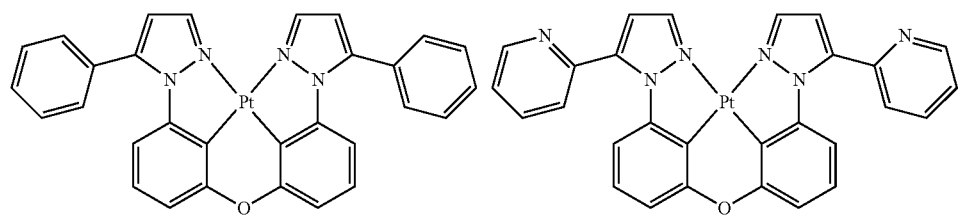
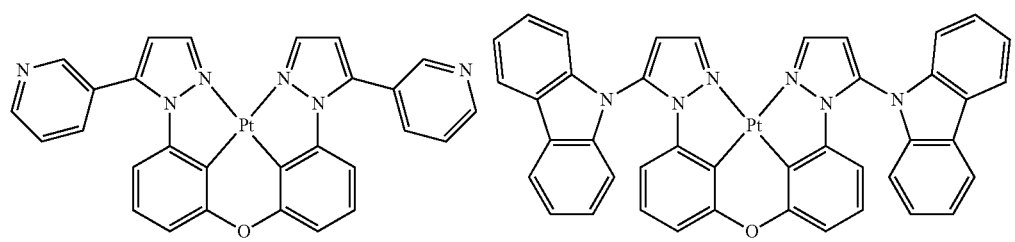

-continued
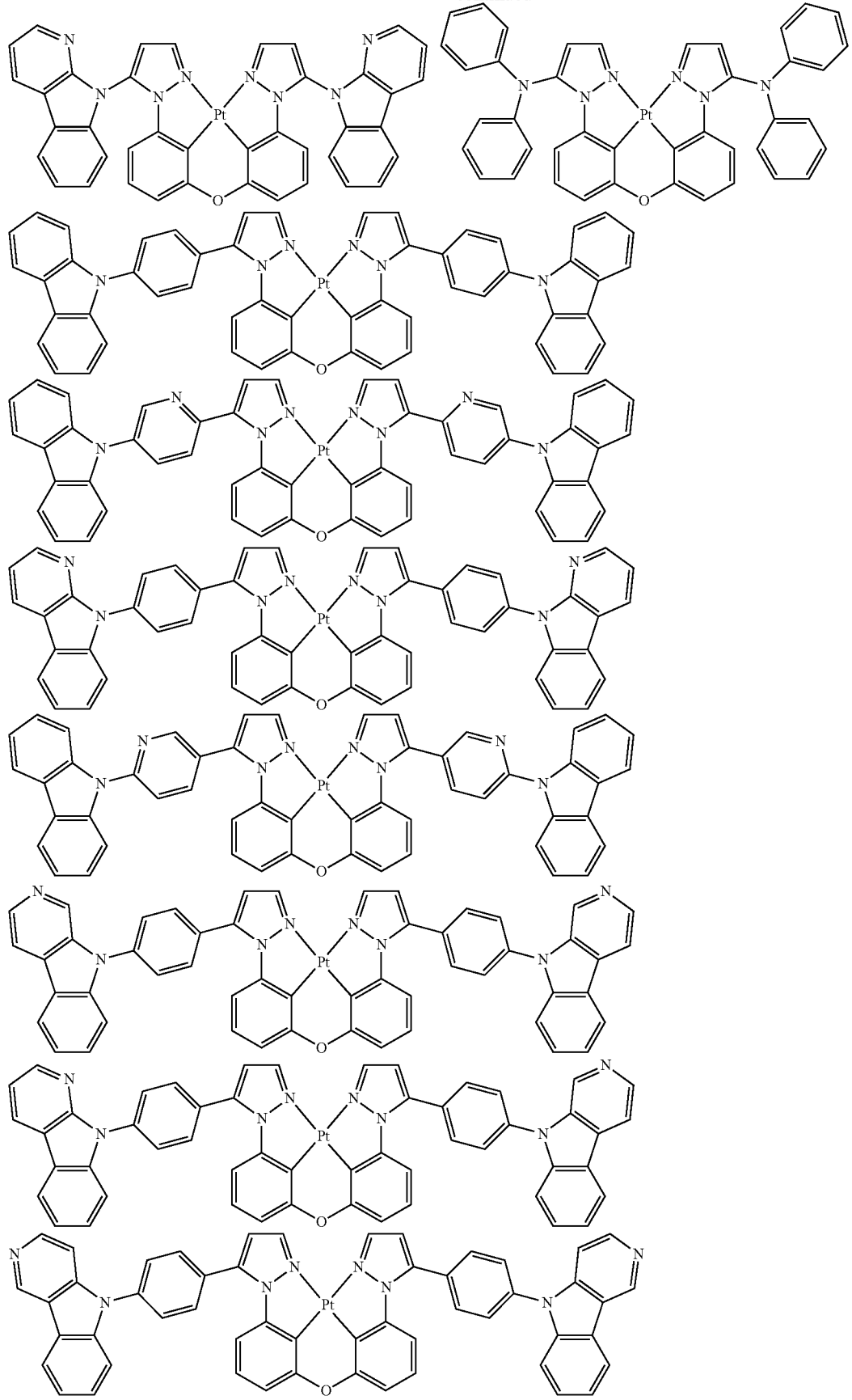

-continued
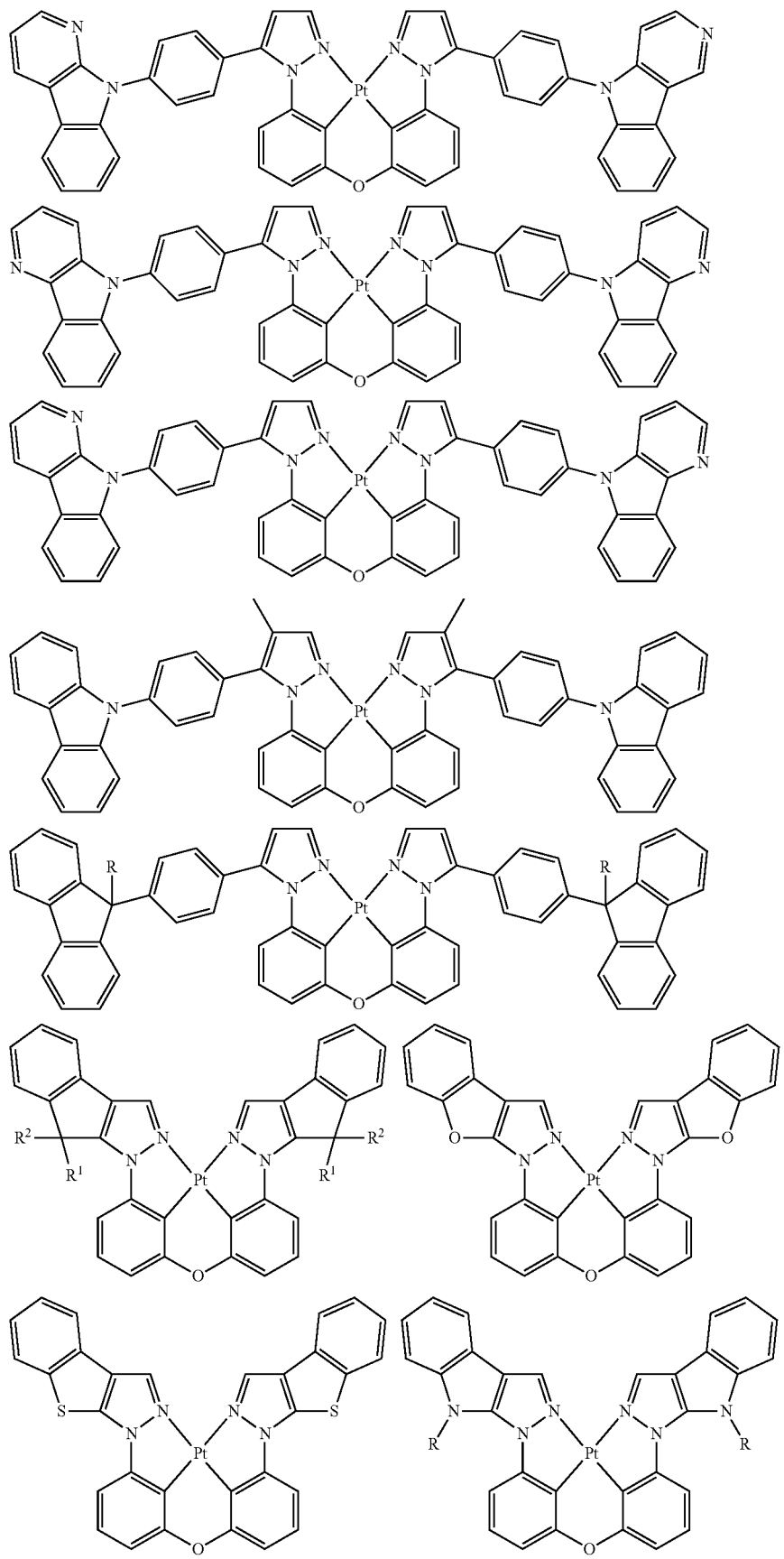

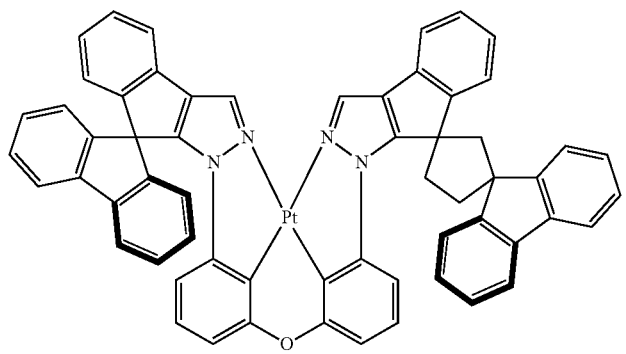
Structure 20
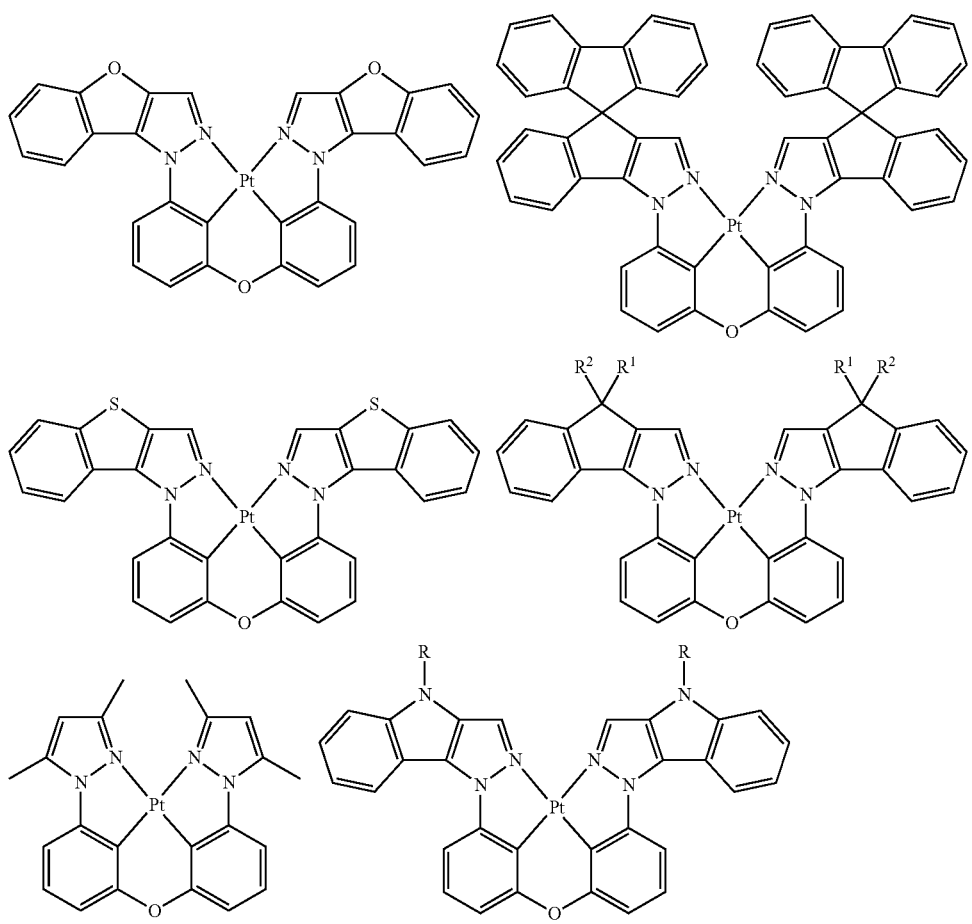
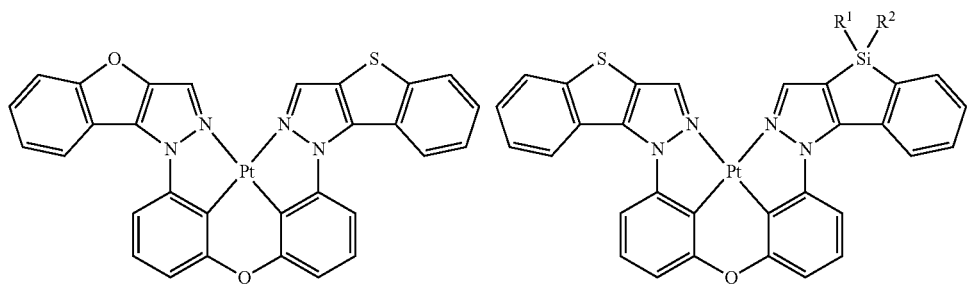

-continued
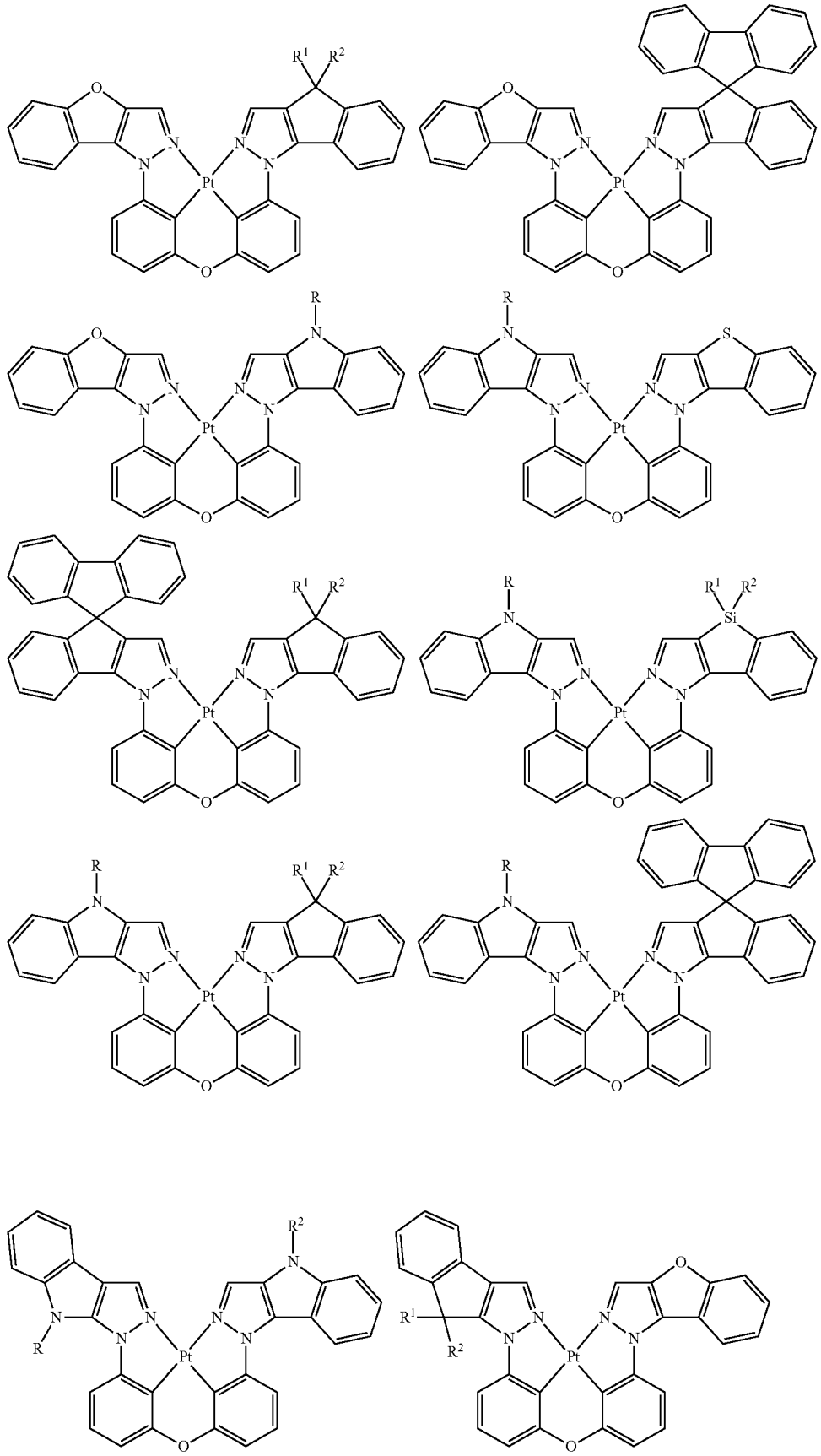

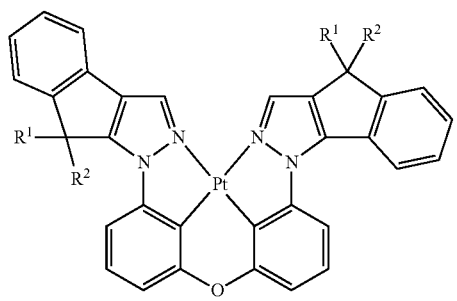
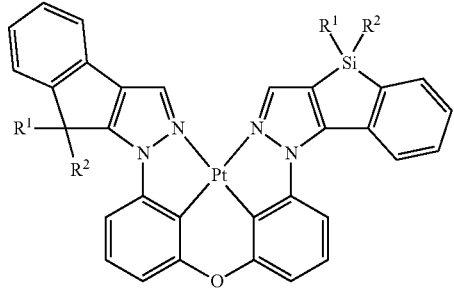
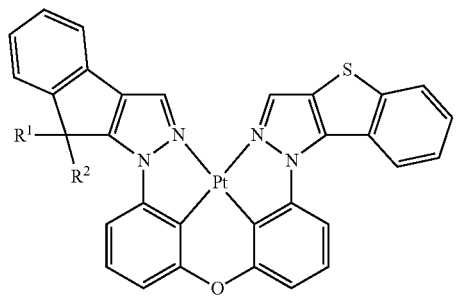
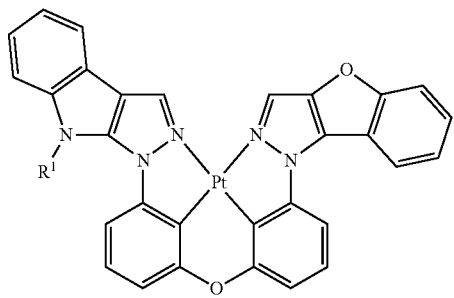
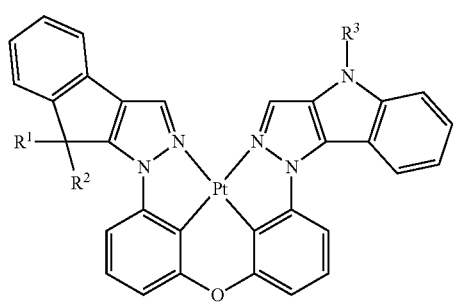
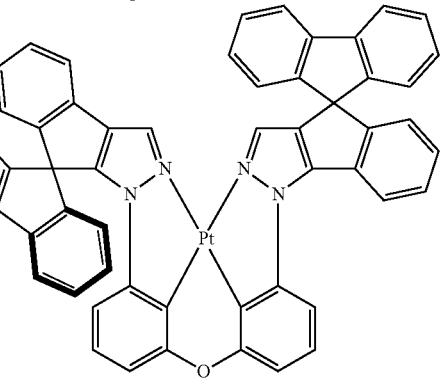
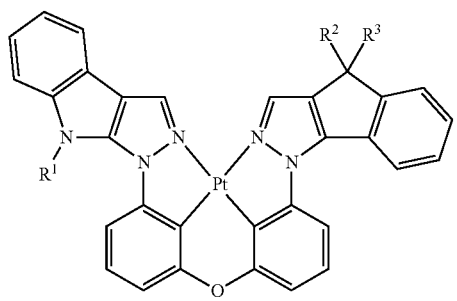
Structures 21
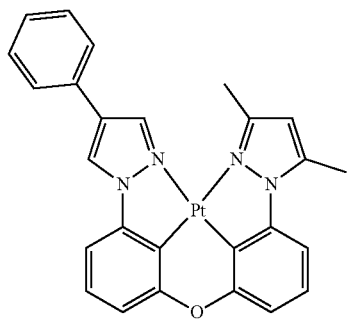
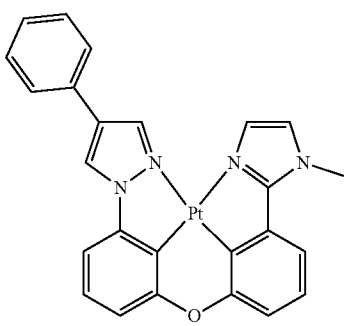

199
-continued
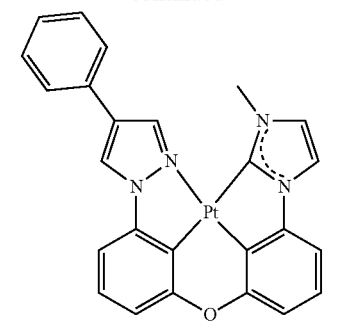
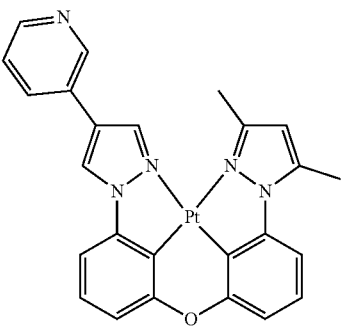
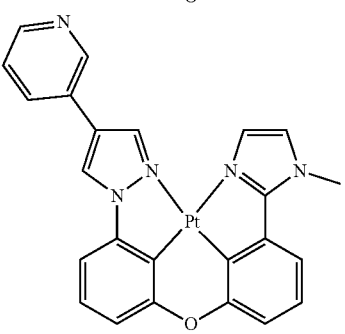
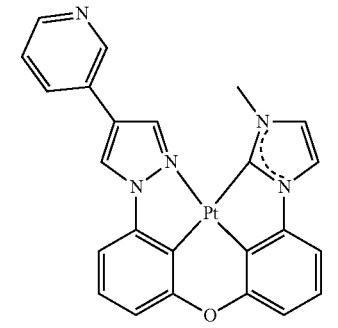
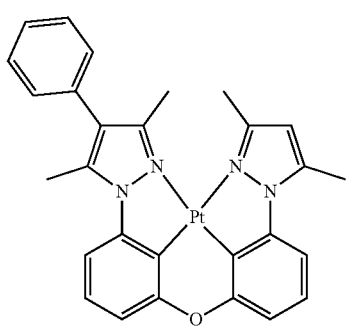
200
-continued
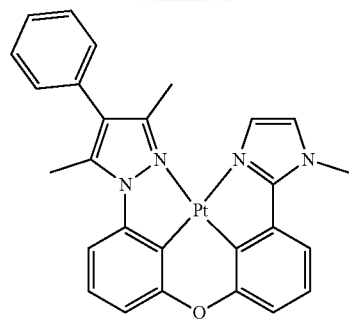
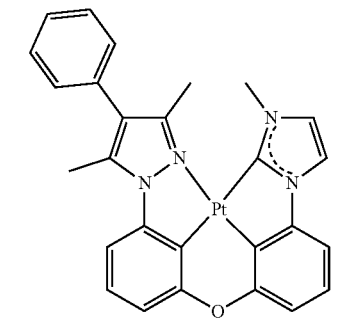
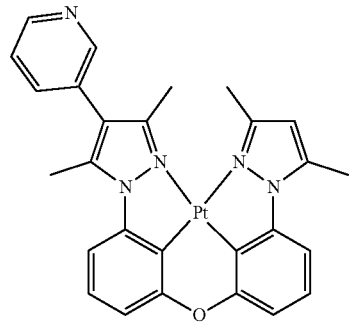
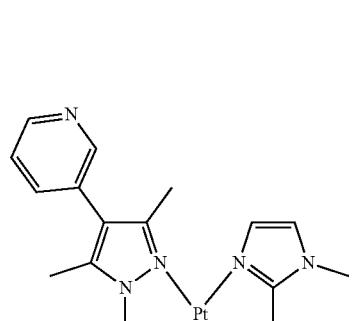
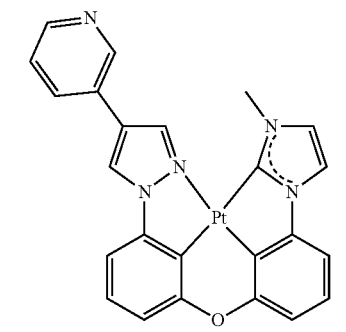

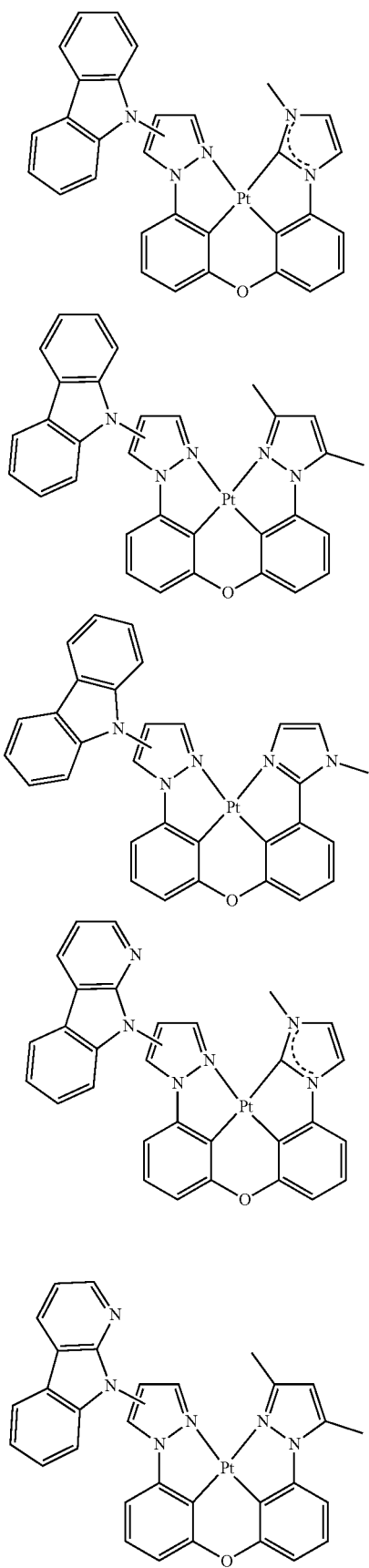
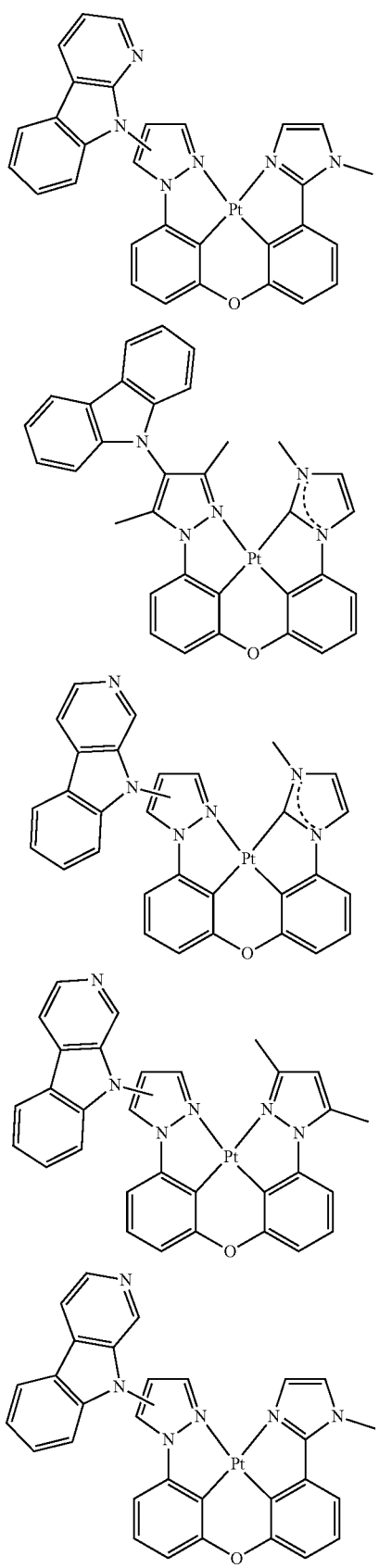

203
-continued
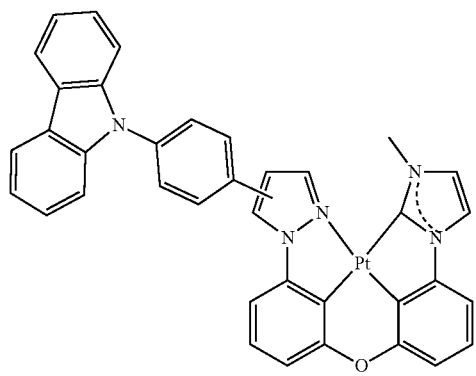
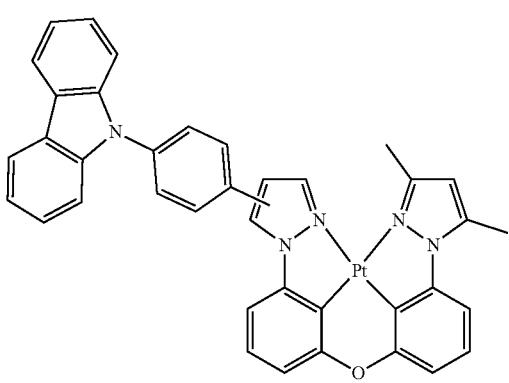
204
-continued
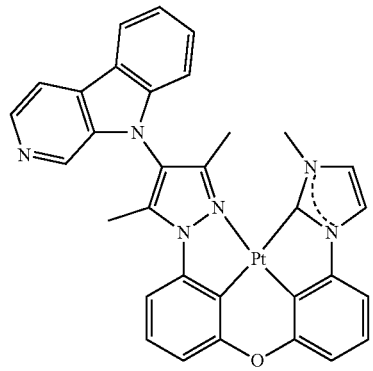
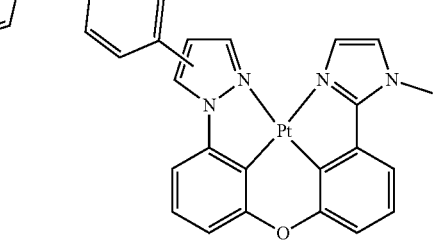
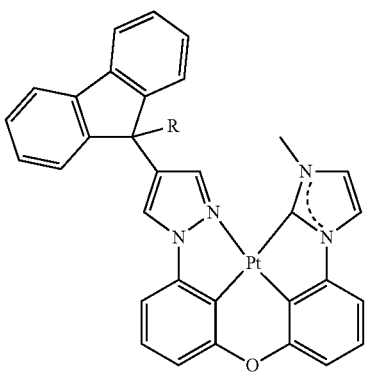
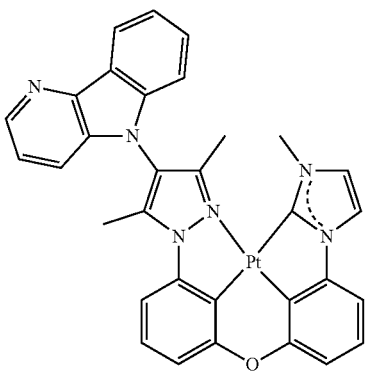

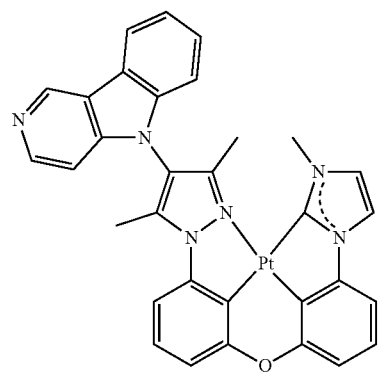
Structures 22
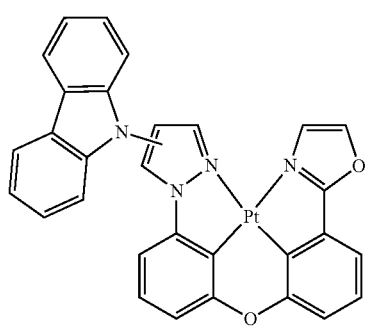
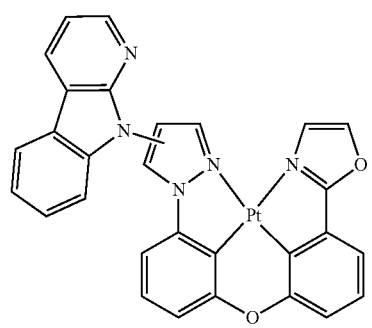
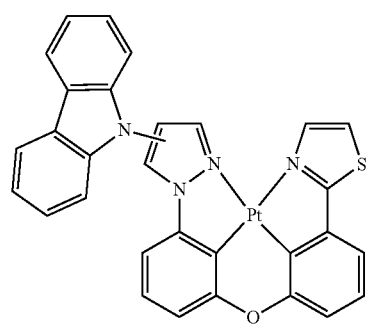
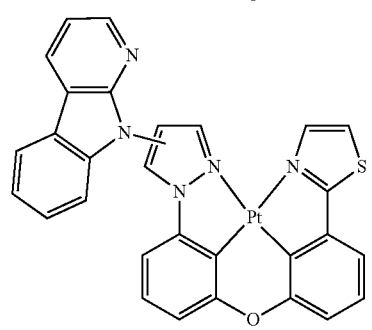
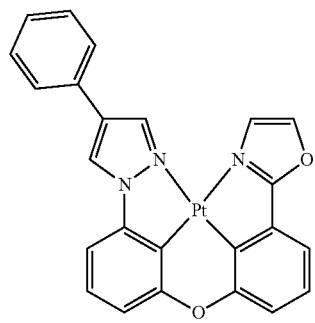
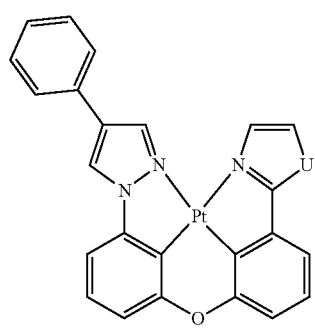
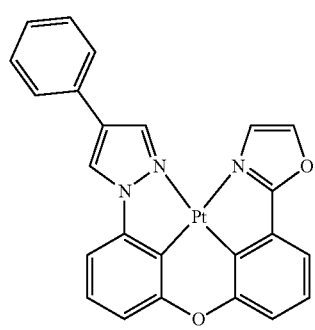
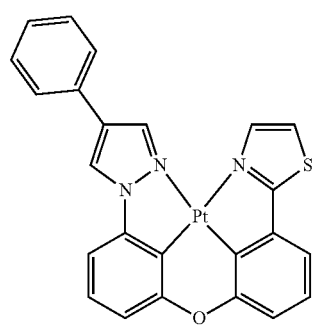
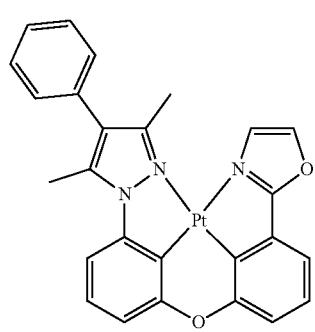

207
-continued
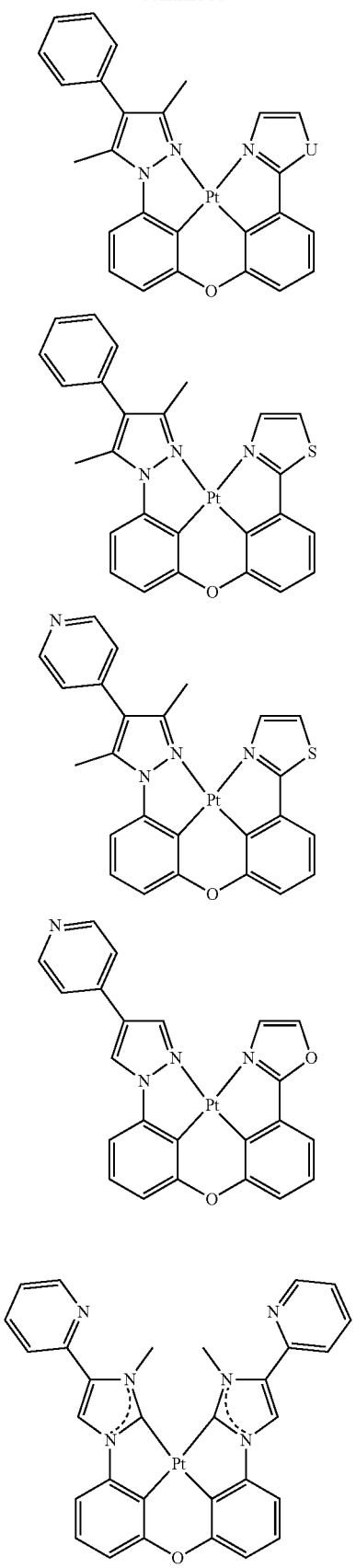
208
-continued
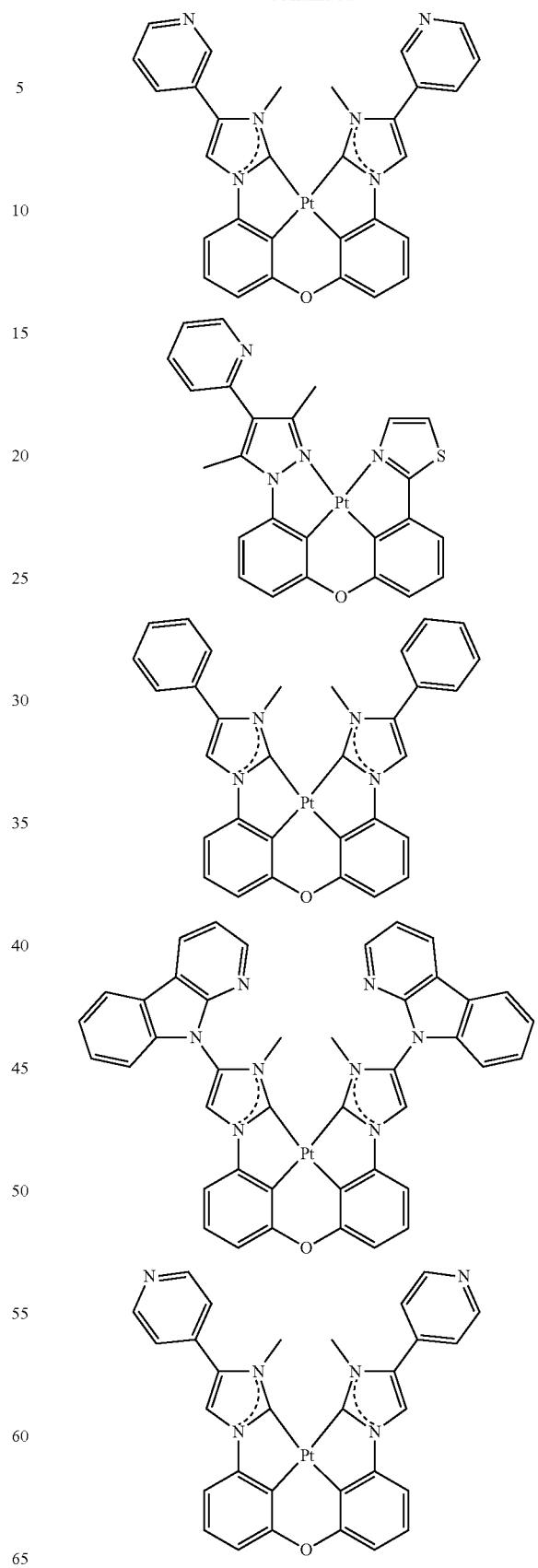

209
-continued
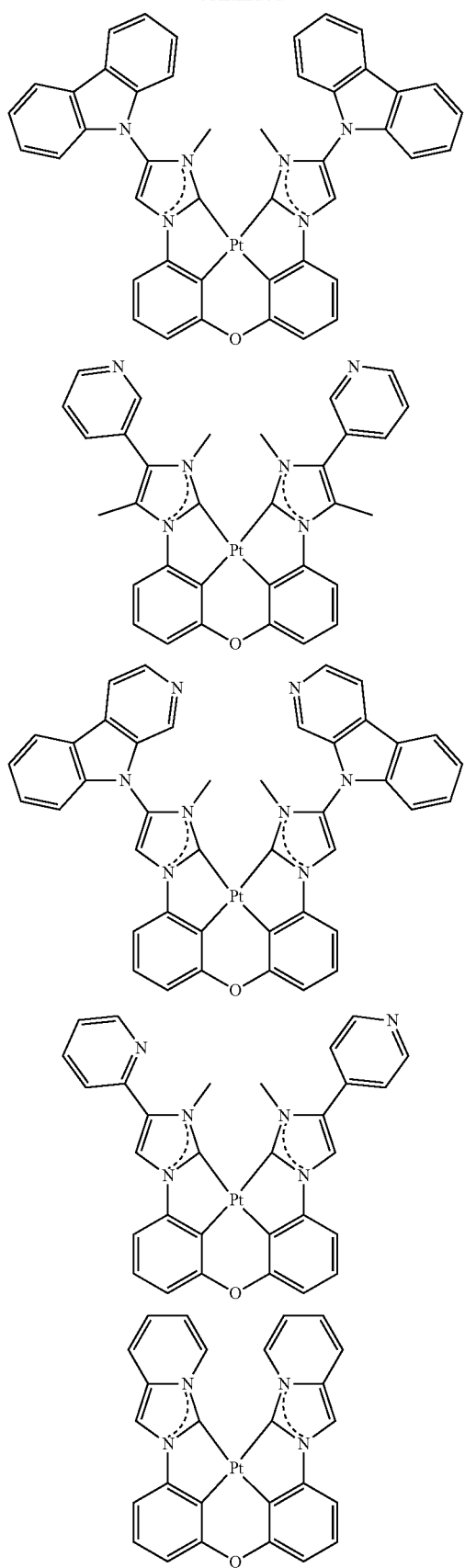
210
-continued
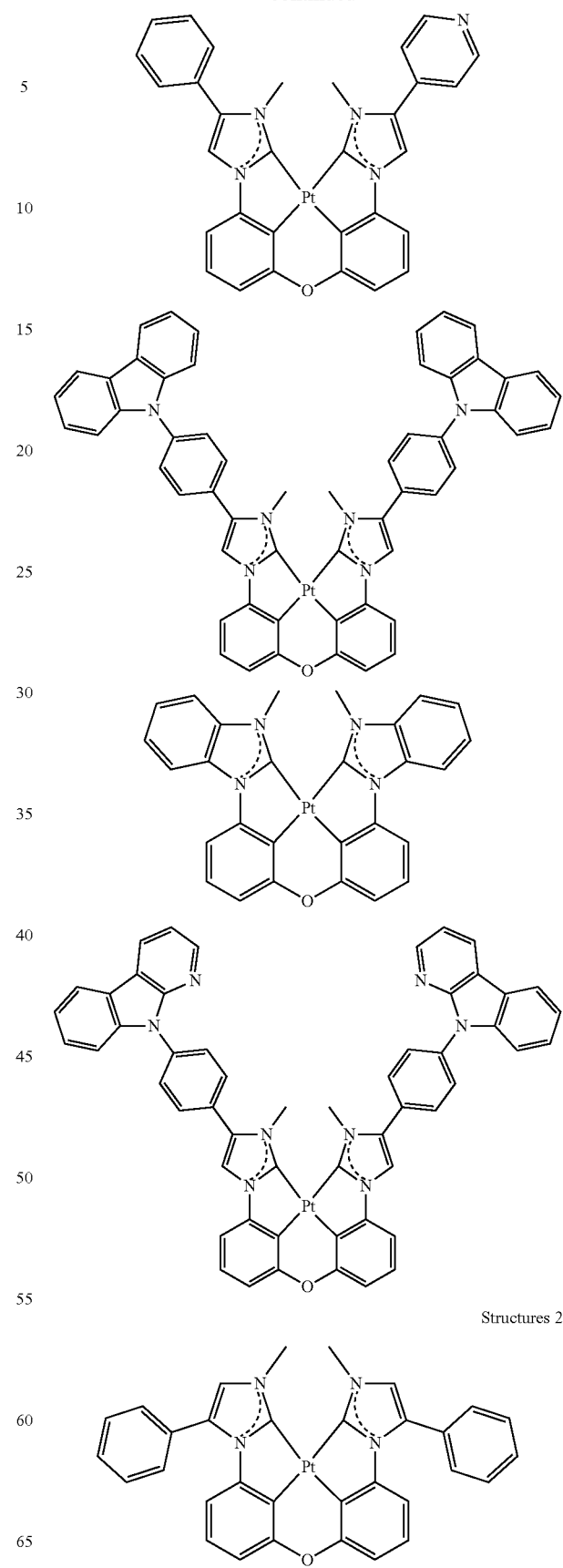
Structures 23

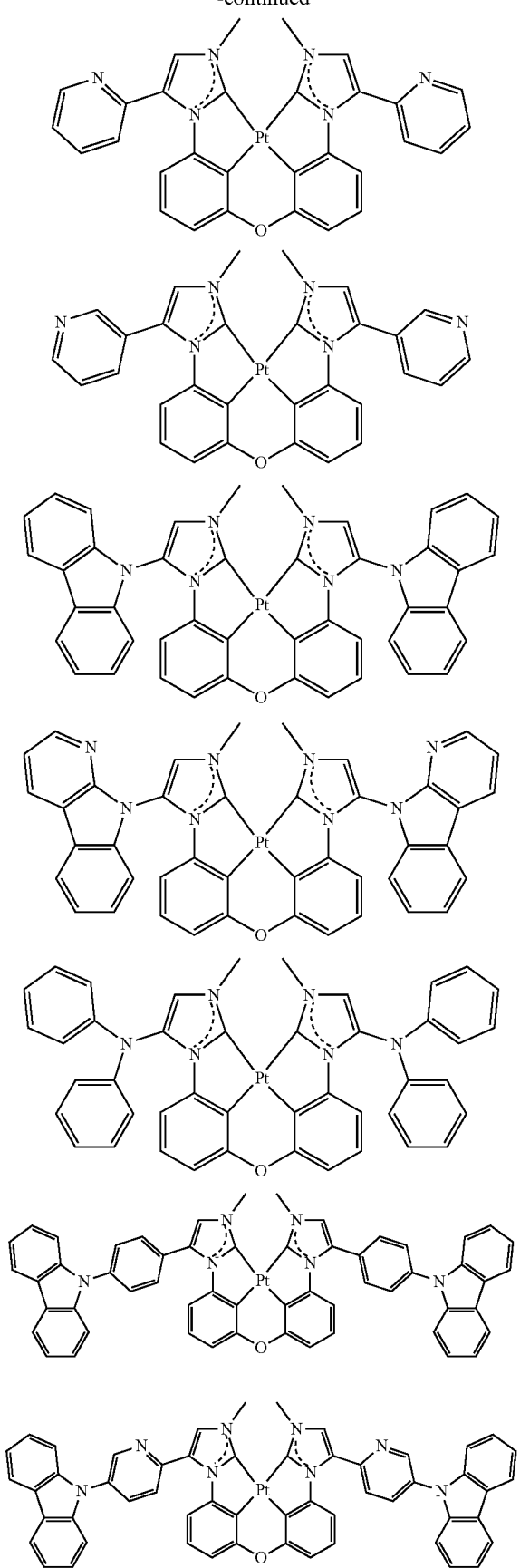
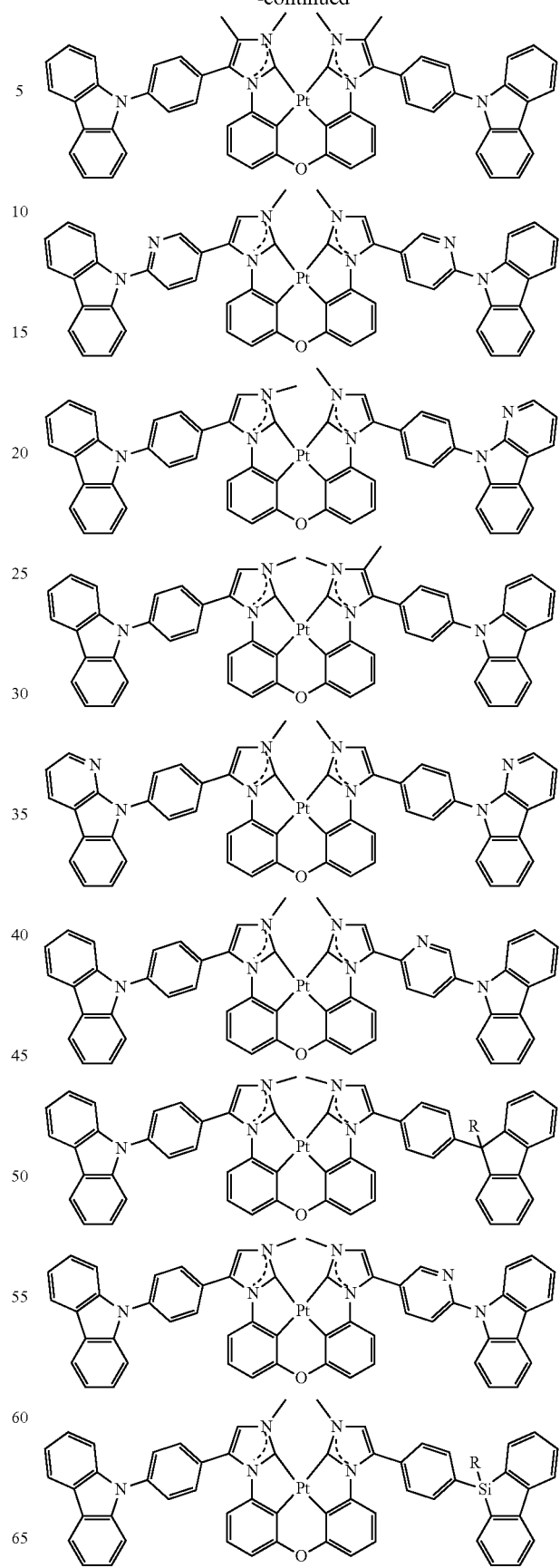

213
-continued
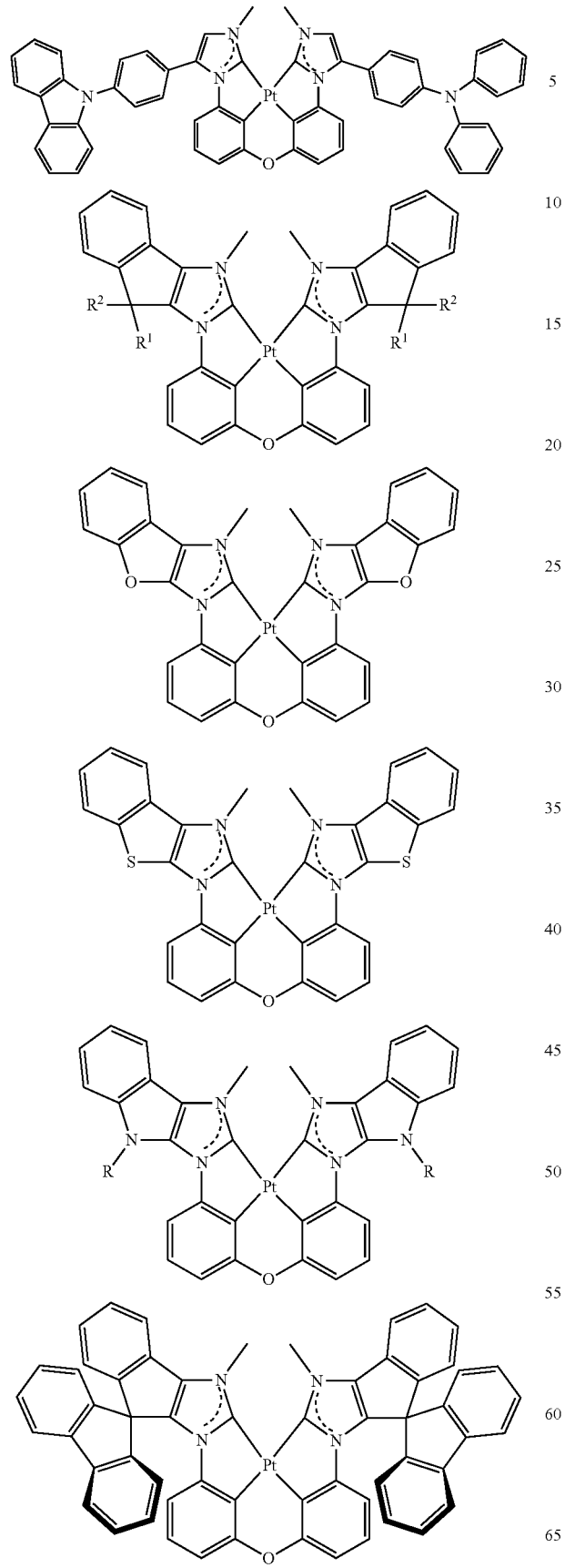
214
-continued
Structures 24
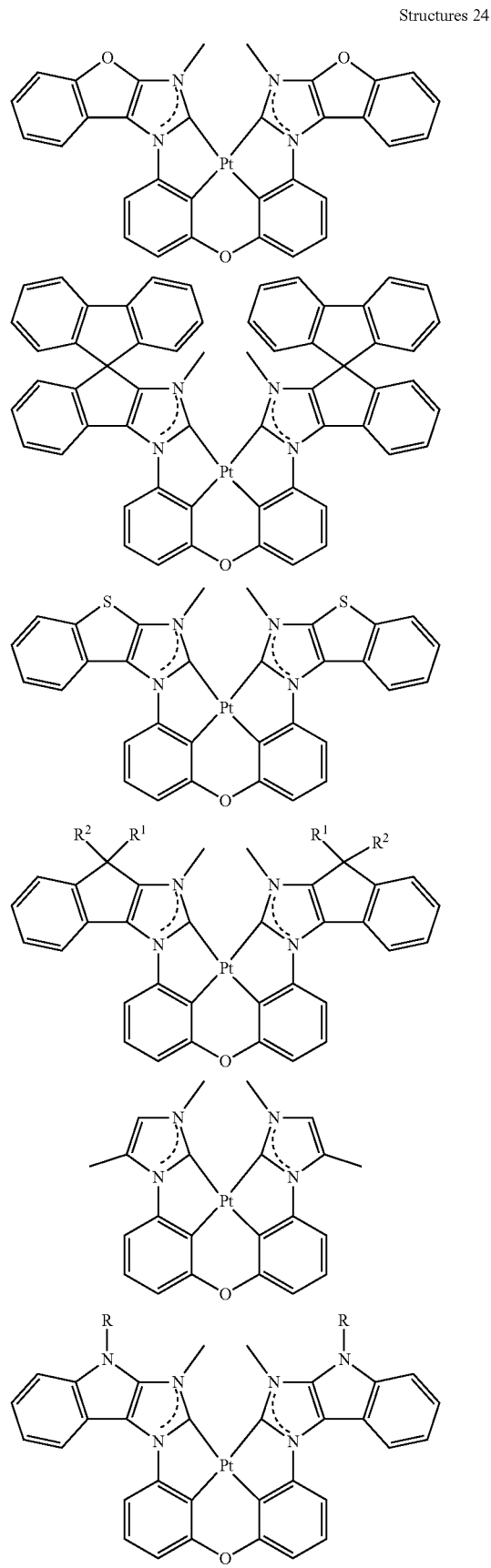

215
-continued
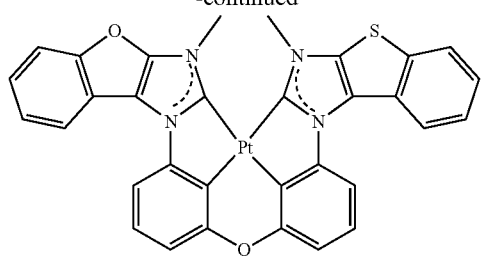
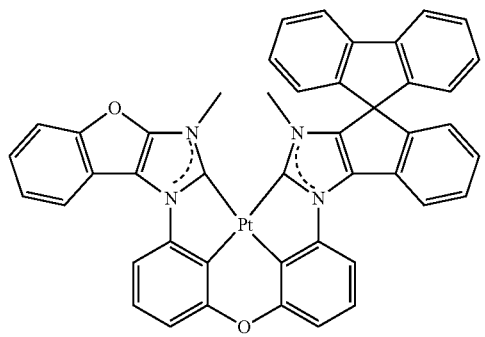
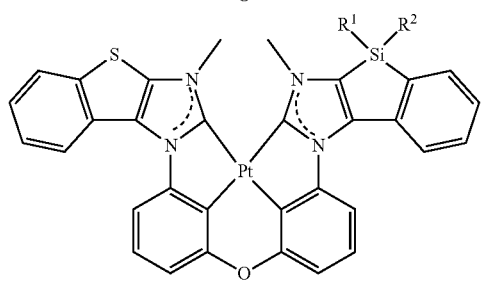
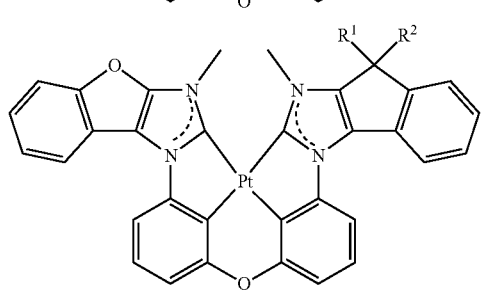
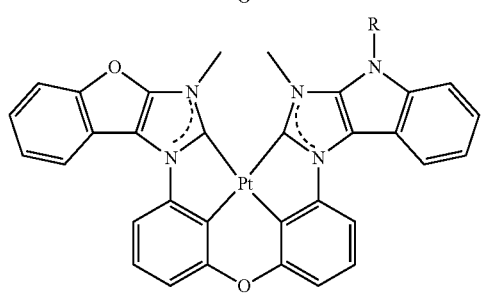
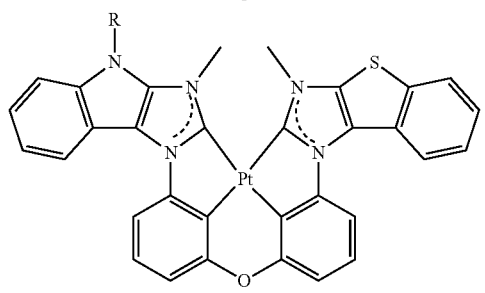
216
-continued
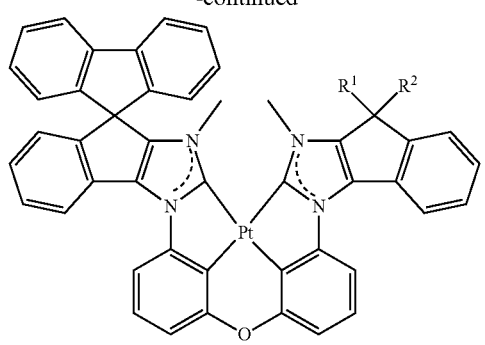
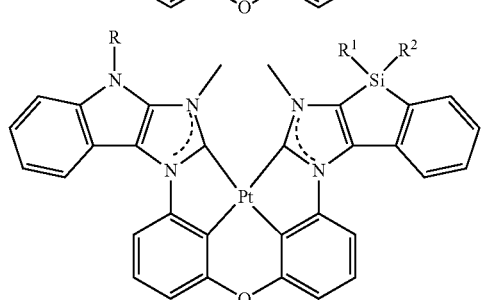
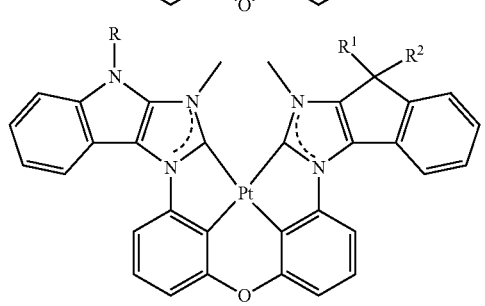
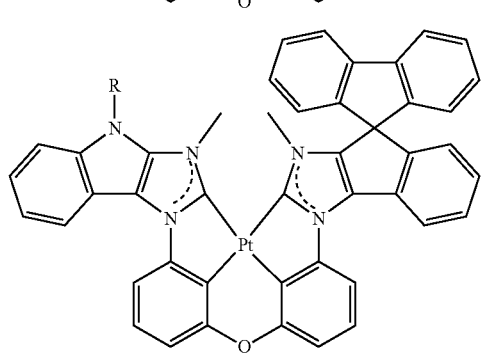
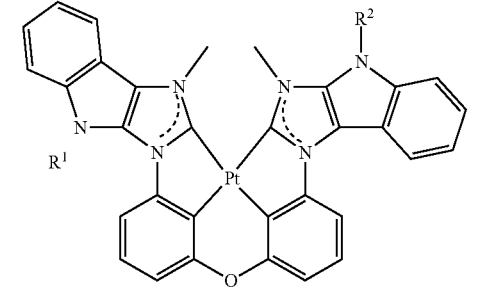

217
-continued
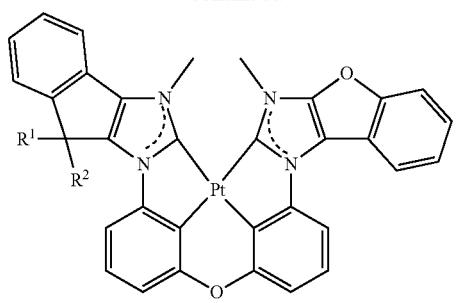
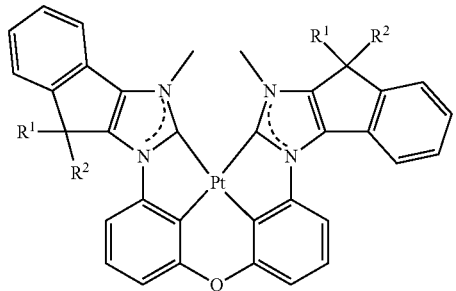
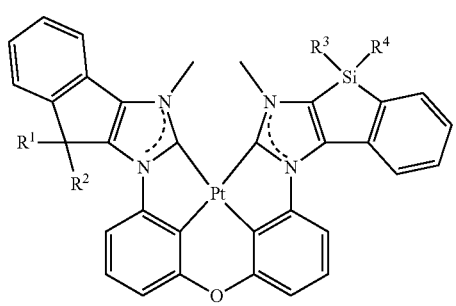
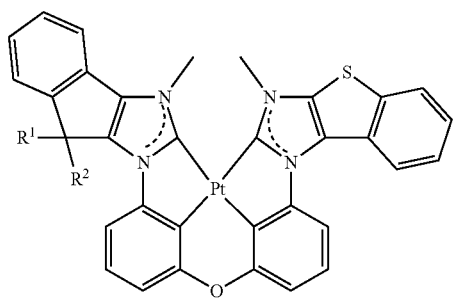
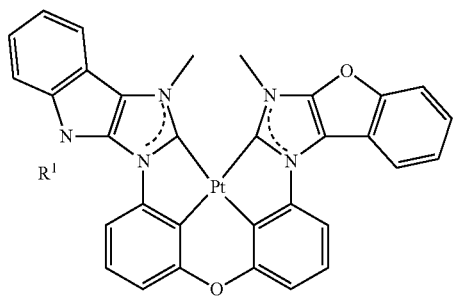
218
-continued
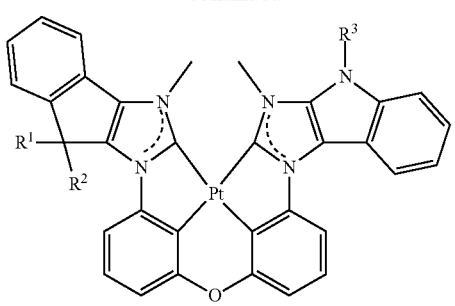
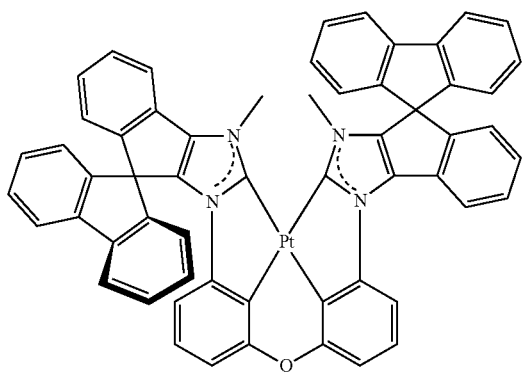
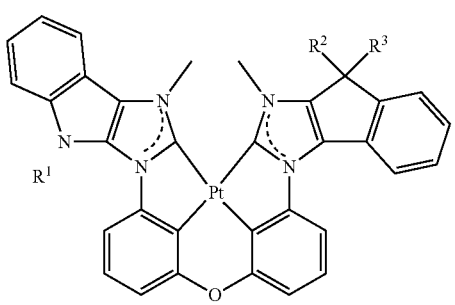
Structures 25
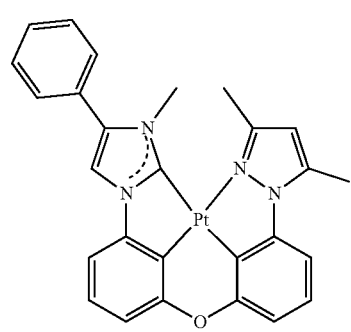
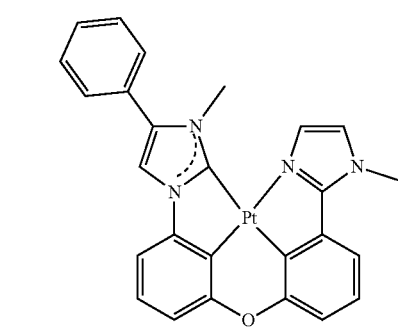

219
-continued
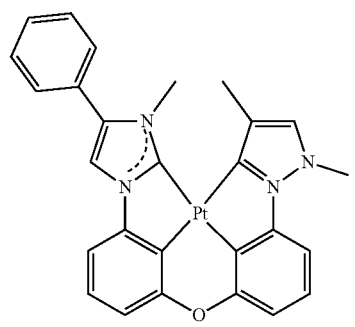
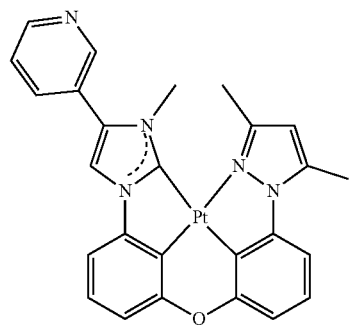
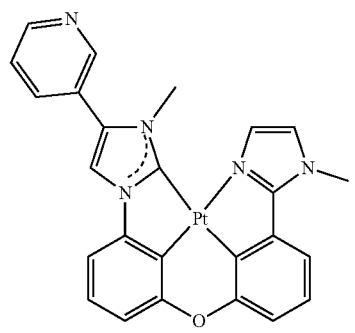
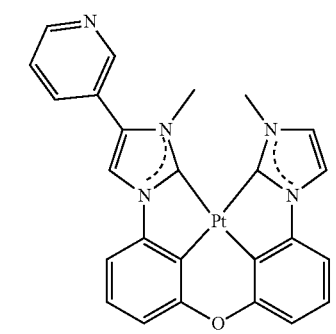
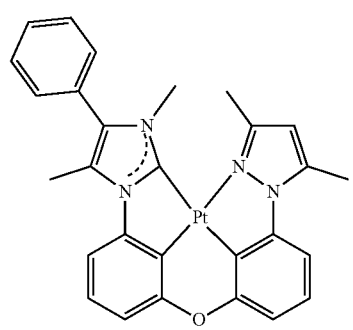
220
-continued
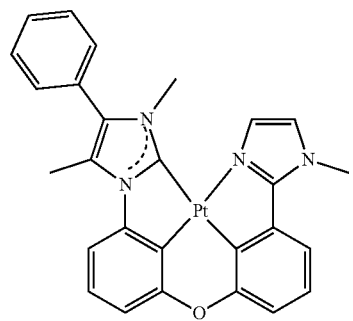
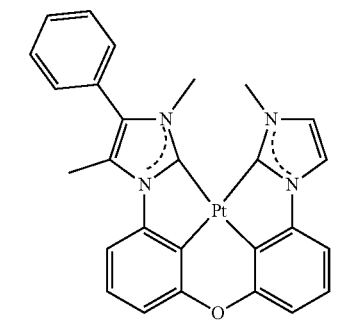
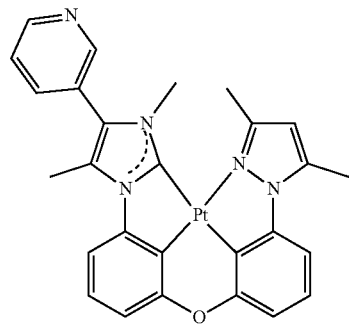
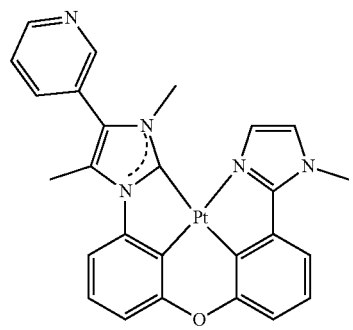
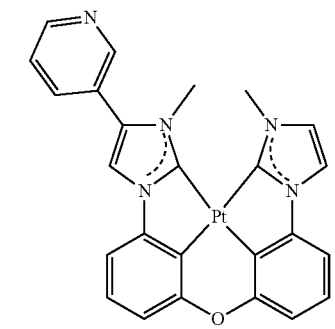

221
-continued
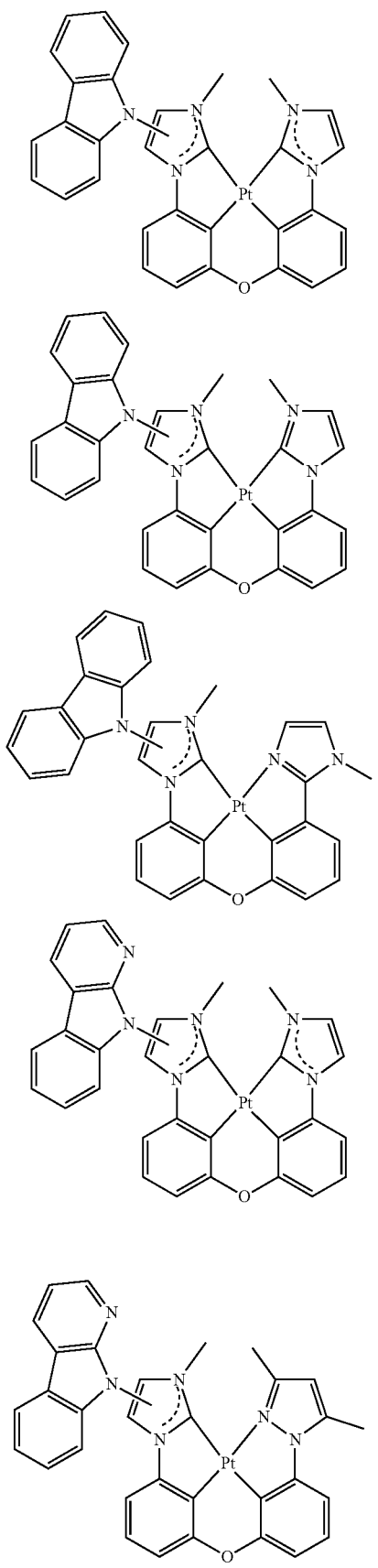
222
-continued
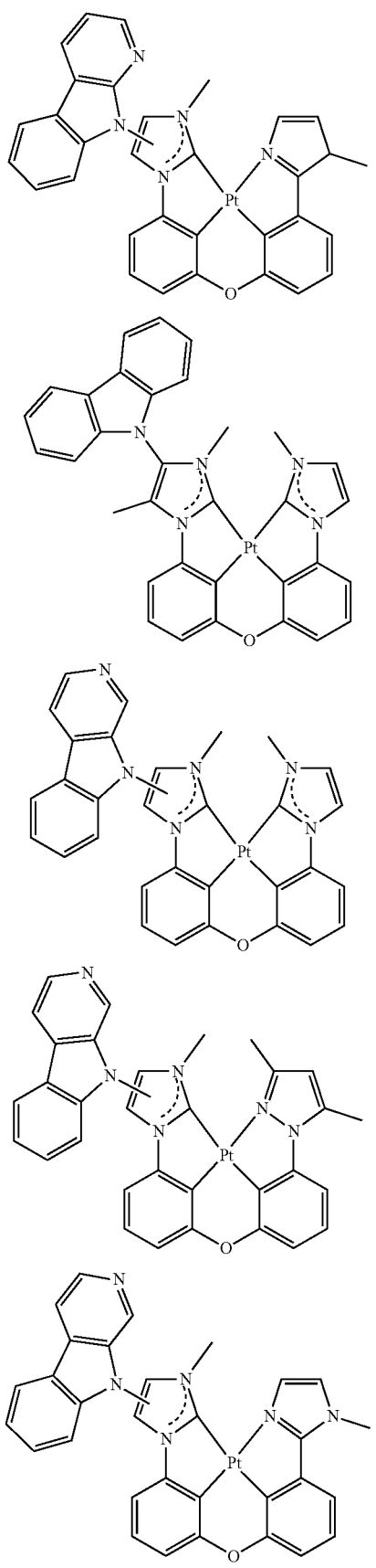

223
-continued
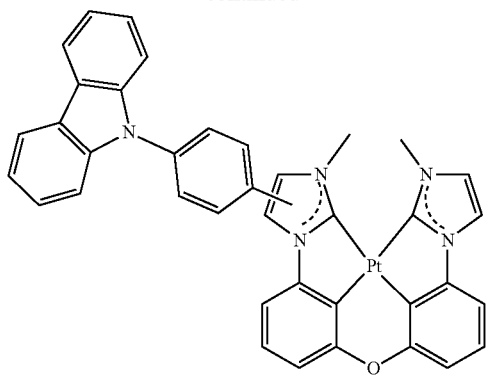
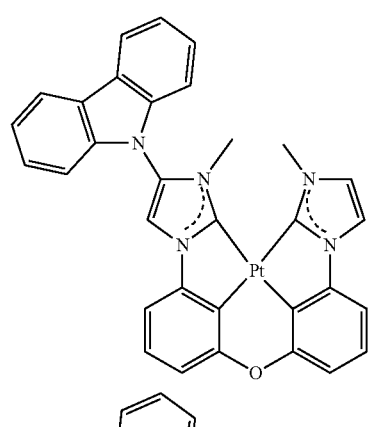
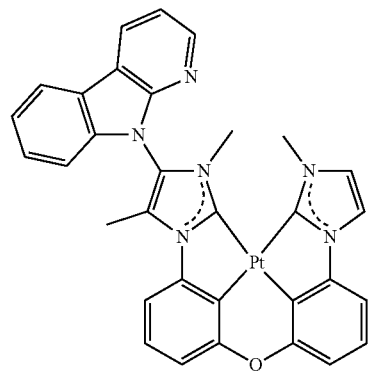
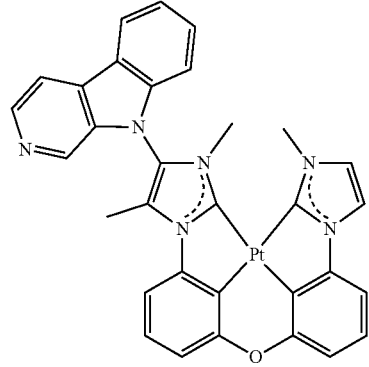
224
-continued
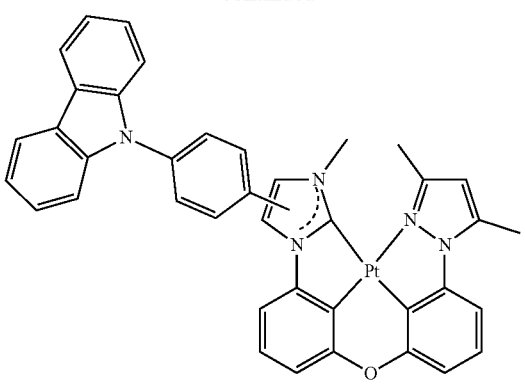
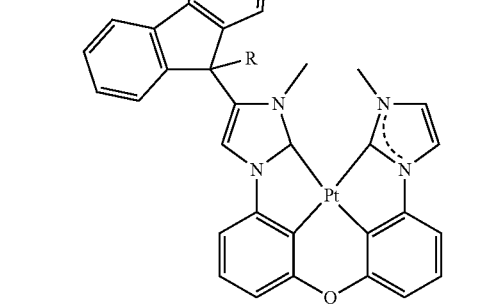

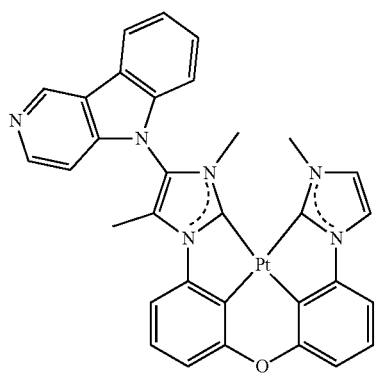
Structure 26
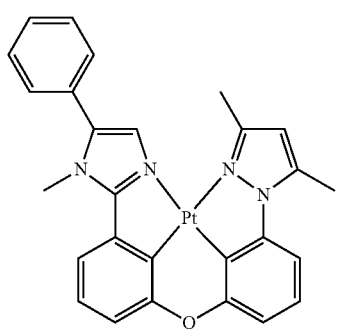
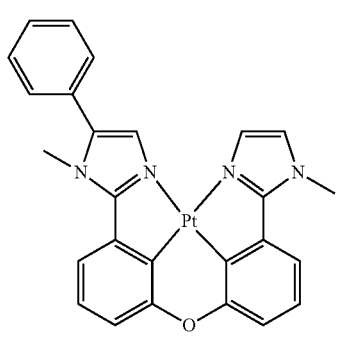
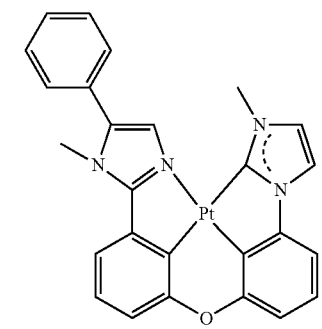
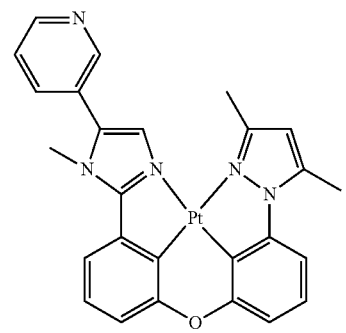
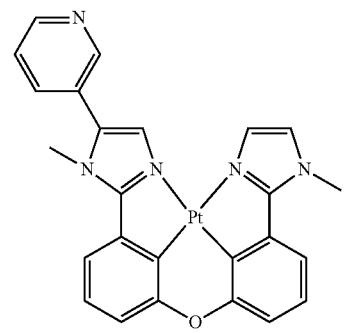
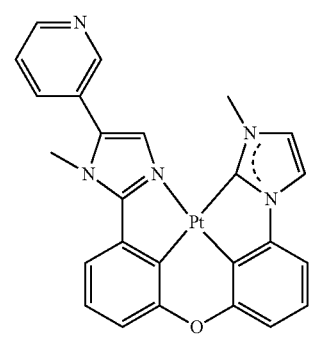
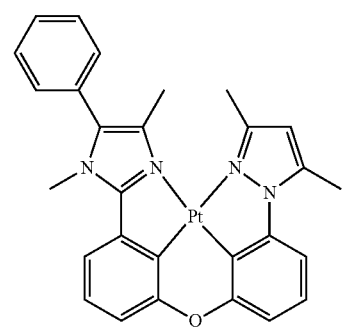
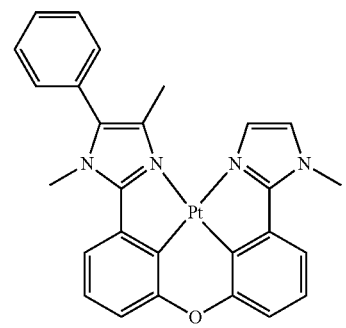

227
-continued
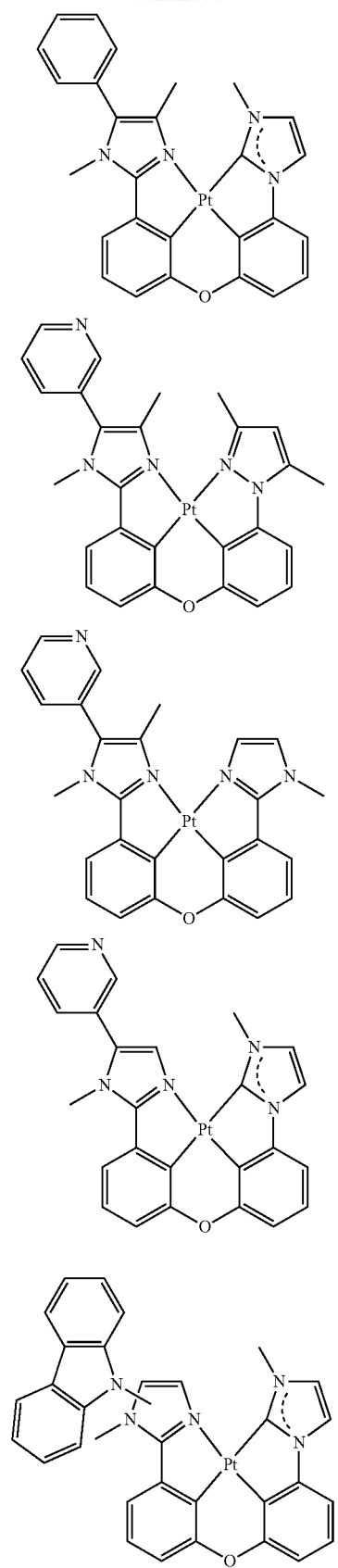
228
-continued
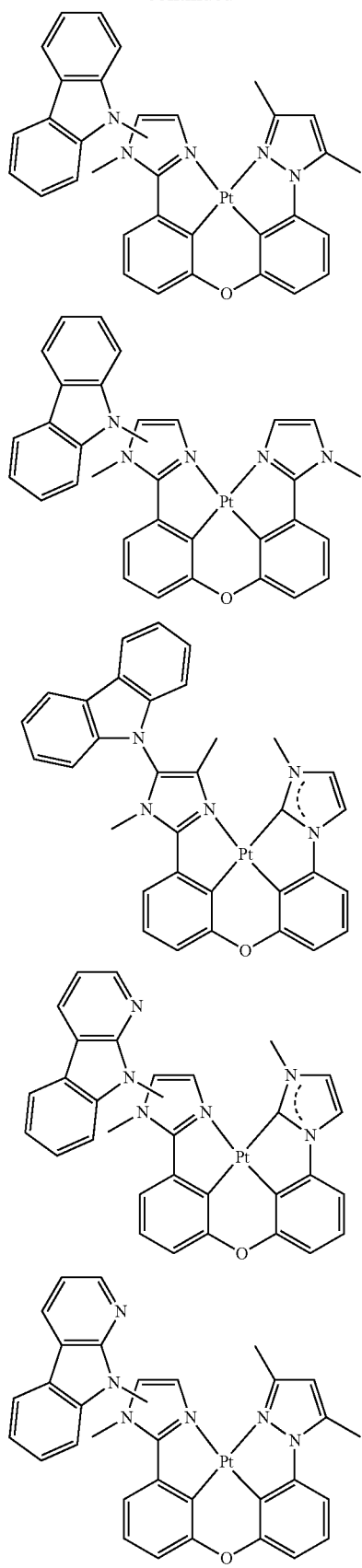

229
-continued
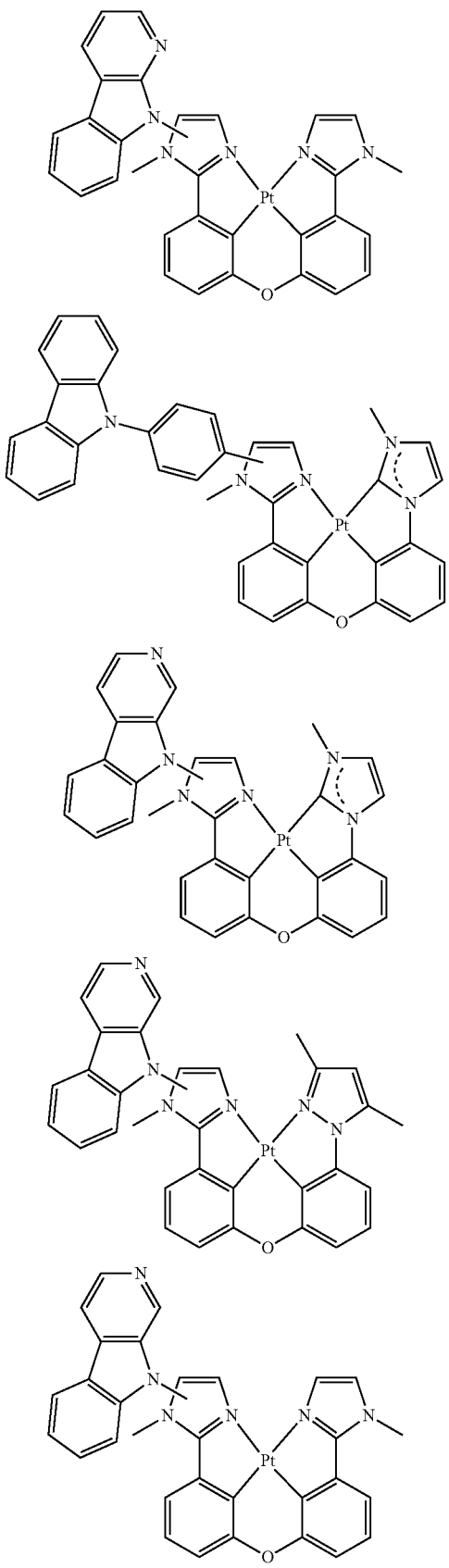
230
-continued
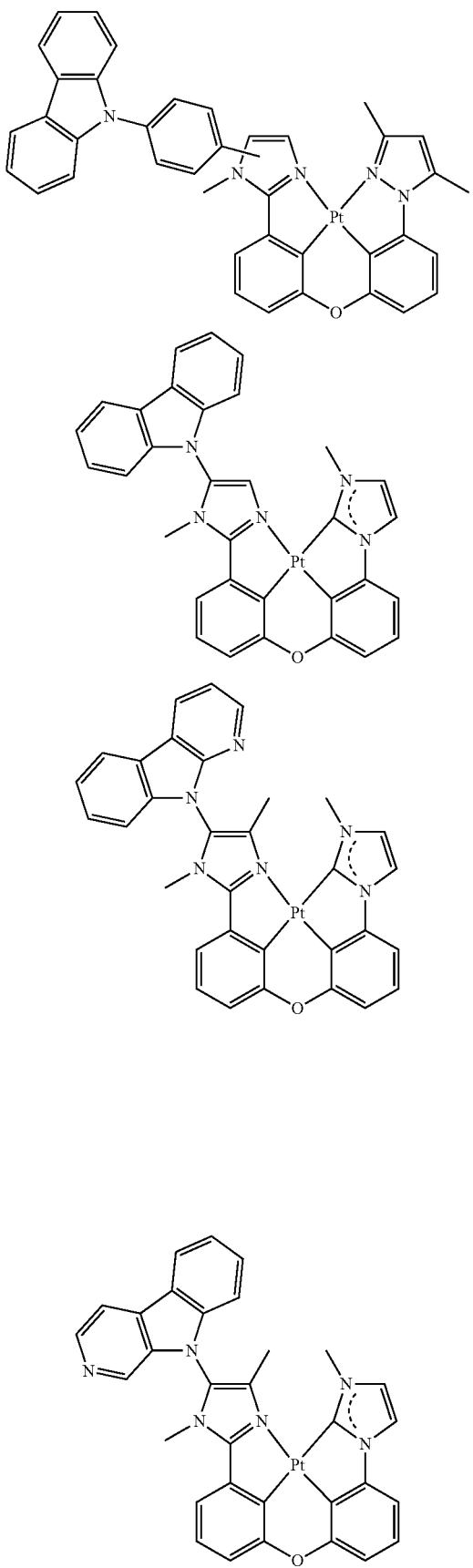

Structure 27
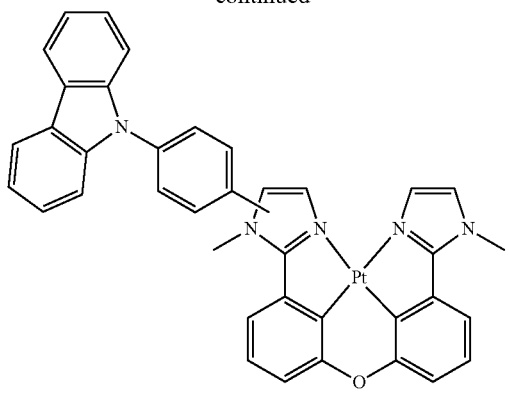
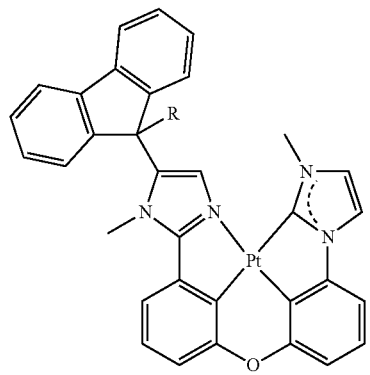
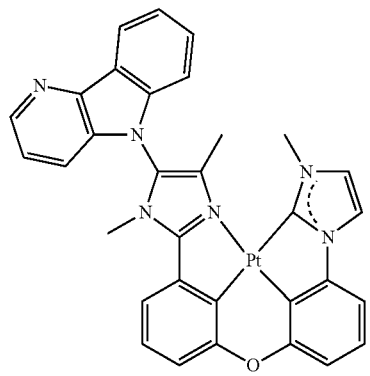
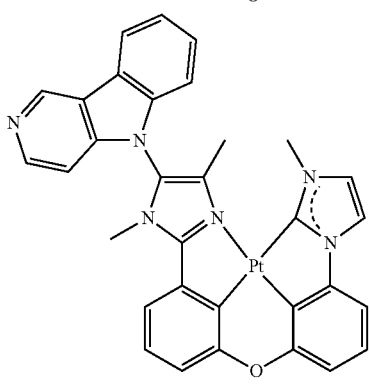
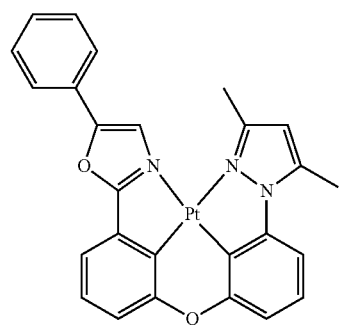
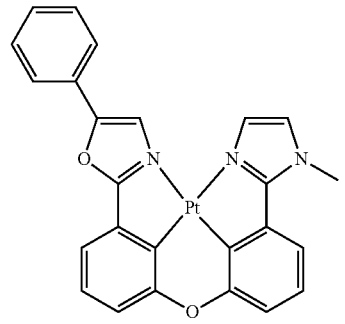
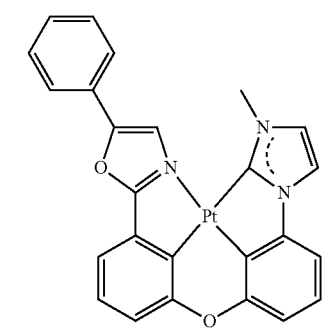
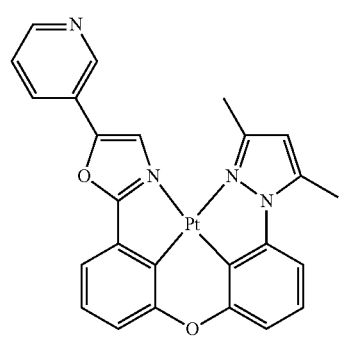
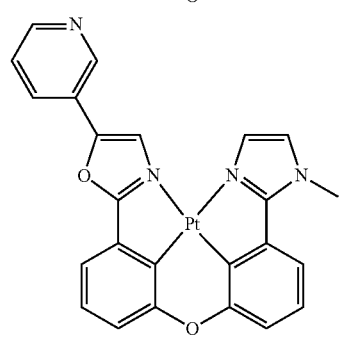

233
-continued
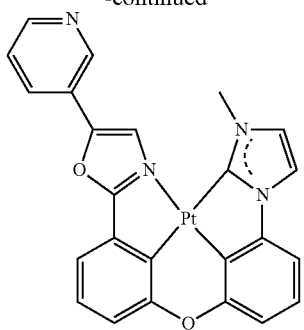
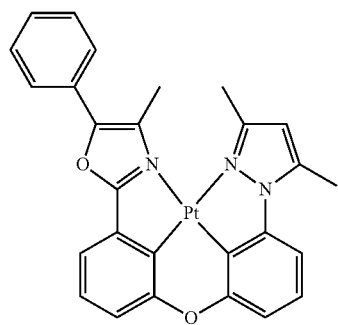
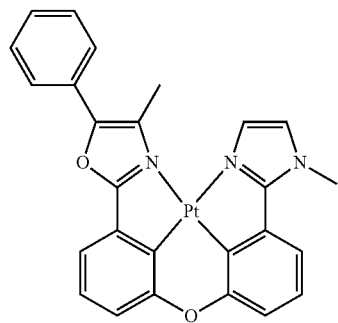
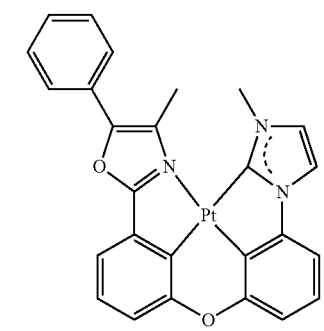
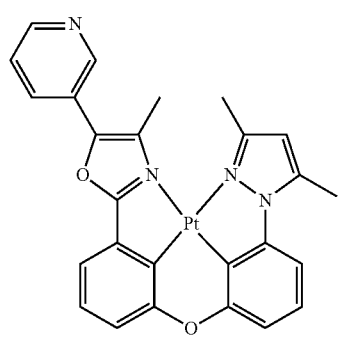
234
-continued
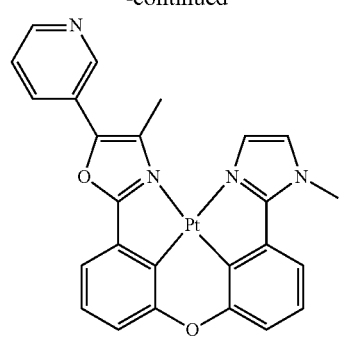
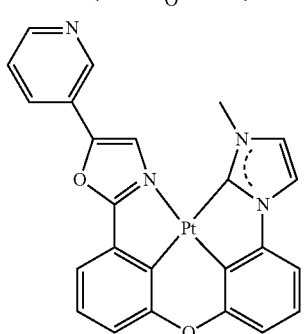
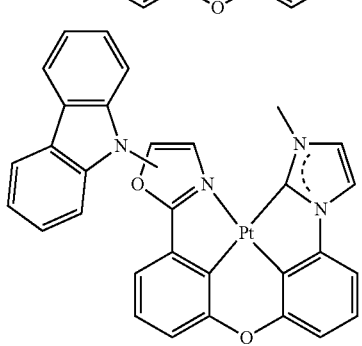
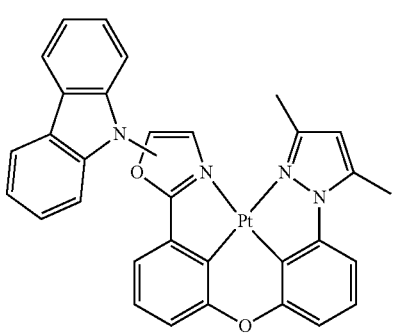
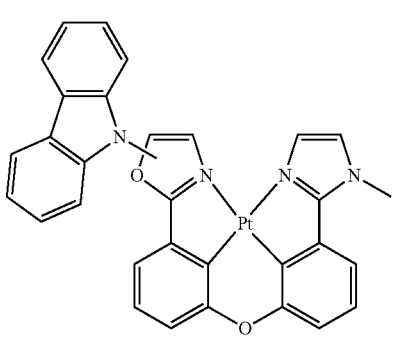

235
236
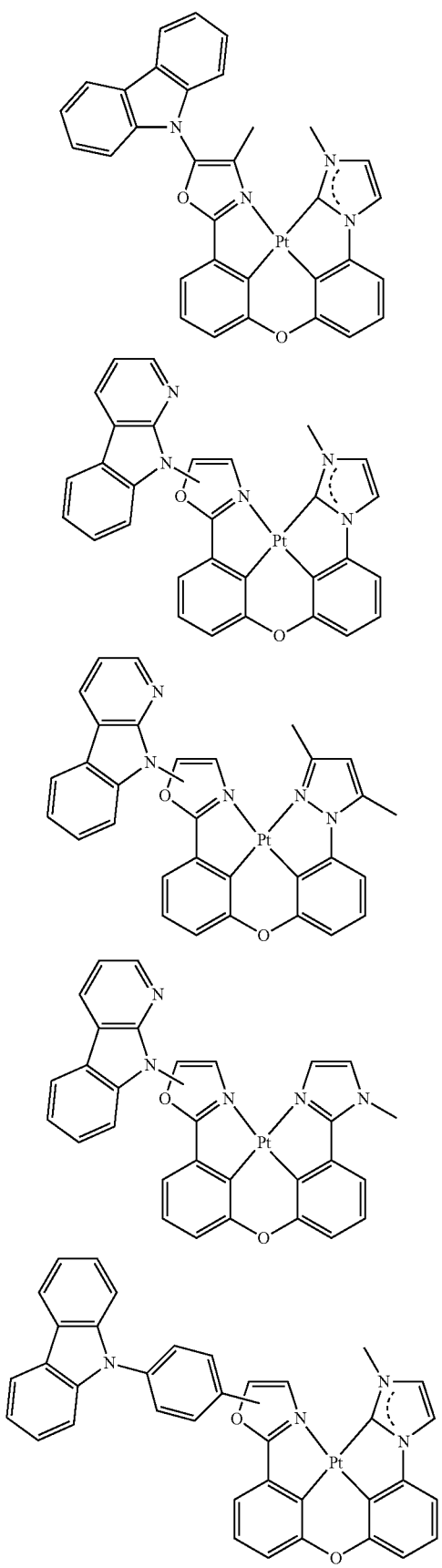
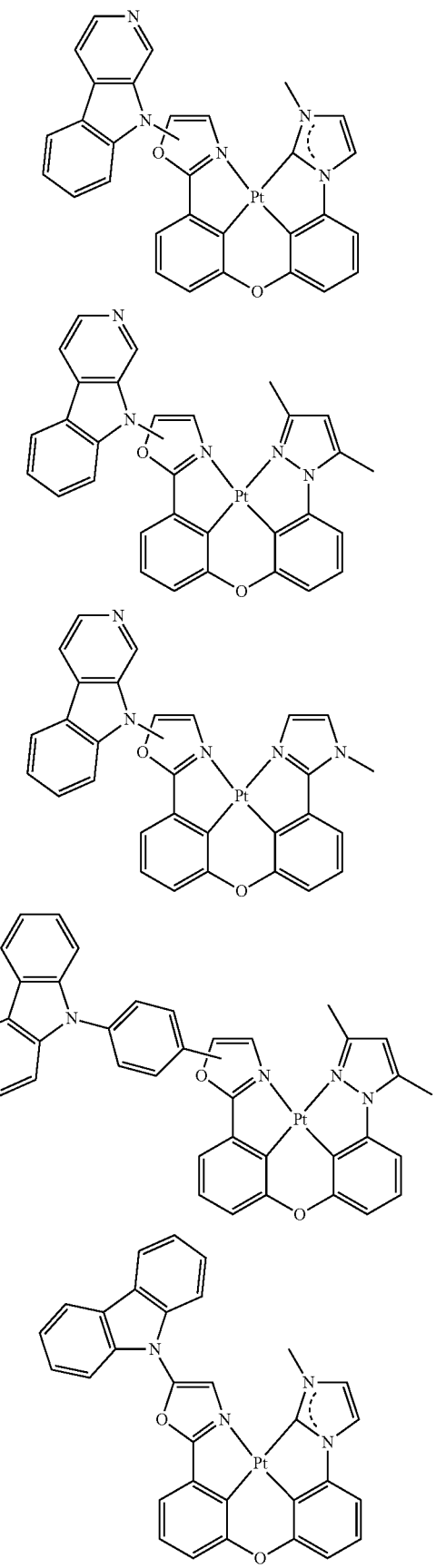

237
-continued
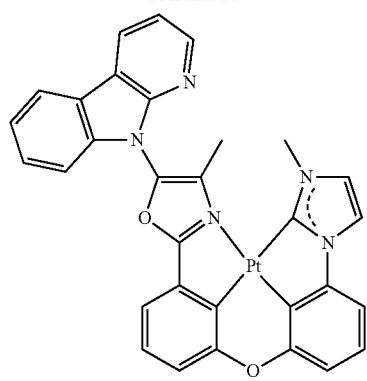
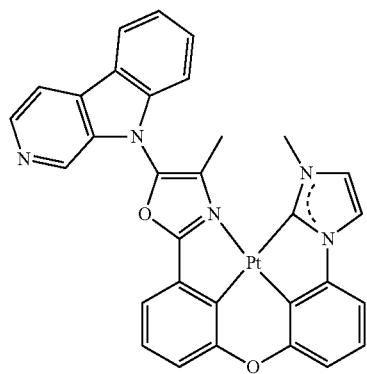
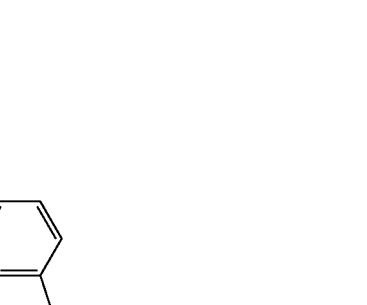
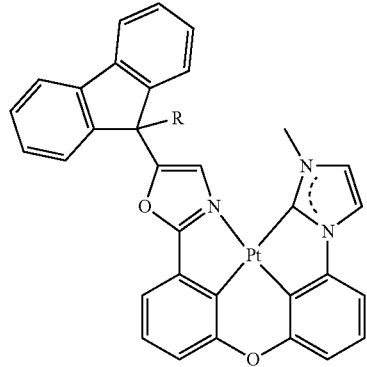
238
-continued
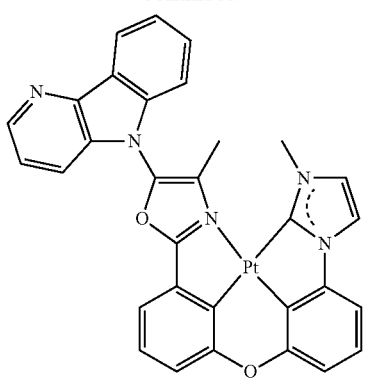
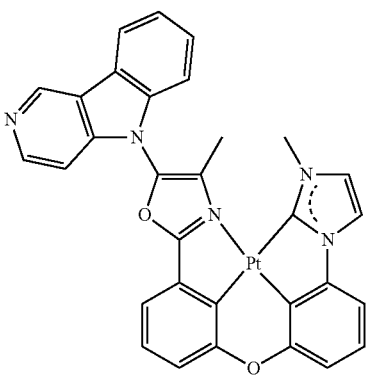
Structures 28
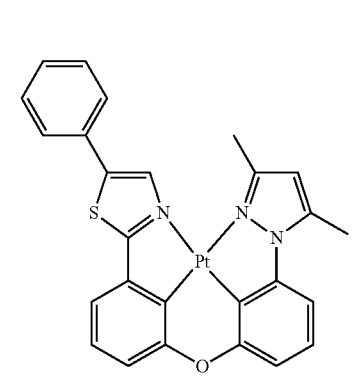
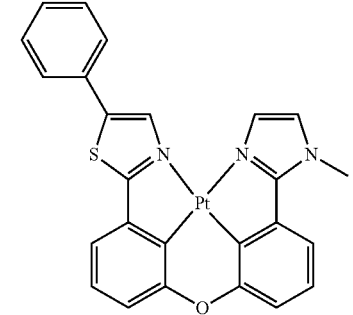

239
-continued
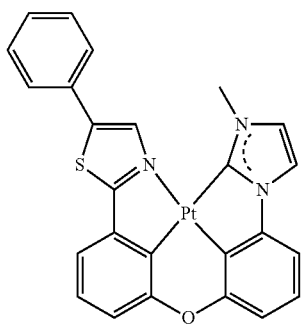
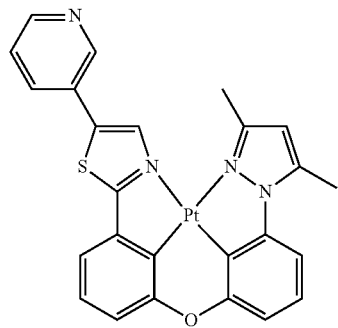
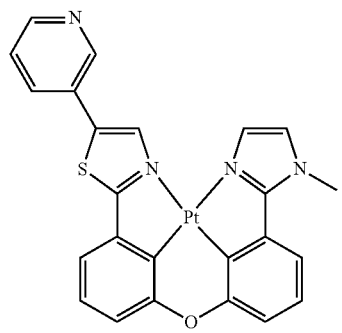
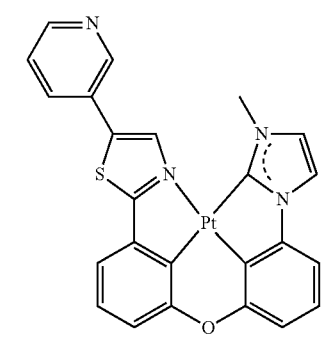
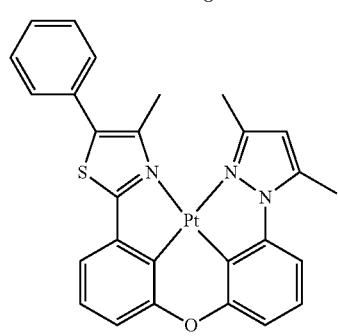
240
-continued
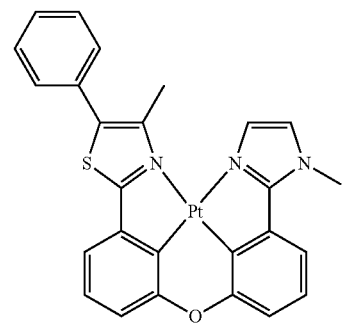
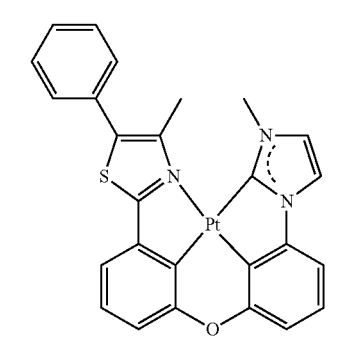
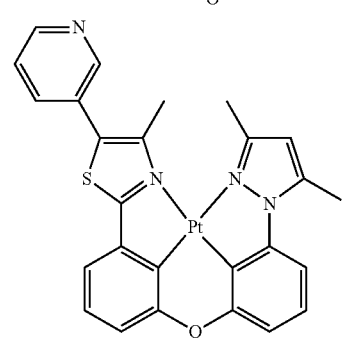
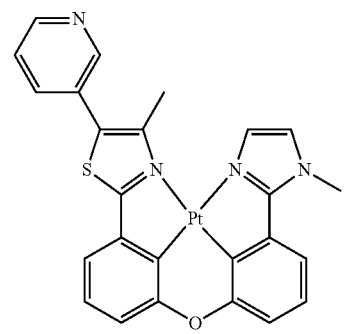
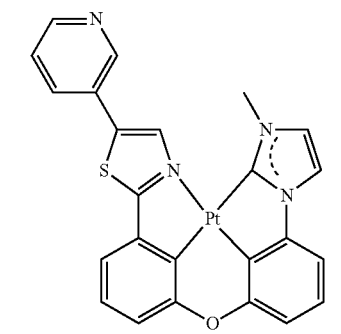

241
-continued
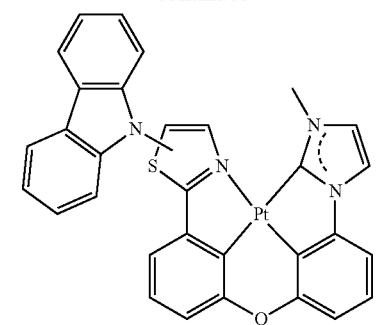
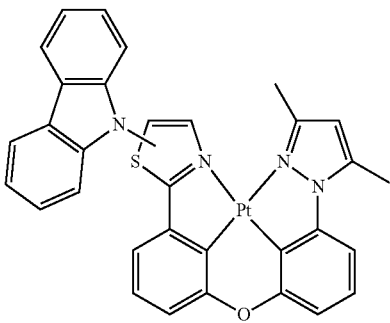
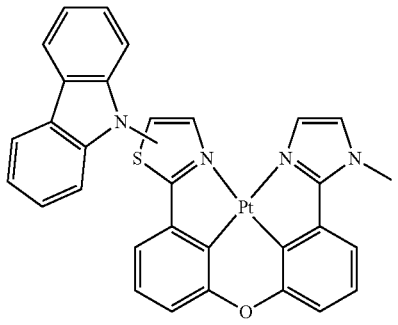
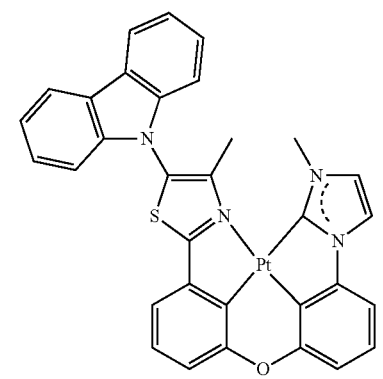
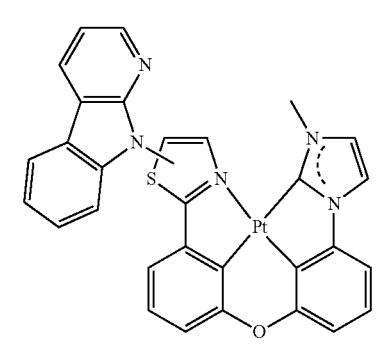
242
-continued
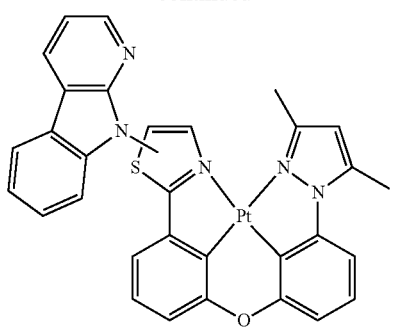
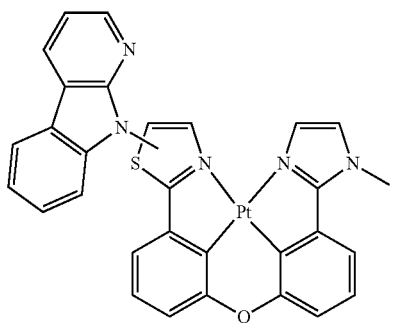
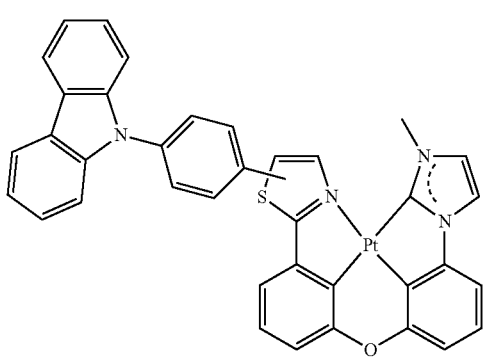
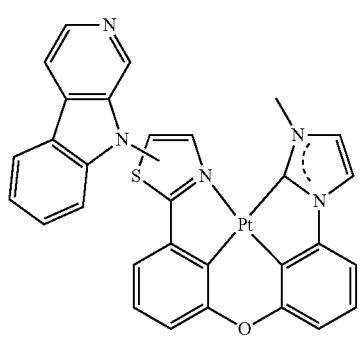
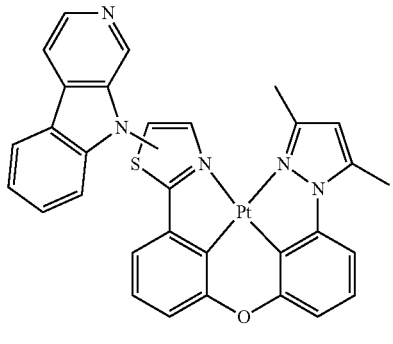

243
-continued
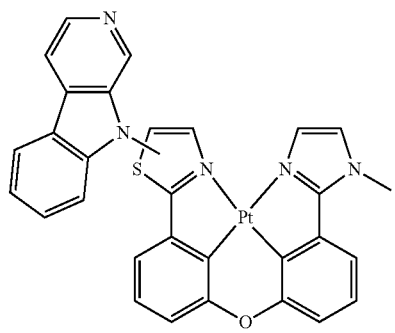
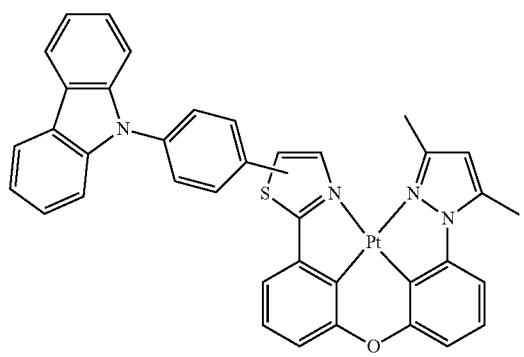
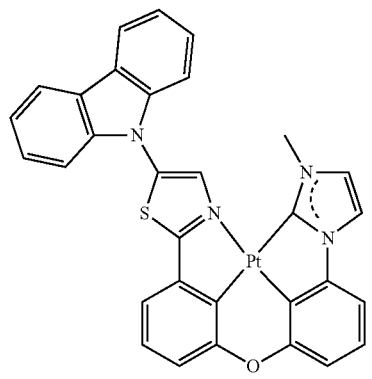
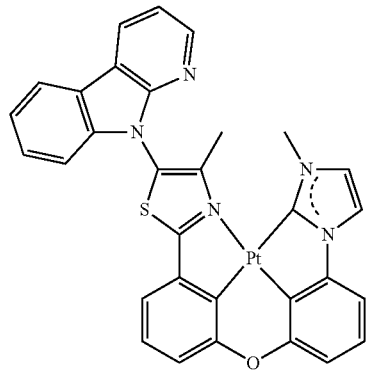
244
-continued
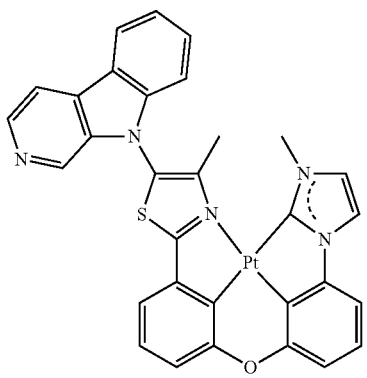
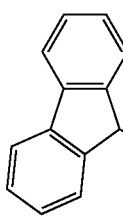
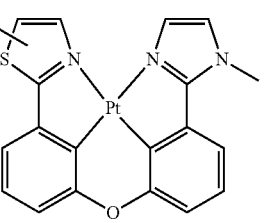
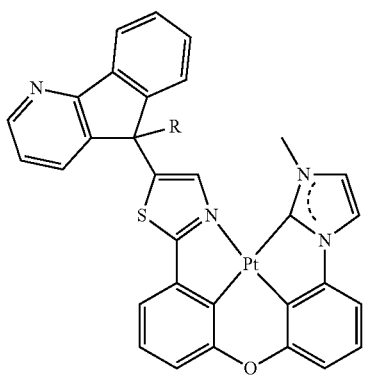
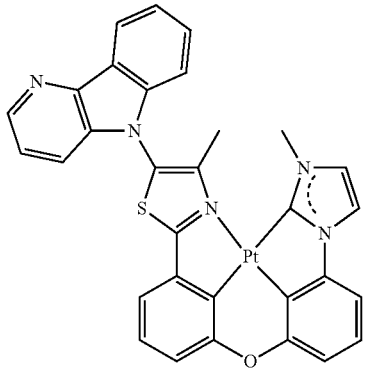

245
-continued
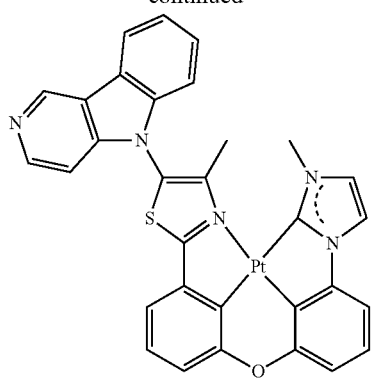
Structure 29
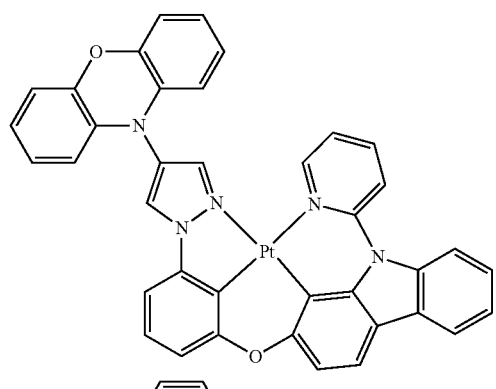
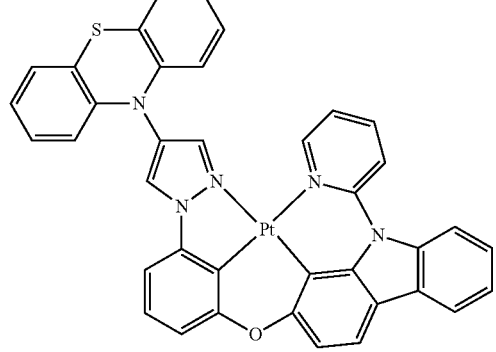
246
-continued
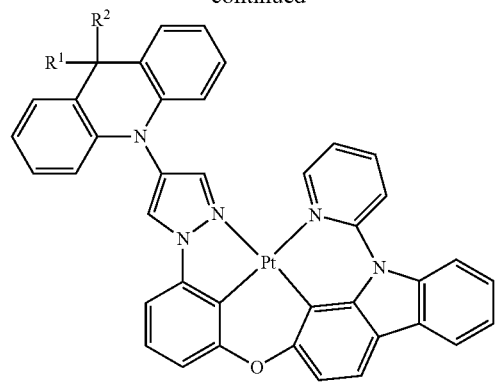
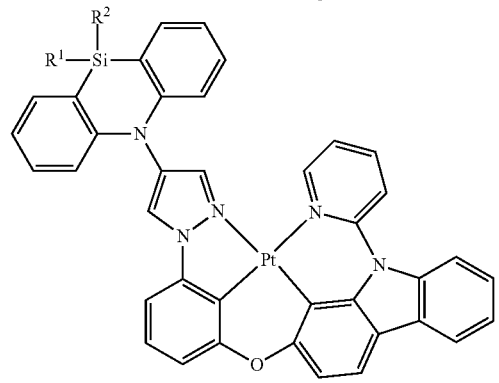
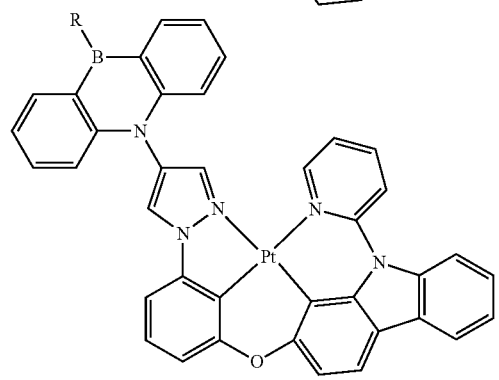
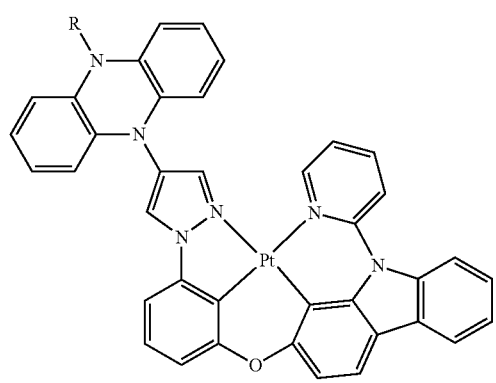
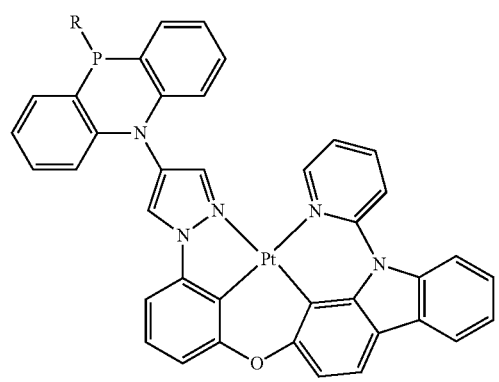

247
-continued
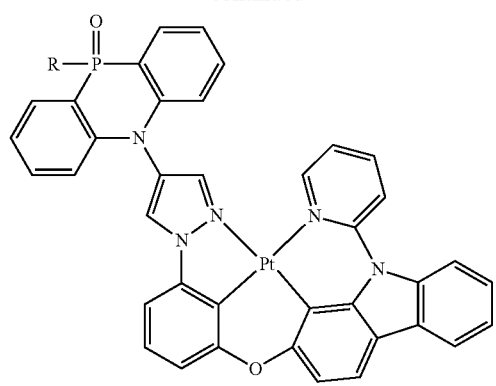
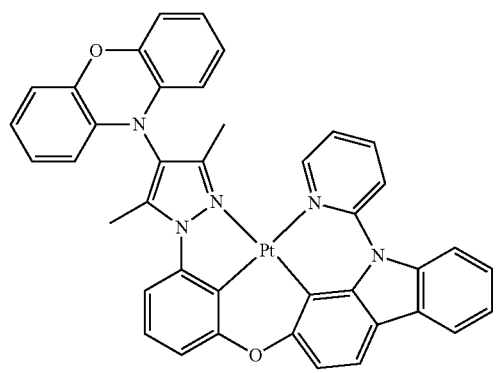
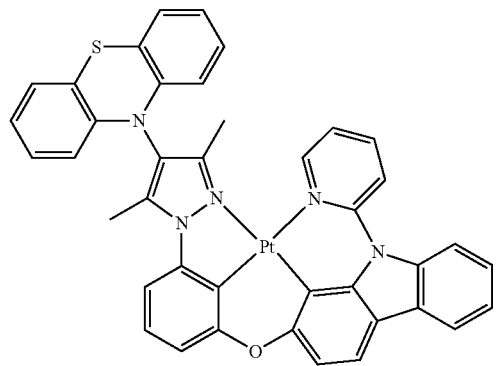
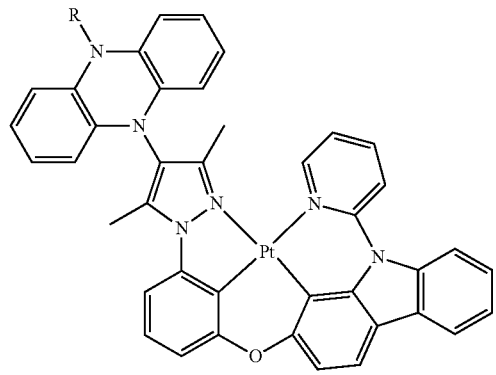
248
-continued
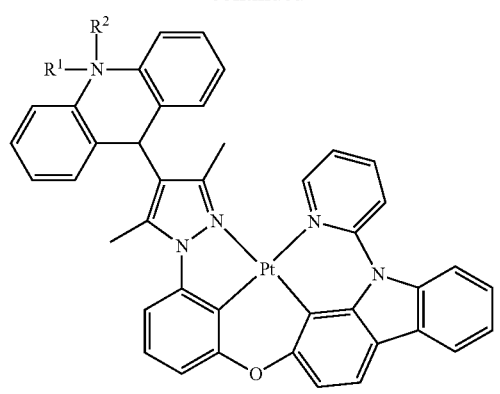
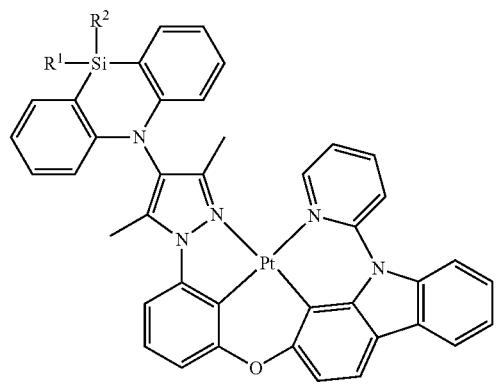
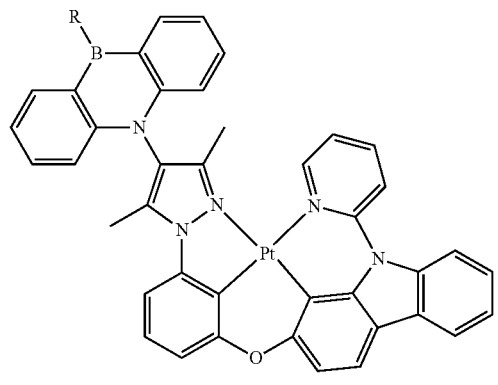
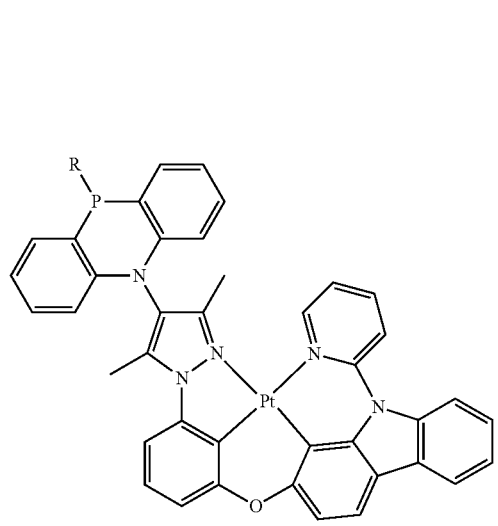

249
-continued
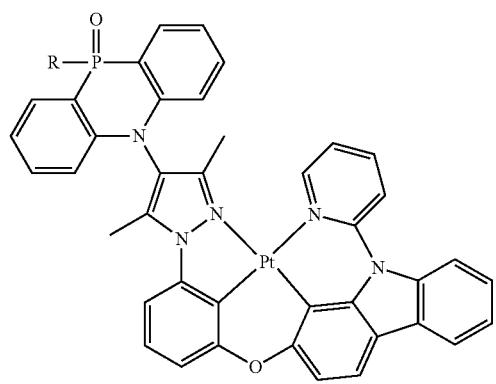
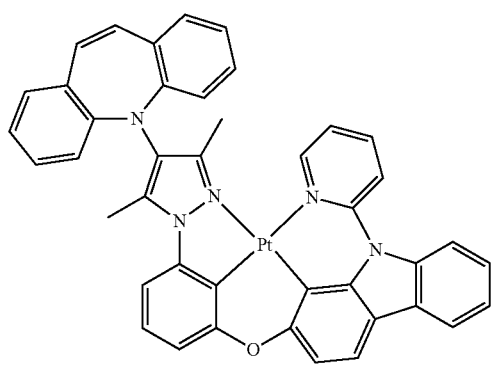
250
-continued
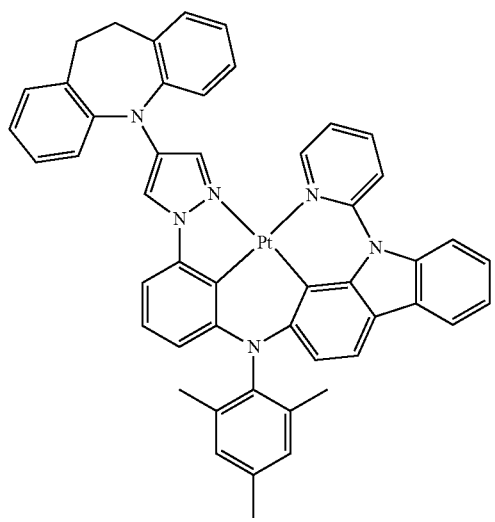

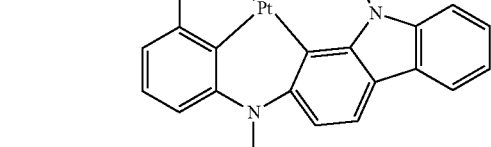

251
-continued
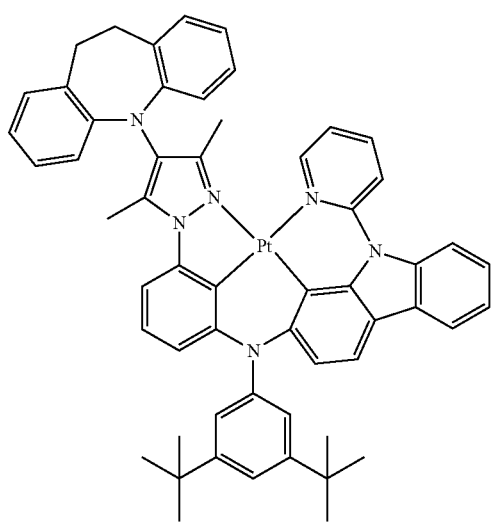
Structures 30
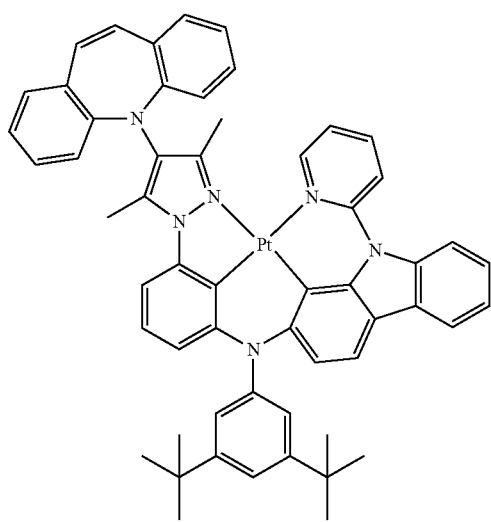
252
-continued
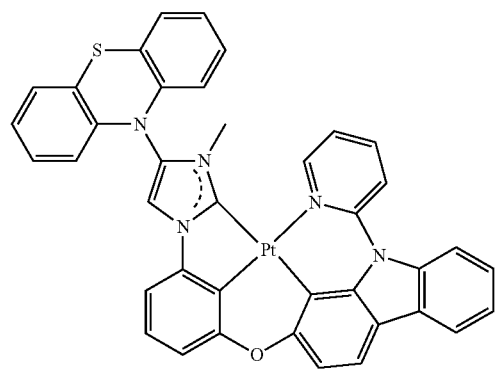
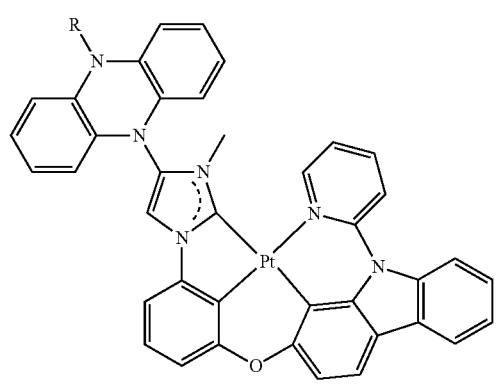
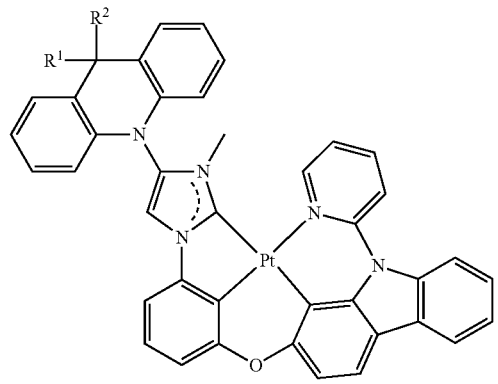
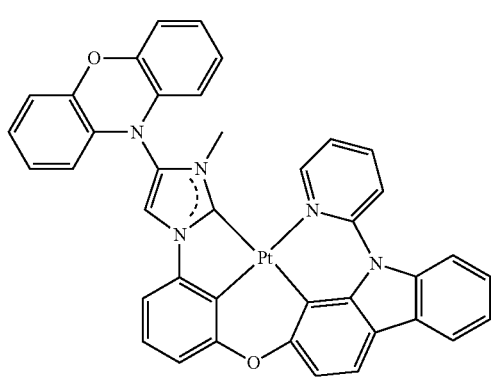
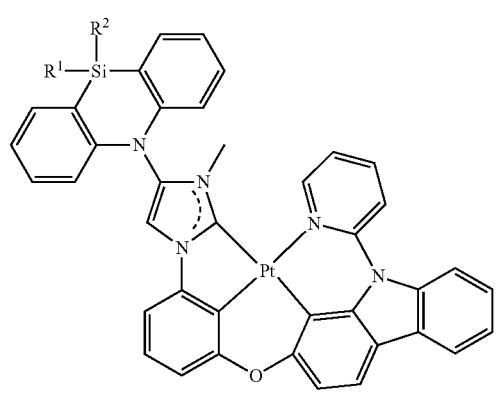

253
-continued
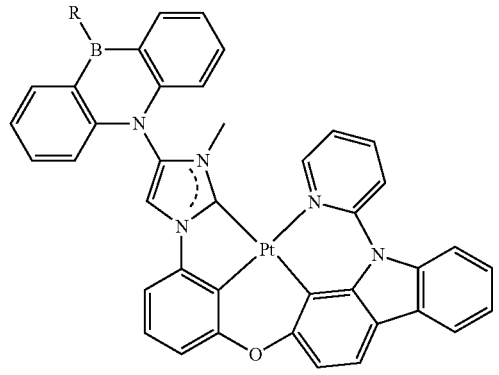
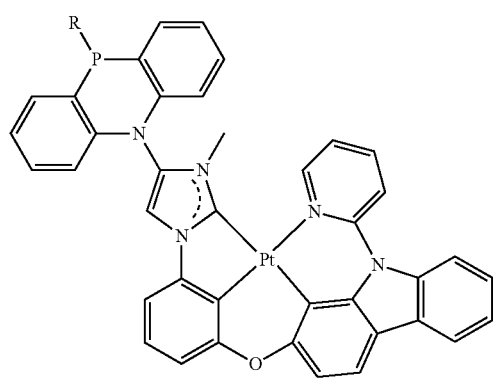
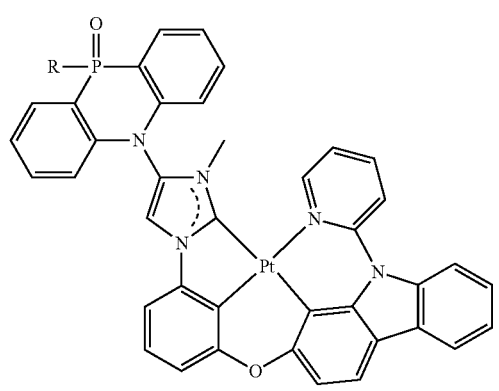
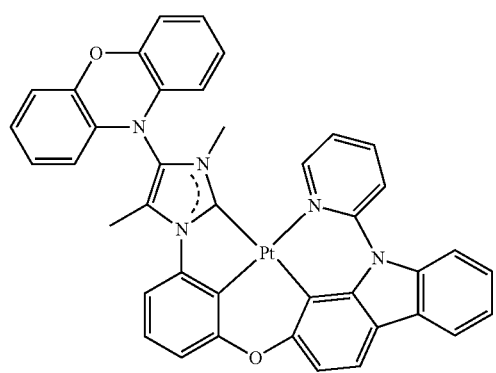
254
-continued
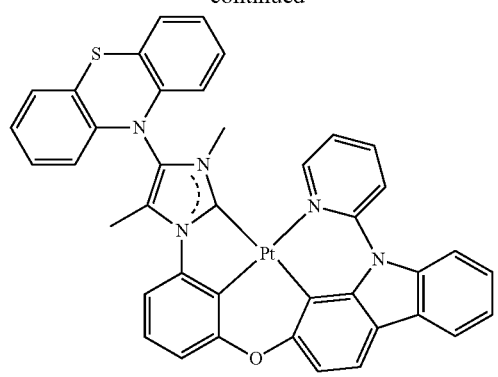
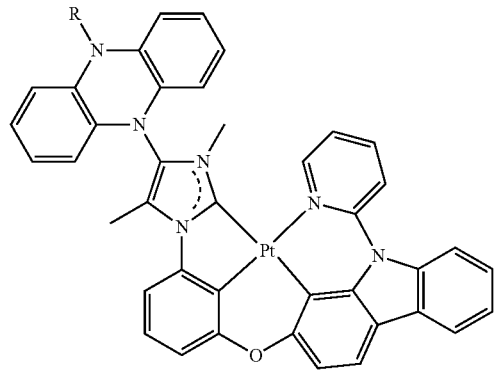
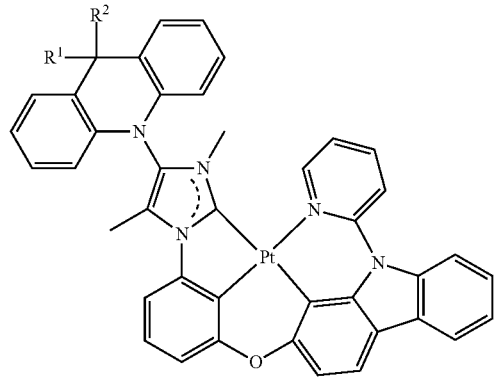
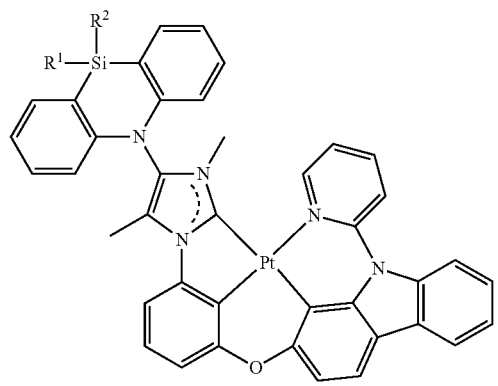

255
-continued
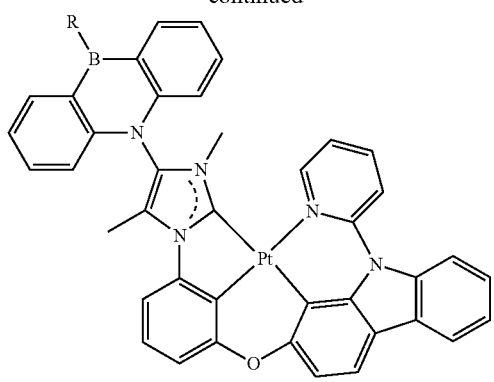
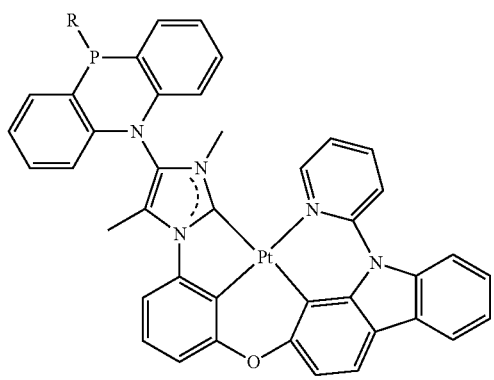
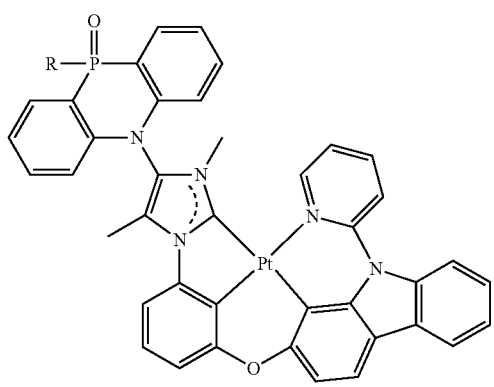
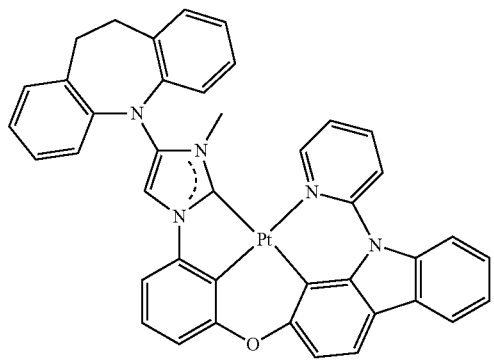
256
-continued
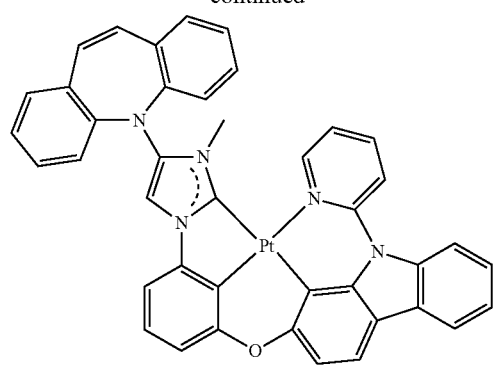
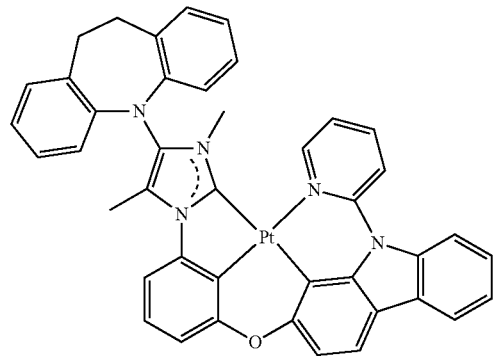
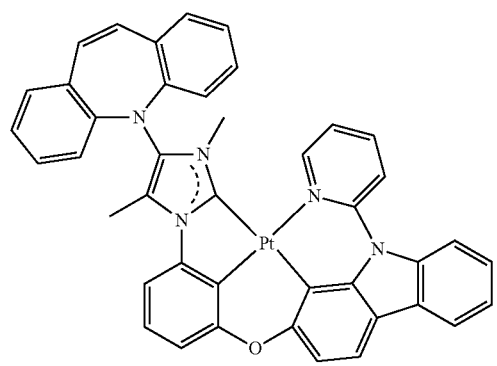

257
-continued
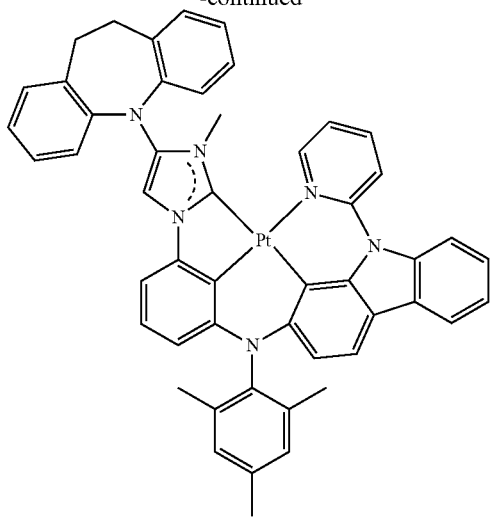
258
-continued
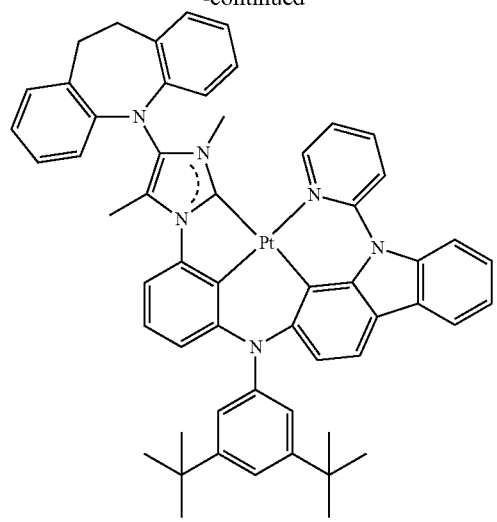
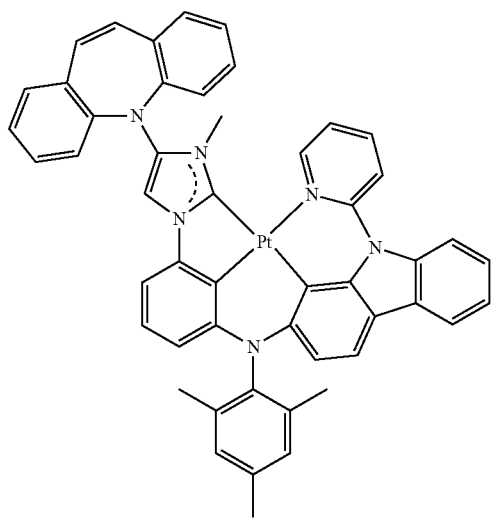
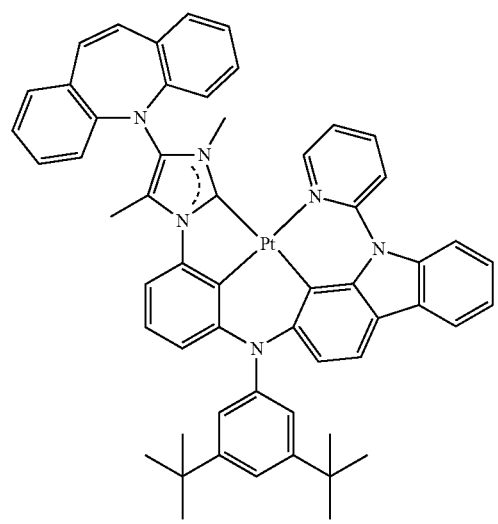
Structures 18
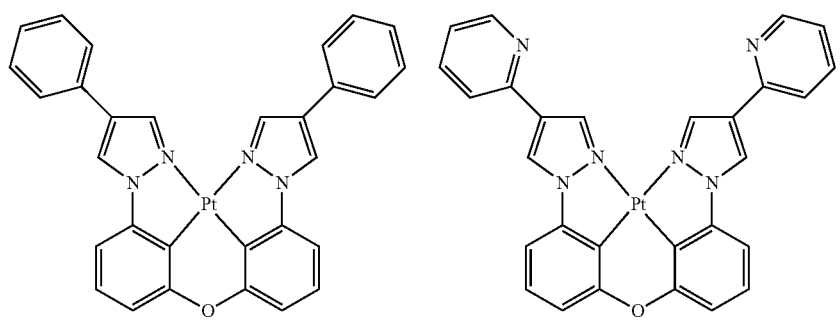

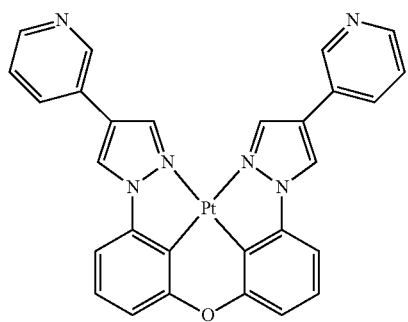
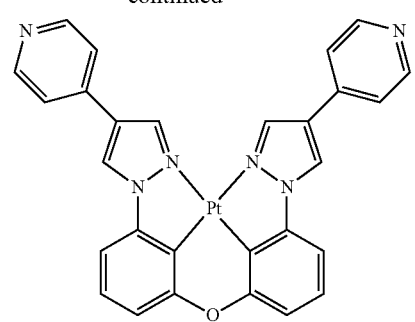
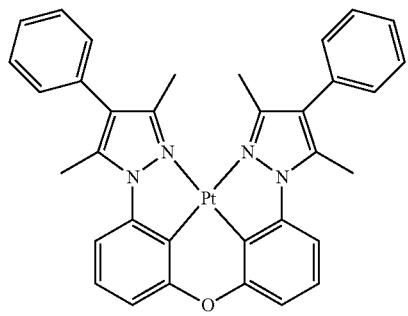
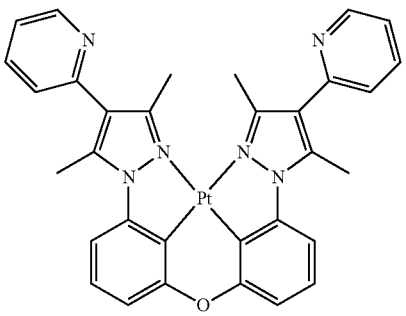
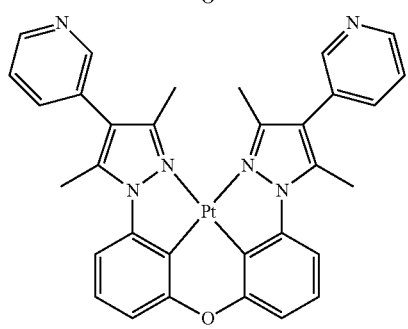
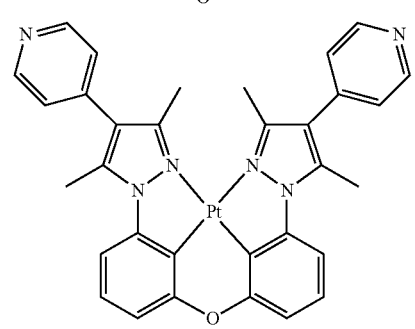
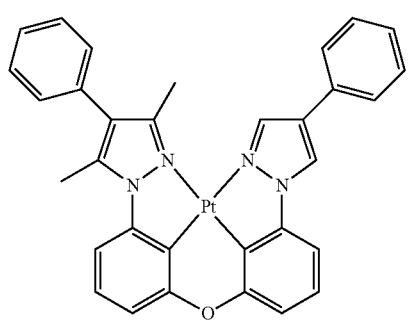
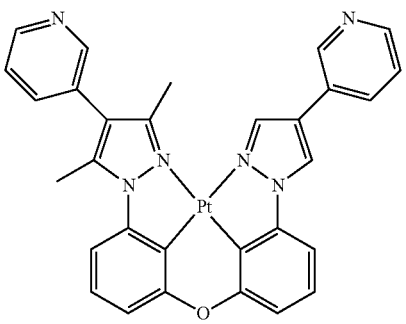
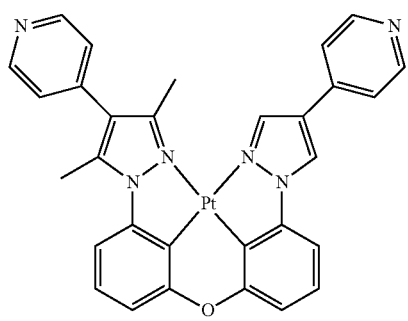
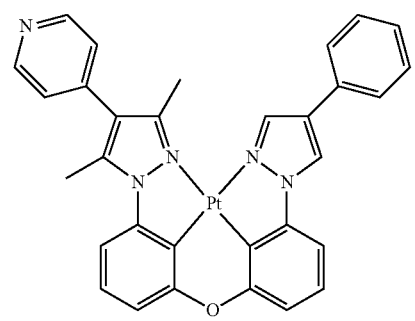

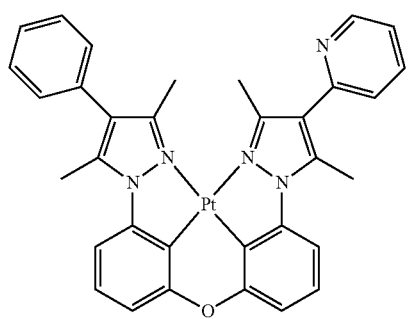
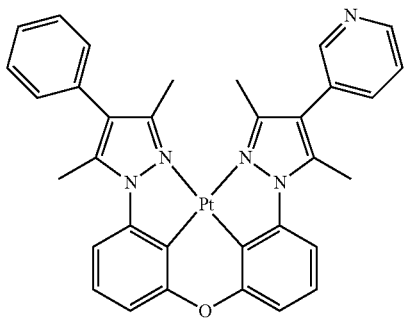
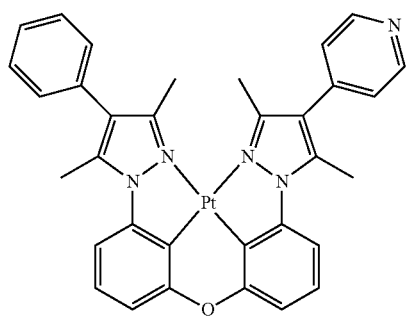
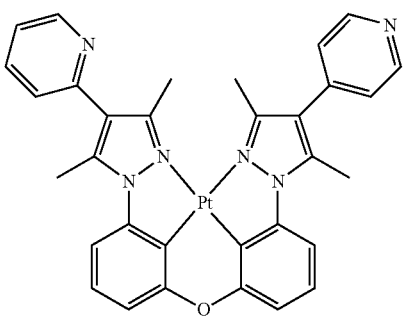
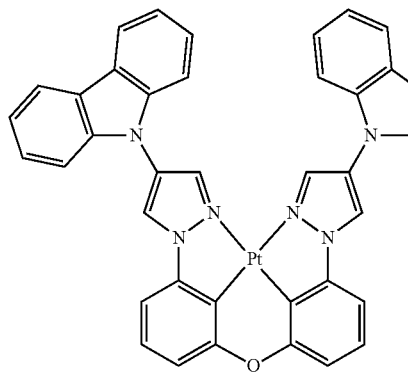
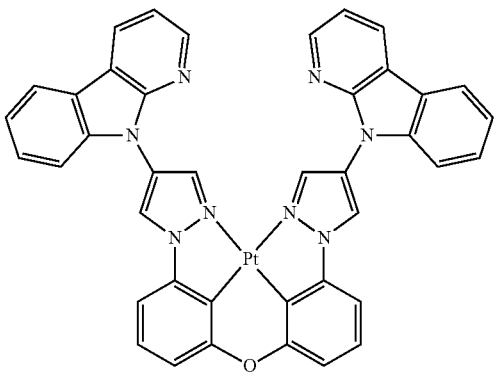
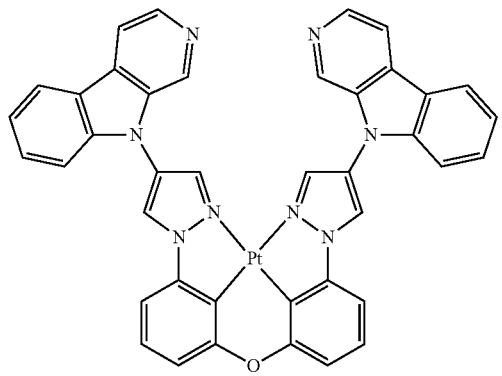

-continued
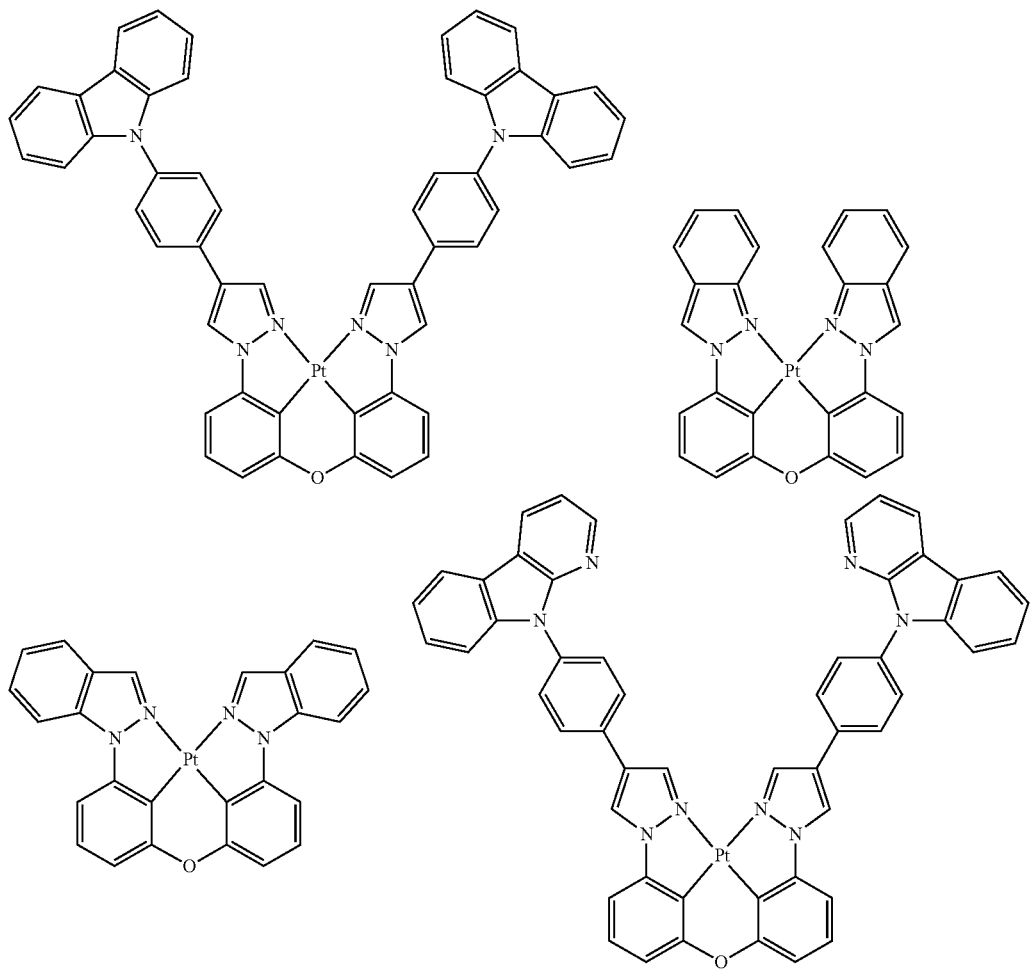
Structures 19
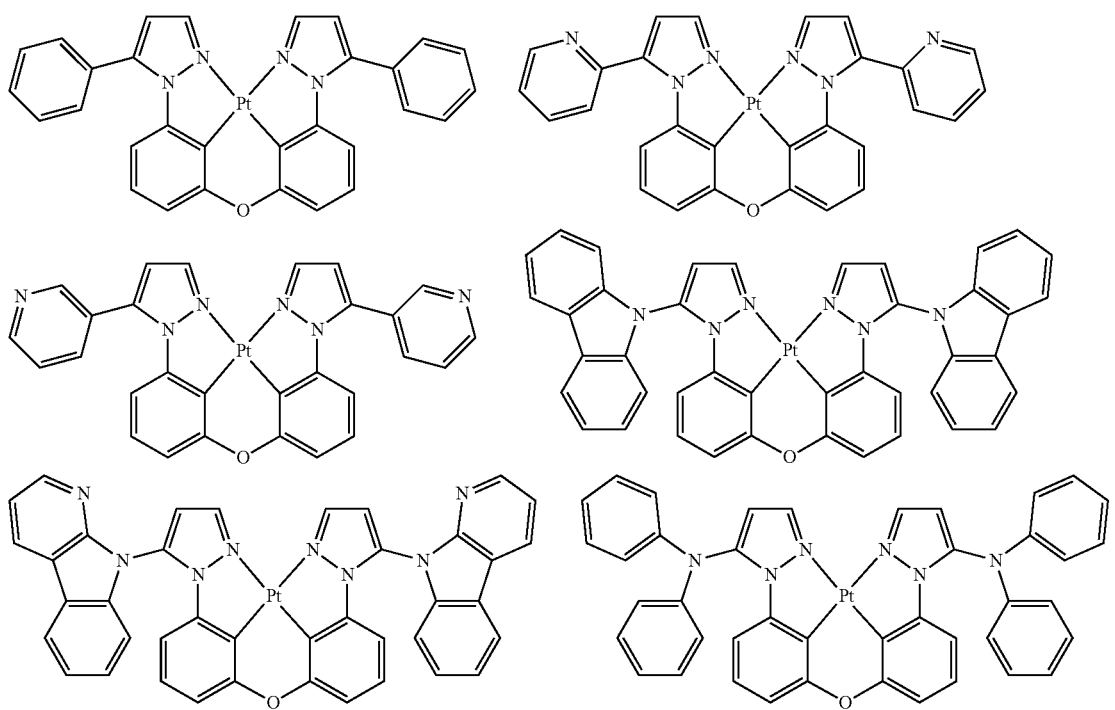

-continued
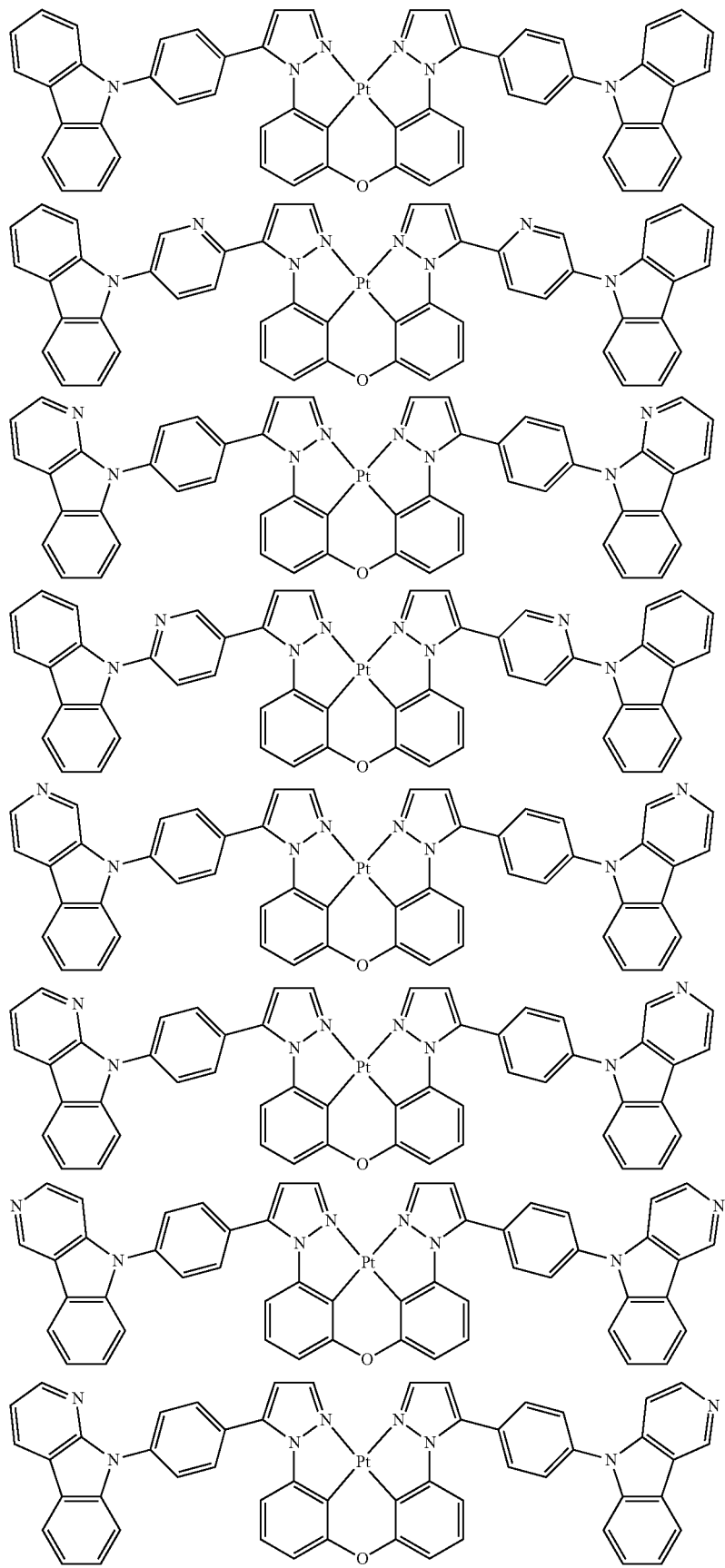

-continued
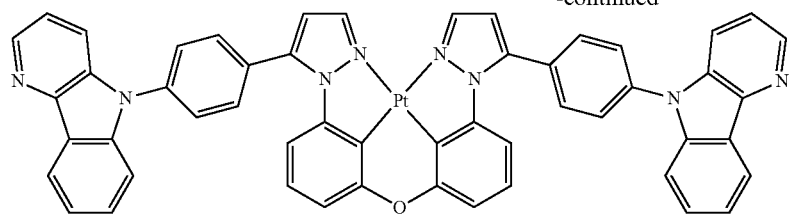
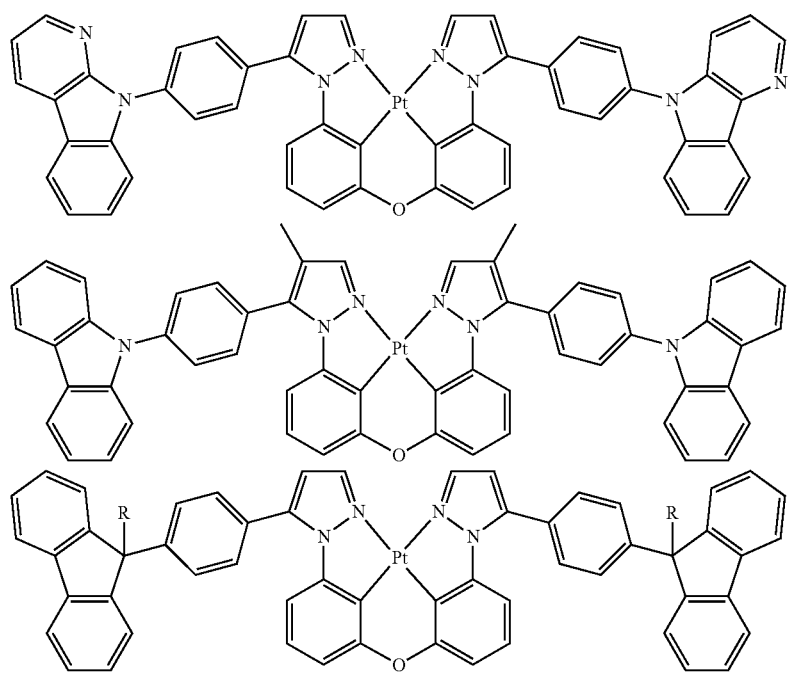
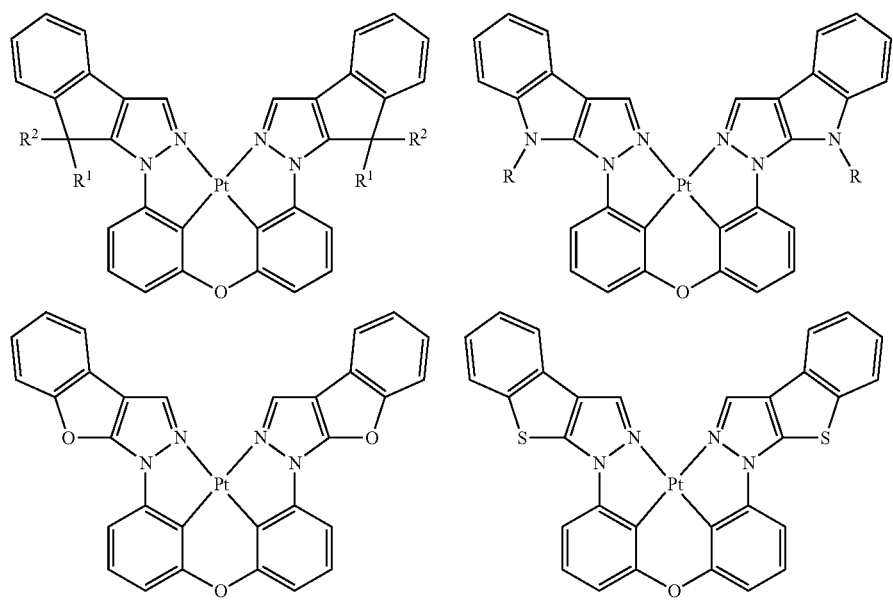

-continued
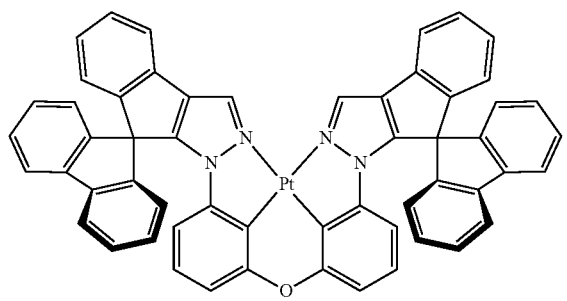
Structures 20
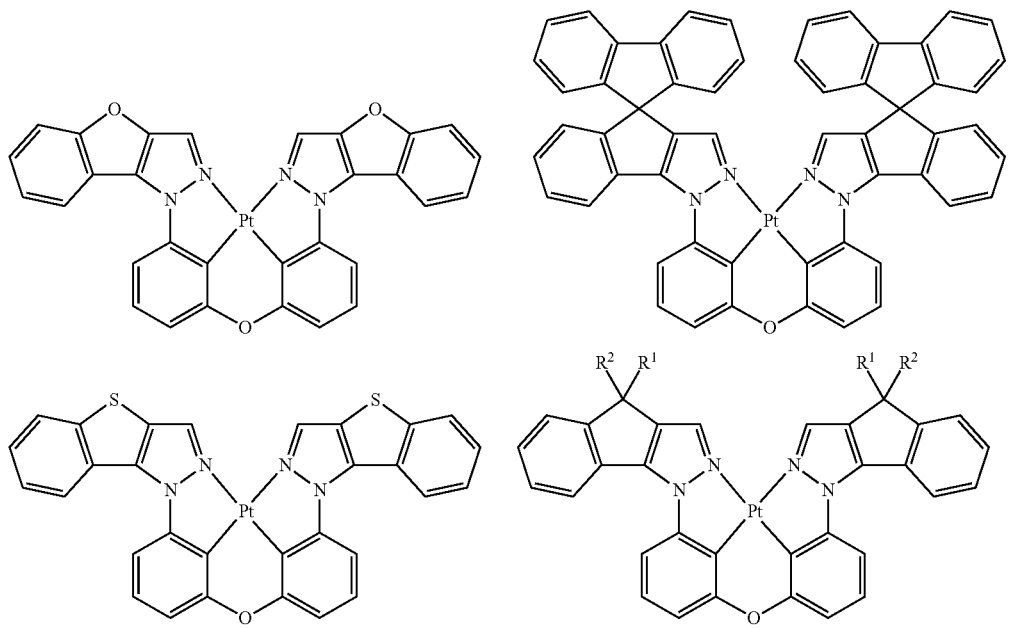
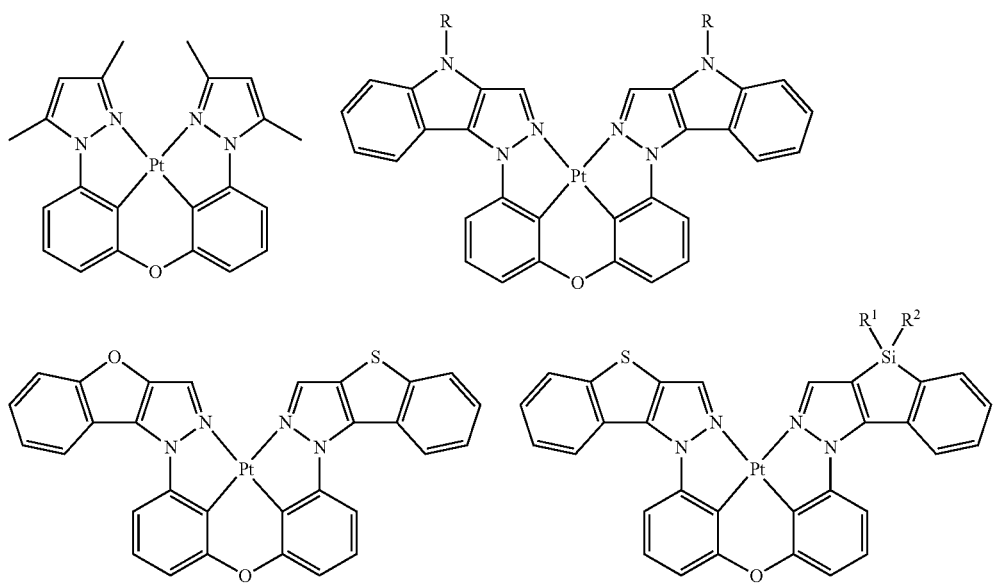

271
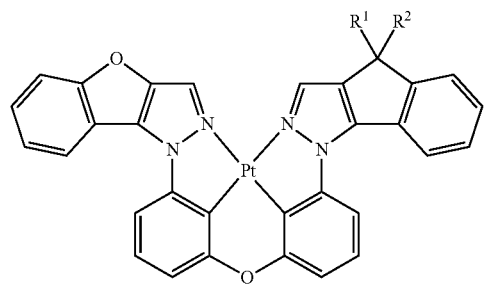
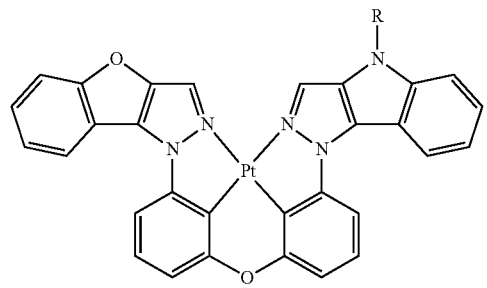
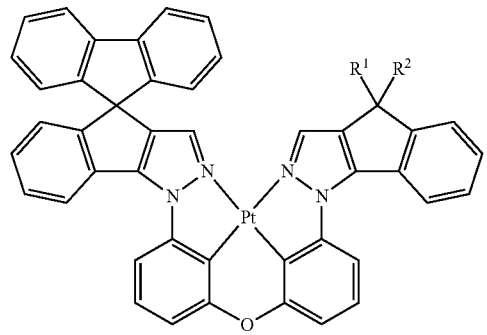
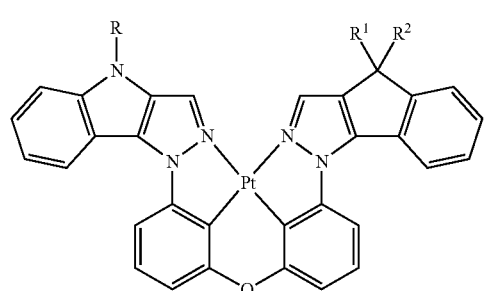
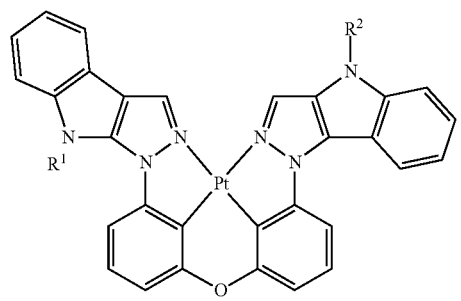
272
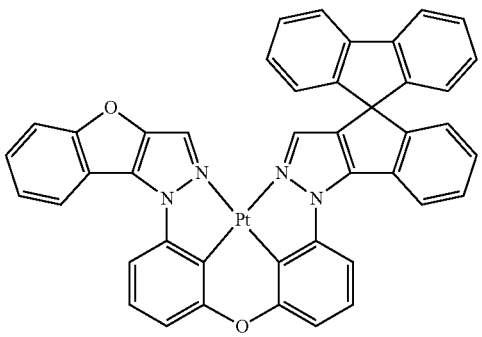
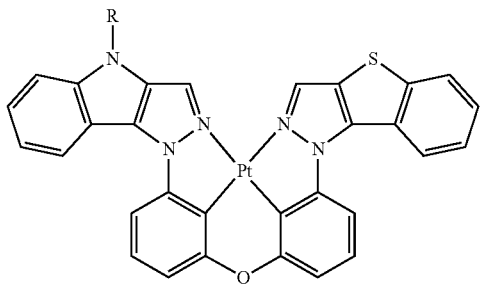
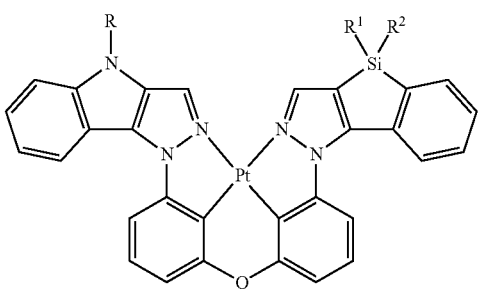
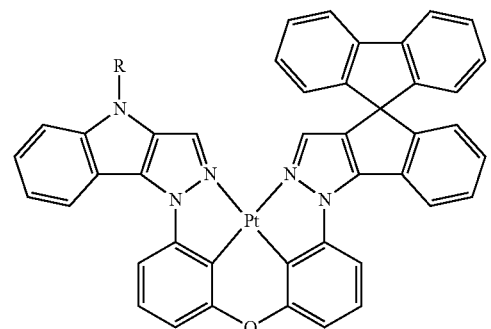
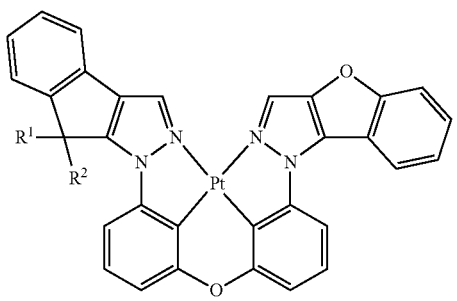

-continued
273
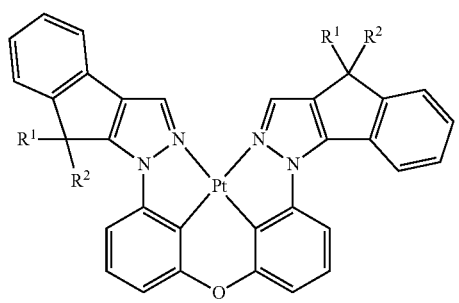
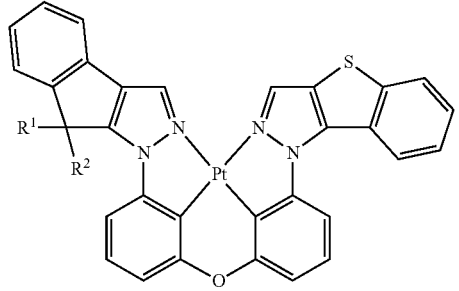
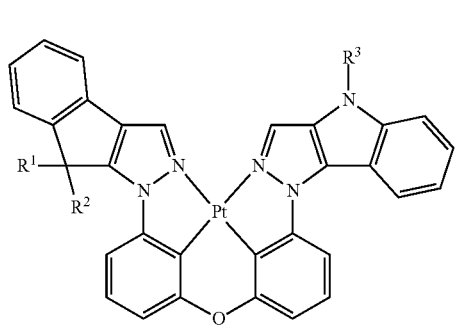
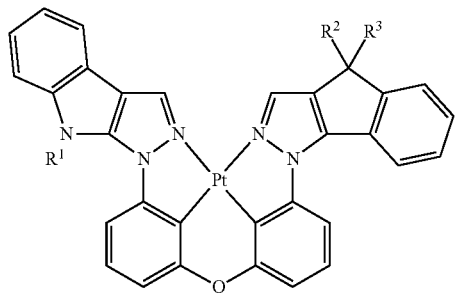
274
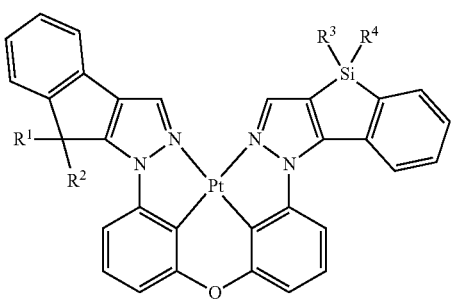
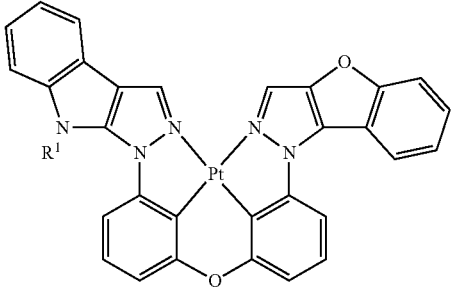
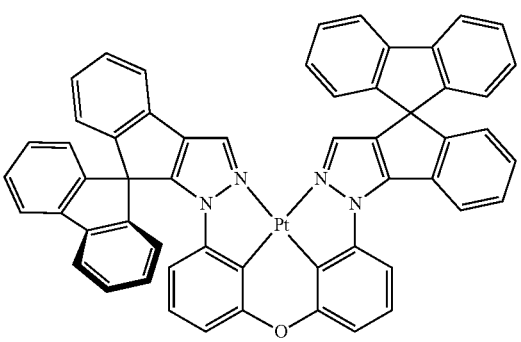
Structures 21
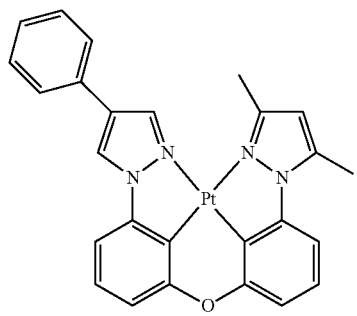
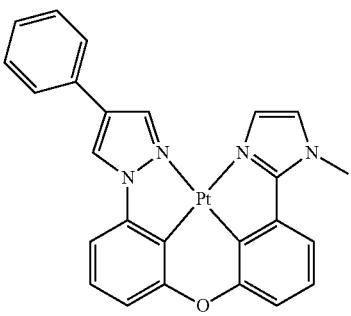
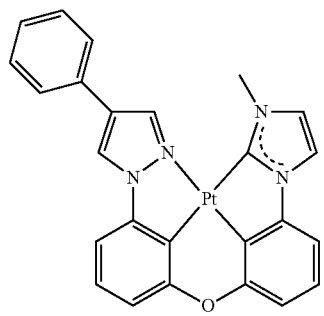

275
276
-continued
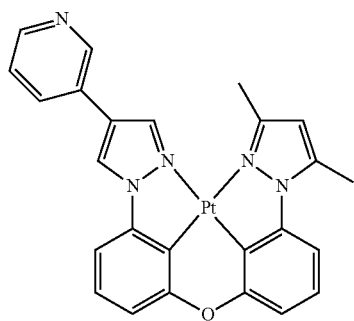
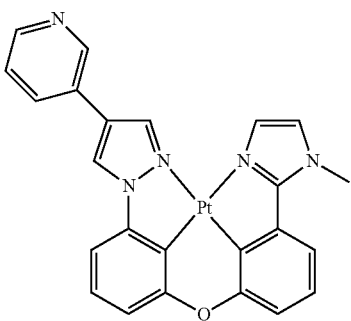
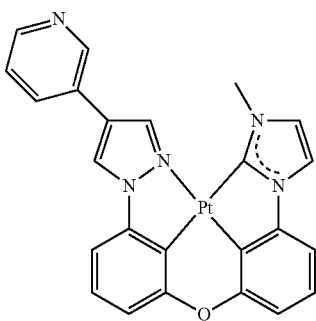
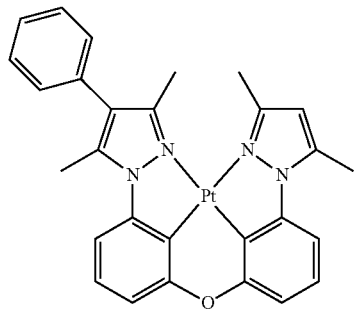
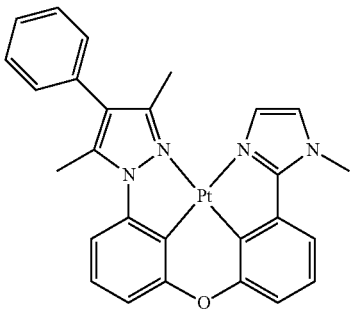
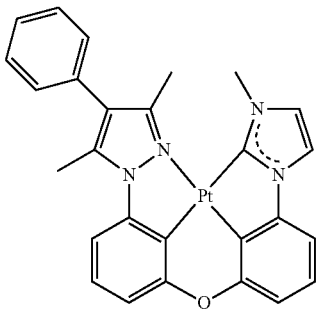
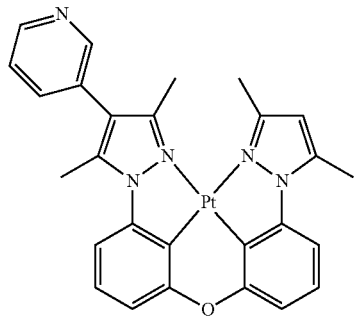
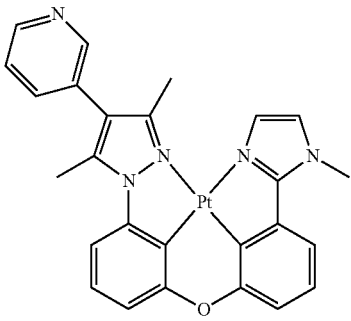
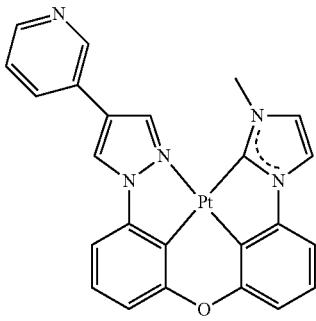
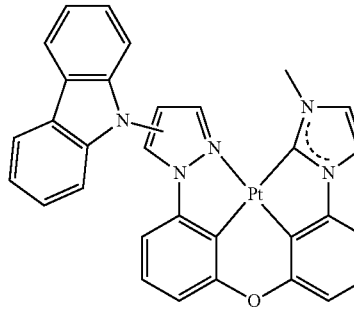
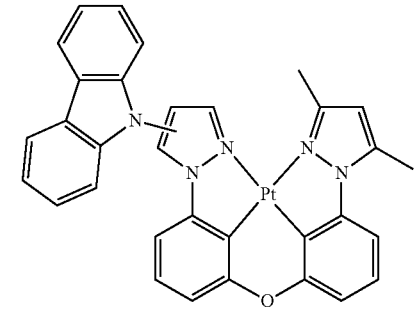
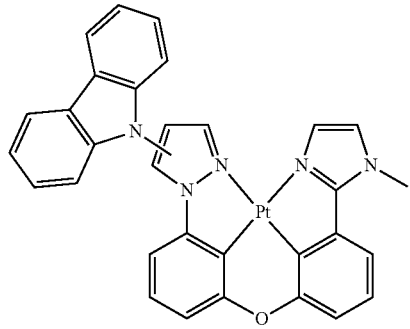
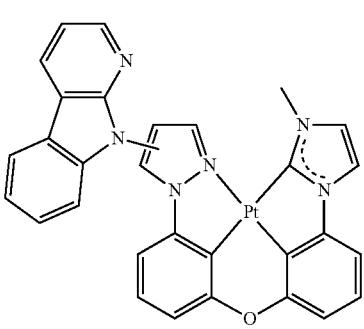

-continued
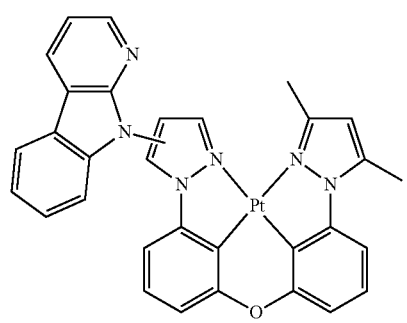
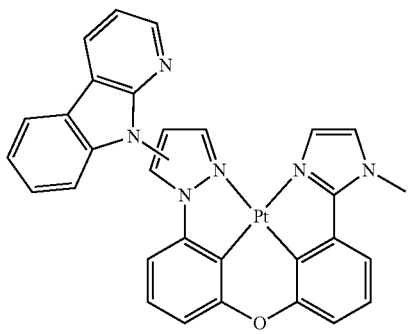
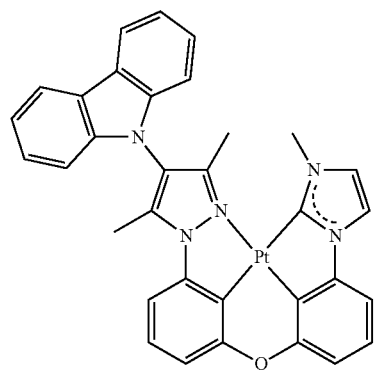
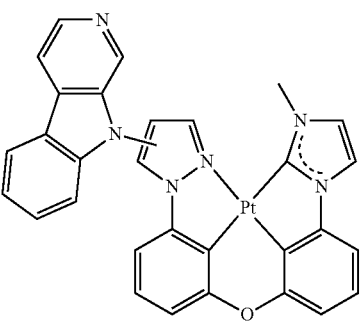
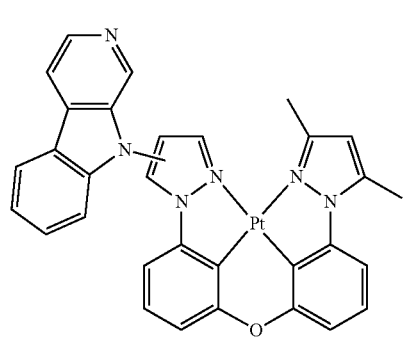
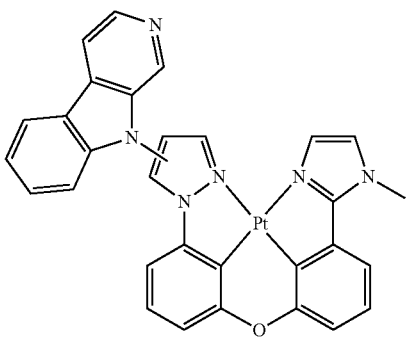
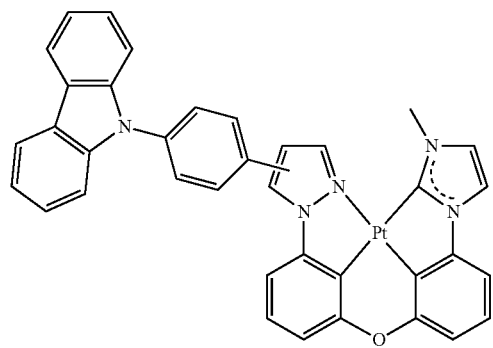
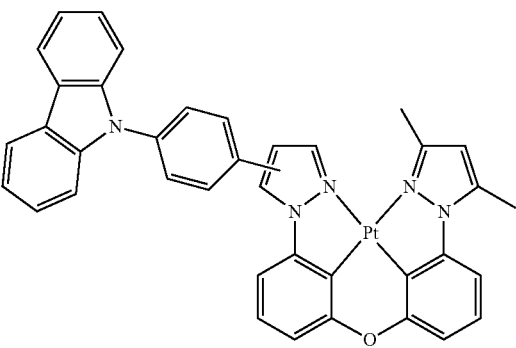

279
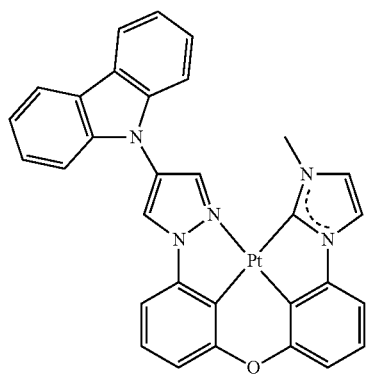
-continued
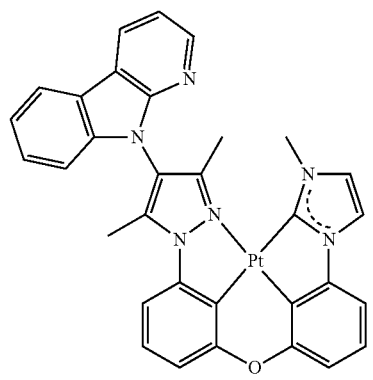
280
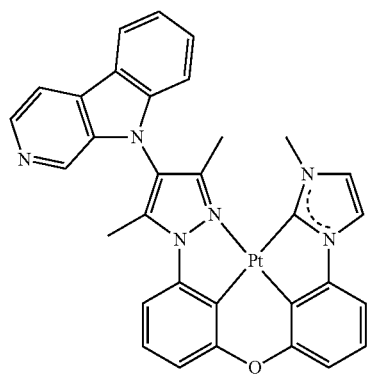
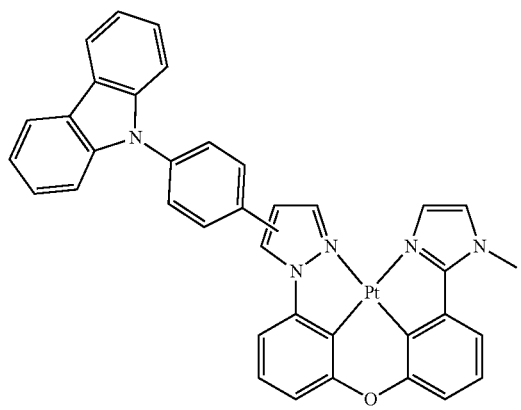
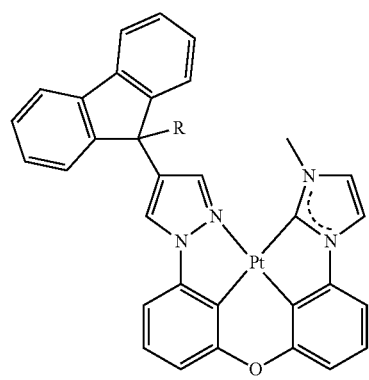
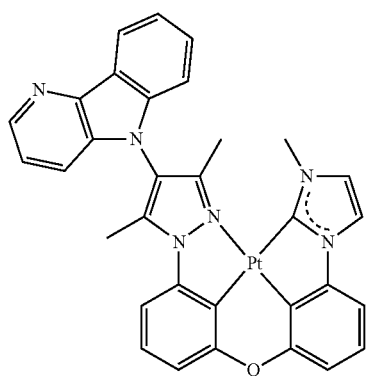
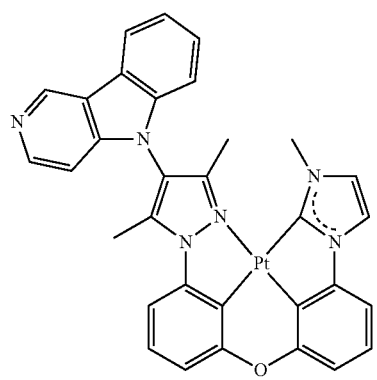
Structures 22
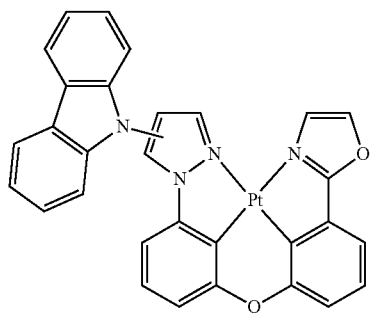
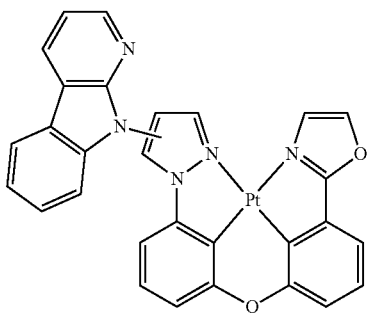
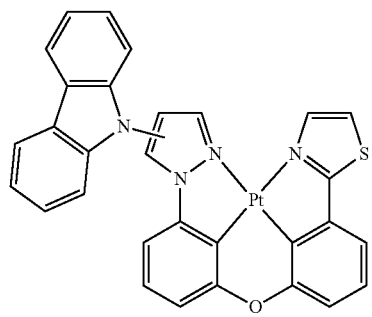

281
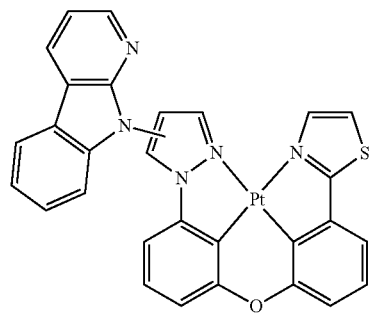
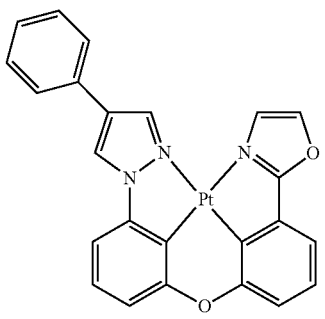
282
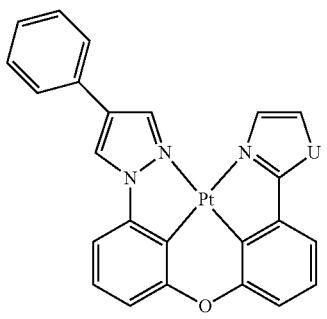
-continued
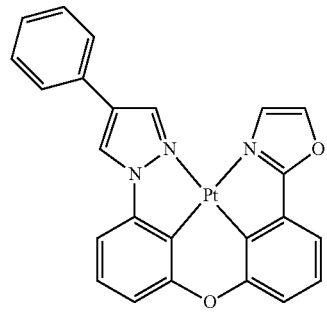
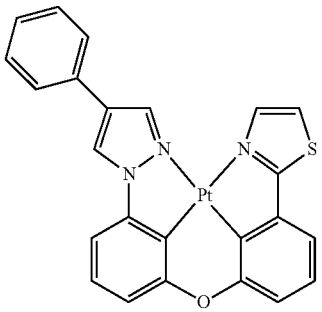
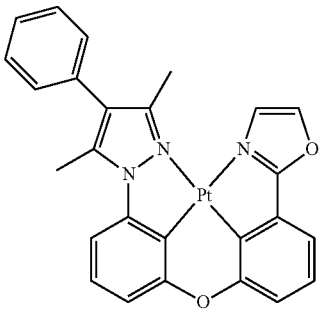
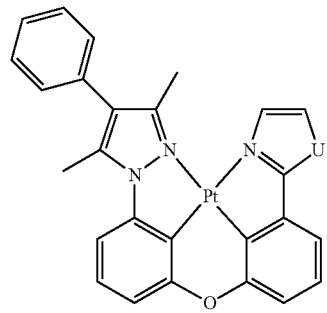
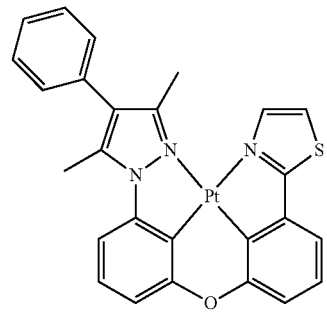
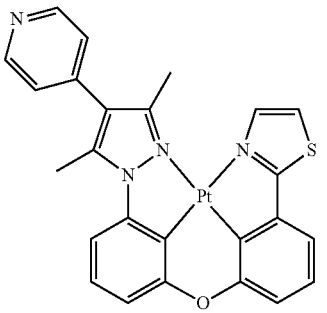
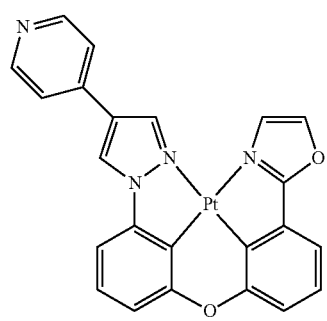
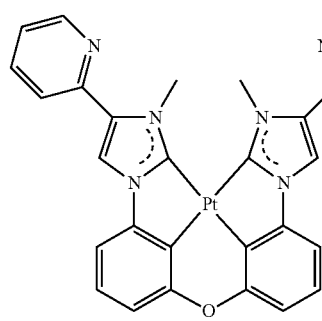
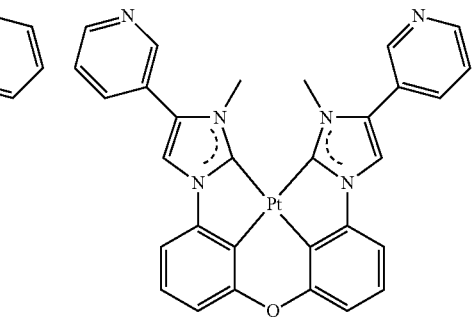
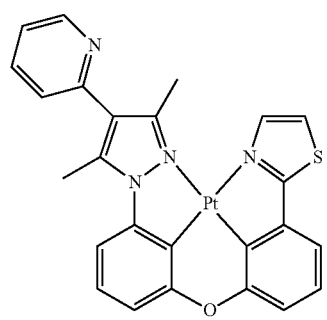
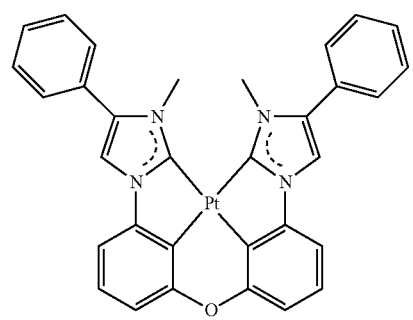

-continued
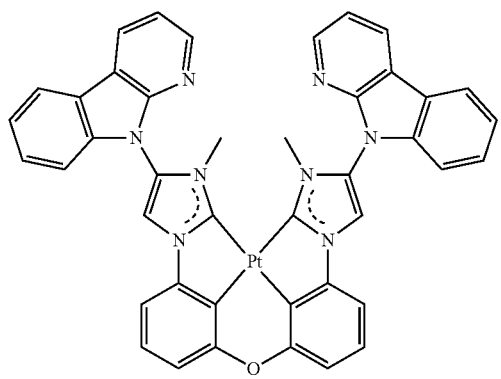 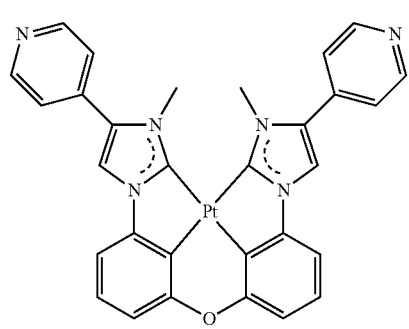
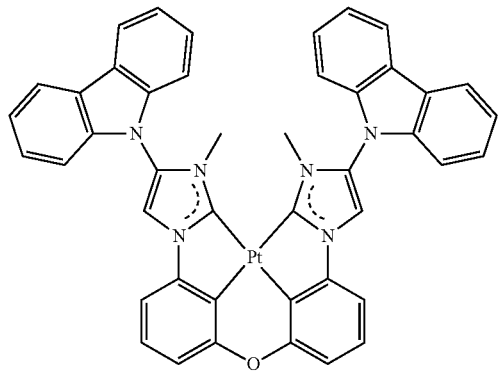 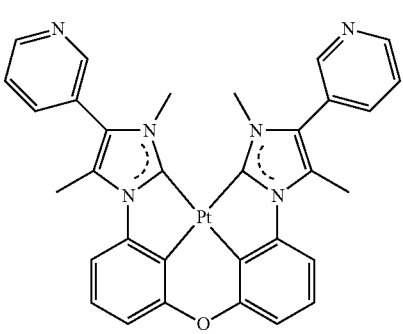
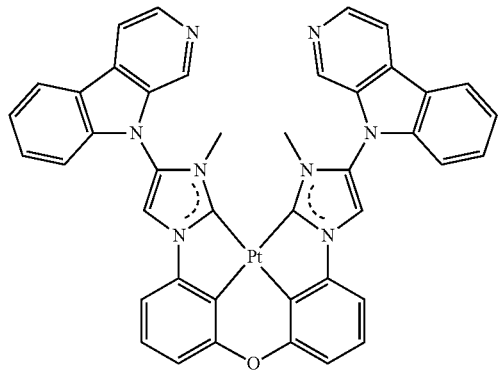 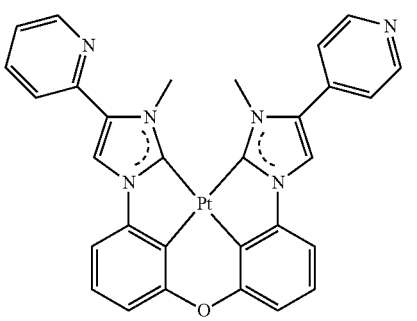 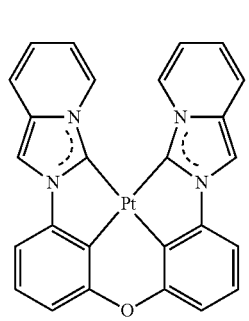
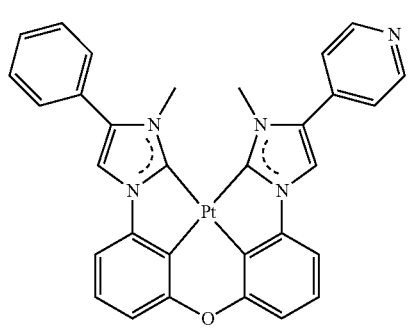 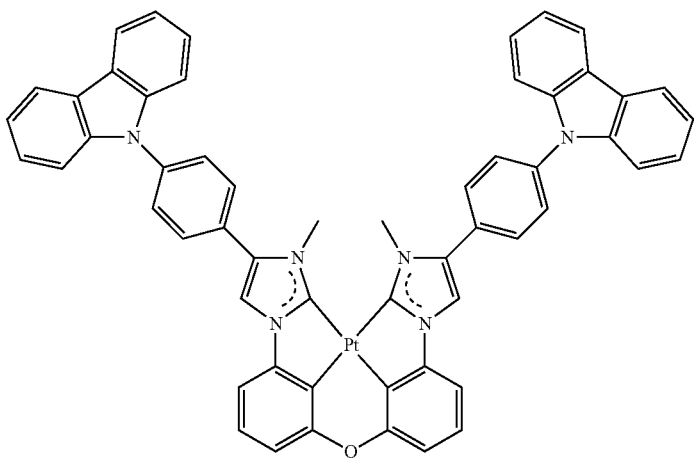

-continued
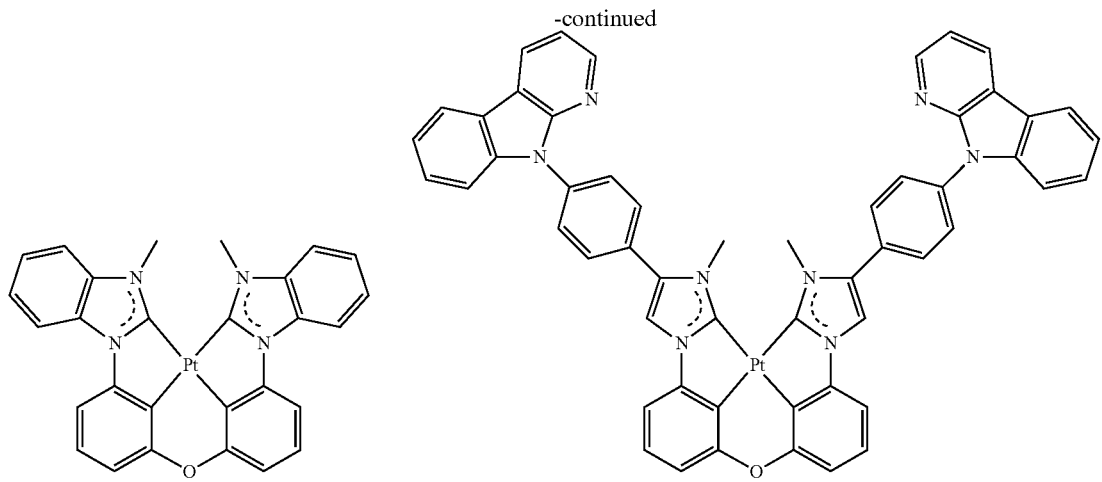
Structures 23
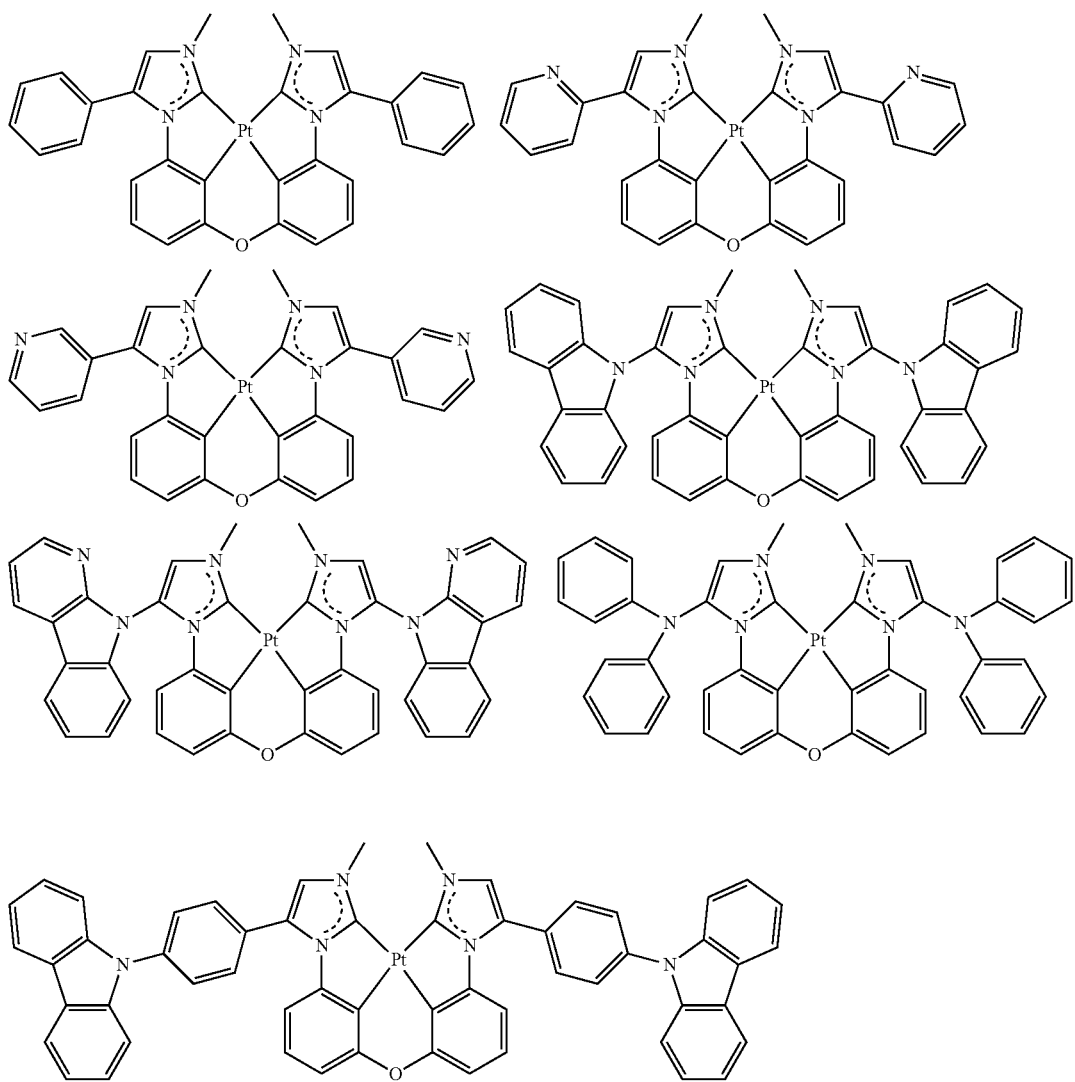

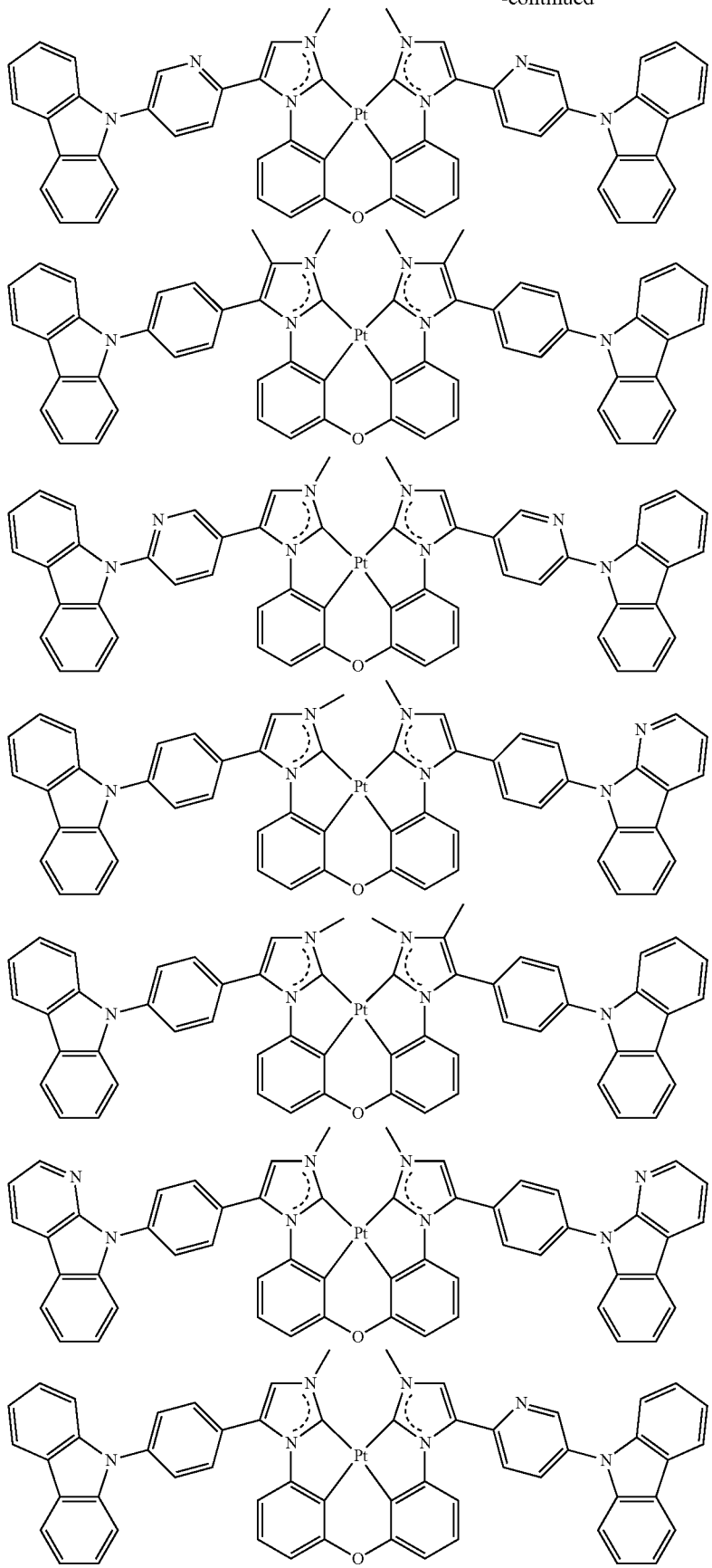

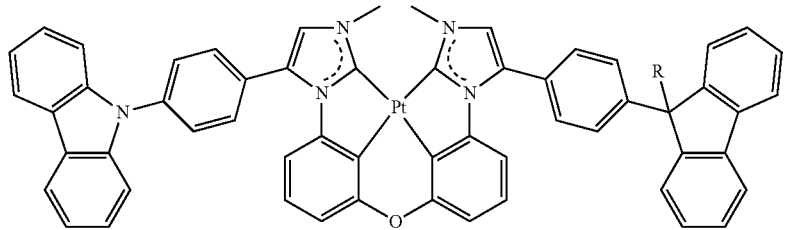
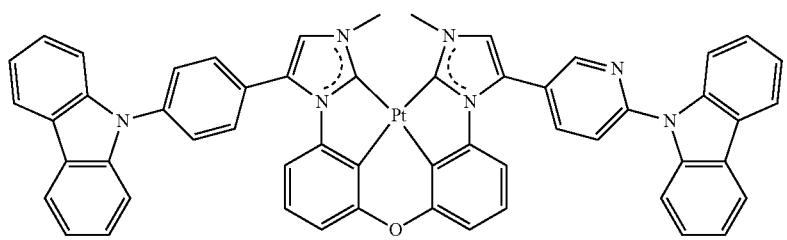
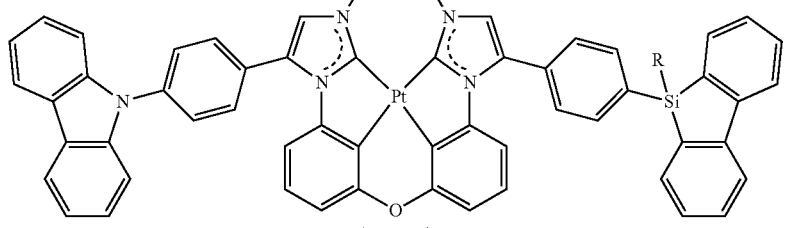
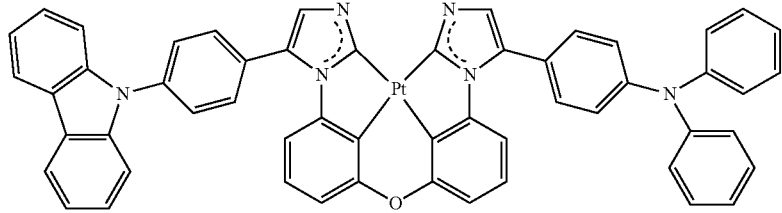
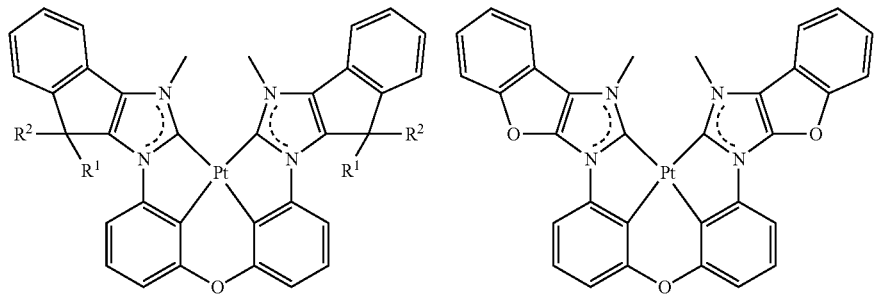
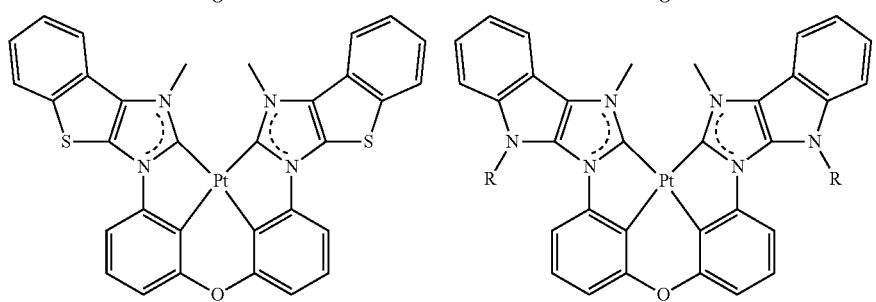

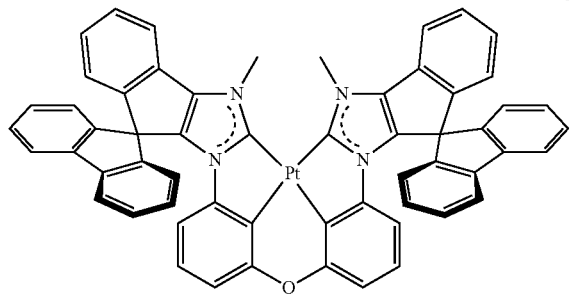
Structures 24
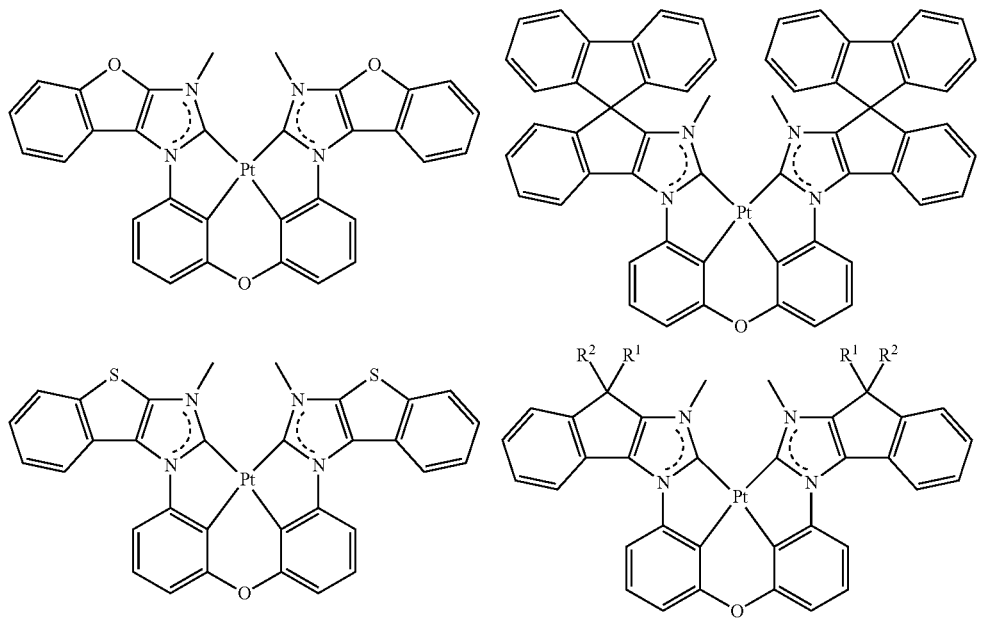
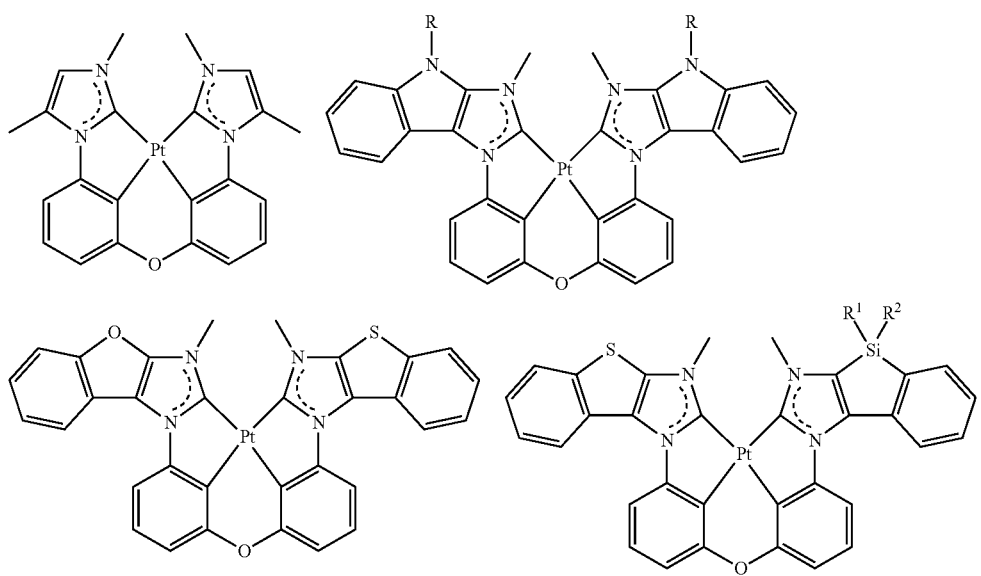

293 294
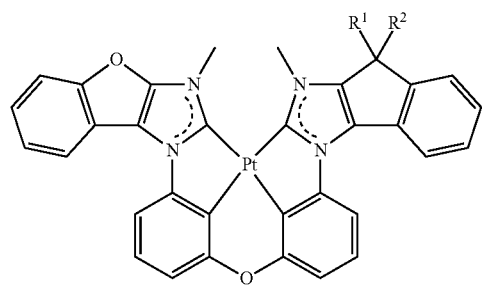 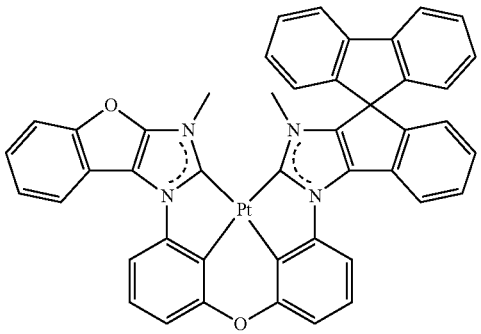
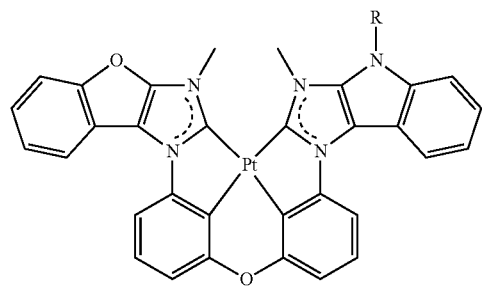 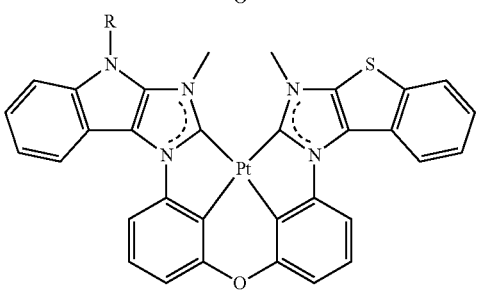
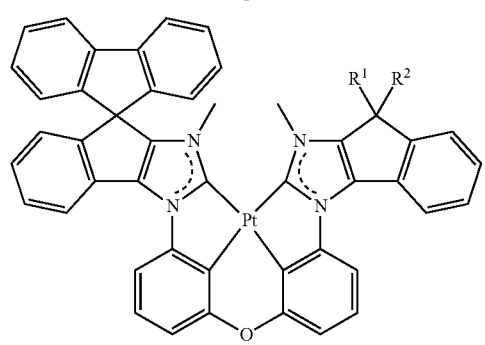 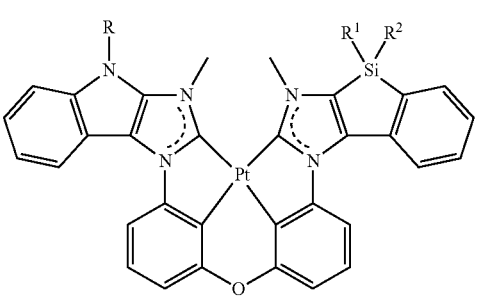
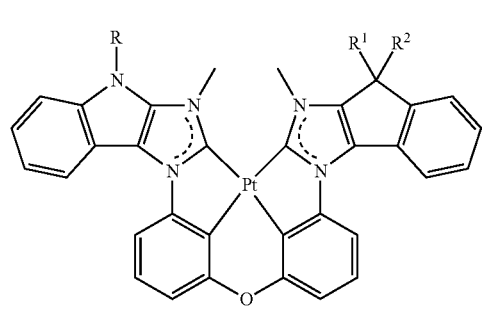 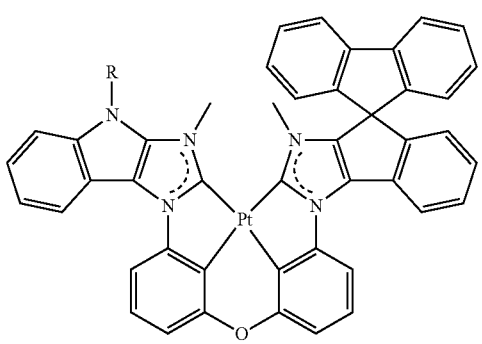
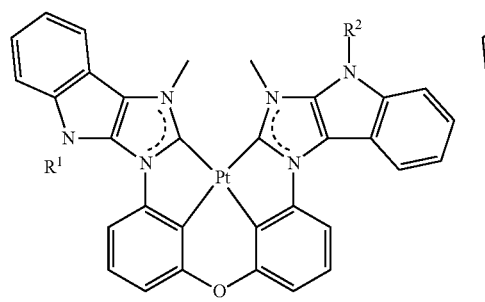 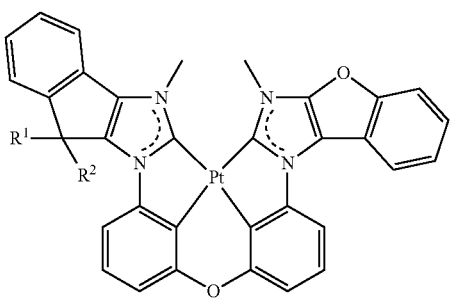

-continued
295
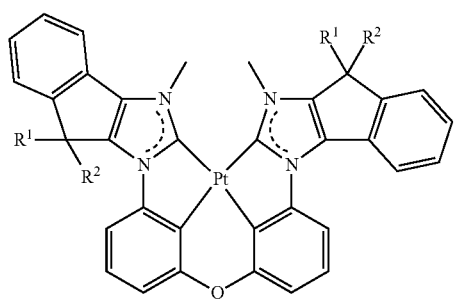
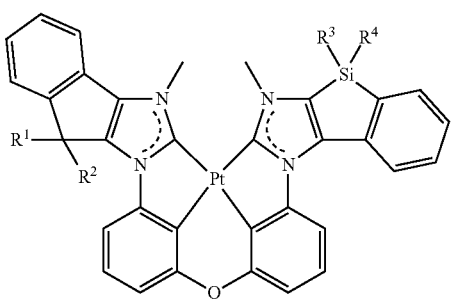
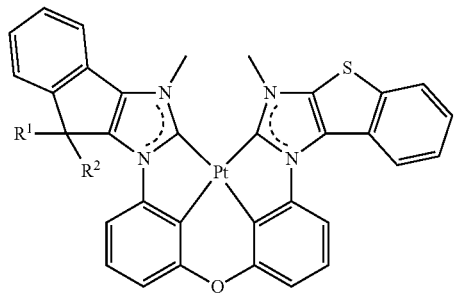
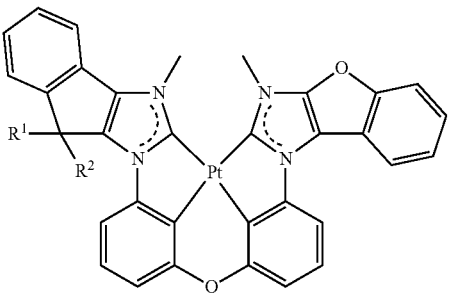
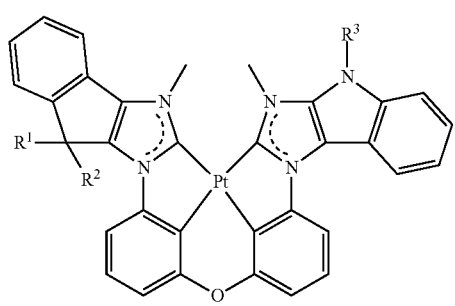
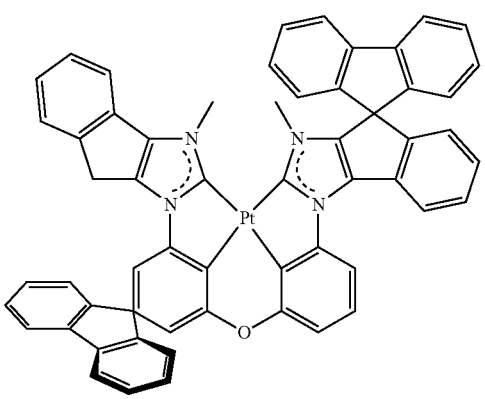
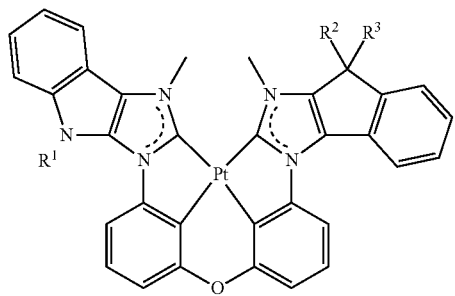
Structures 25
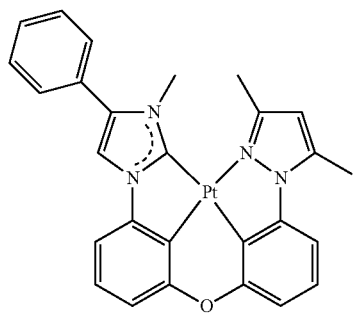
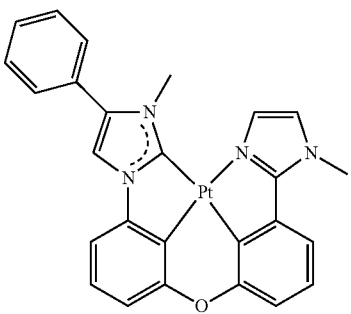
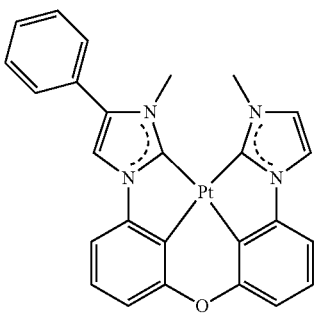
296

297
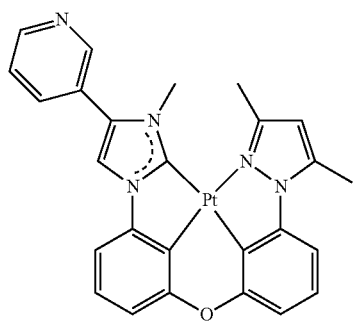 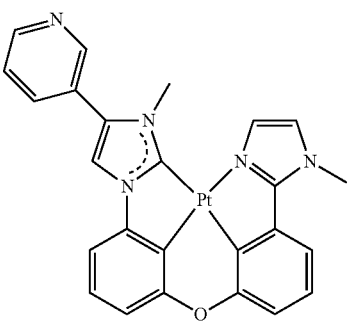 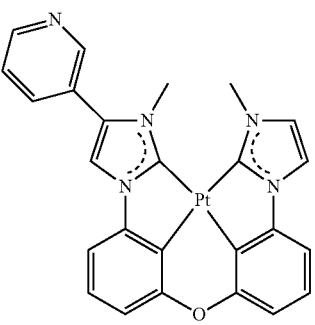
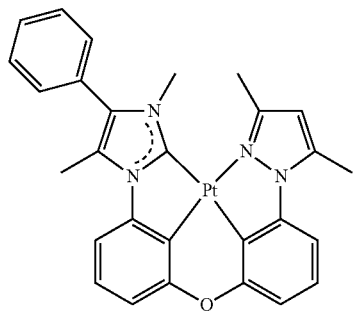 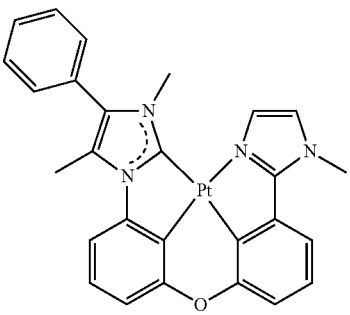 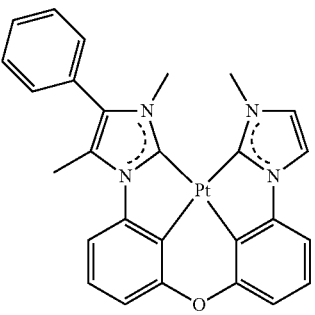
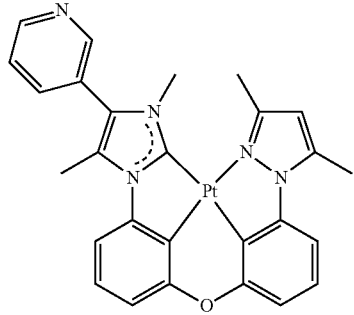 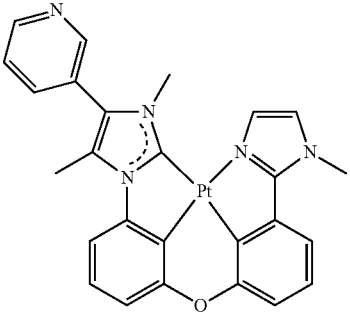 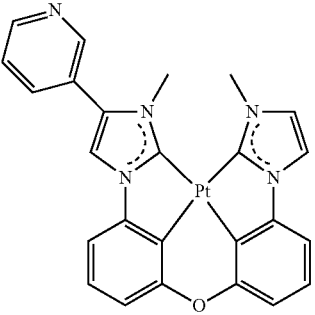
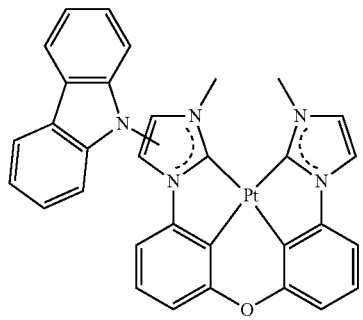 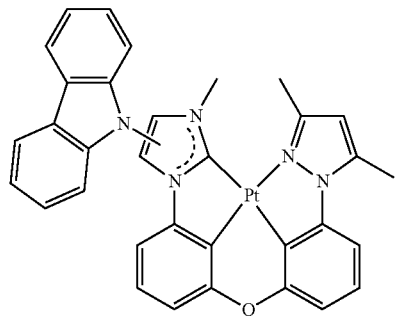 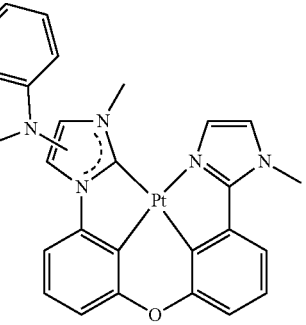
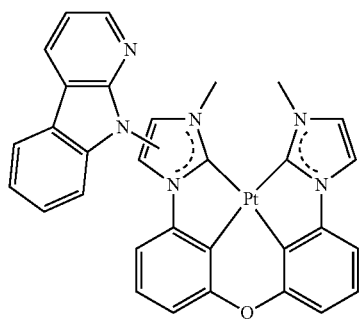 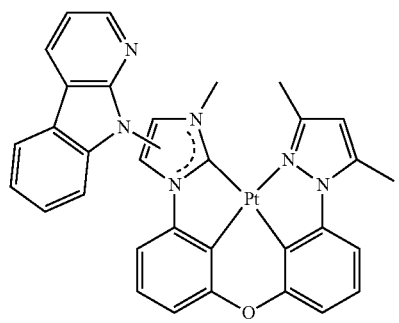 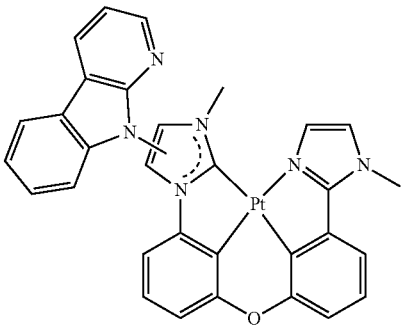
298

-continued
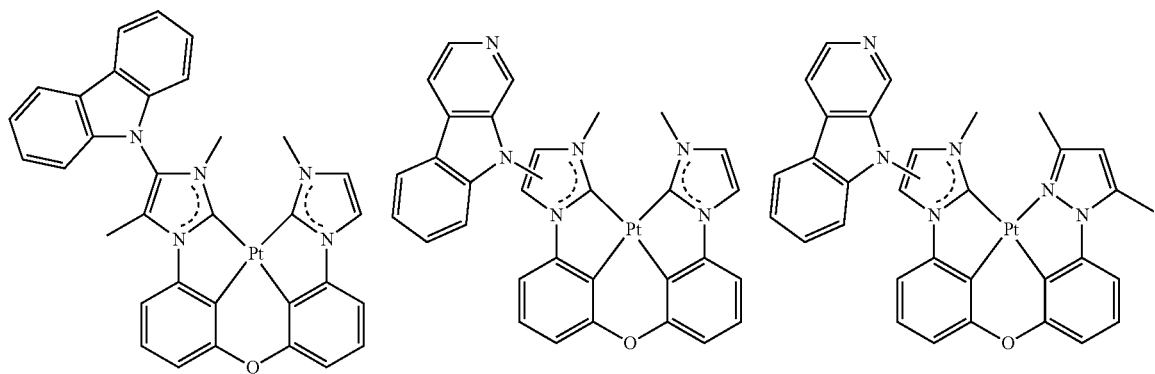
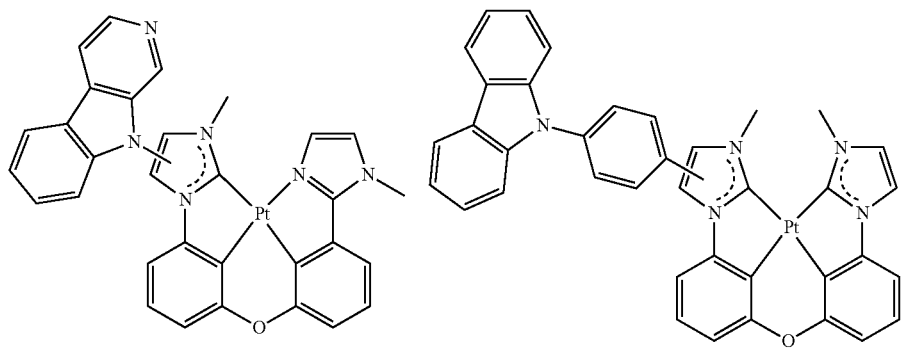
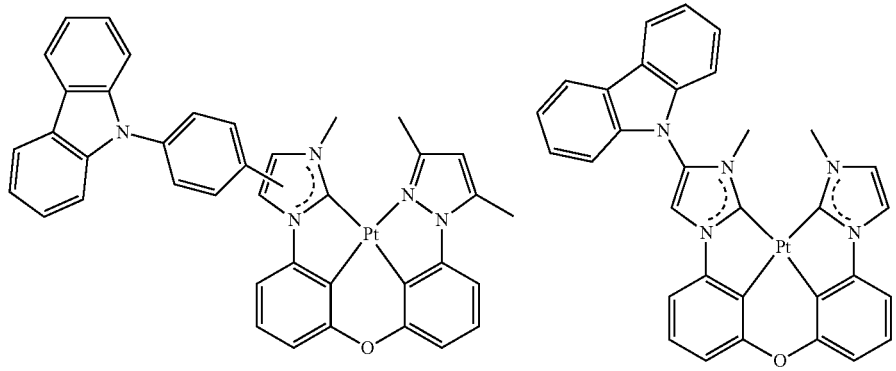
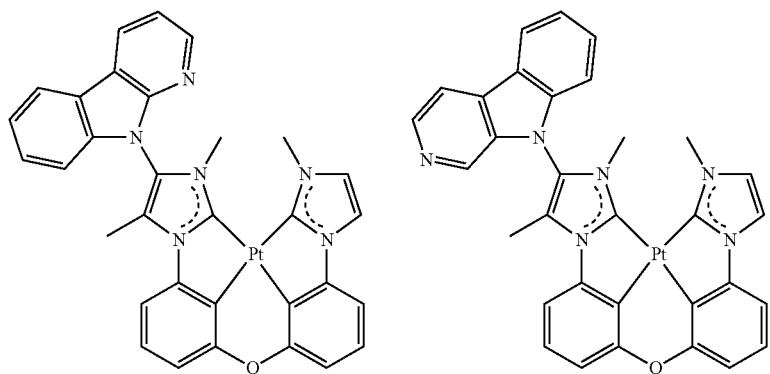

301
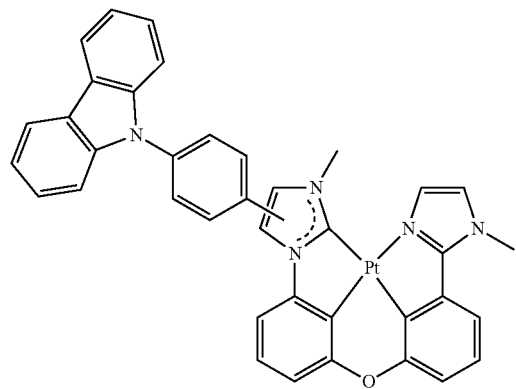
302
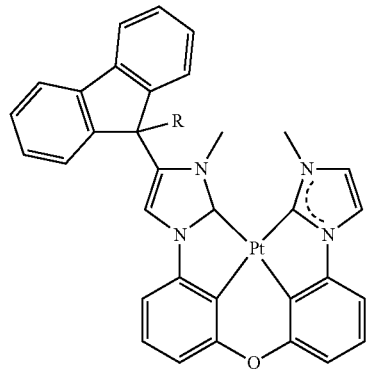
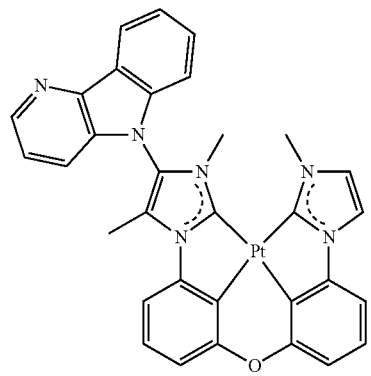
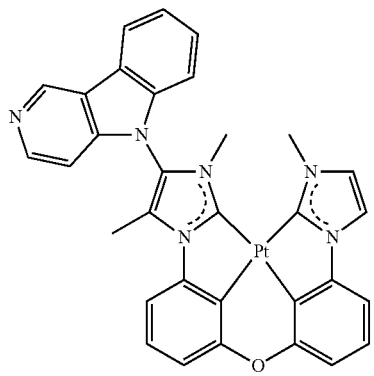
Structures 26
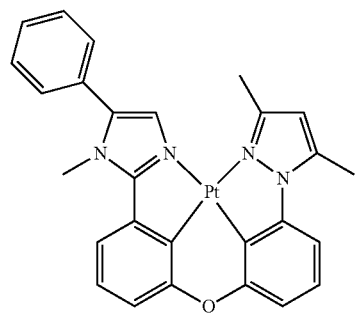
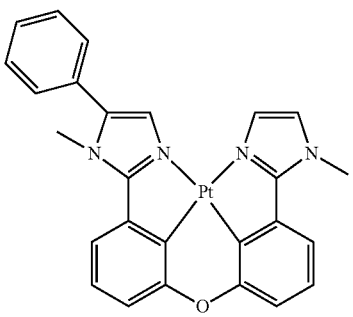
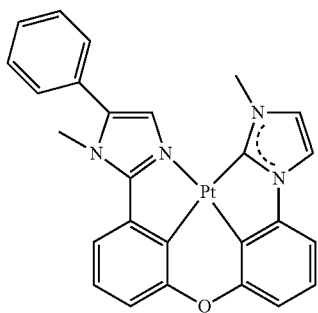
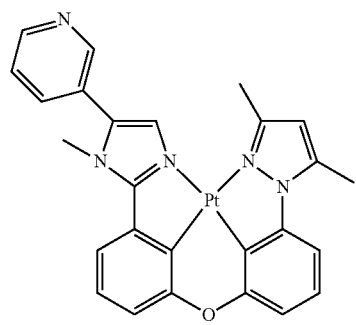
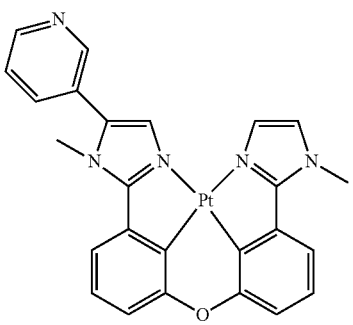
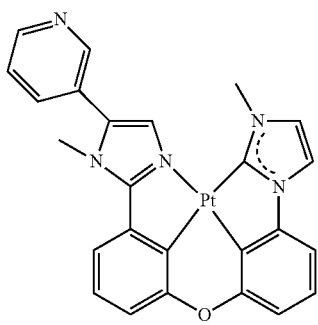

303        -continued        304
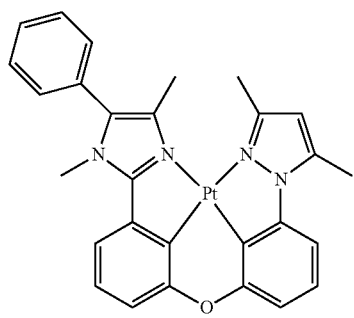 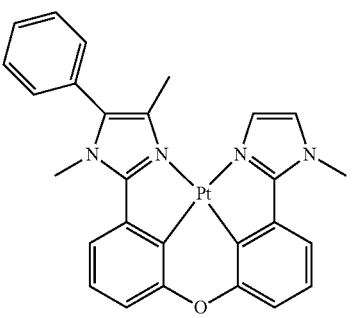 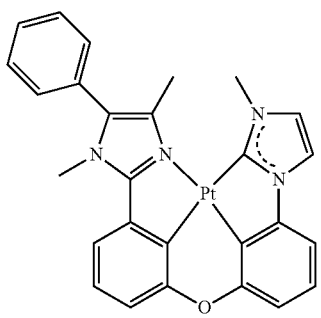
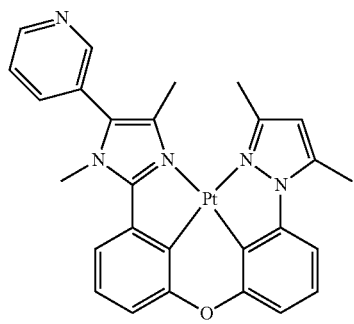 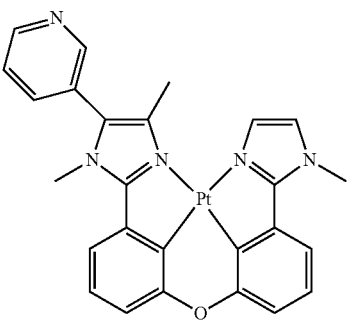 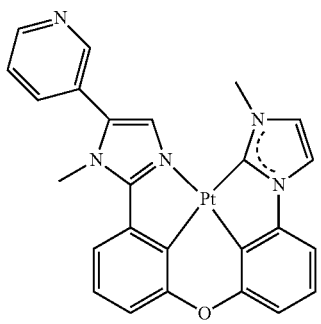
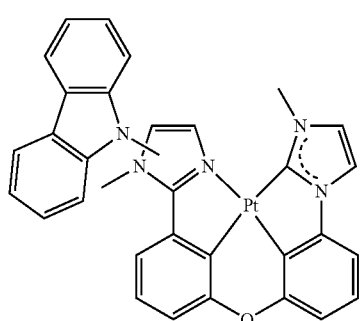 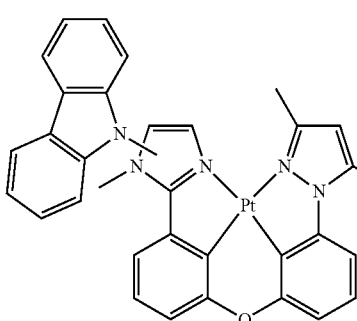 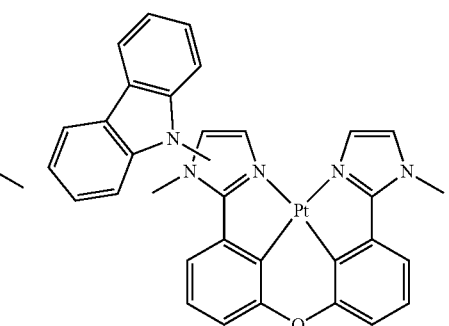
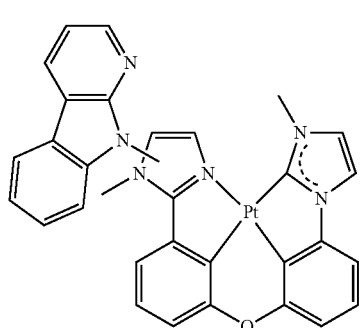 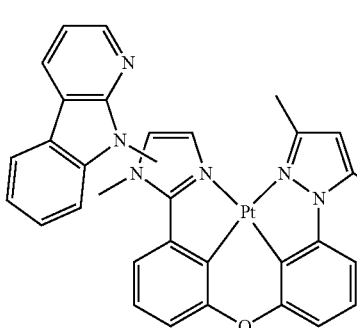 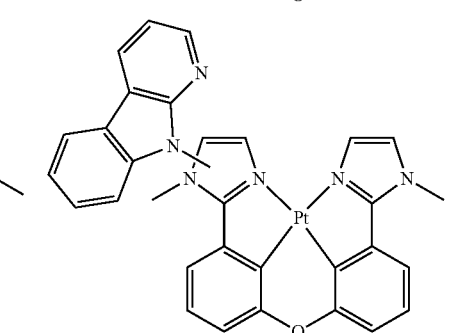
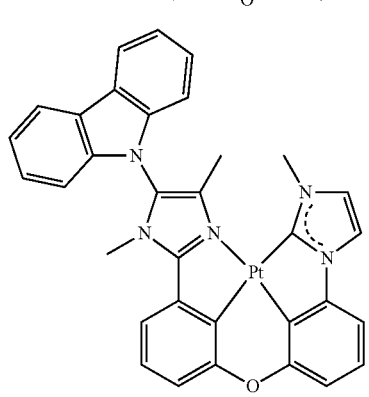 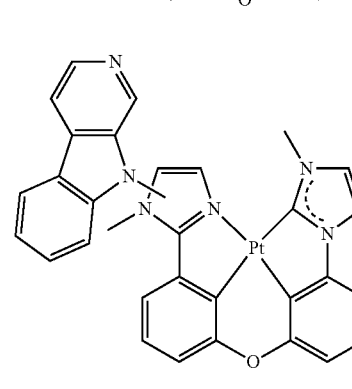 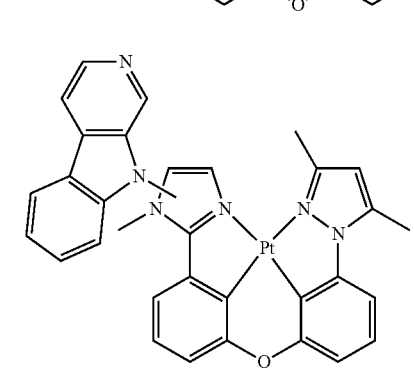

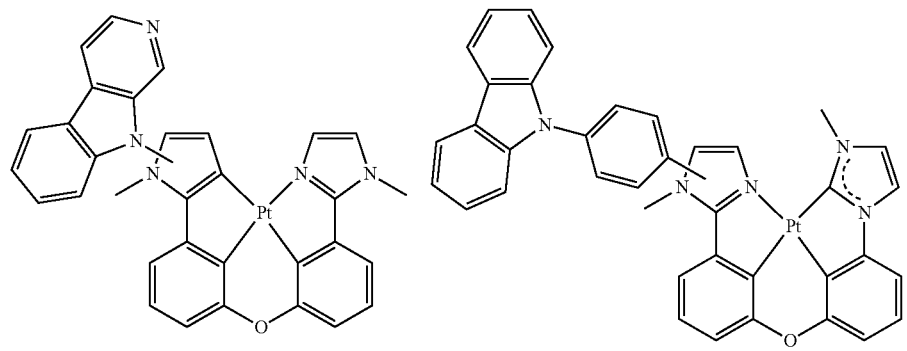
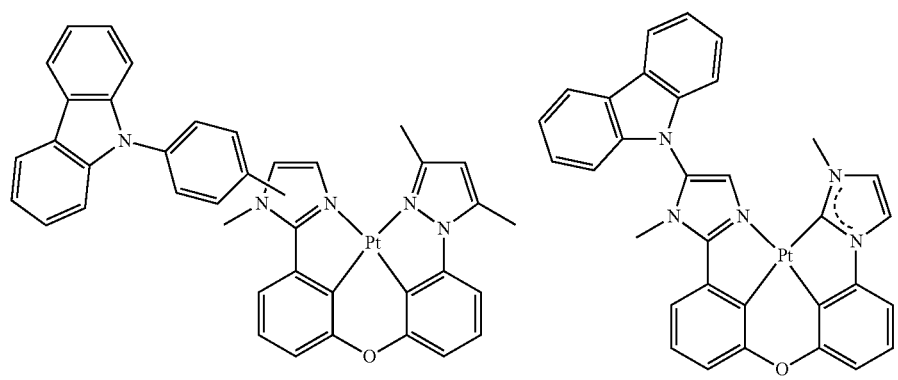
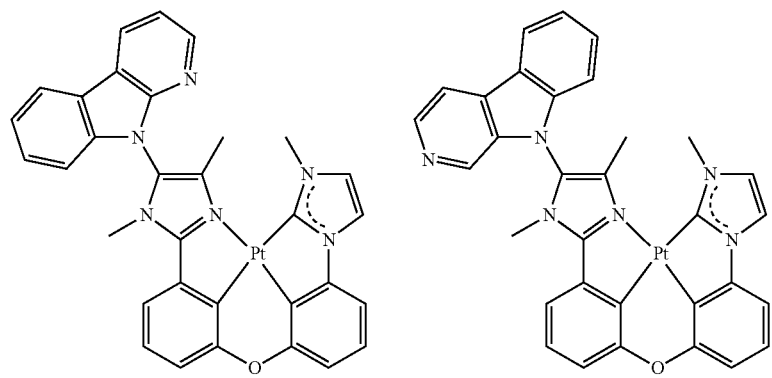
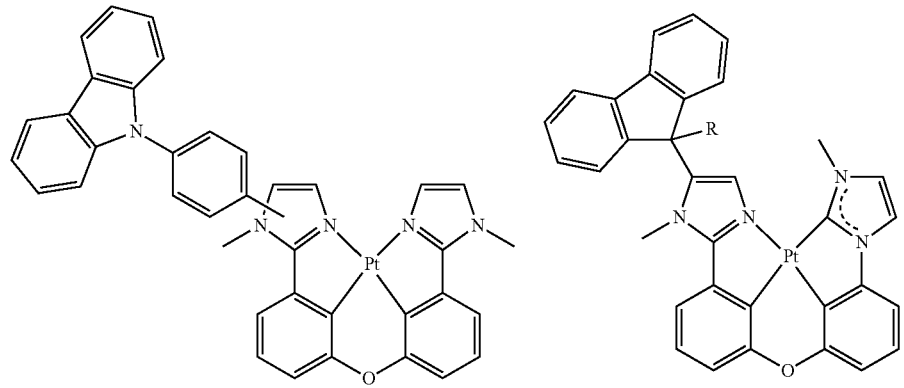

-continued
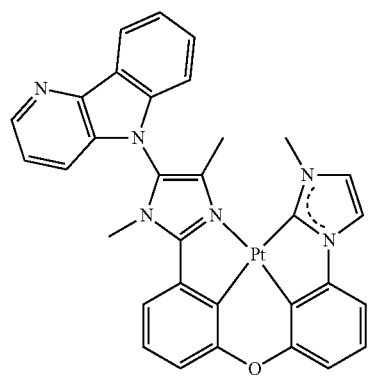
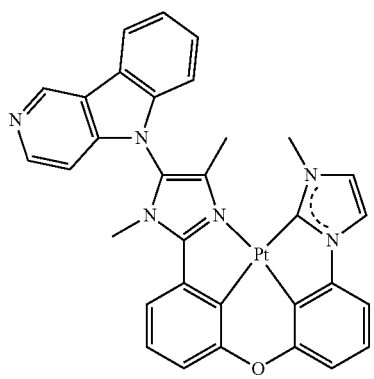
Structures 27
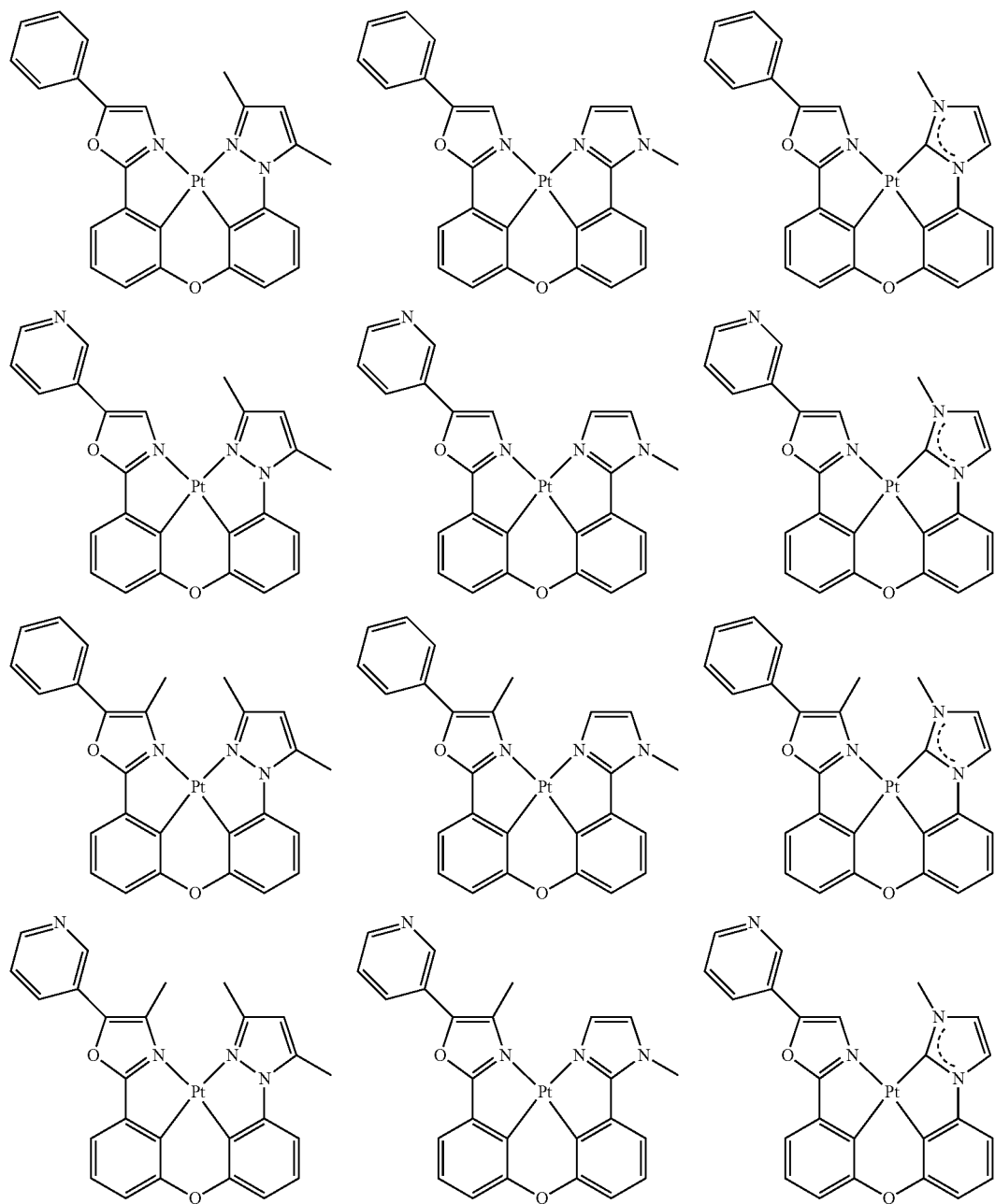

-continued
| 309 | | 310 |
|---|---|---|
| 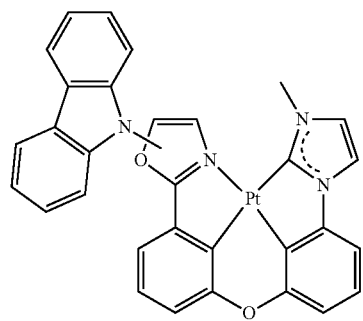 | 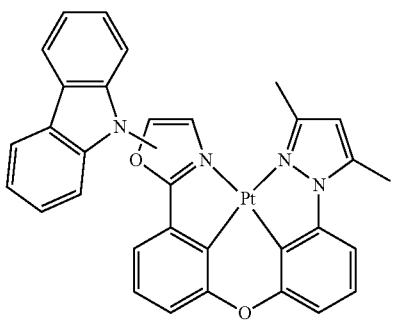 | 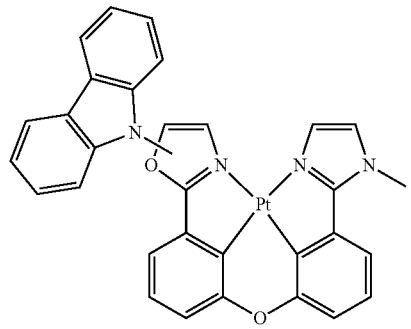 |
| 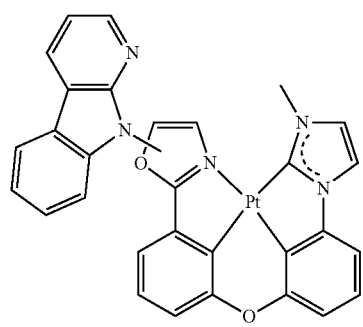 | 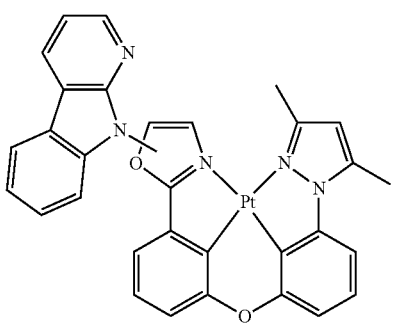 | 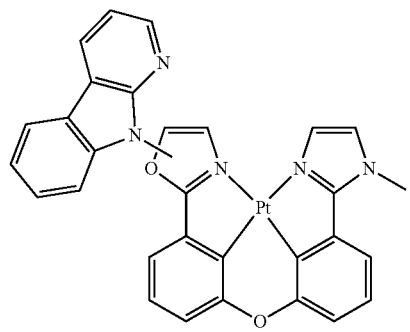 |
| 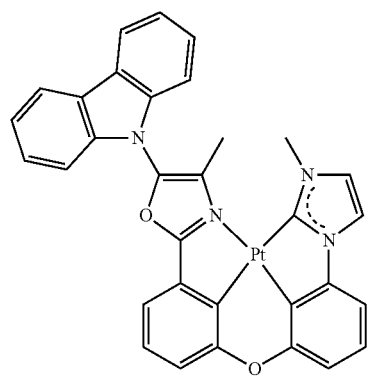 | 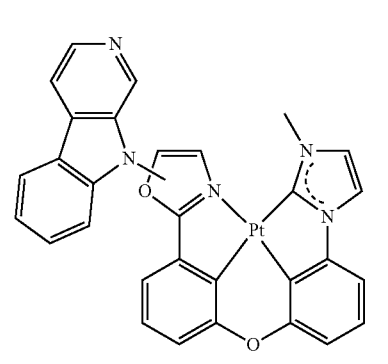 | 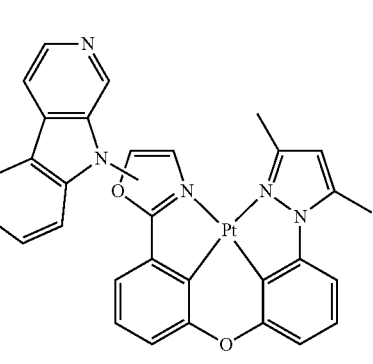 |
| 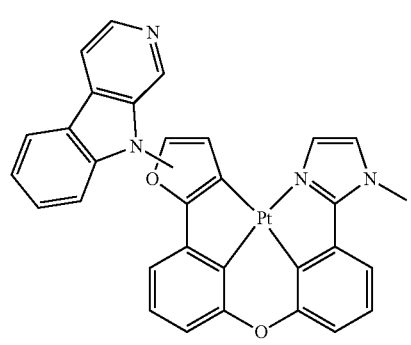 | 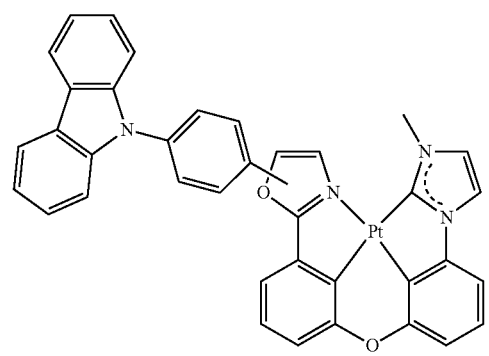 | |

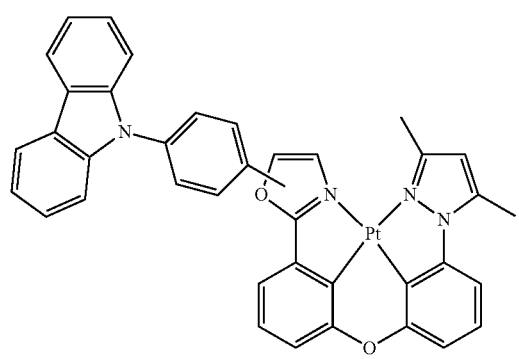
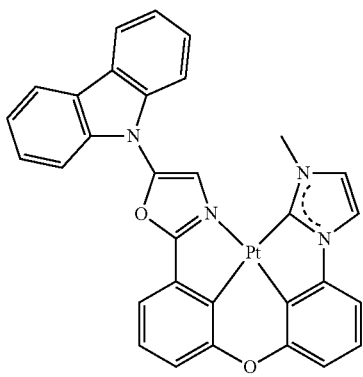
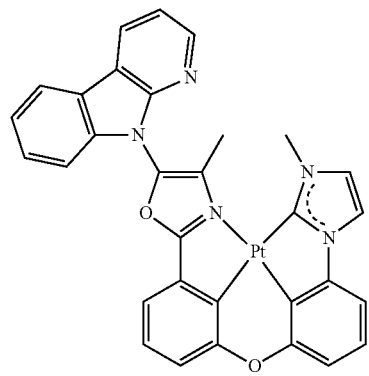
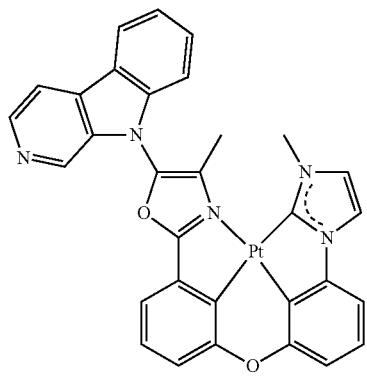
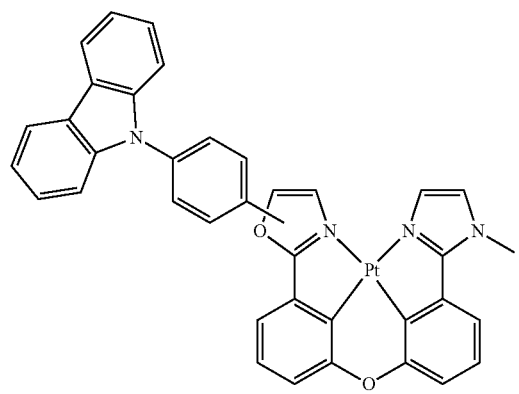
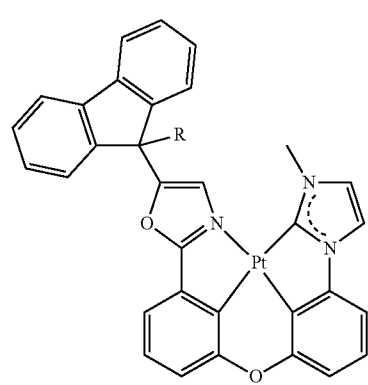
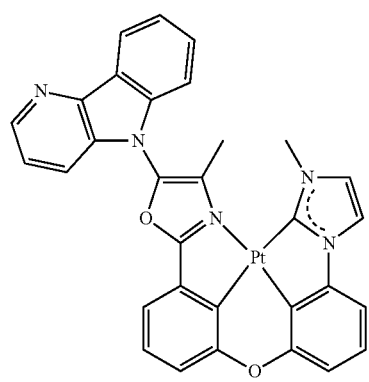
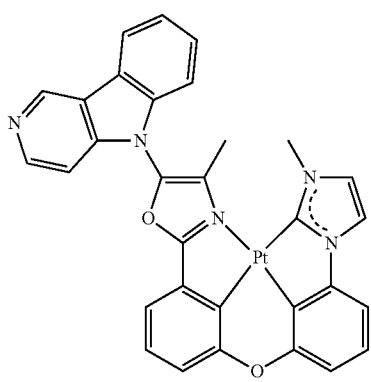

Structures 28
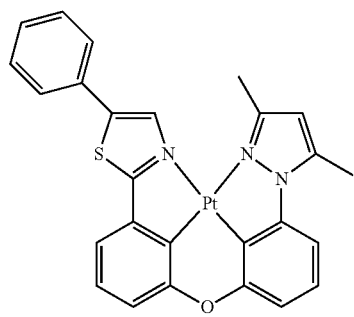
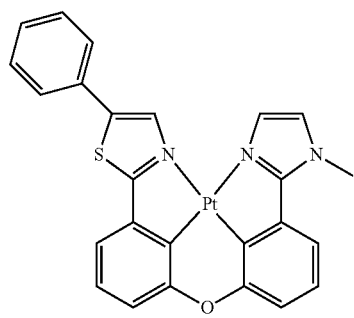
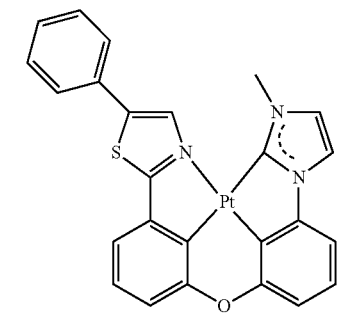
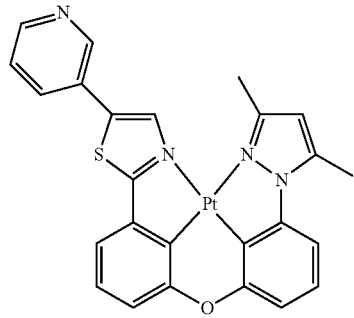
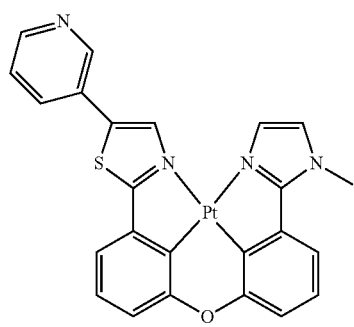
-continued
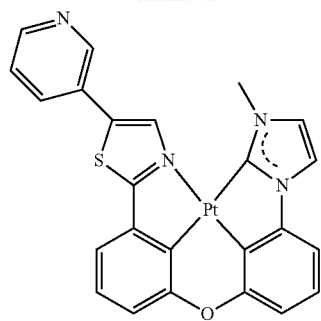
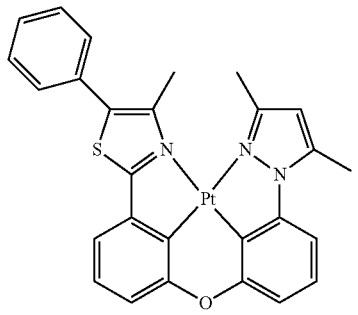
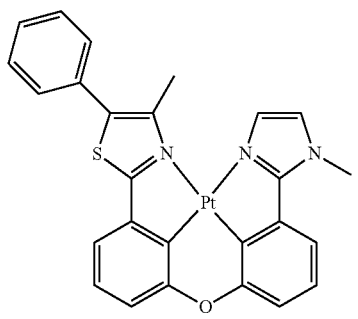
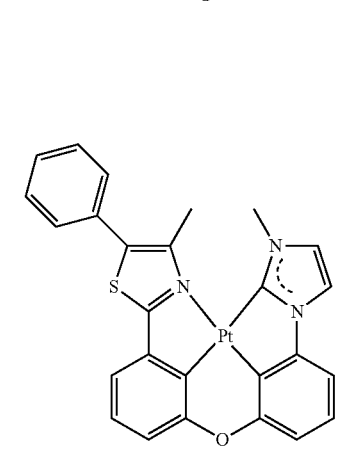
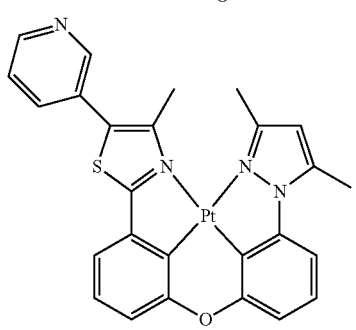

315
-continued
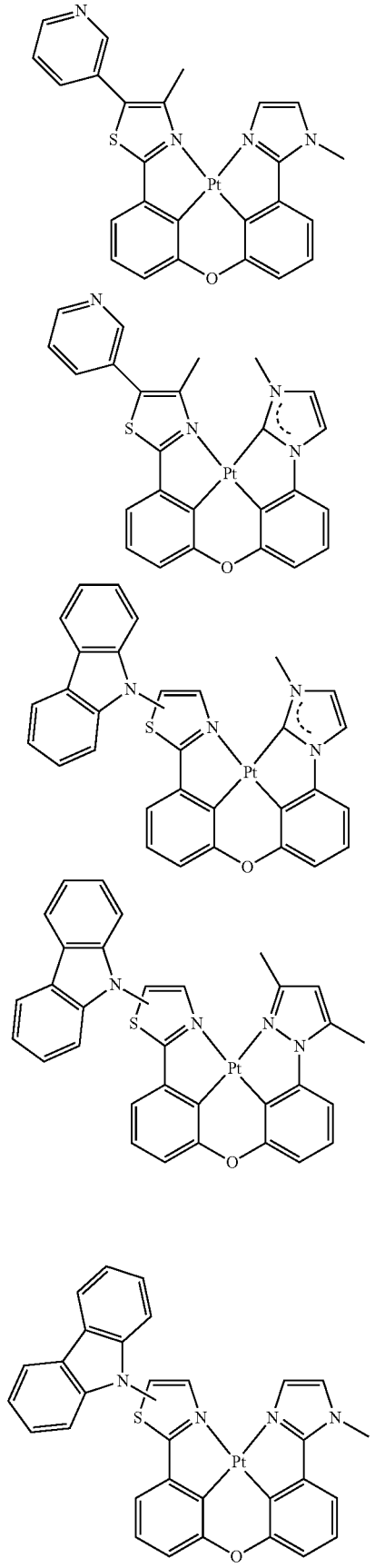
316
-continued
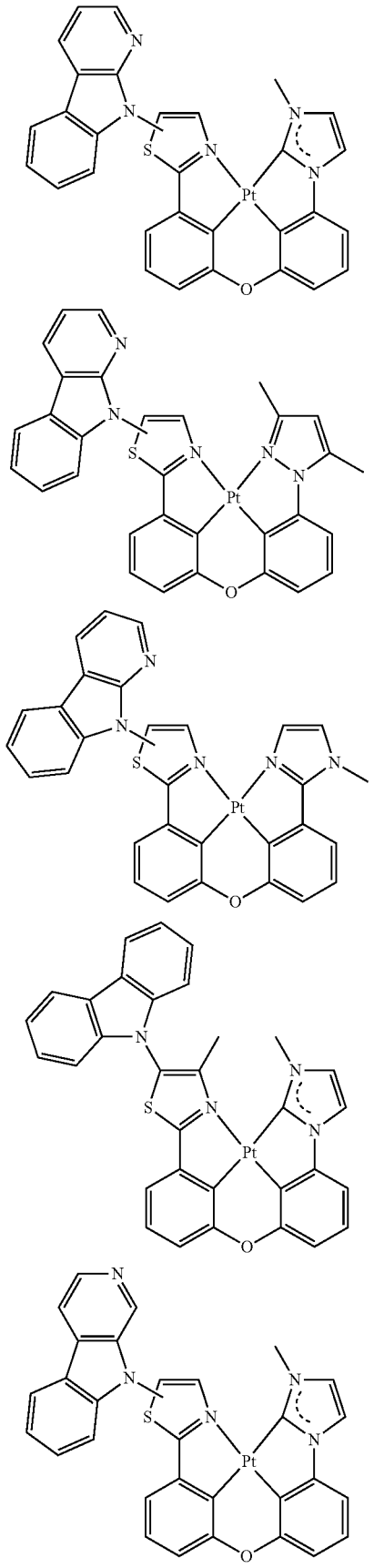

317
-continued
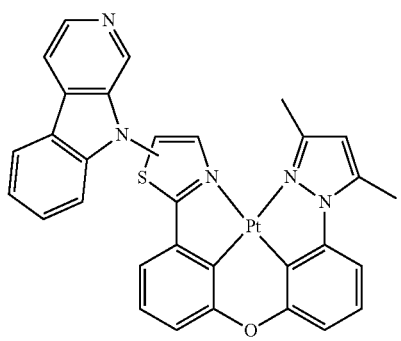
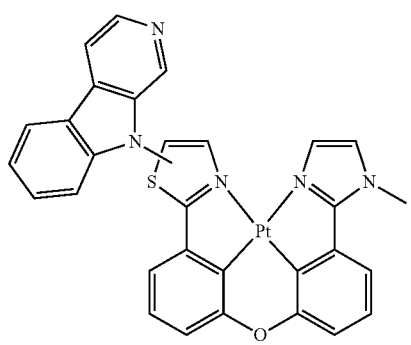
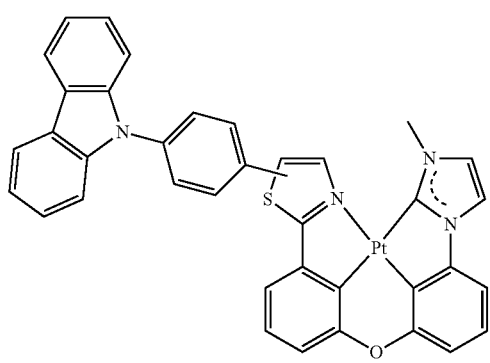
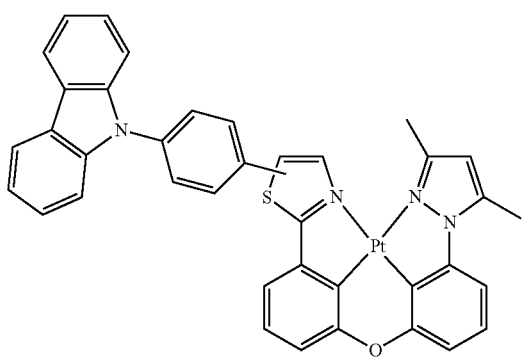
318
-continued
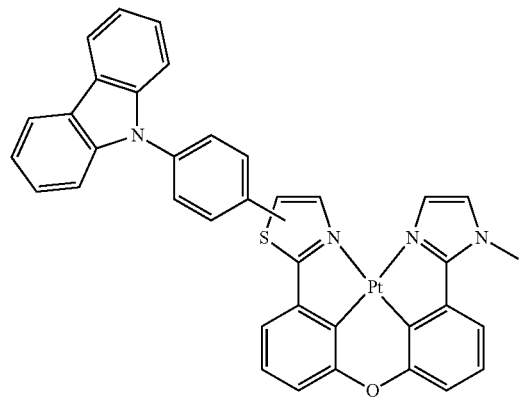
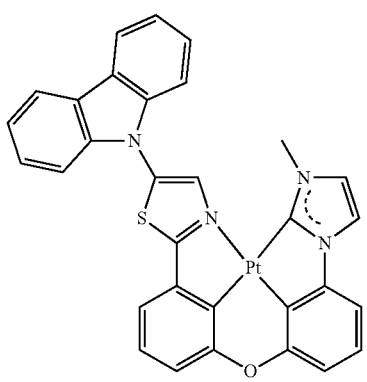
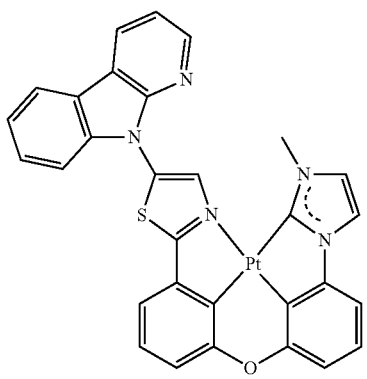
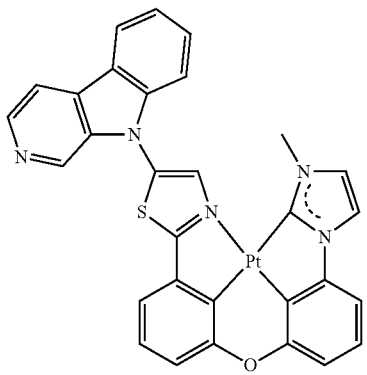

319
-continued
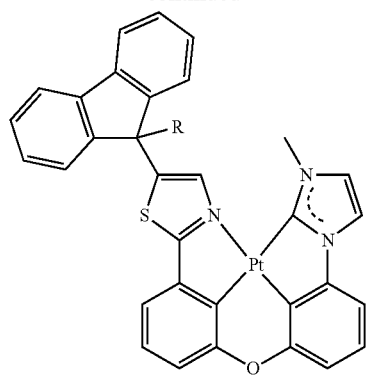
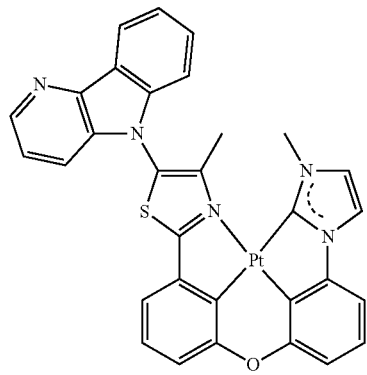
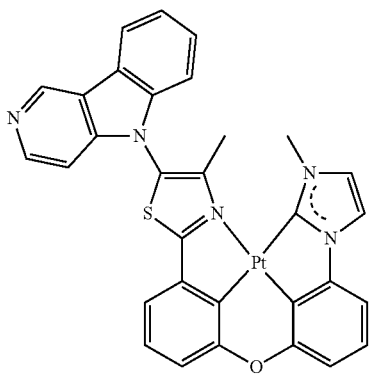
Structures 29
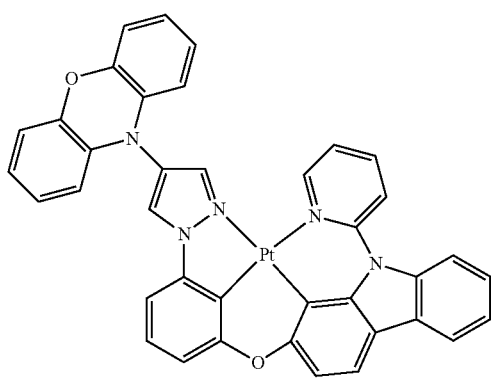
320
-continued
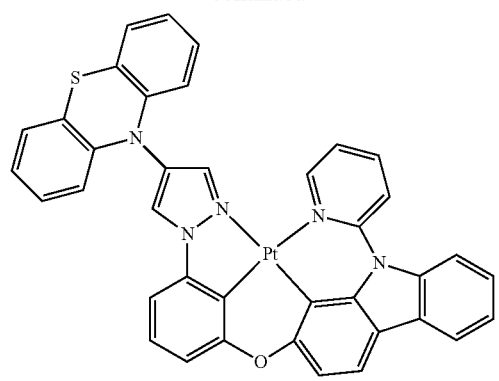
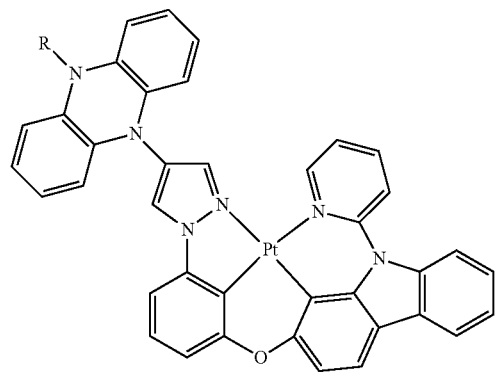
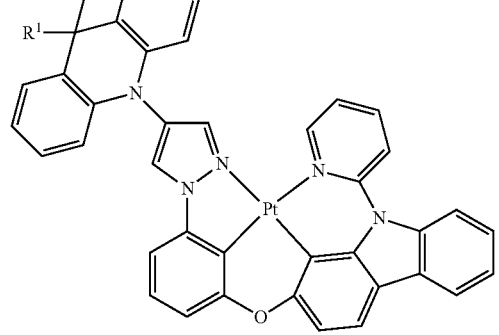
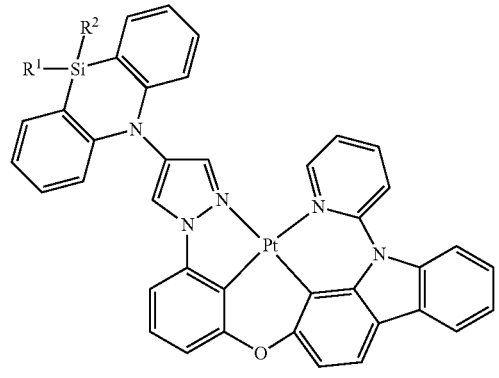

321
-continued
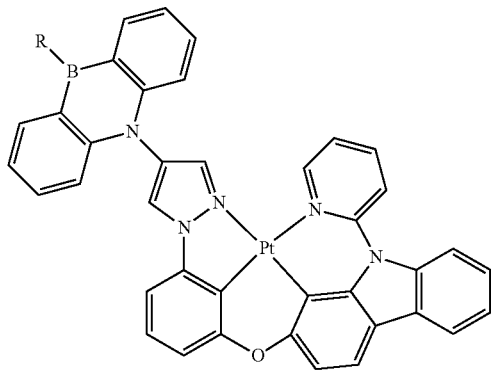
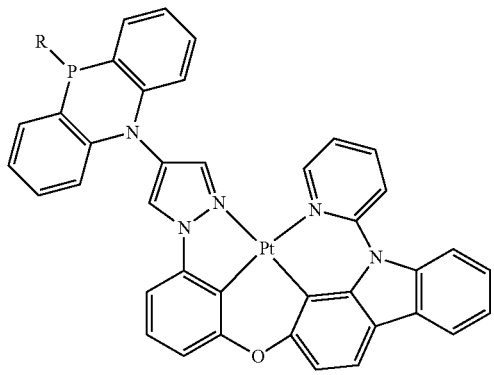
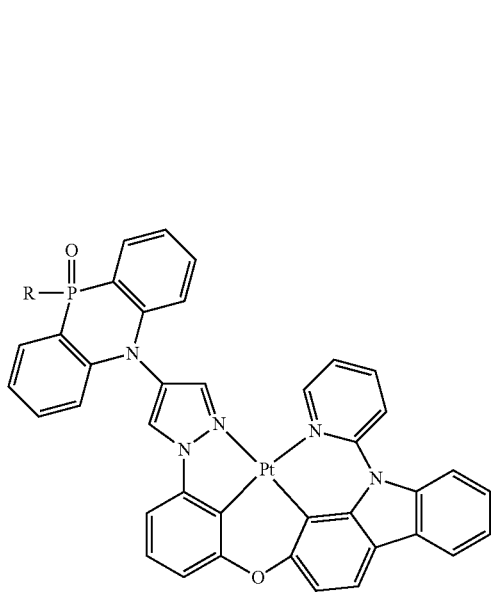
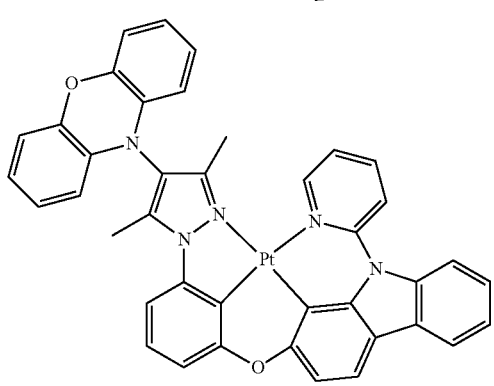
322
-continued
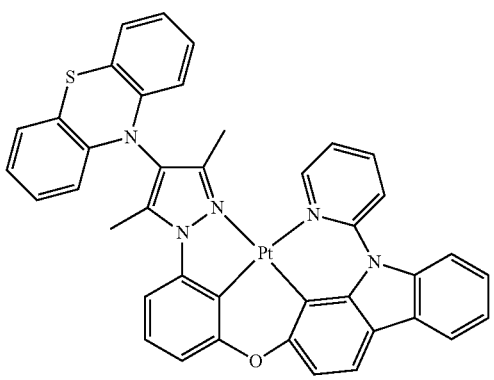
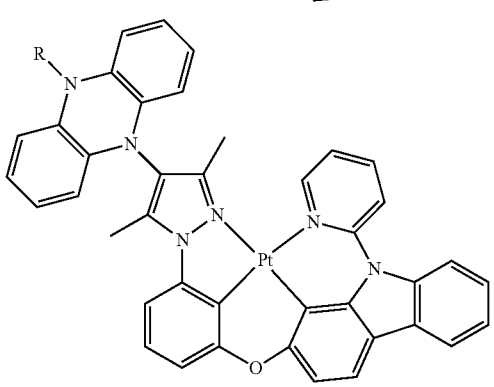
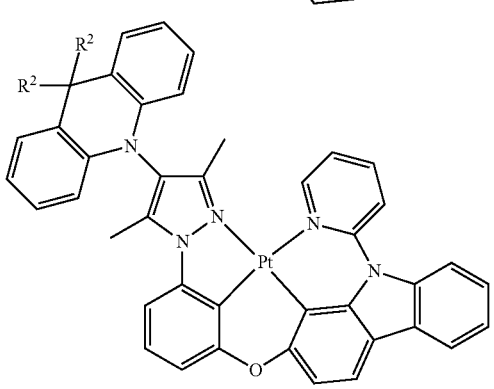
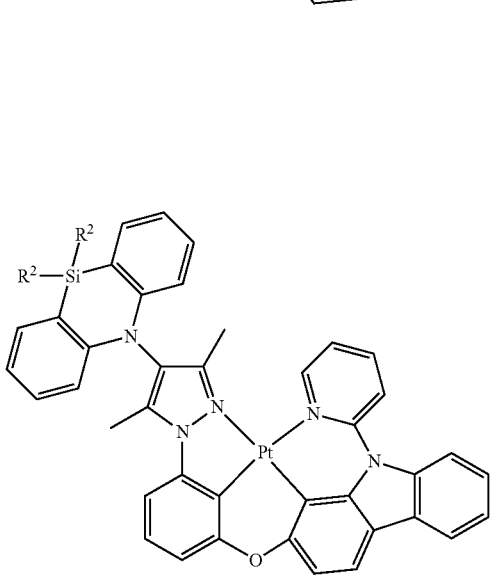

323
-continued
324
-continued
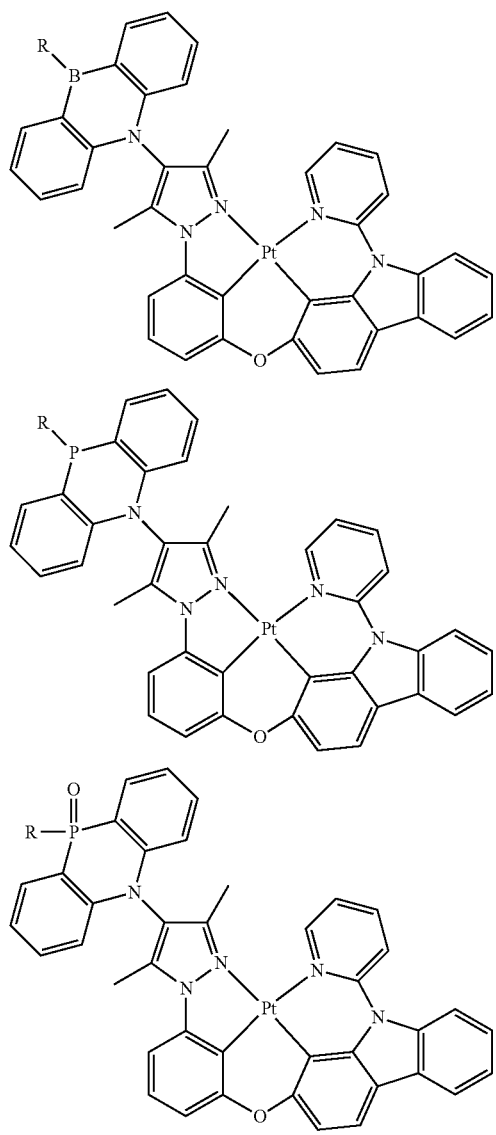
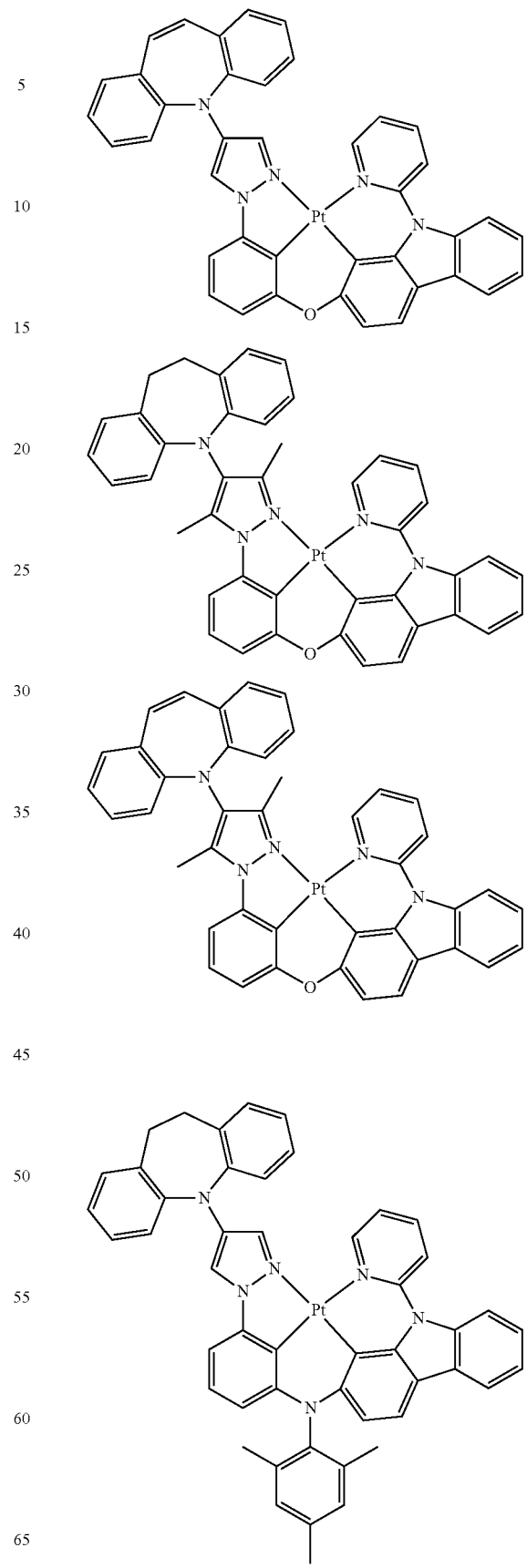

325
-continued
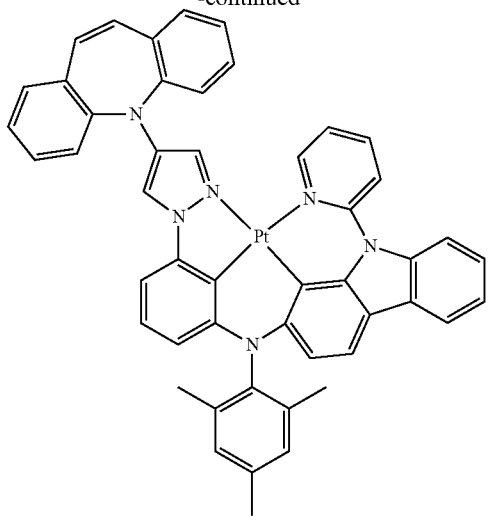

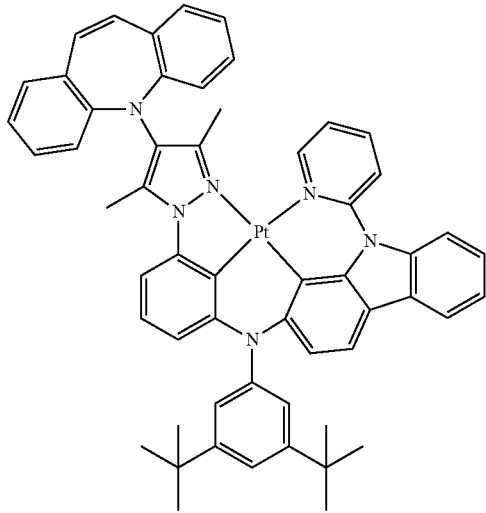
326
-continued
Structures 30
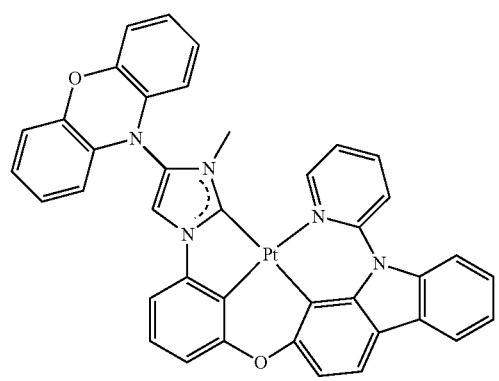
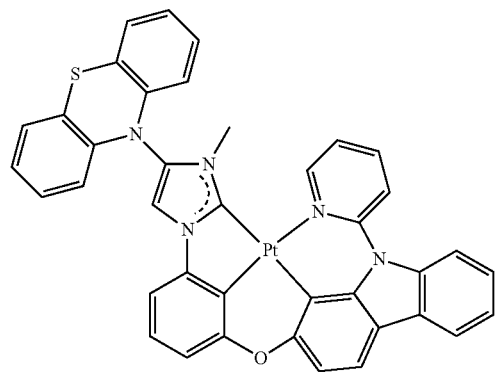
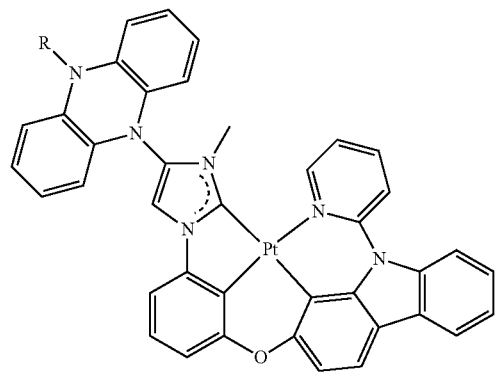
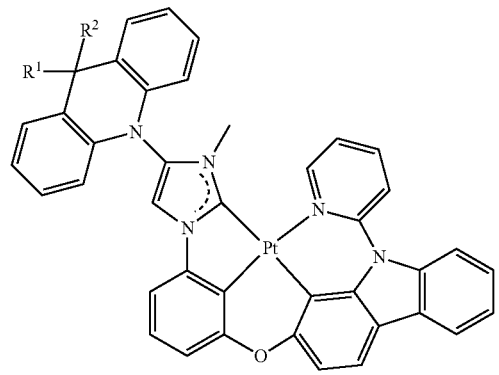

327
-continued
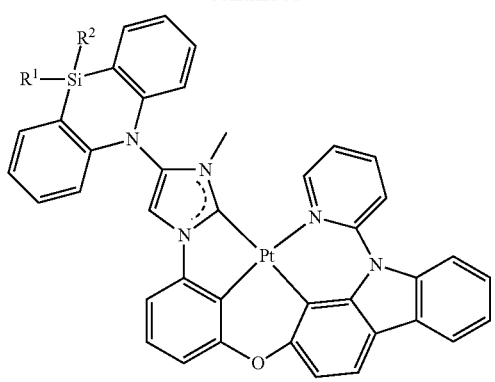
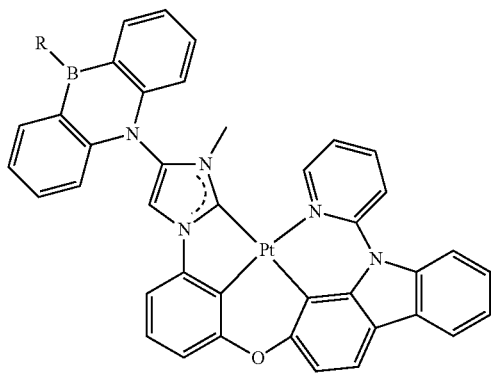
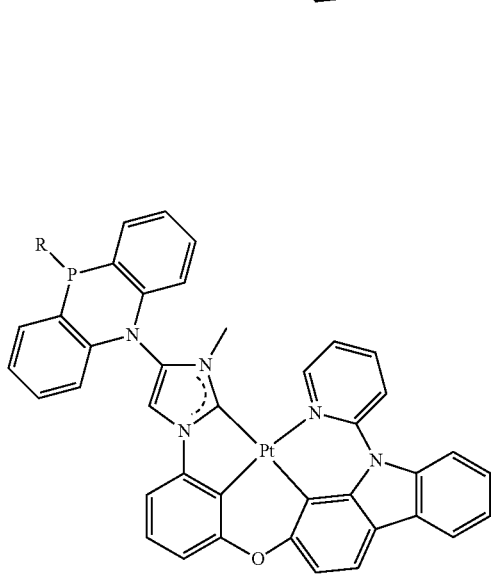
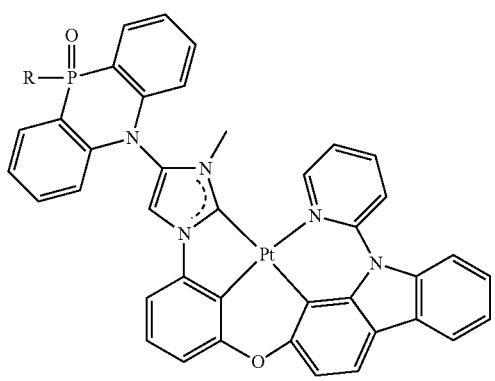
328
-continued
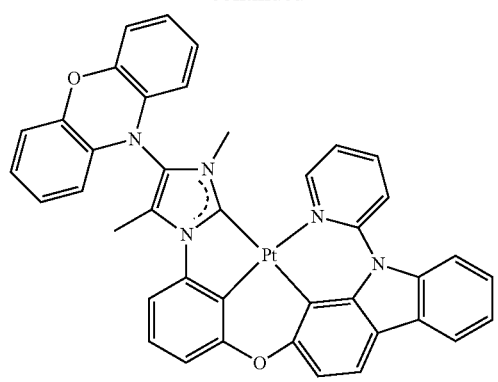
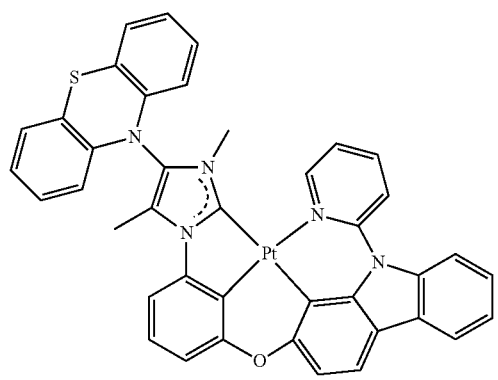
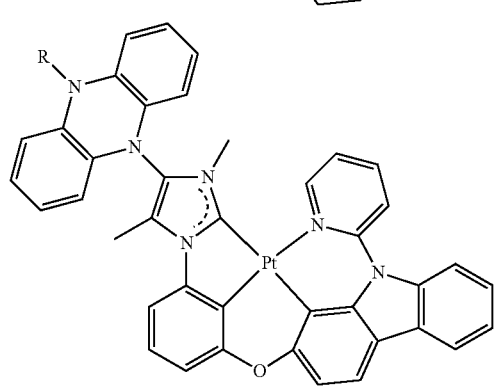
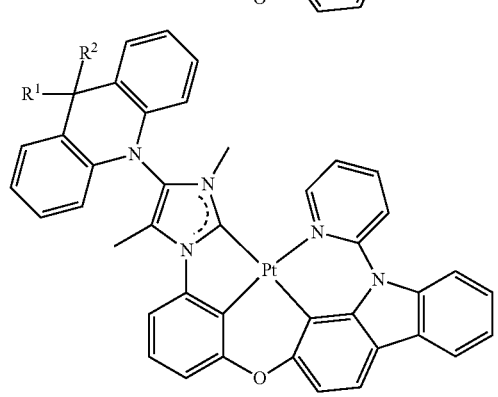

-continued
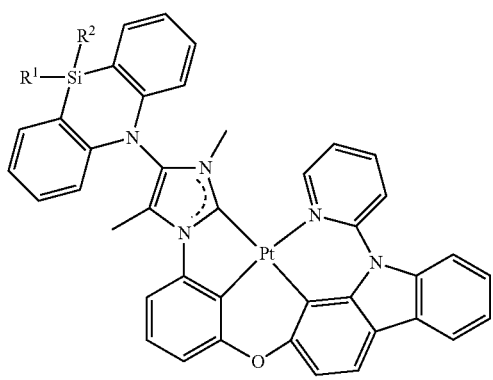
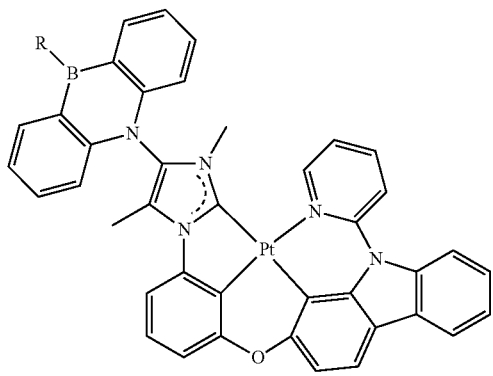
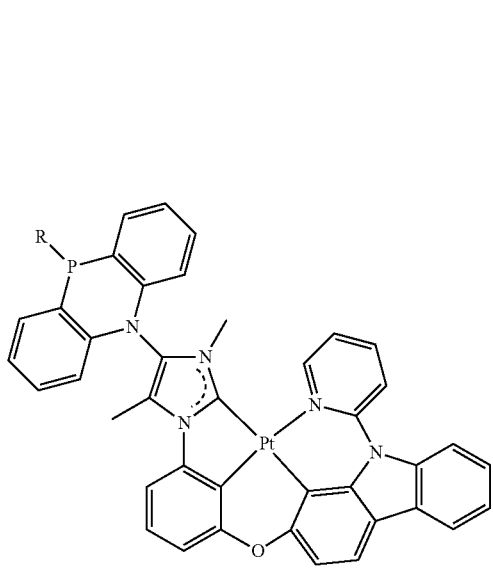
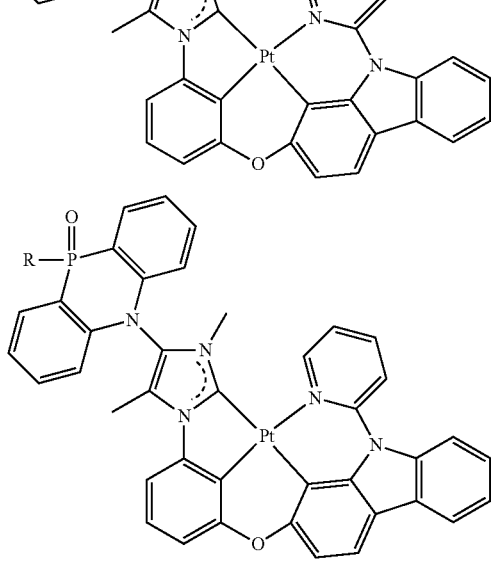
-continued
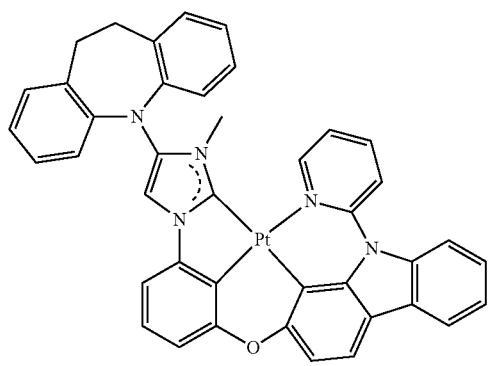
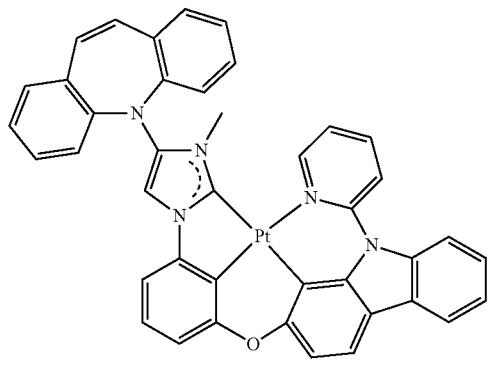
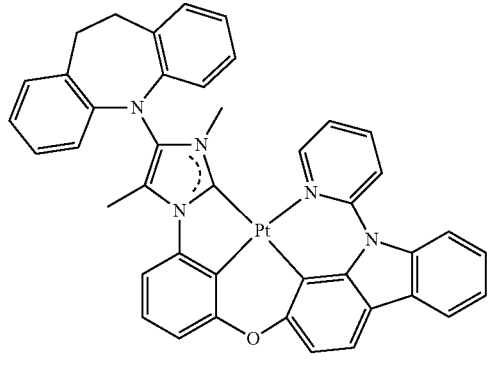
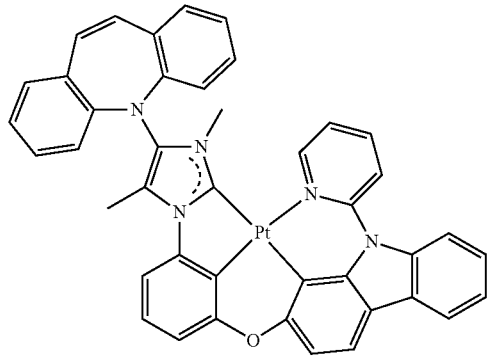

| 331 -continued | 332 -continued |
|---|---|
| 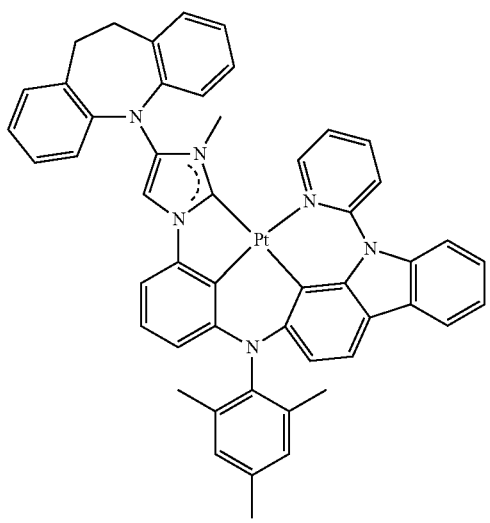 | 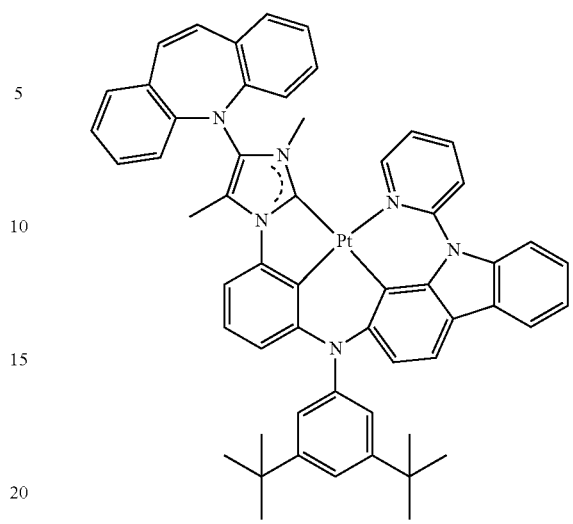 |
| 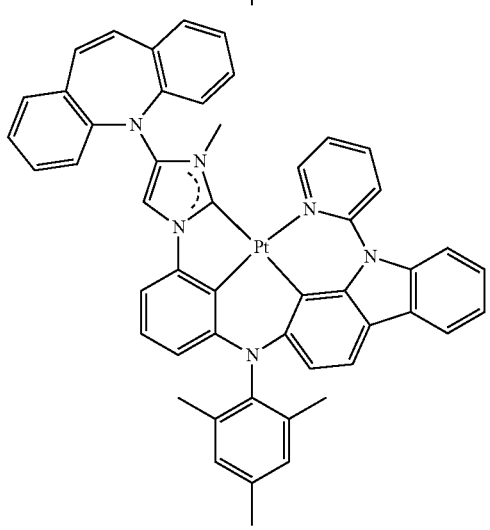 | Structures 31<br>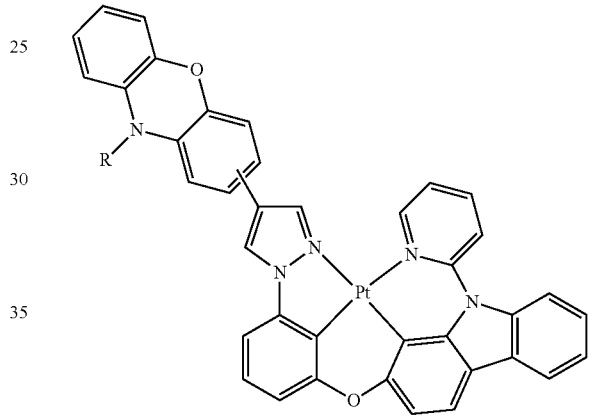 |
| 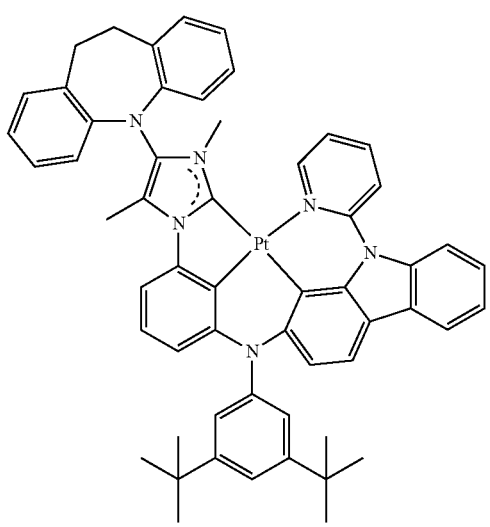 | 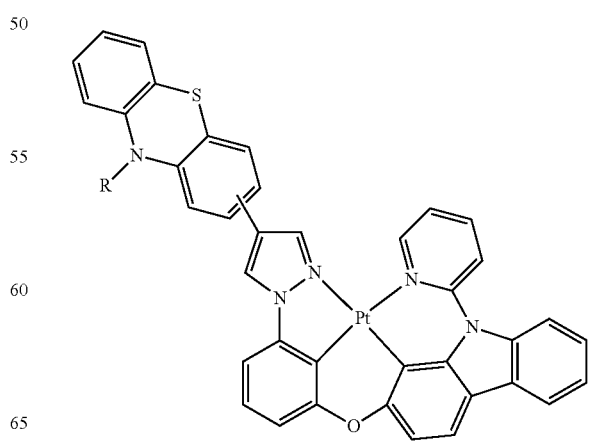 |

333
-continued
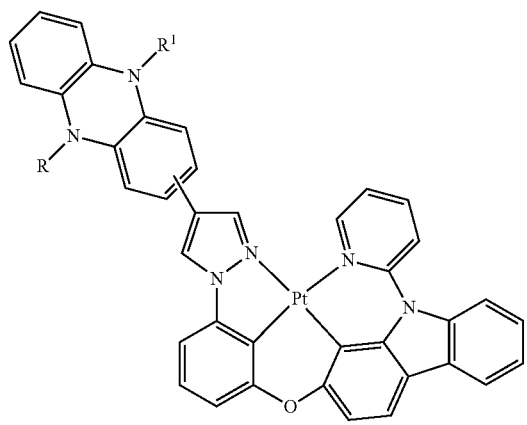
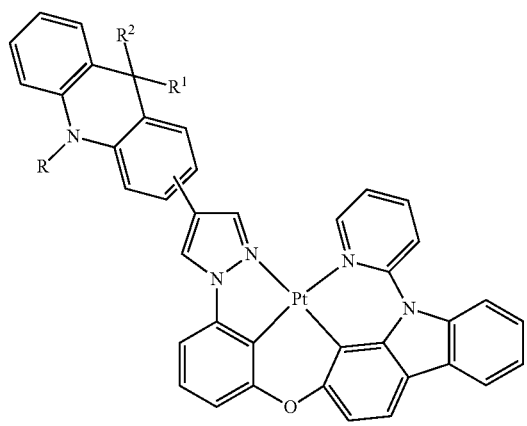
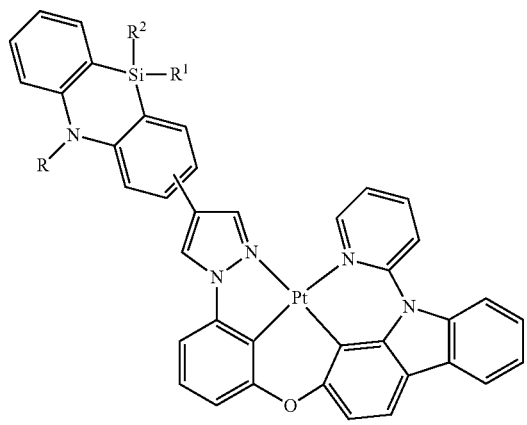
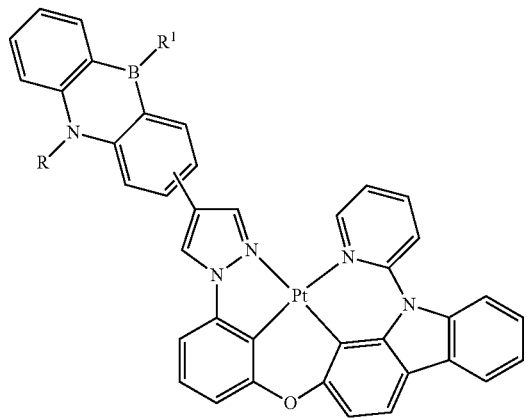
334
-continued
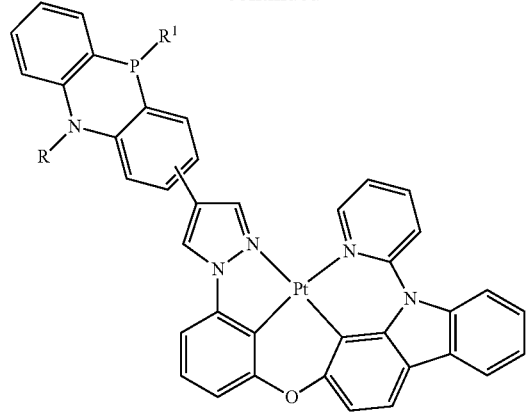
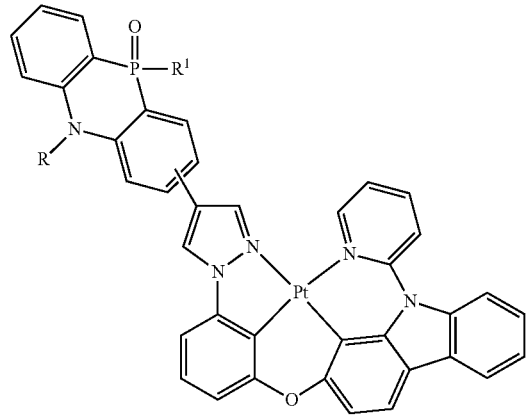
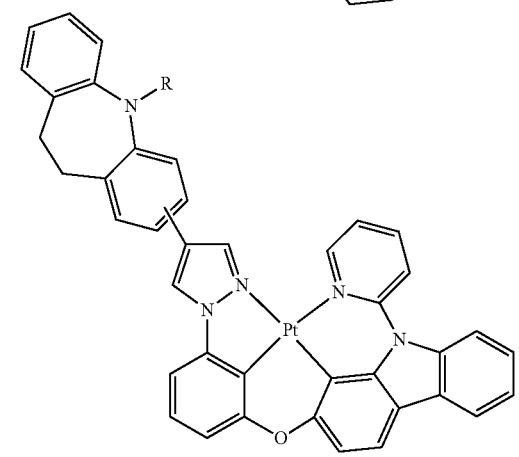
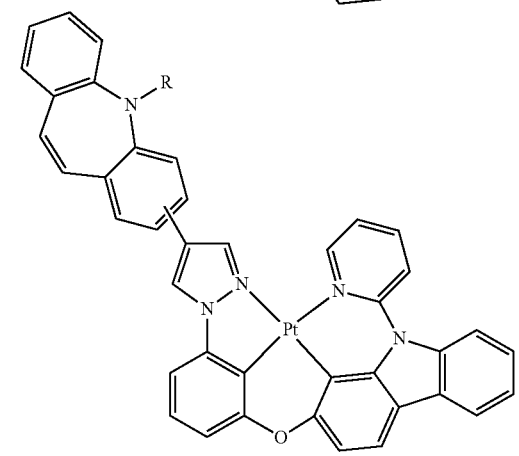

335
-continued
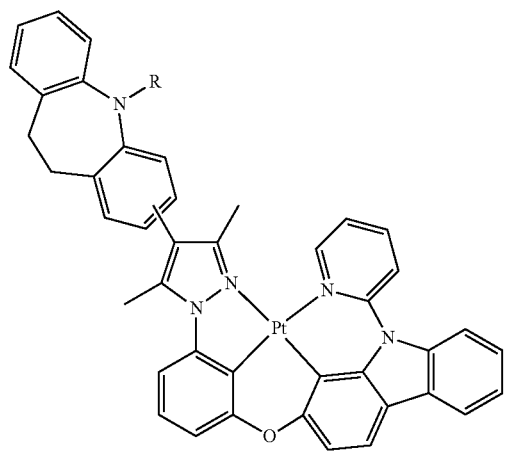
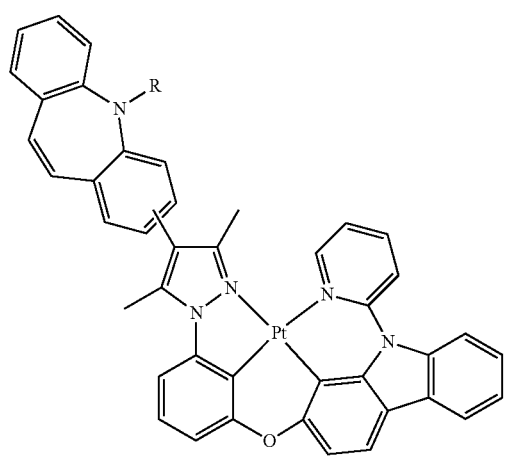
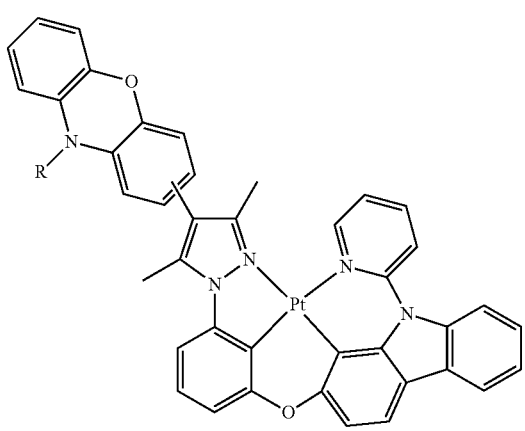
336
-continued
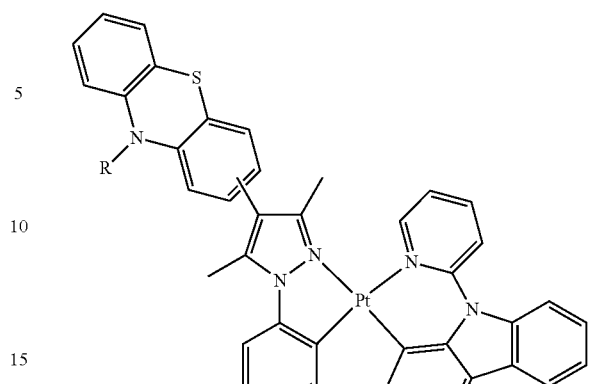
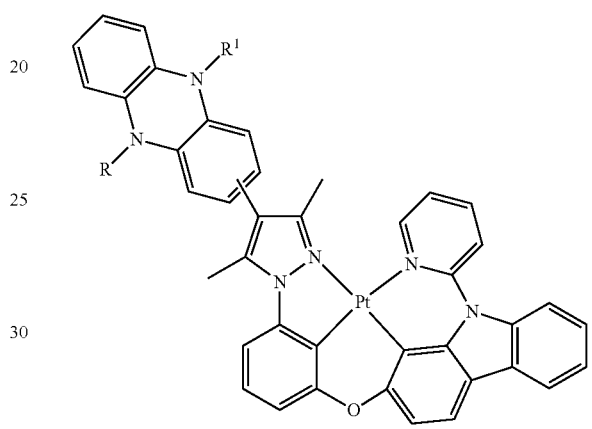
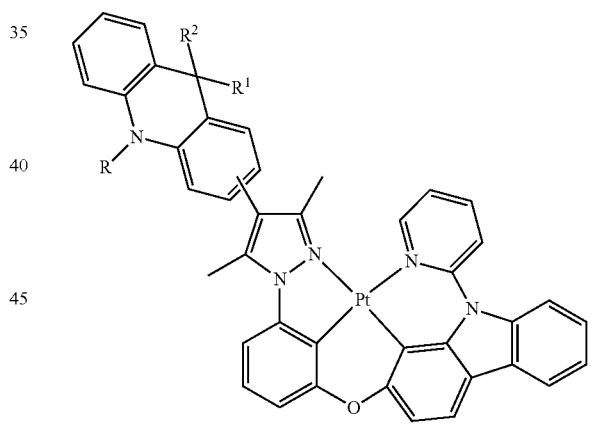
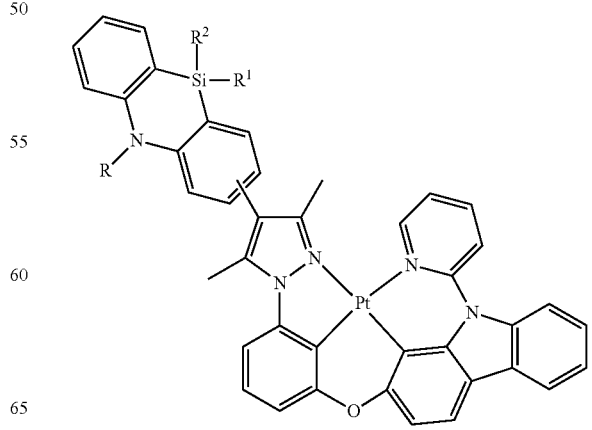

337
-continued
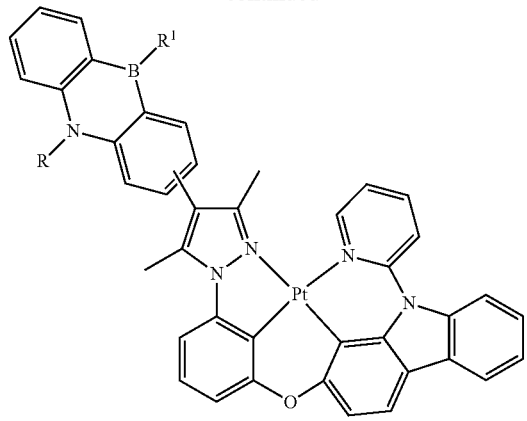
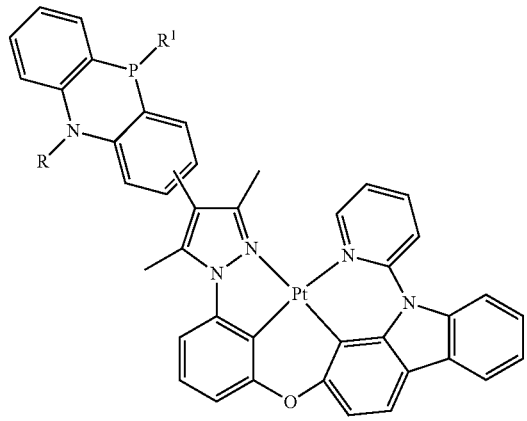
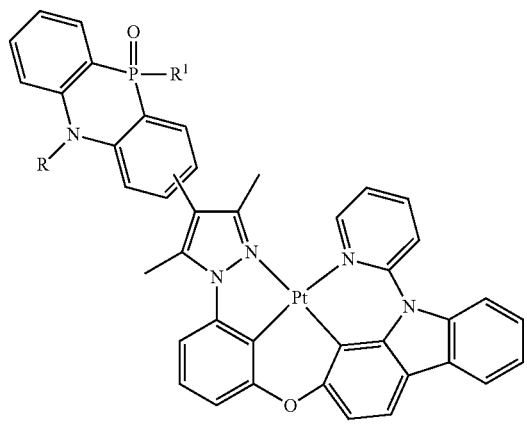
Structures 32
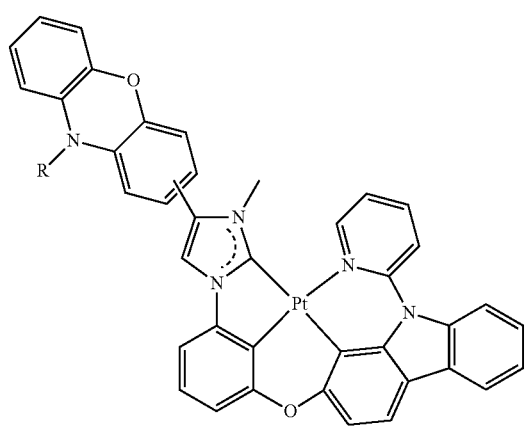
338
-continued
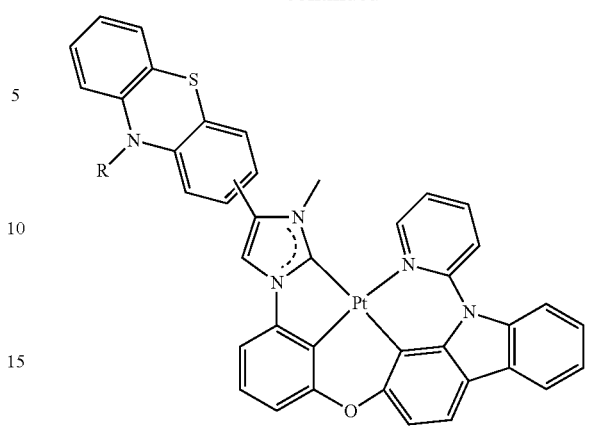
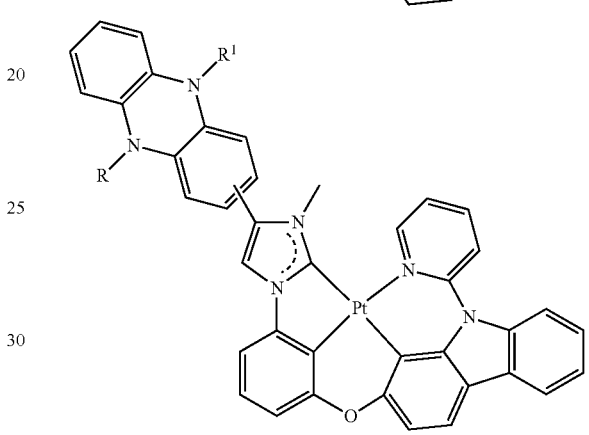
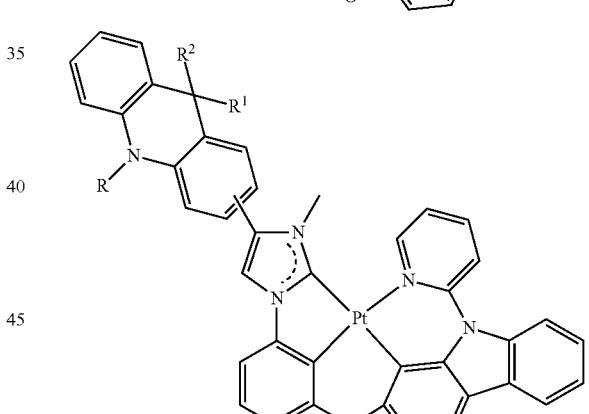
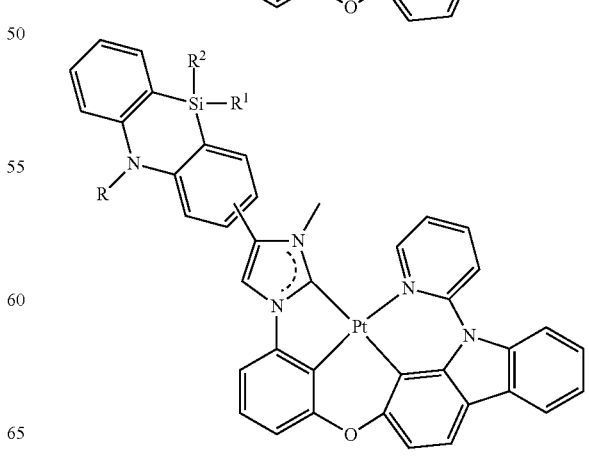

339
-continued
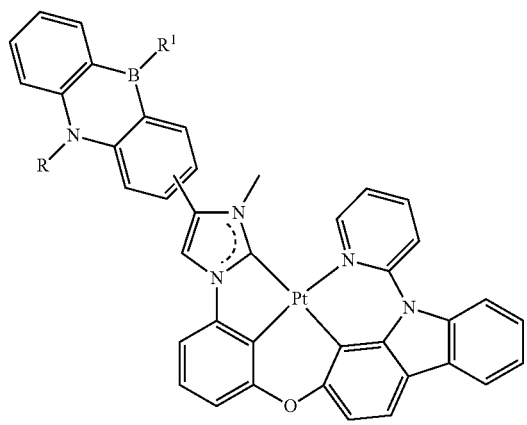
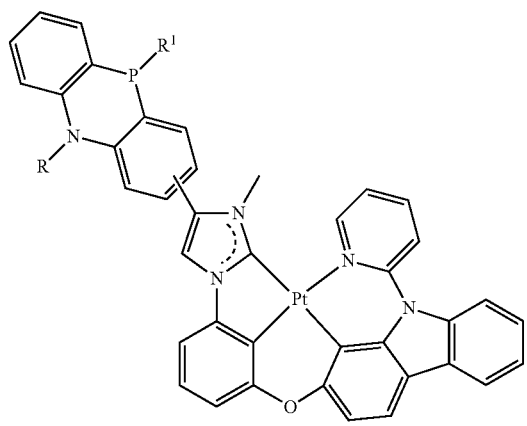
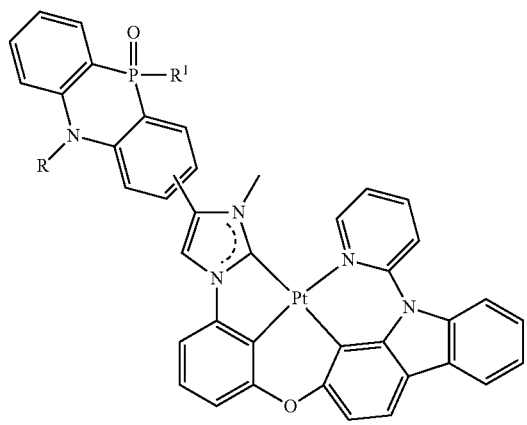
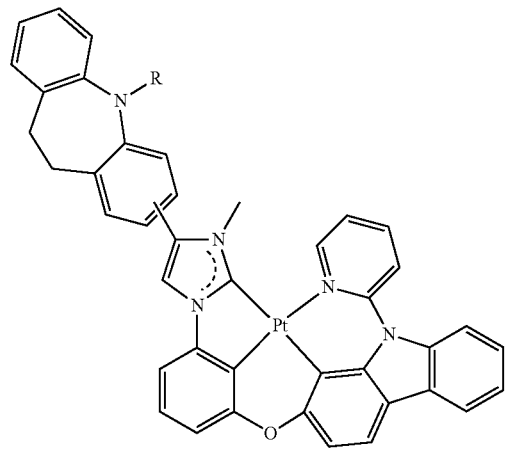
340
-continued
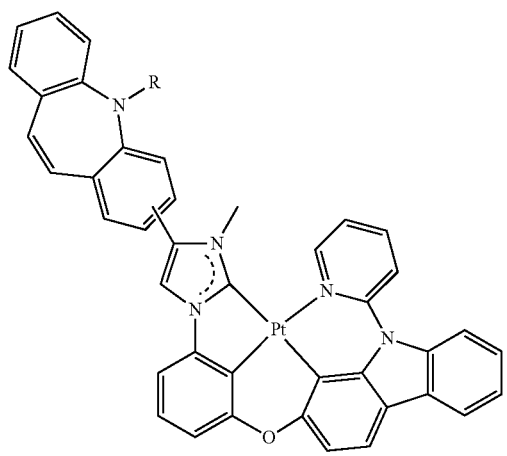
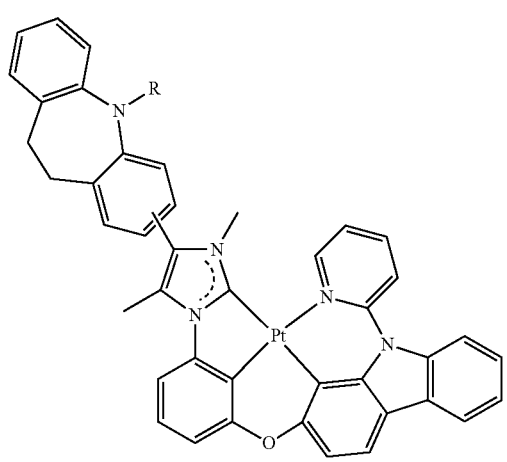
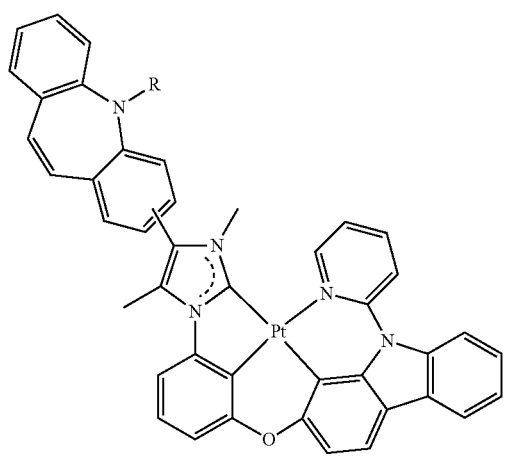

341
-continued
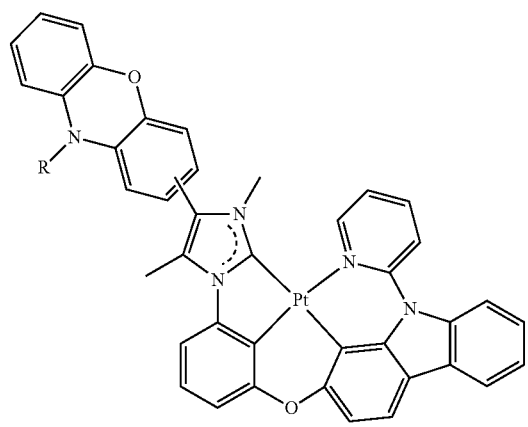
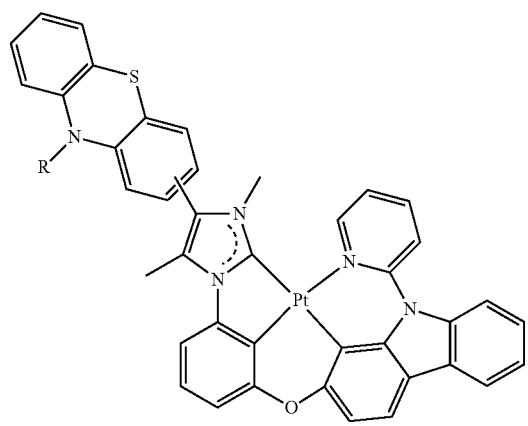
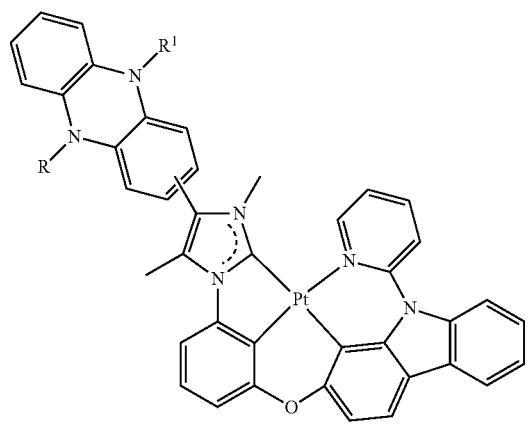
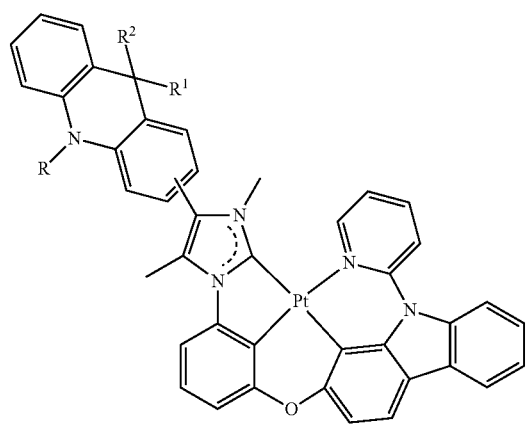
342
-continued
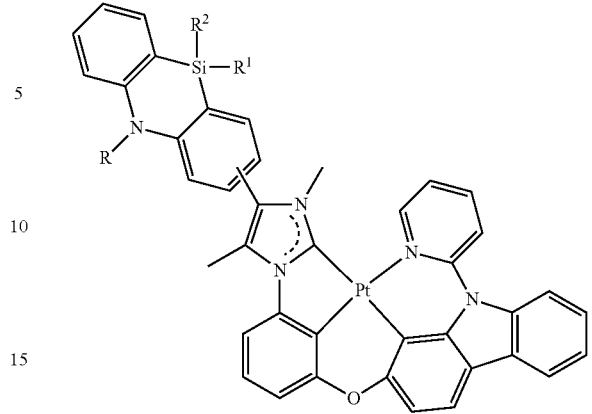
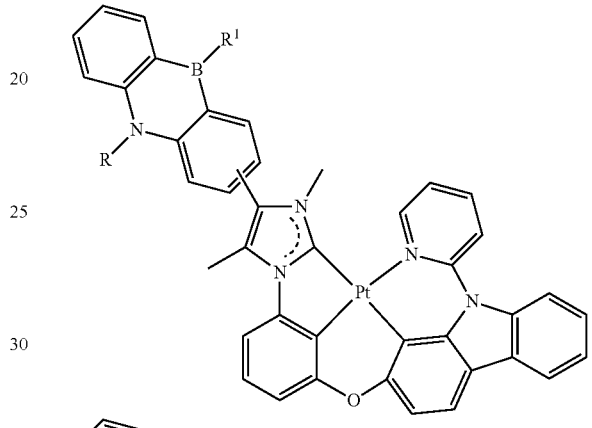

In one aspect, for any of the platinum complexes illustrated in this disclosure, Formula II can include one or more of the following structures depicted collectively below as Structures 1-60. In another aspect, structures of Formula II can also include other structures or portions thereof not specifically recited herein, and the present disclosure is not intended to be limited to those structures or portions thereof specifically recited.
Structures 1
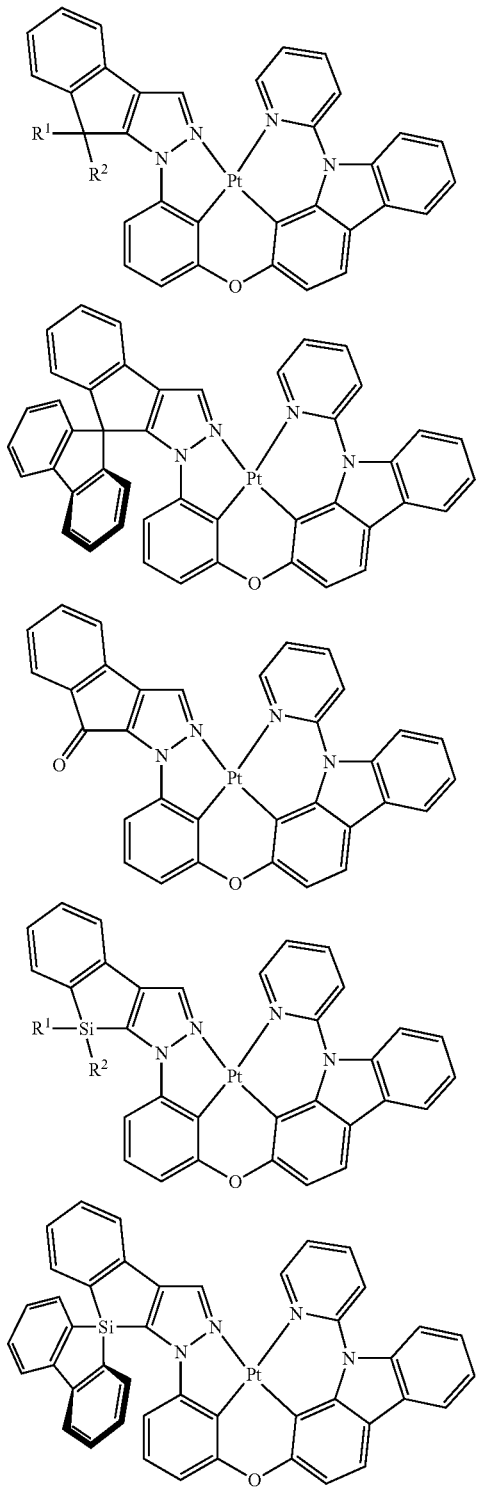
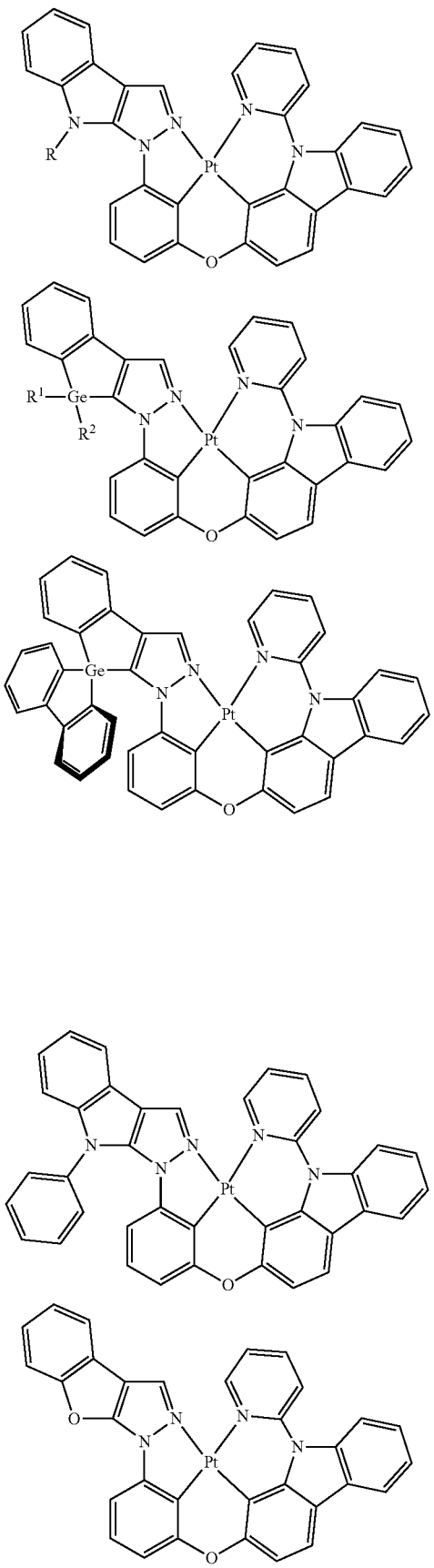

345
-continued
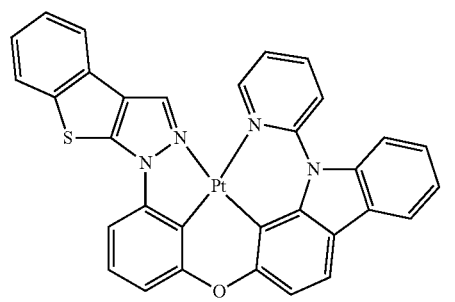
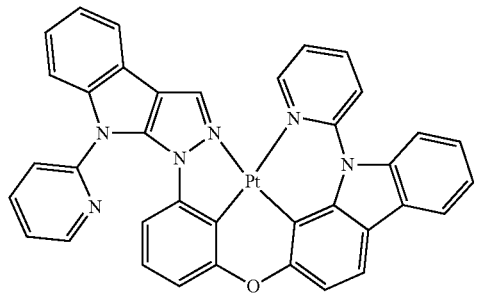
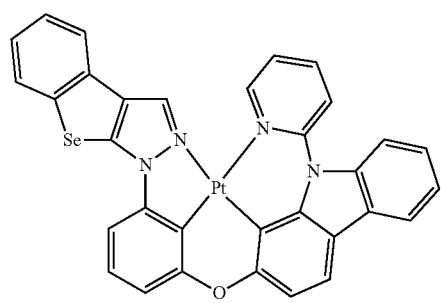
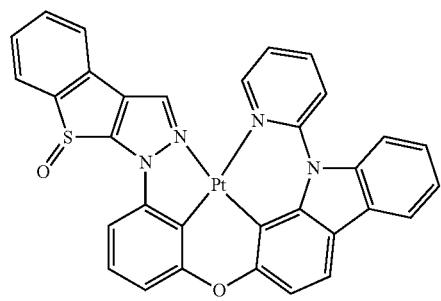
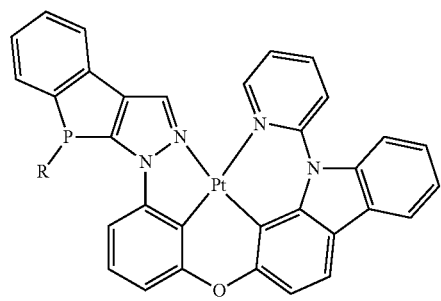
346
-continued
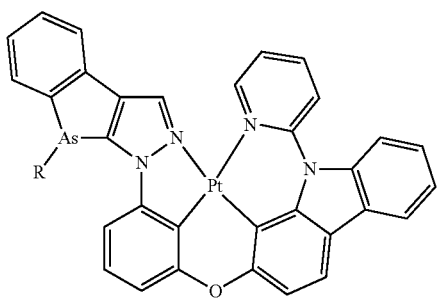
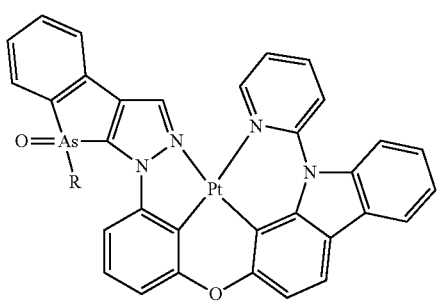
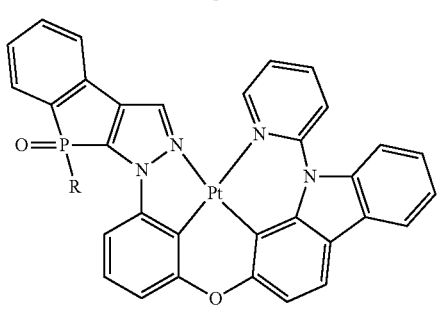
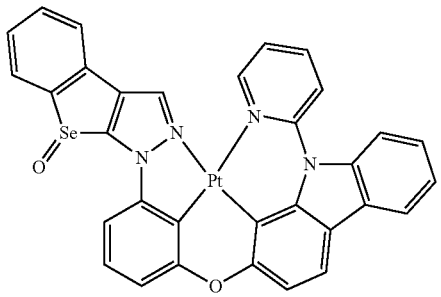
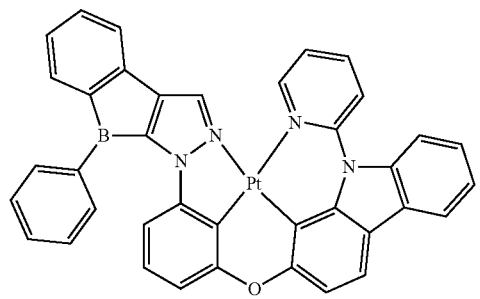

347
-continued
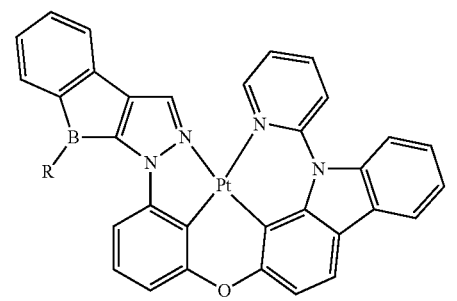
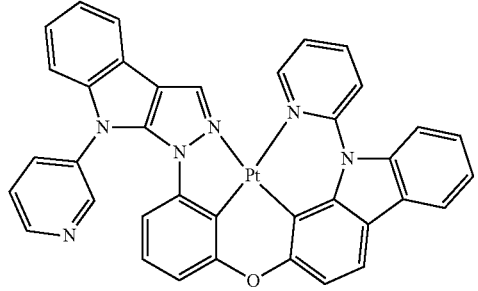
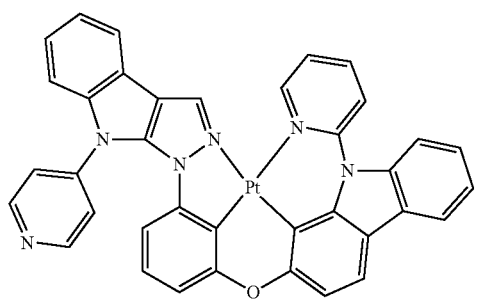
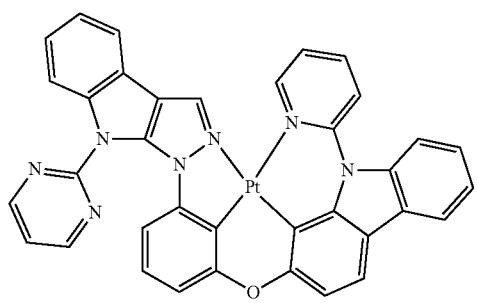
Structures 2
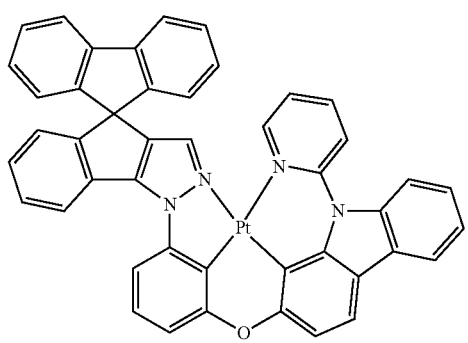
348
-continued
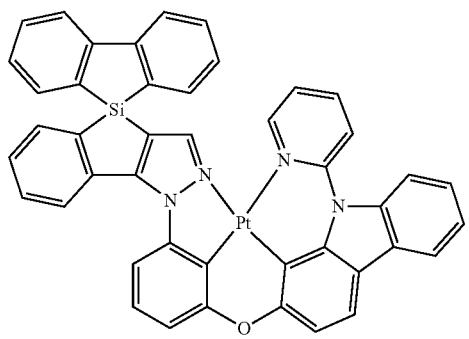
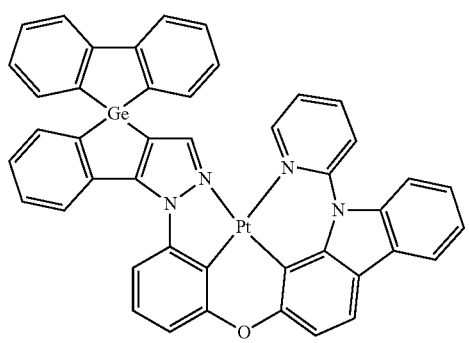
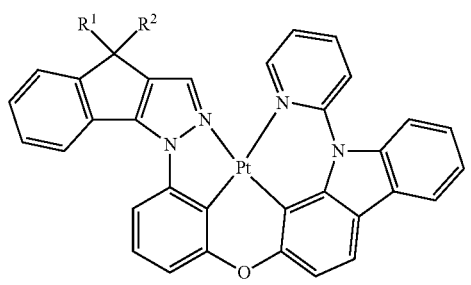
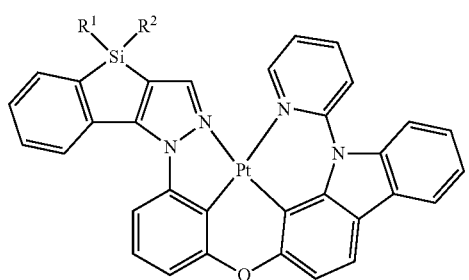
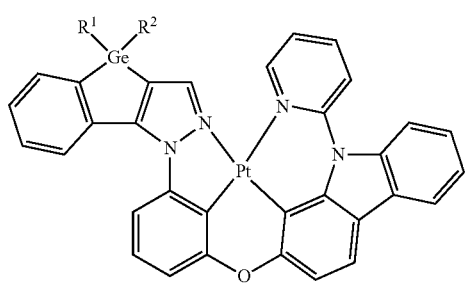

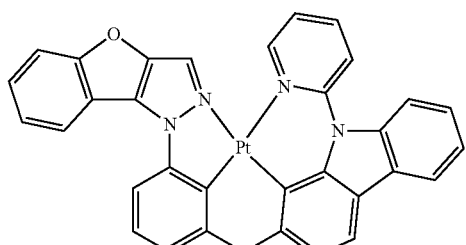
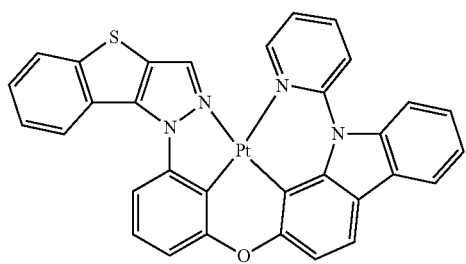
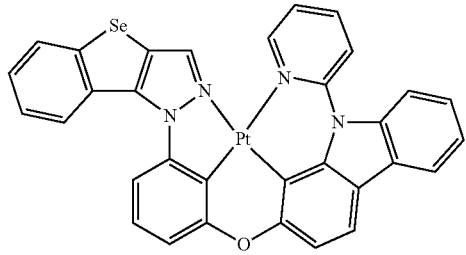
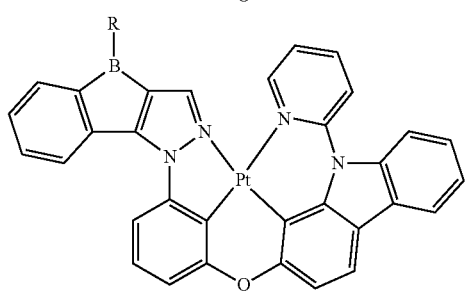
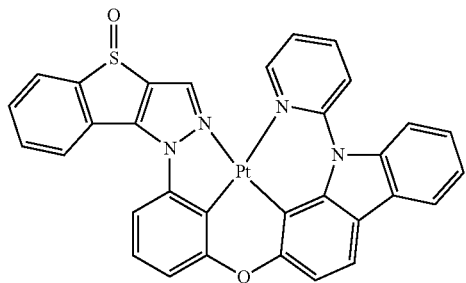
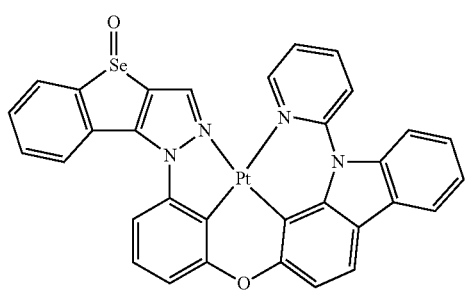
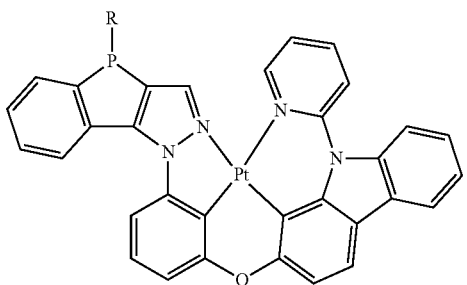
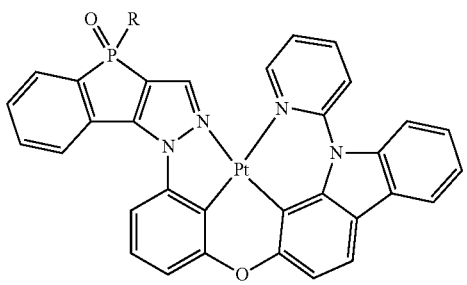
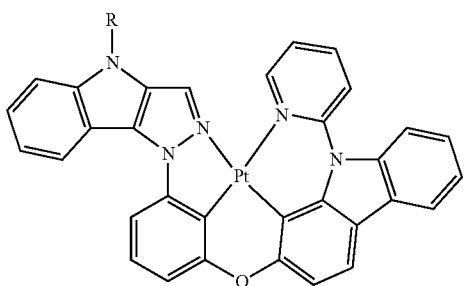
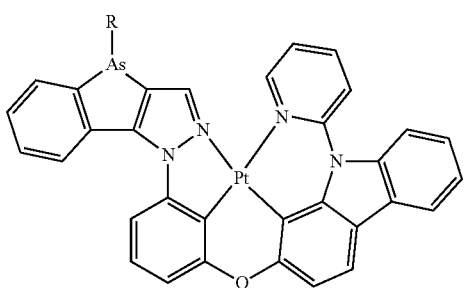
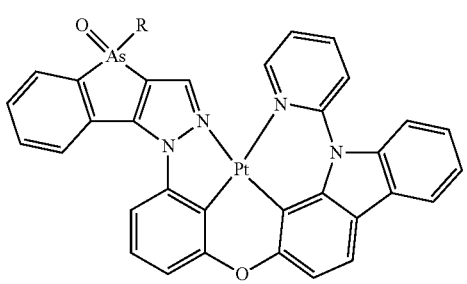

351
-continued
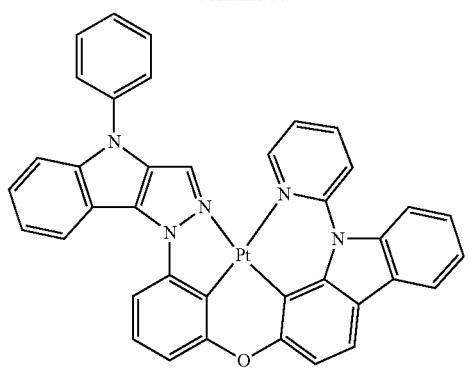
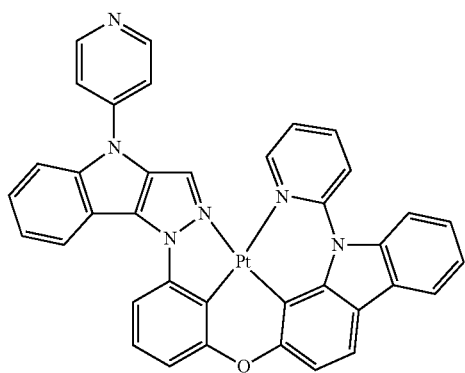
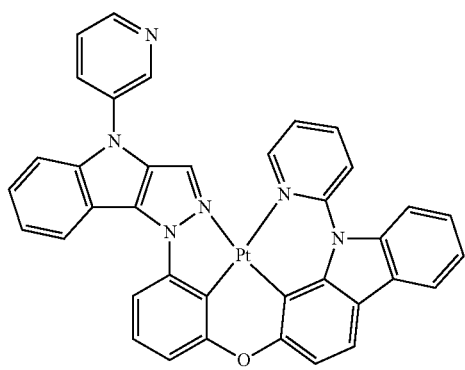
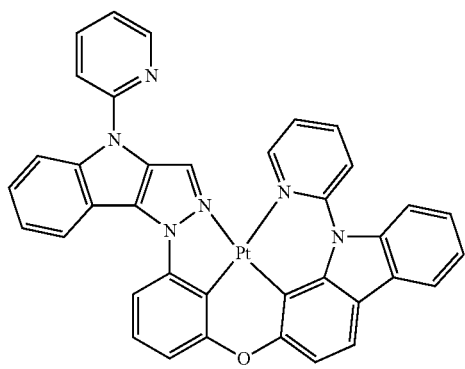
352
-continued
Structures 3
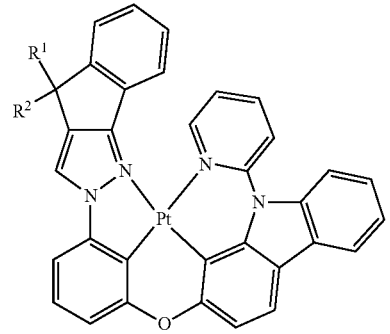
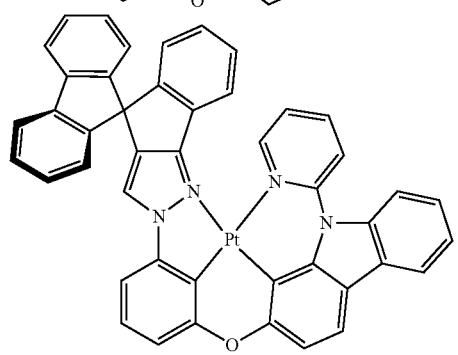
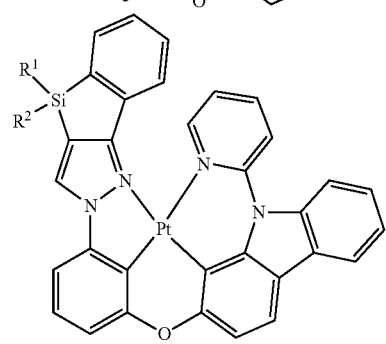
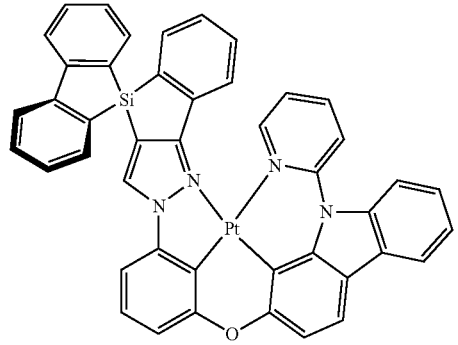
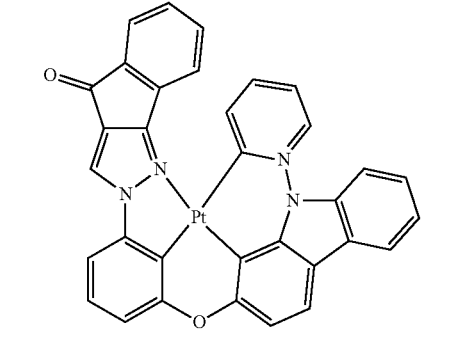

353
-continued
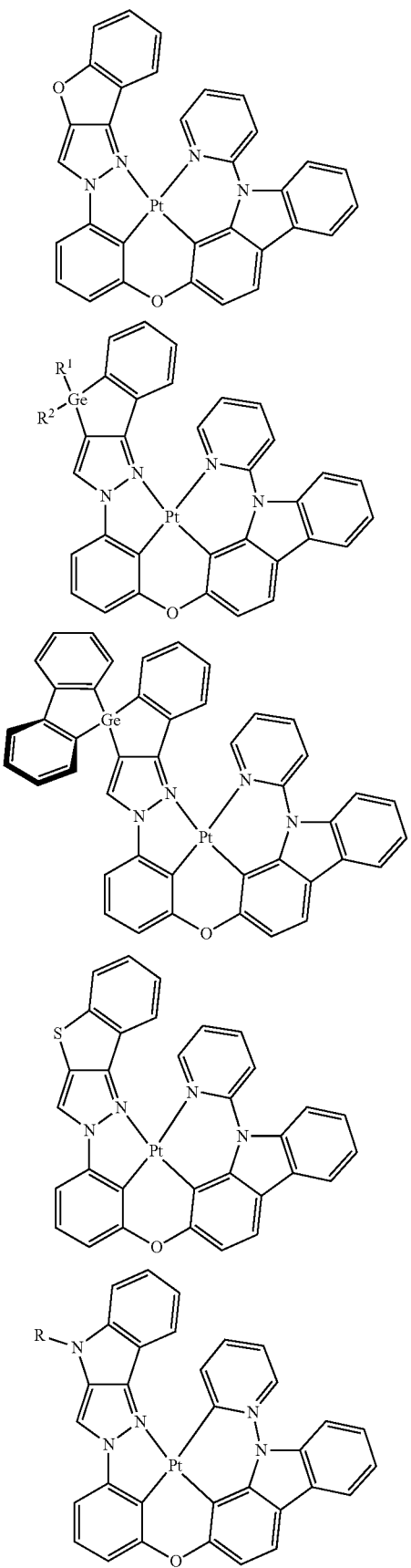
354
-continued
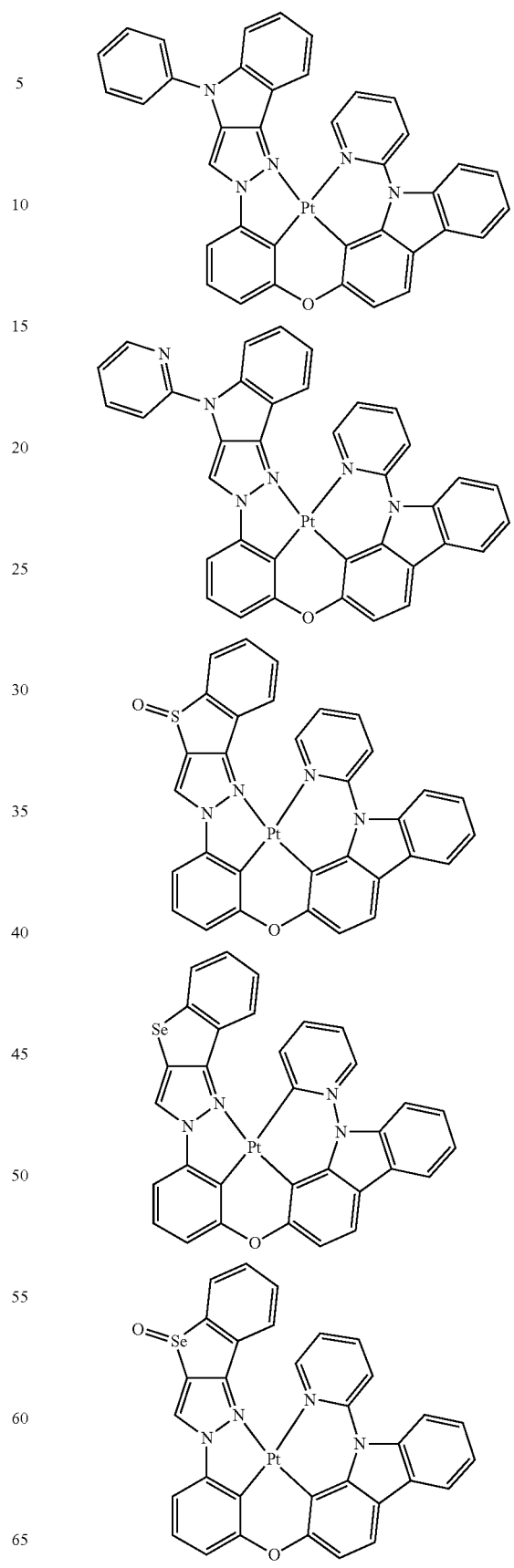

355
-continued
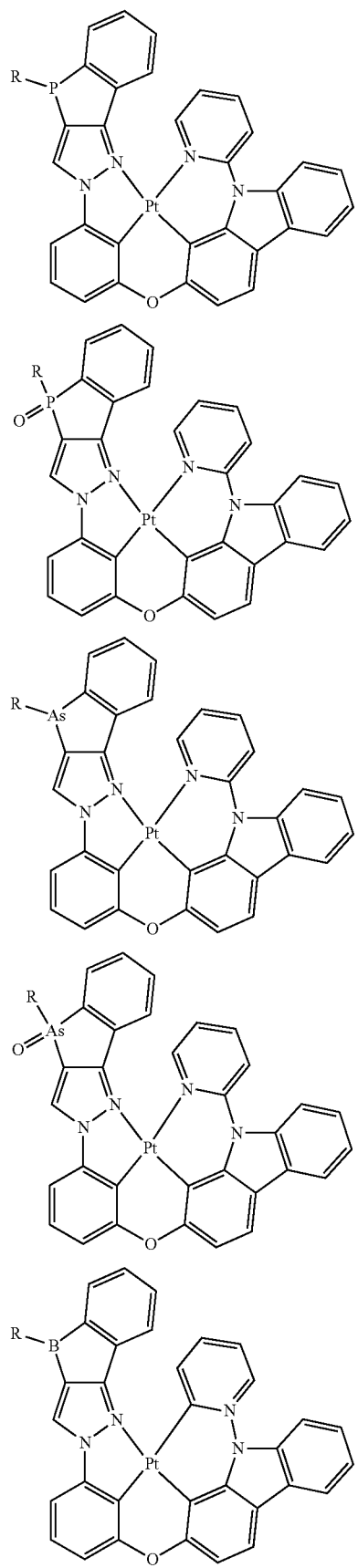
356
-continued
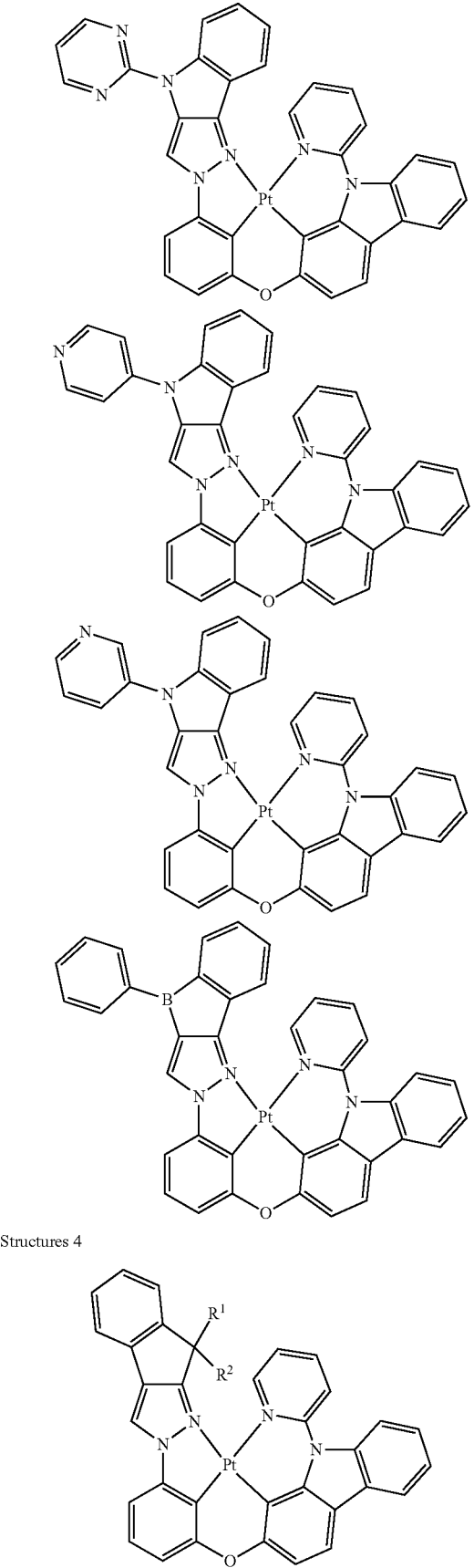
Structures 4

357
-continued
358
-continued
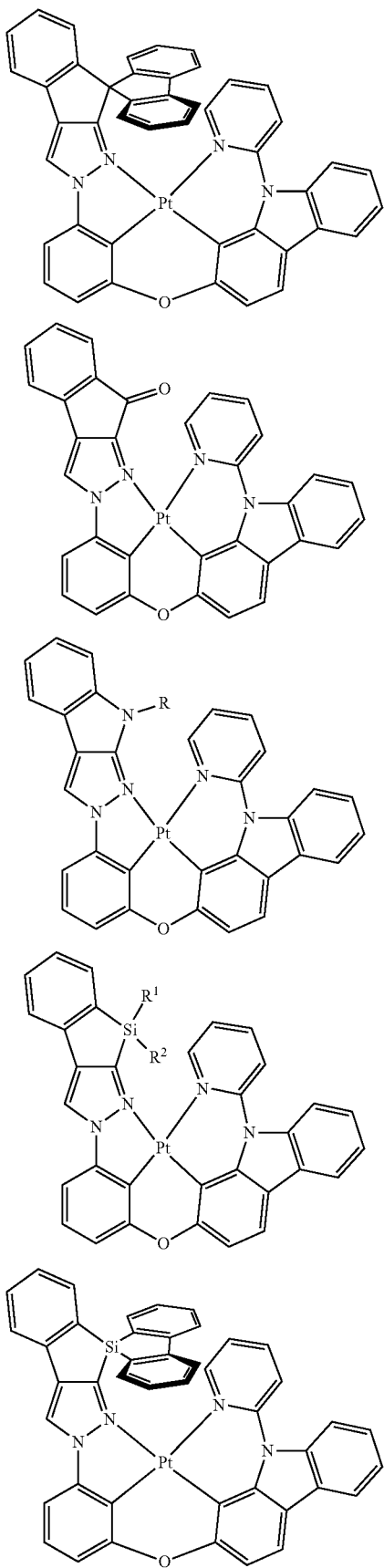
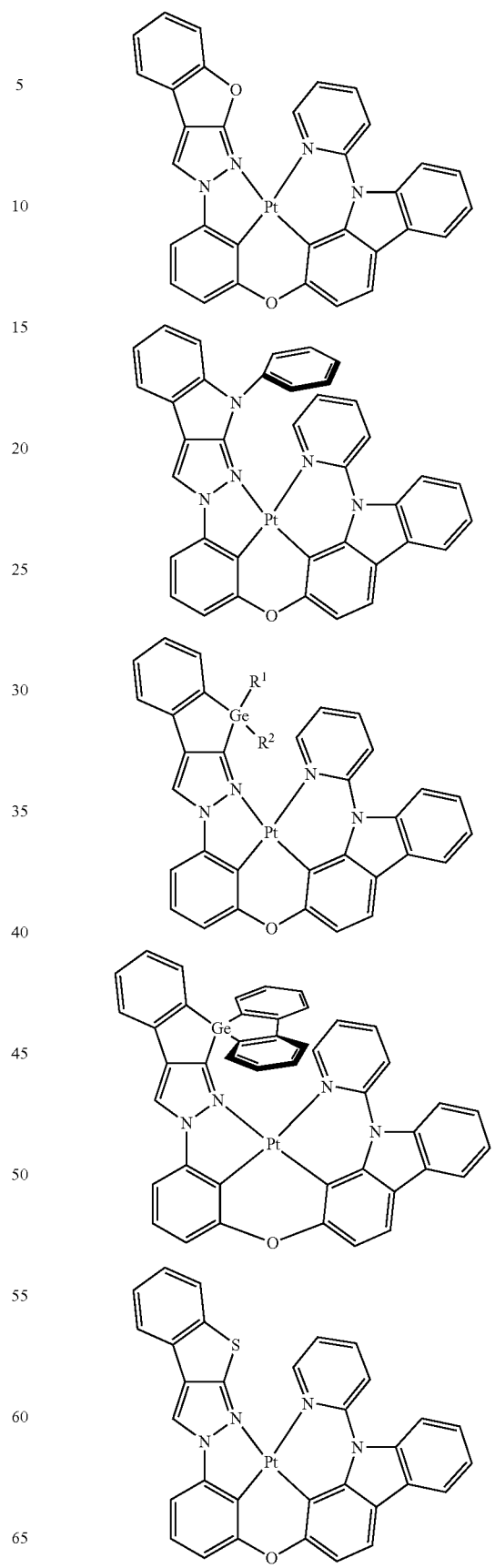

359
-continued
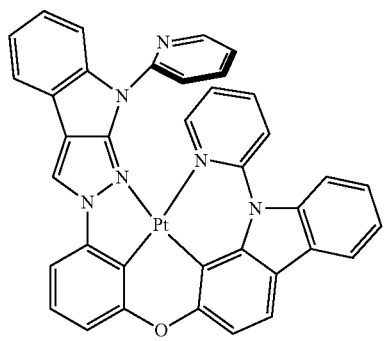
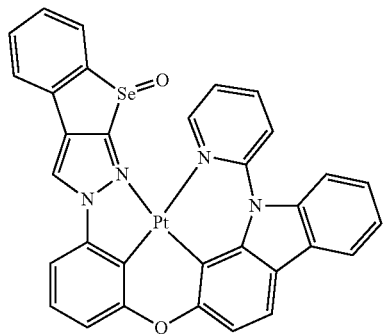
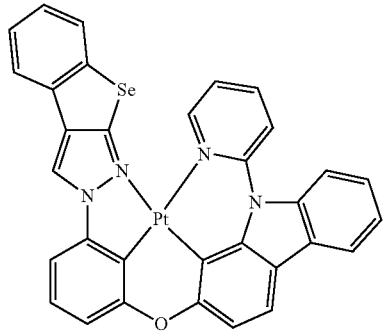
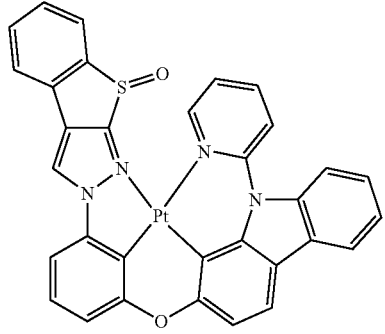
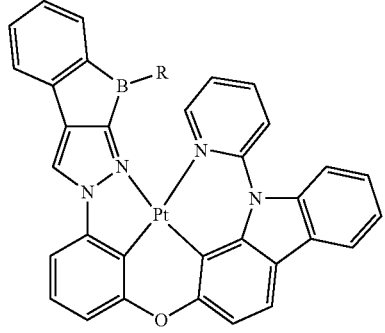
360
-continued
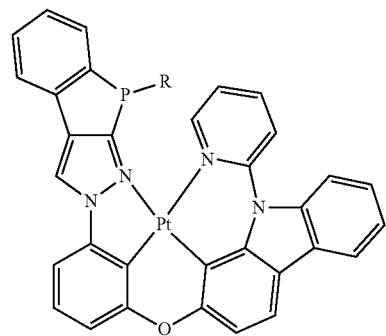
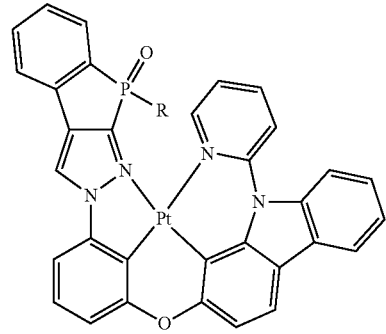
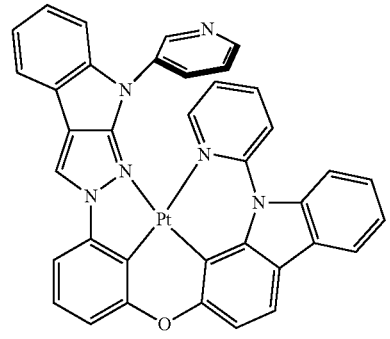
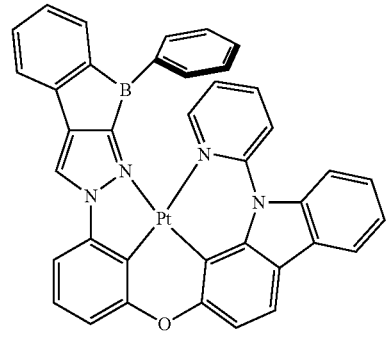

361
-continued
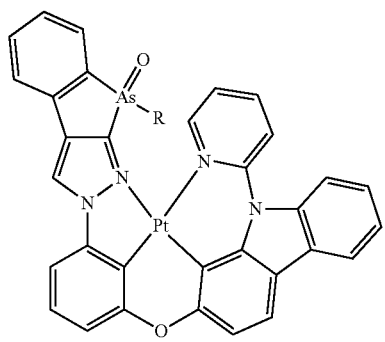
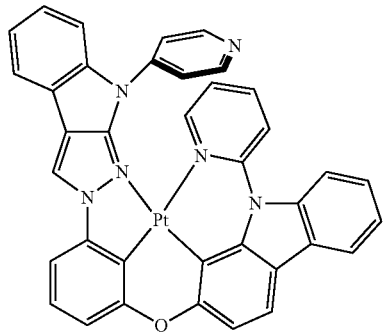
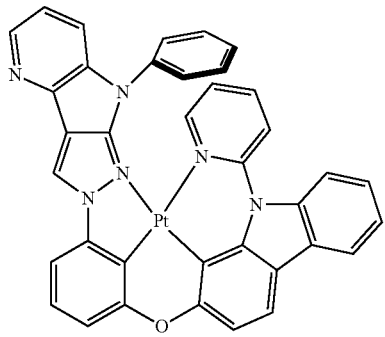
Structures 5
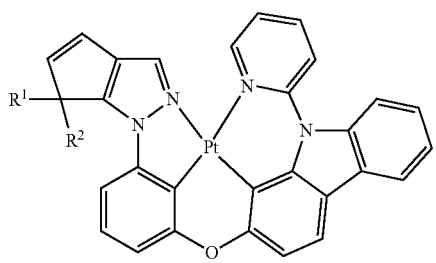
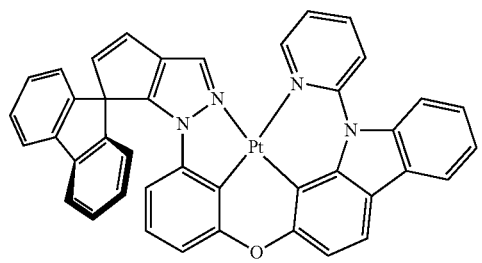
362
-continued
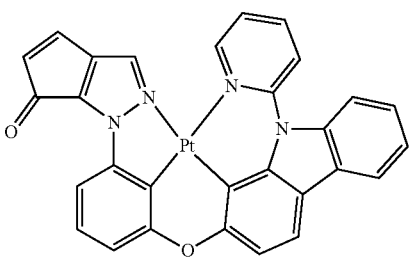
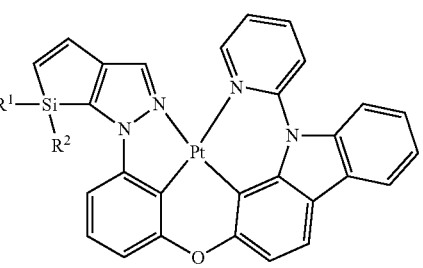
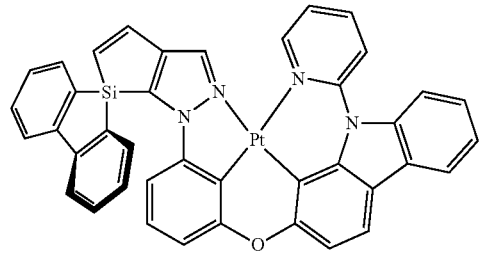
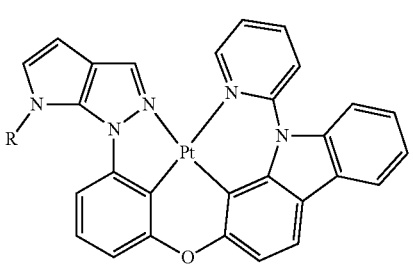
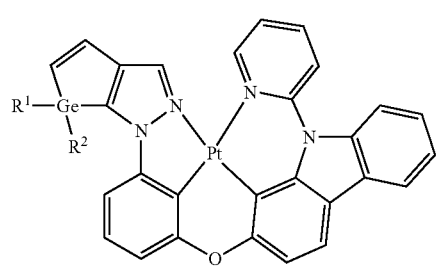
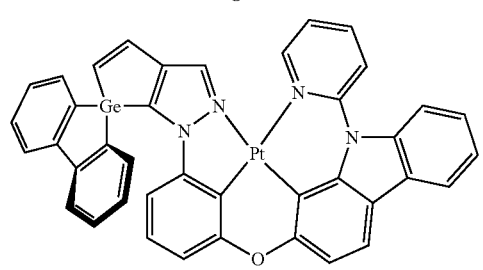

363
-continued
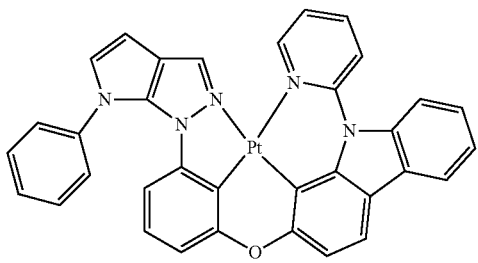
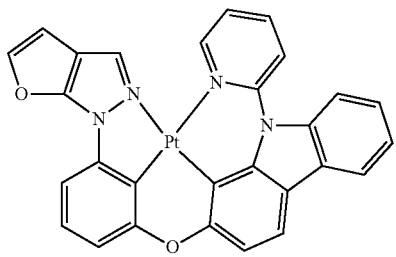
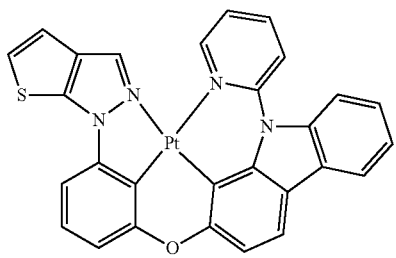
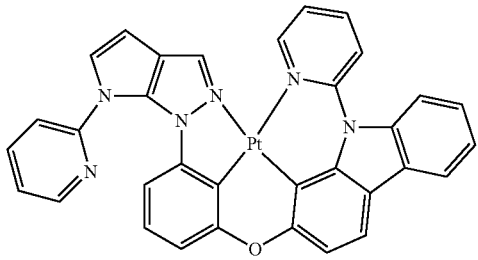
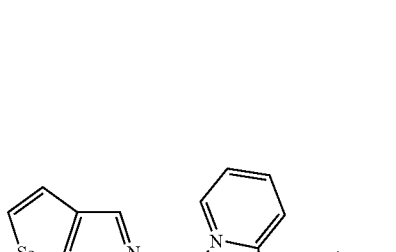
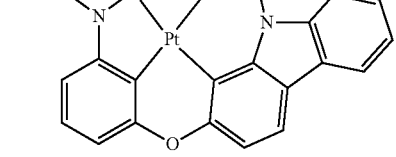
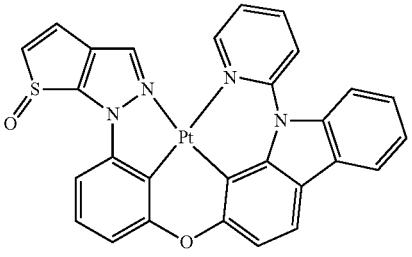
364
-continued
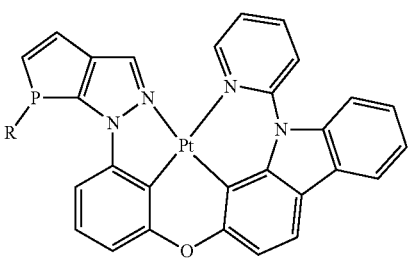
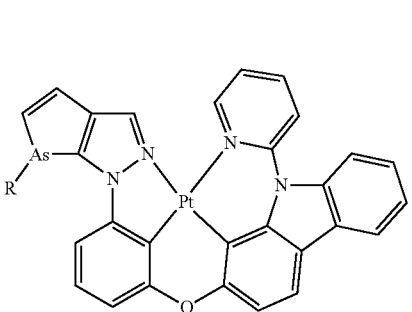
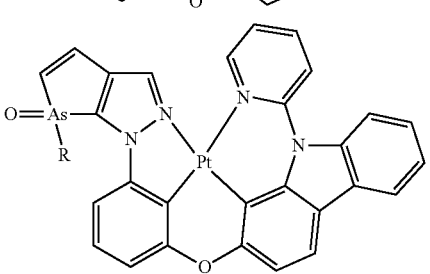
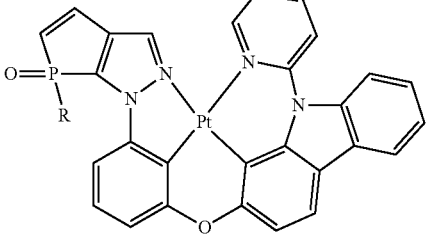
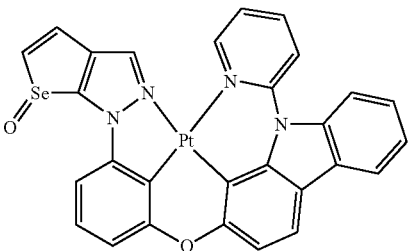
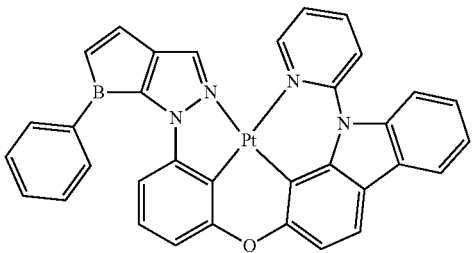

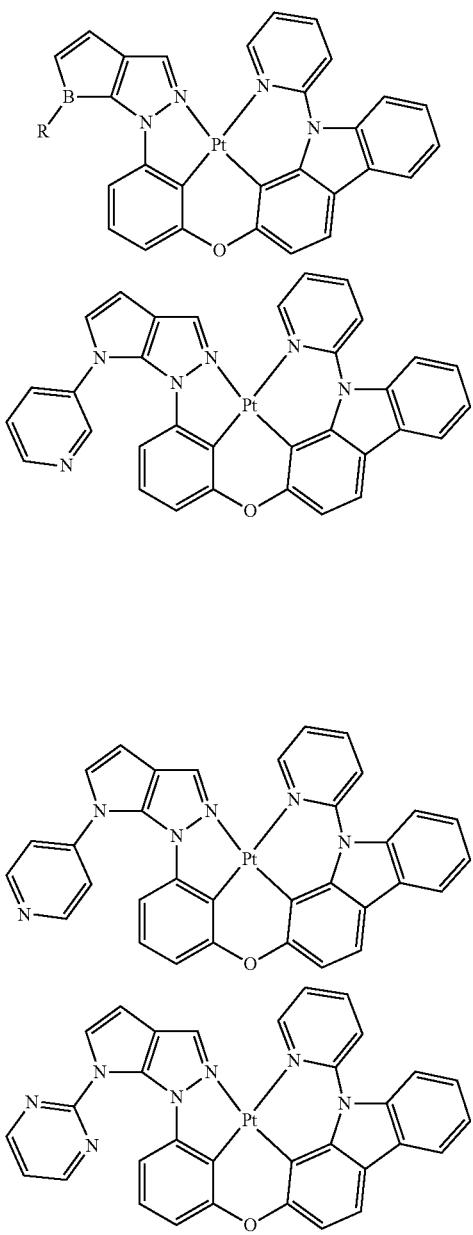
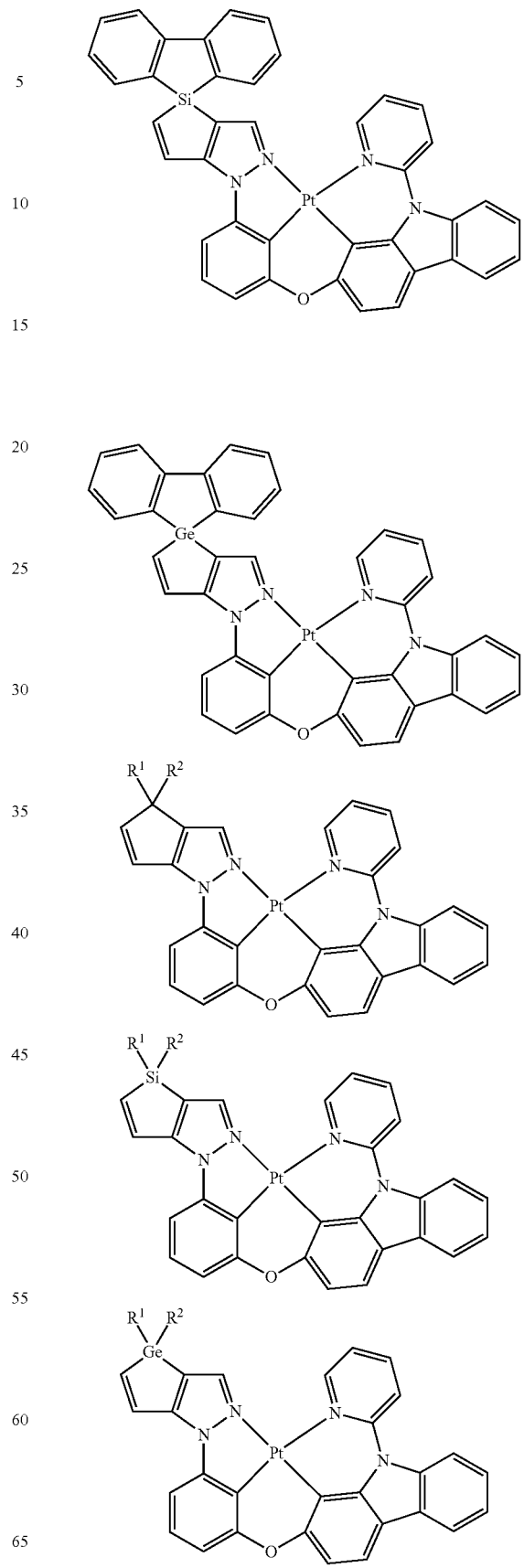
Structures 6
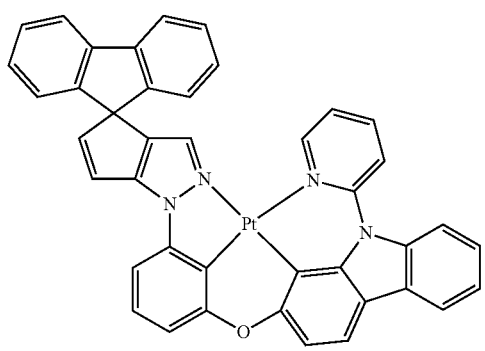

367
-continued
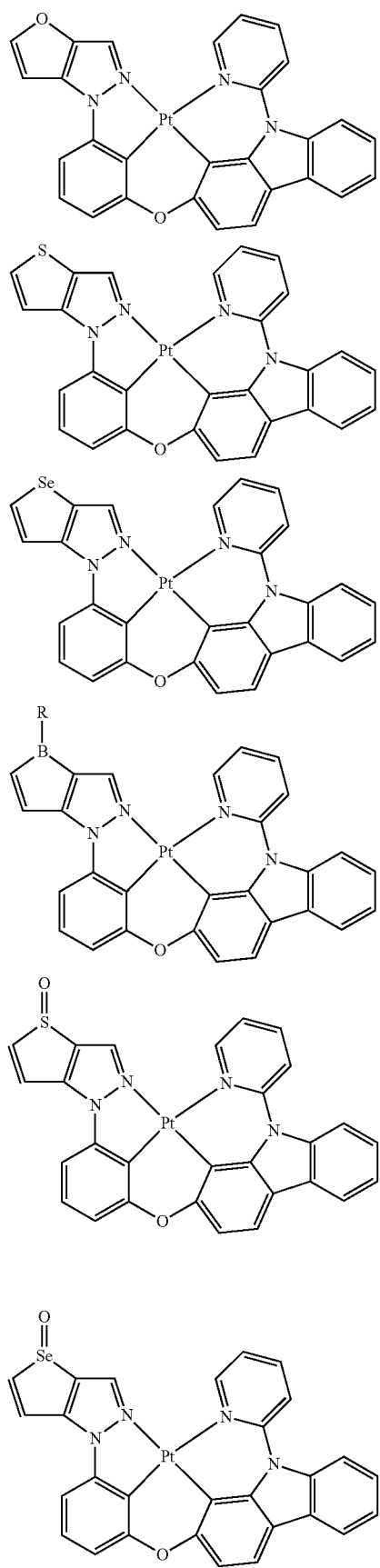
368
-continued
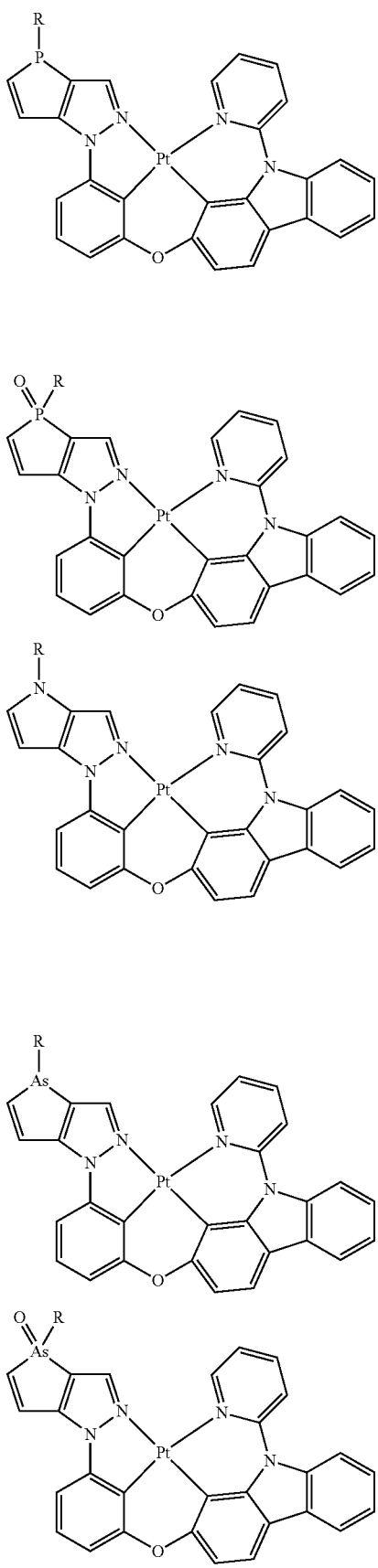

-continued
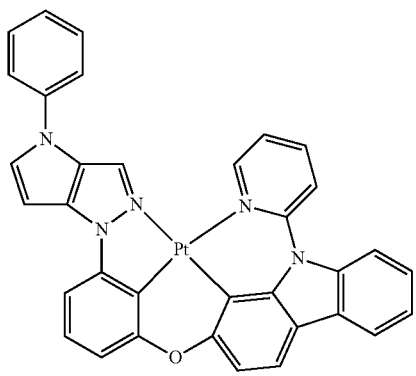
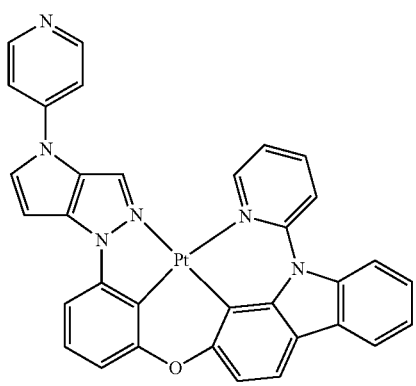
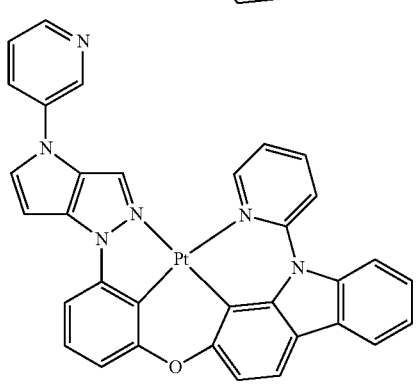
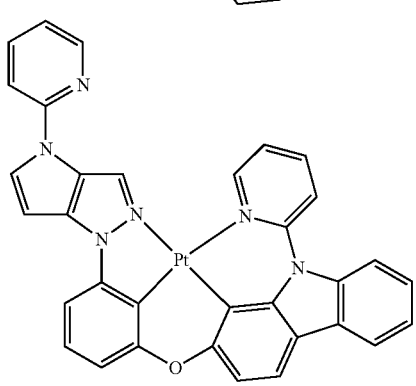
-continued
Structures 7
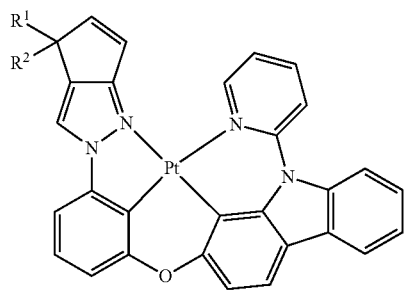
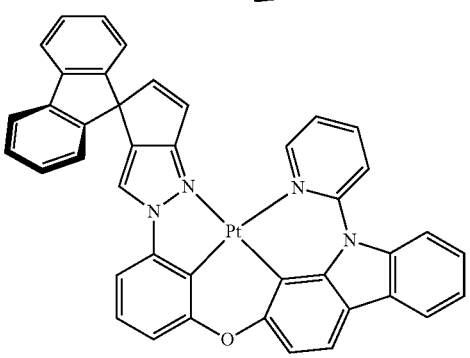
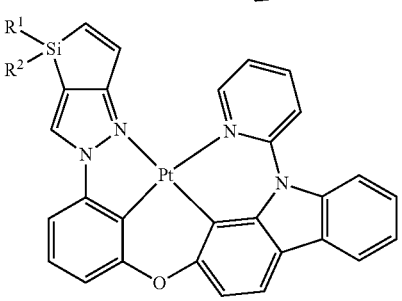
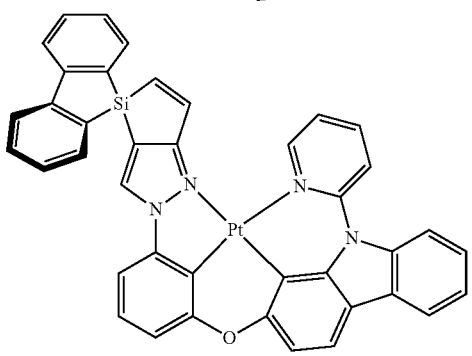
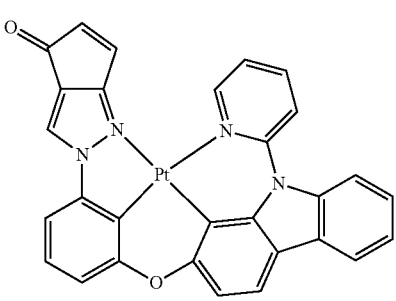

371
-continued
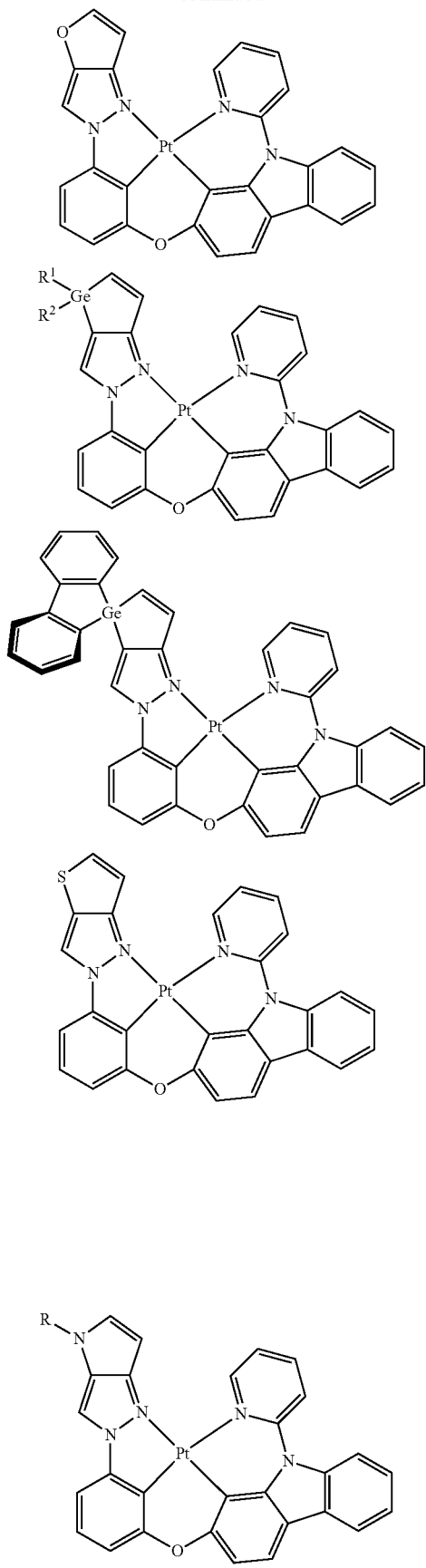
372
-continued
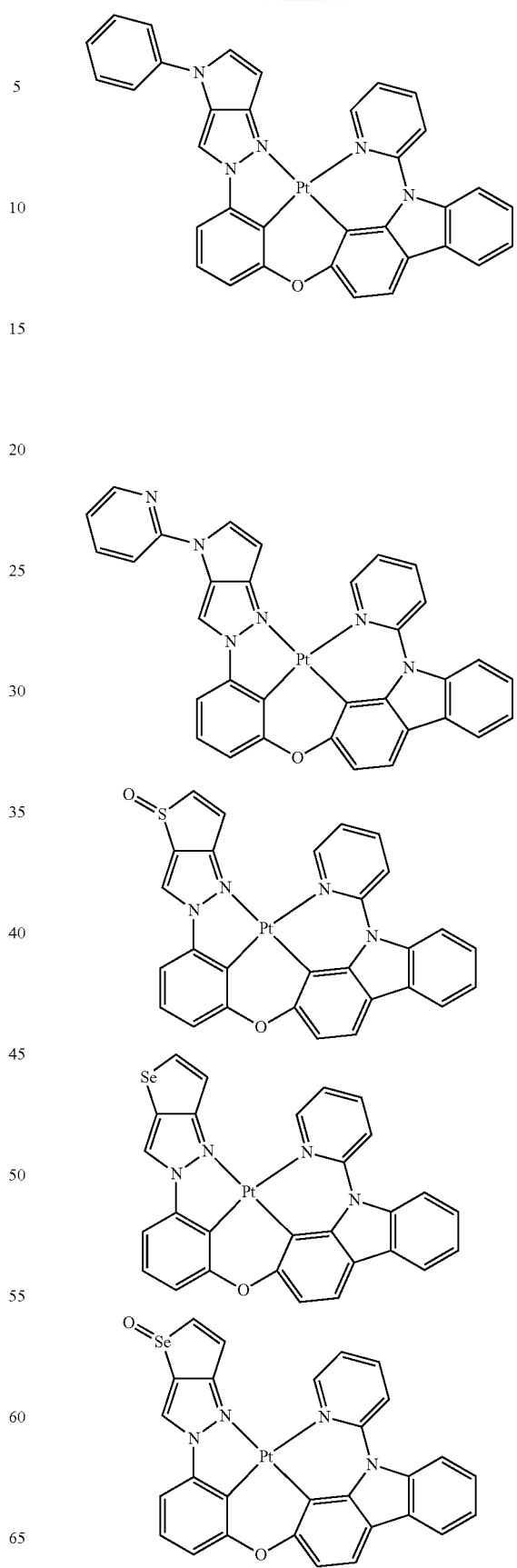

373
-continued
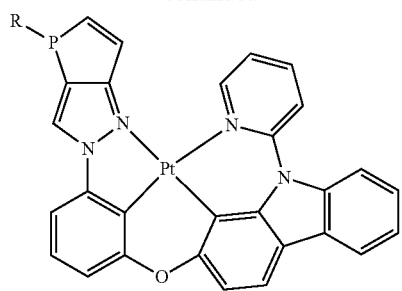
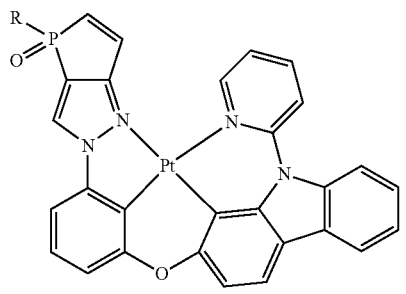
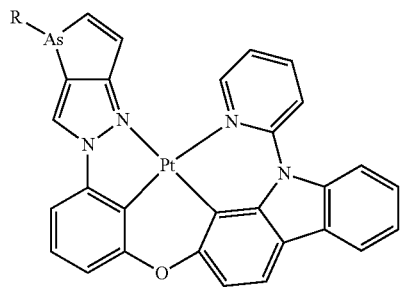
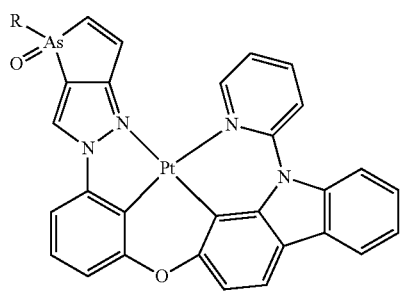
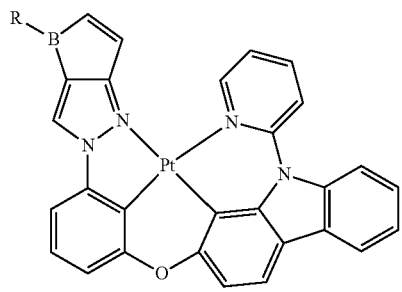
374
-continued
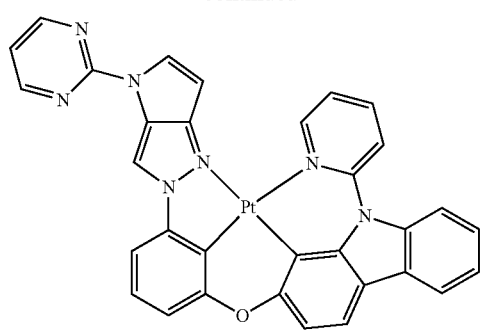
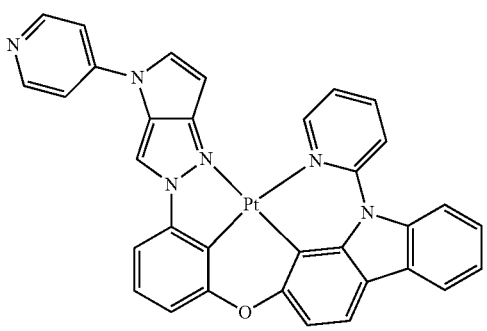
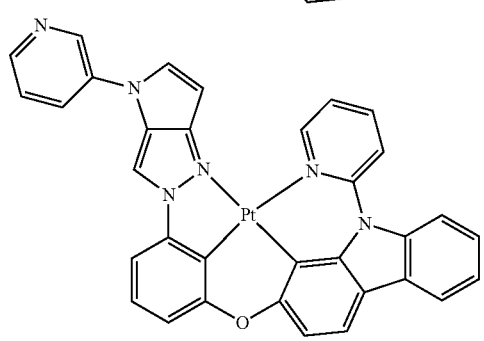
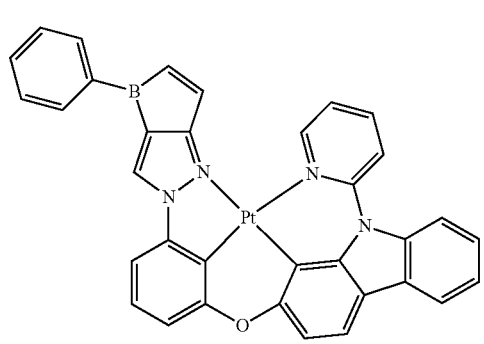
Structures 8
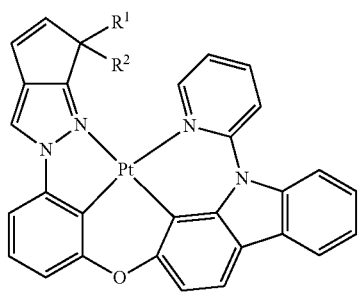

| 375 -continued | 376 -continued |
|---|---|
| 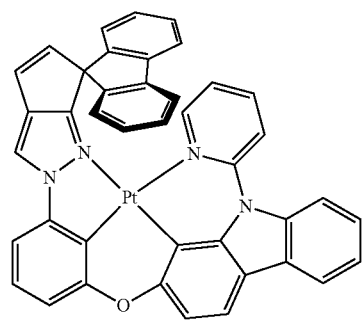 | 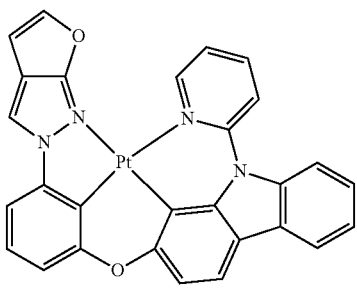 |
| 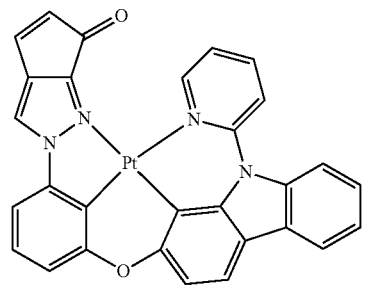 | |
| 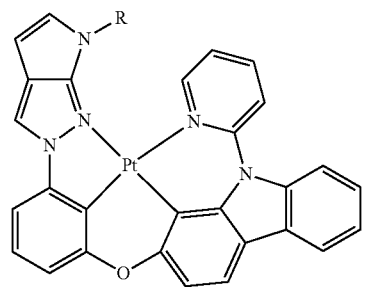 | 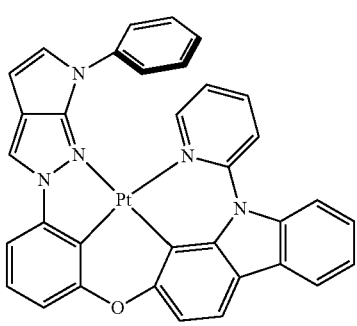 |
| 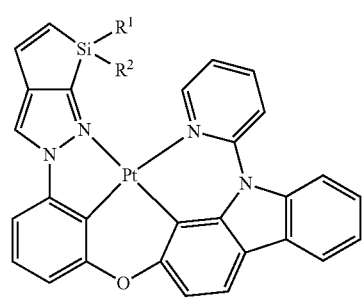 | 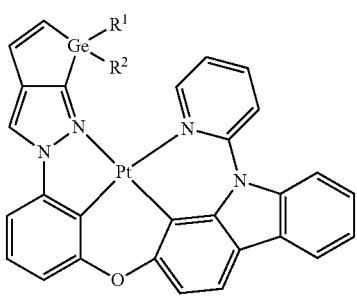 |
| | 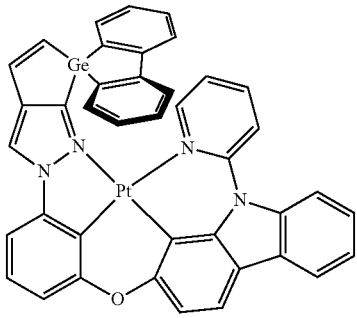 |
| 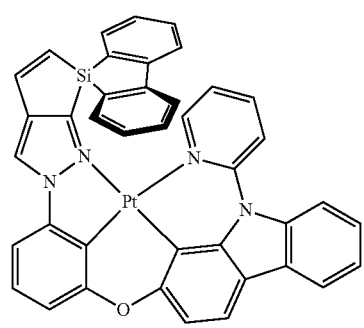 | 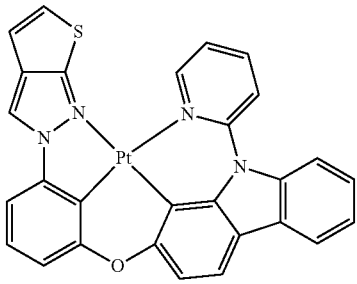 |

377
-continued
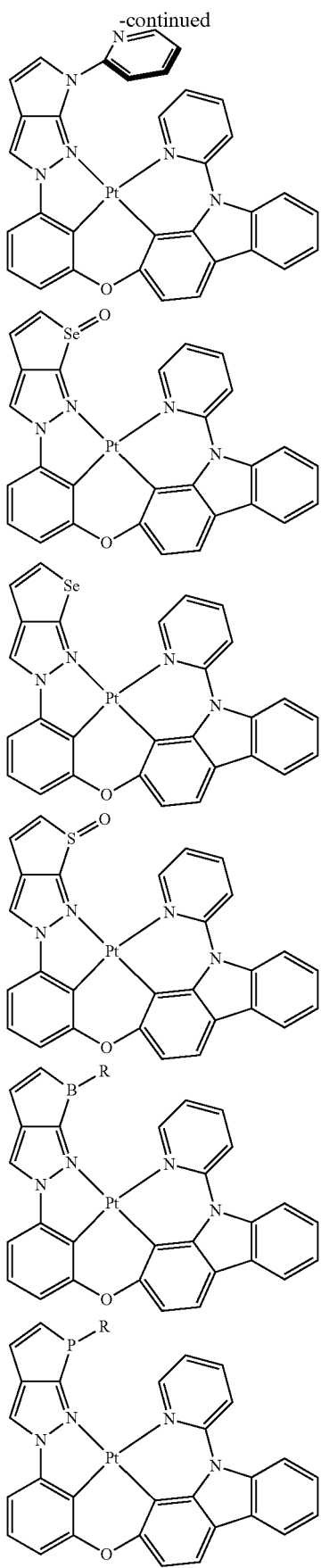
378
-continued
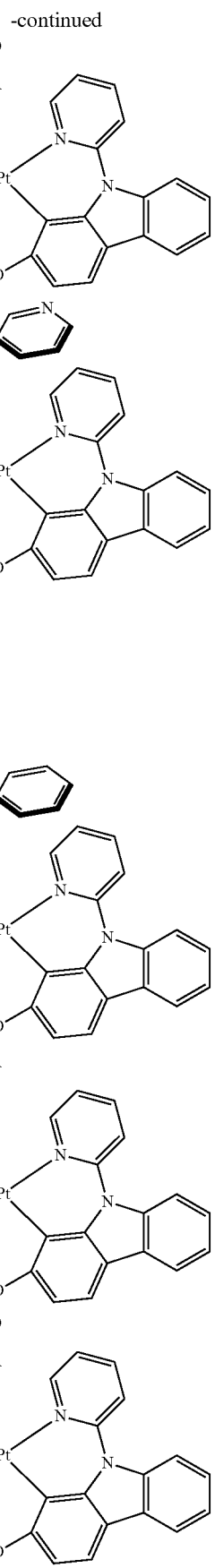

-continued
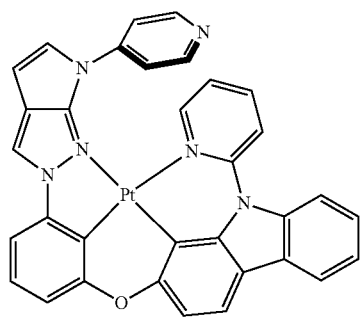
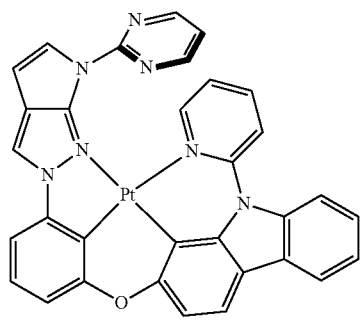
Structures 9
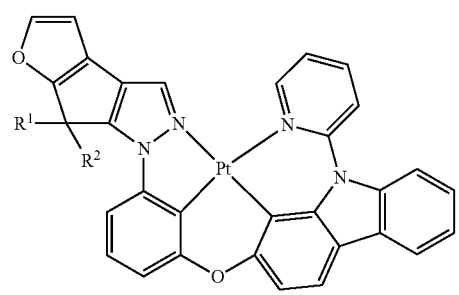
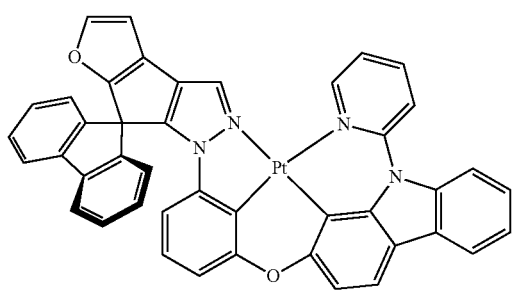
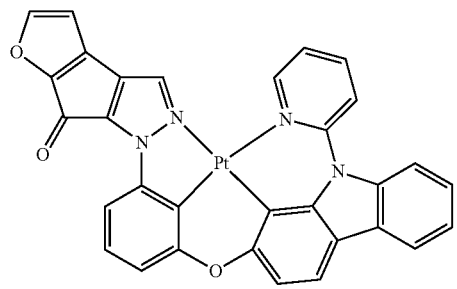
-continued
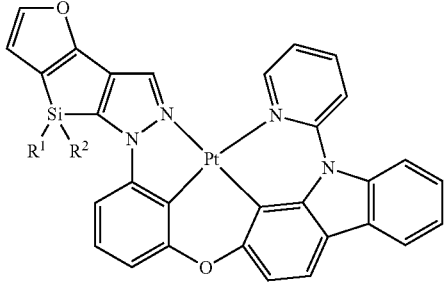
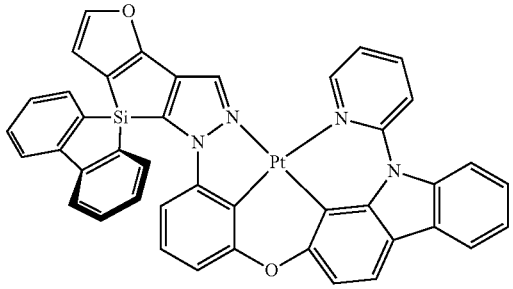
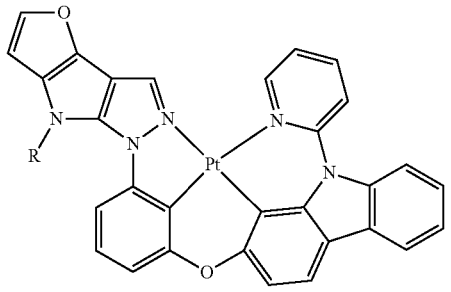
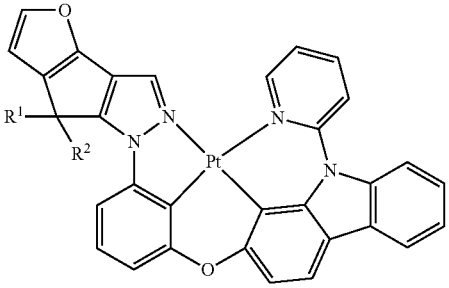
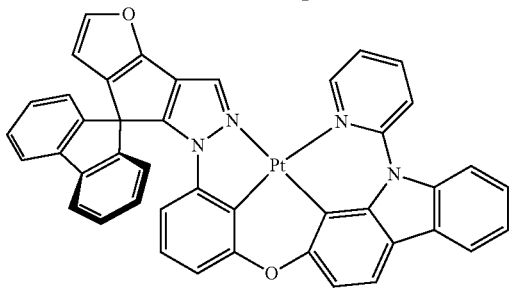
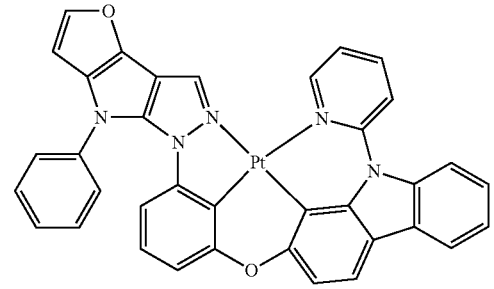

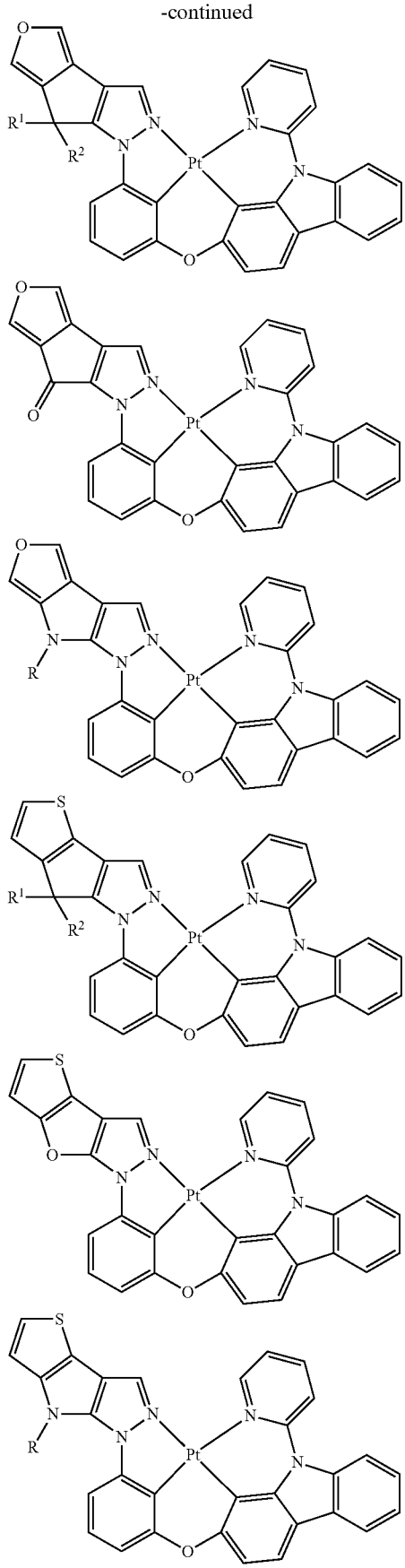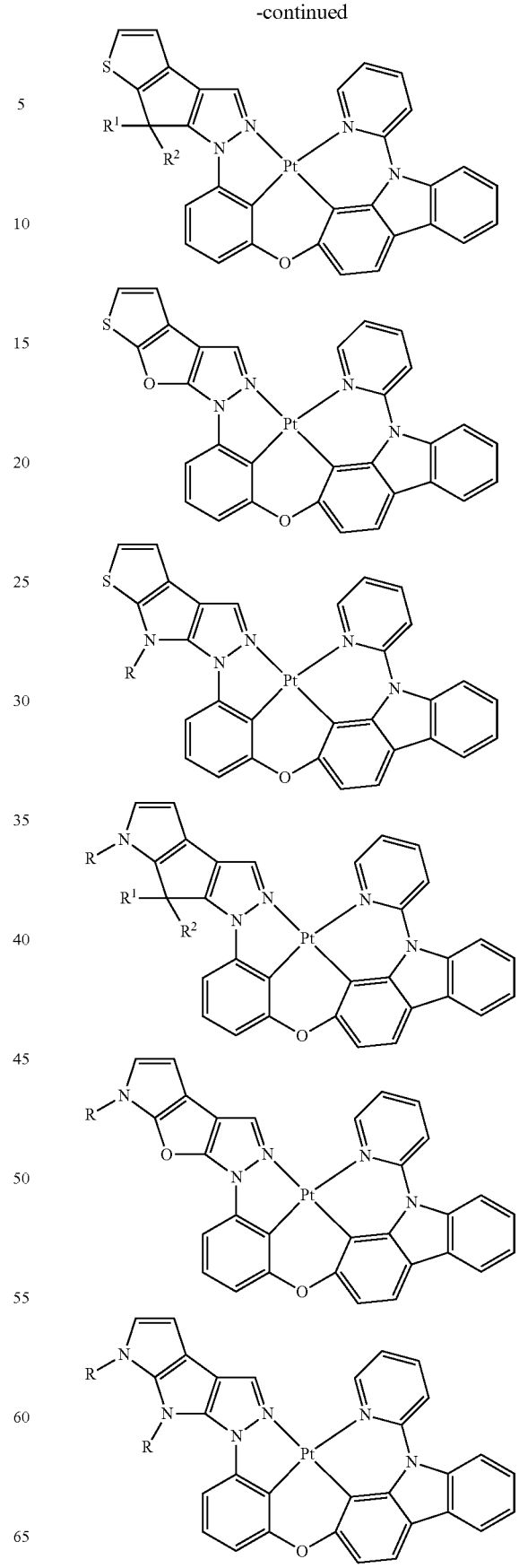

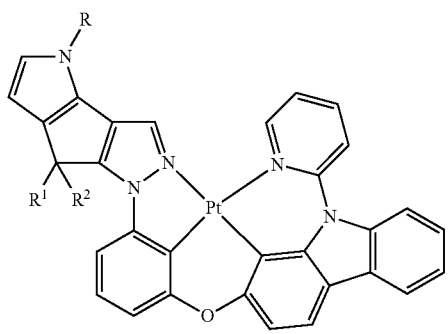
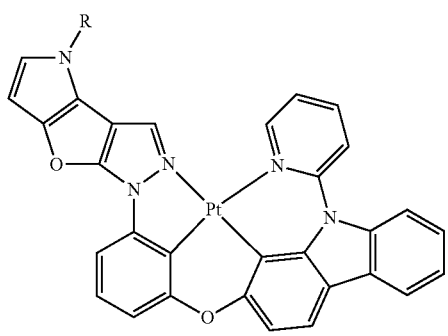
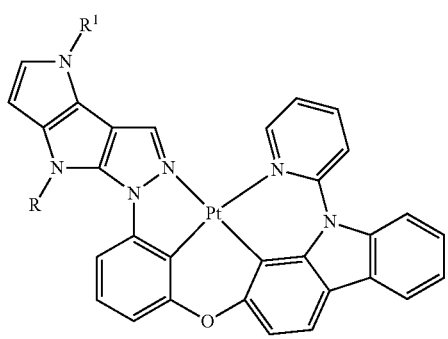
Structures 10
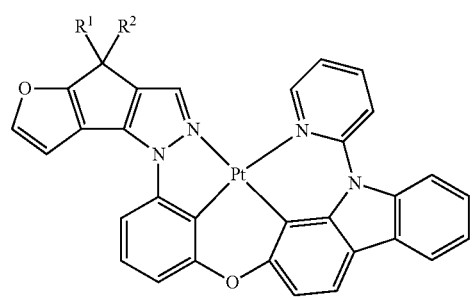
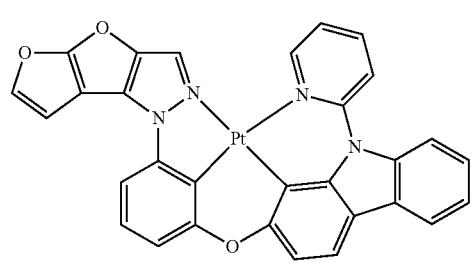
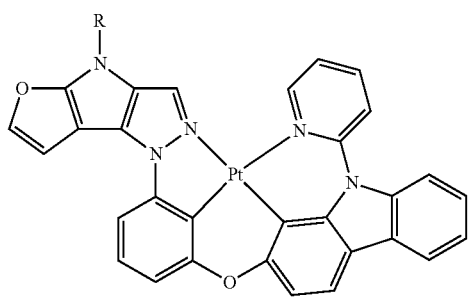
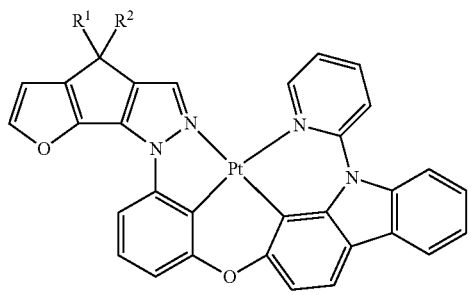
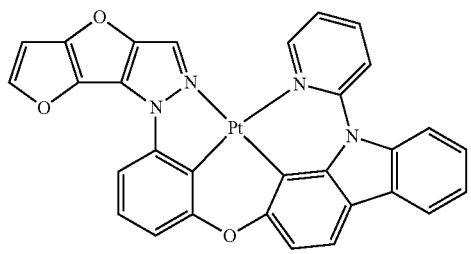
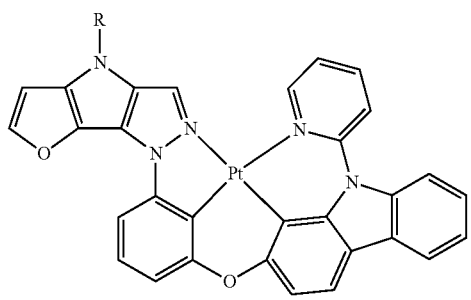
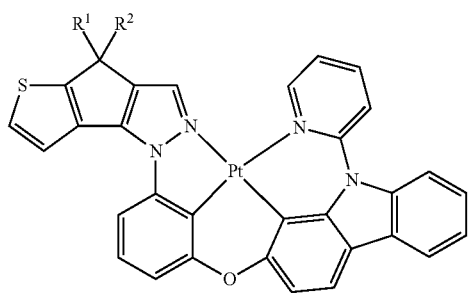
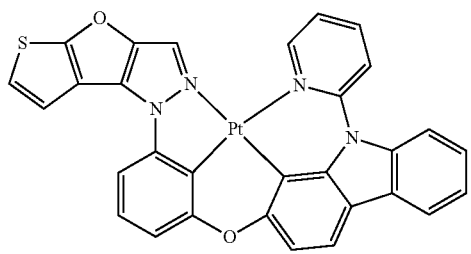

385
-continued
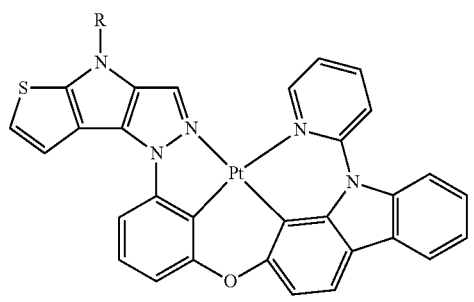
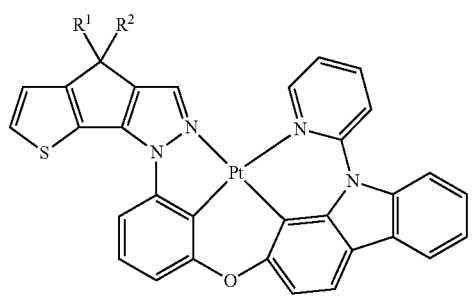
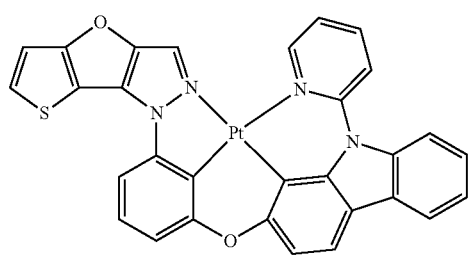
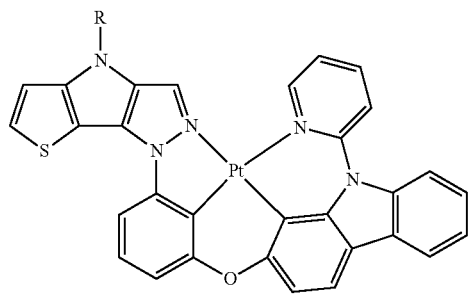
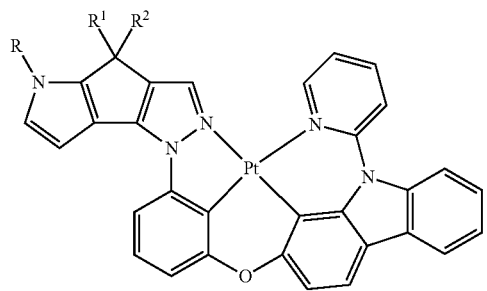
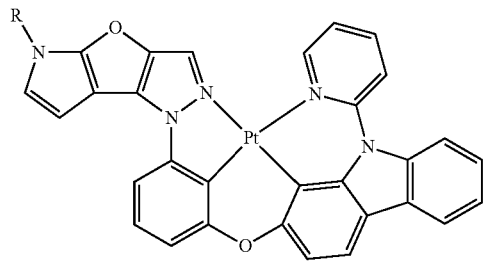
386
-continued
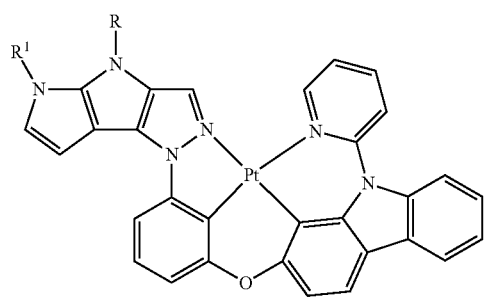
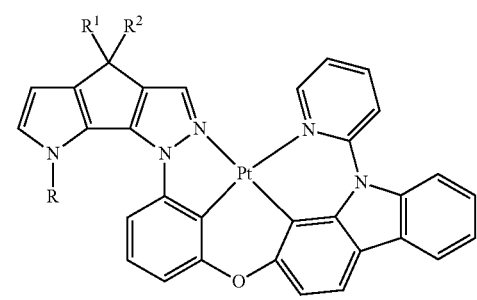
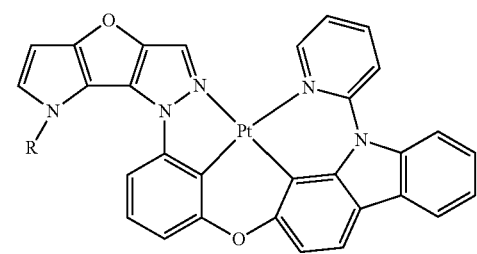
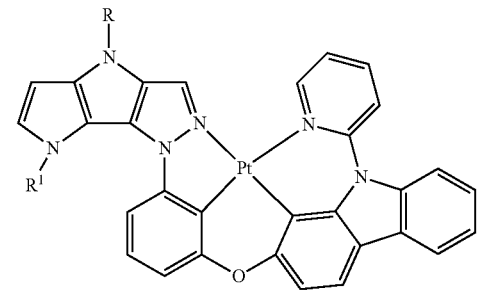
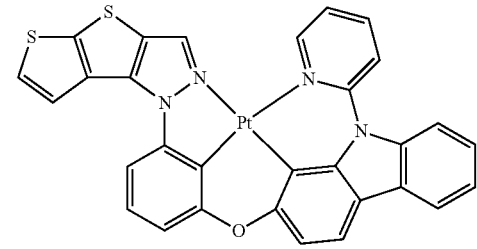
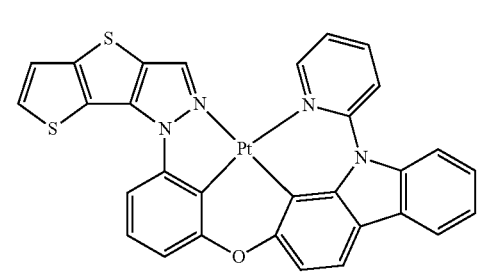

387
-continued
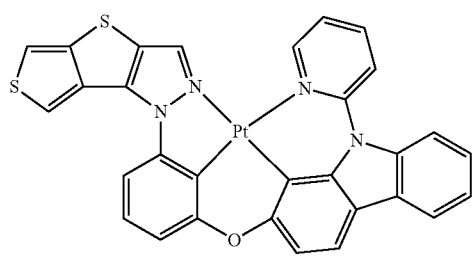
Structures 11
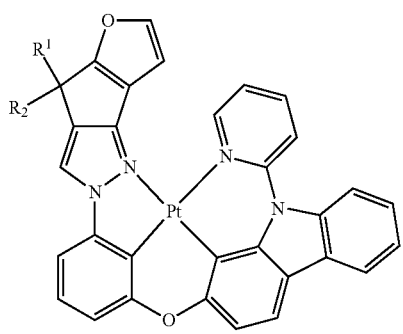
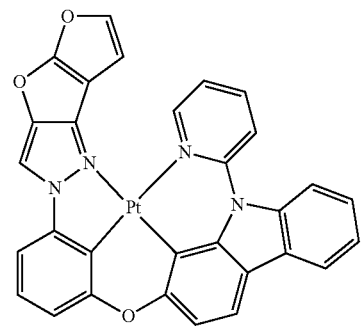
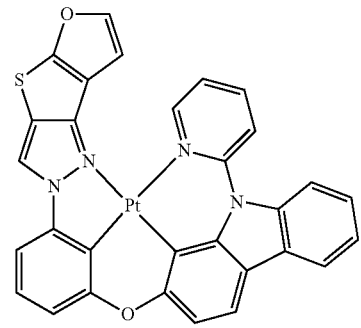
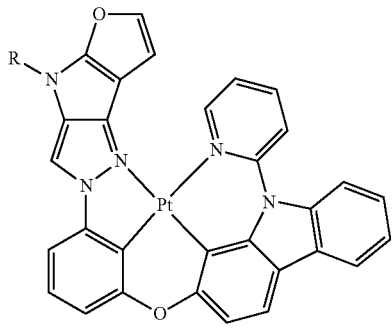
388
-continued
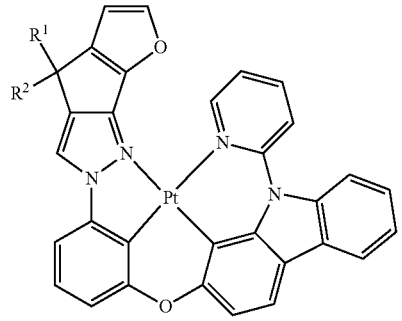
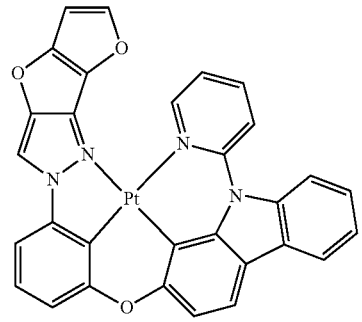
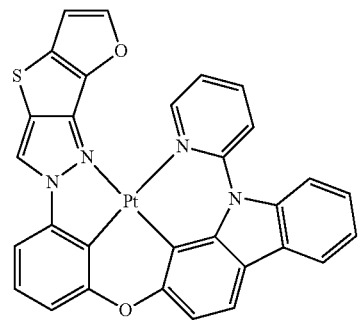
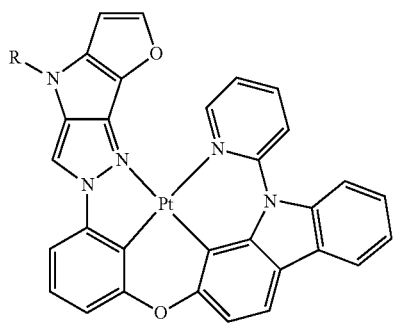
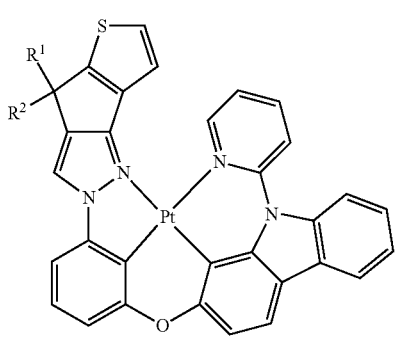

389
-continued
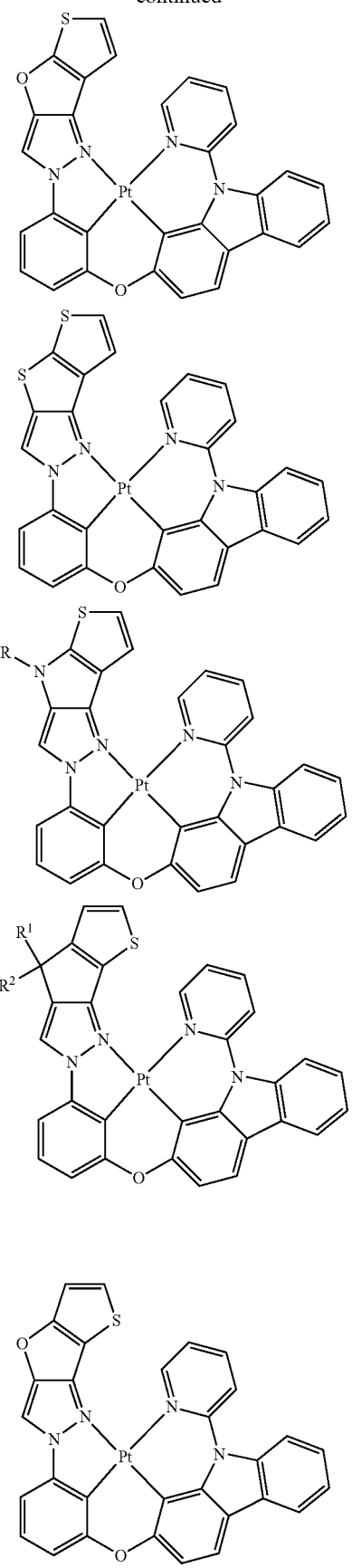
390
-continued
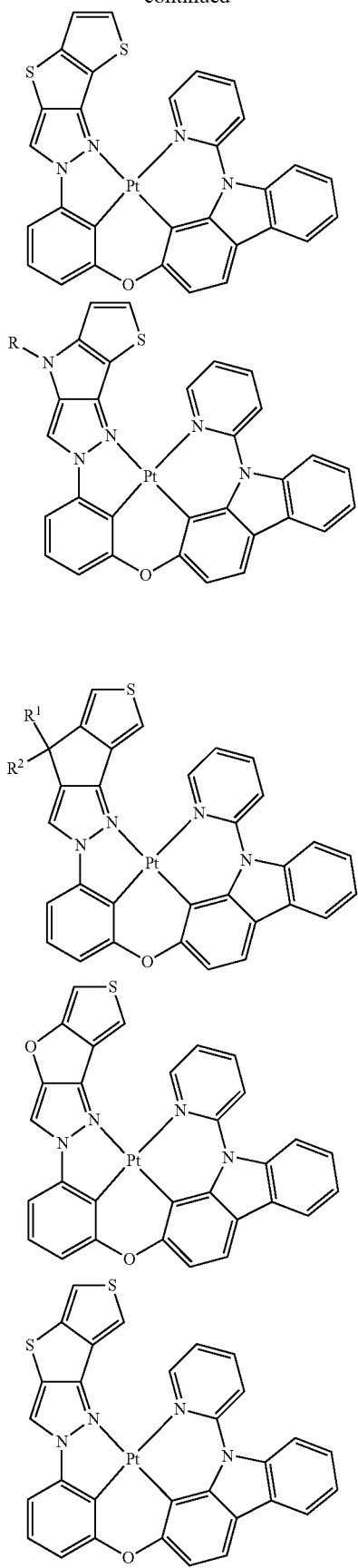

391
-continued
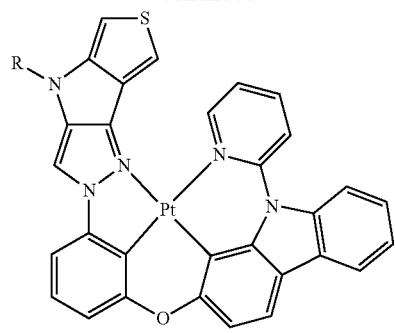
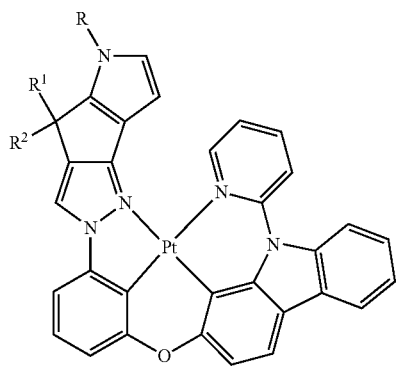
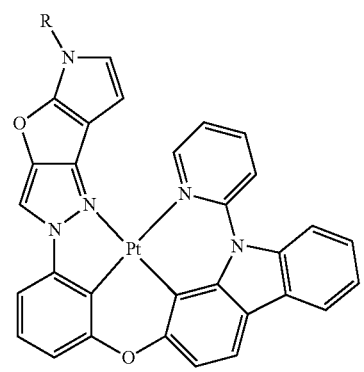
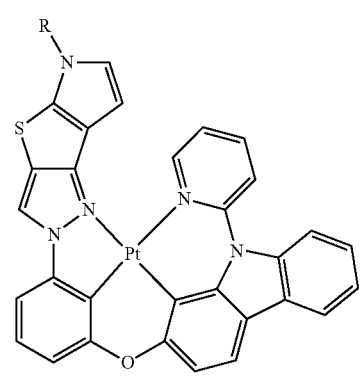
392
-continued
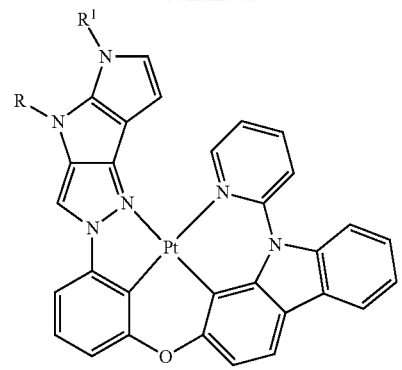
Structures 12
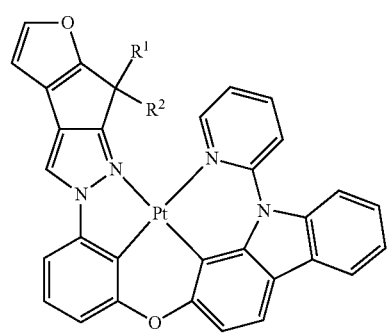
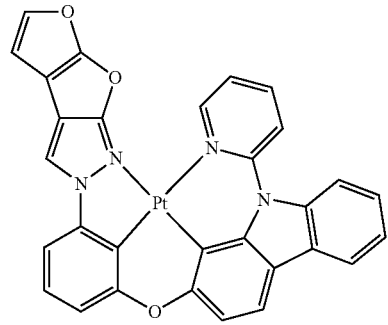
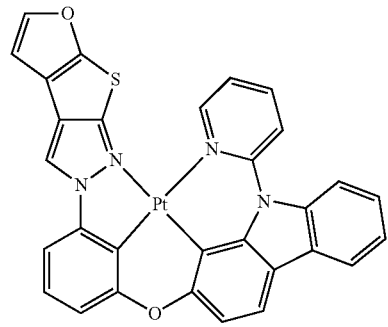
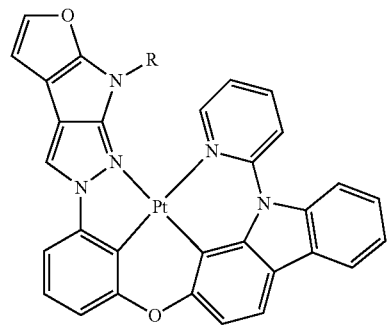

393
-continued
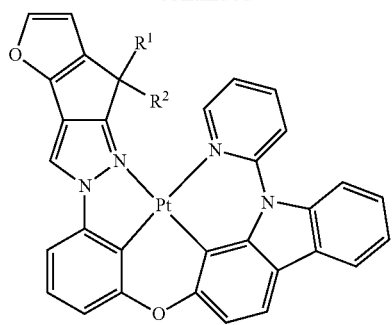
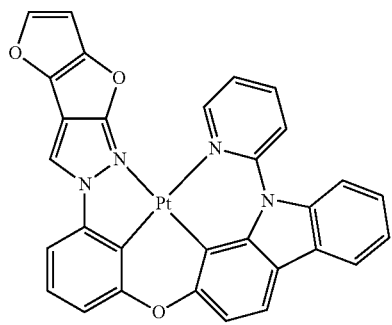
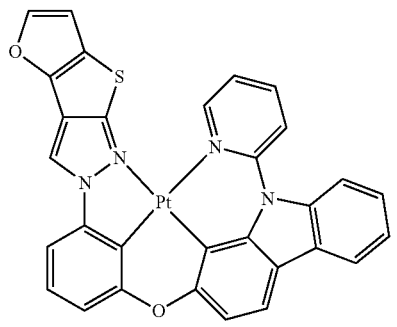
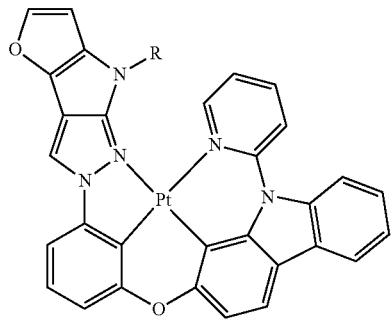
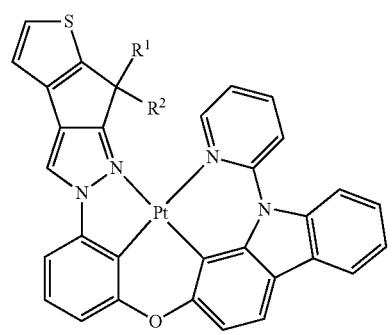
394
-continued
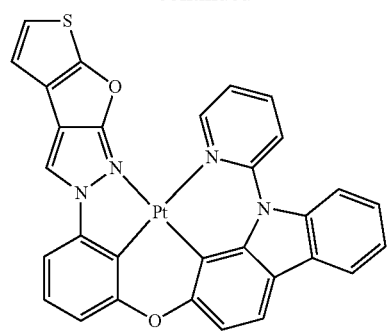
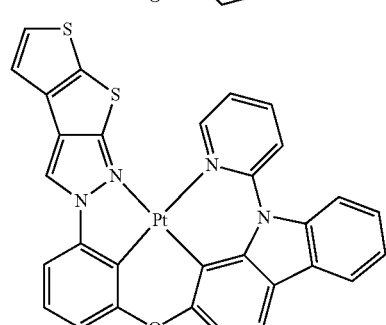
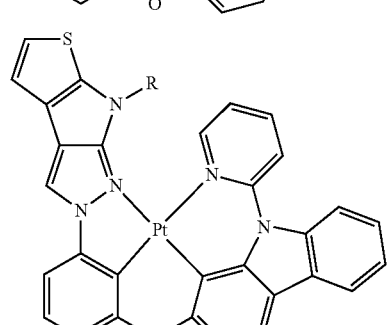
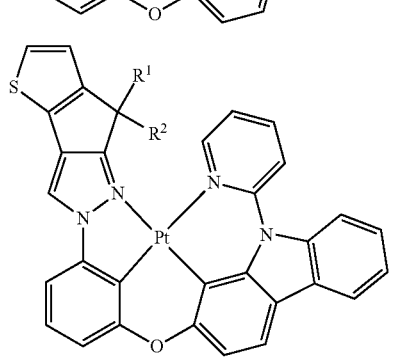
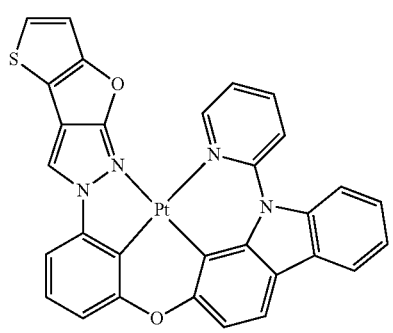

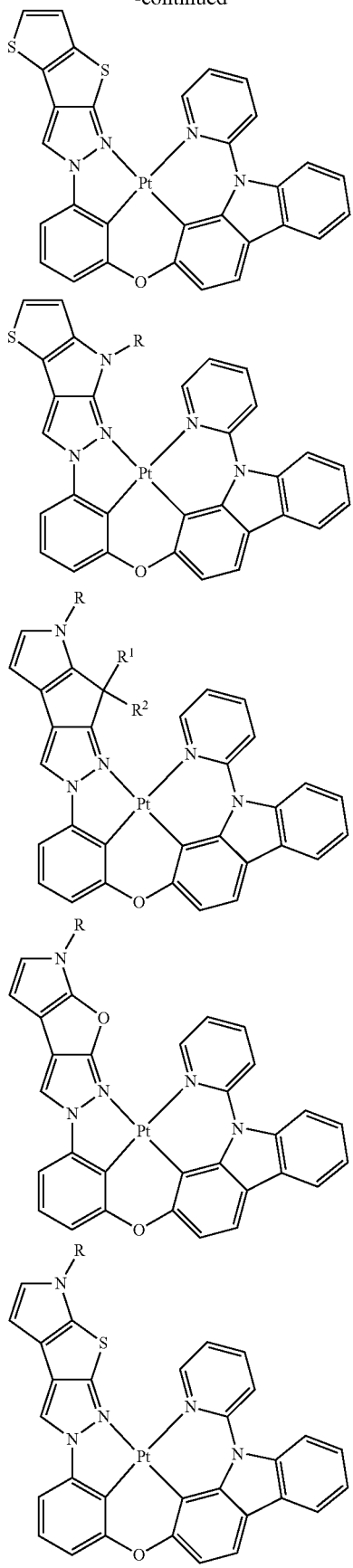
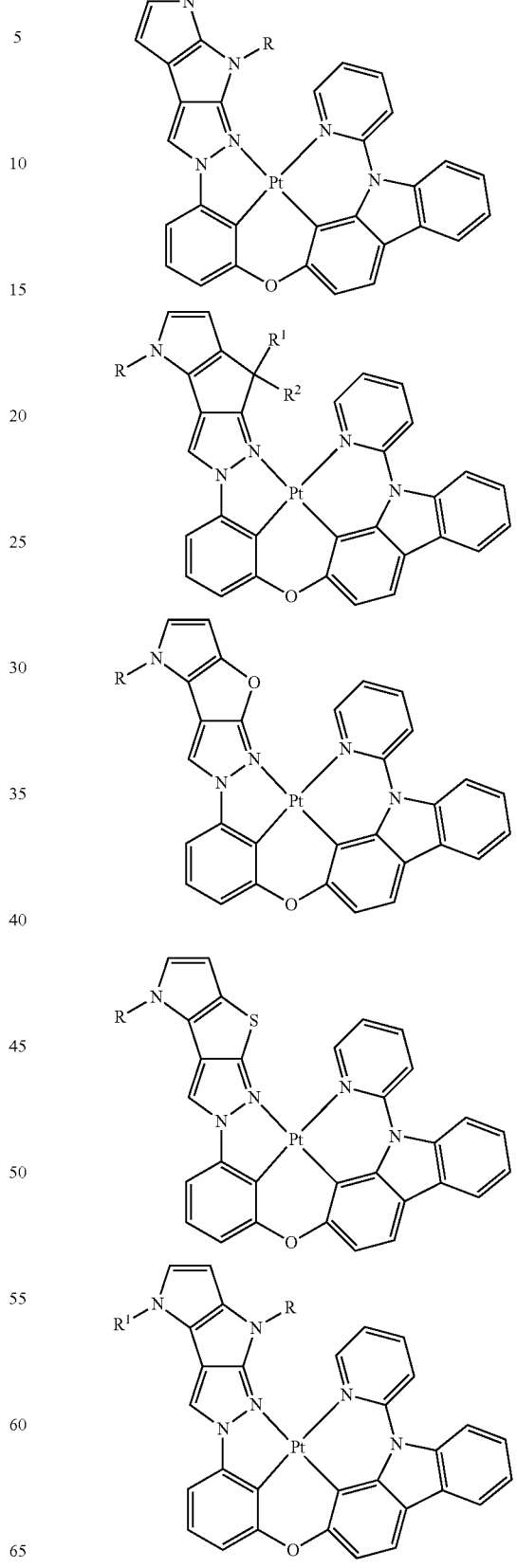

397
-continued
Structures 13
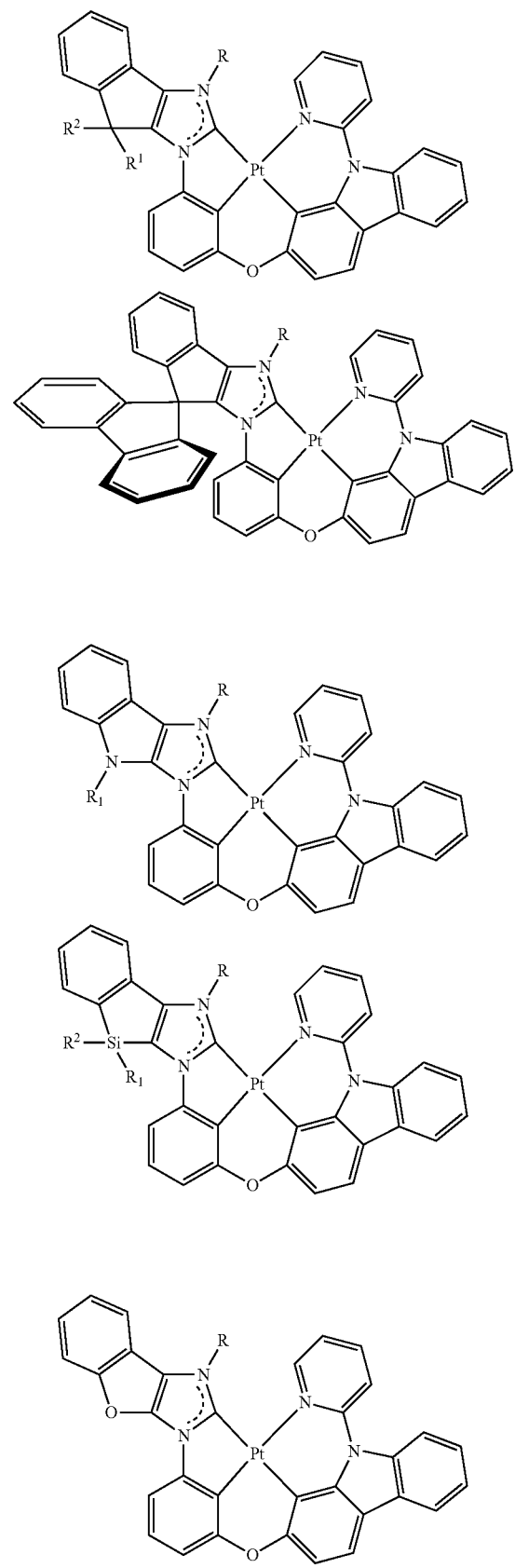
398
-continued
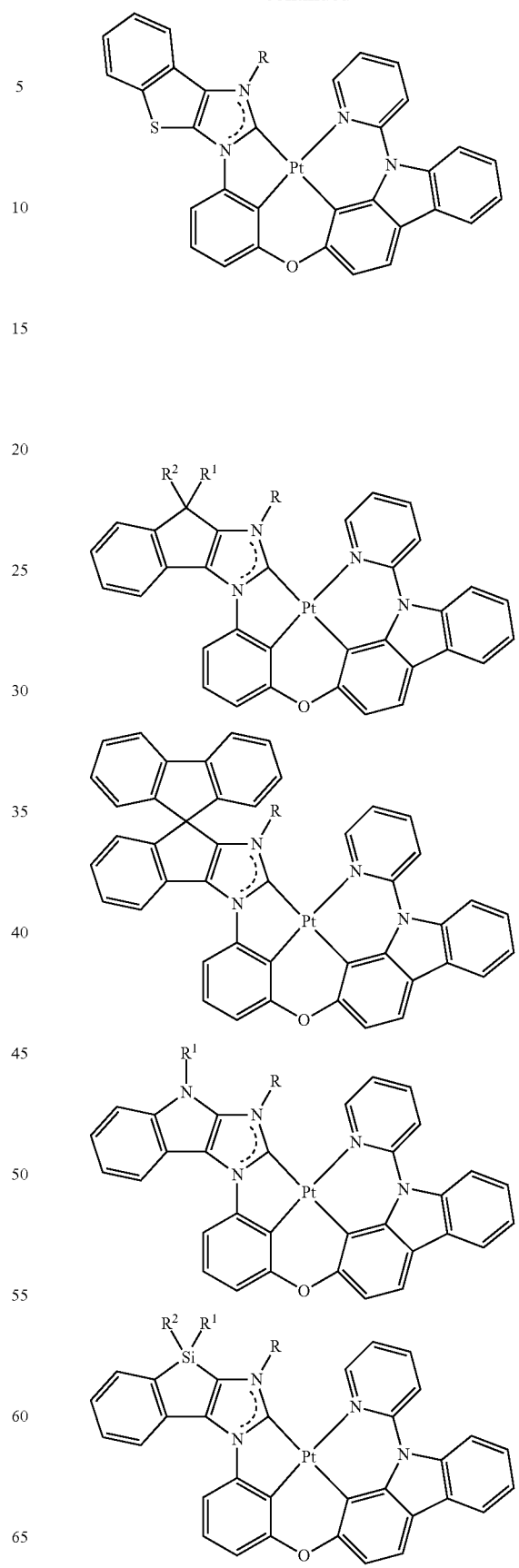

399
-continued
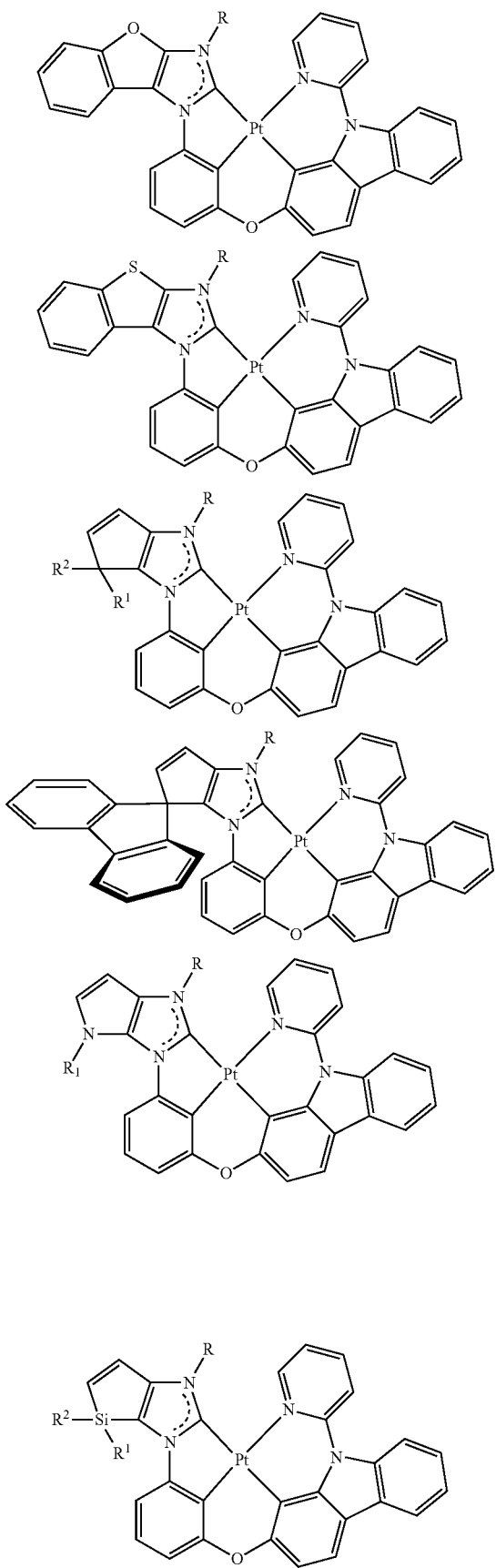
400
-continued
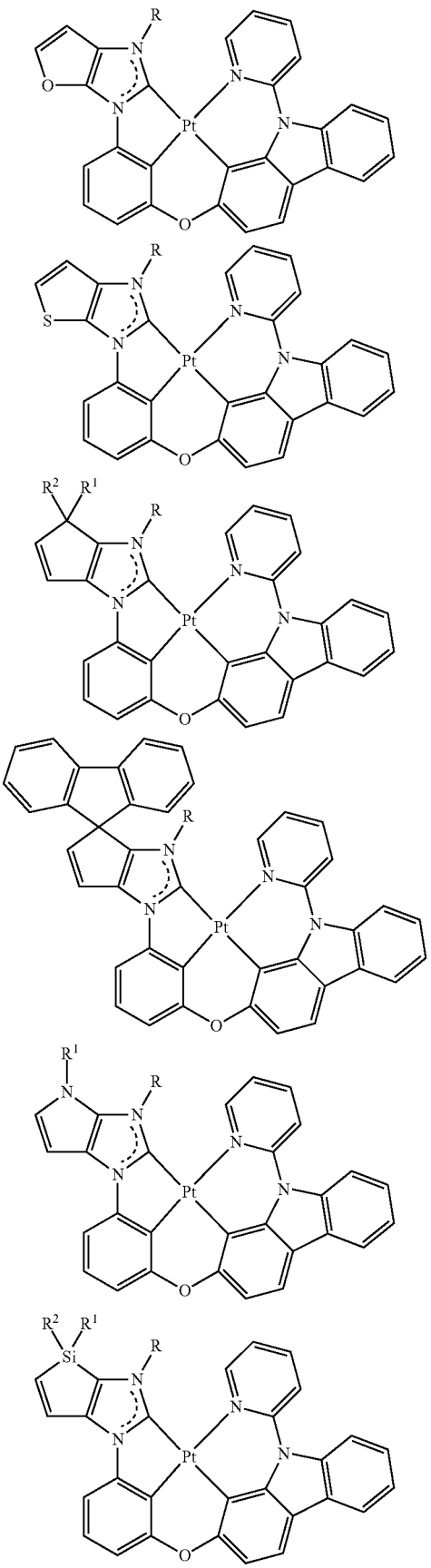

401
-continued
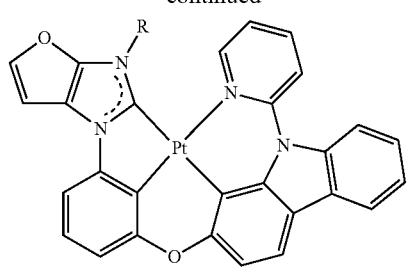
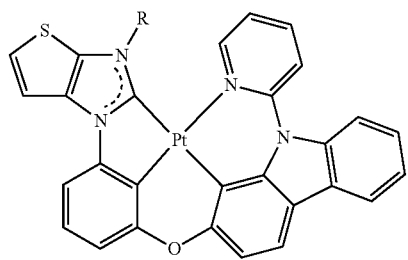
Structures 14
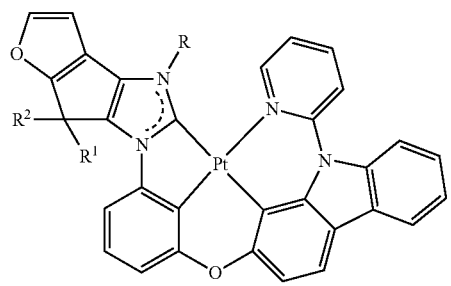
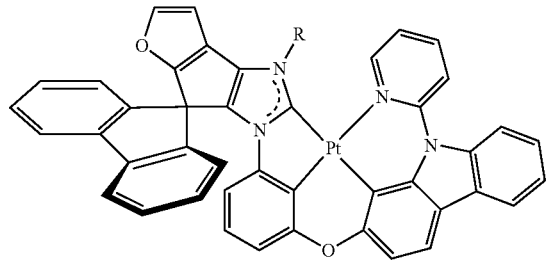
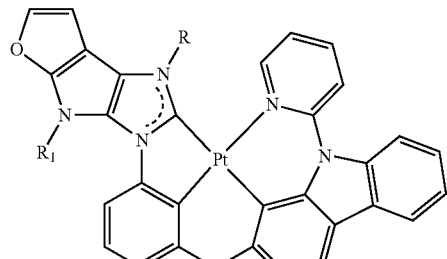
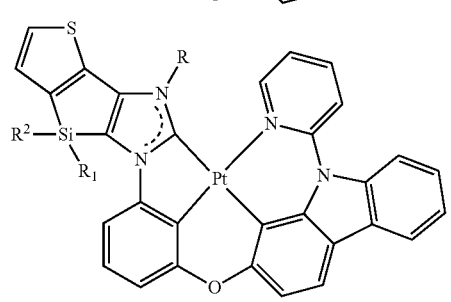
402
-continued
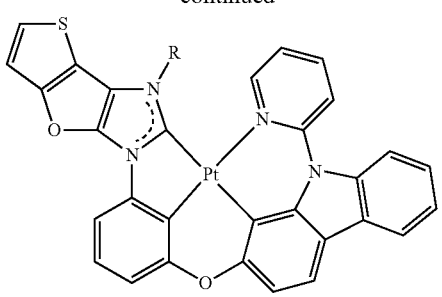
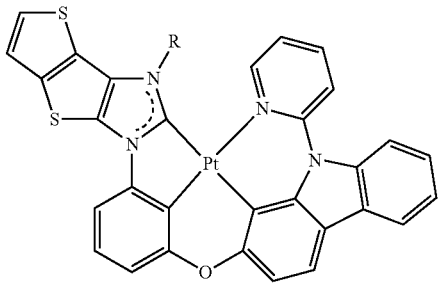
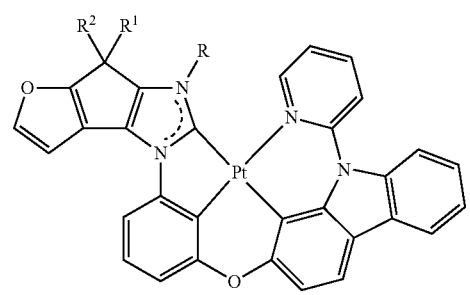
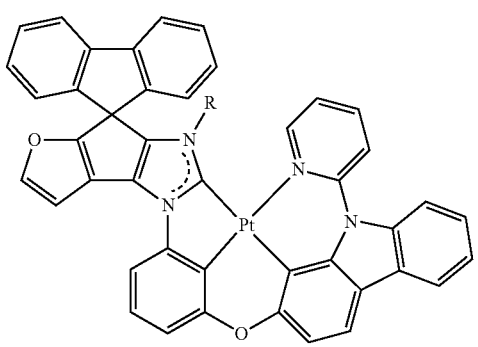
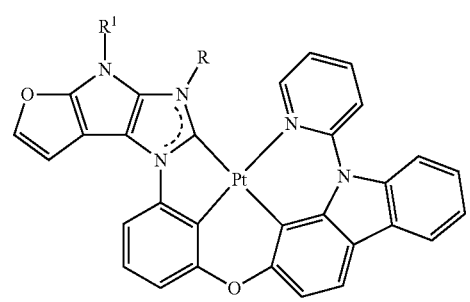

403
-continued
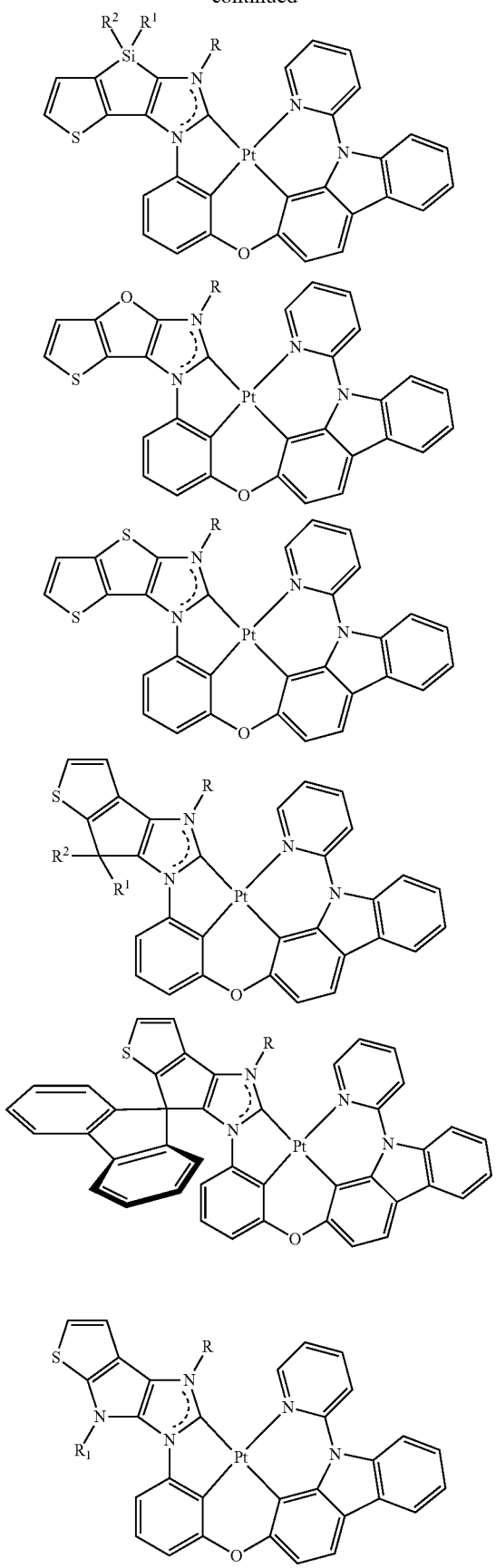
404
-continued
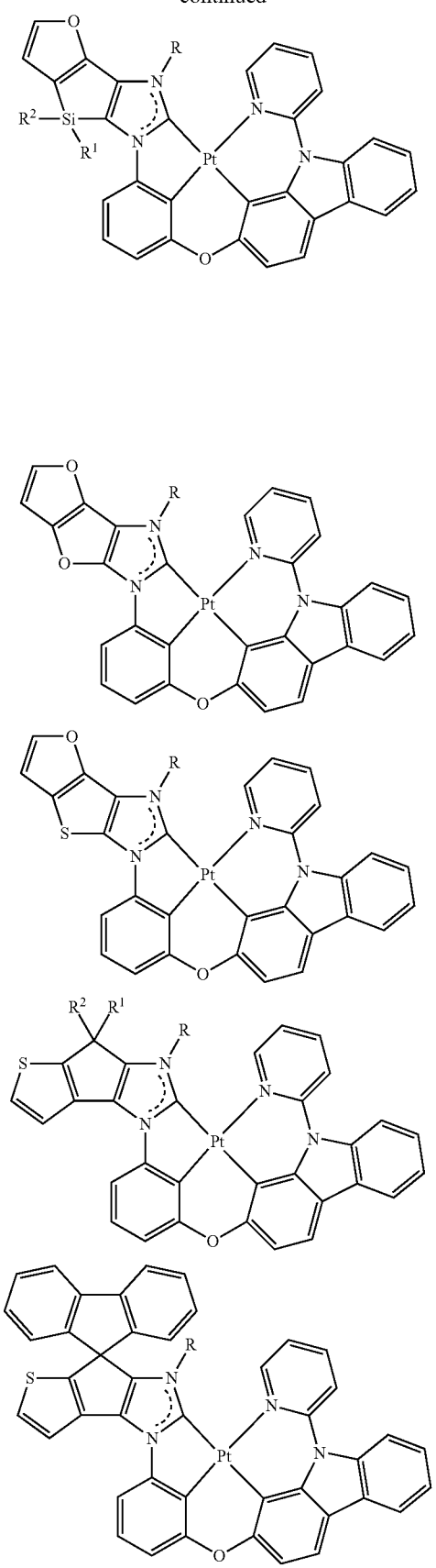

405
-continued
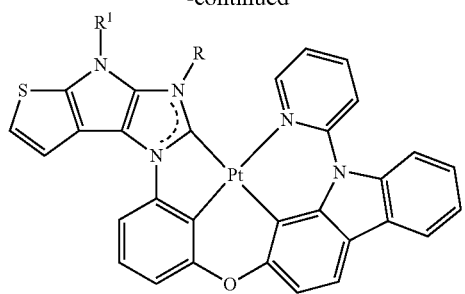
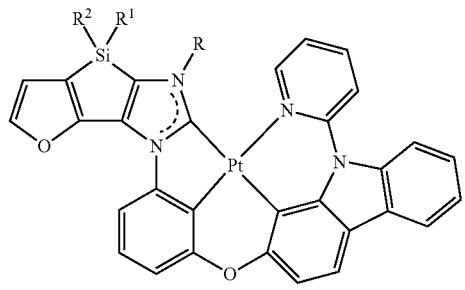
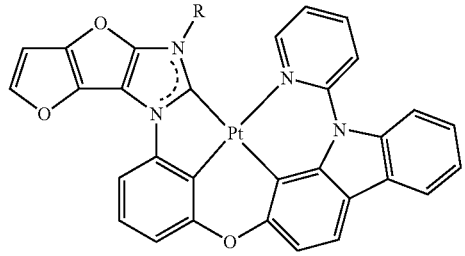
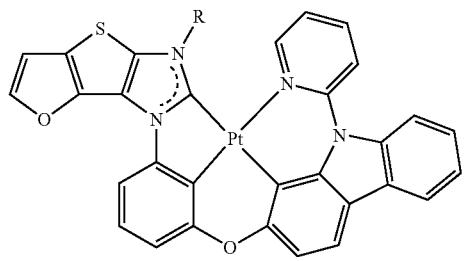
Structures 15
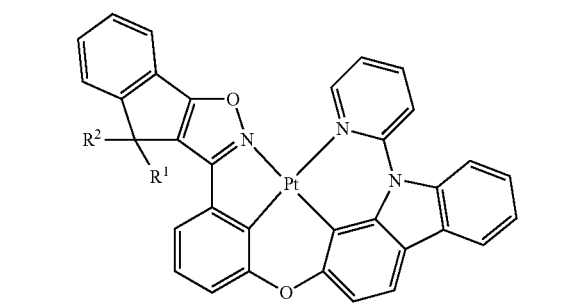
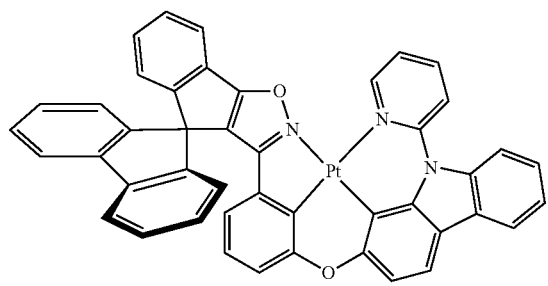
406
-continued
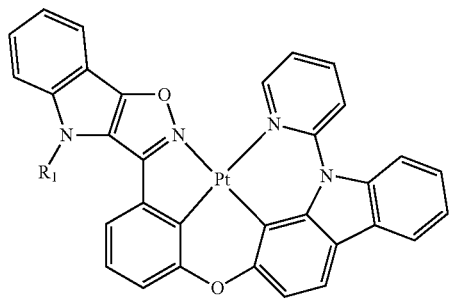
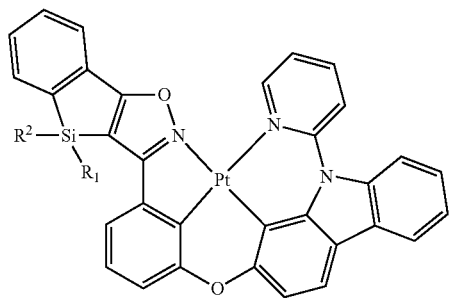
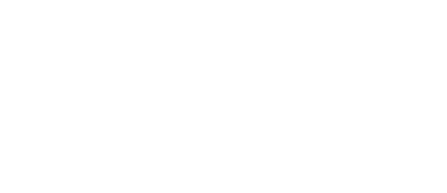
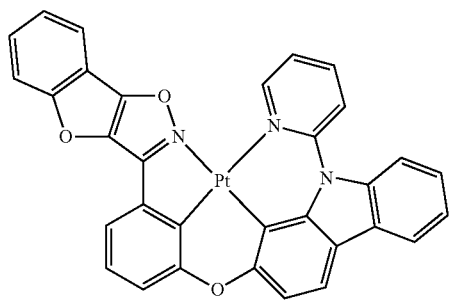
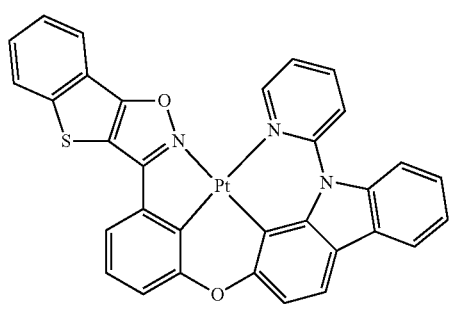
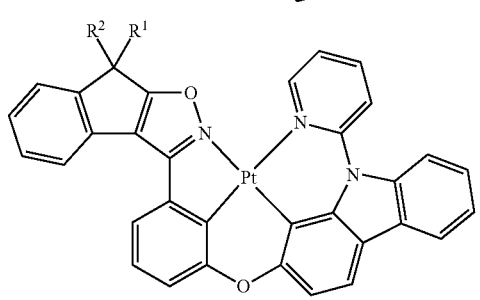

407
-continued
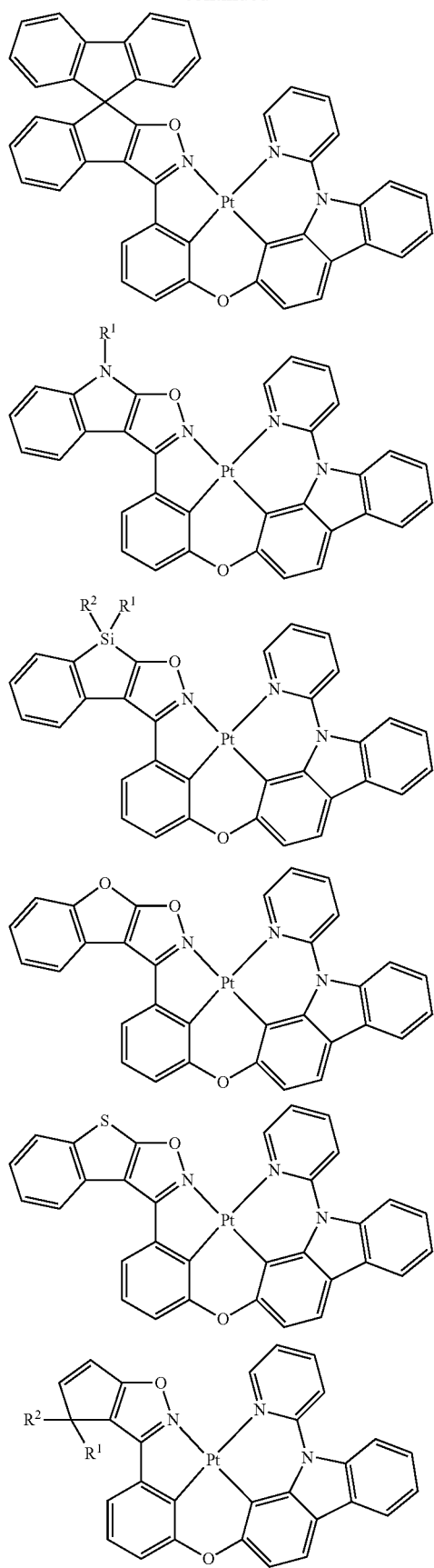
408
-continued
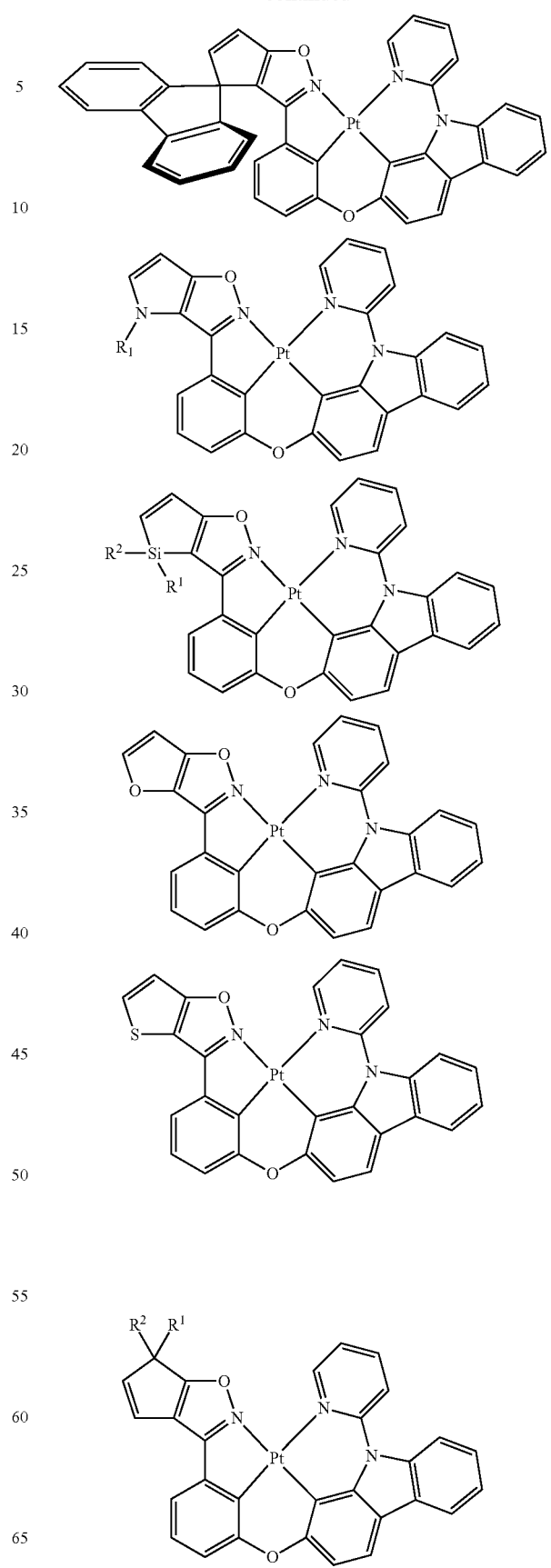

-continued
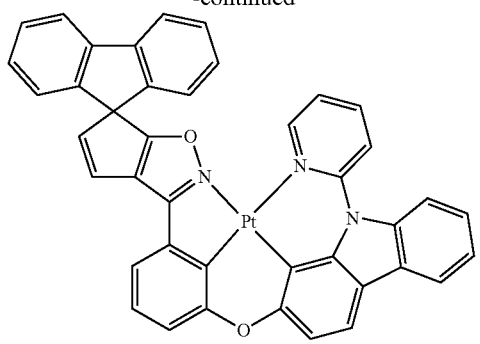
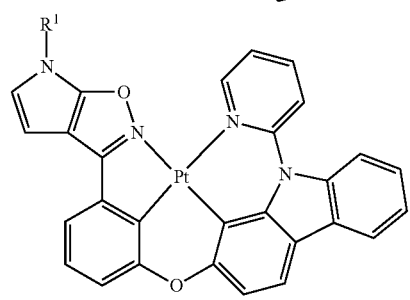
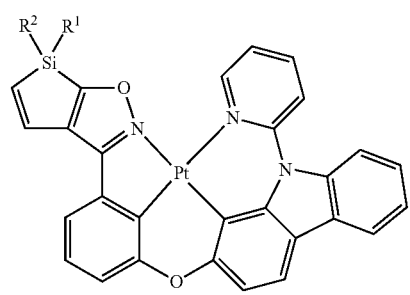
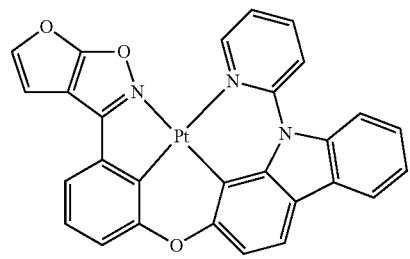

Structures 16
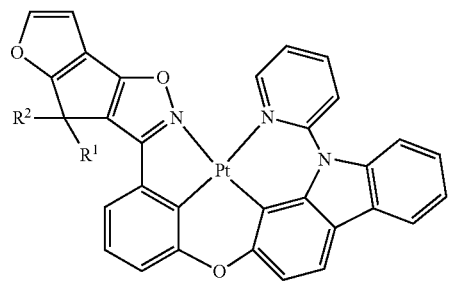
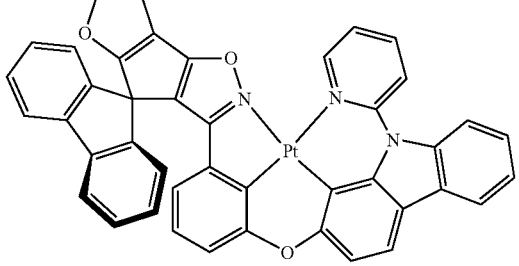
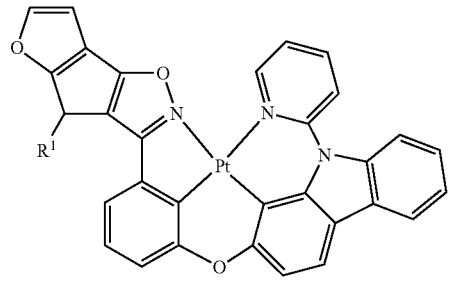
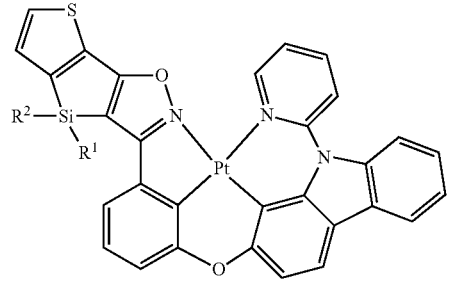
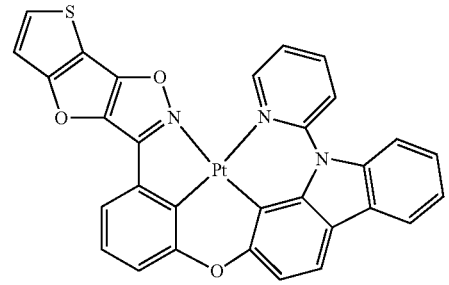
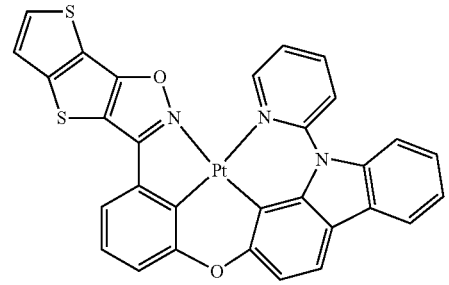

411
-continued
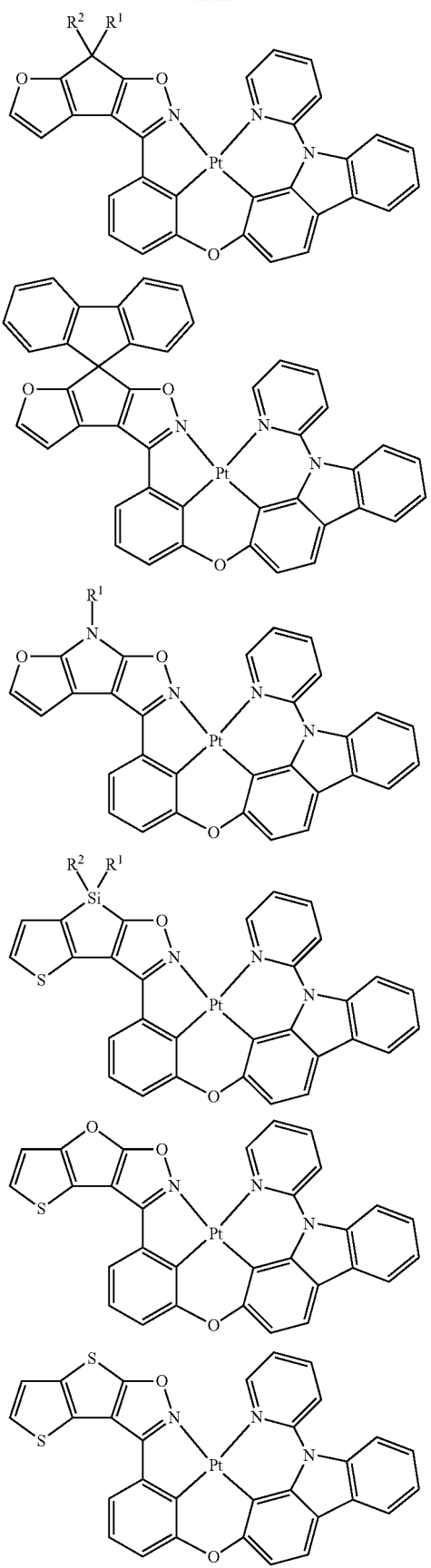
412
-continued
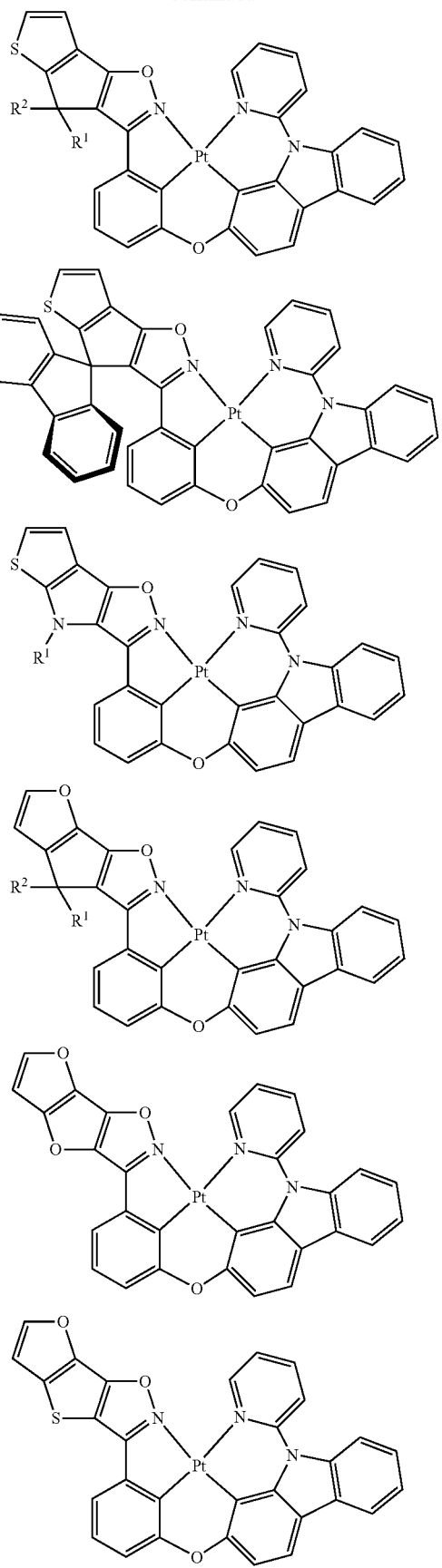

413
-continued
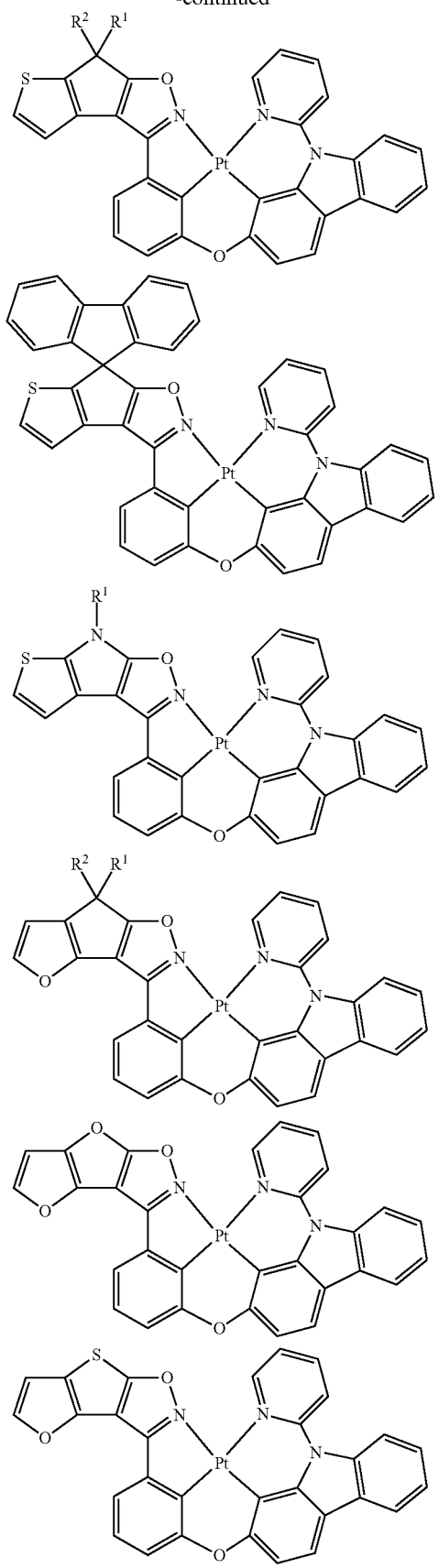
414
-continued
Structures 17
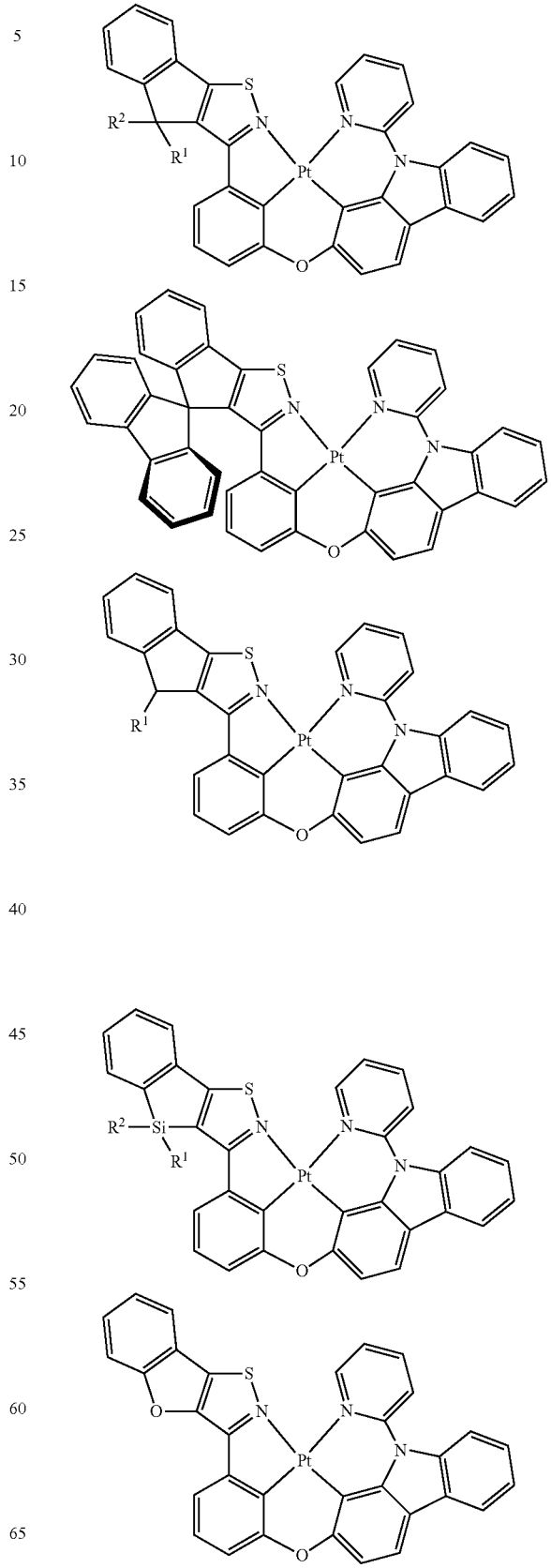

415
-continued
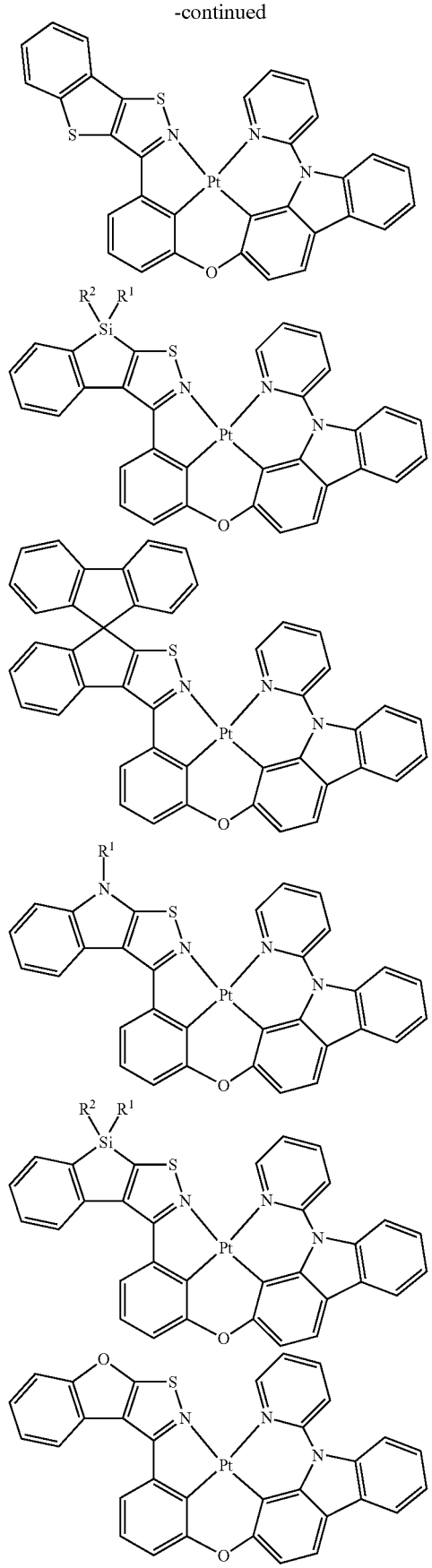
416
-continued
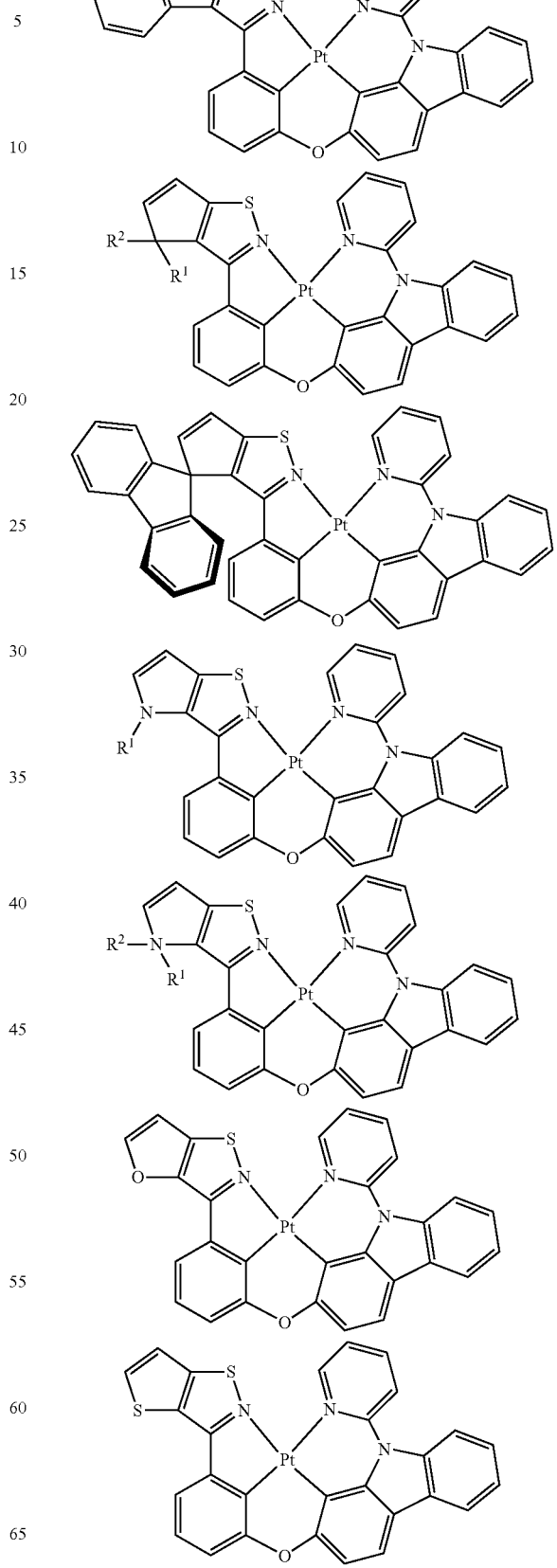

417
-continued
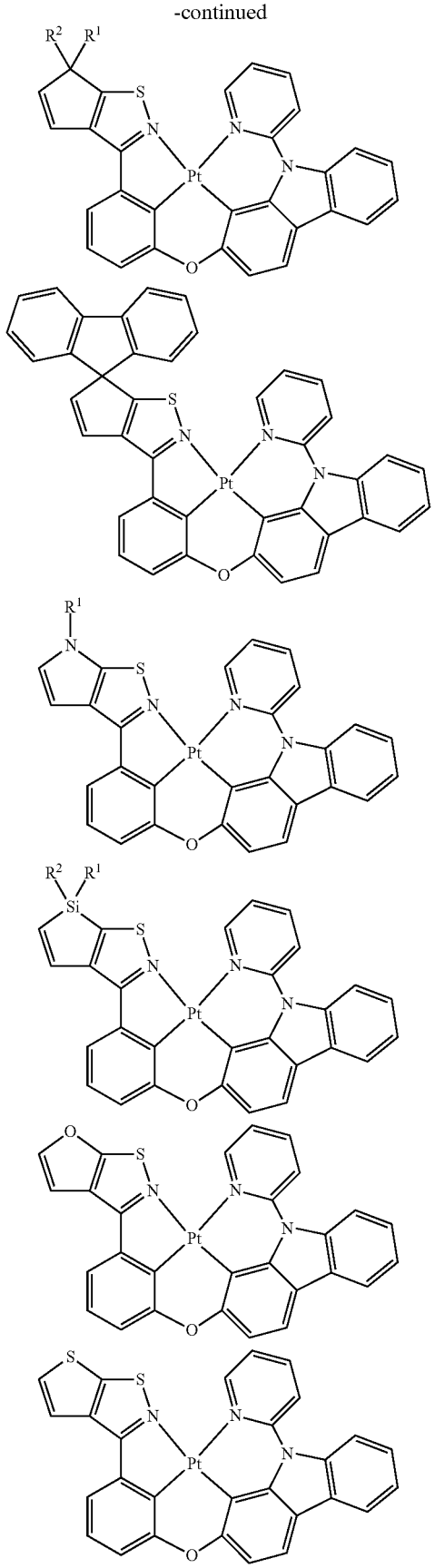
418
-continued
Structures 18
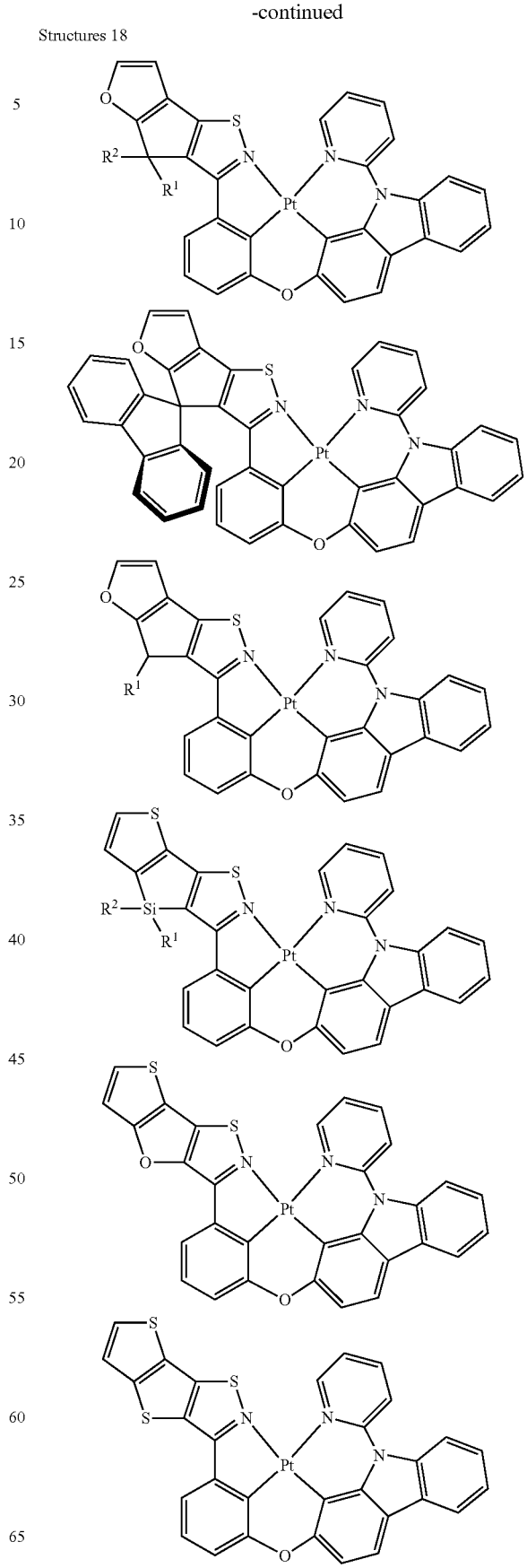

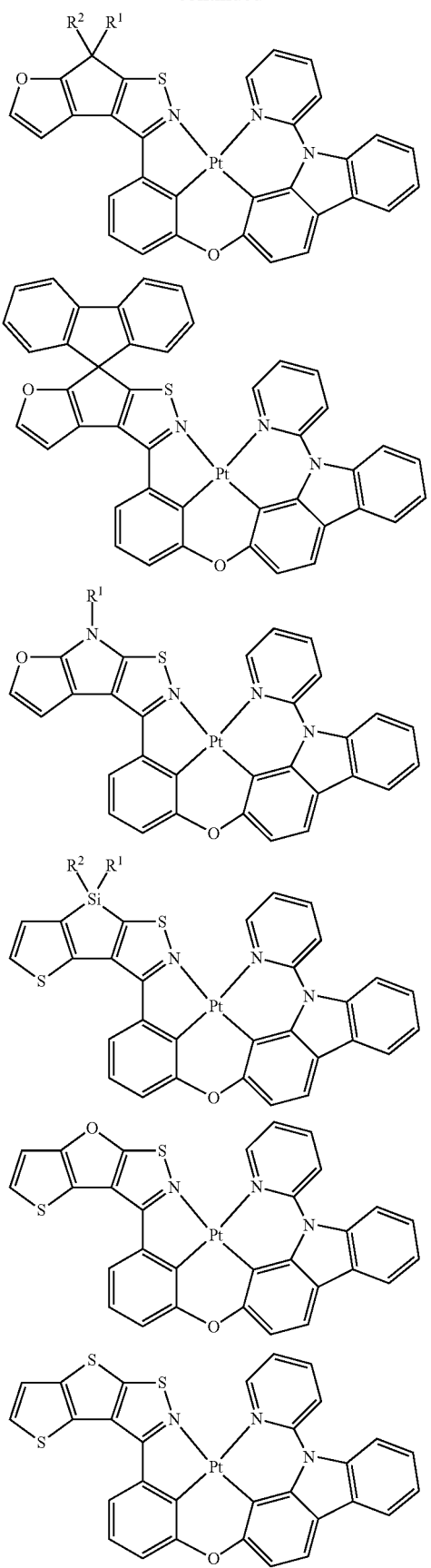
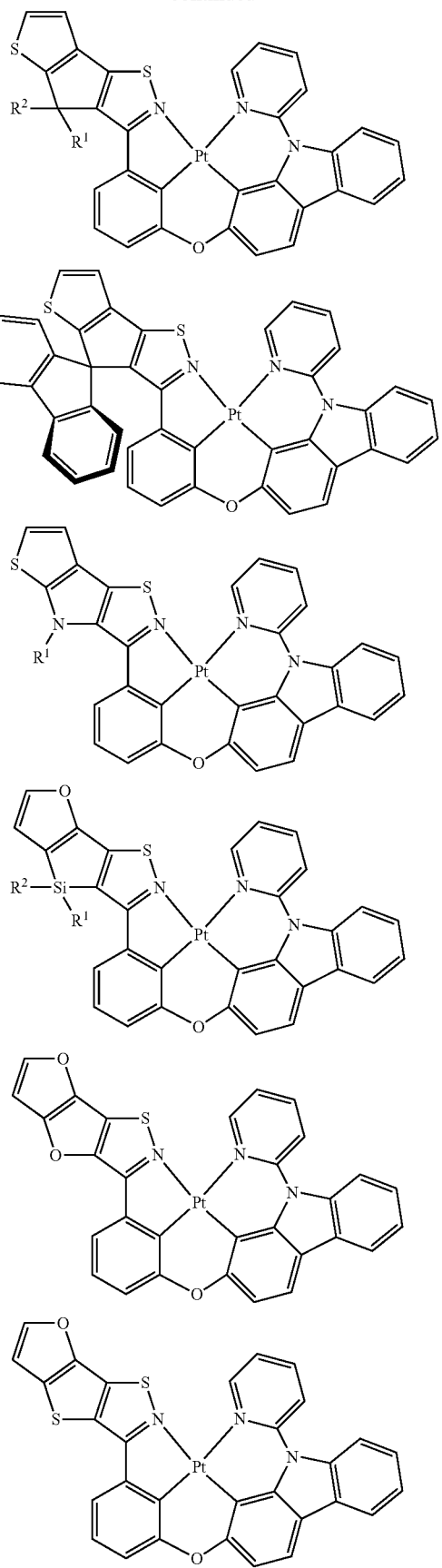

Structures 19
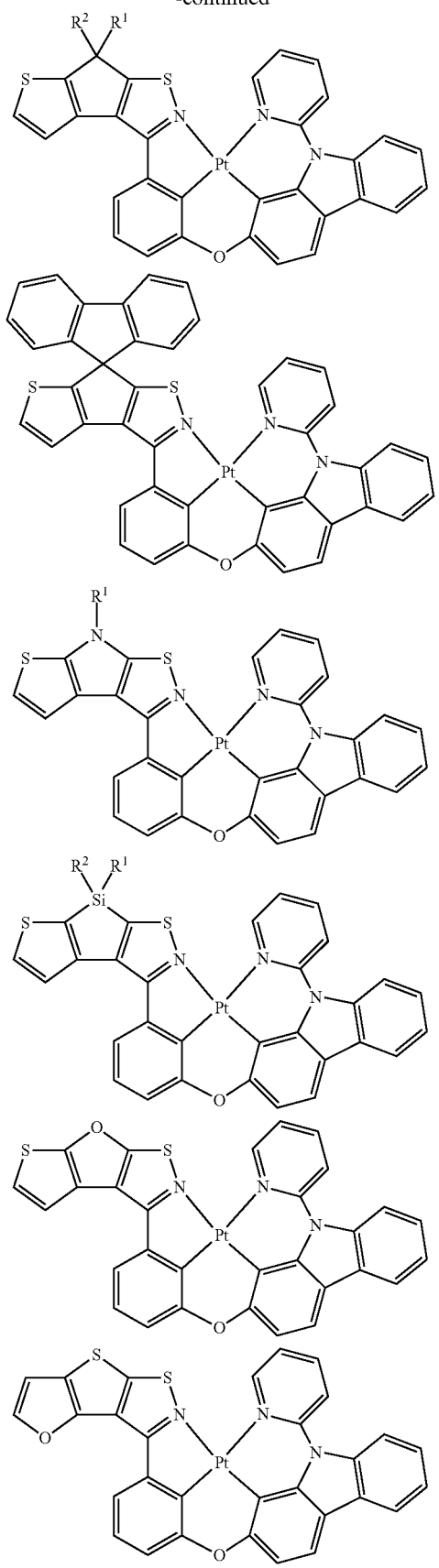
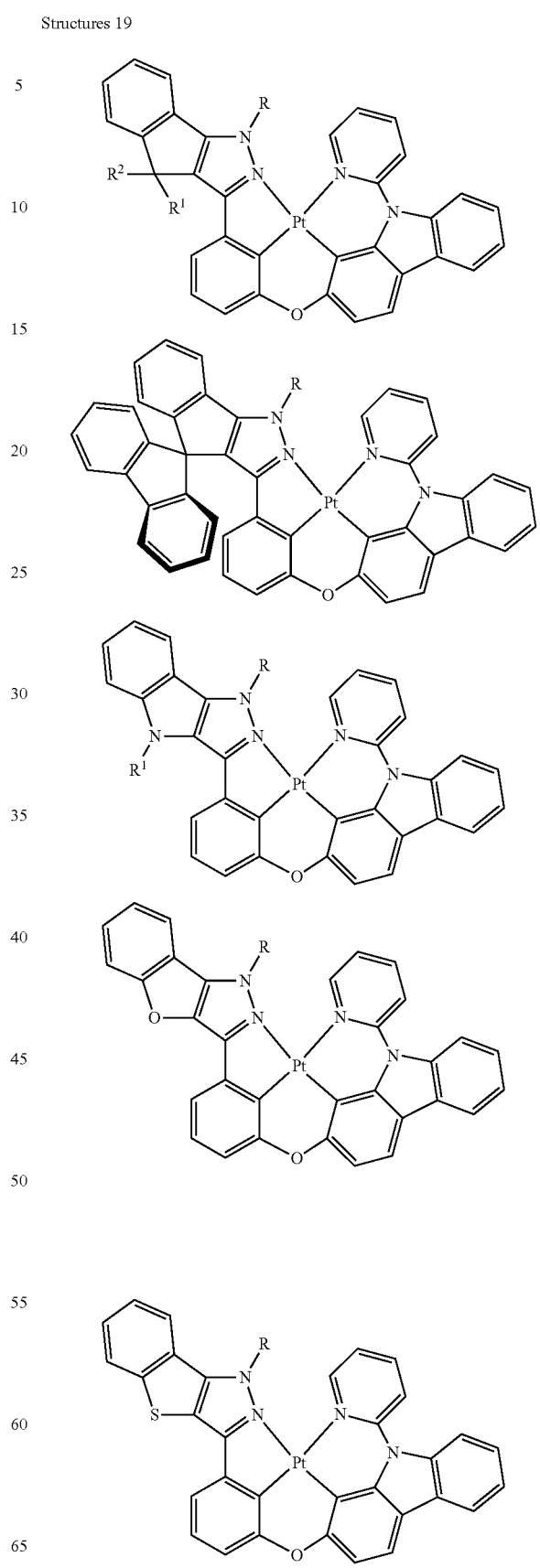

423
-continued
424
-continued
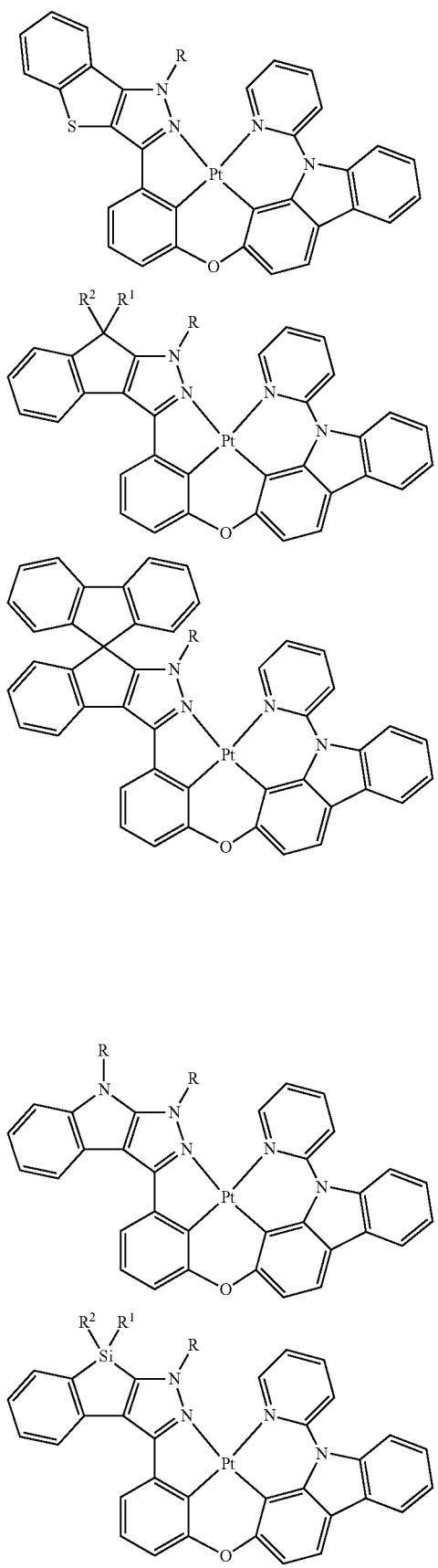
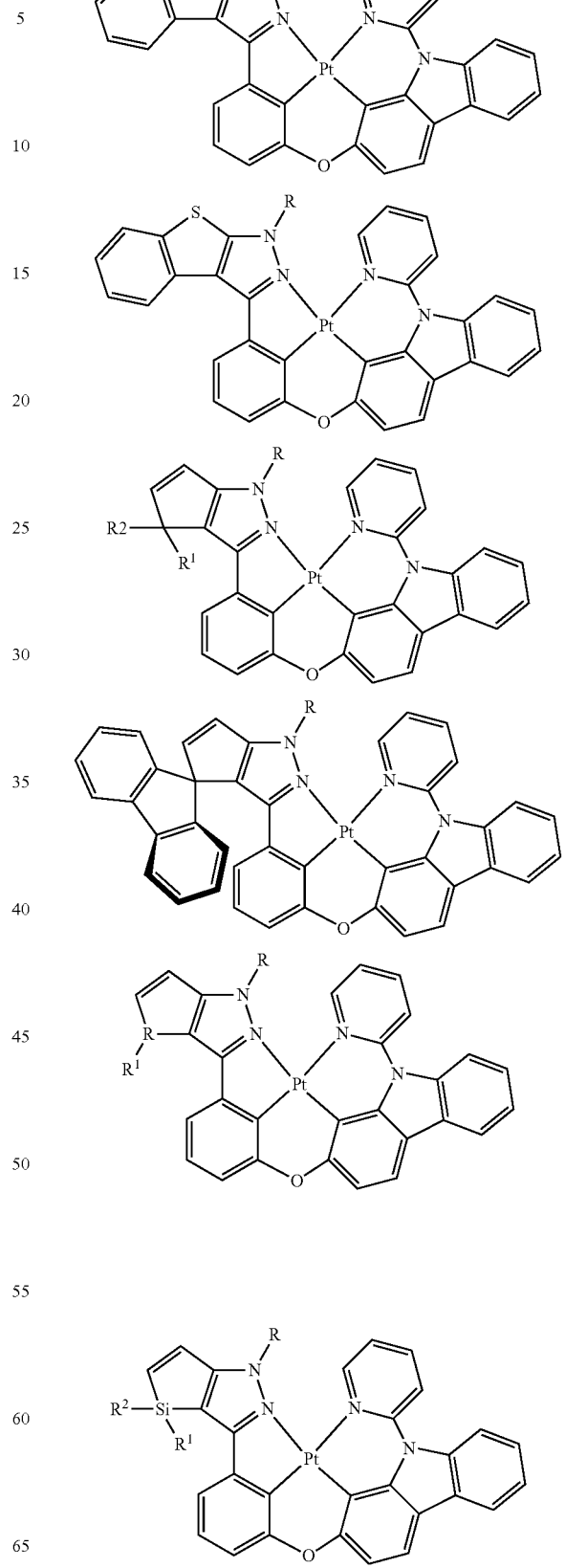

425
-continued
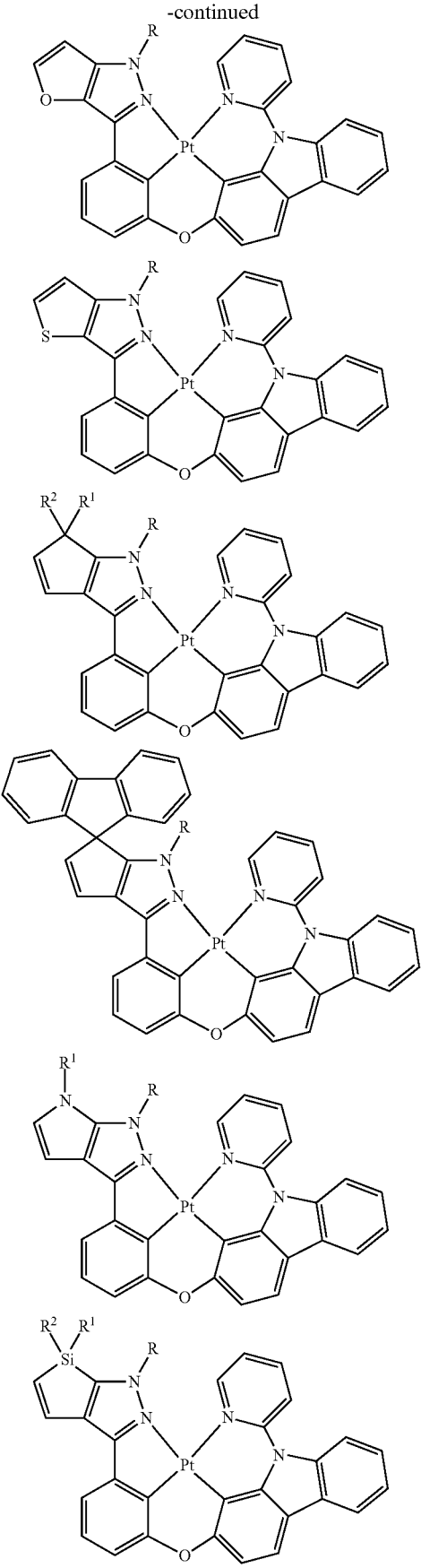
426
-continued
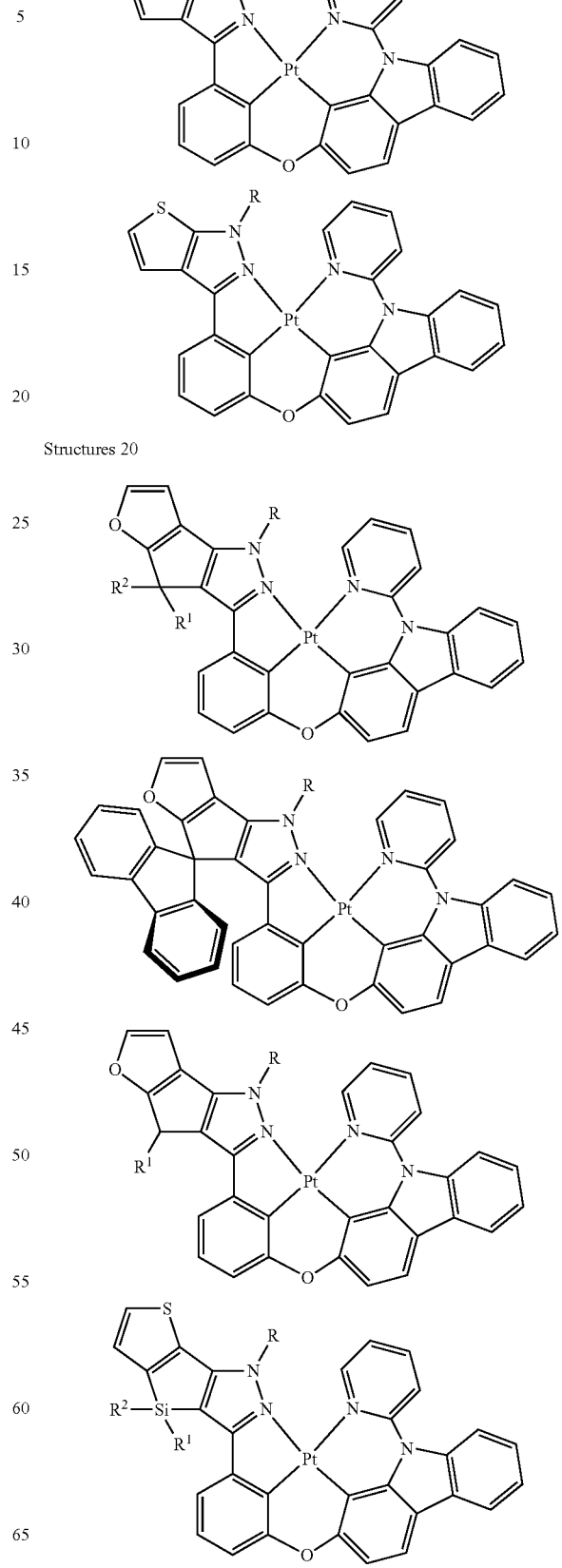
Structures 20

427
-continued
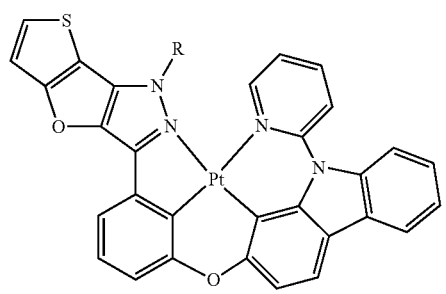
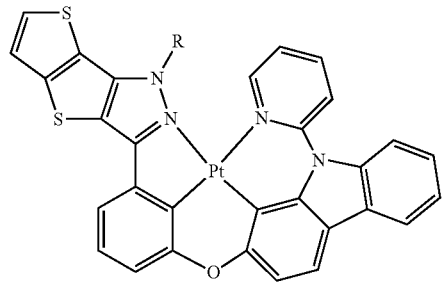
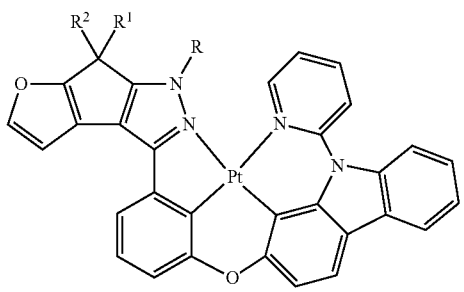
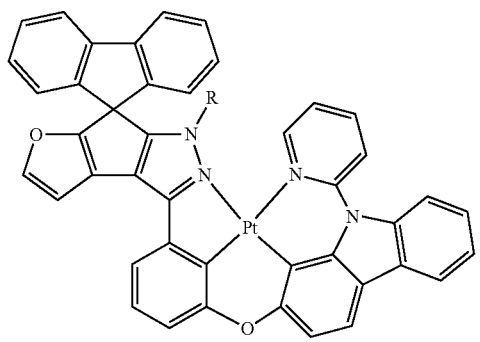
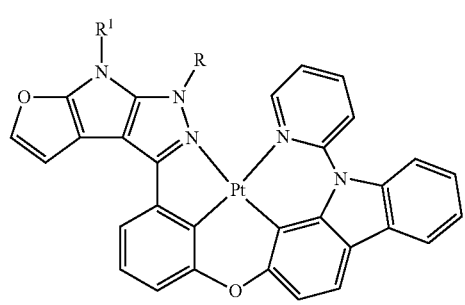
428
-continued
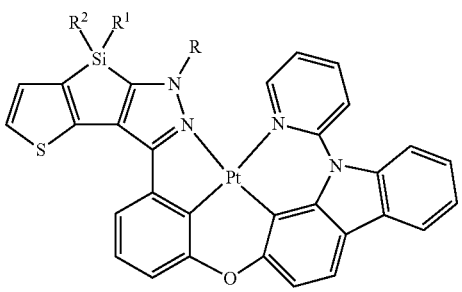
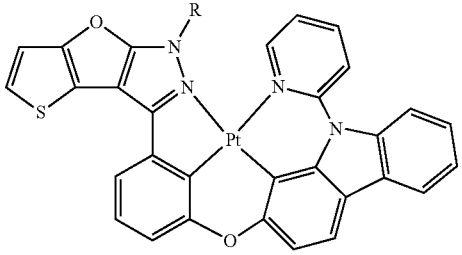
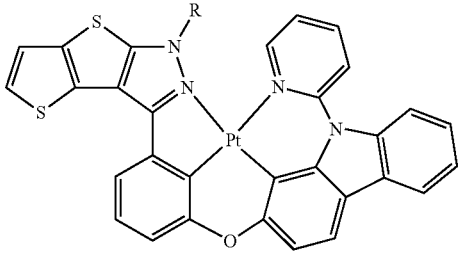
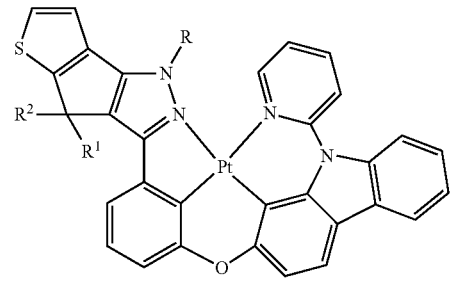
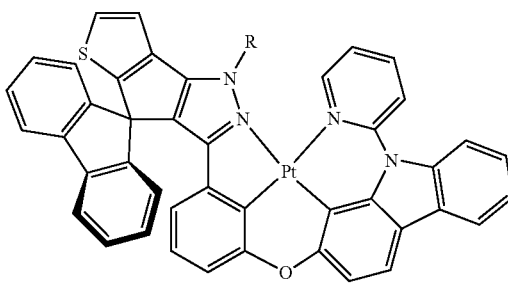
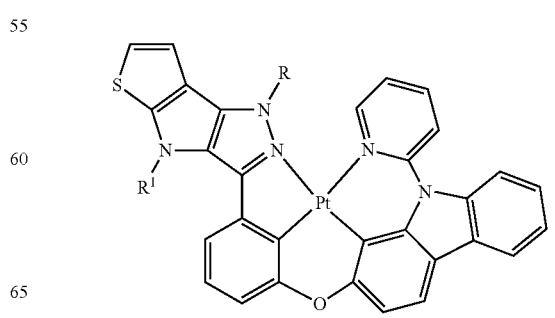

429
-continued
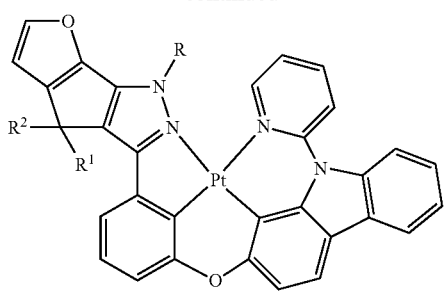
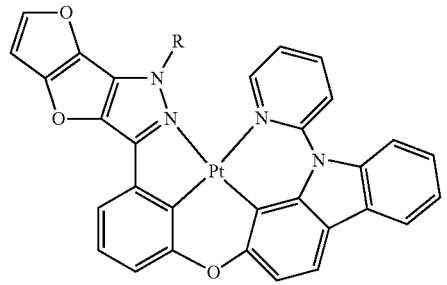
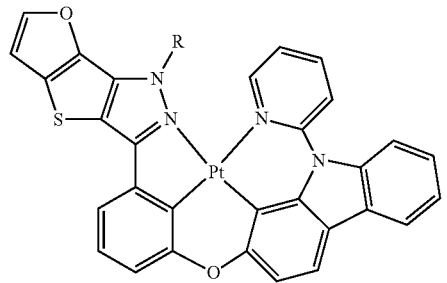
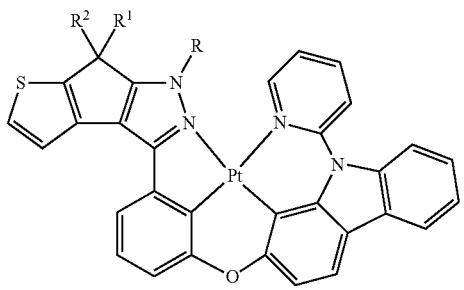
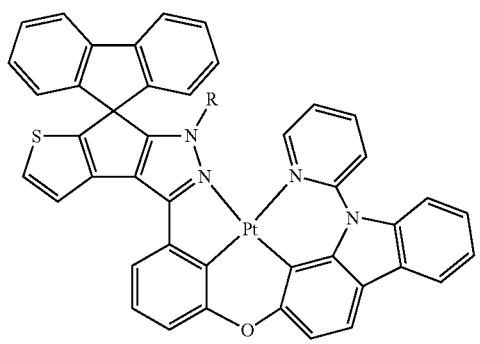
430
-continued
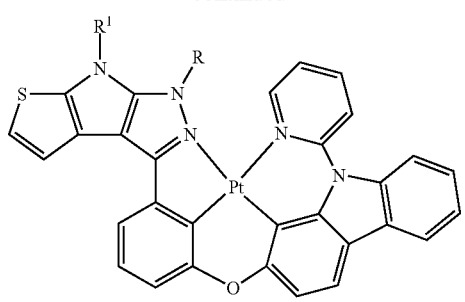
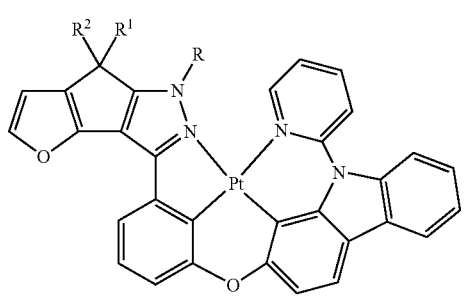
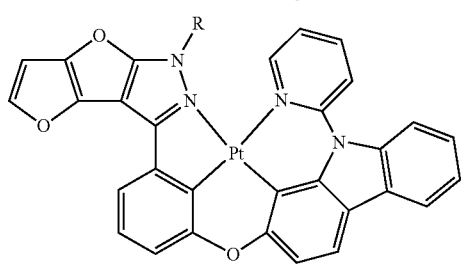
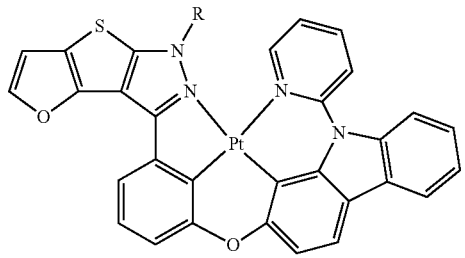
Structures 21
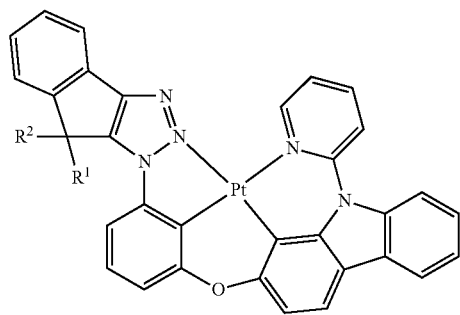

431
-continued
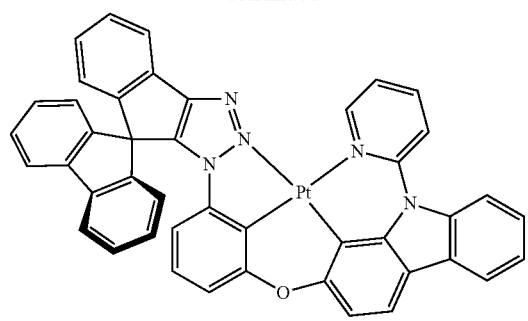
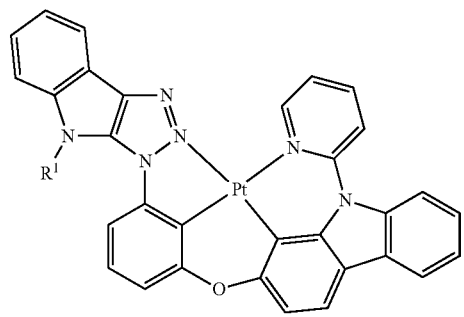
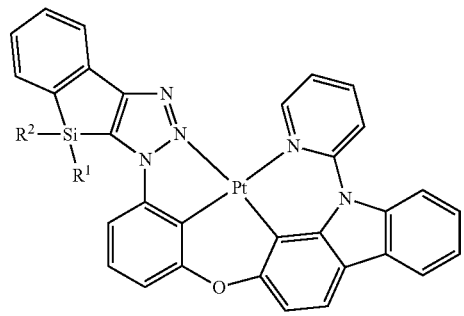

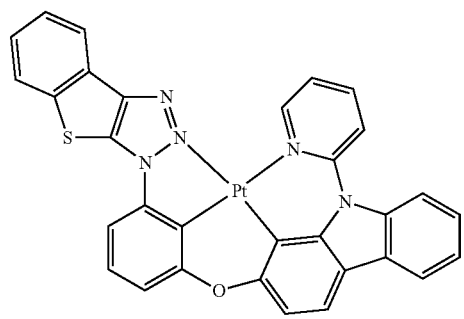
432
-continued
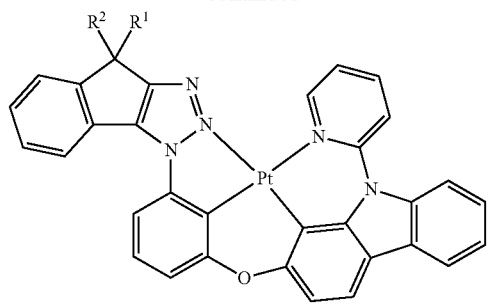
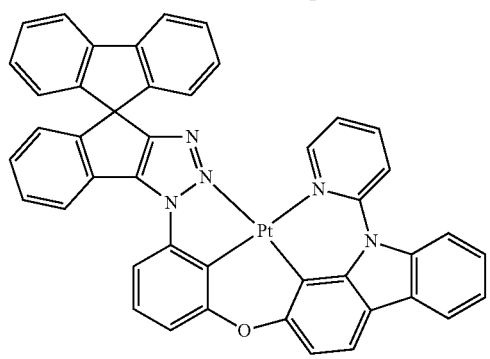
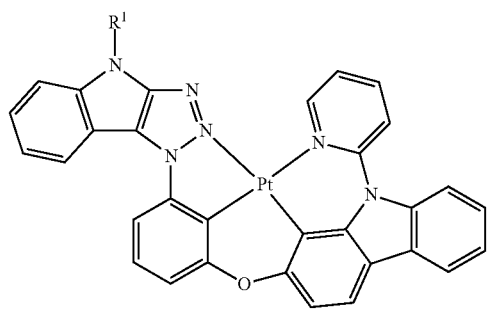
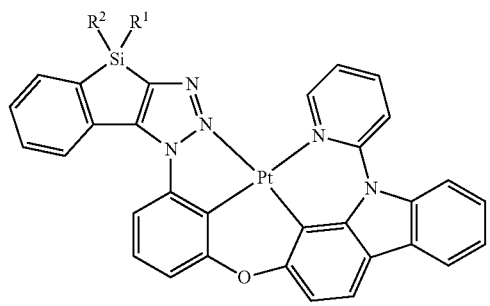
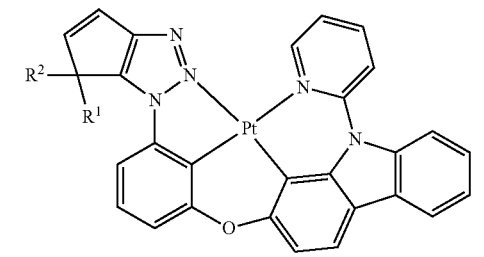

433
-continued
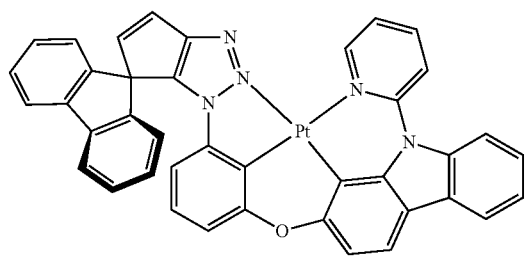
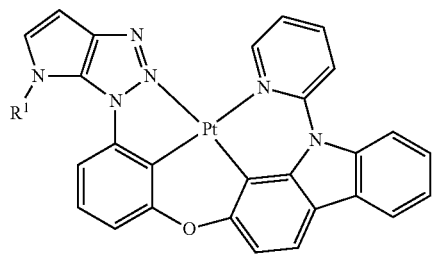
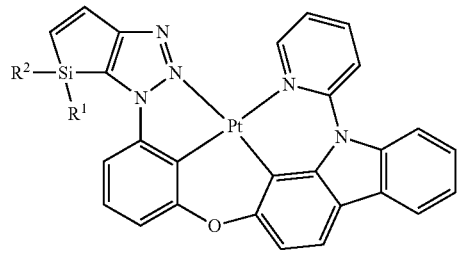
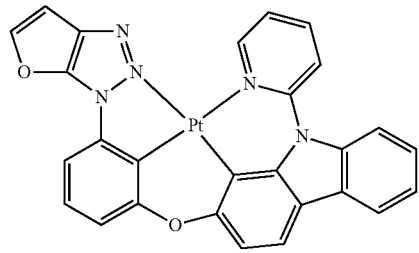
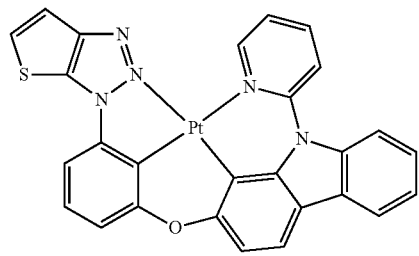
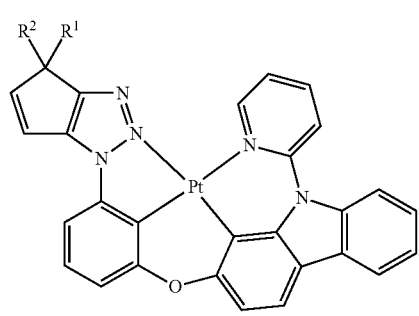
434
-continued
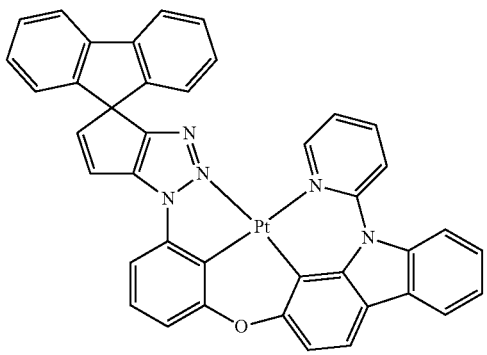
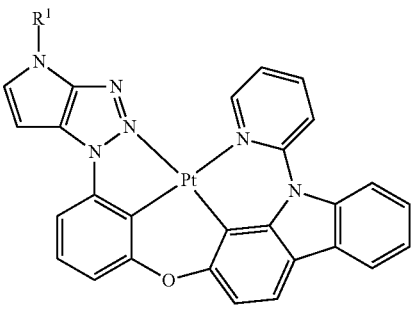
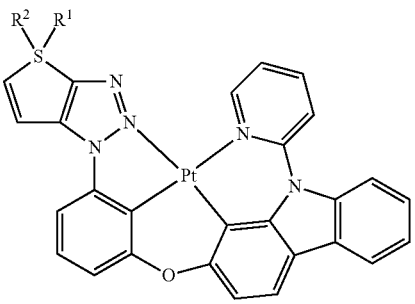
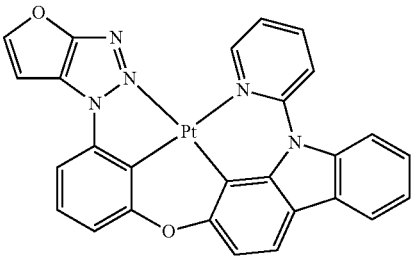
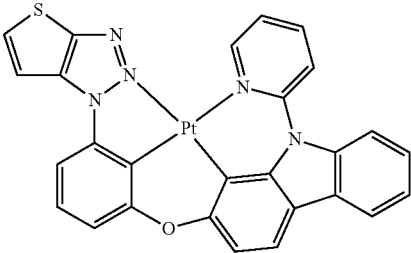

Structures 22
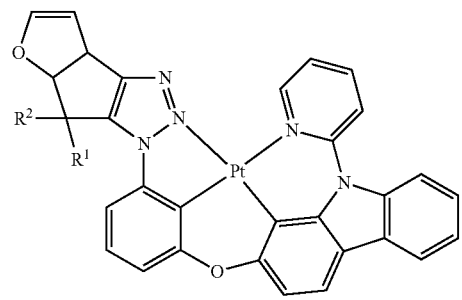
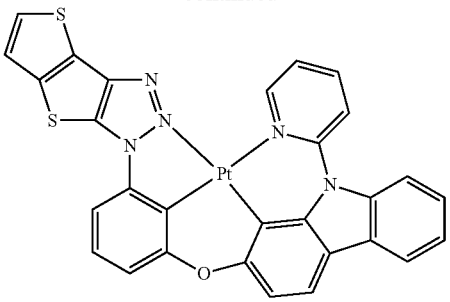
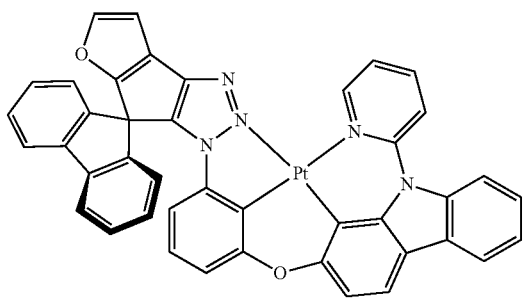
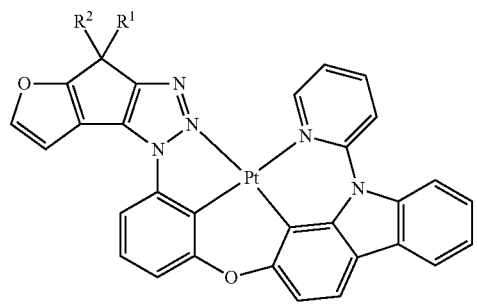
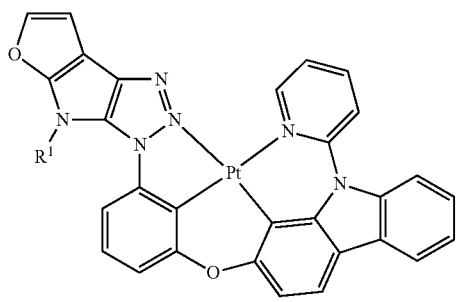
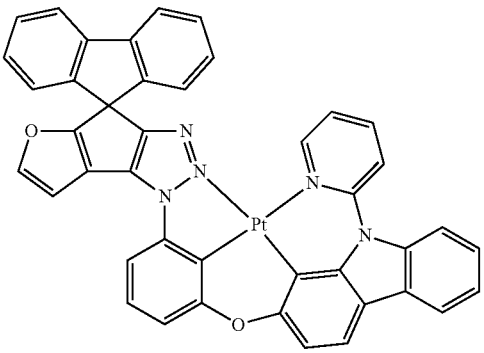
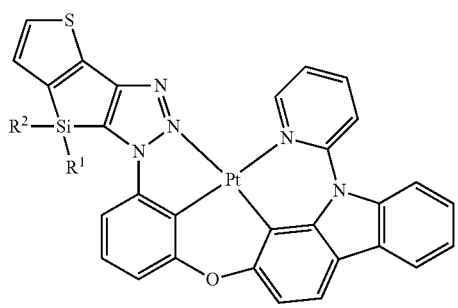
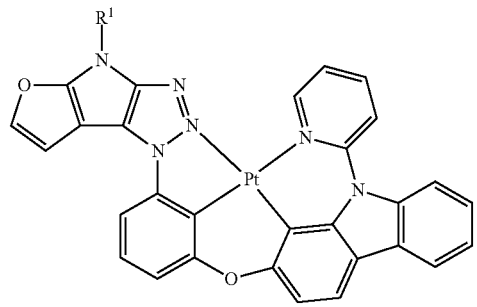
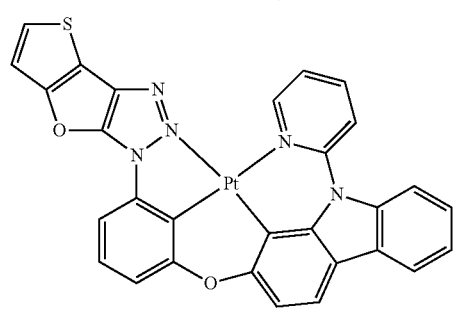
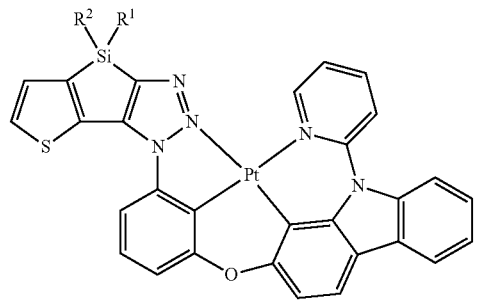

437
-continued
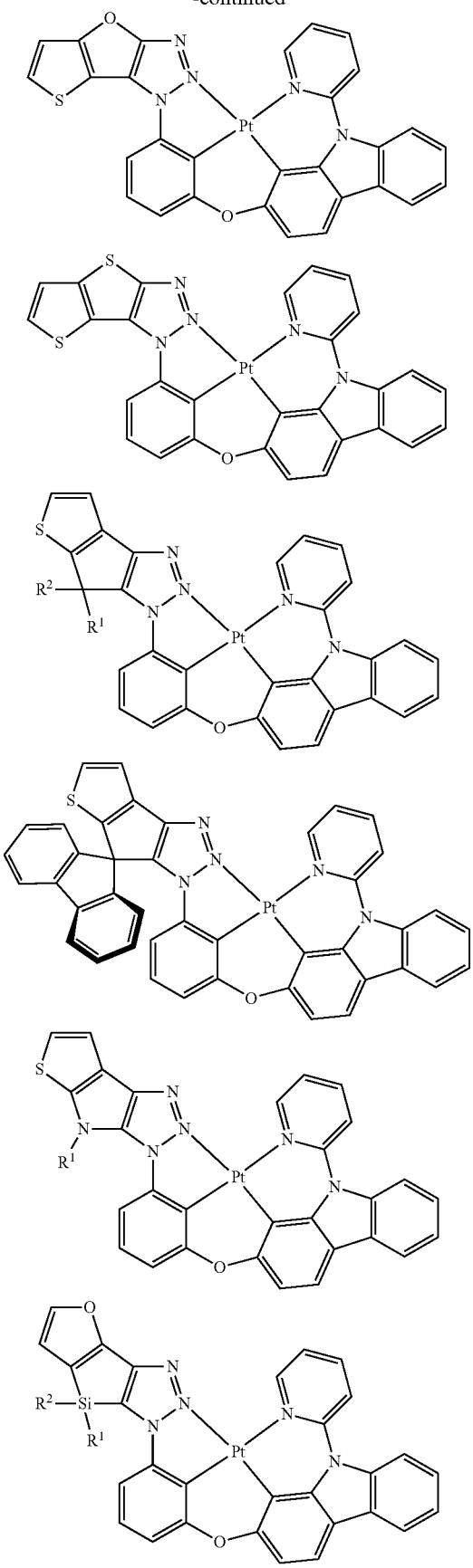
438
-continued
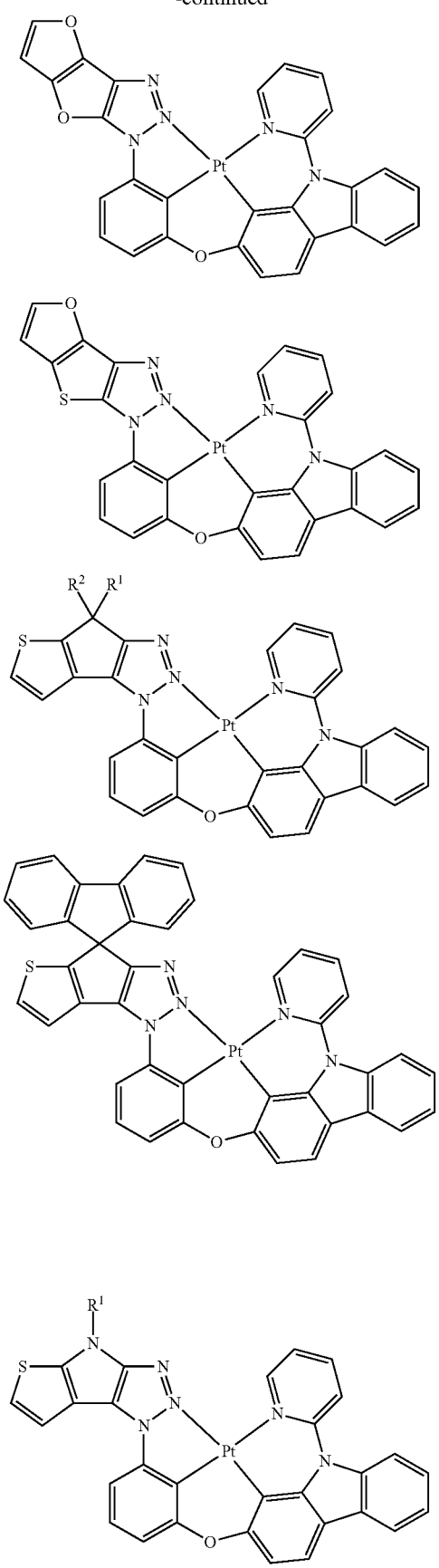

439
-continued
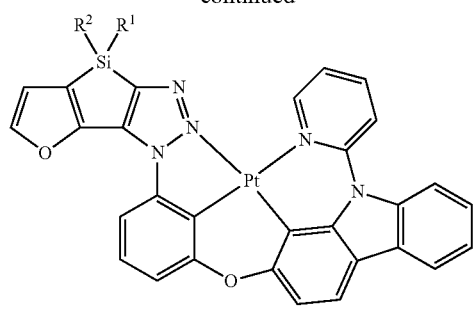
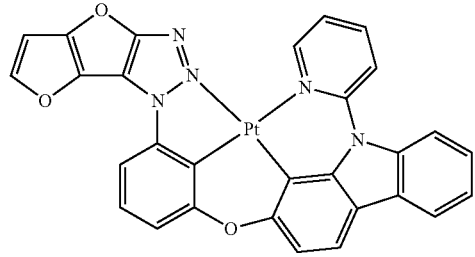
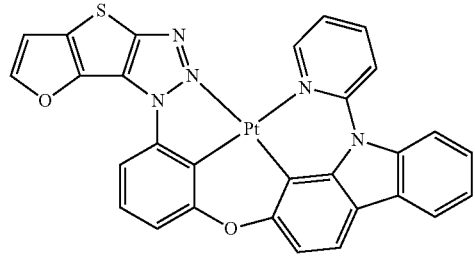
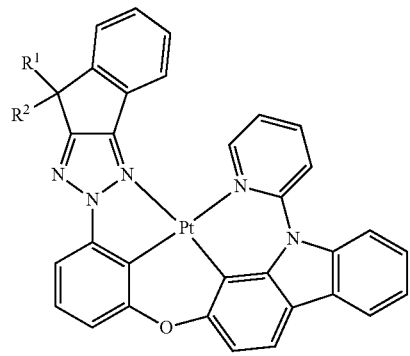
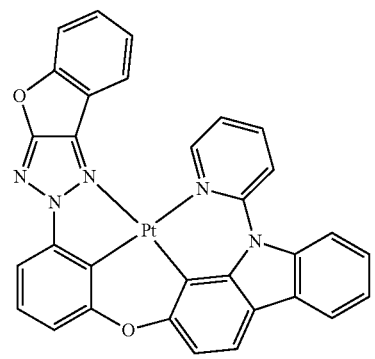
440
-continued
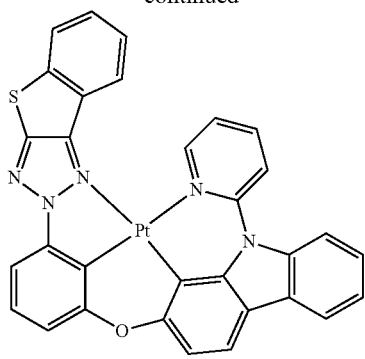
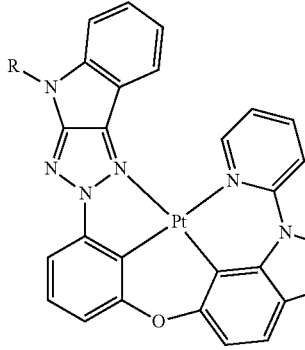
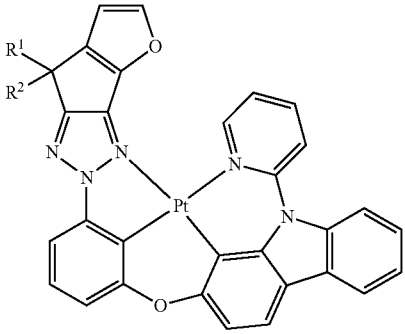
Structures 23
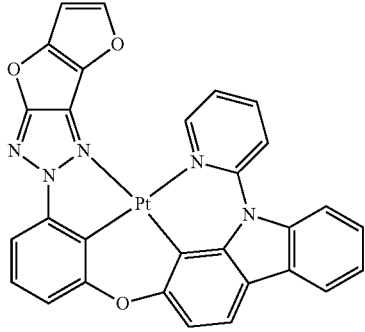
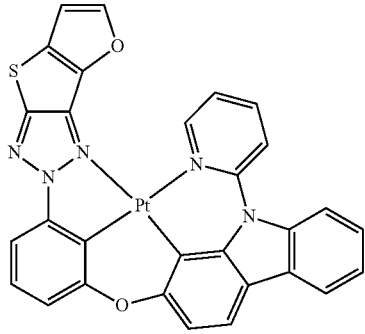

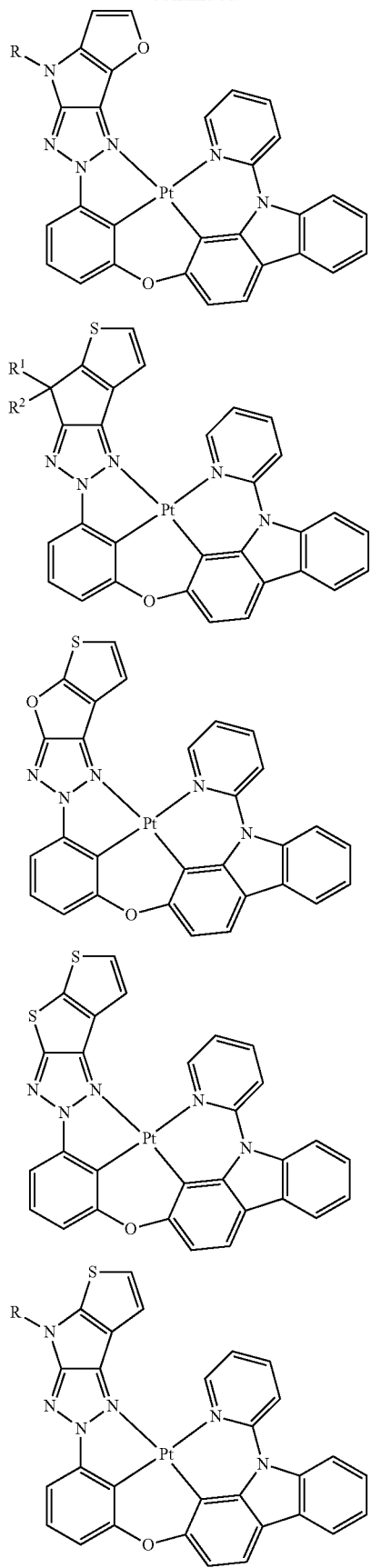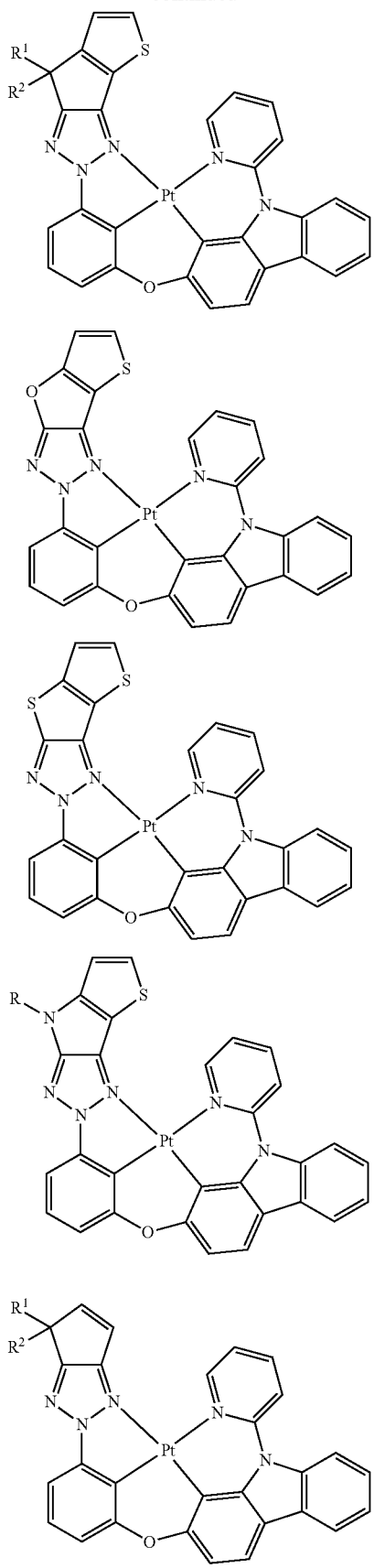

443
-continued
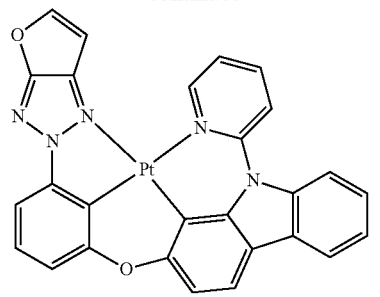
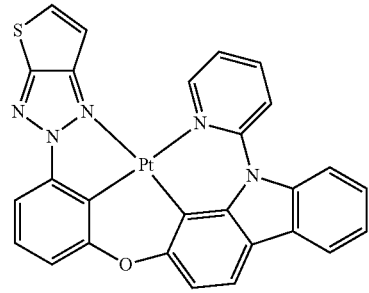
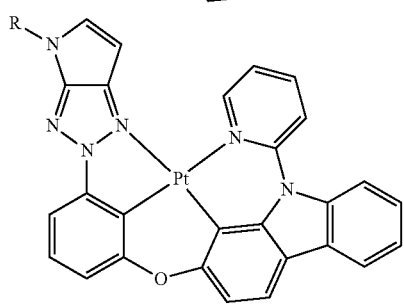
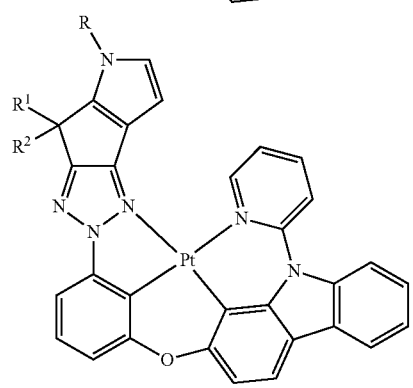
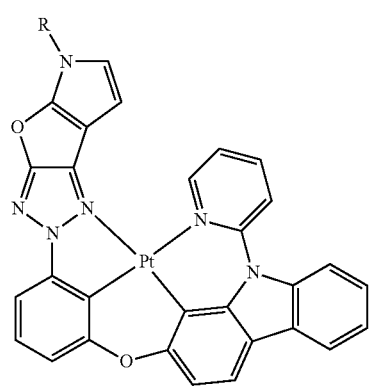
444
-continued
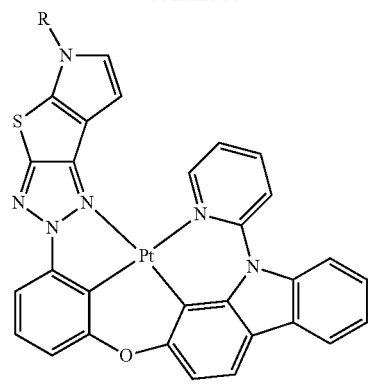
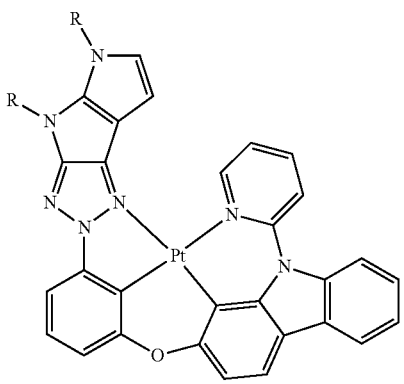
Structures 24
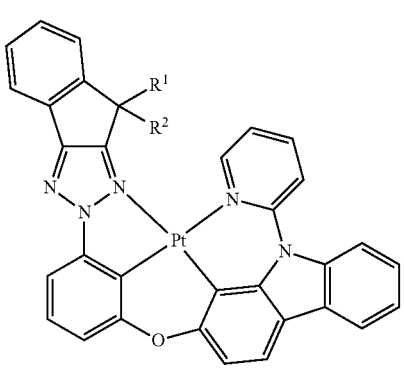
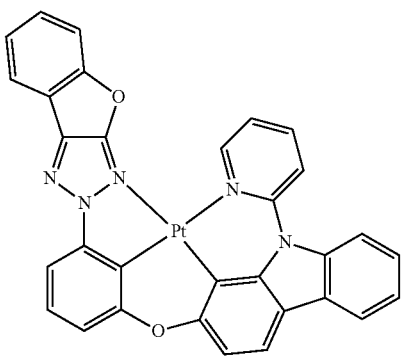

445
-continued
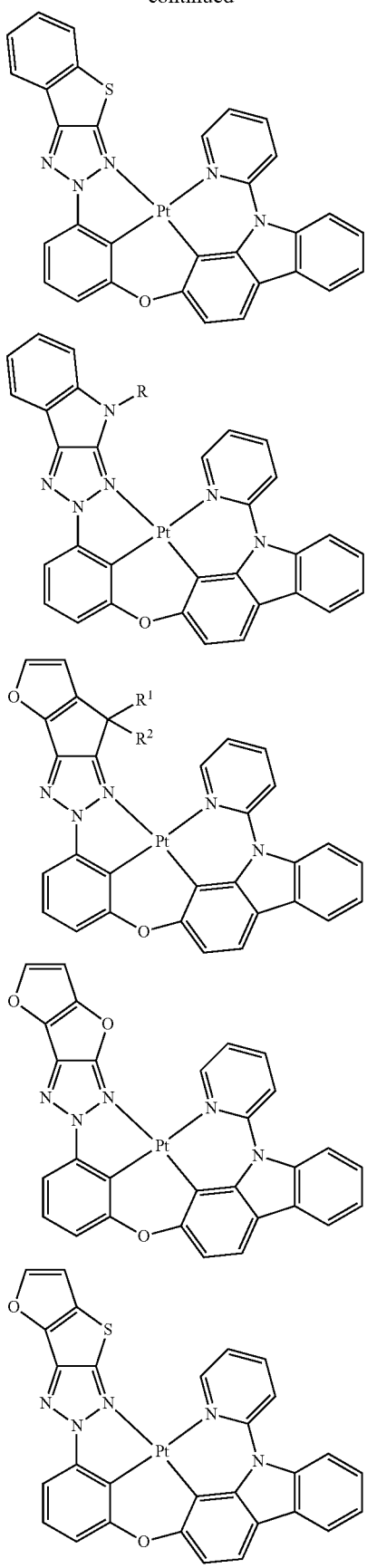
446
-continued
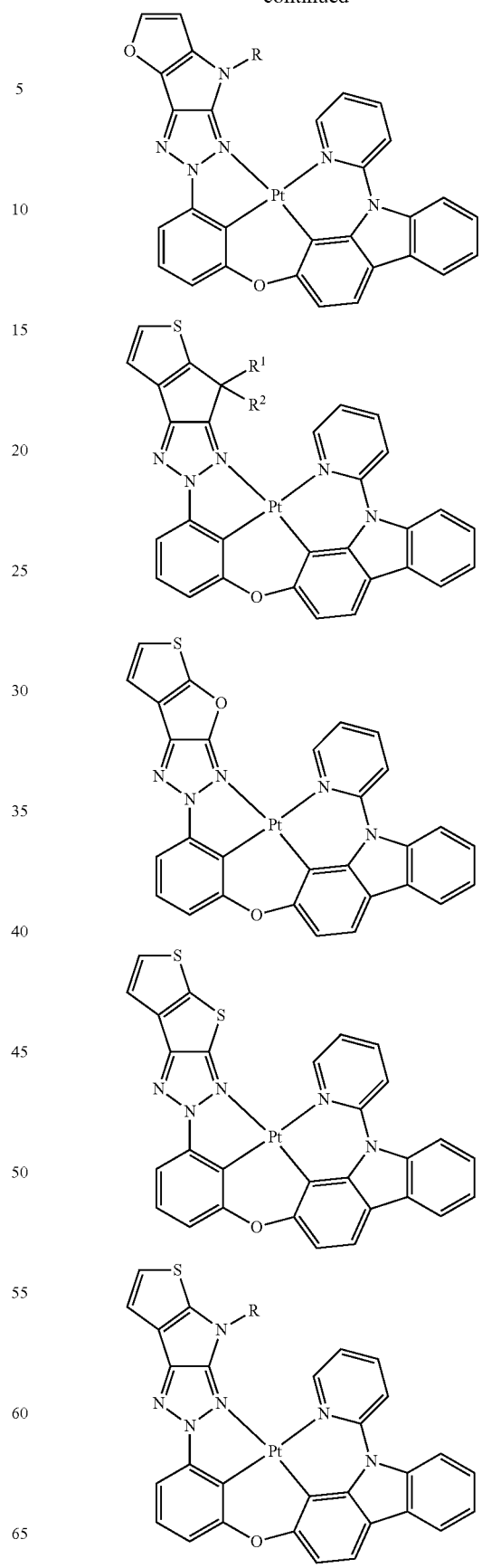

447
-continued
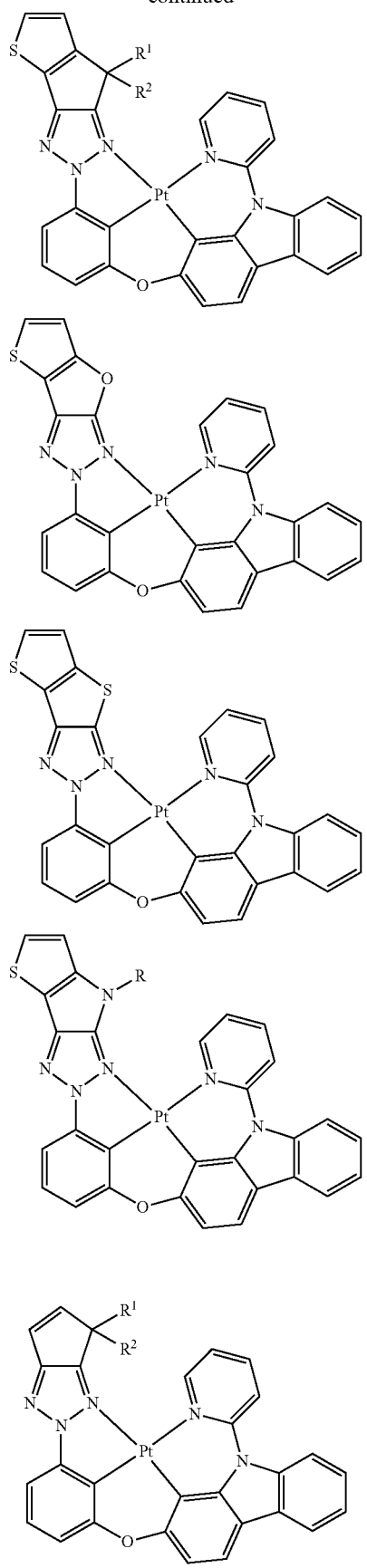
448
-continued
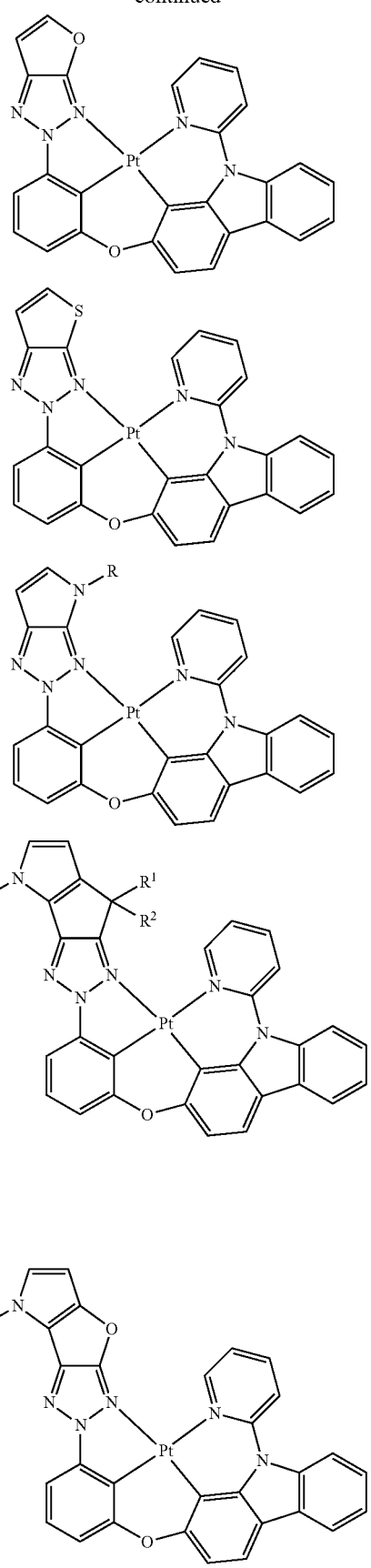

449
-continued
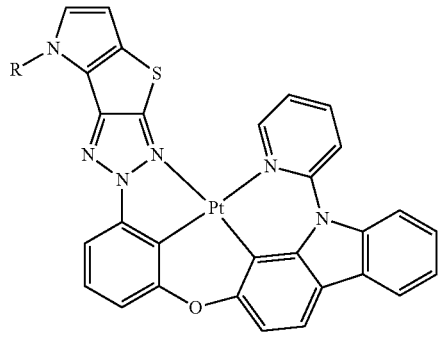
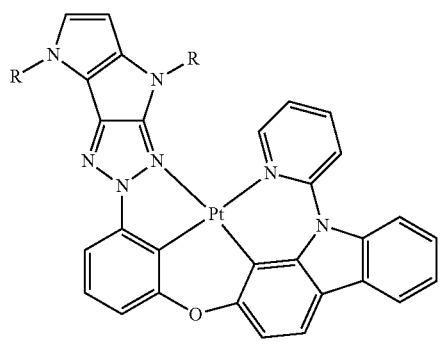
Structures 25
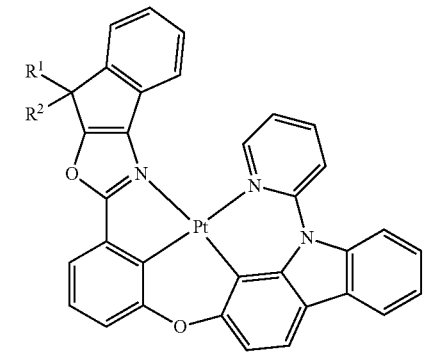
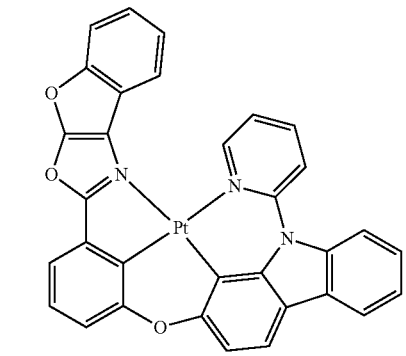
450
-continued
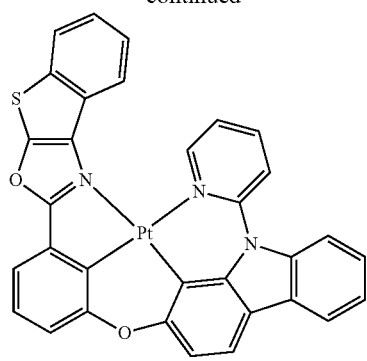
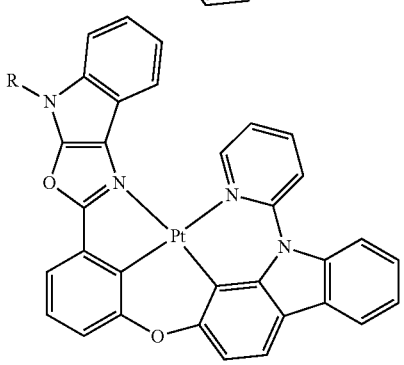
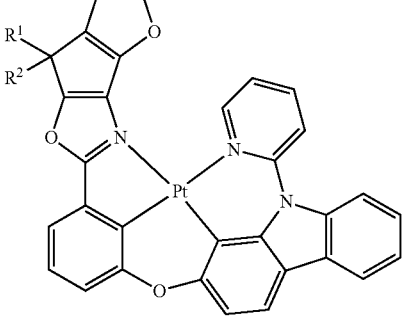
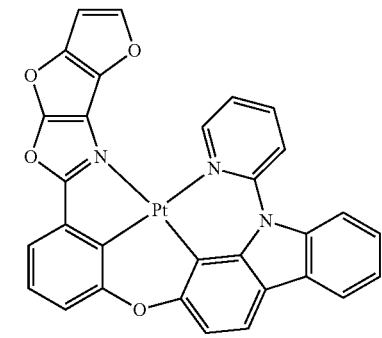
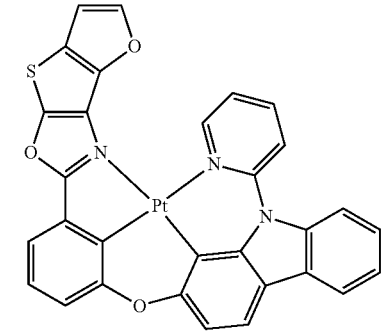

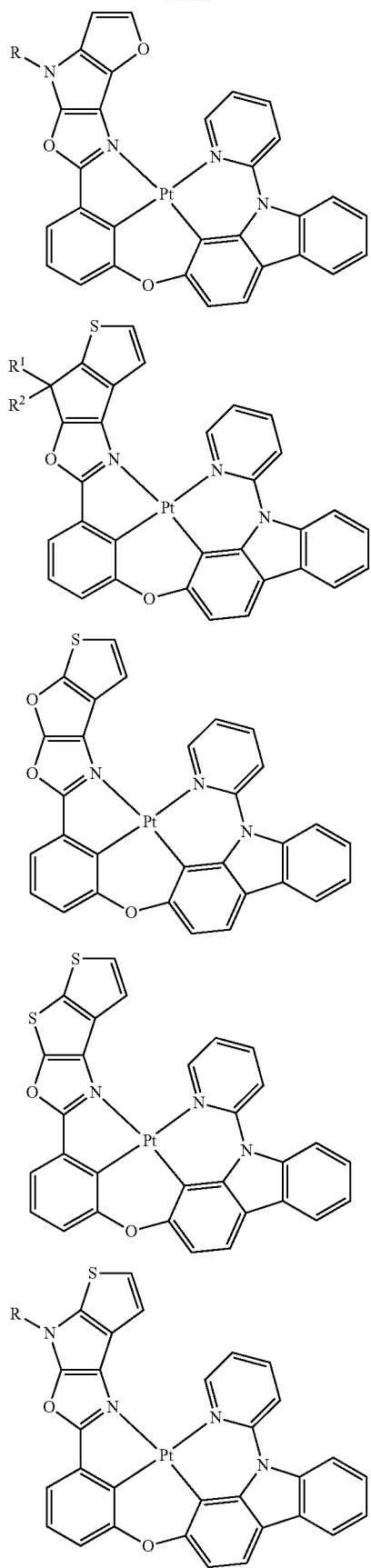
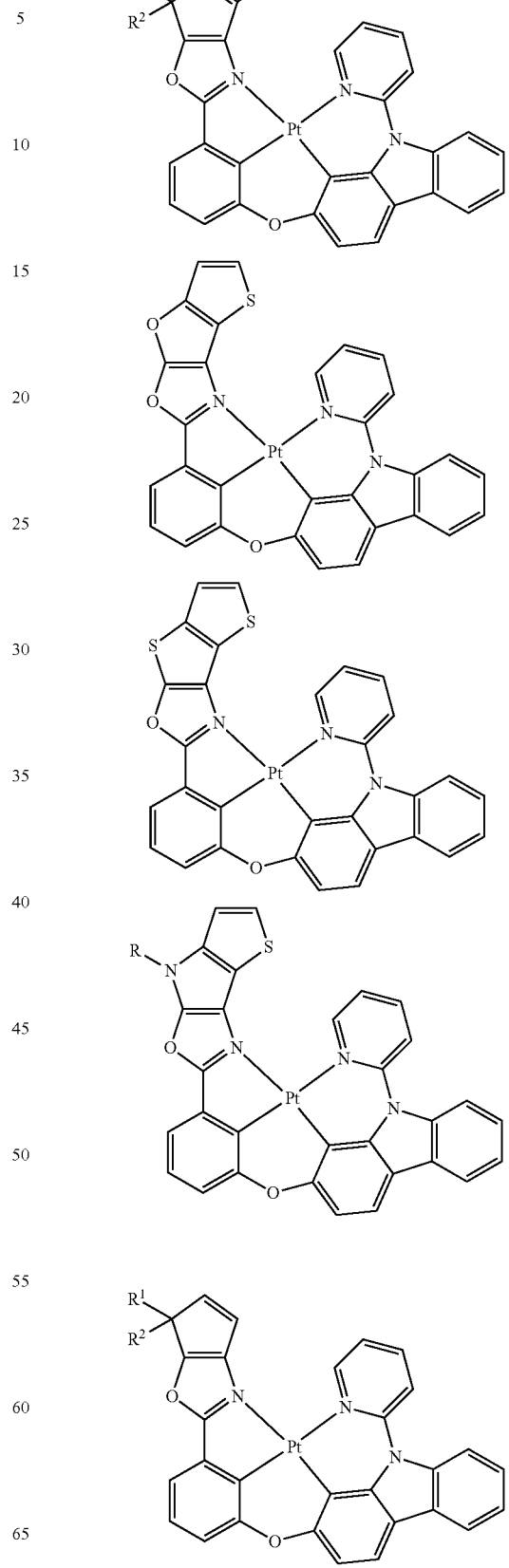

453
-continued
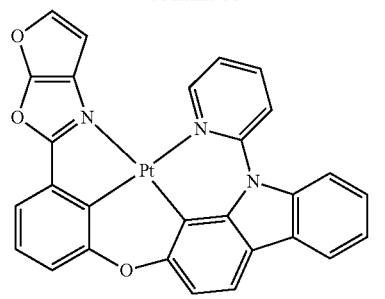
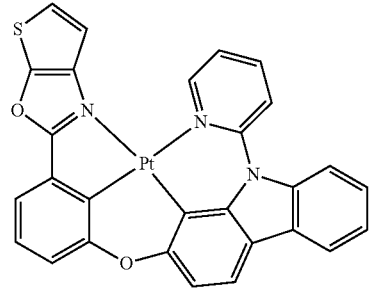
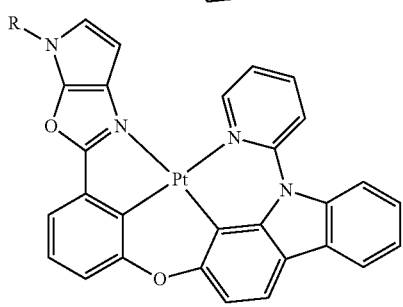
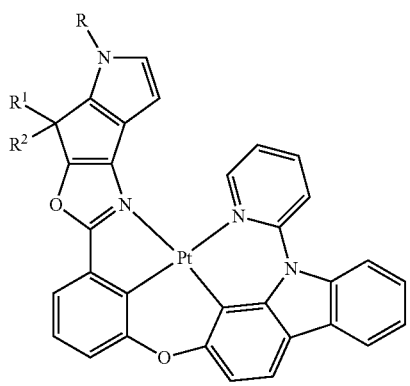
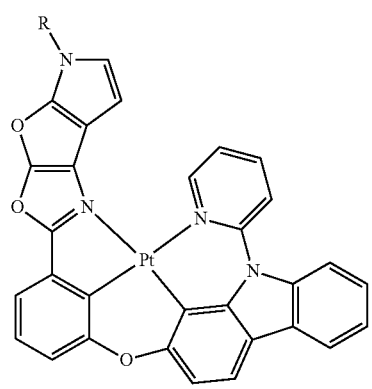
454
-continued
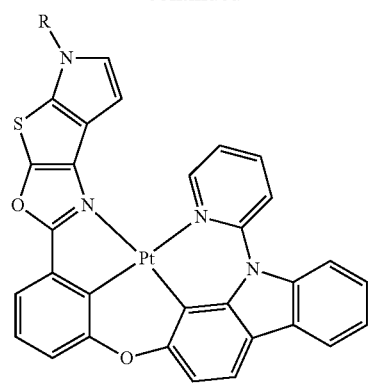
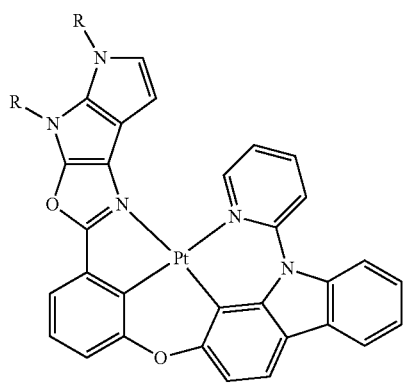
Structures 26
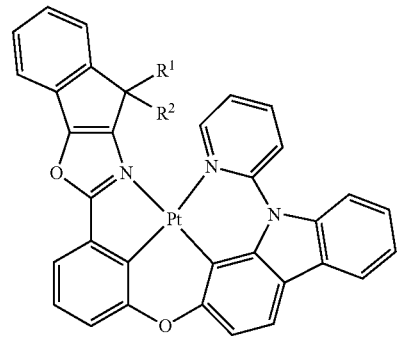
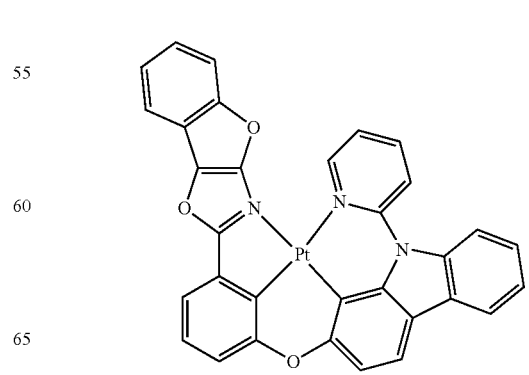

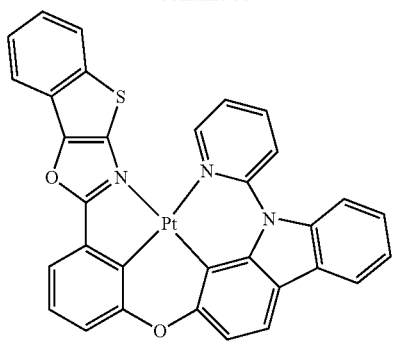
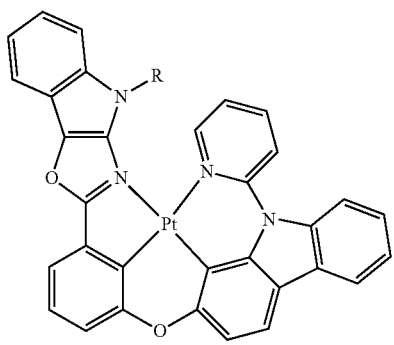
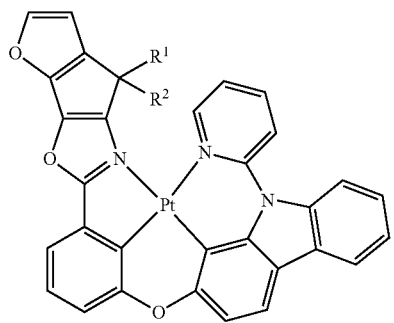
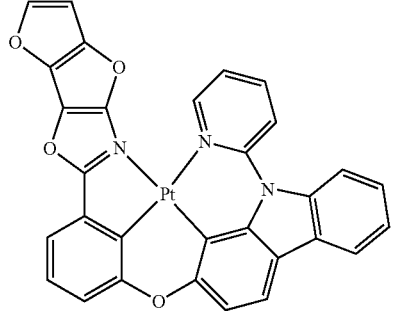
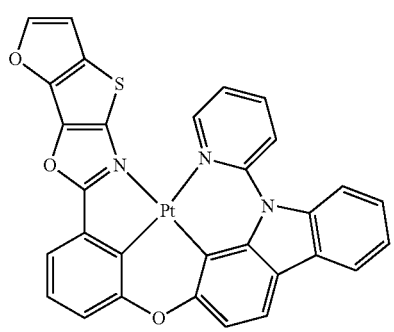
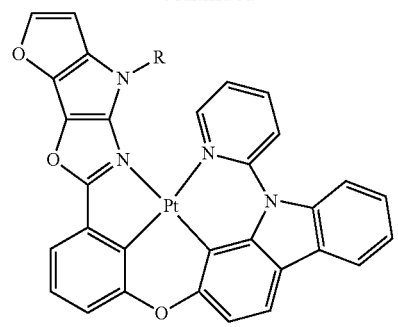
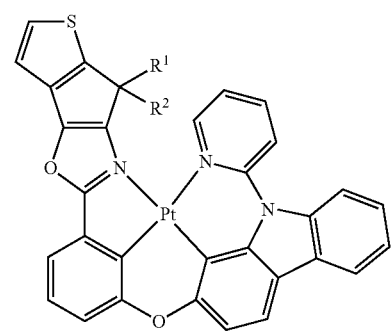
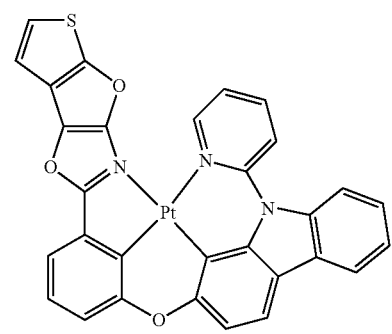
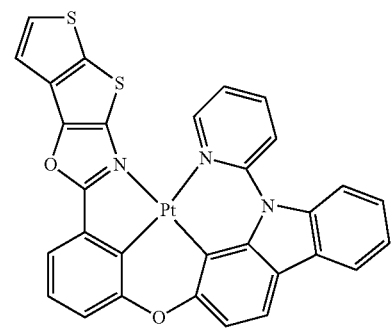
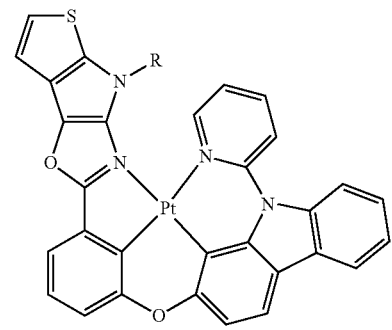

457
-continued
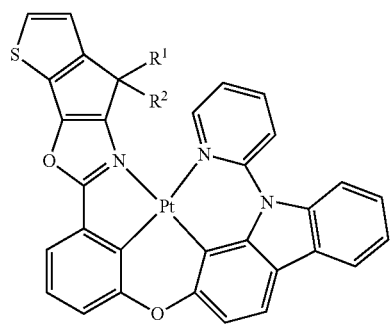
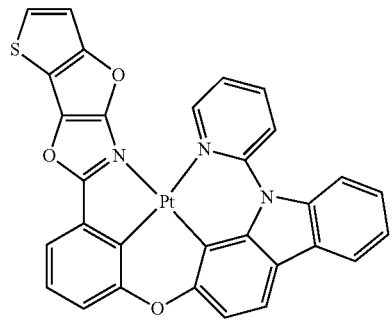
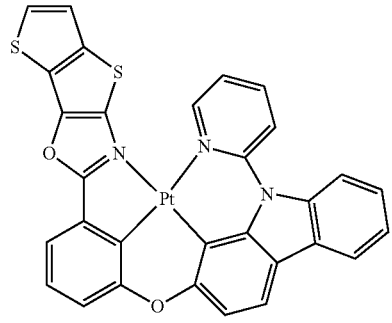
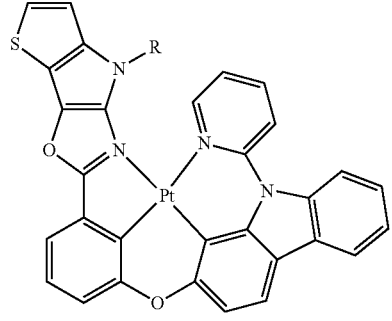
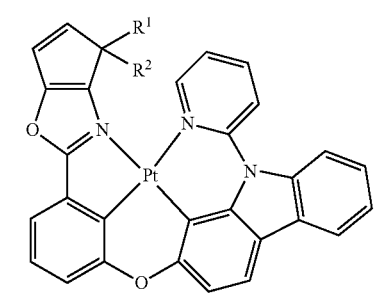
458
-continued
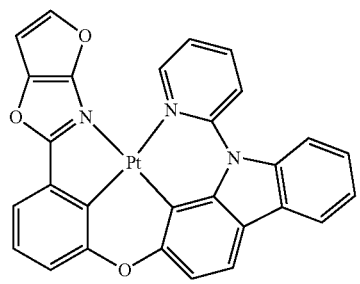
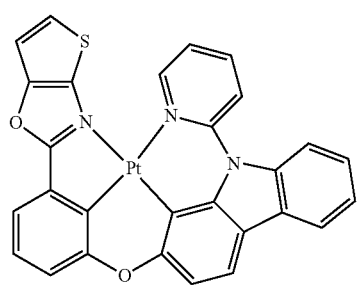
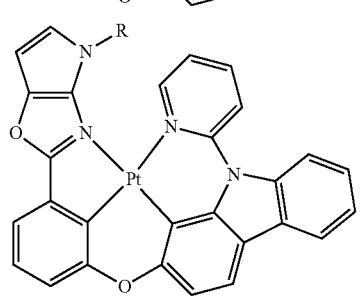
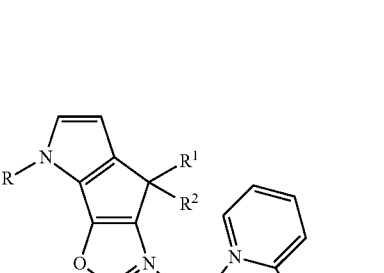
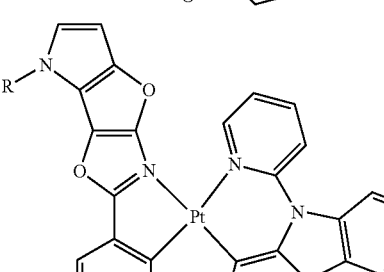

-continued
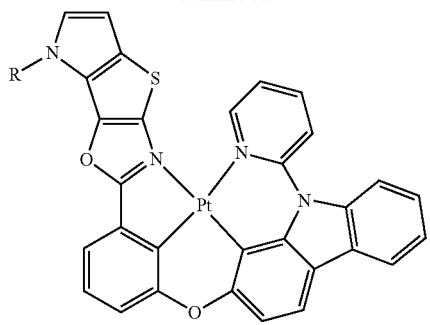
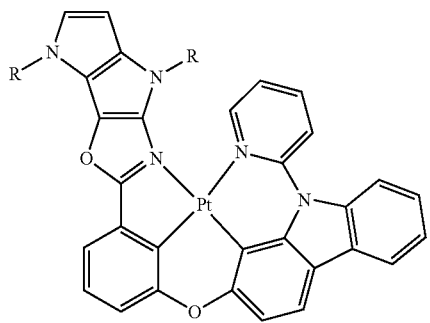
Structures 27
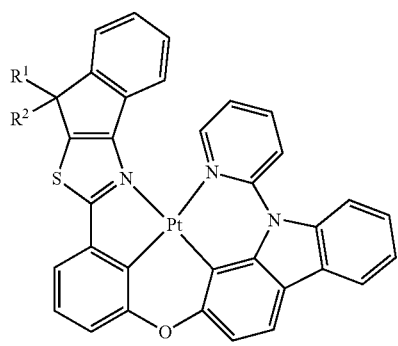
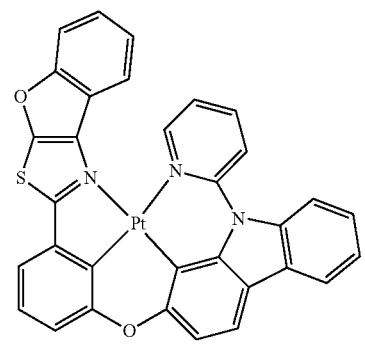
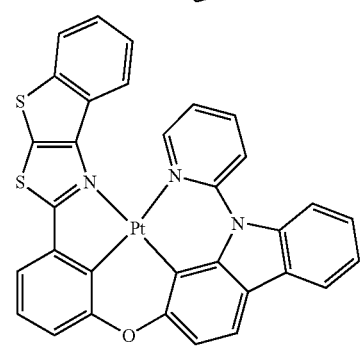
-continued
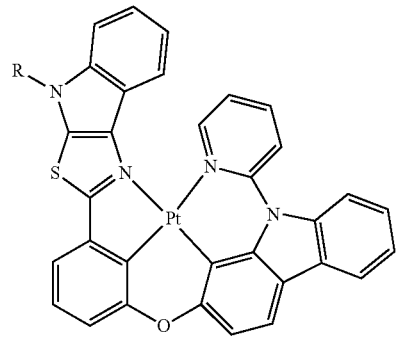
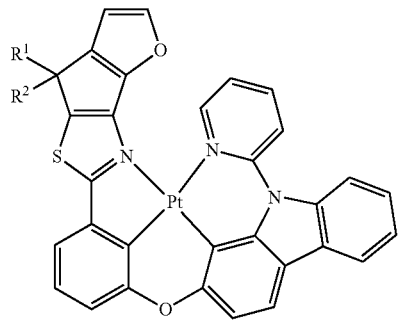
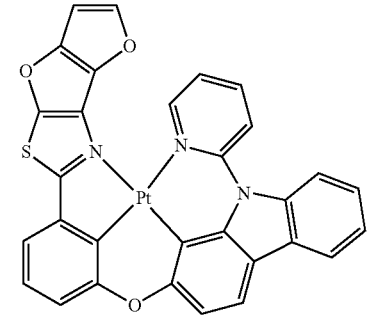
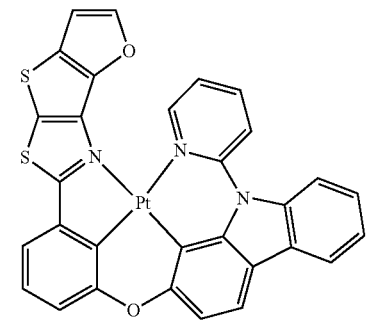
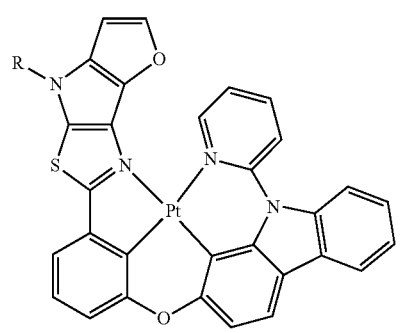

461
-continued
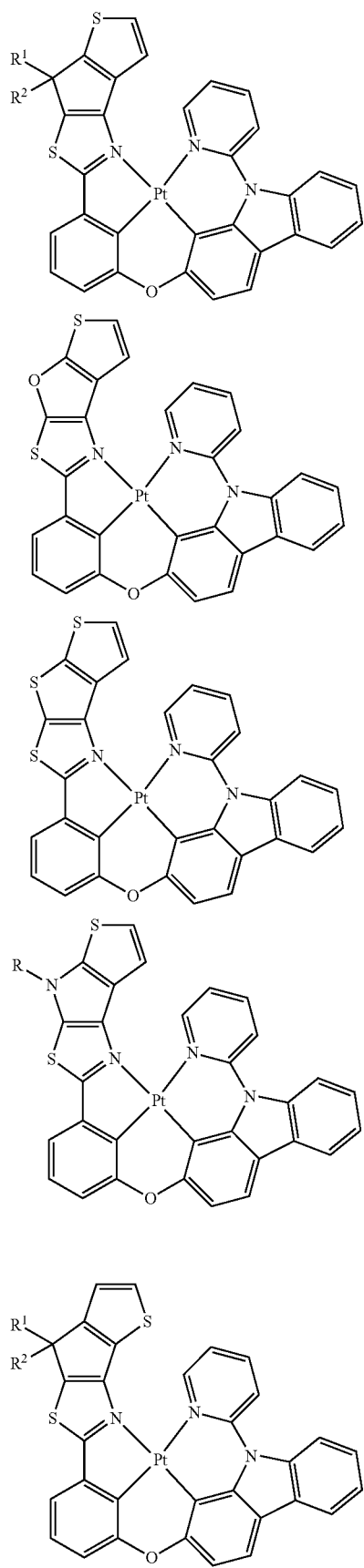
462
-continued
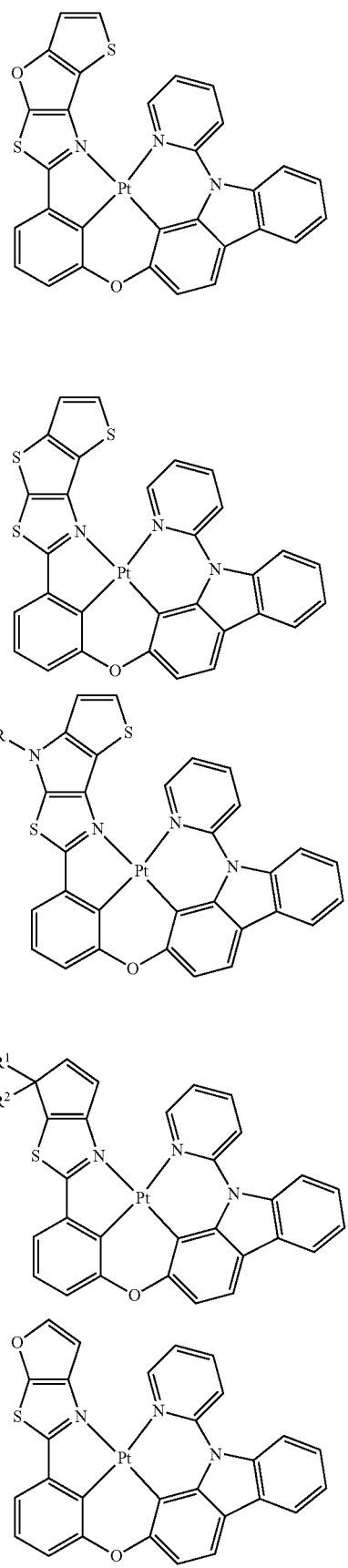

-continued
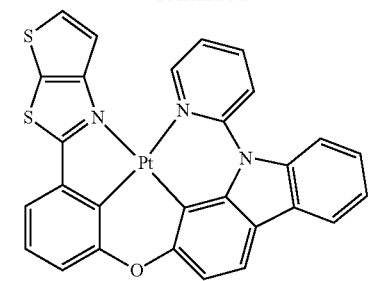
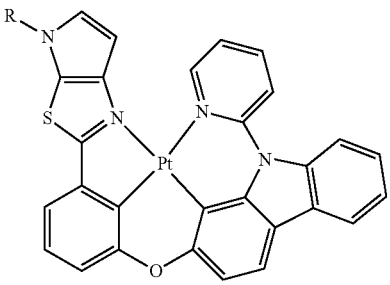
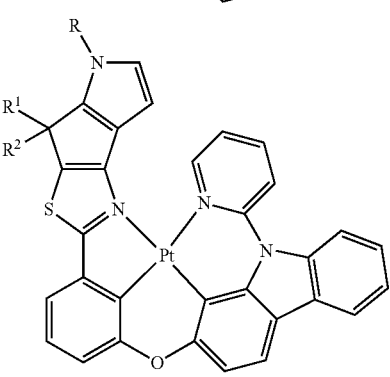
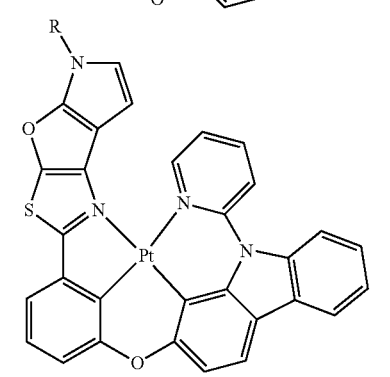
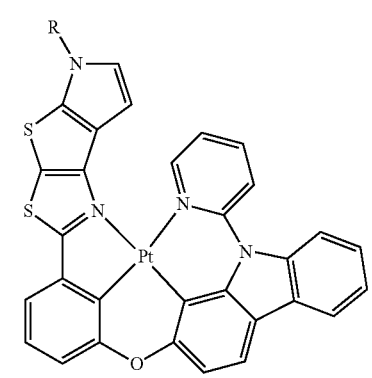
-continued
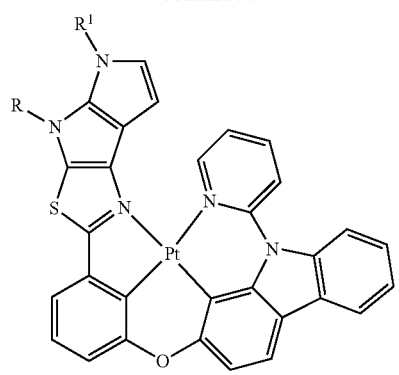
Structures 28
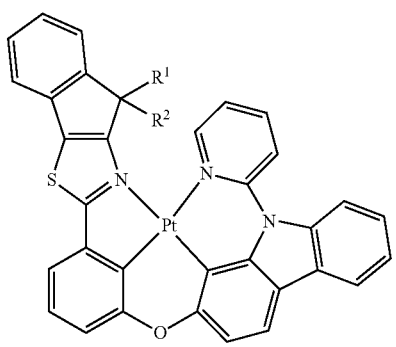
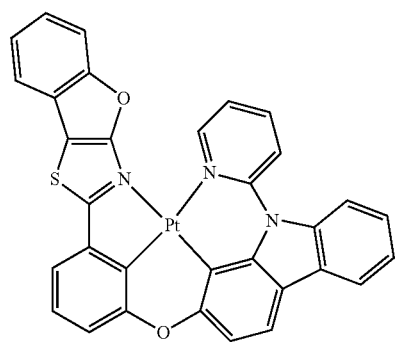
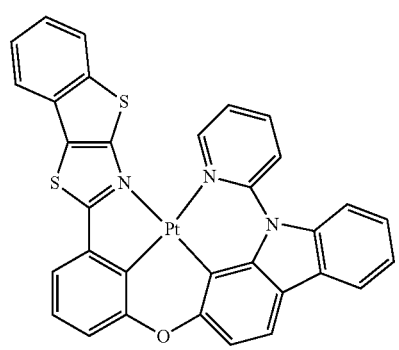

465
-continued
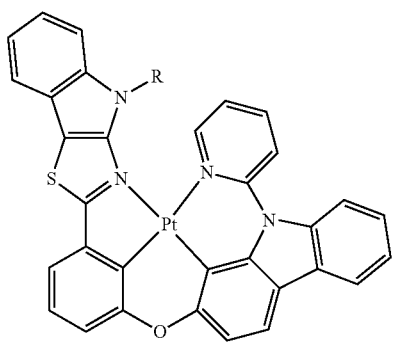
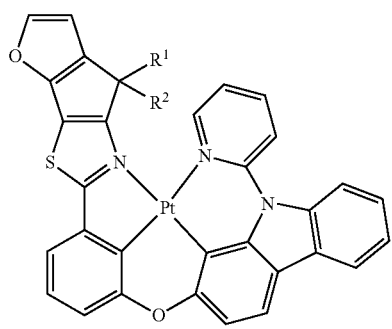
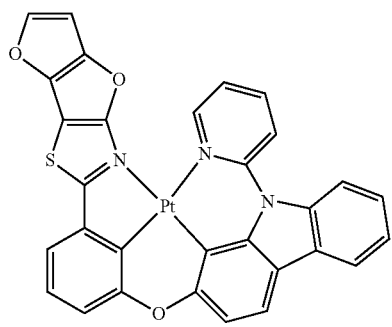
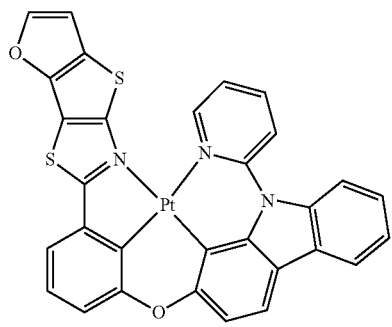
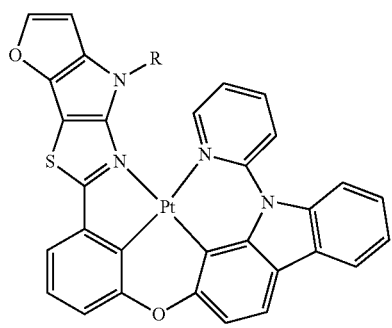
466
-continued
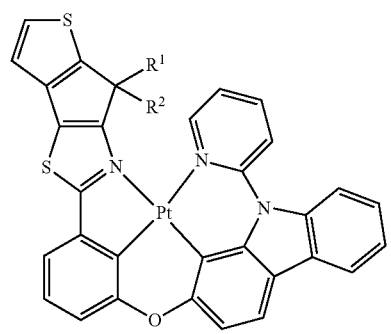
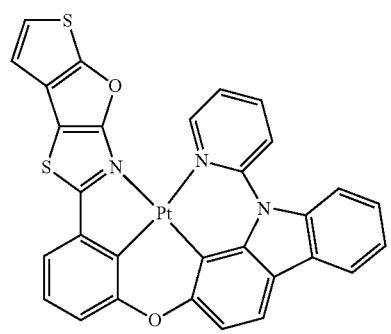
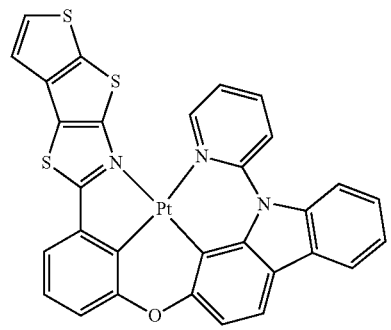
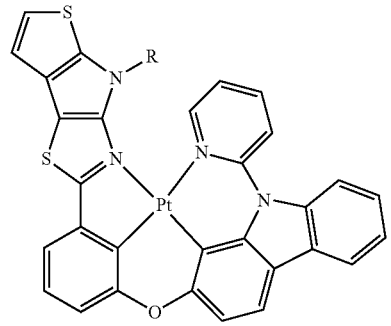
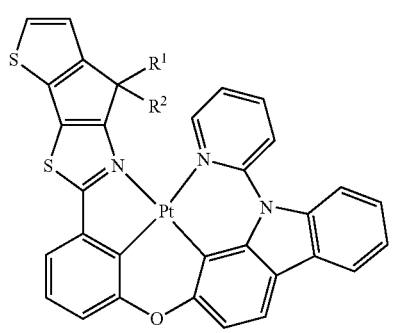

467
-continued
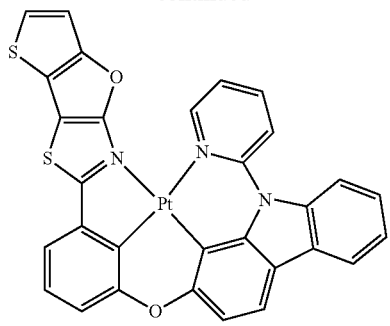
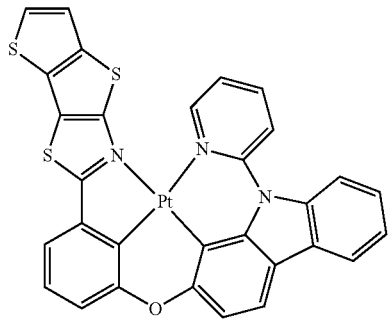
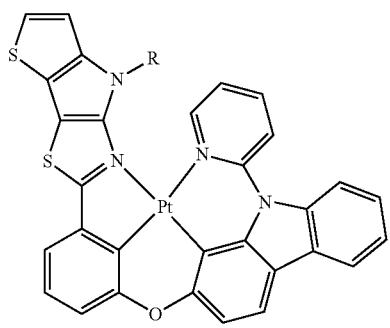
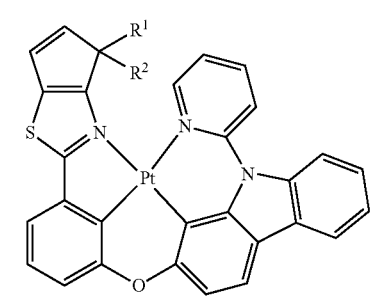
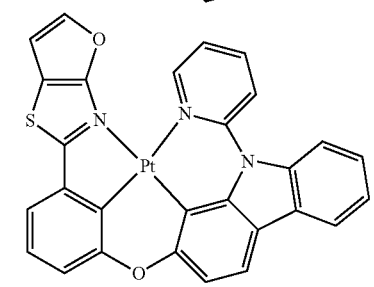
468
-continued
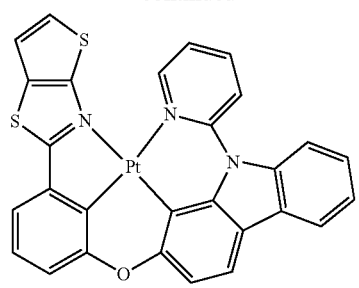
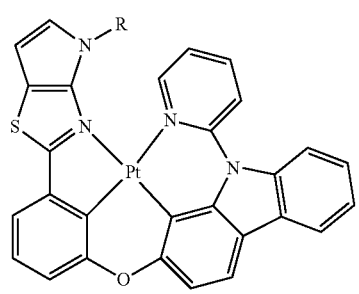
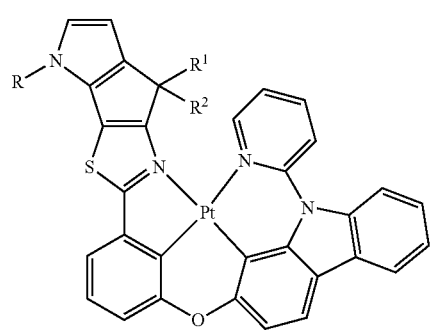
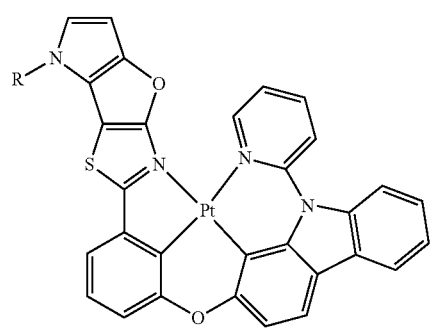
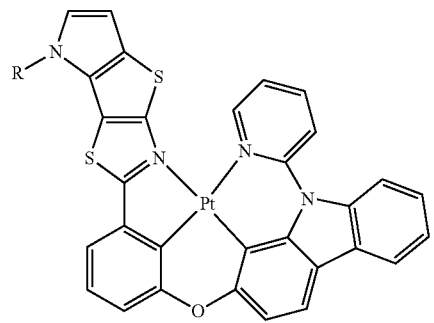

469
-continued
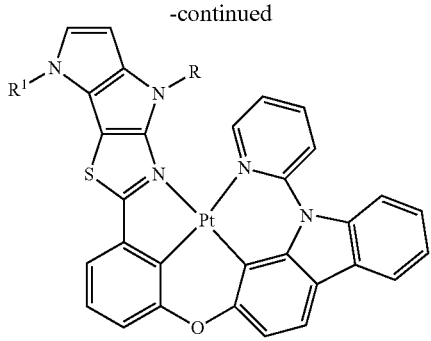
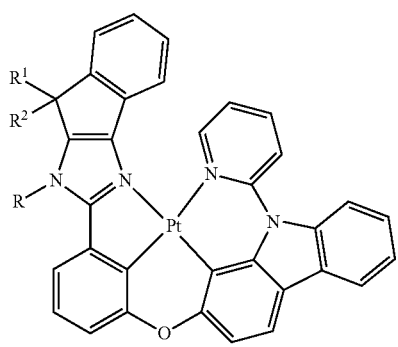
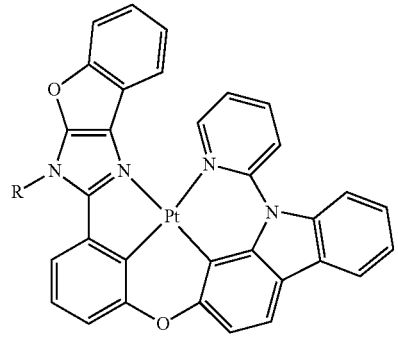
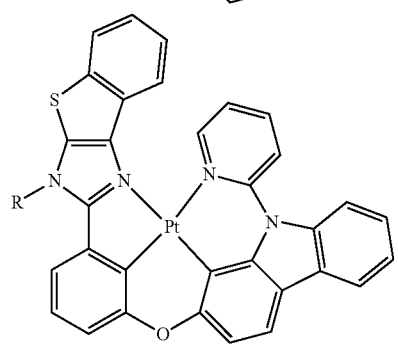
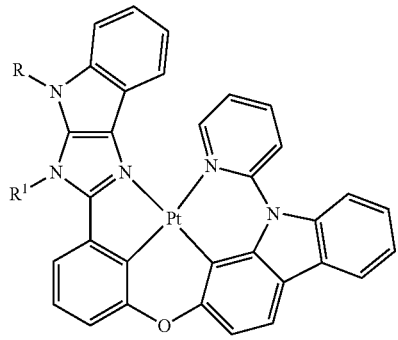
470
-continued
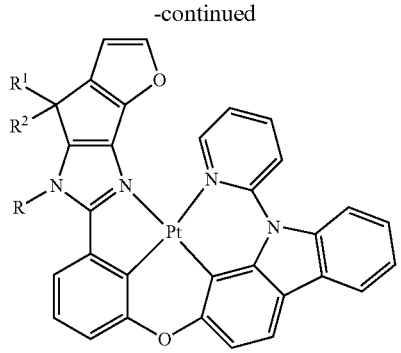
Structures 29
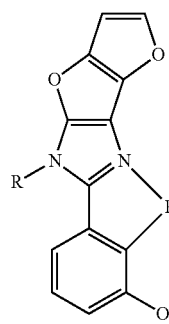
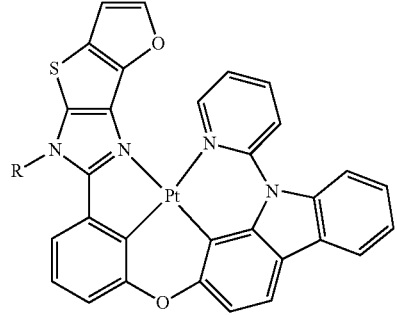
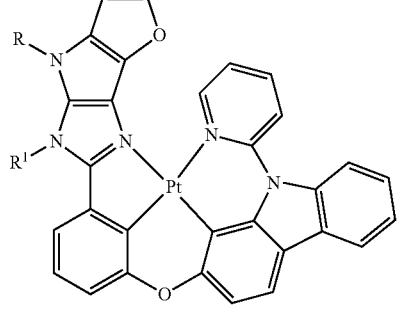
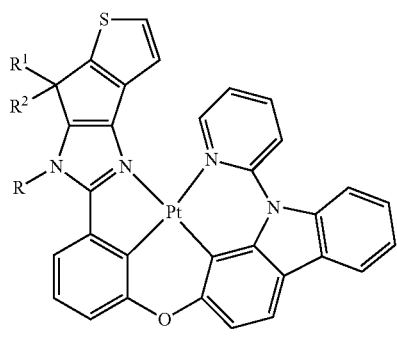

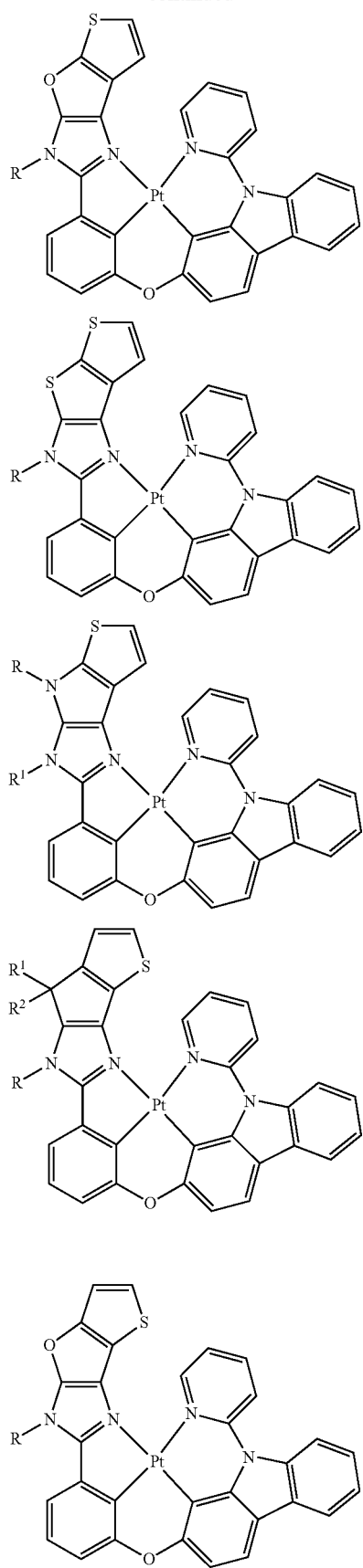
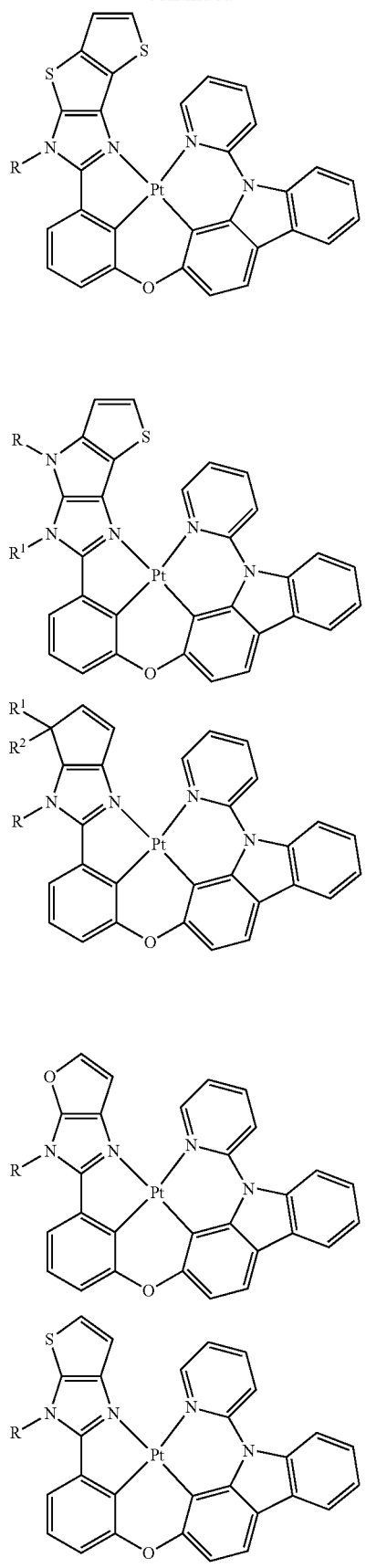

473
-continued
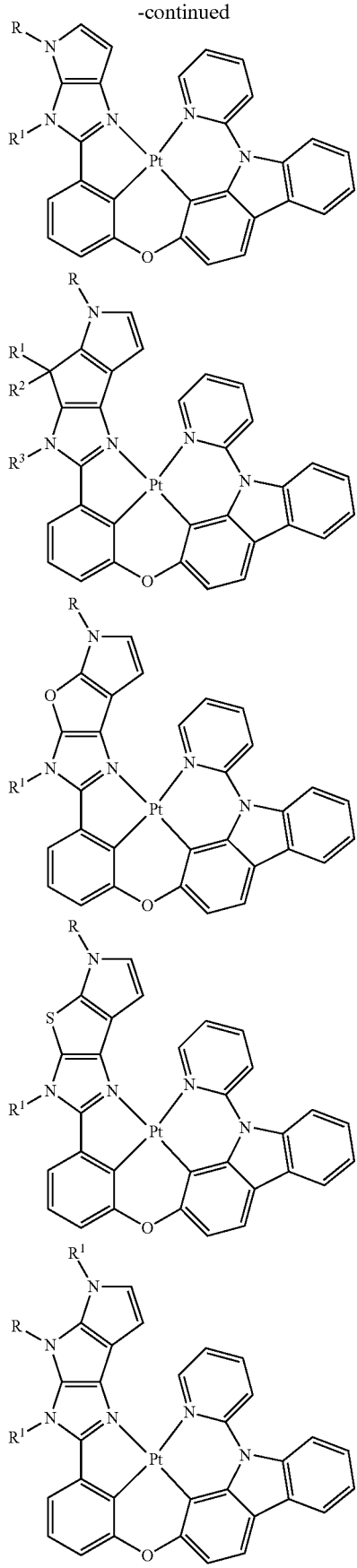
474
-continued
Structures 30
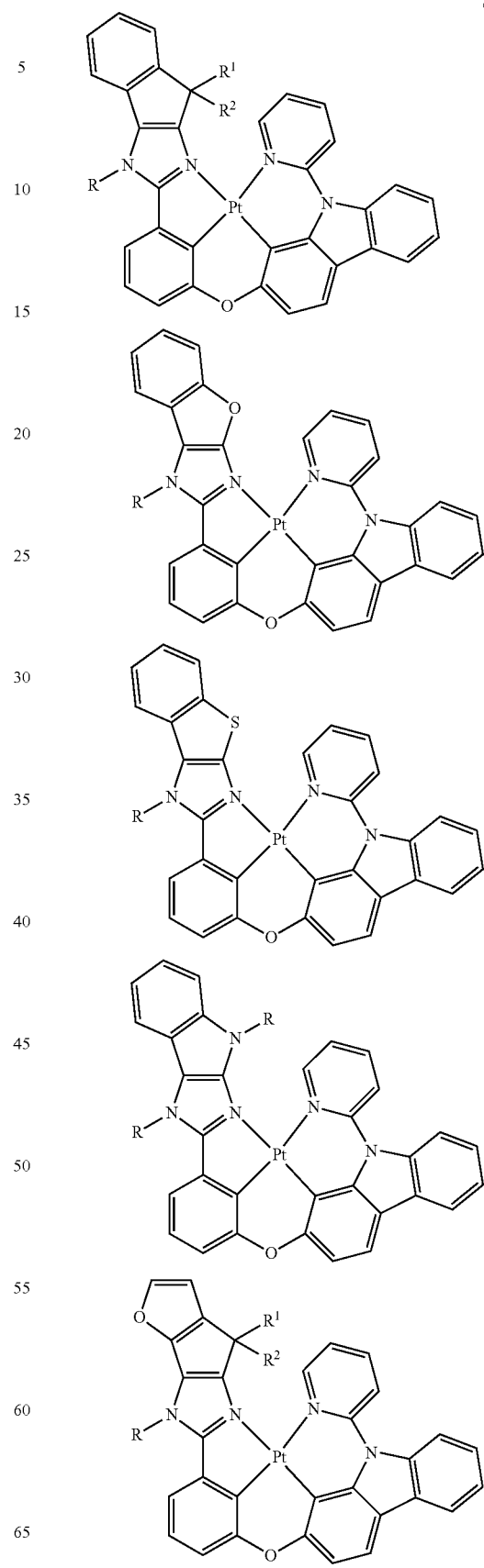

475
-continued
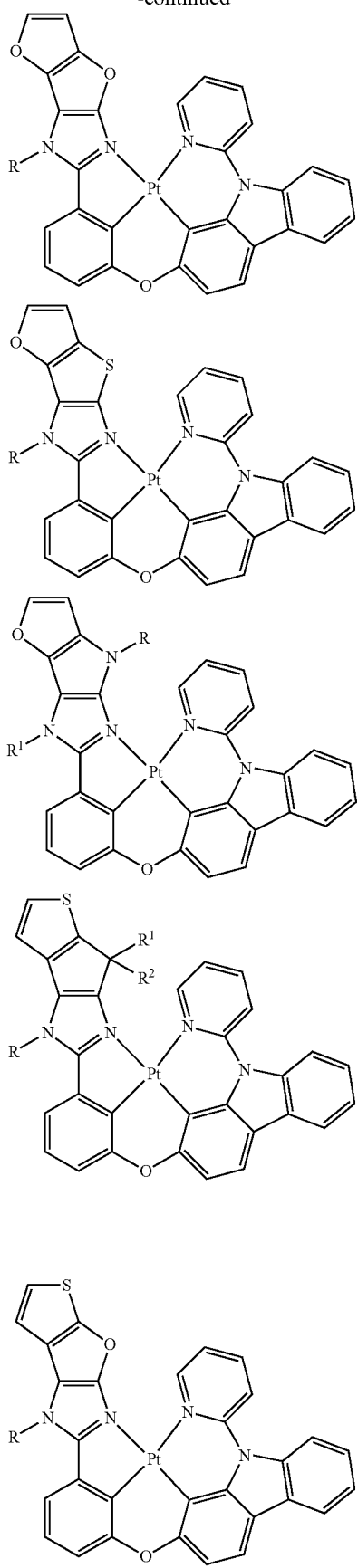
476
-continued
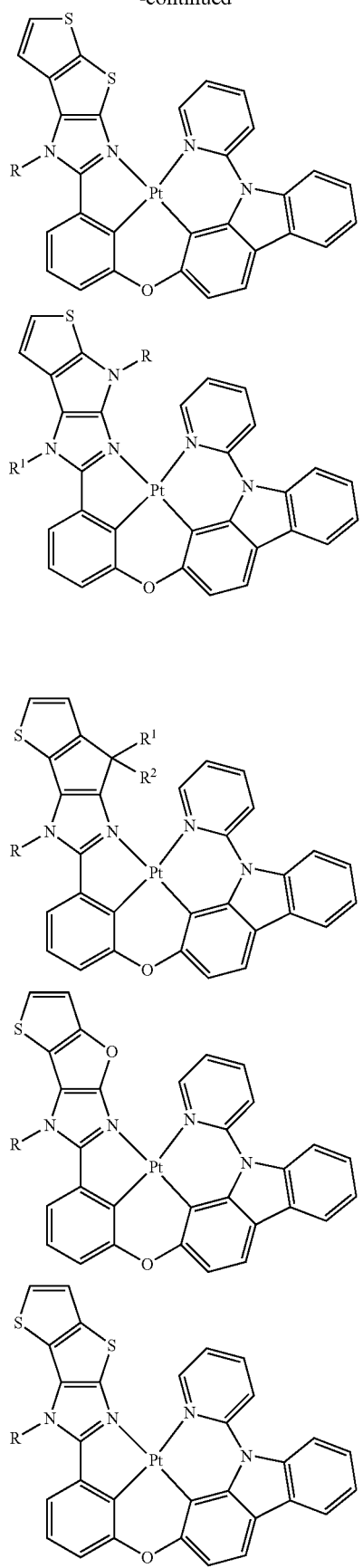

477
-continued
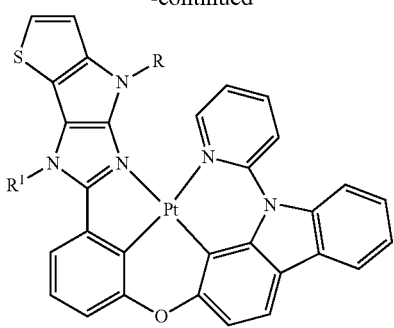
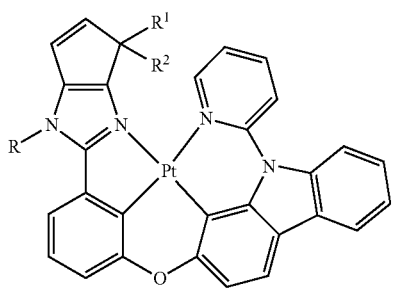
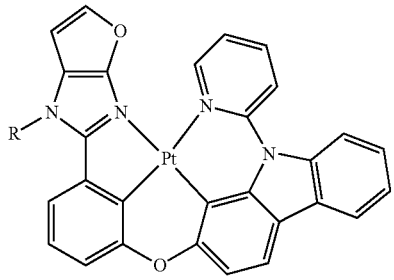
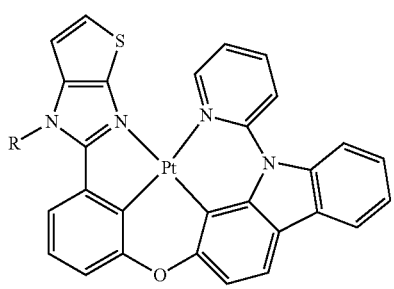
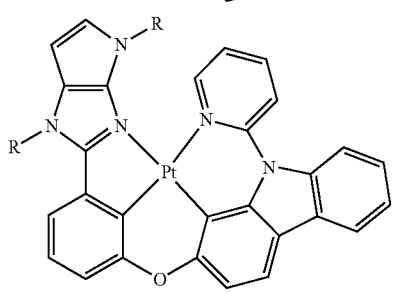
478
-continued
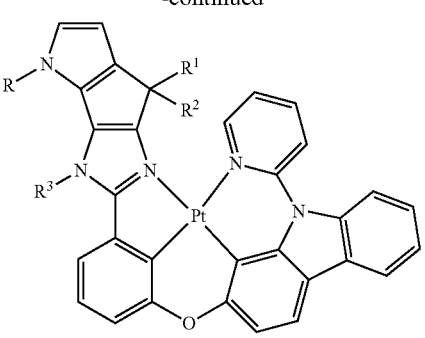
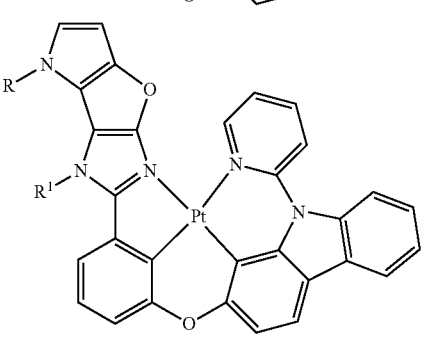
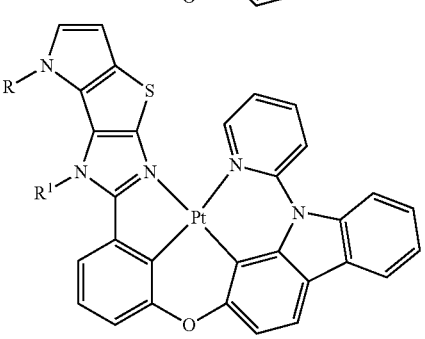
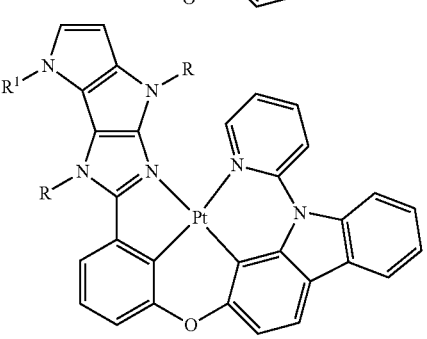
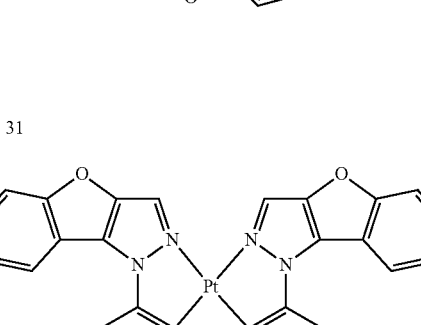
Structures 31
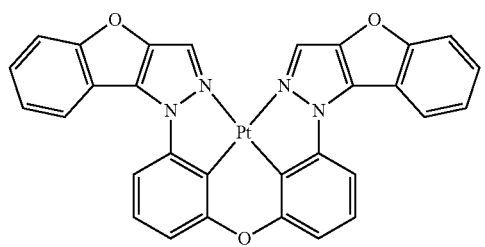

479
-continued
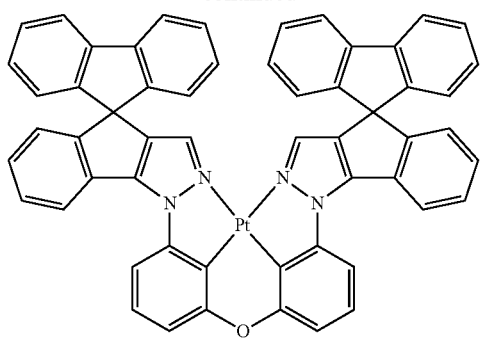
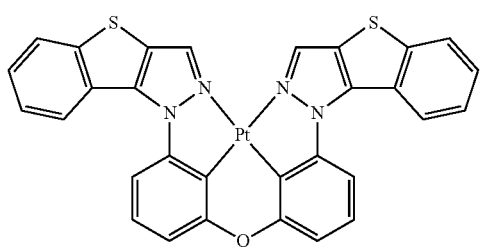
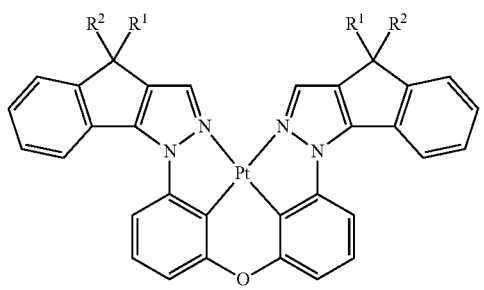
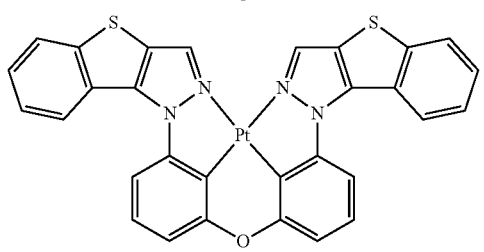
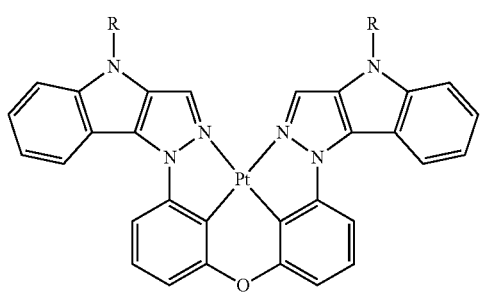
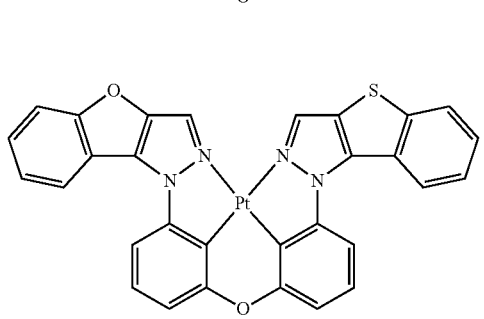
480
-continued
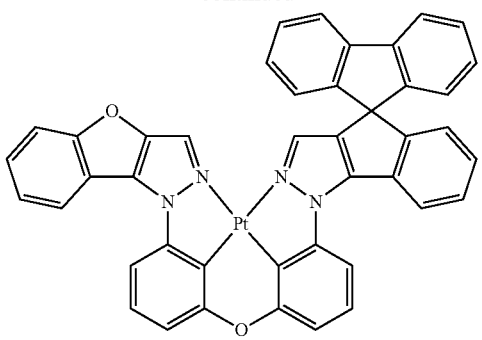
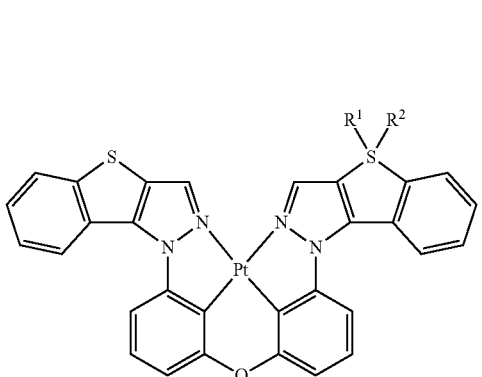
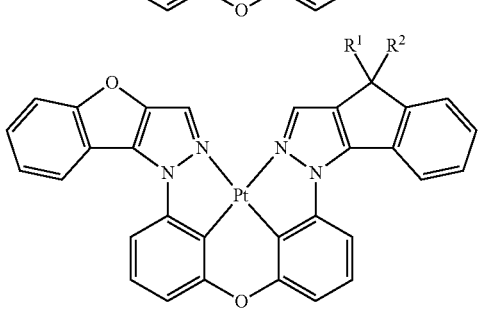
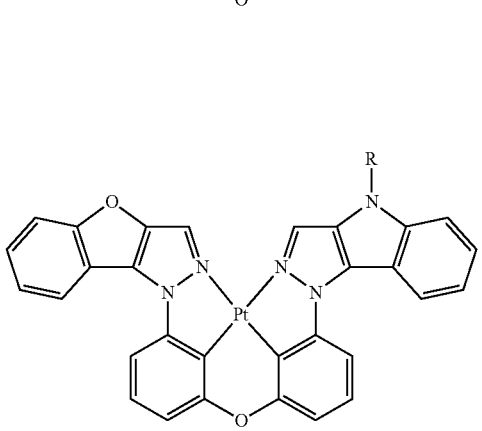
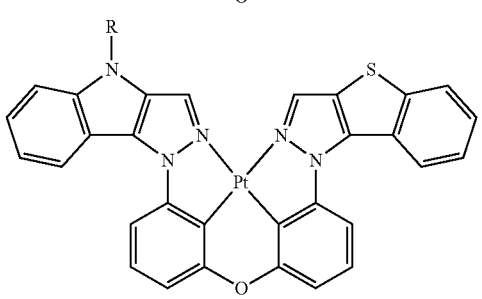

481
-continued
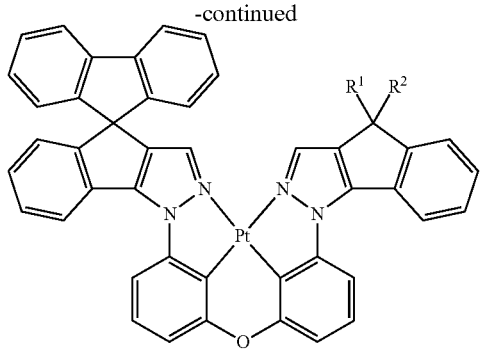
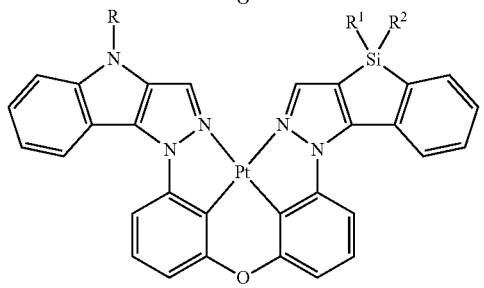
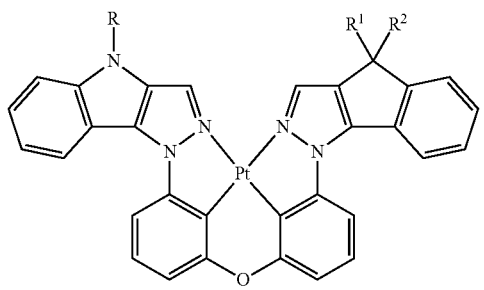
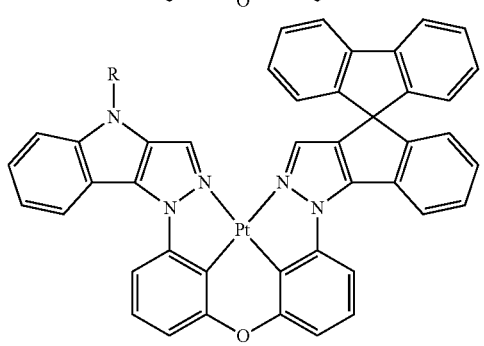
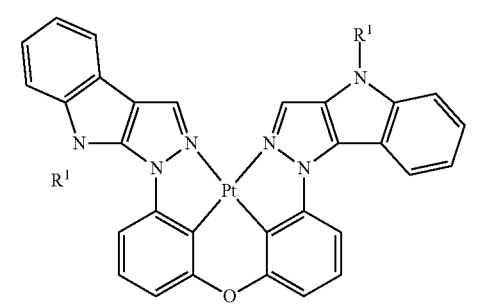
482
-continued
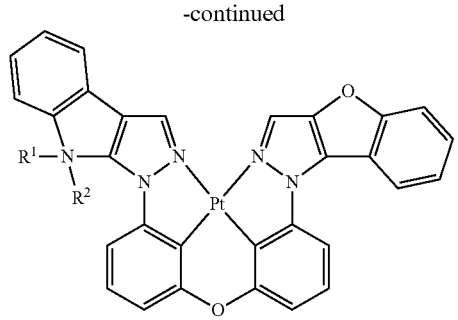
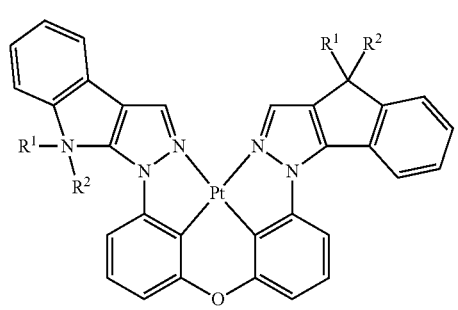
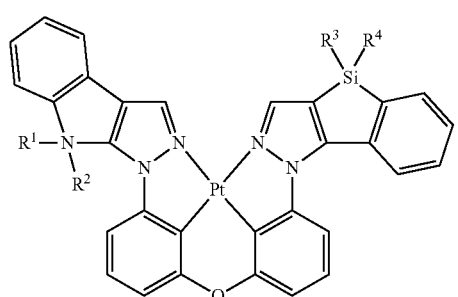
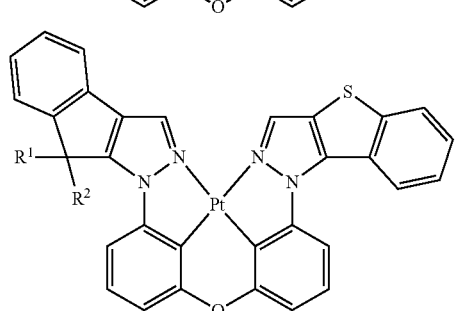
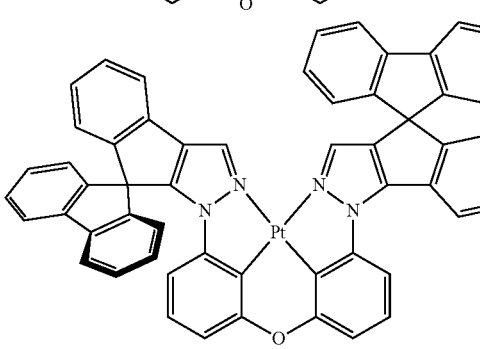

483
-continued
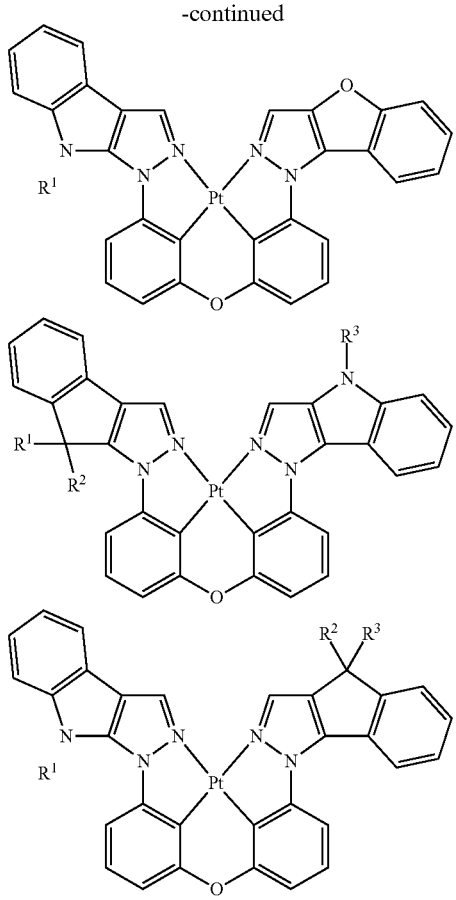
Structures 32
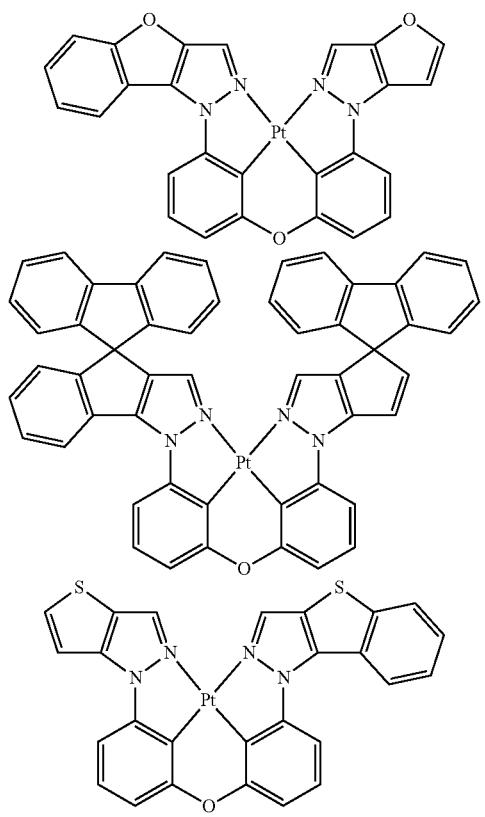
484
-continued
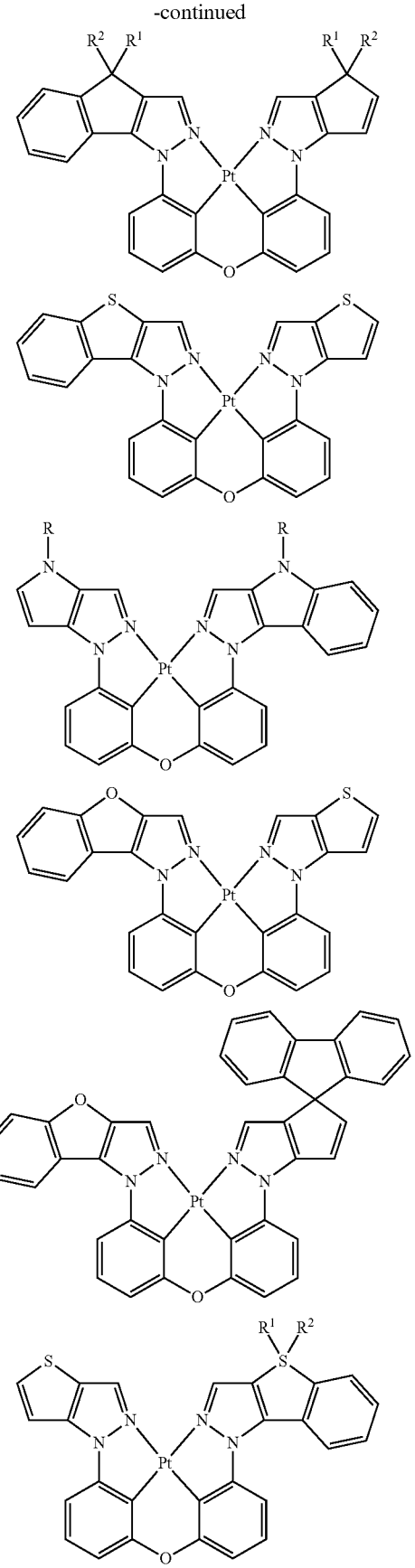

485
-continued
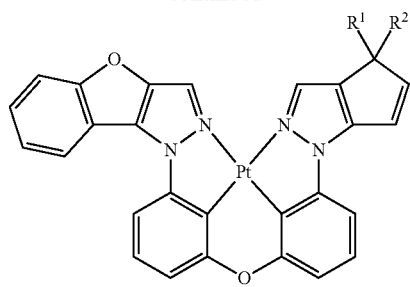
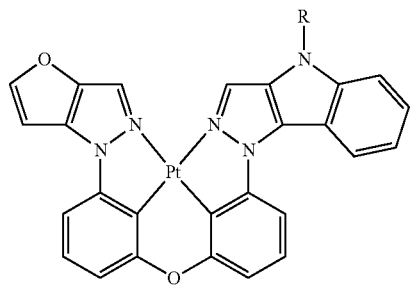
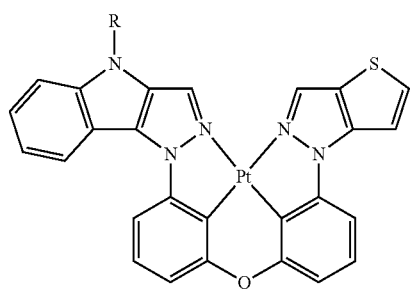
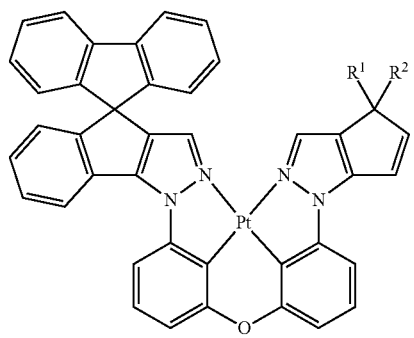
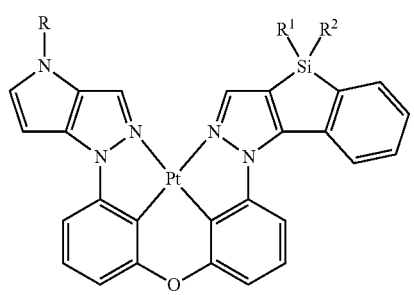
486
-continued
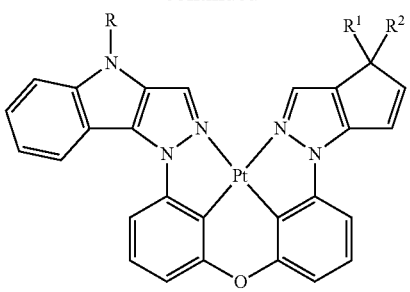
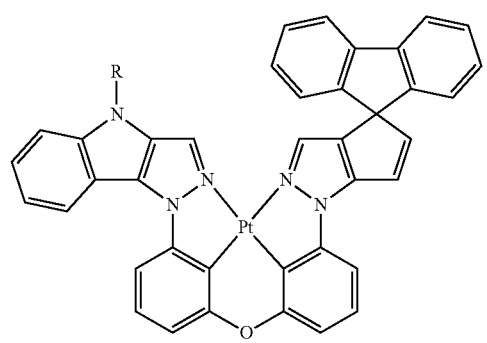
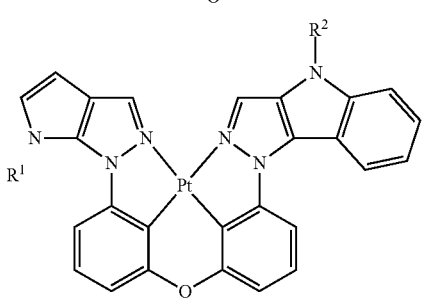
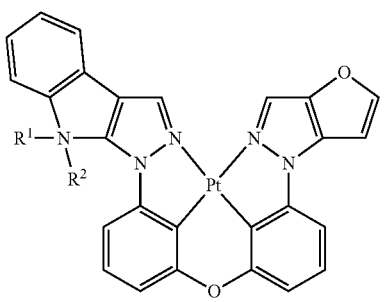
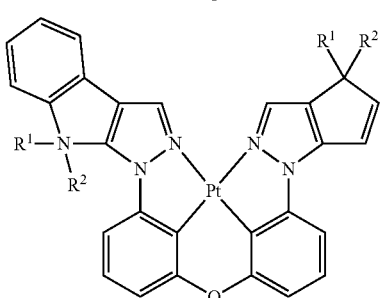

487
-continued
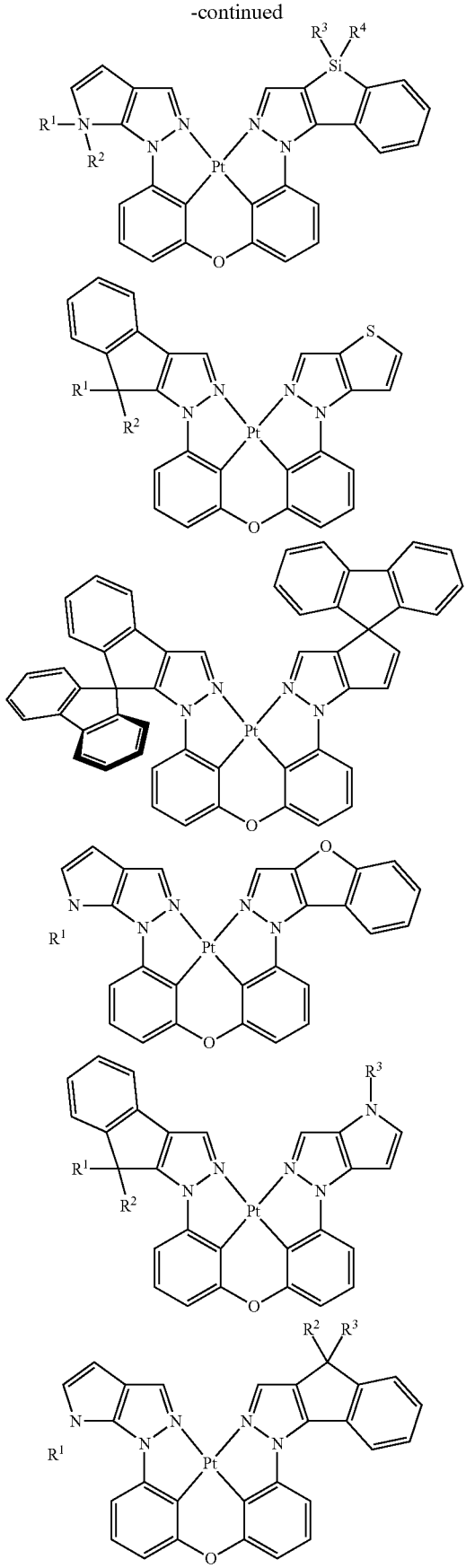
488
-continued
Structures 33
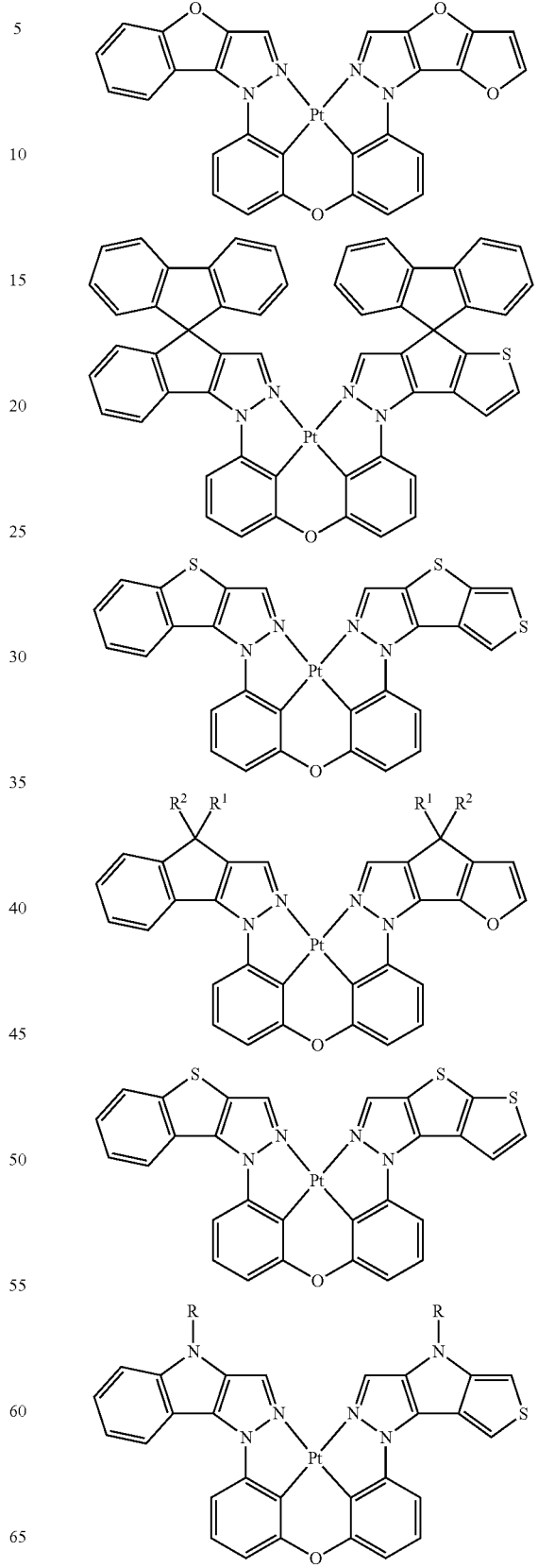

489
-continued
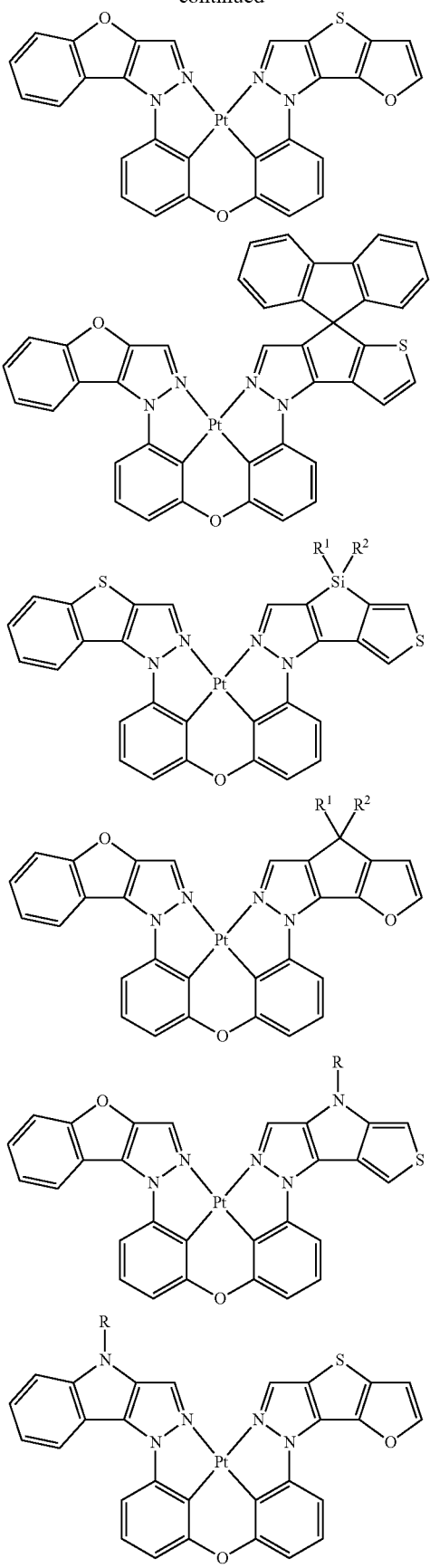
490
-continued
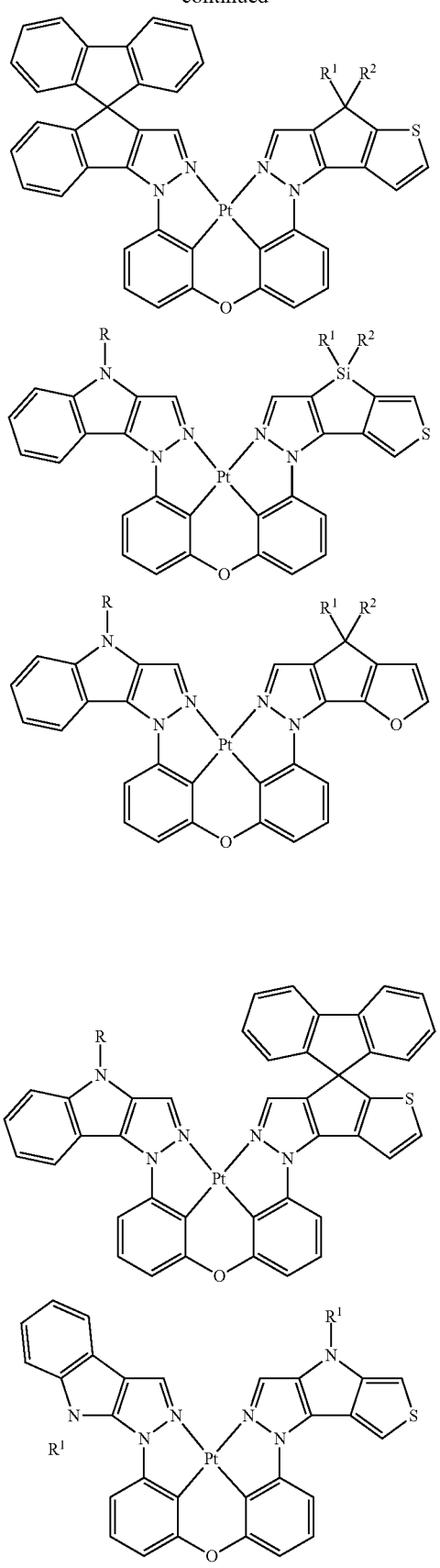

491
-continued
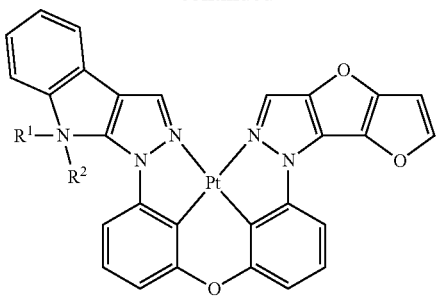
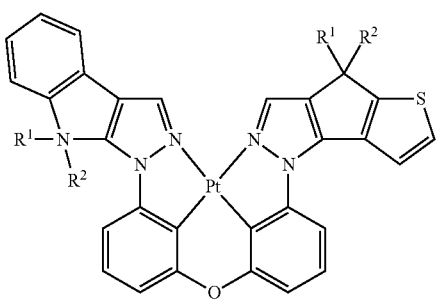
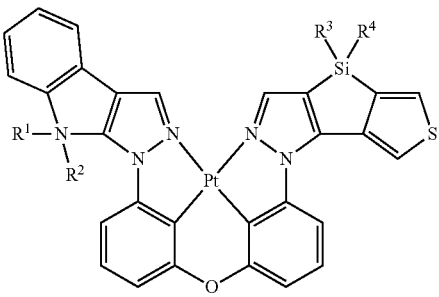
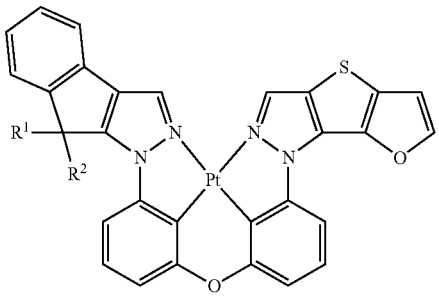
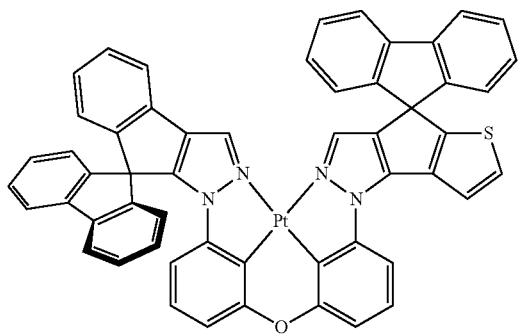
492
-continued
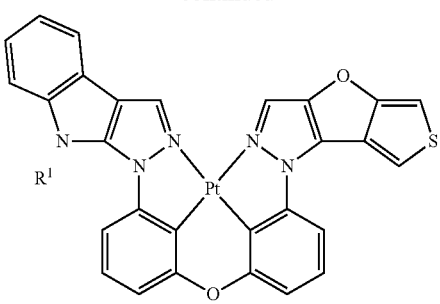
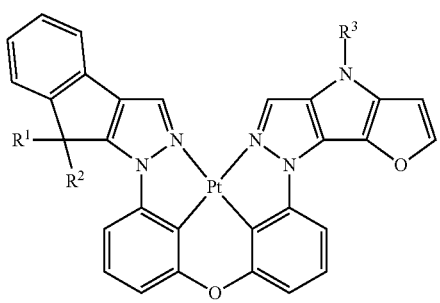
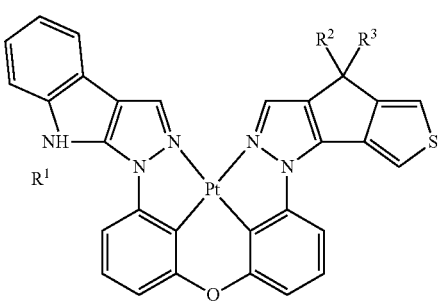
Structures 34
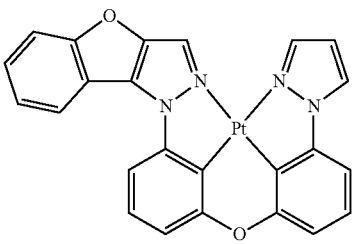
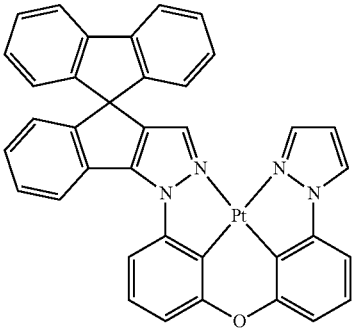

493
-continued
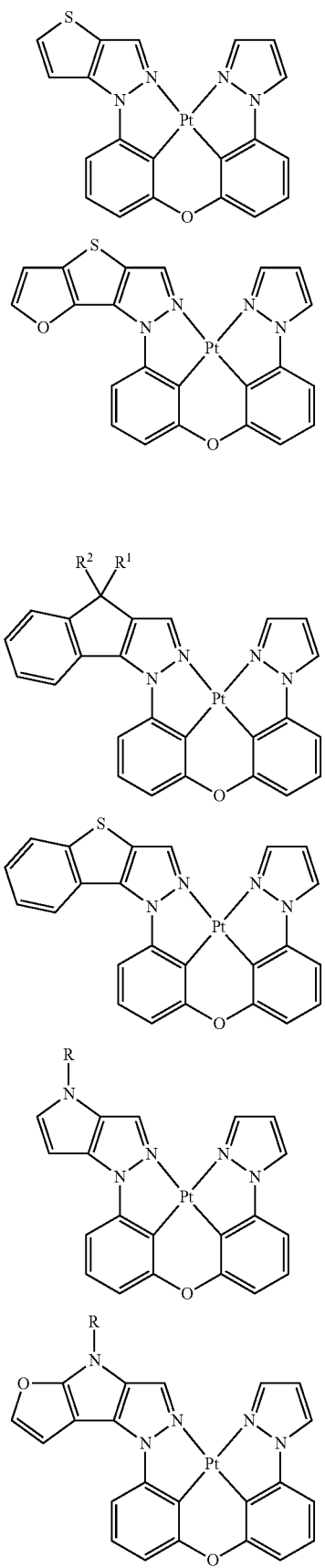
494
-continued
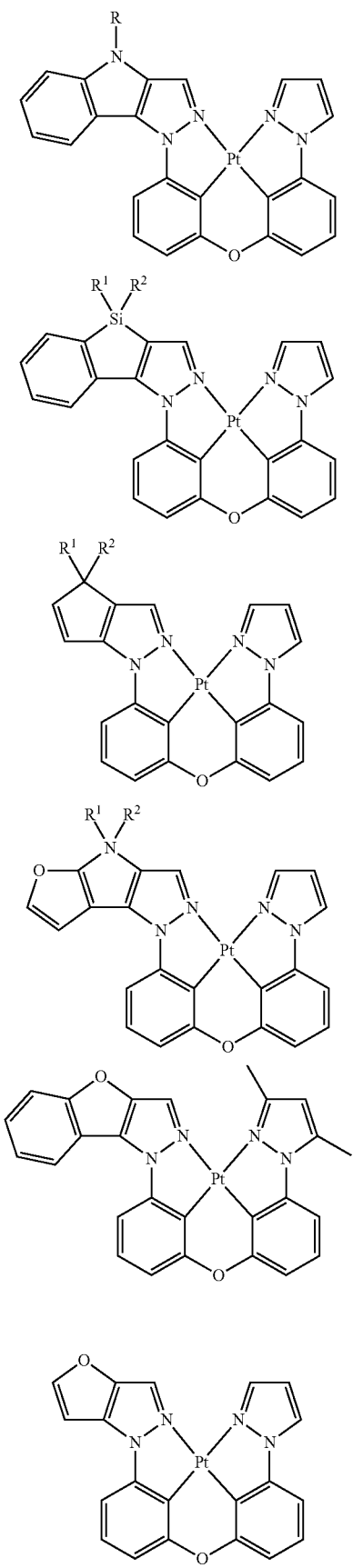

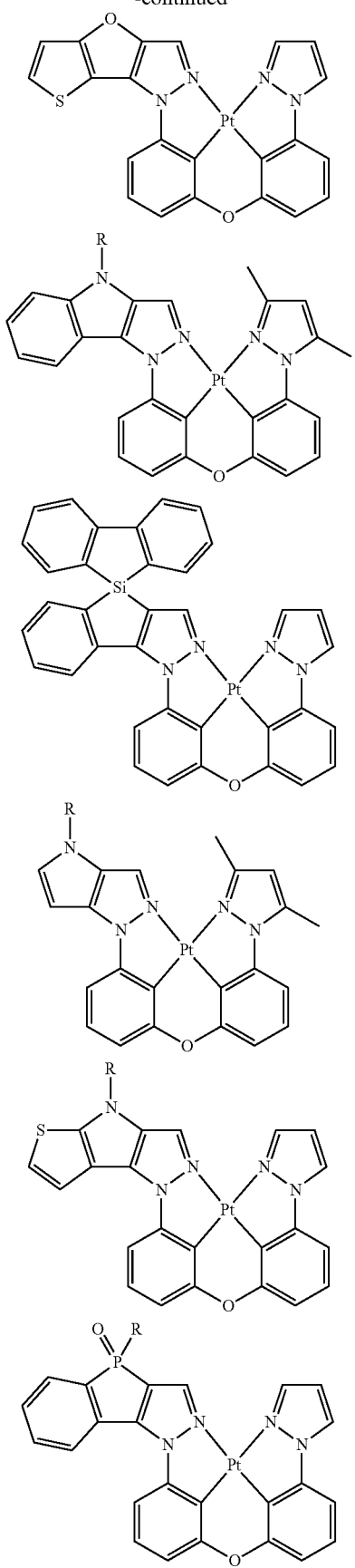
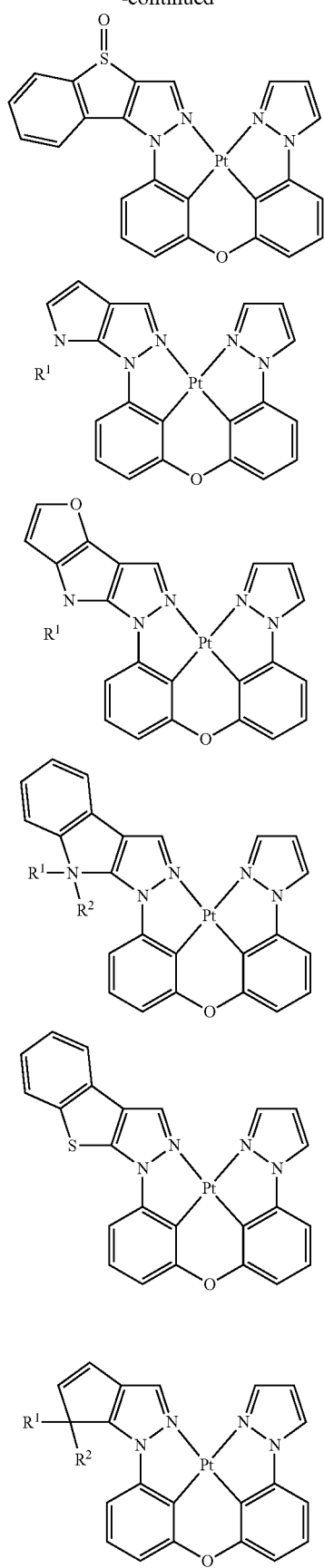

497
-continued
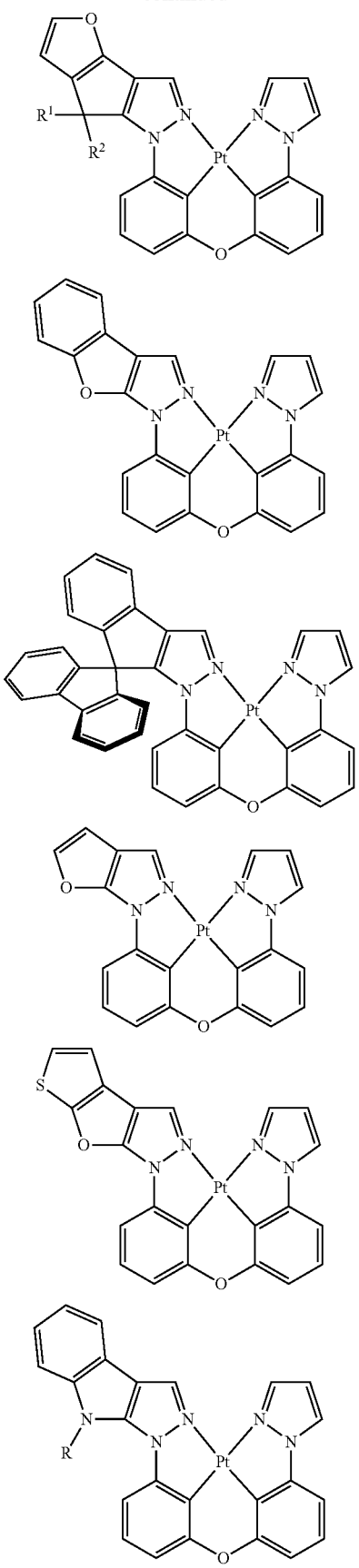
498
-continued
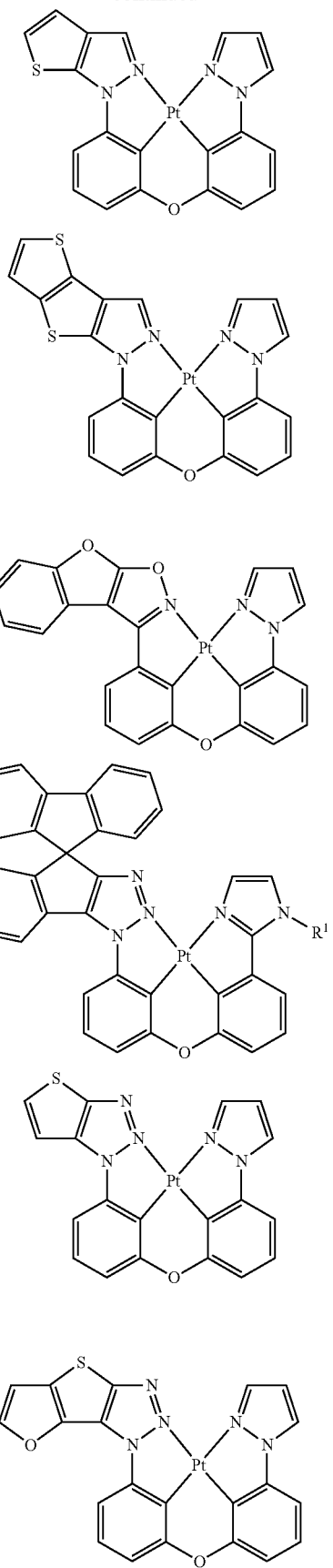
Structures 35

499
-continued
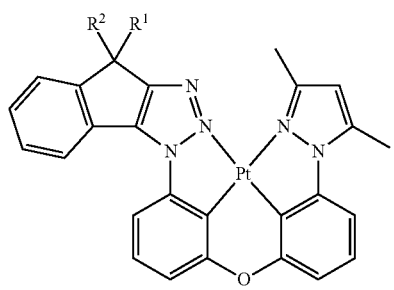
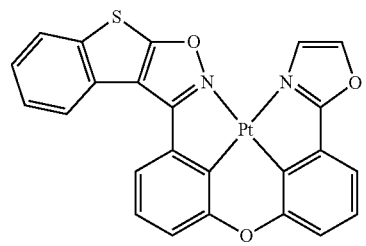
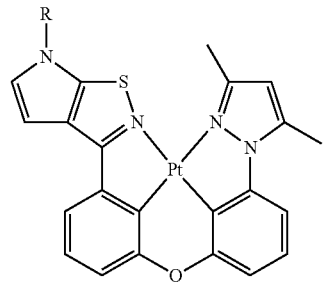
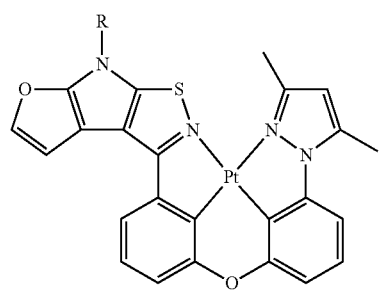
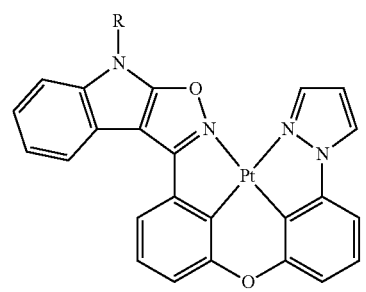
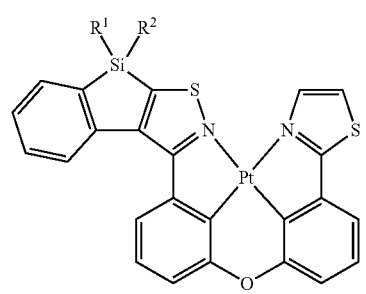
500
-continued
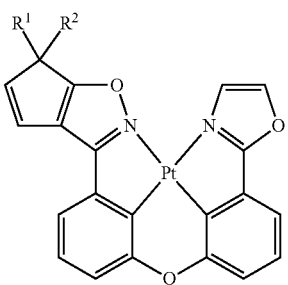
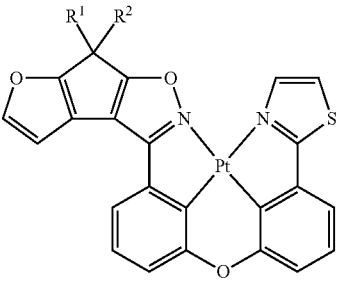
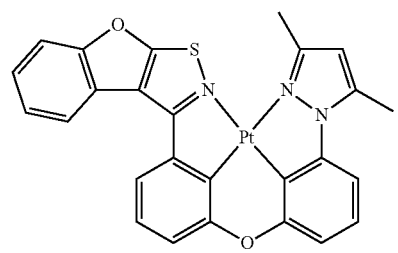
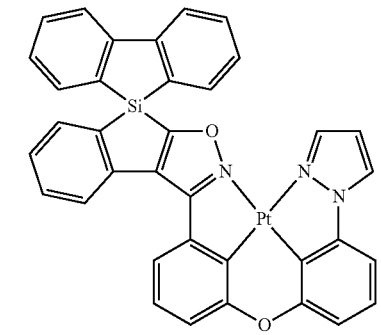
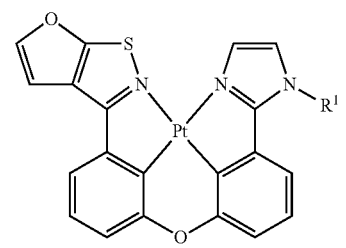
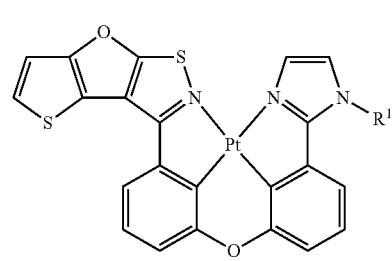

501
-continued
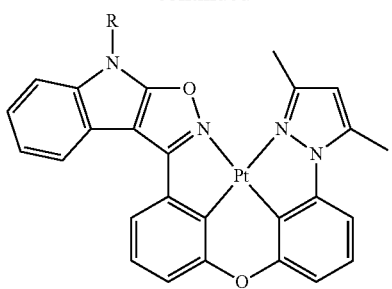
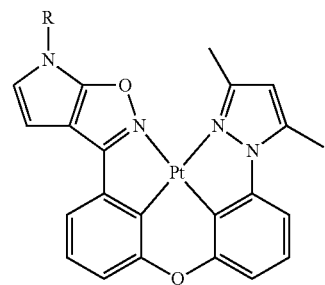
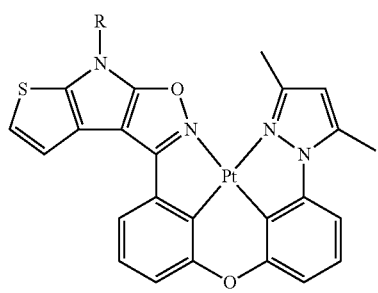
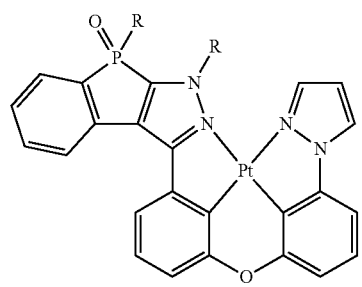
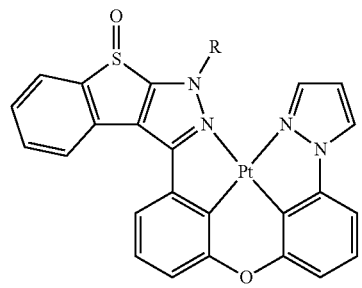
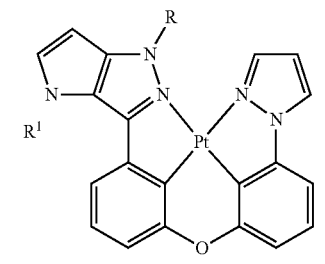
502
-continued
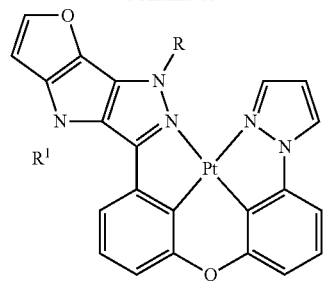
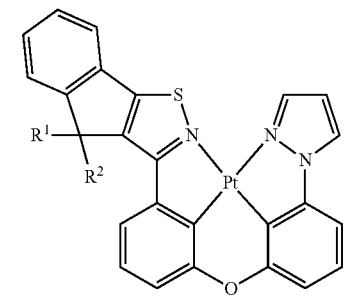
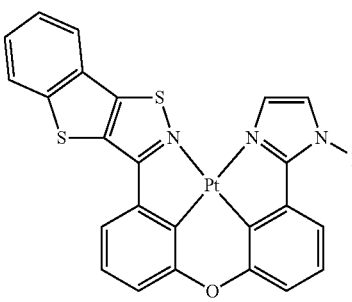
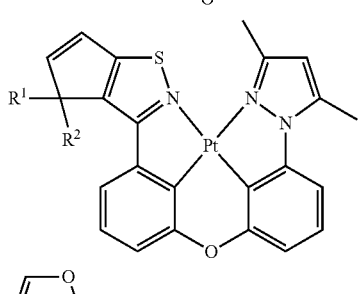
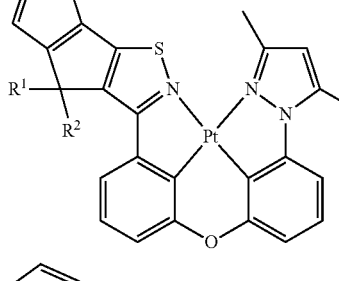
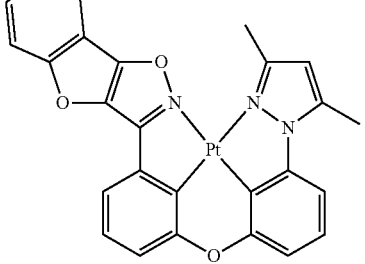

-continued
Structures 36
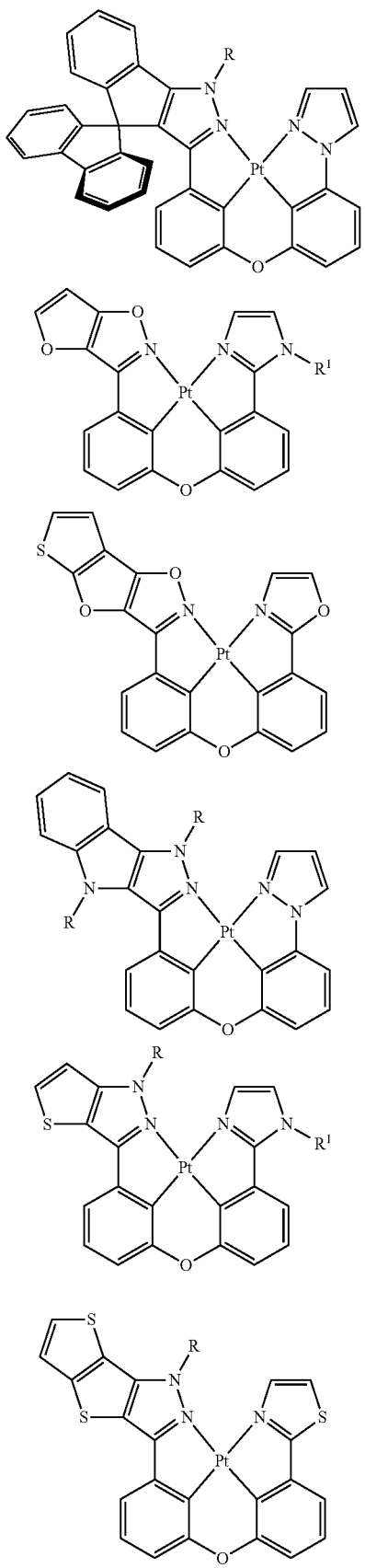
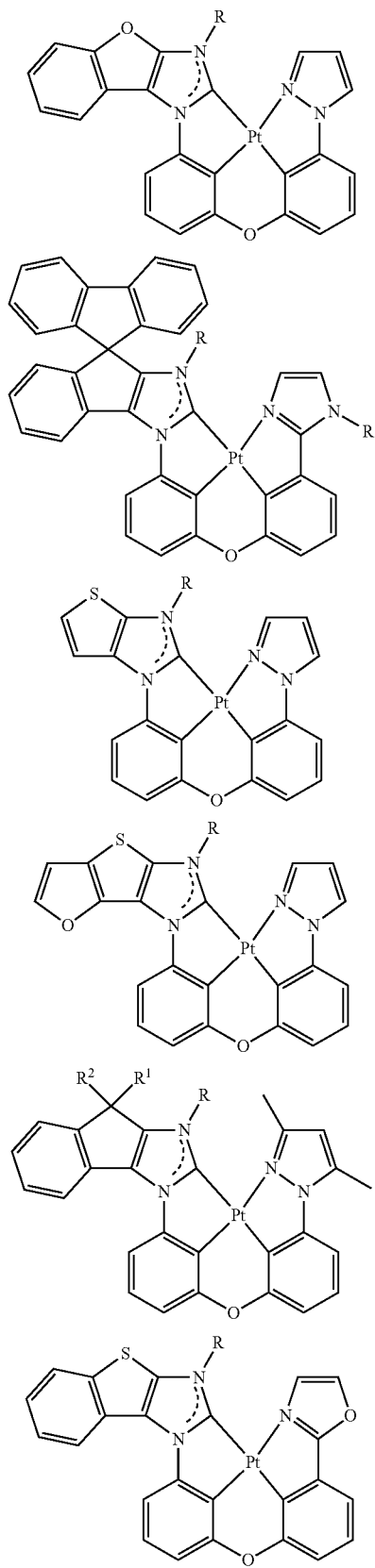

505
-continued
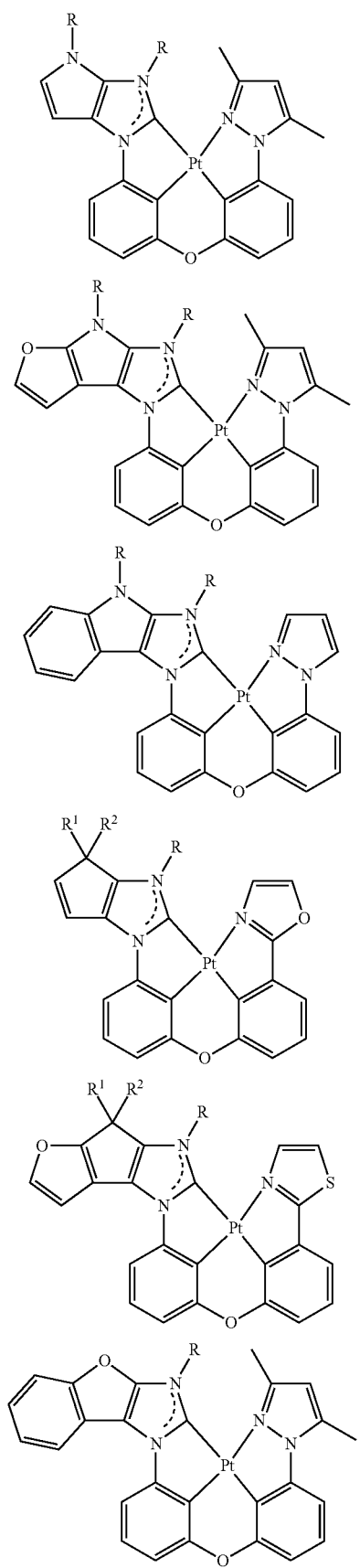
506
-continued
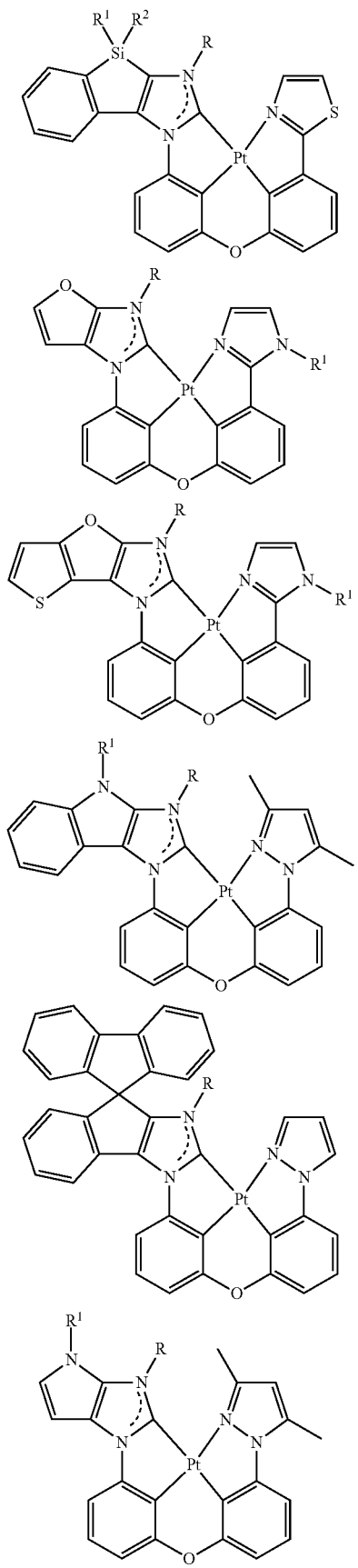

507
-continued
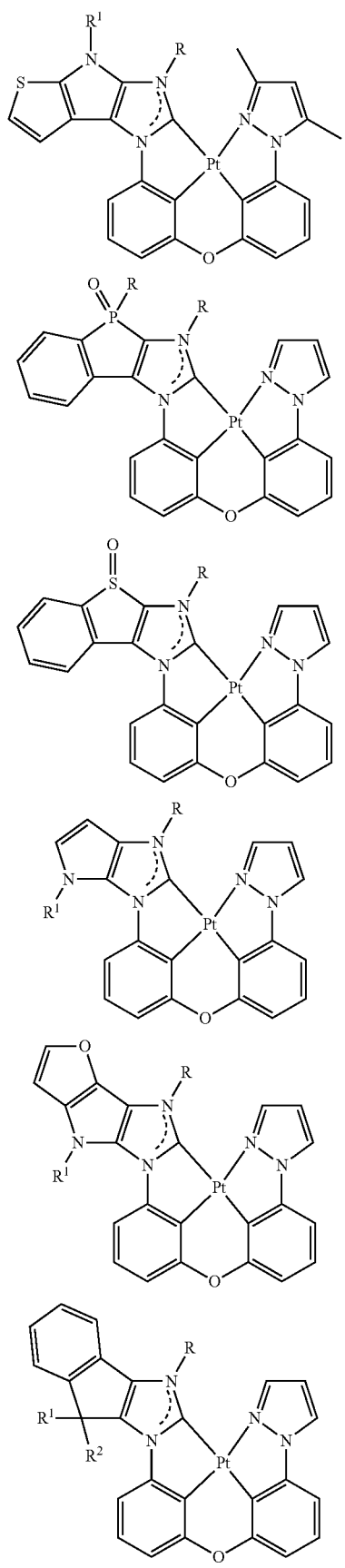
508
-continued
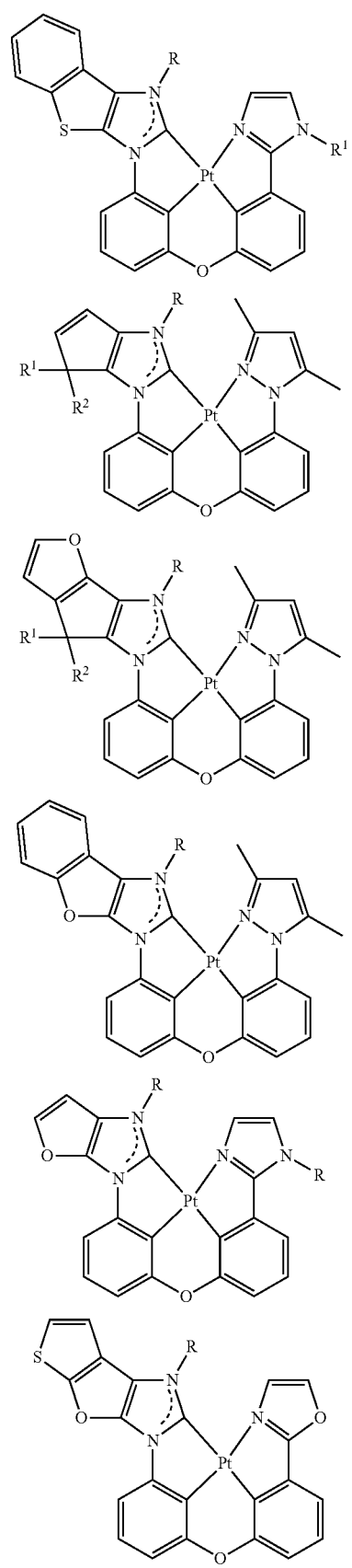

509
-continued
510
-continued
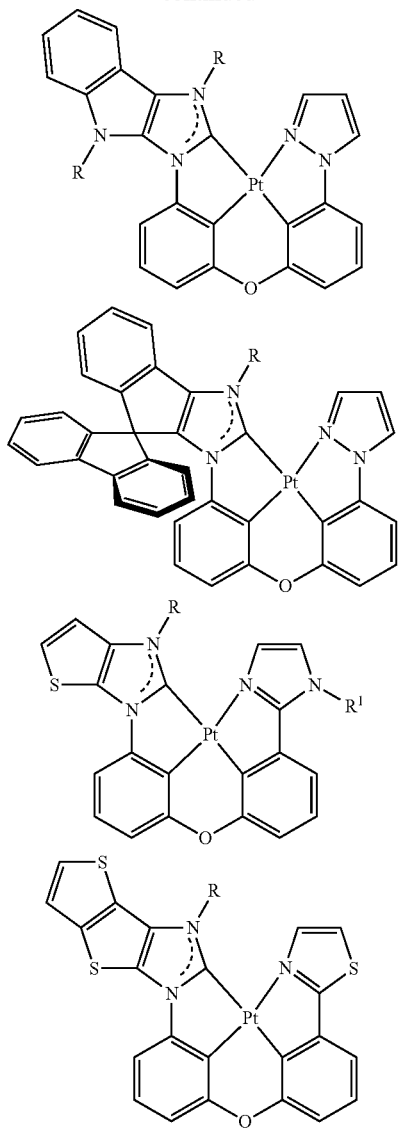
Structures 37
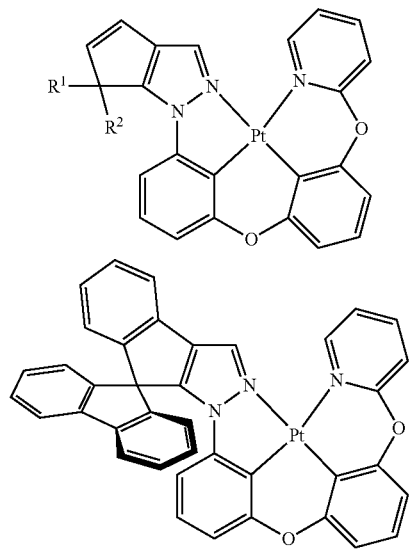
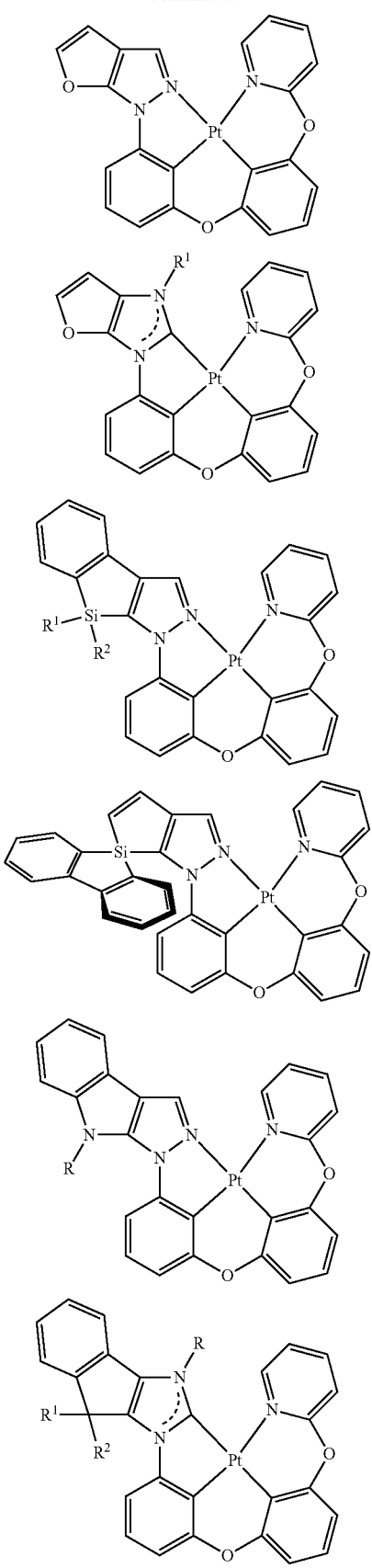

511
-continued
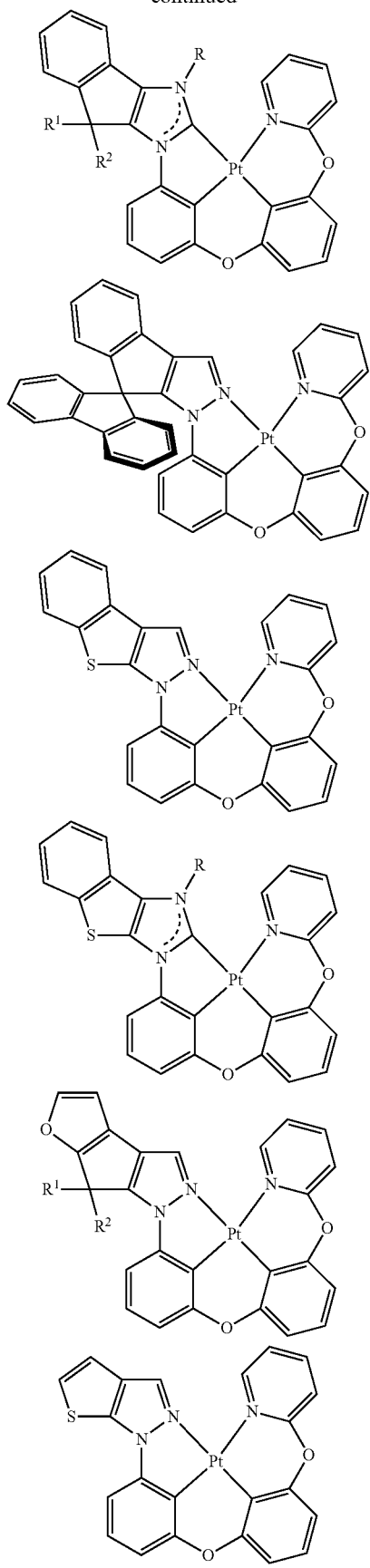
512
-continued
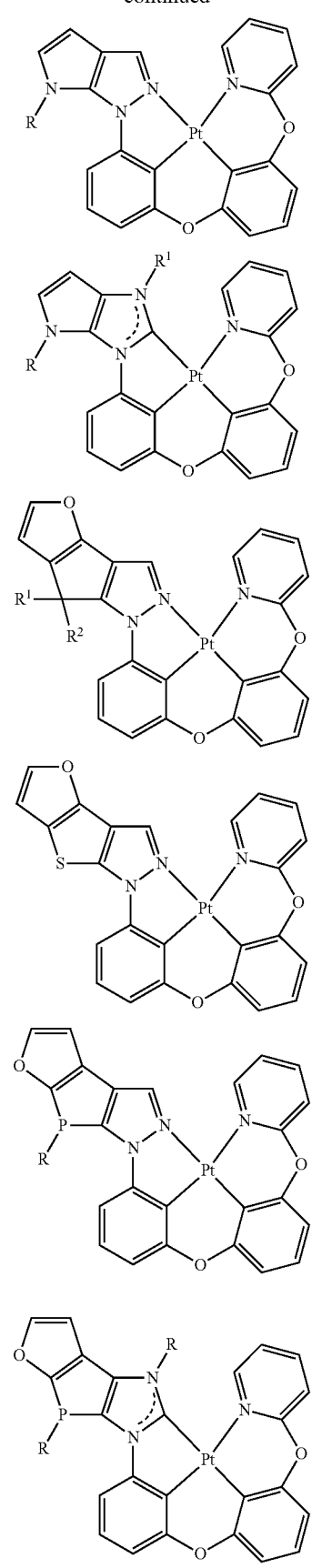

513
-continued
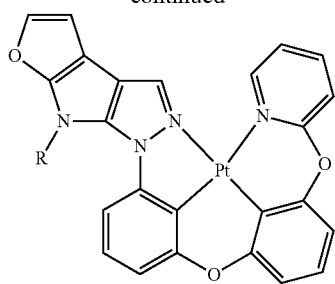
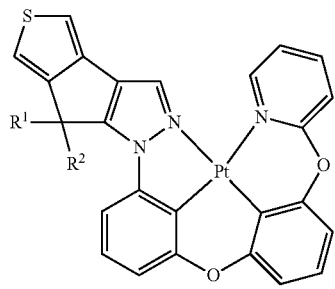
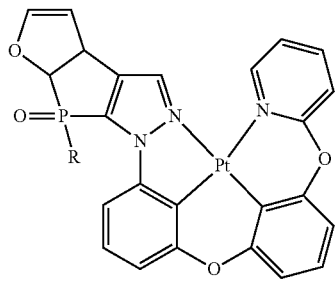
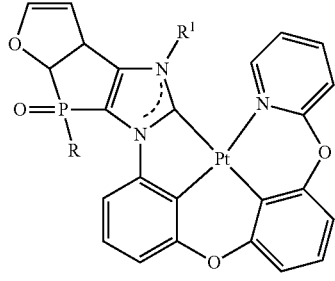
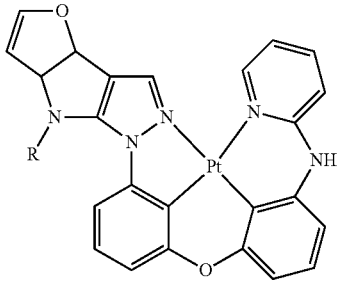
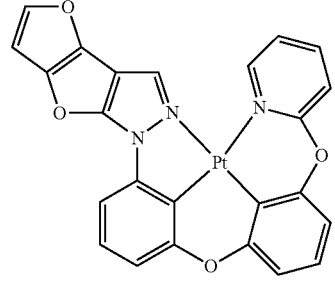
514
-continued
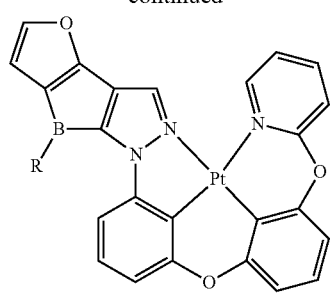
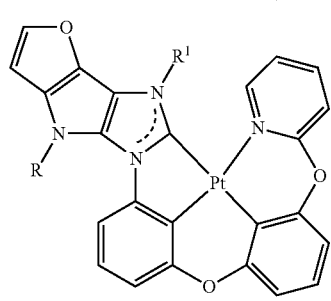
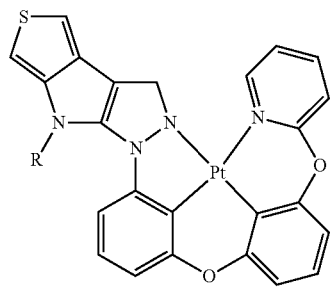
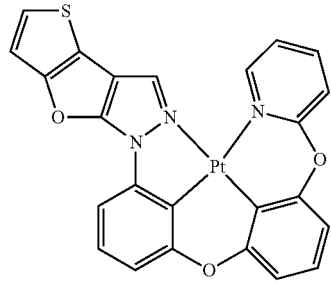
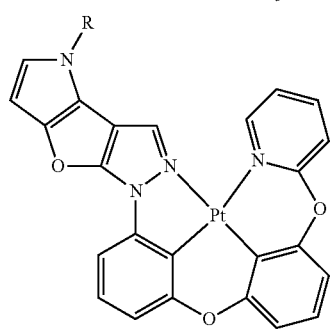

515
-continued
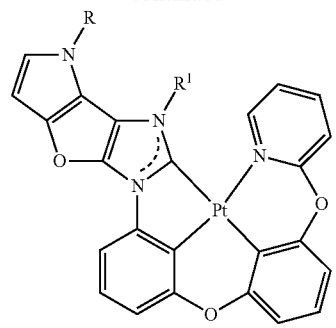
Structures 38
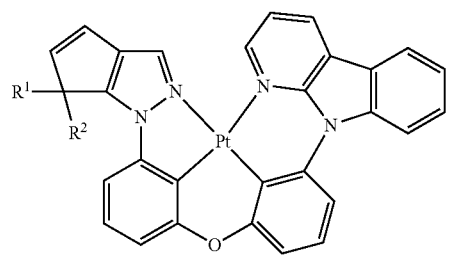
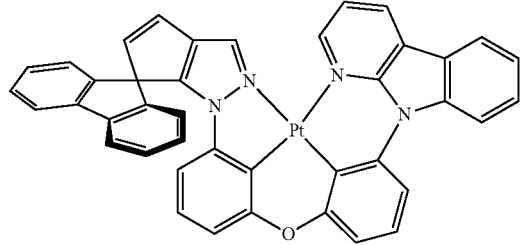
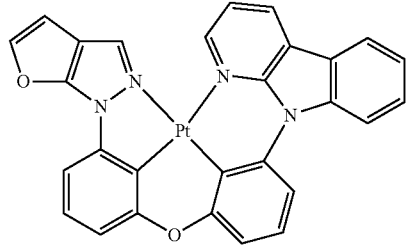
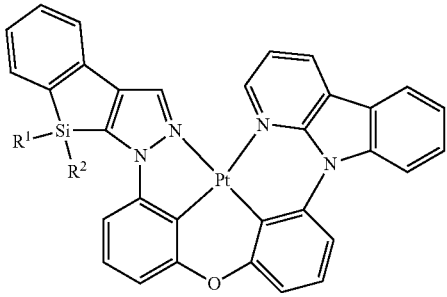
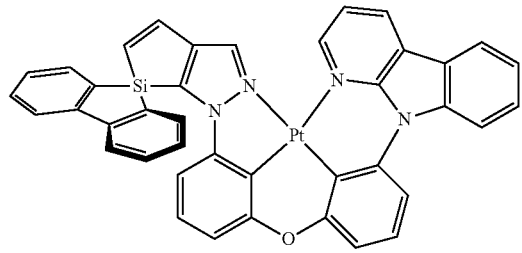
516
-continued
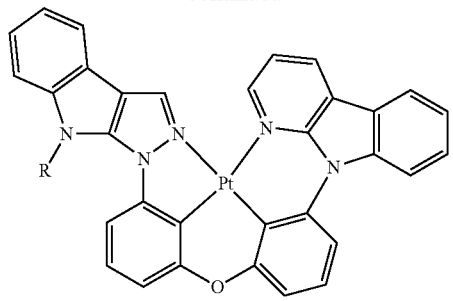
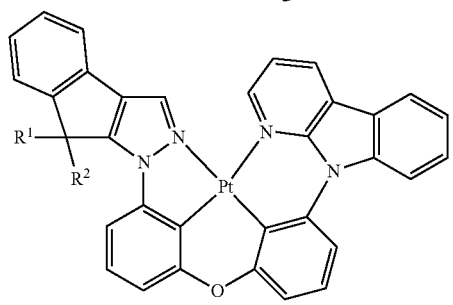
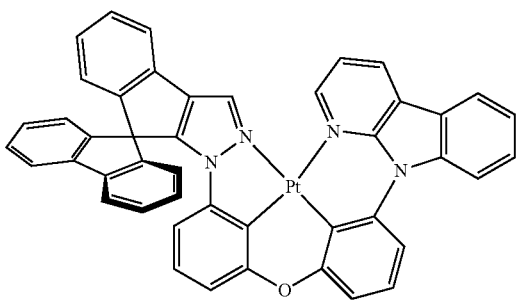
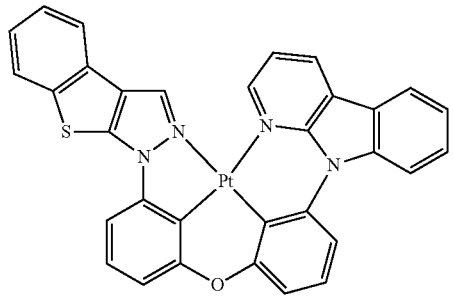
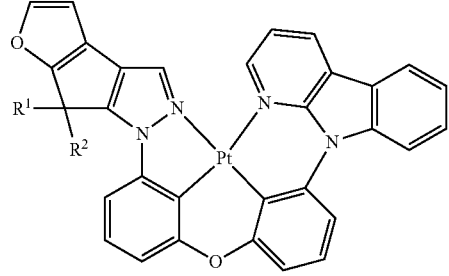
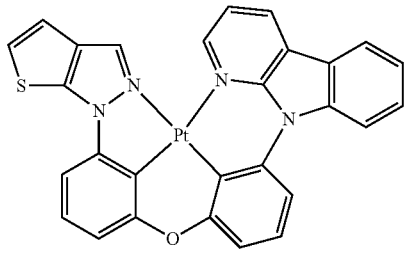

517
-continued
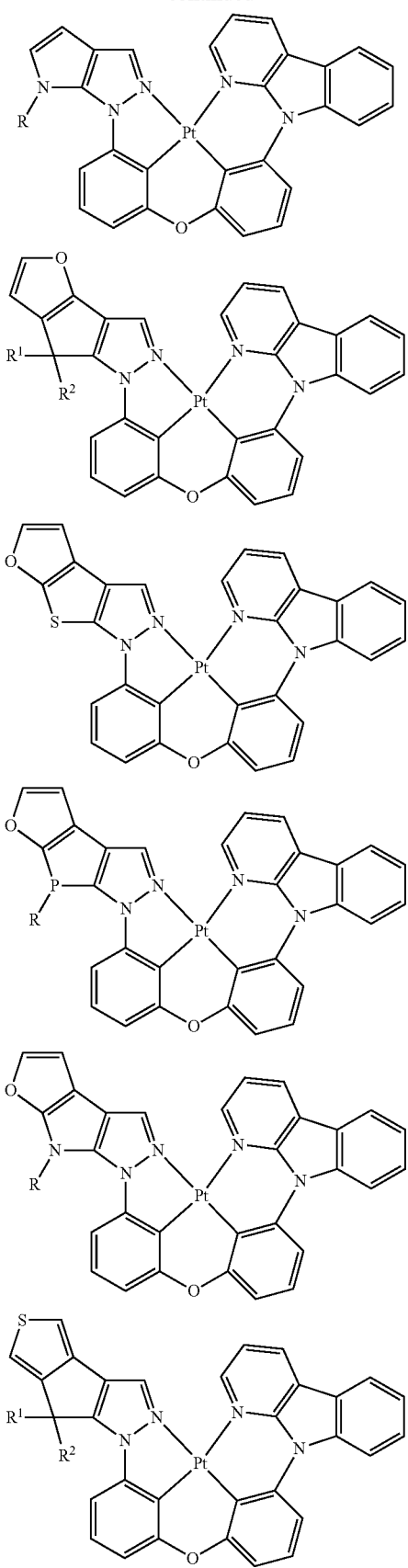
518
-continued
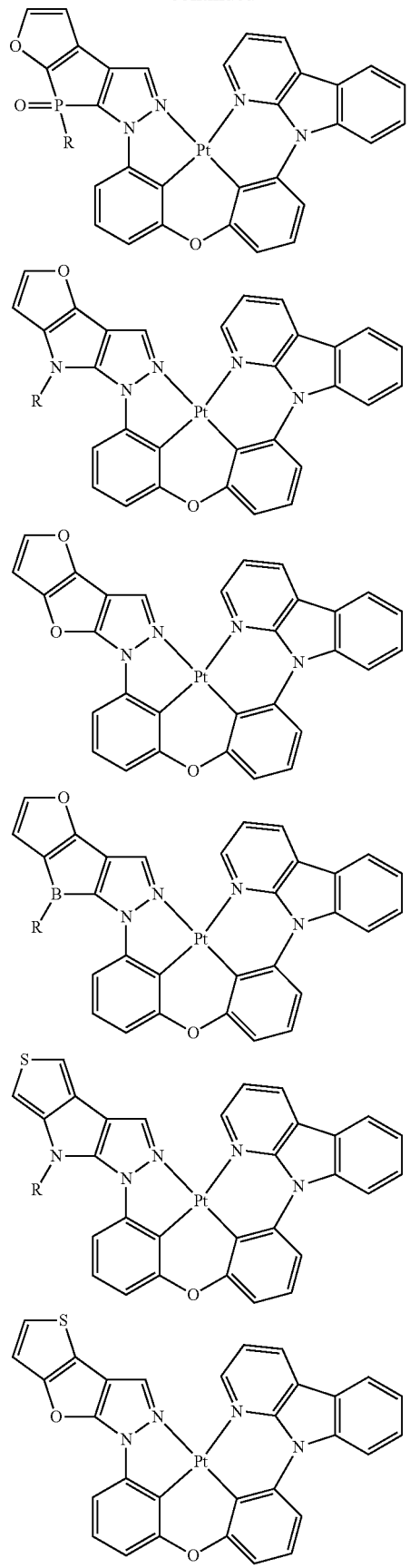

519
-continued
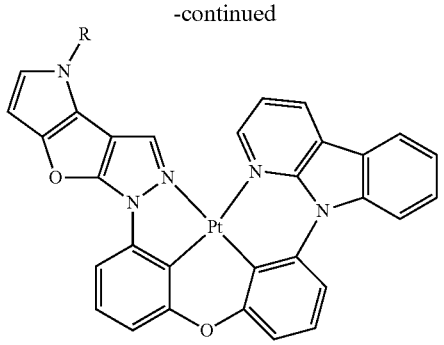
Structure 39
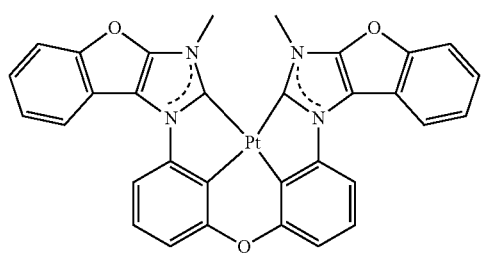
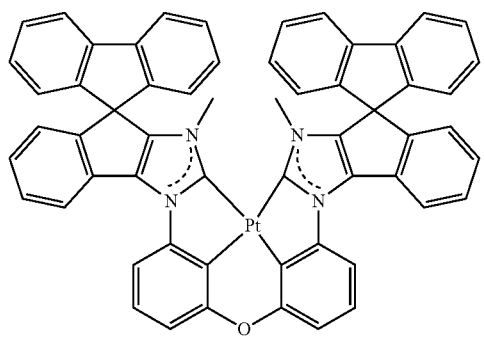
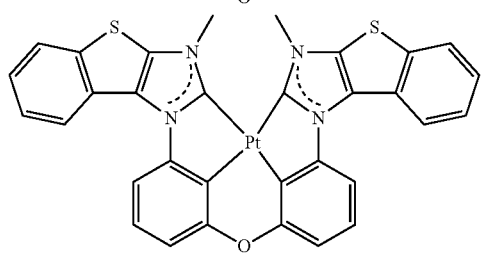
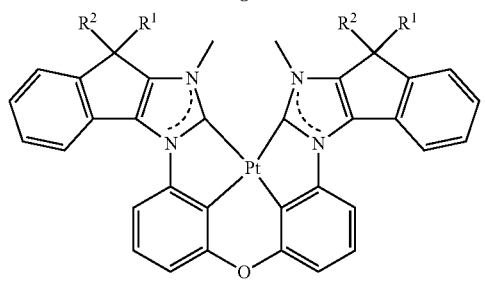
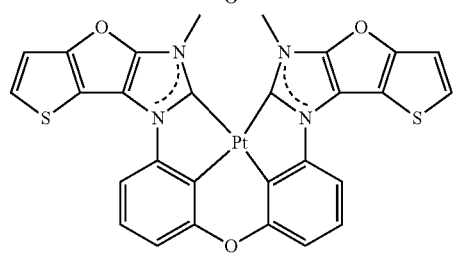
520
-continued
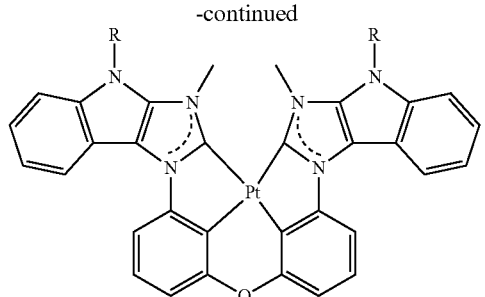
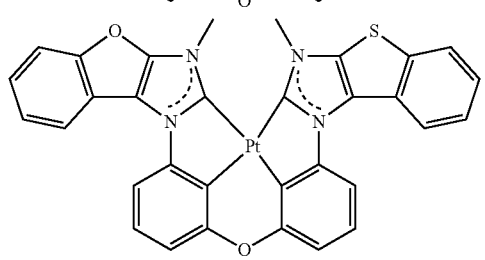
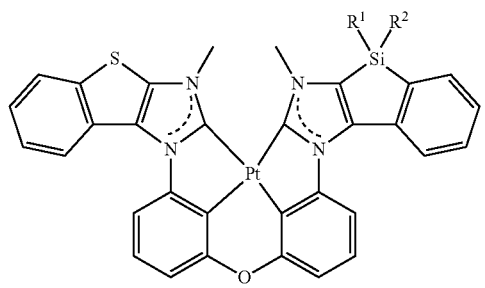
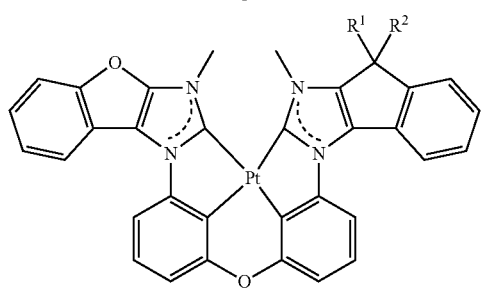
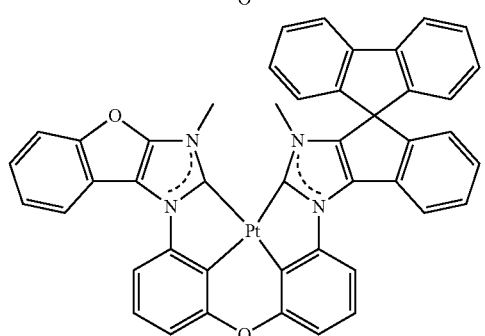
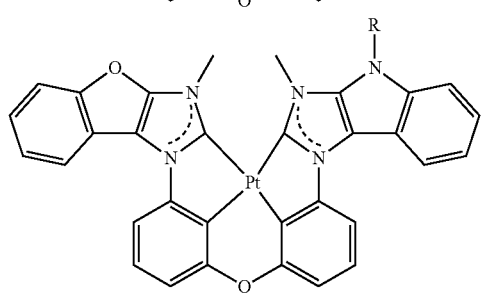

521
-continued
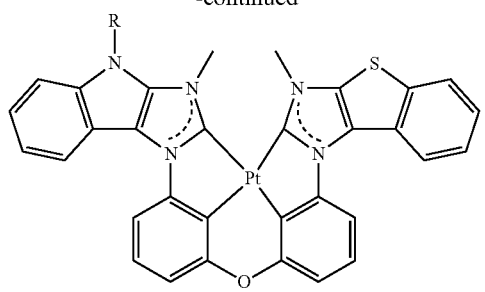
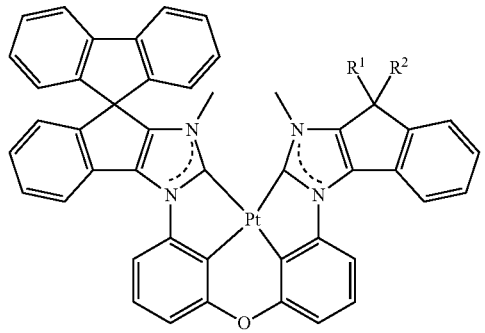
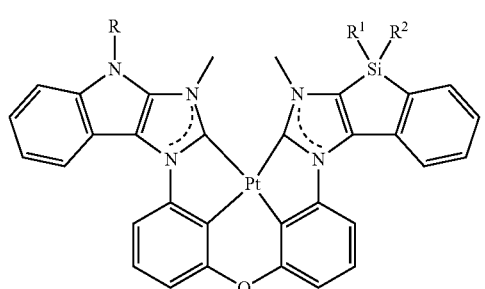
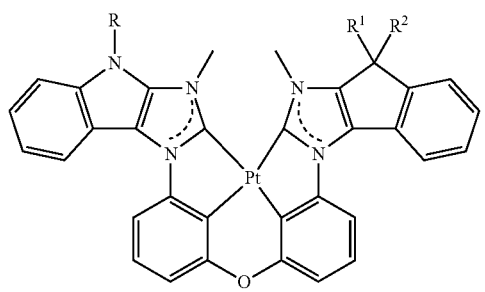
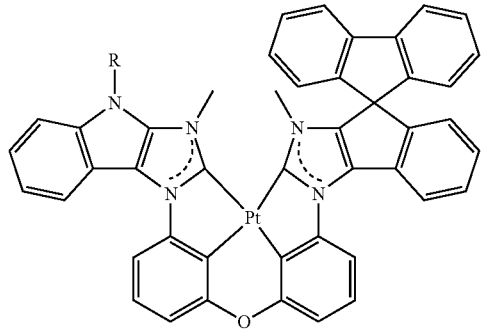
522
-continued
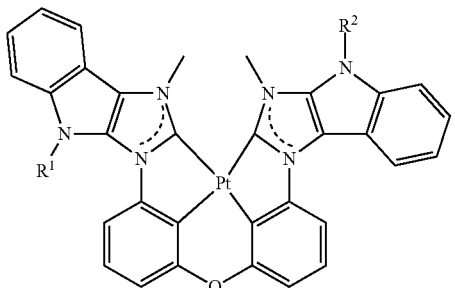
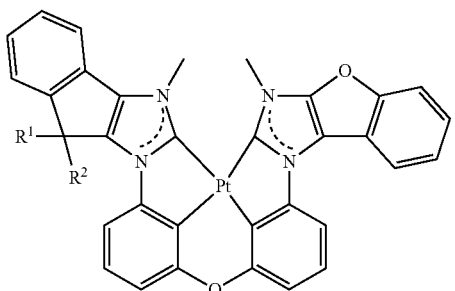
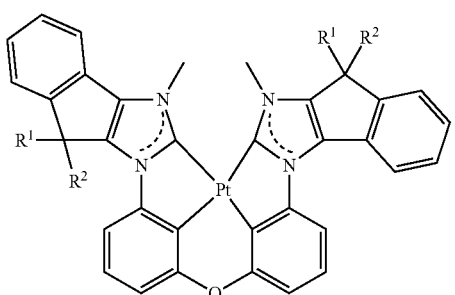
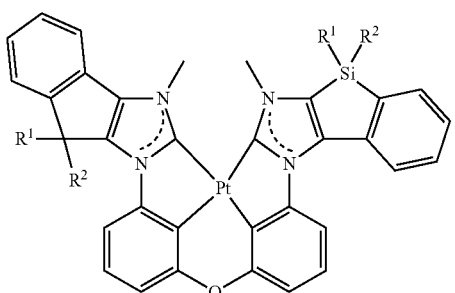
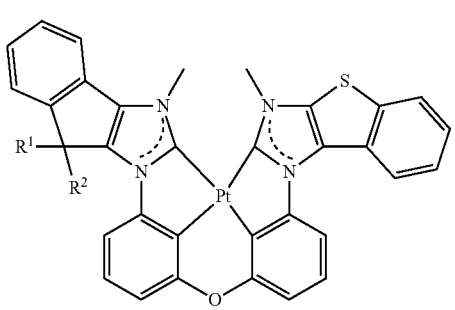

523
-continued
524
-continued
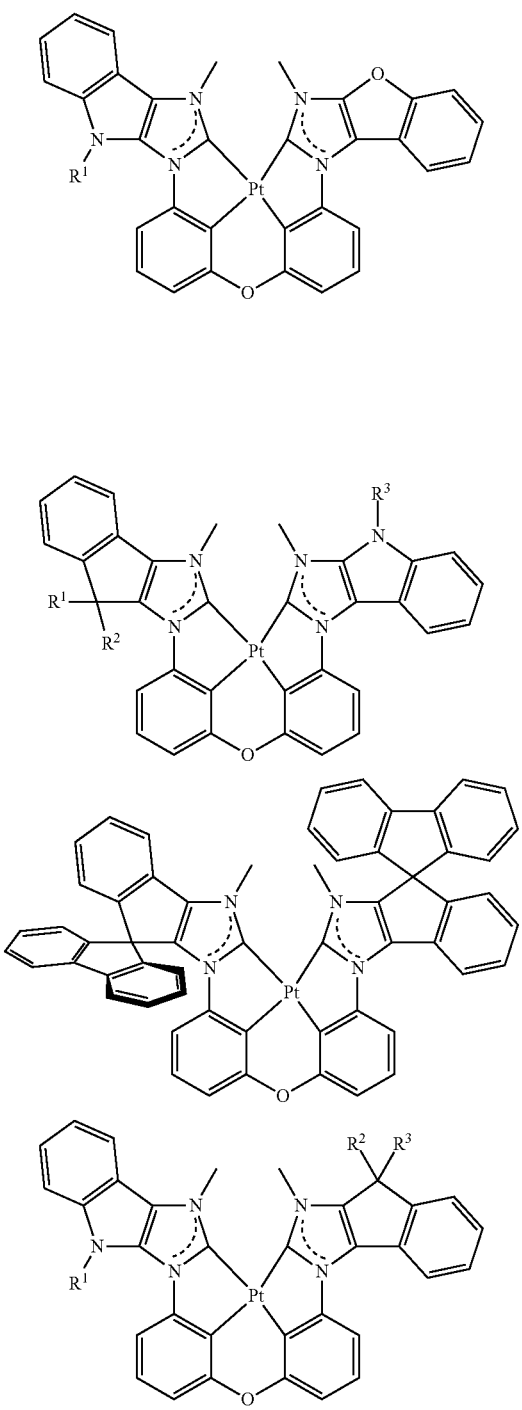
Structures 40
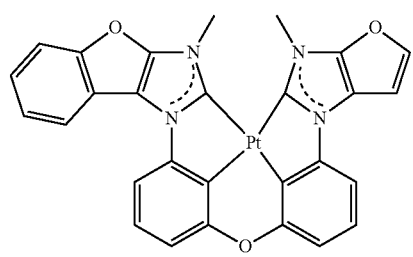
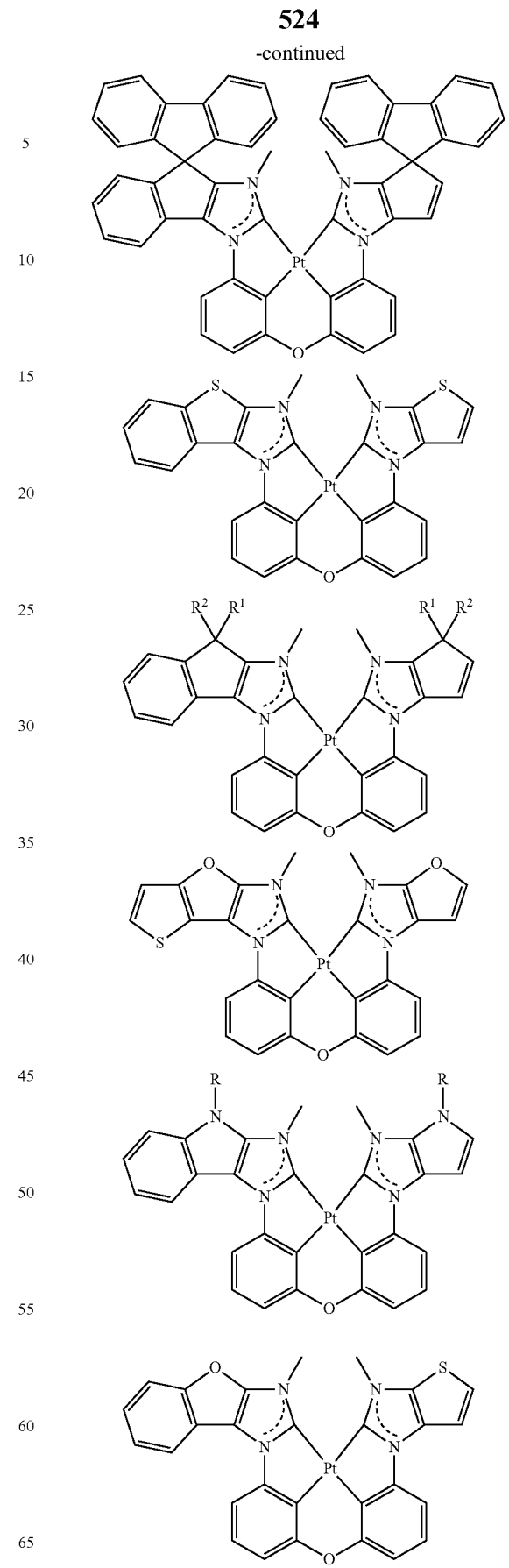

525
-continued
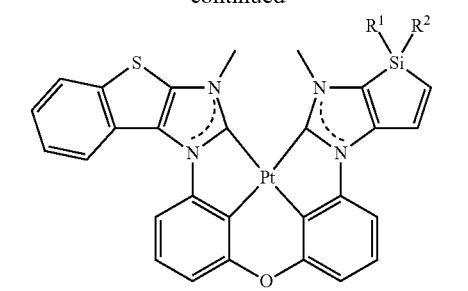
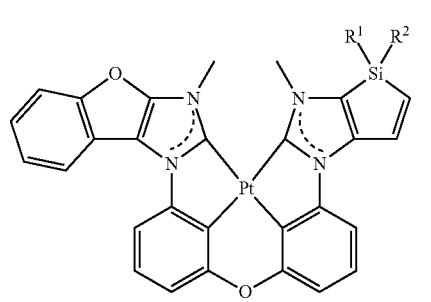
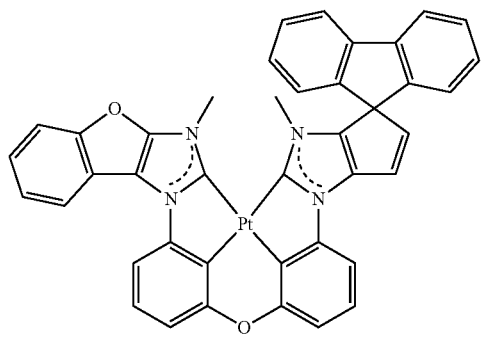
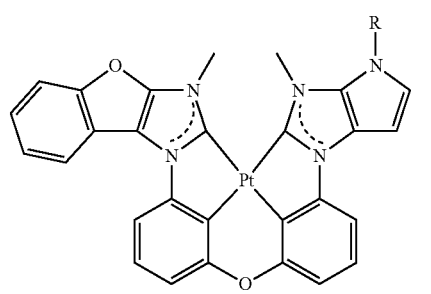
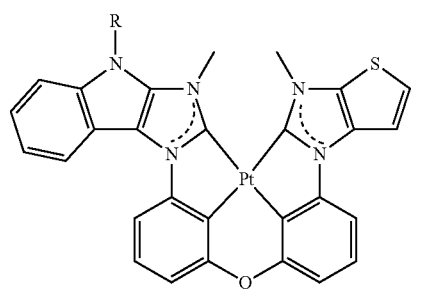
526
-continued
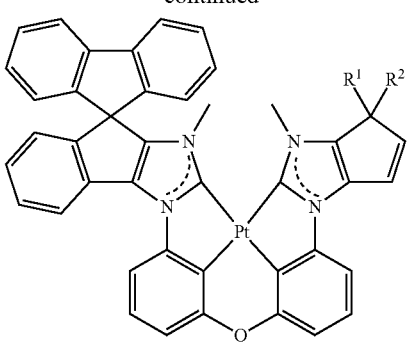
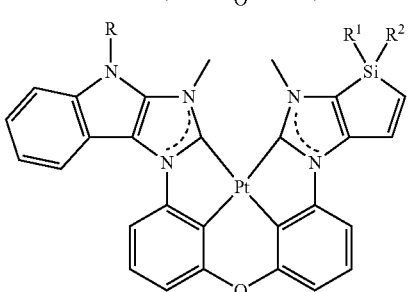
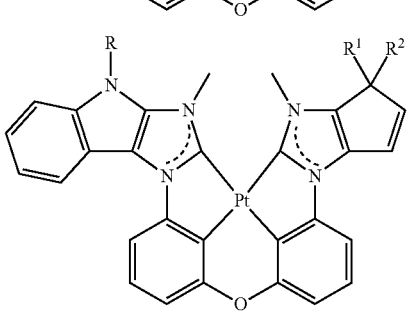
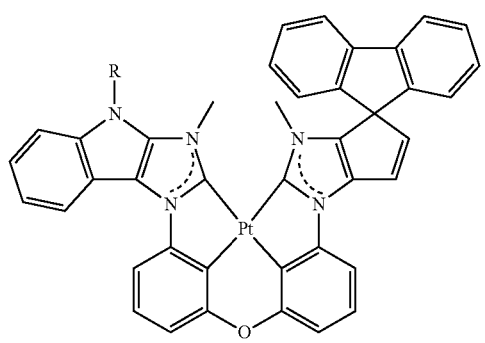
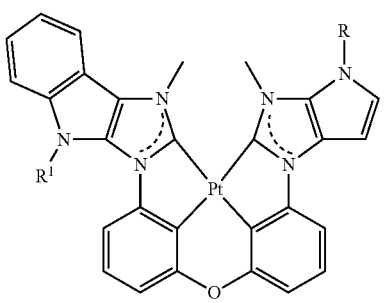

527
-continued
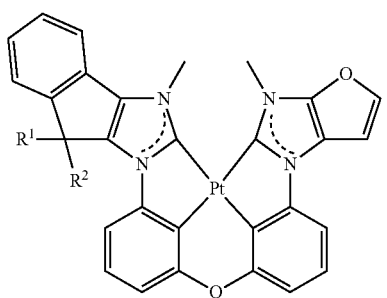
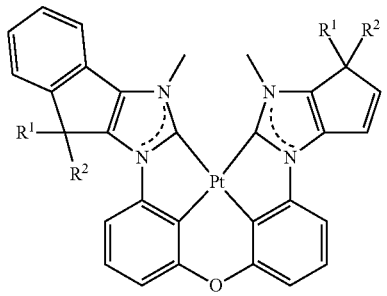
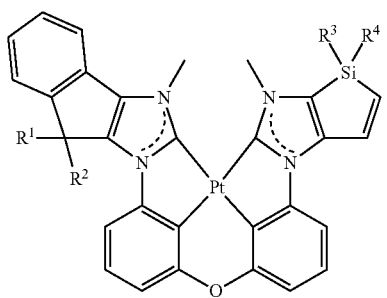
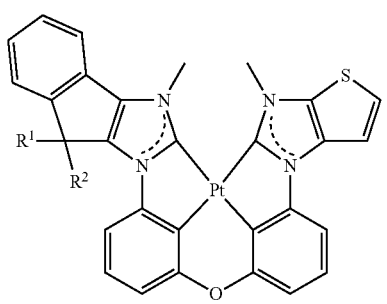
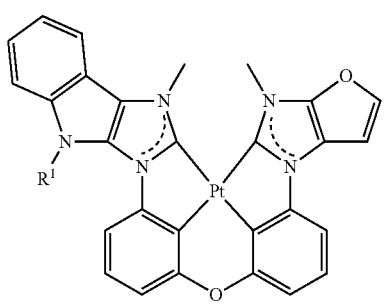
528
-continued
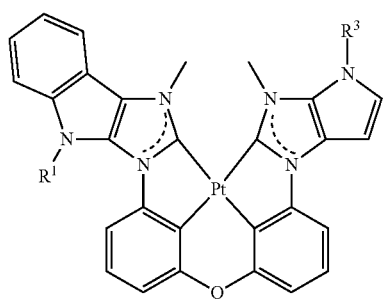
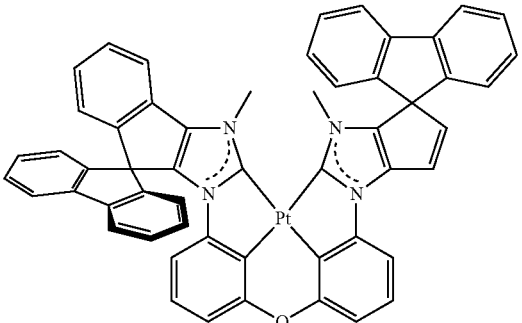
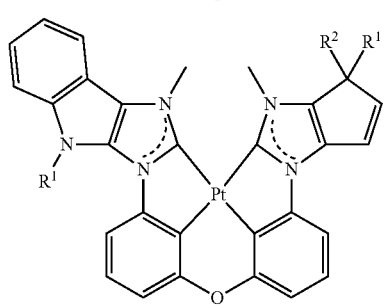
Structures 41
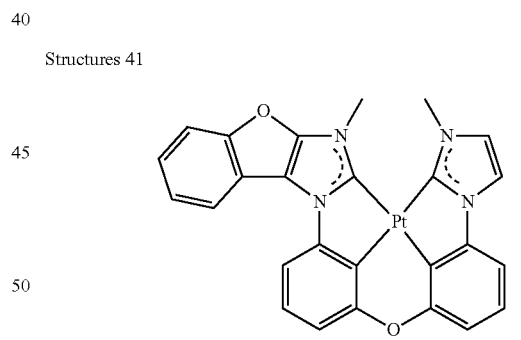
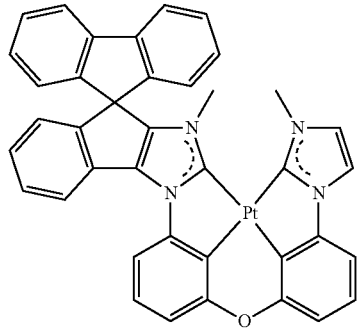

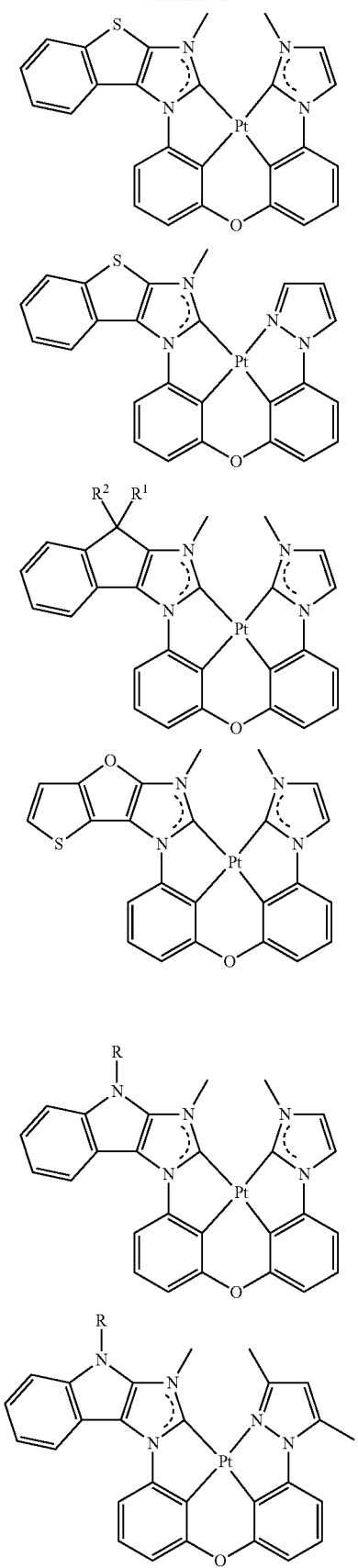
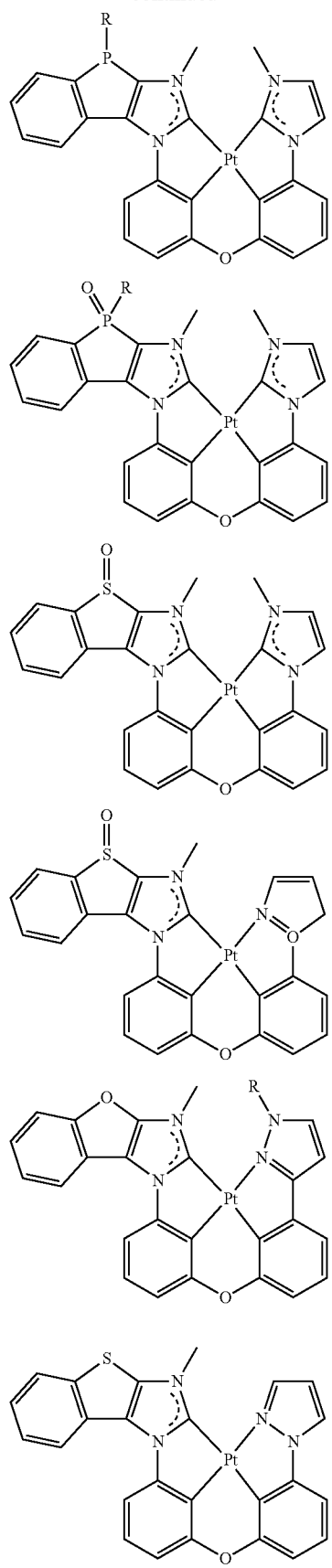

531
-continued
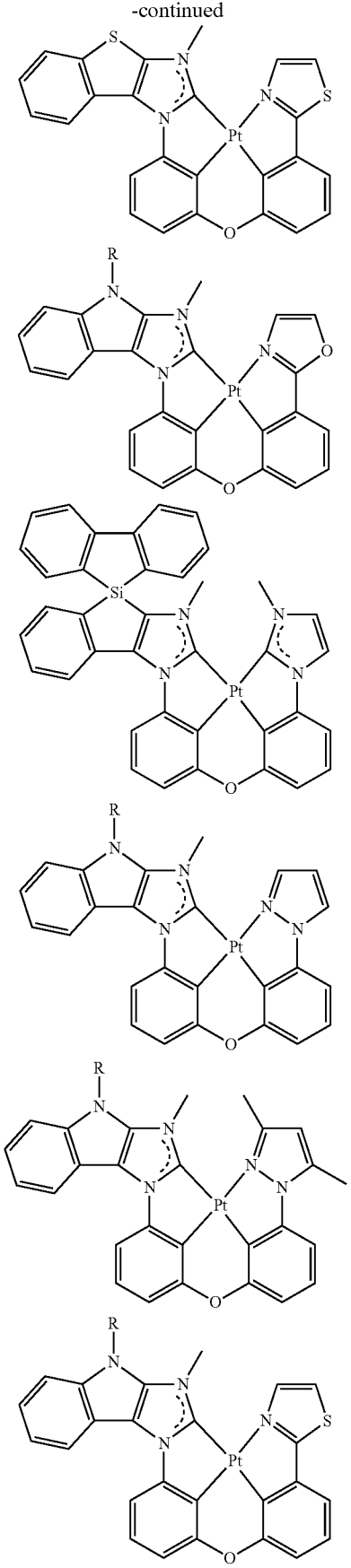
532
-continued
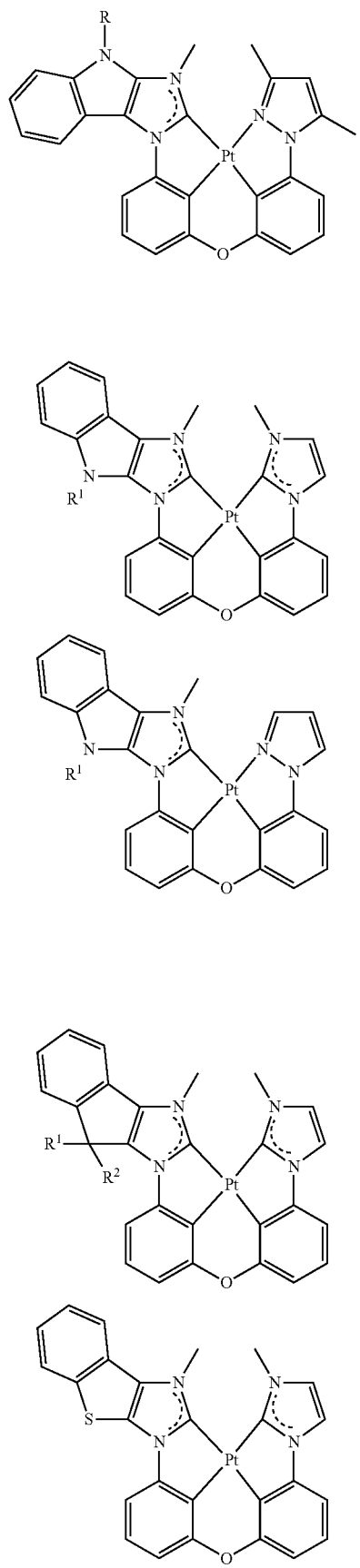

533
-continued
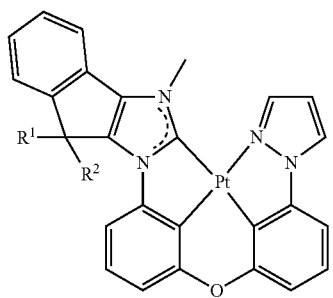
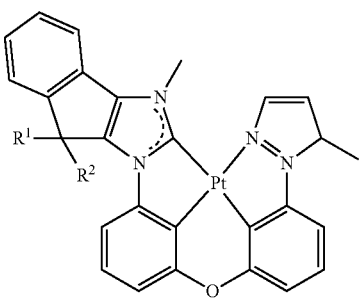
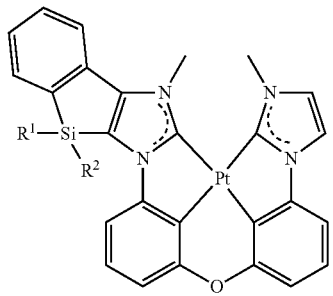
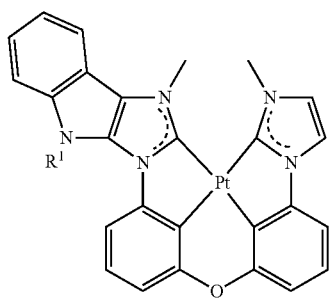
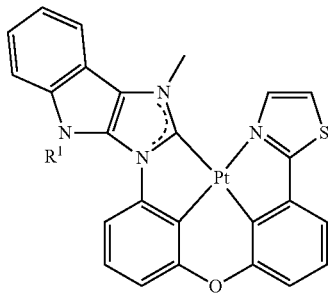
534
-continued
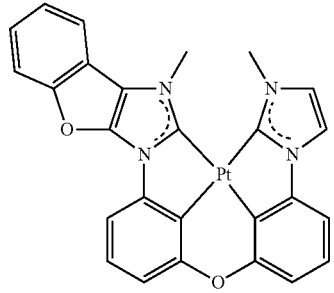
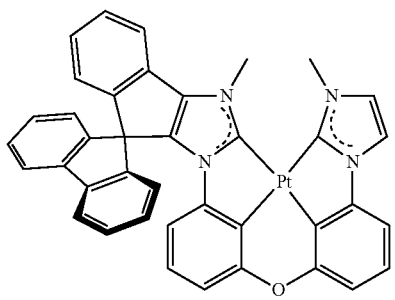
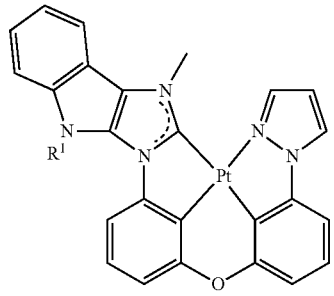
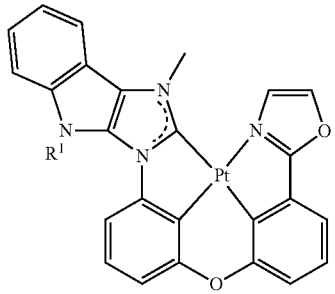
Structures 42
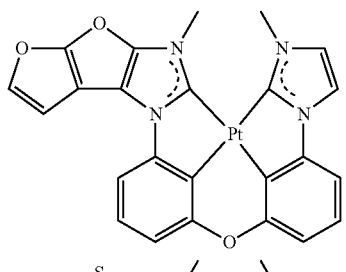
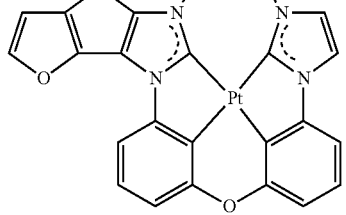

535
-continued
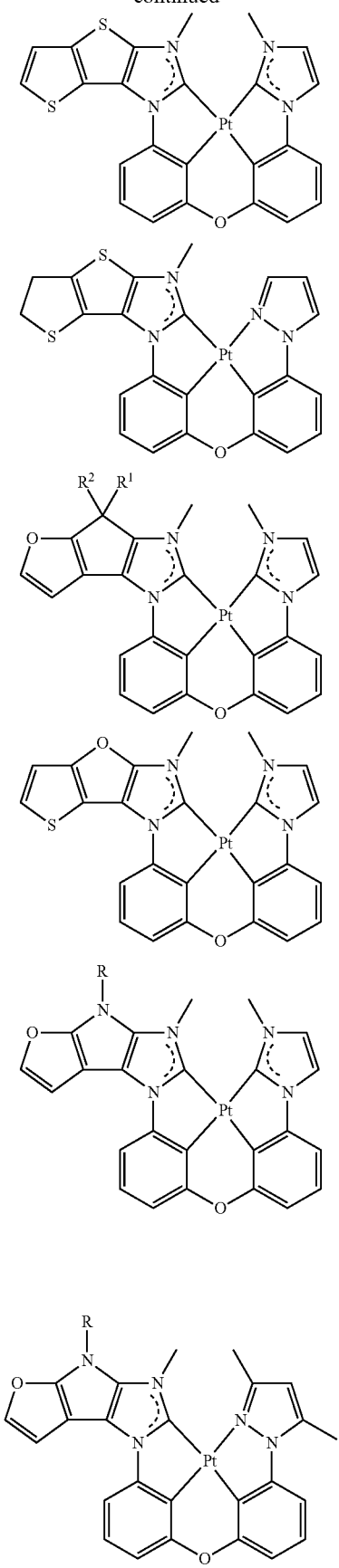
536
-continued
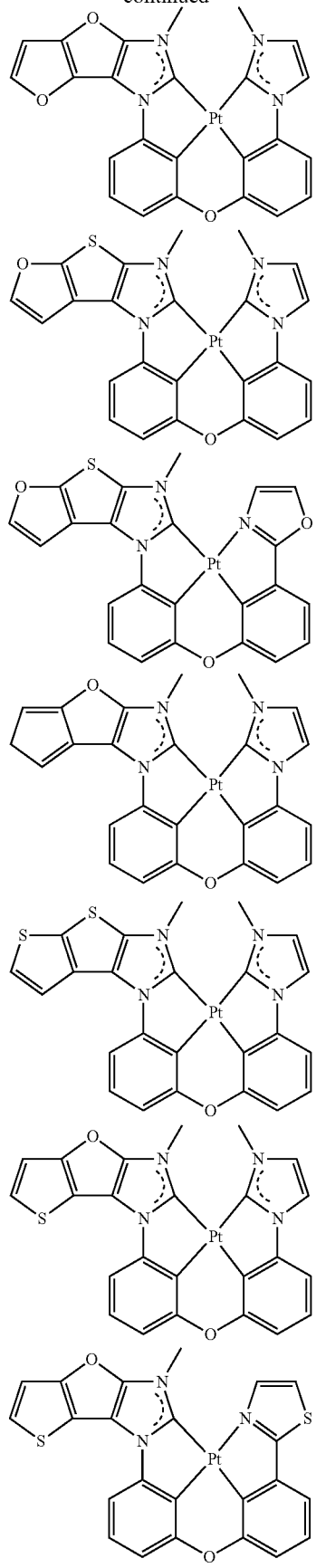

537
-continued
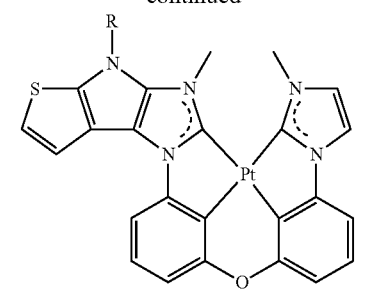
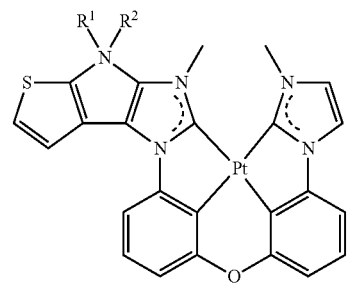
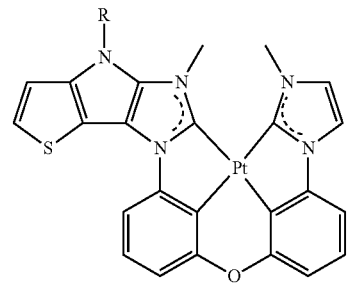
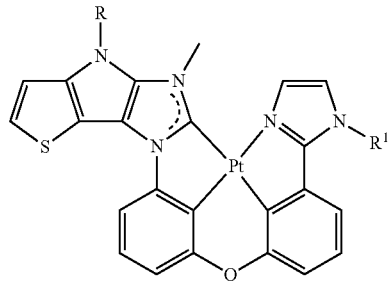
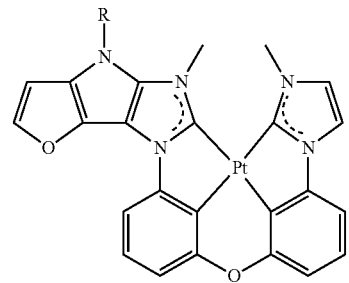
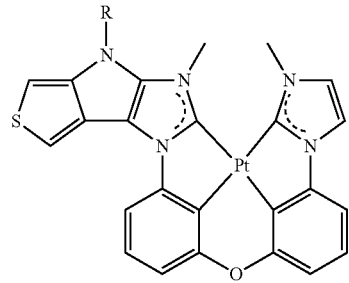
538
-continued
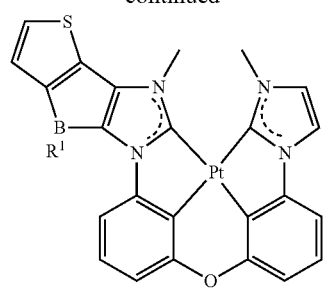
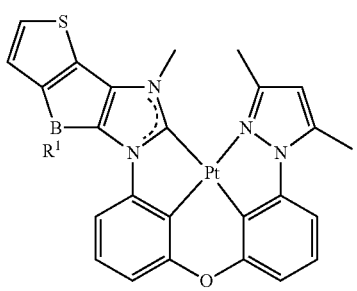
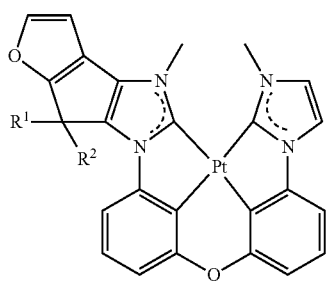
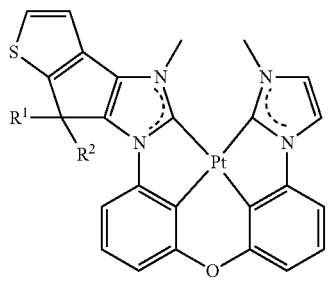
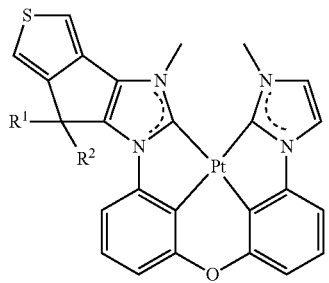
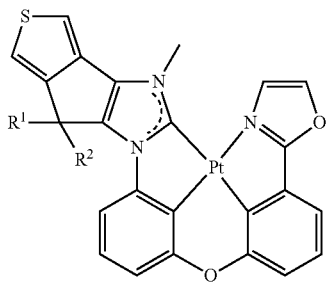

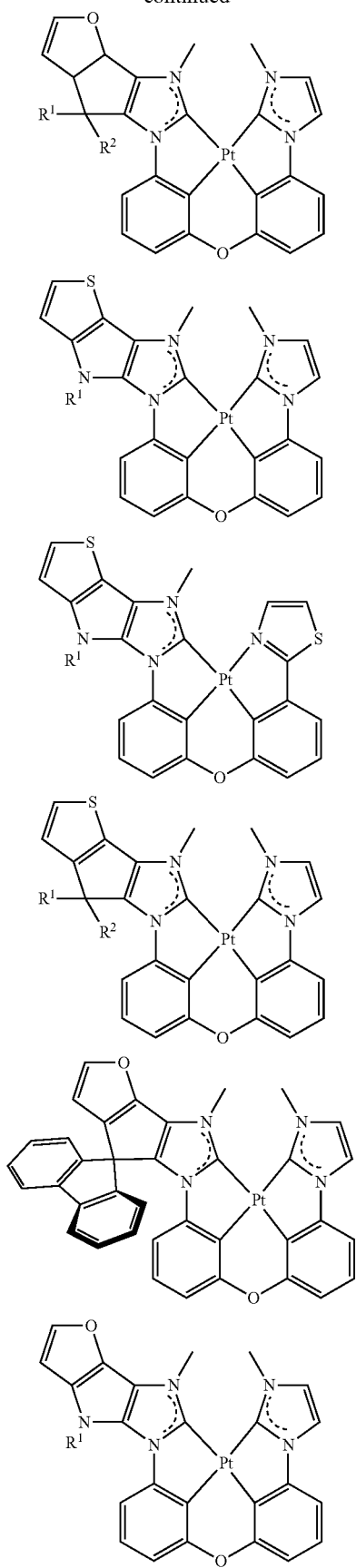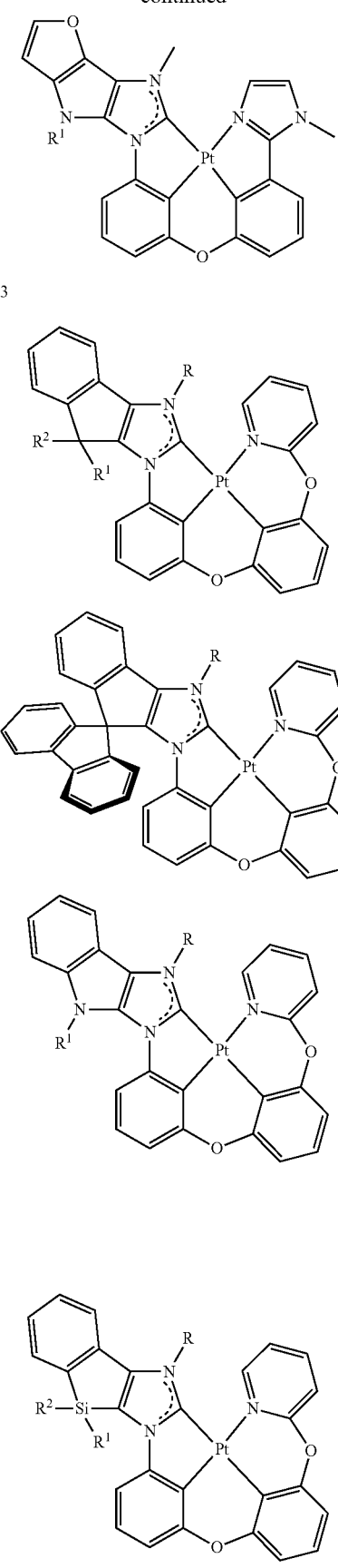
Structures 43

541
-continued
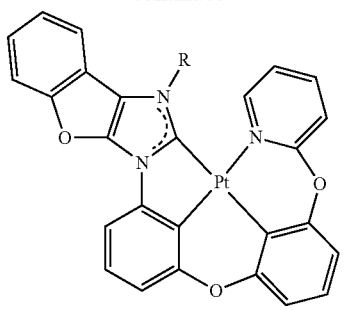
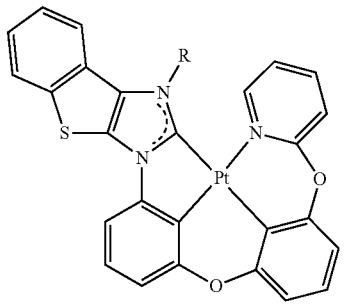
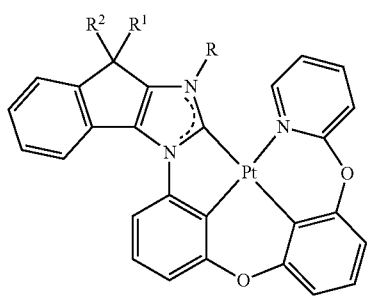
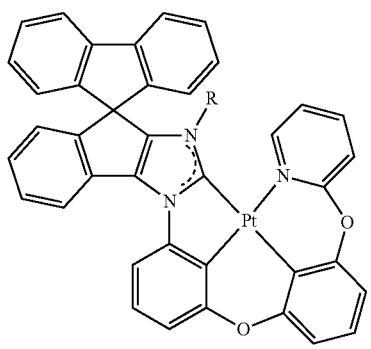
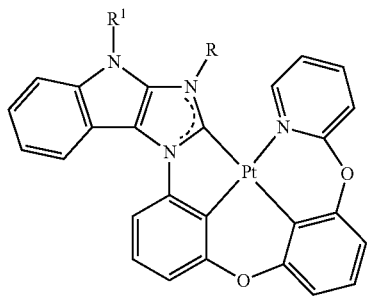
542
-continued
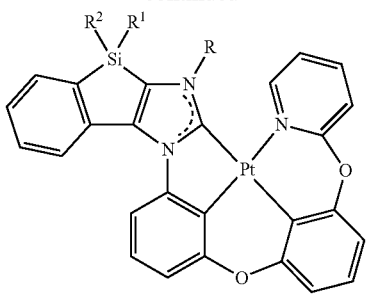
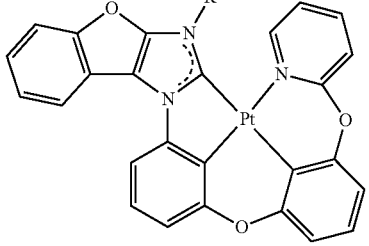
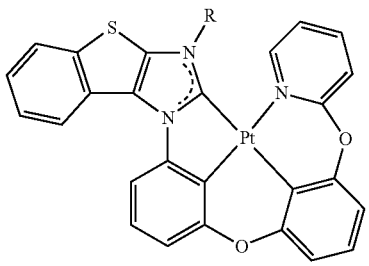
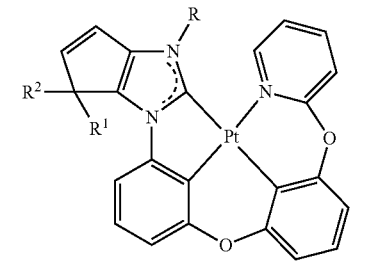
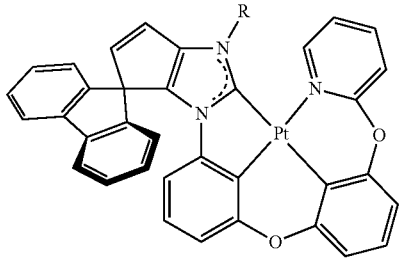
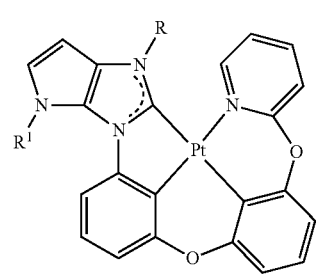

543
-continued
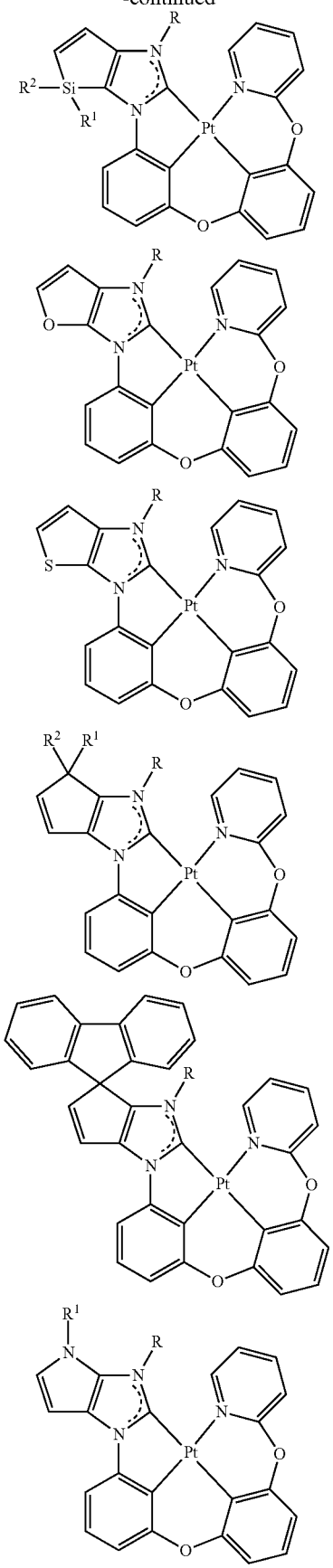
544
-continued
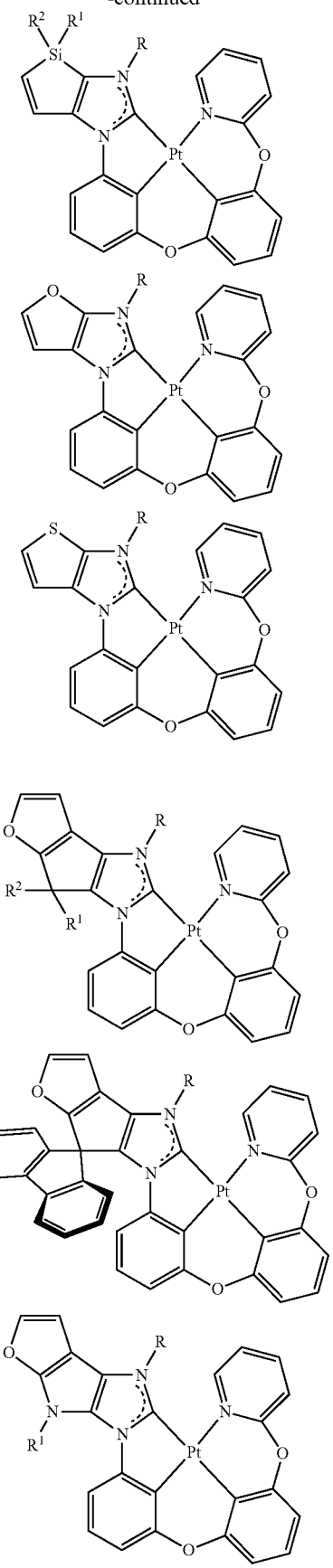
Structures 44

545
-continued
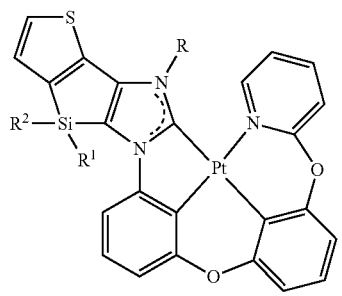
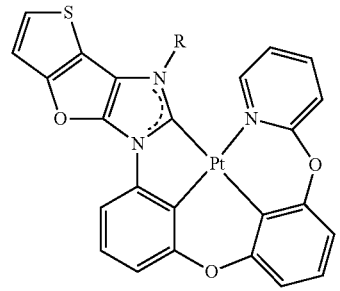
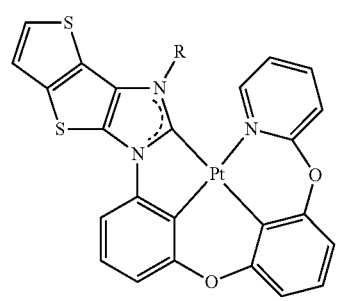
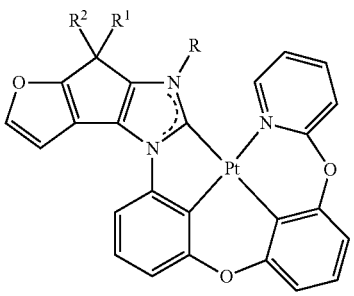
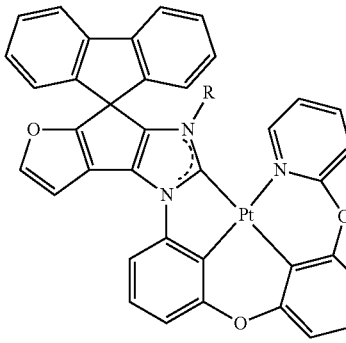
546
-continued
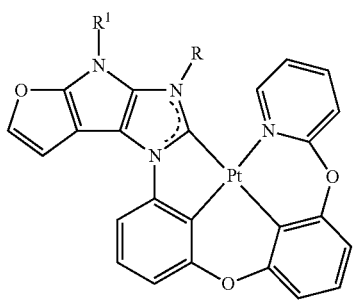
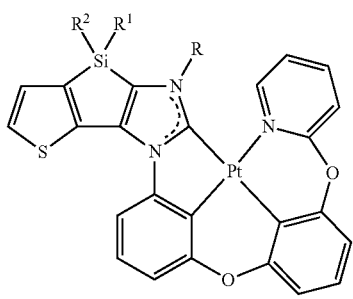
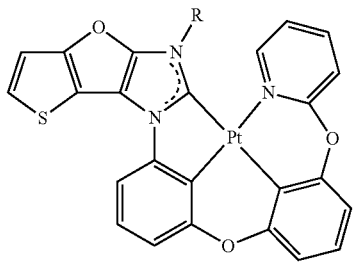
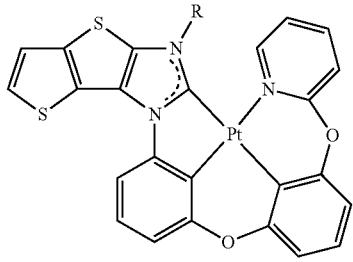
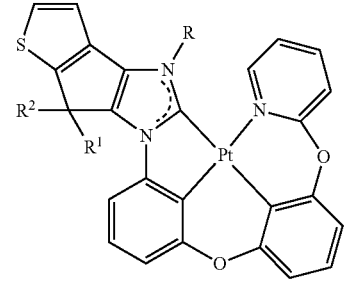
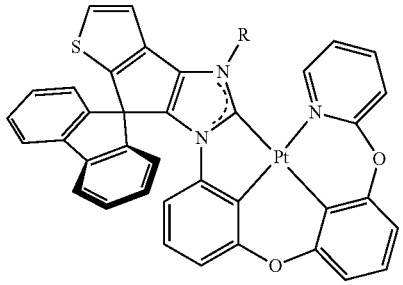

547
-continued
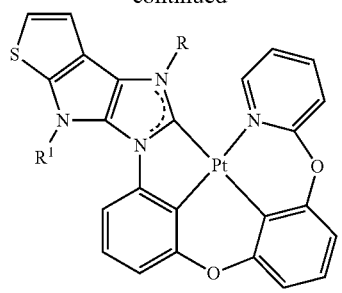
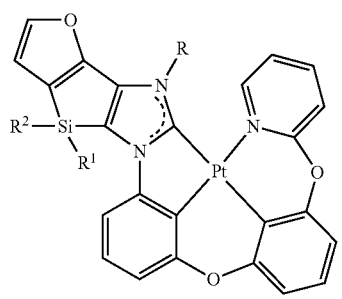
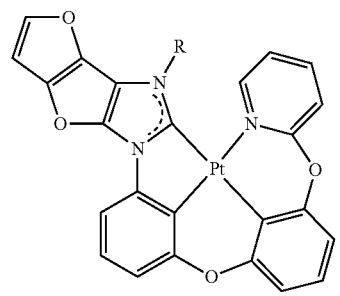
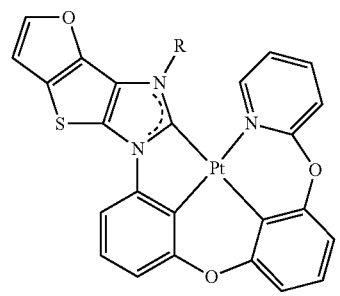
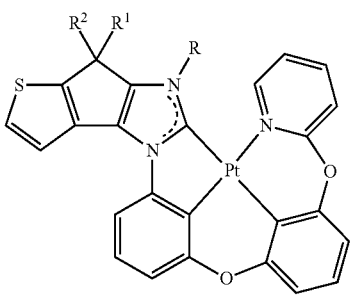
548
-continued
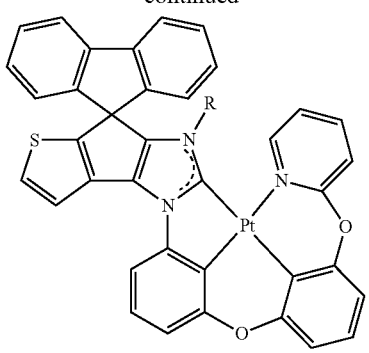
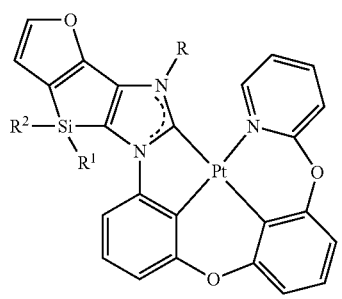
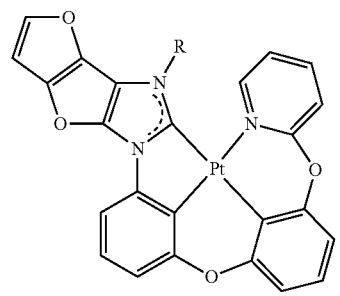
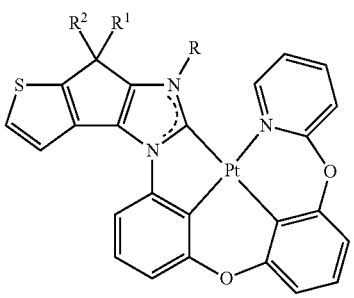

Structures 45
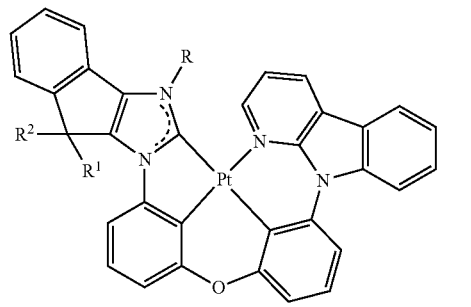
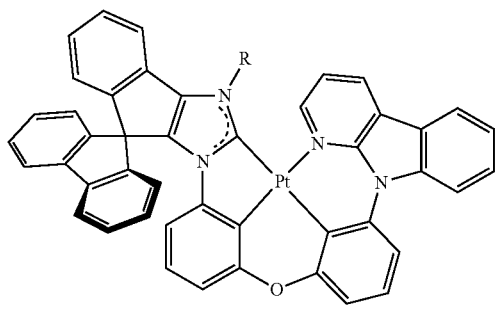
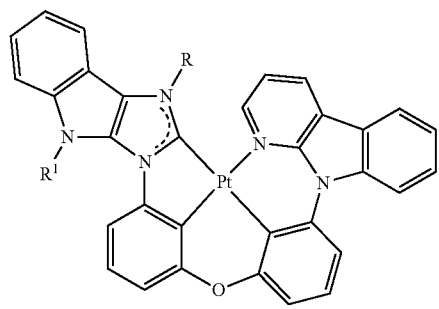
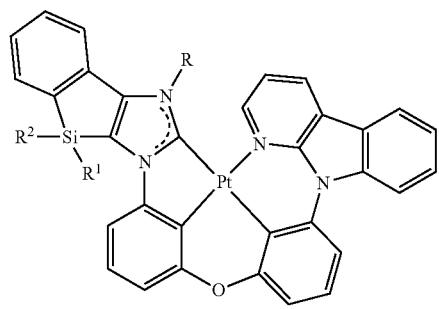
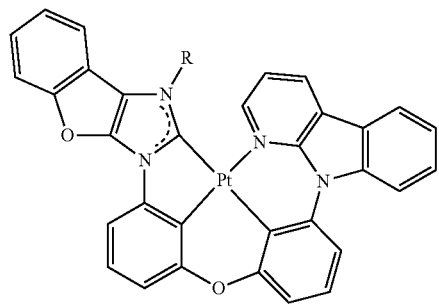
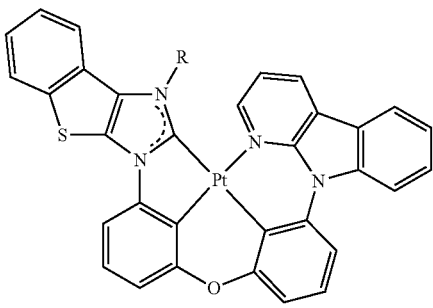
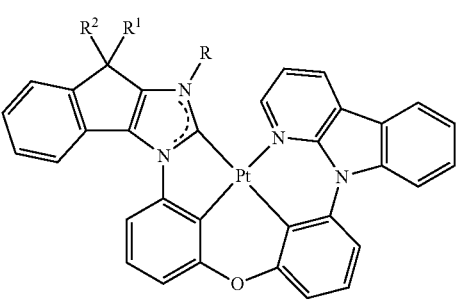
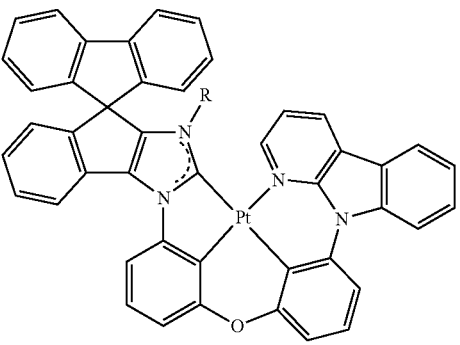
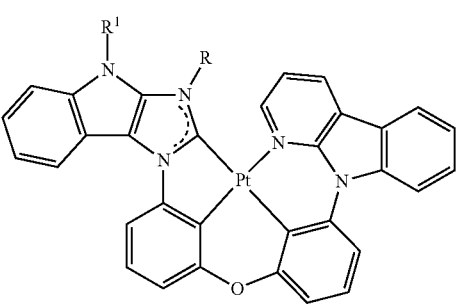
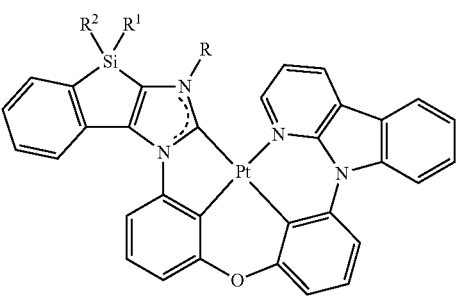

551
-continued
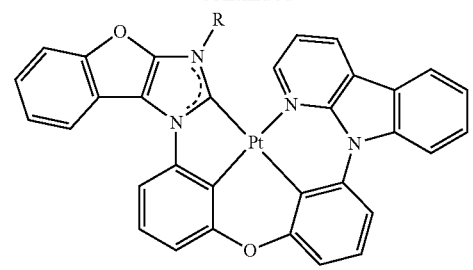
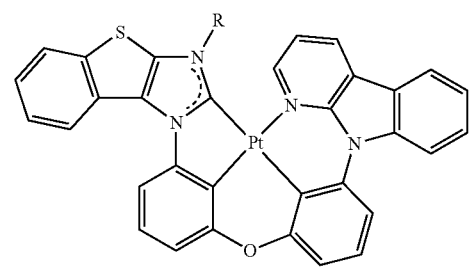
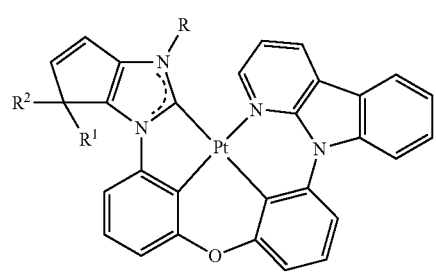
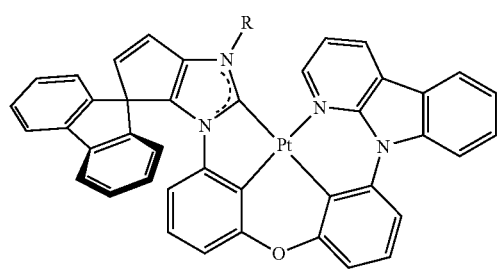
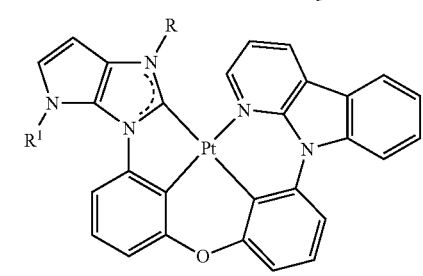
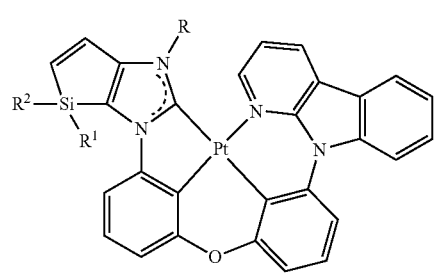
552
-continued
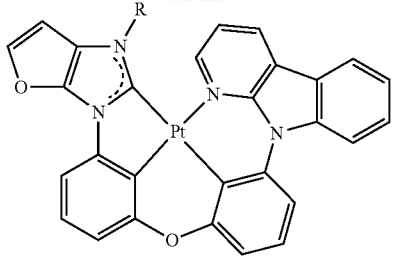
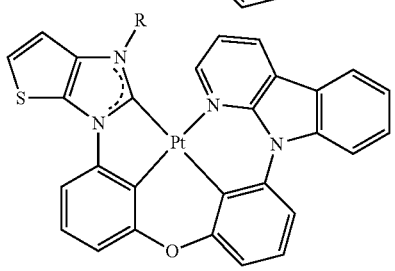
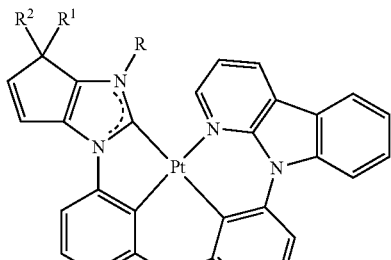
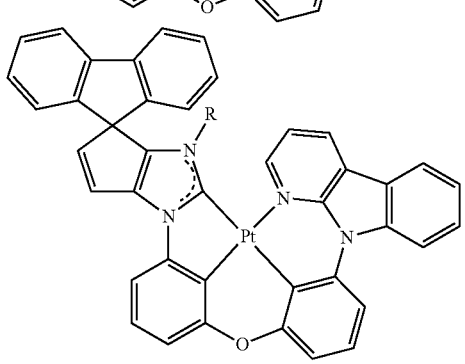
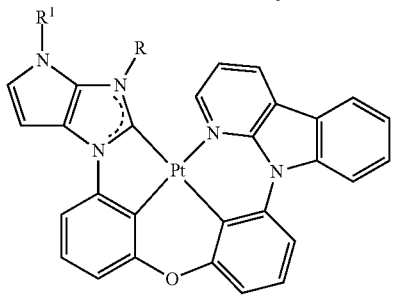
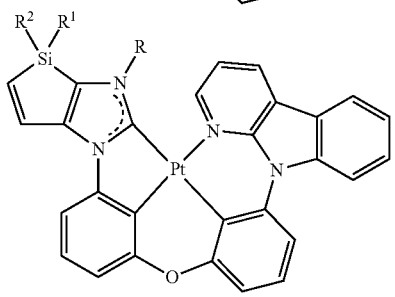

553
-continued
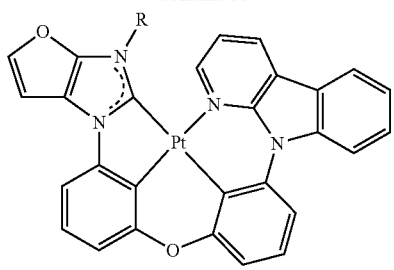
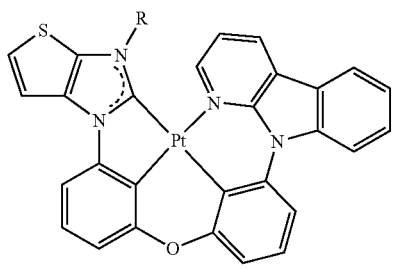
Structures 46
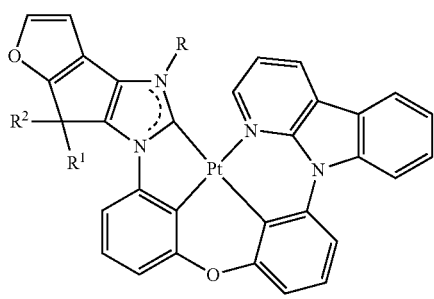
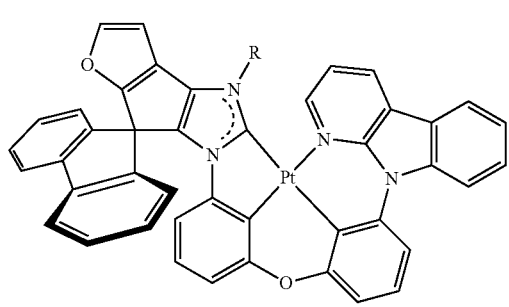
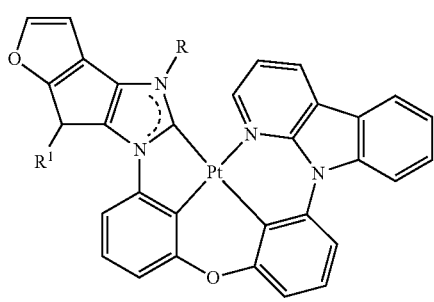
554
-continued
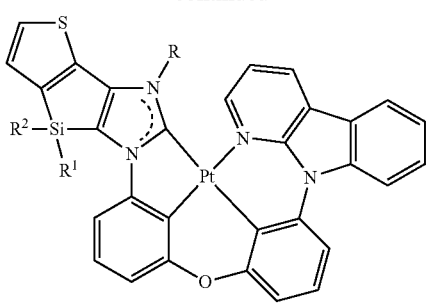
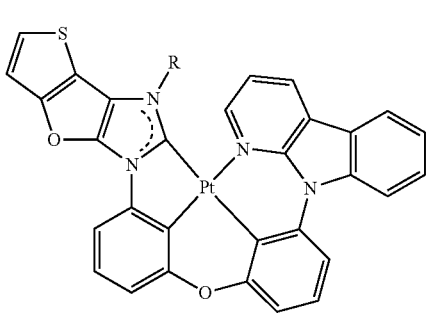
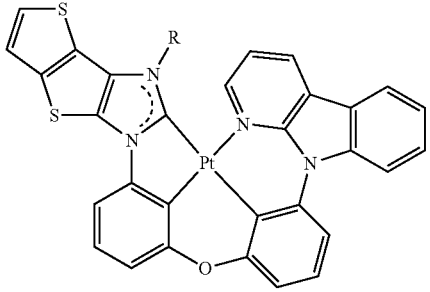
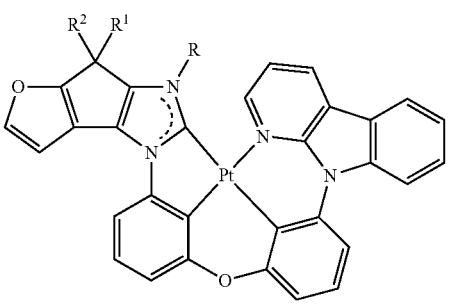
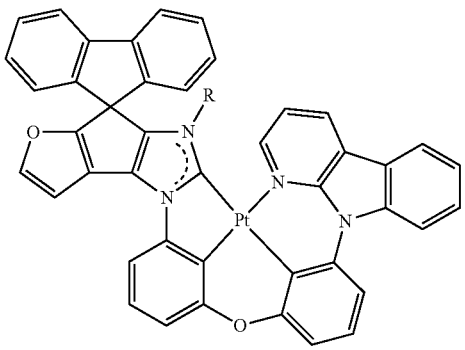

555
-continued
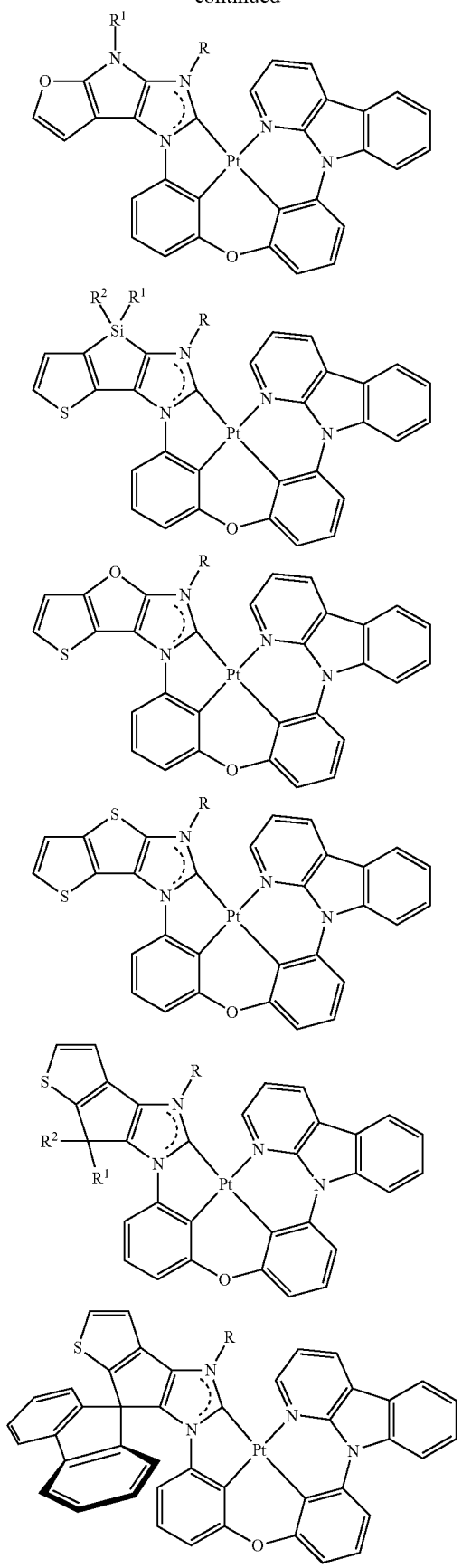
556
-continued
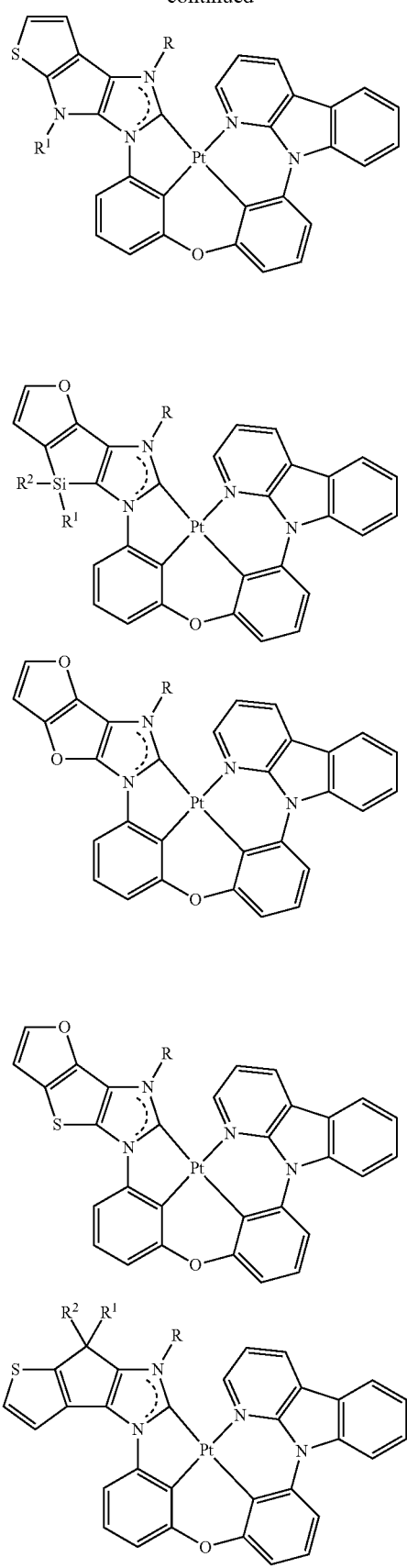

557
-continued
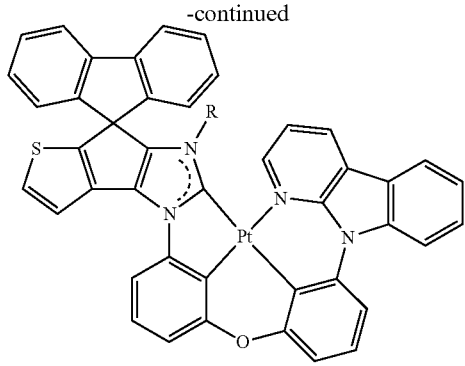
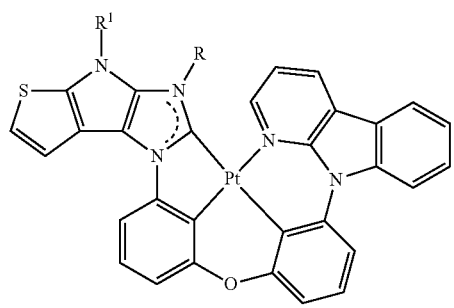
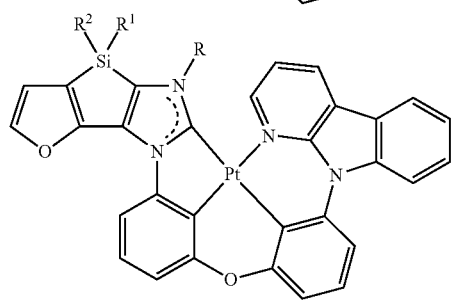
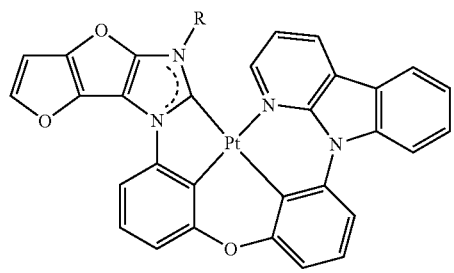
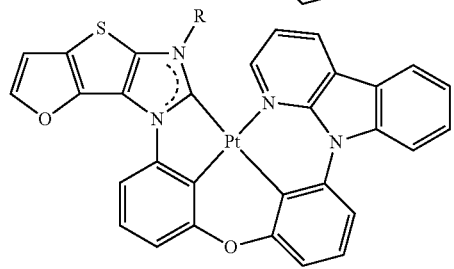
558
-continued
Structures 47
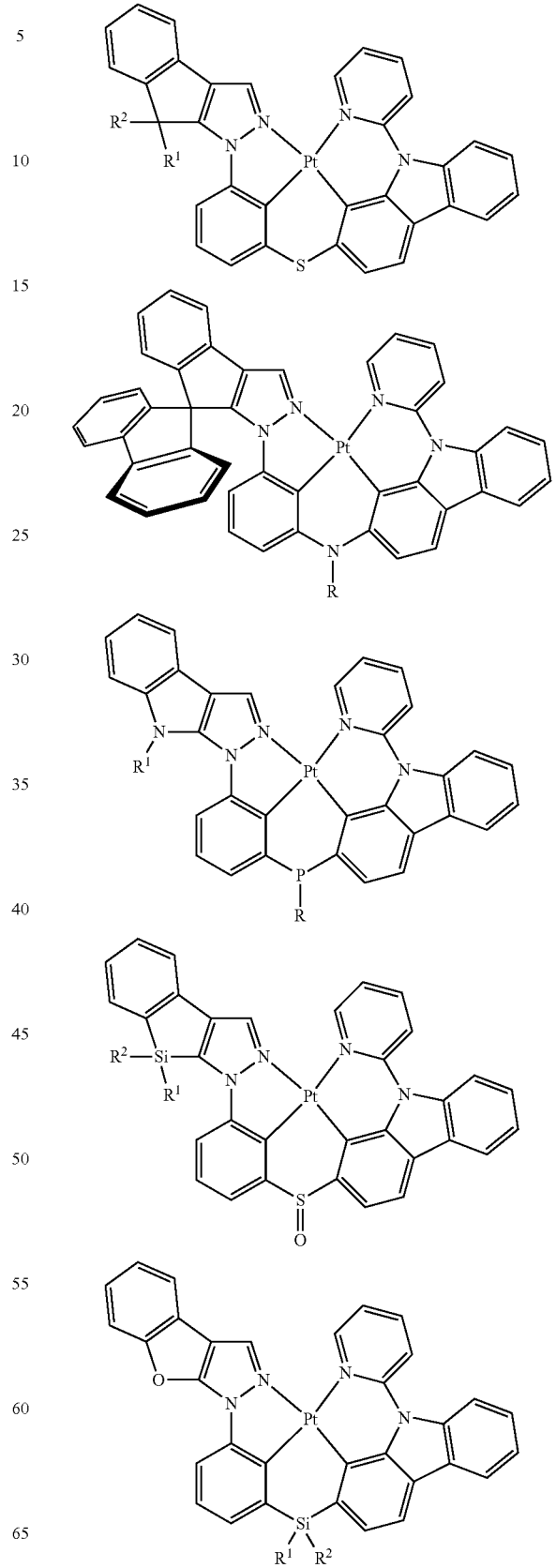

559
-continued
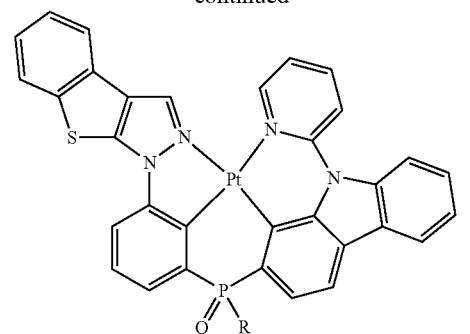
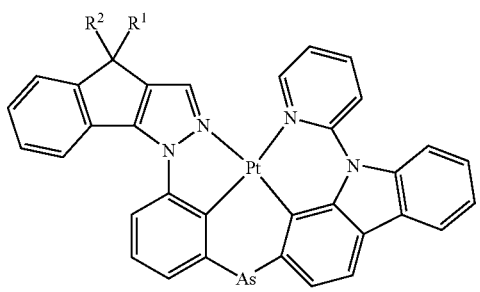
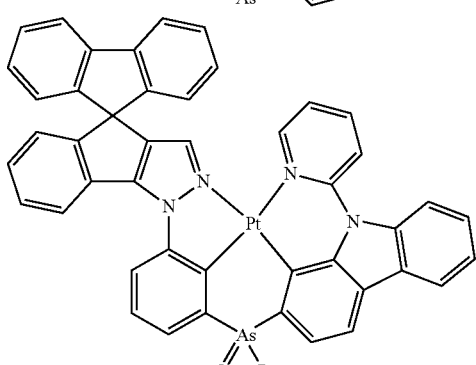
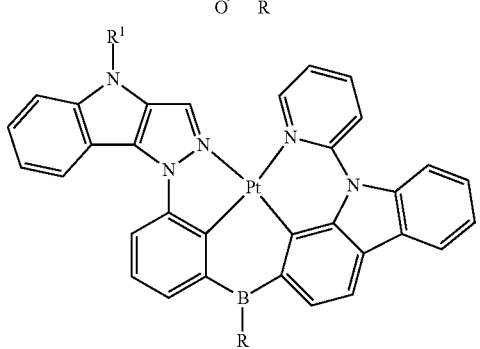
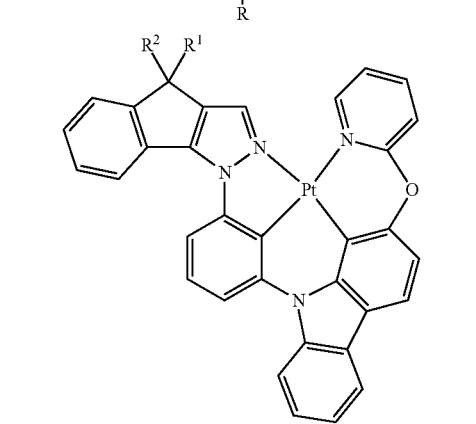
560
-continued
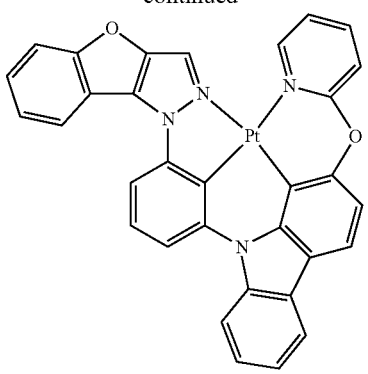
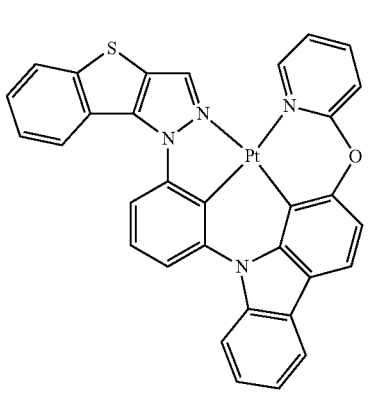
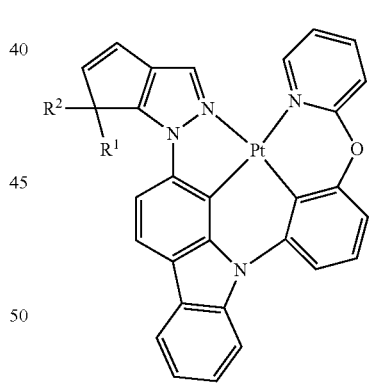
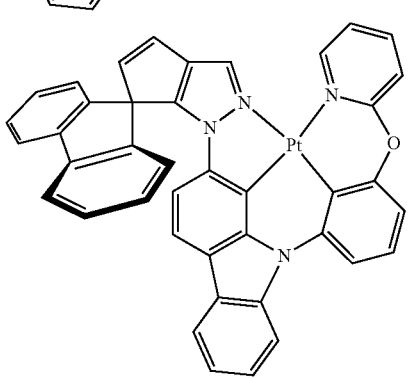

561
-continued
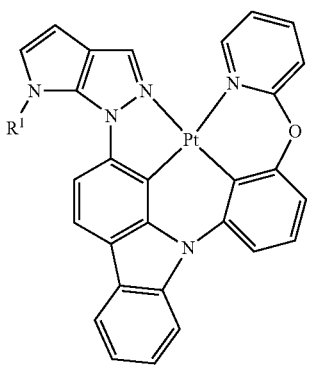
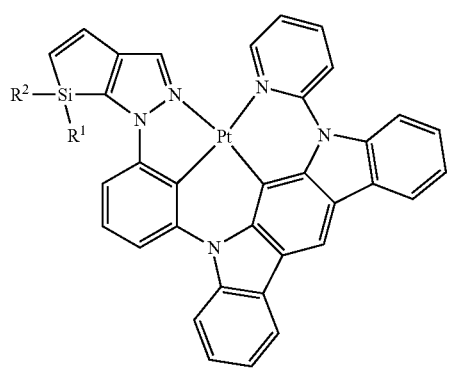
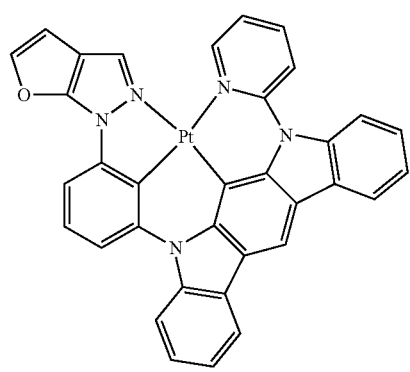
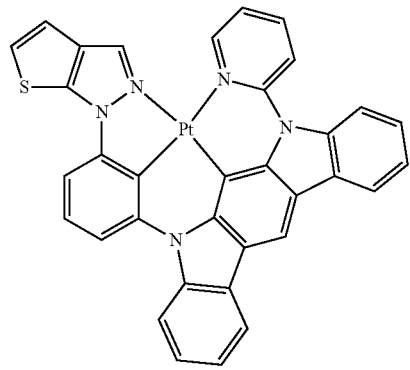
562
-continued
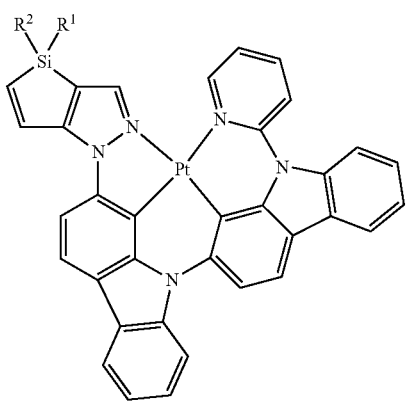
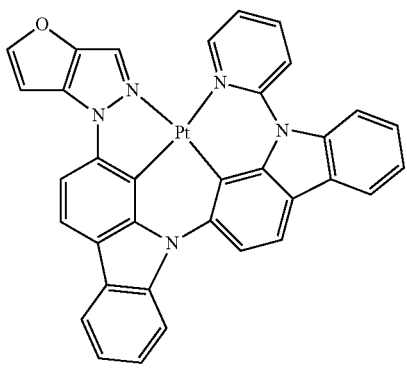
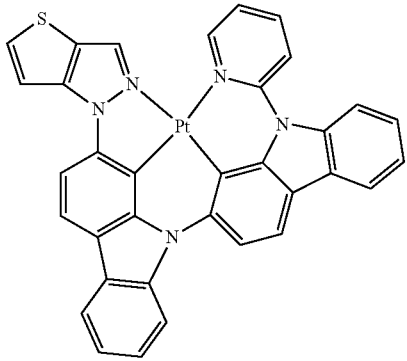
Structures 48
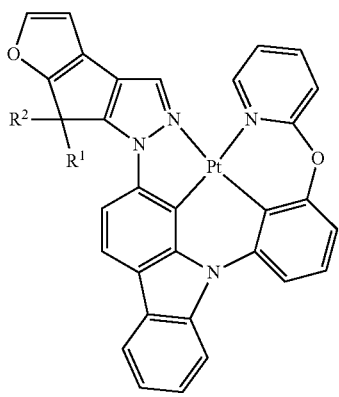

563
-continued
564
-continued
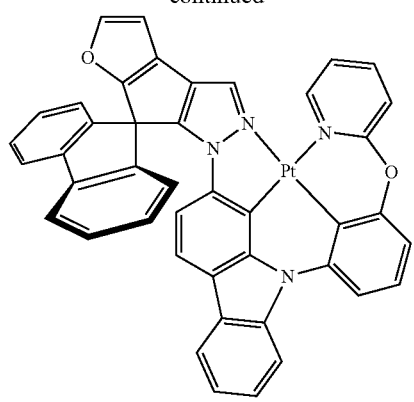
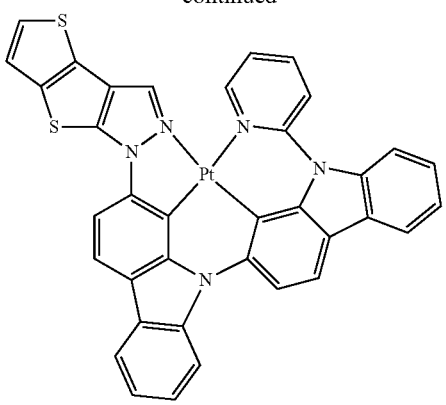
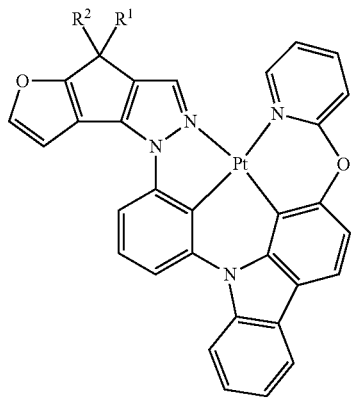
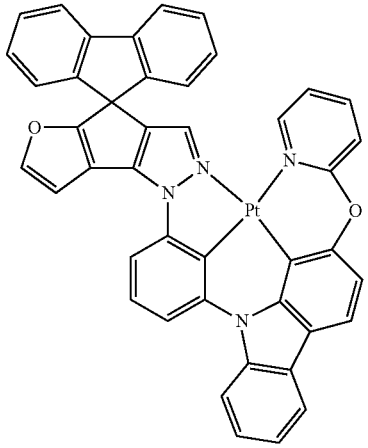
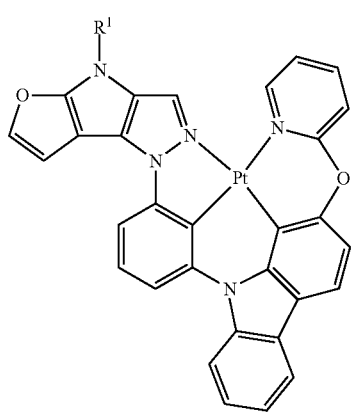

565
-continued
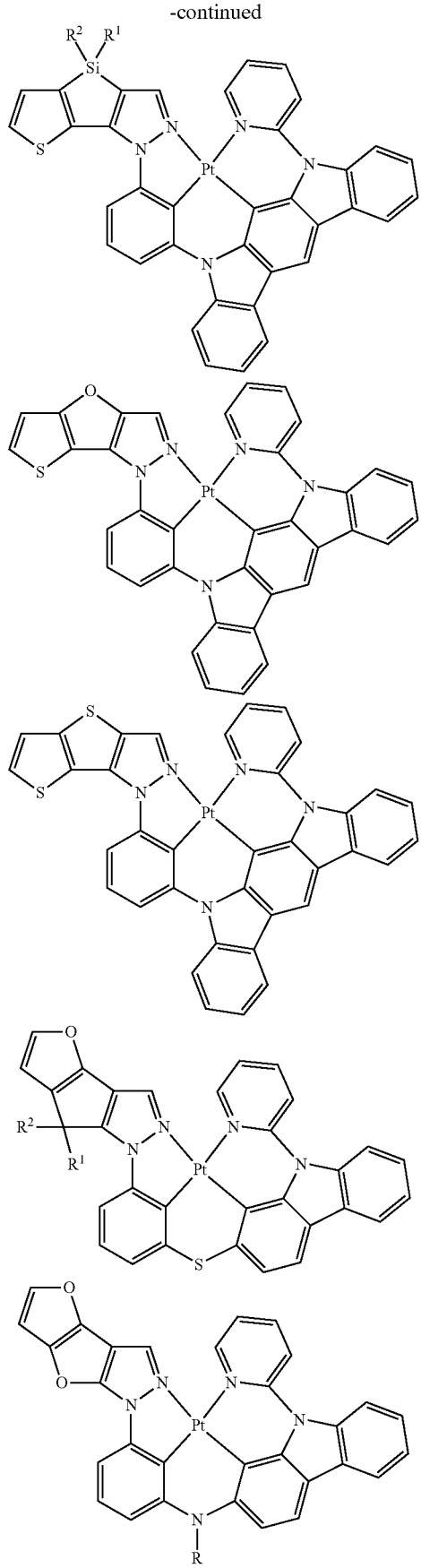
566
-continued
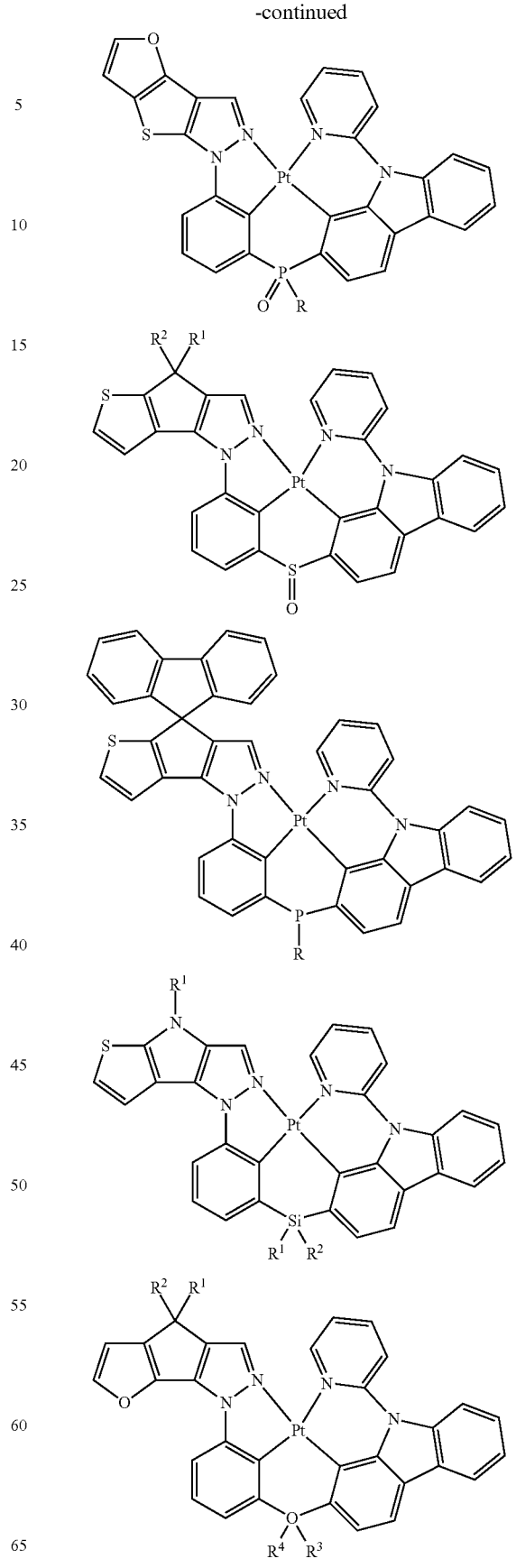

567
-continued
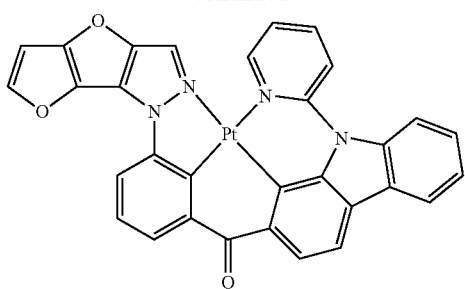
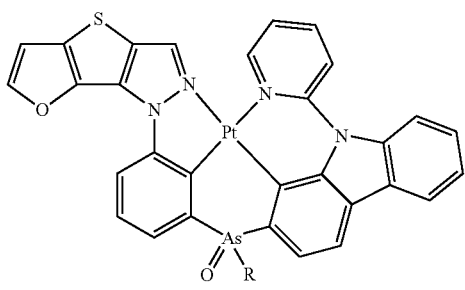
Structures 49
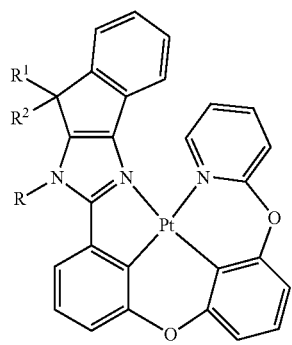
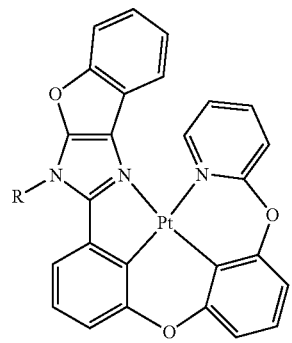
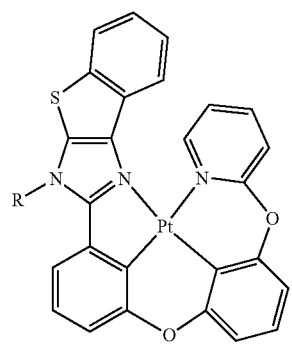
568
-continued
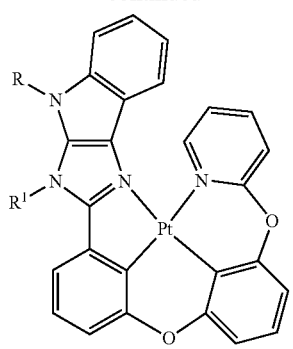
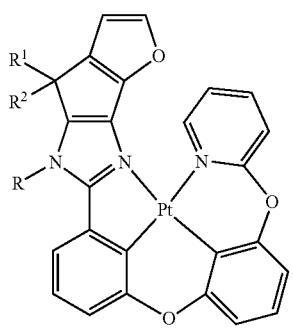
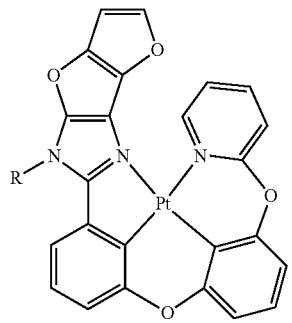
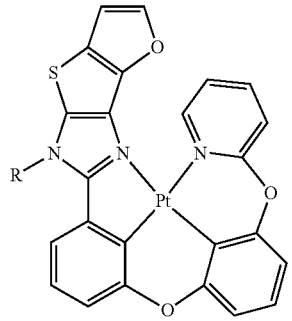
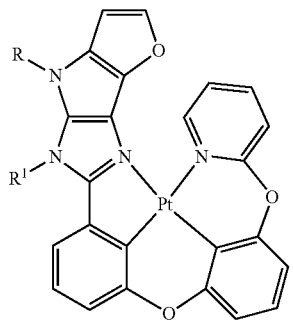

-continued
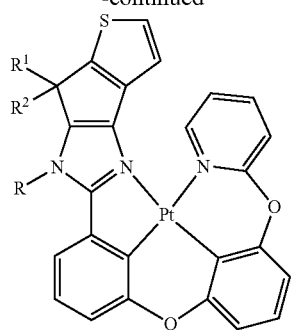
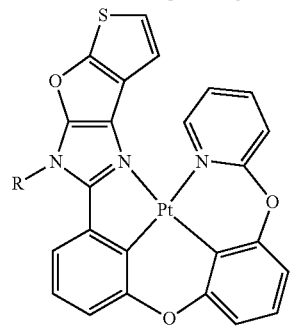
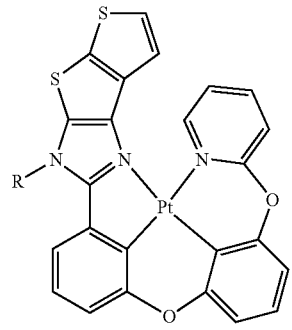
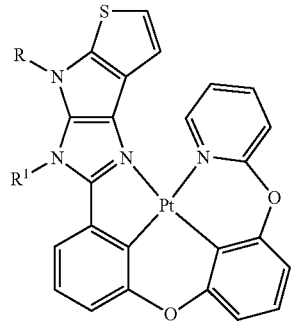
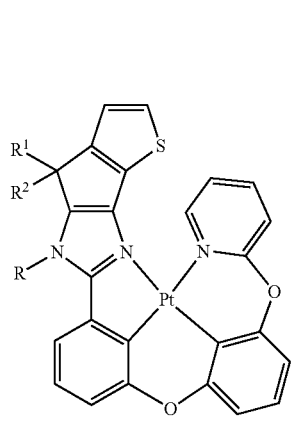
-continued
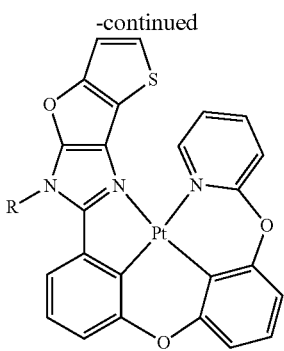
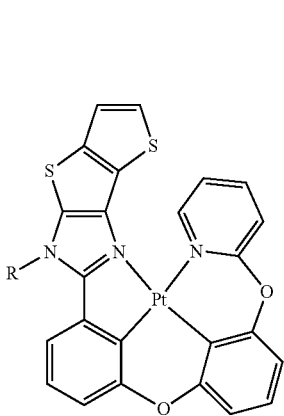
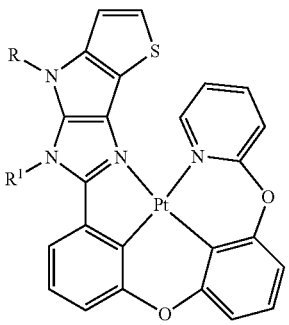
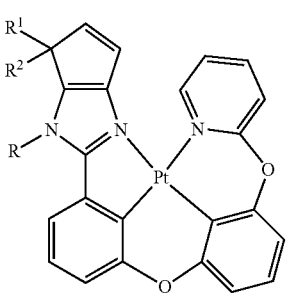
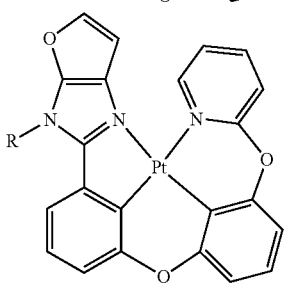

-continued
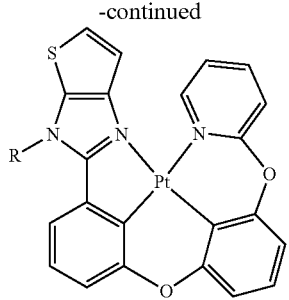
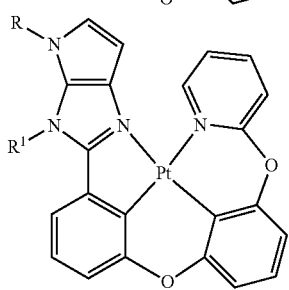
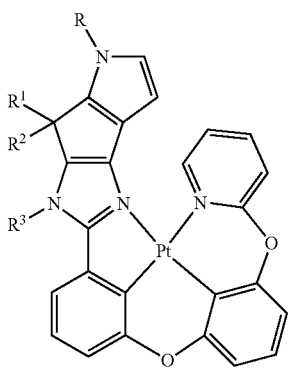
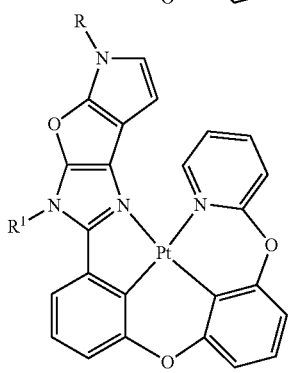
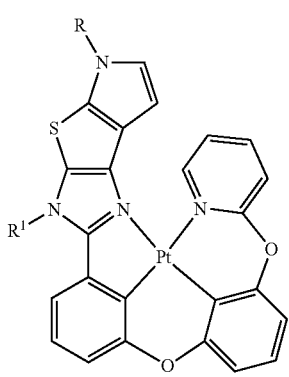
-continued
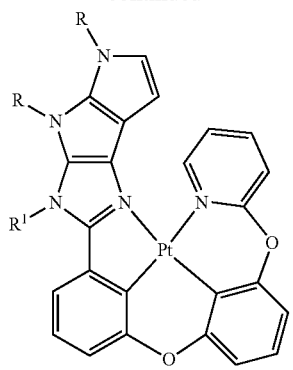
Structures 50
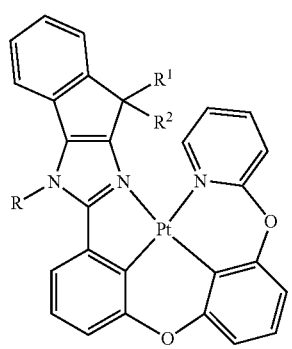
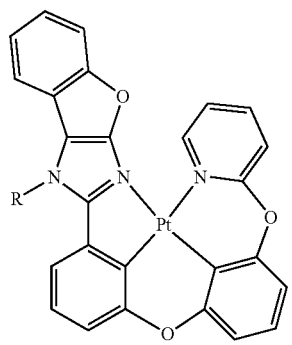
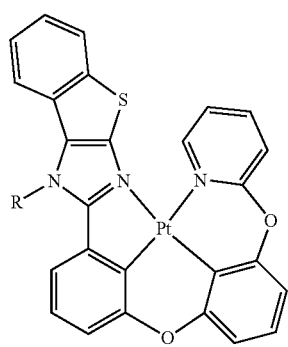

573
-continued
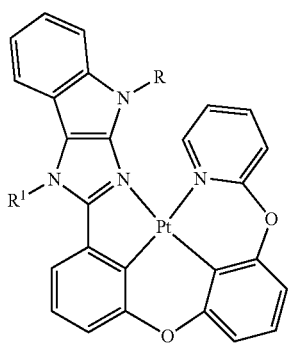
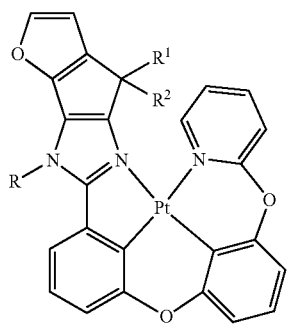
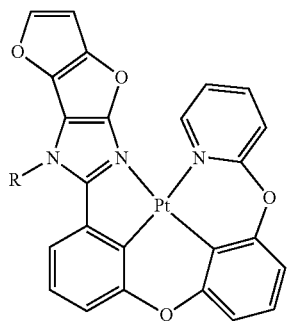
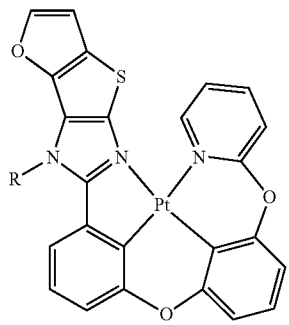
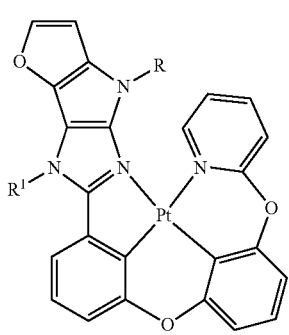
574
-continued
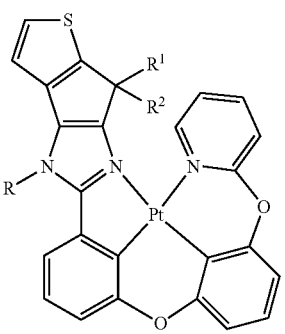
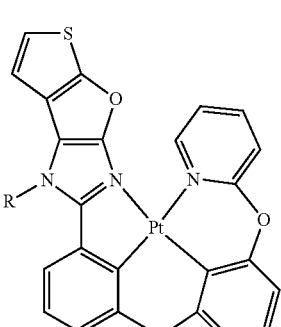
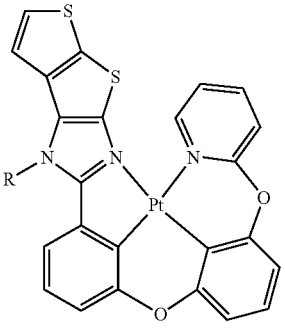
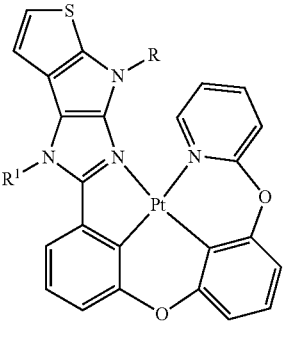
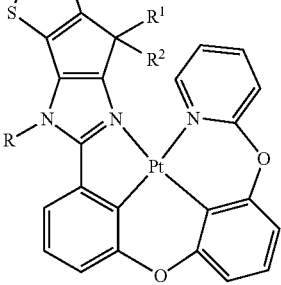

575
-continued
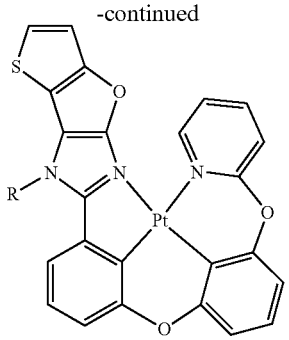
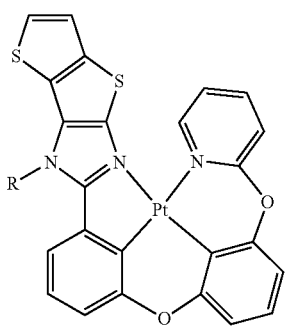
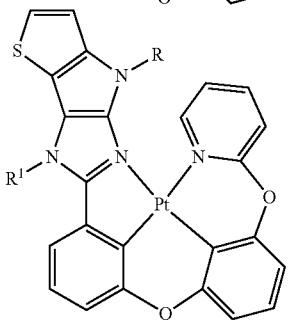
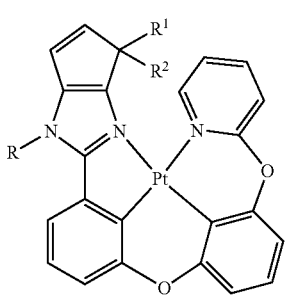
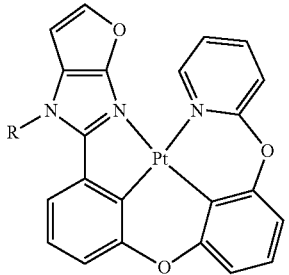
576
-continued
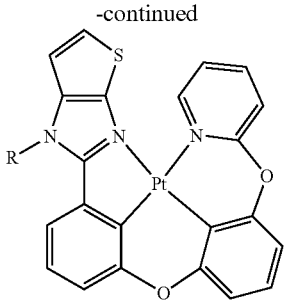
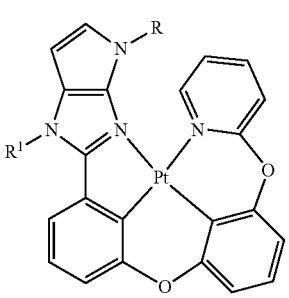
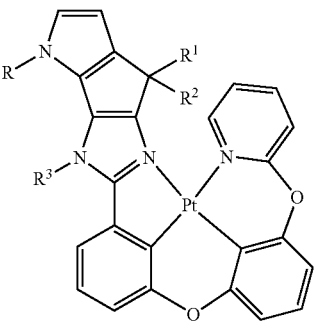
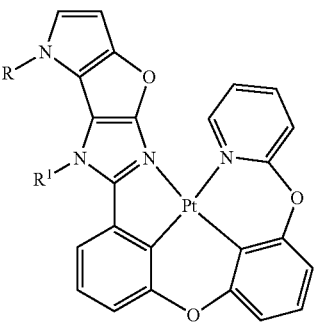
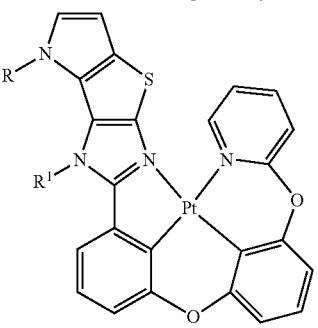

577
-continued
578
-continued
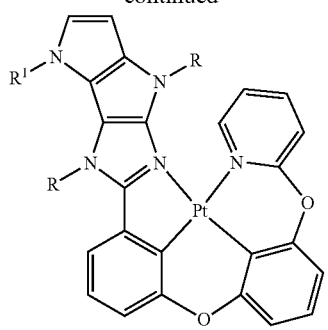
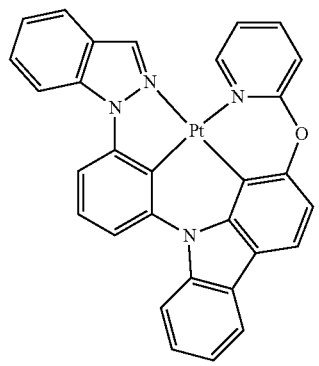
Structure 51
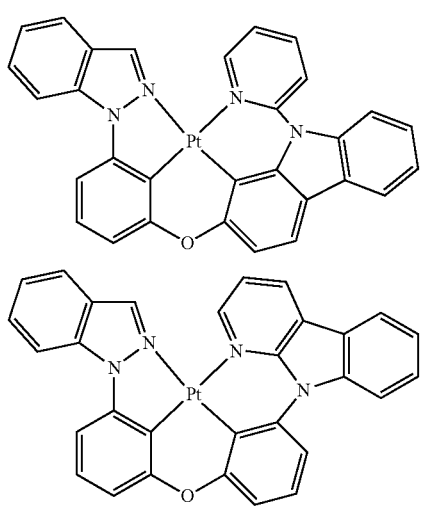
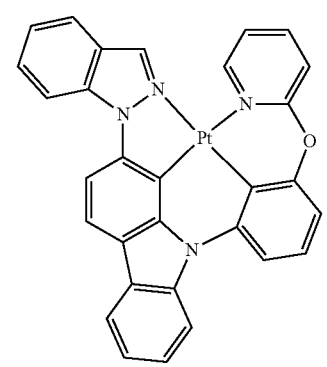
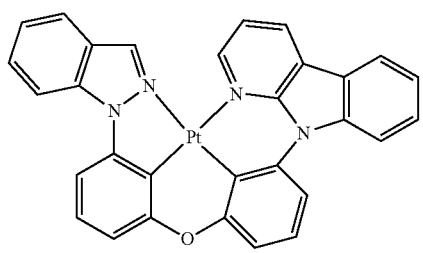
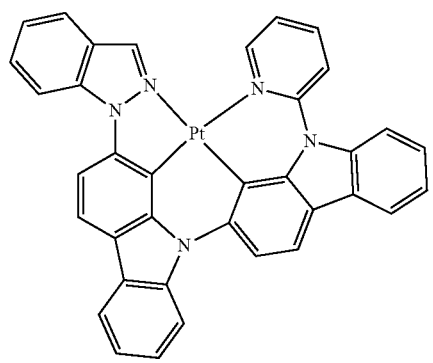
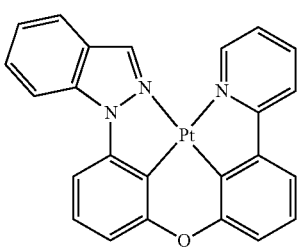
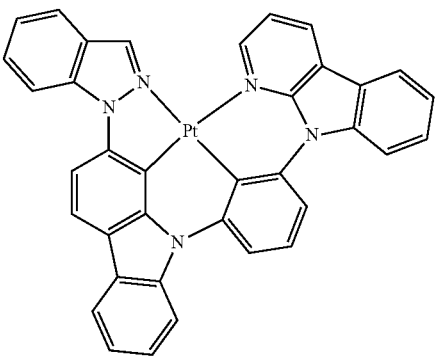

579
-continued
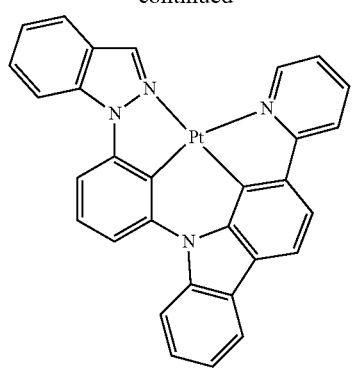
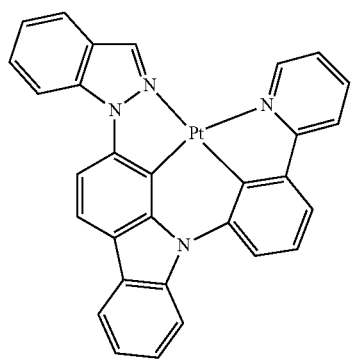
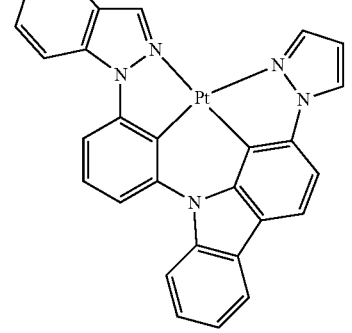
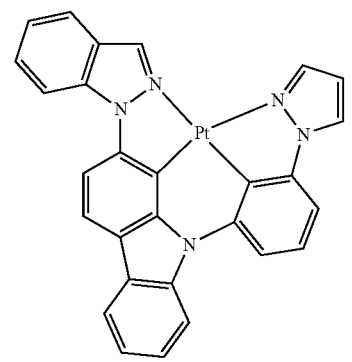
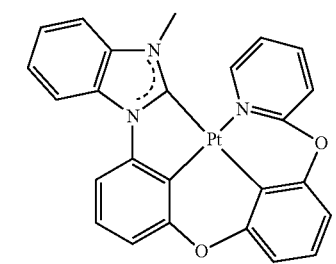
580
-continued
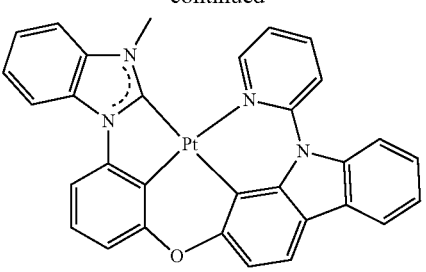
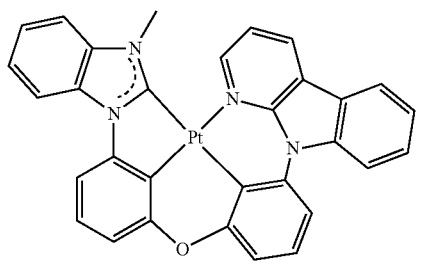
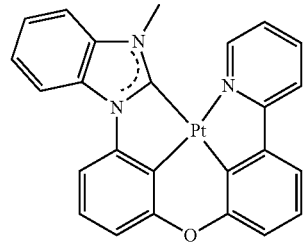
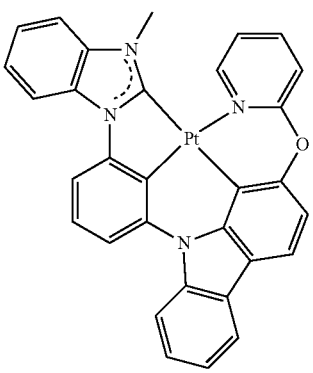
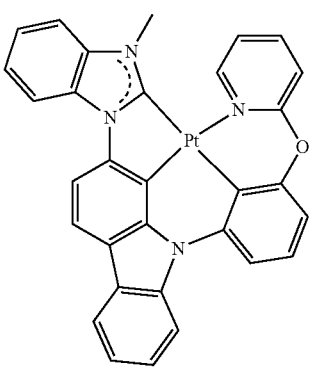

581
-continued
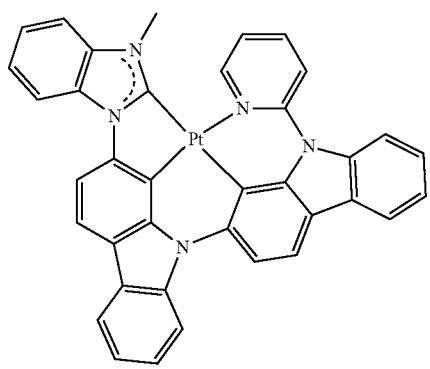
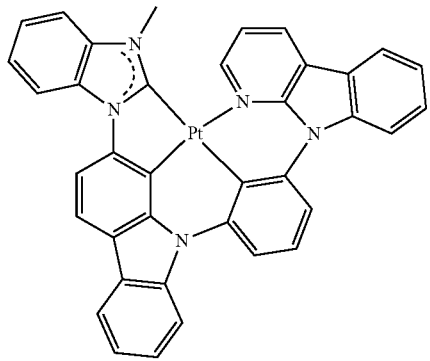
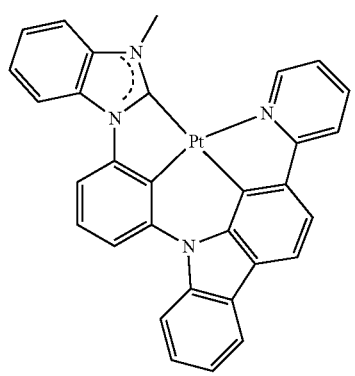
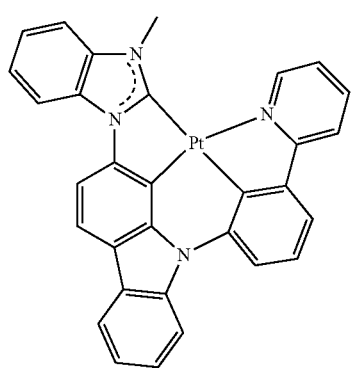
582
-continued
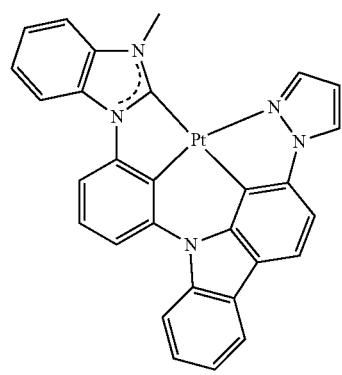
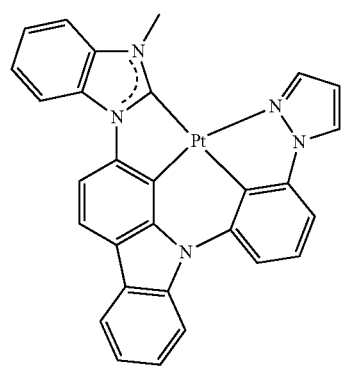
Structures 52
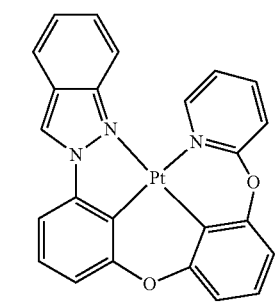
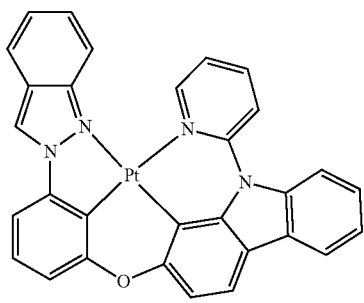
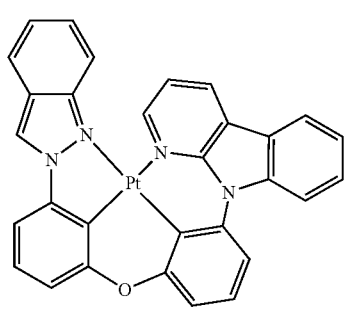

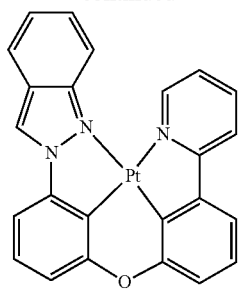
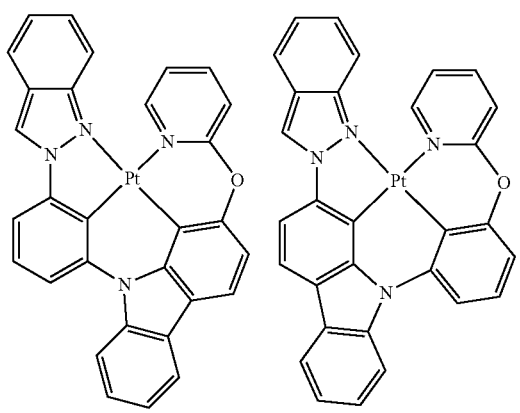
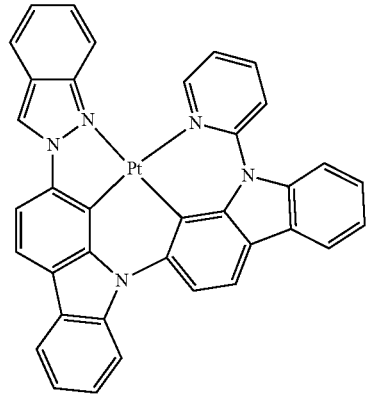
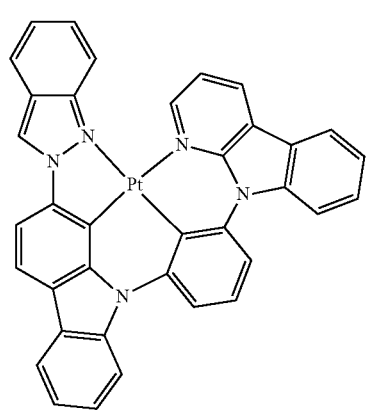
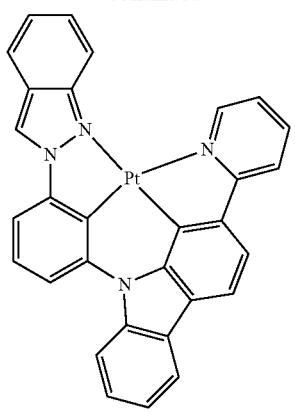
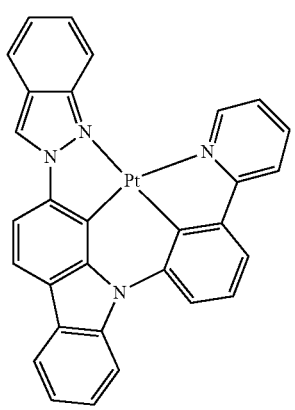
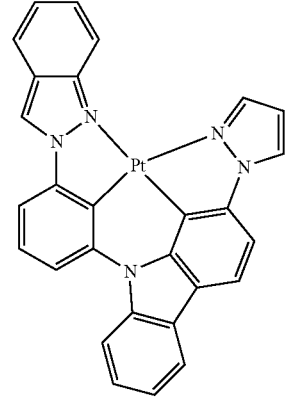
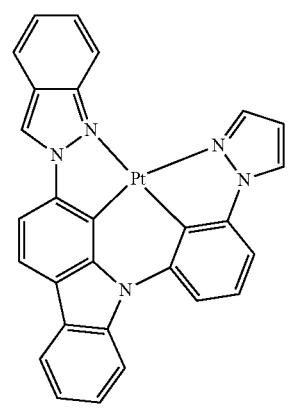

585
-continued
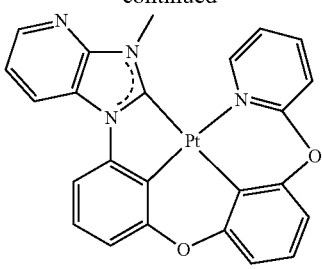
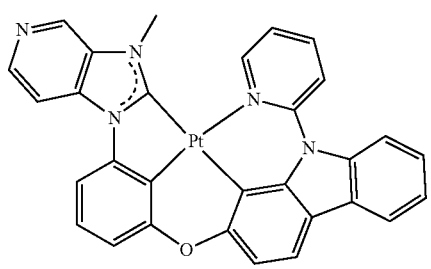
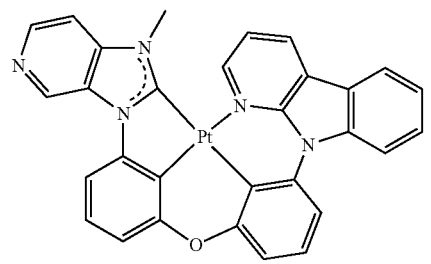
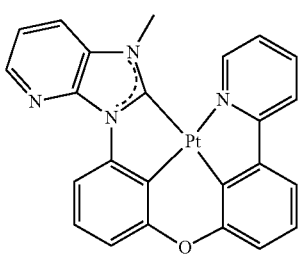
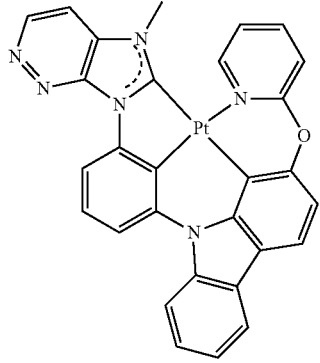
586
-continued
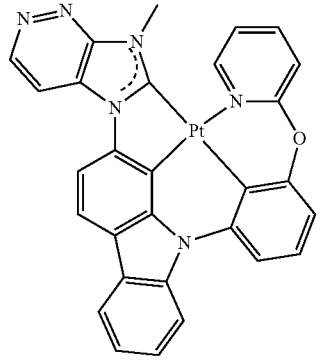
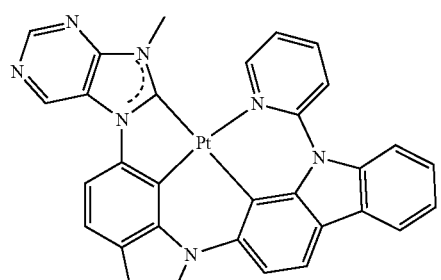
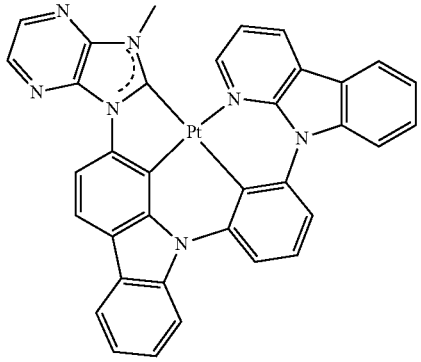
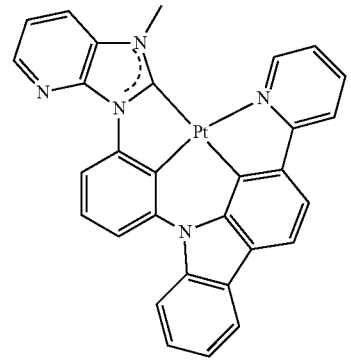

587
-continued
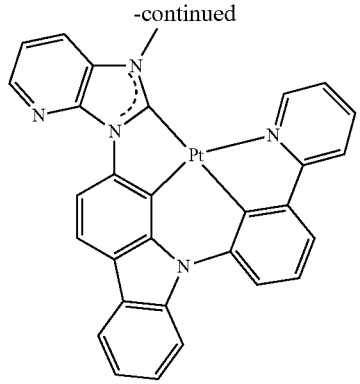
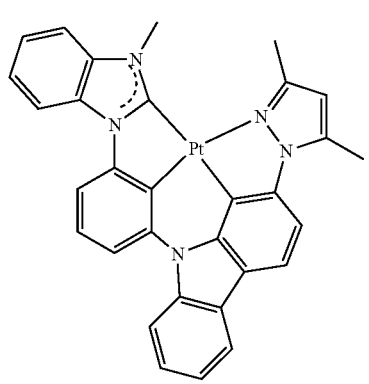
Structures 53
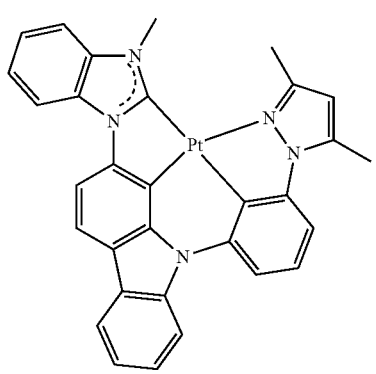
588
-continued
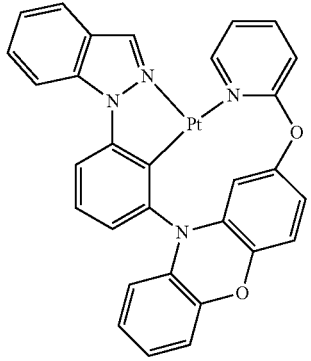
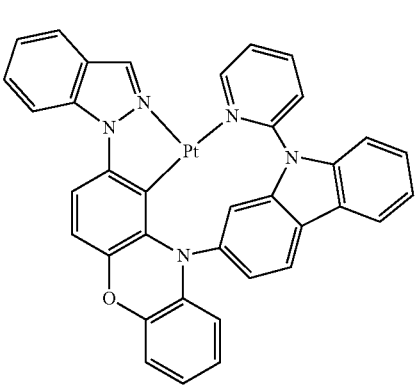
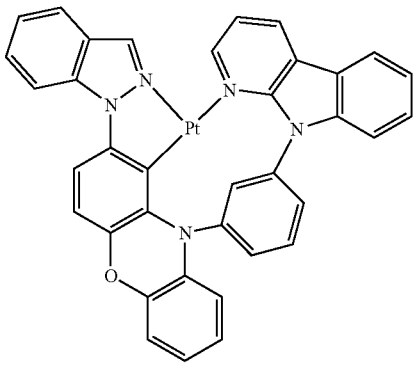
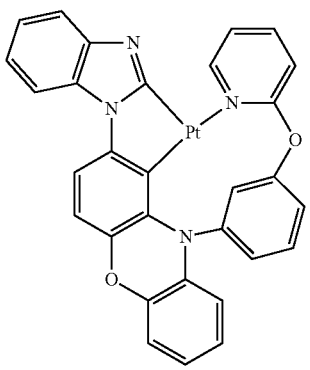
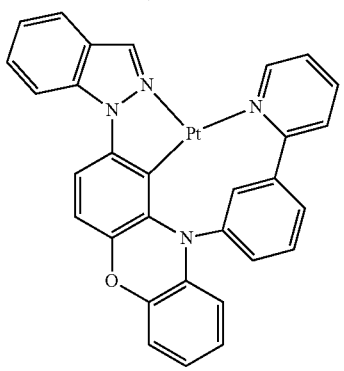

| 589 -continued | 590 -continued |
|---|---|
| 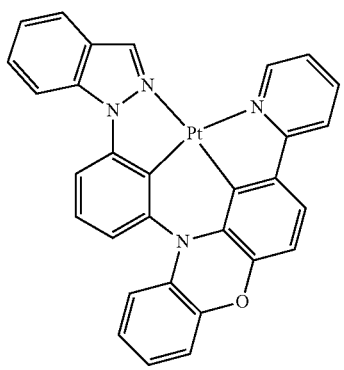 | 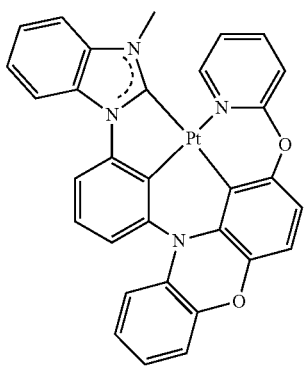 |
| 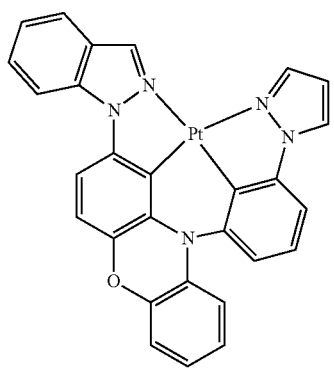 | 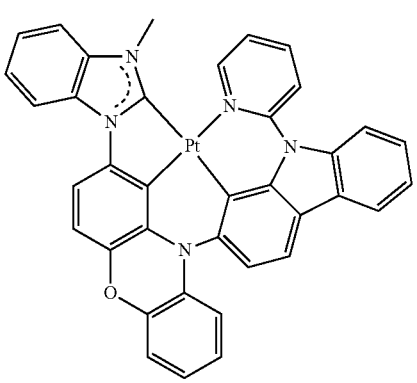 |
| 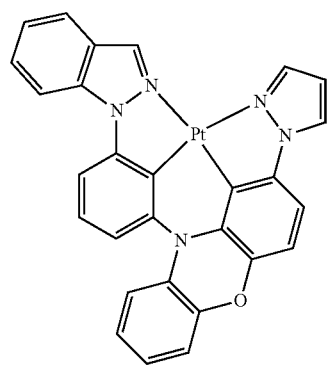 | 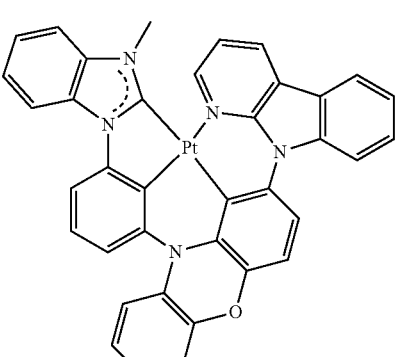 |
| 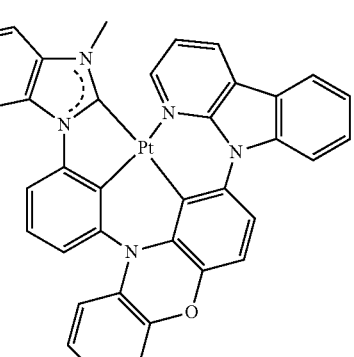 | 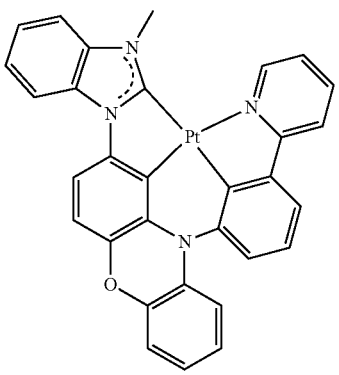 |

591
-continued
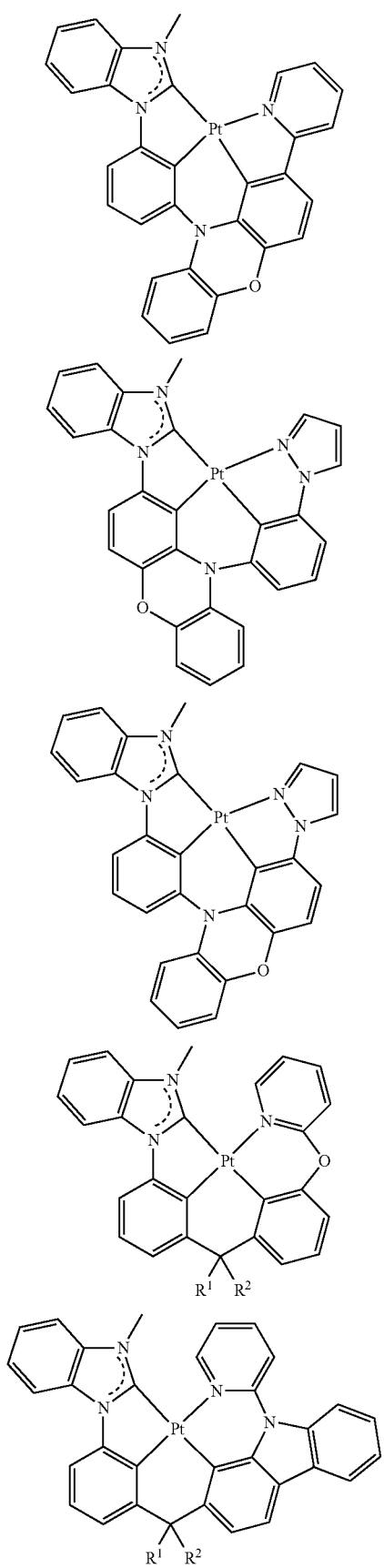
592
-continued
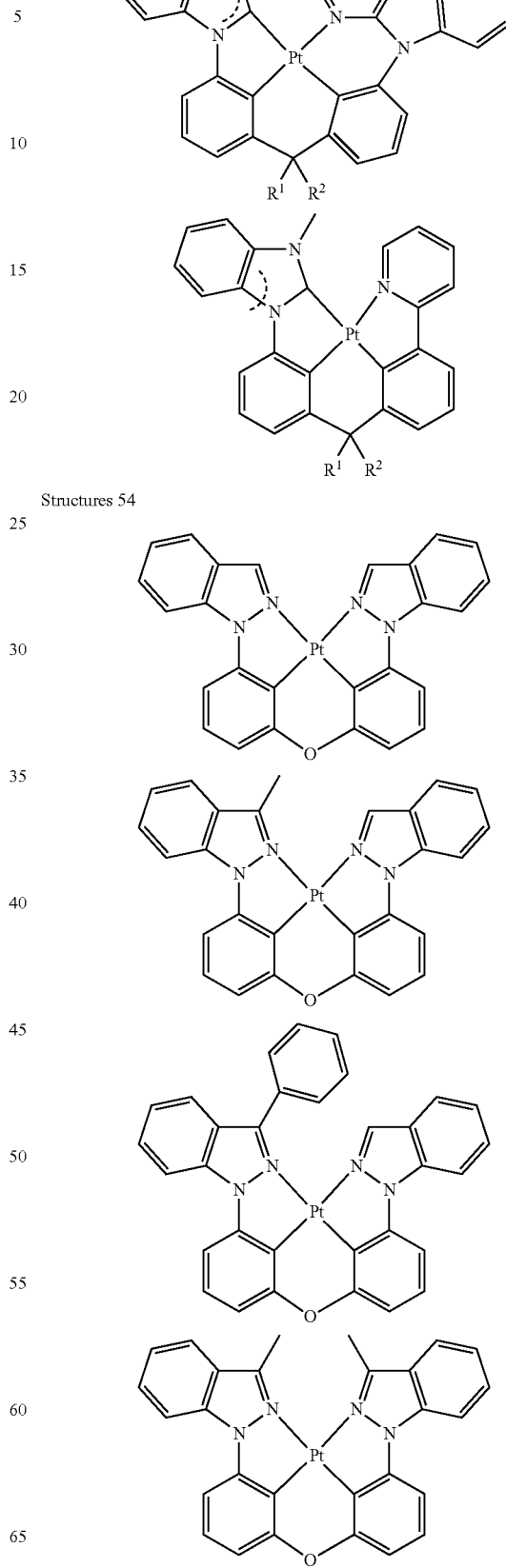
Structures 54

593
-continued
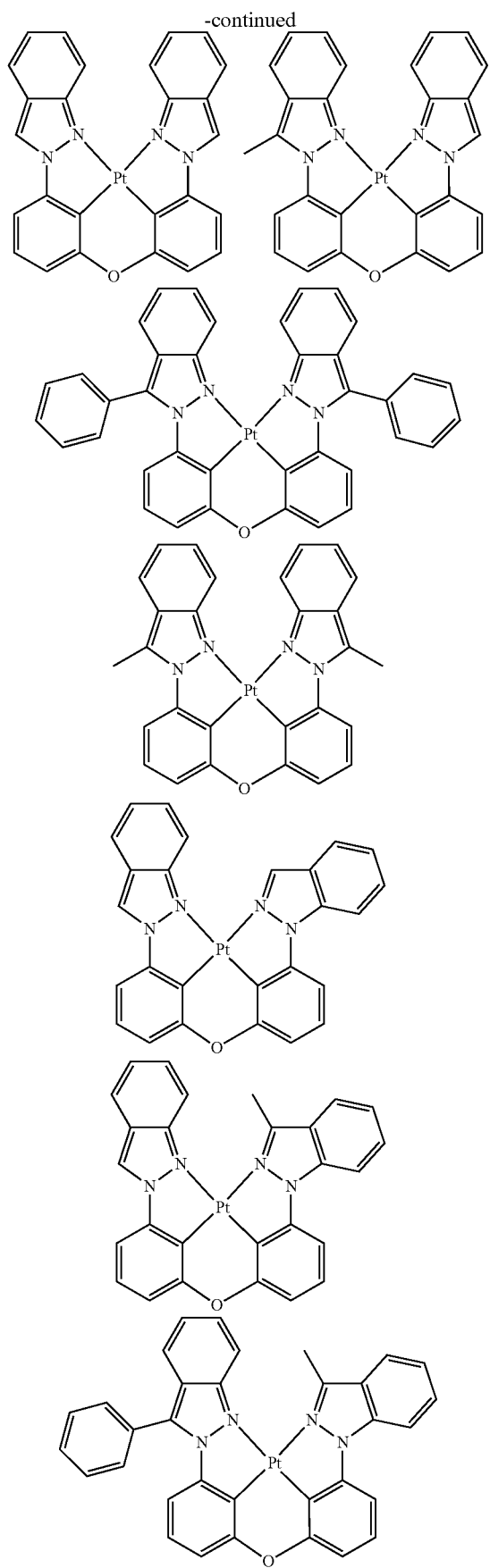
594
-continued
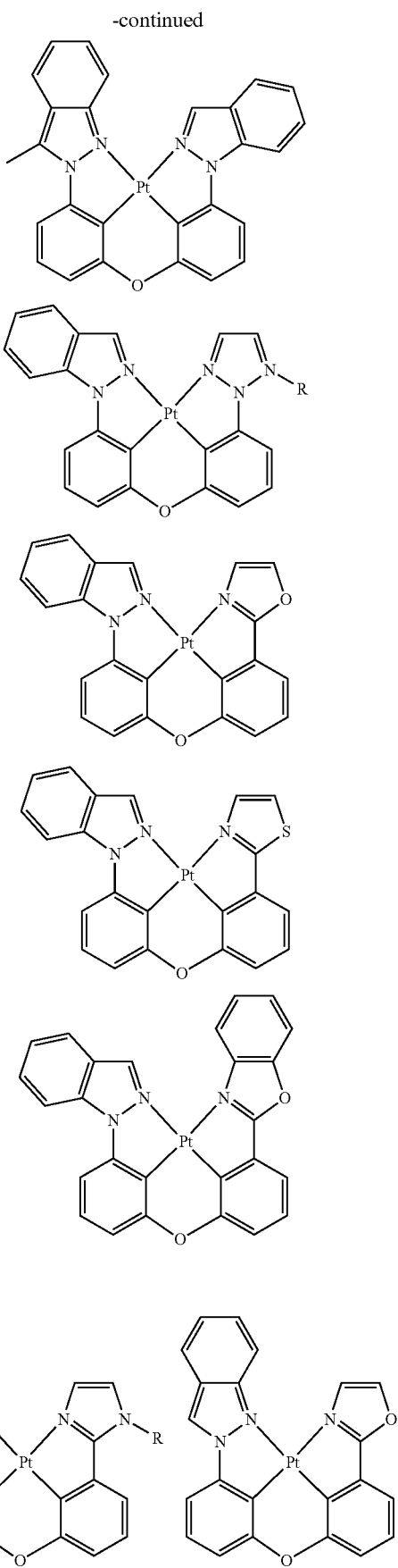

595
-continued
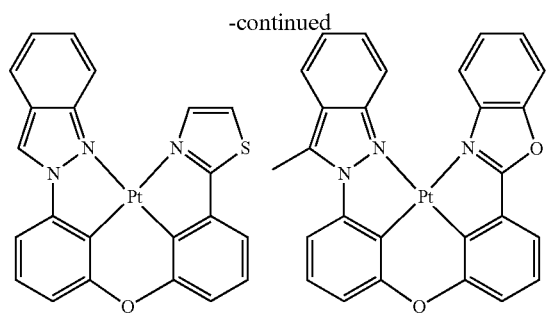
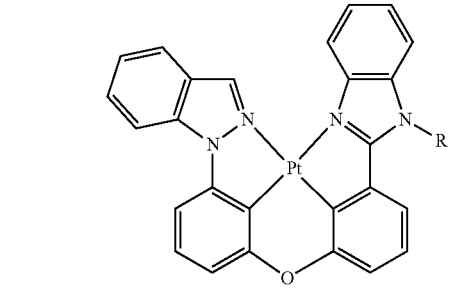
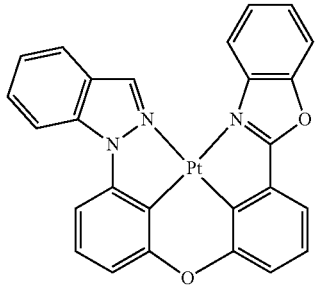
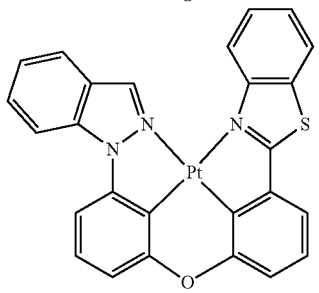
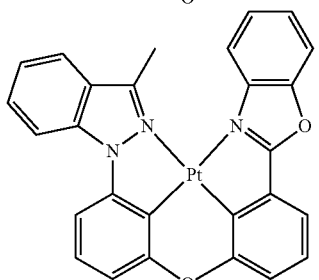
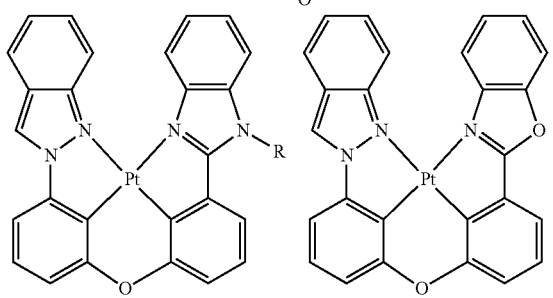
596
-continued
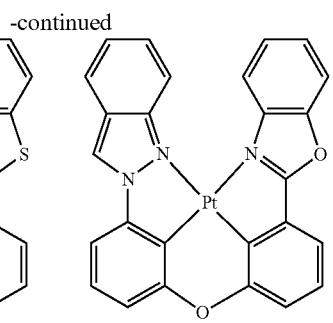
Structures 55
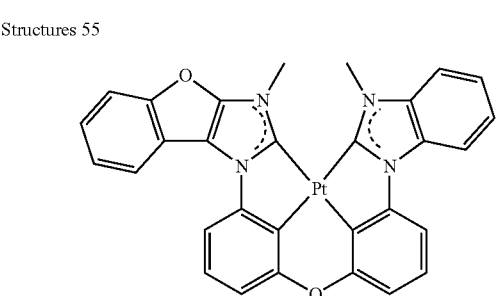
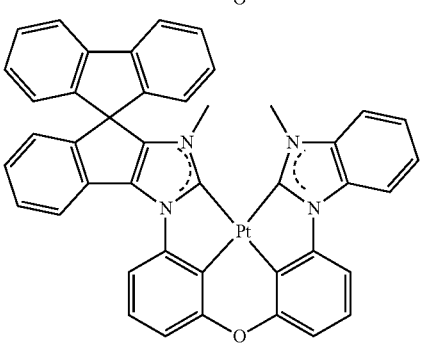
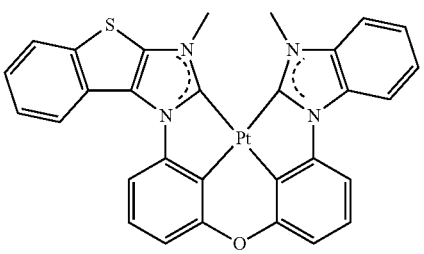
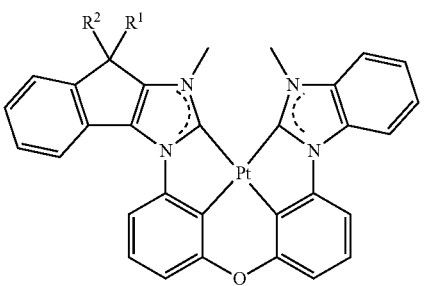
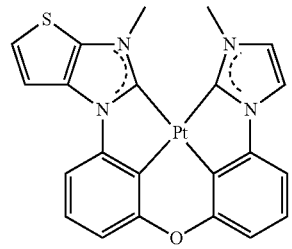

597
-continued
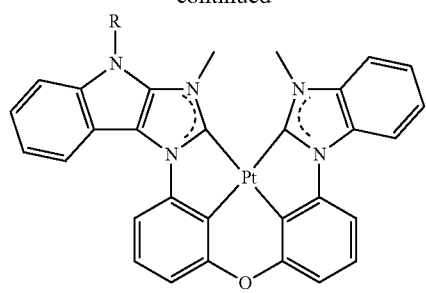
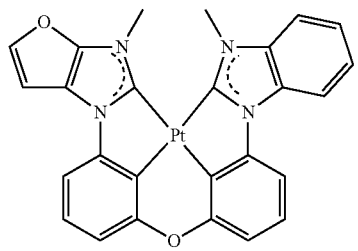
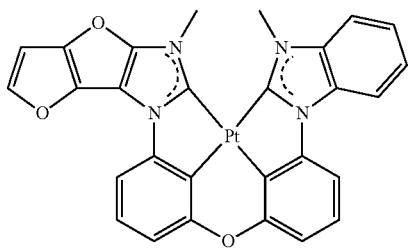
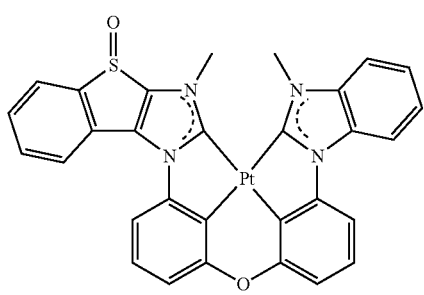
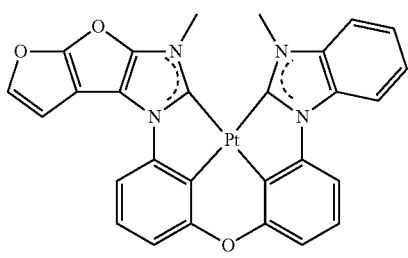
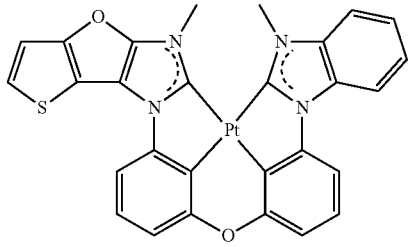
598
-continued
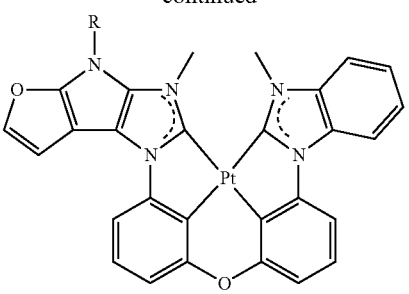
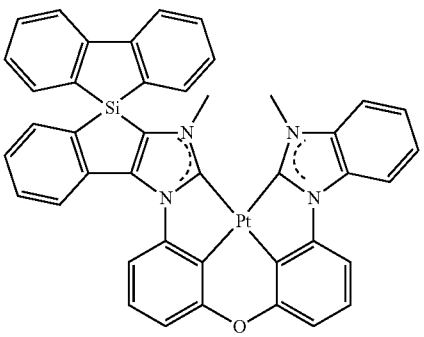
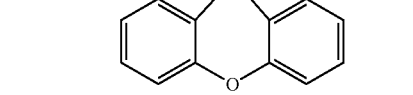
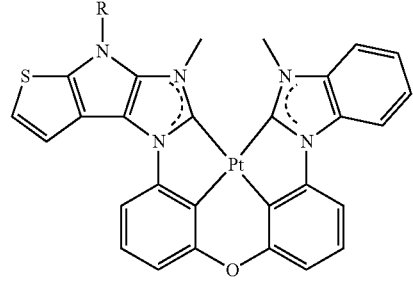
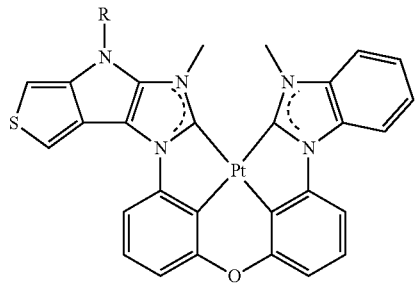

| 599 -continued | 600 -continued |
|---|---|
| 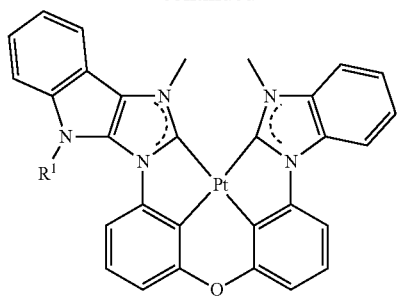 | 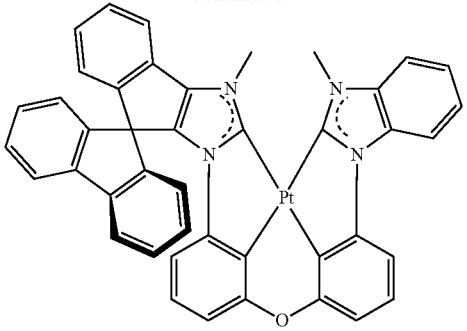 |
| 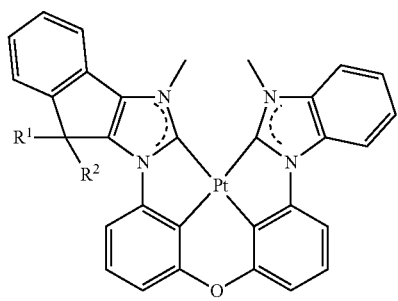 | 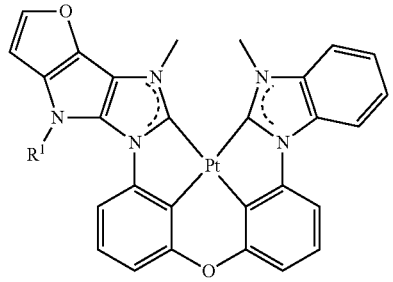 |
| 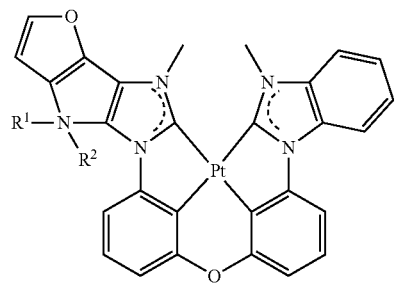 | 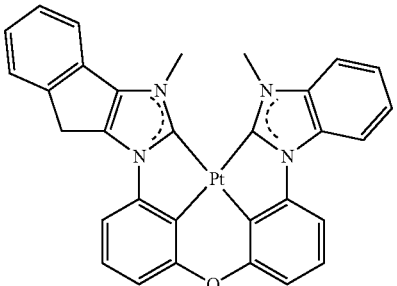 |
| 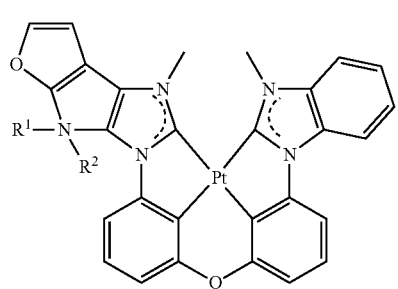 | 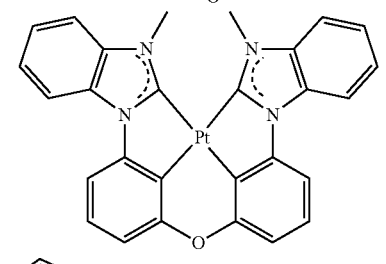 |
| 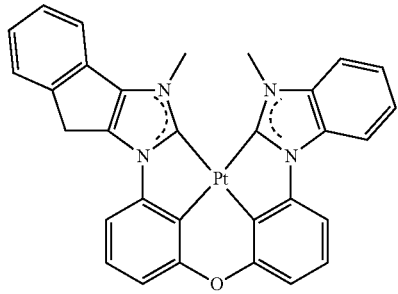 | 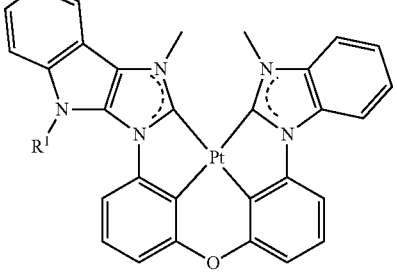 |

Structures 56
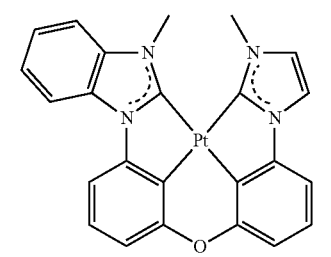
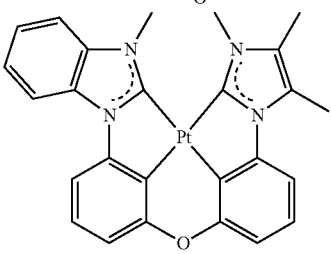
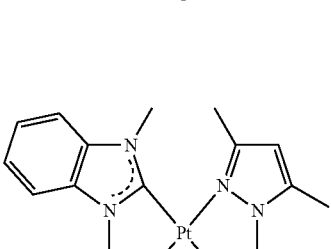
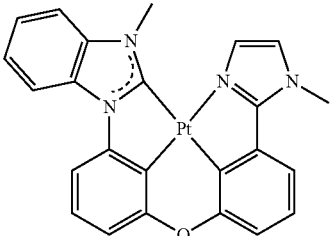
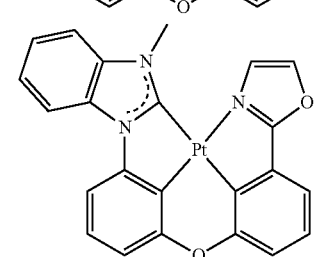
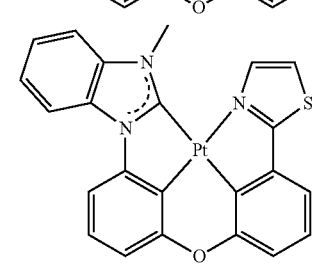
-continued
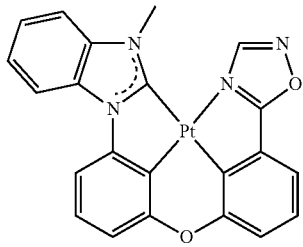
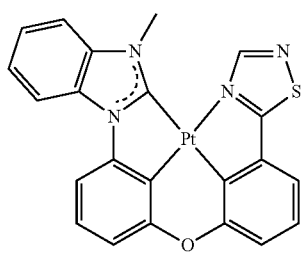
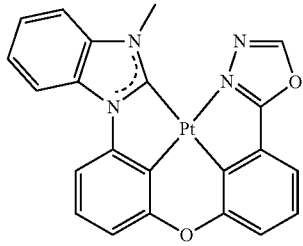
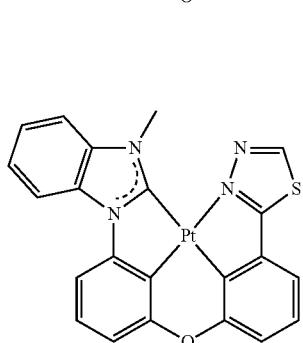
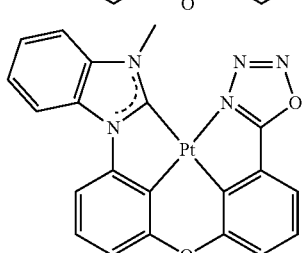
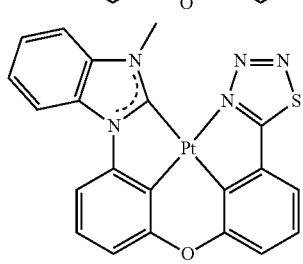

603
-continued
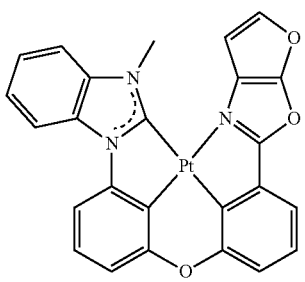
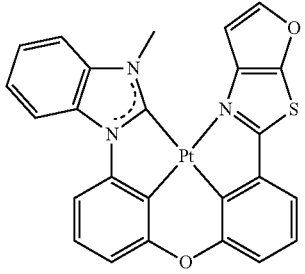
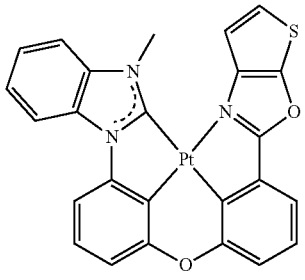
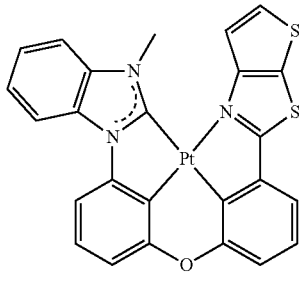
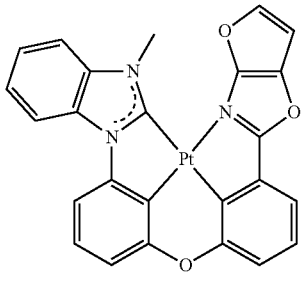
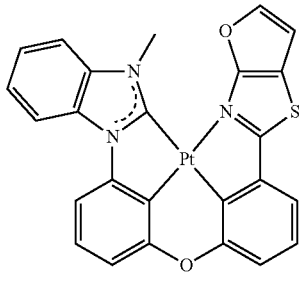
604
-continued
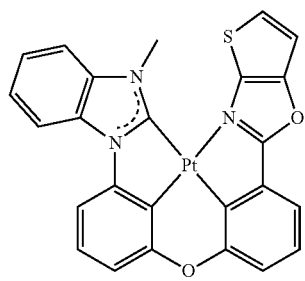
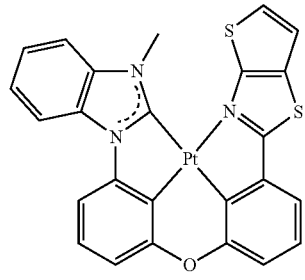
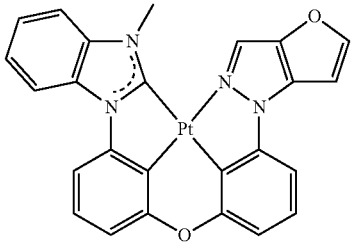
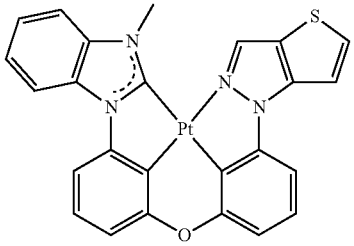
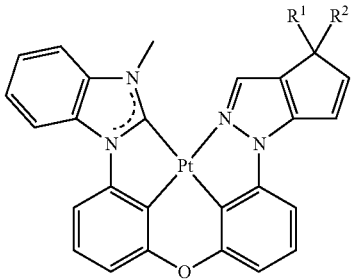
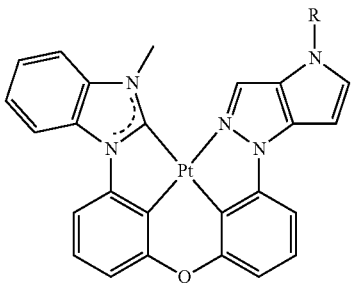

605
-continued
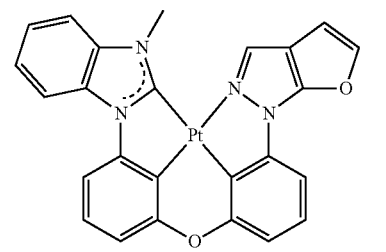
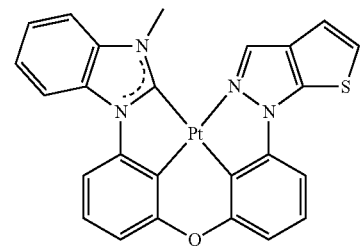
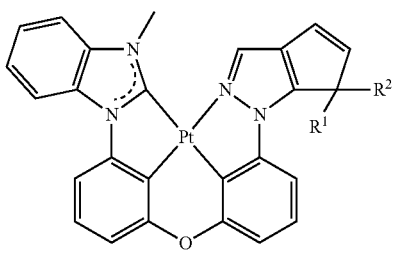
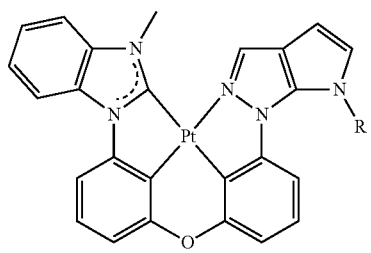
Structures 57
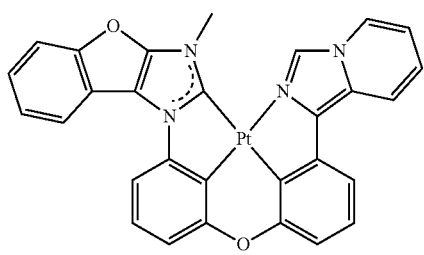
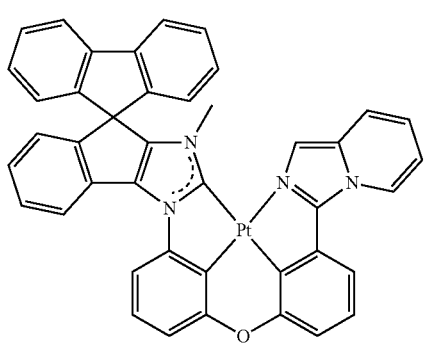
606
-continued
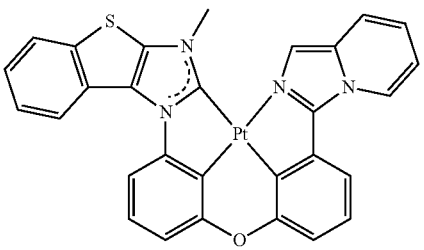
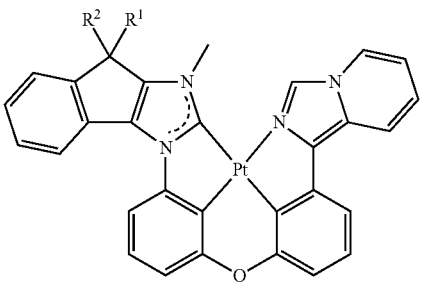
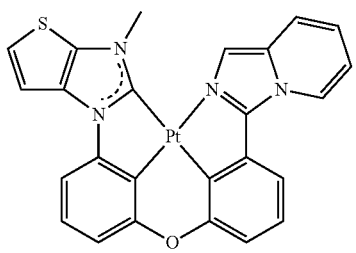
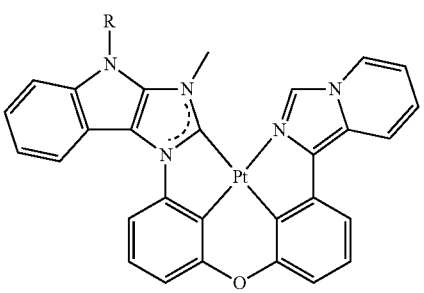
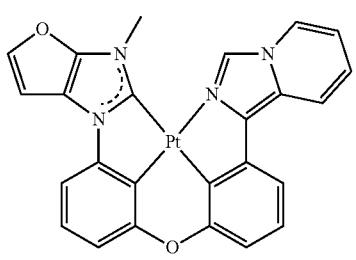
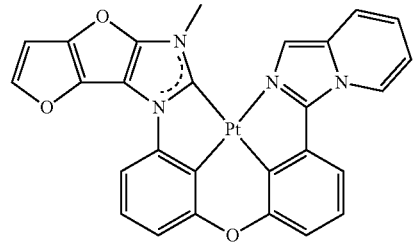

607
-continued
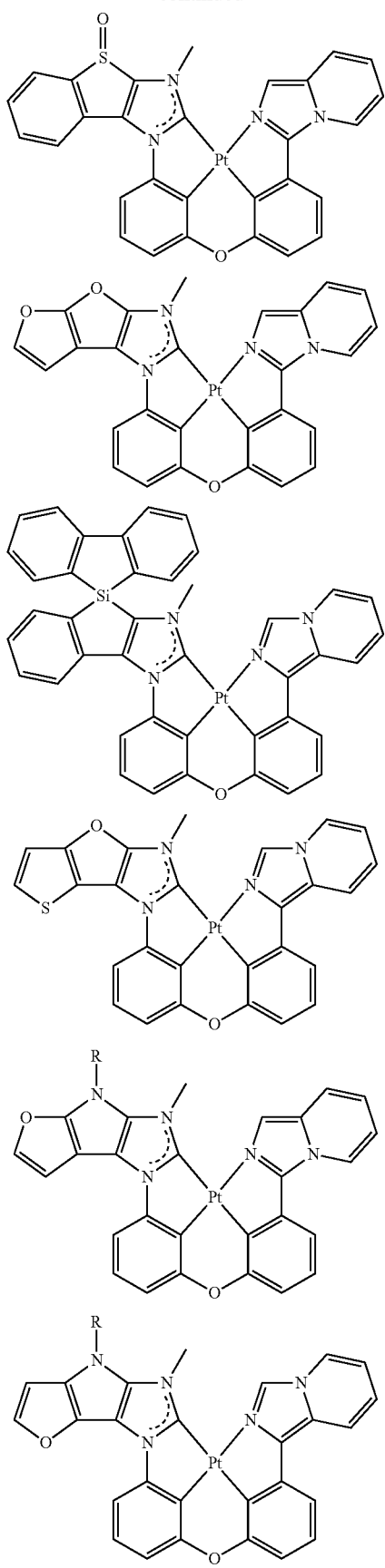
608
-continued
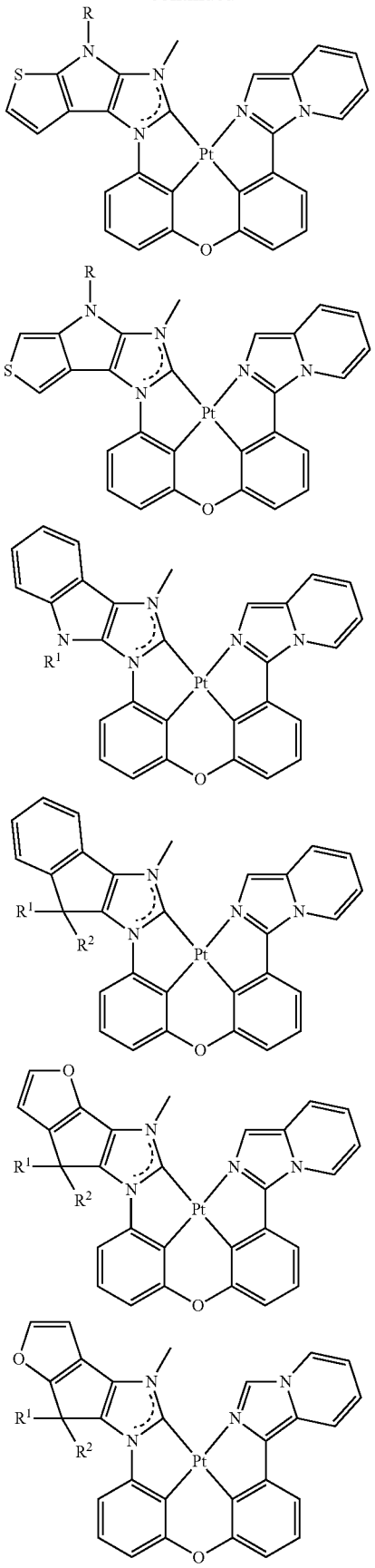

609
-continued
Structures 58
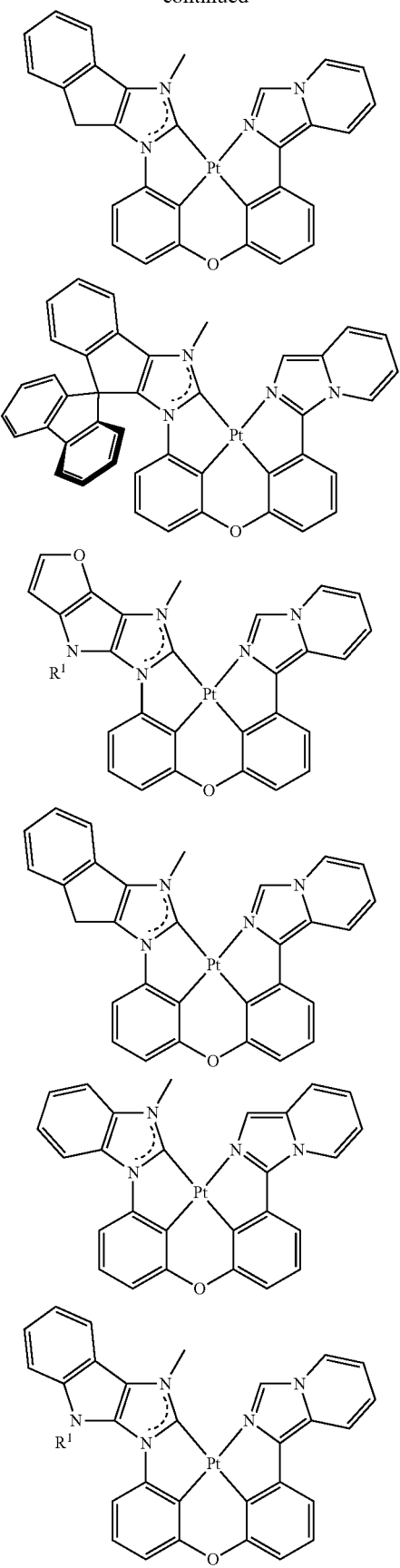
610
-continued
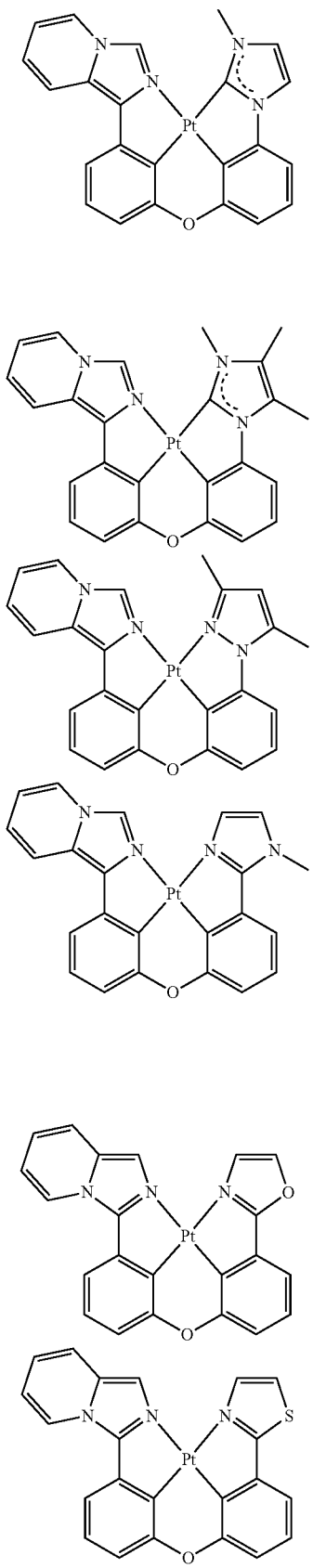

611
-continued
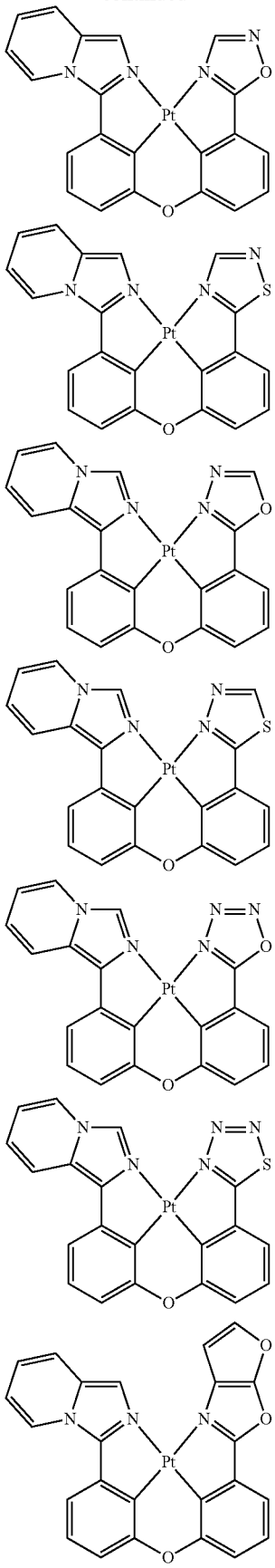
612
-continued
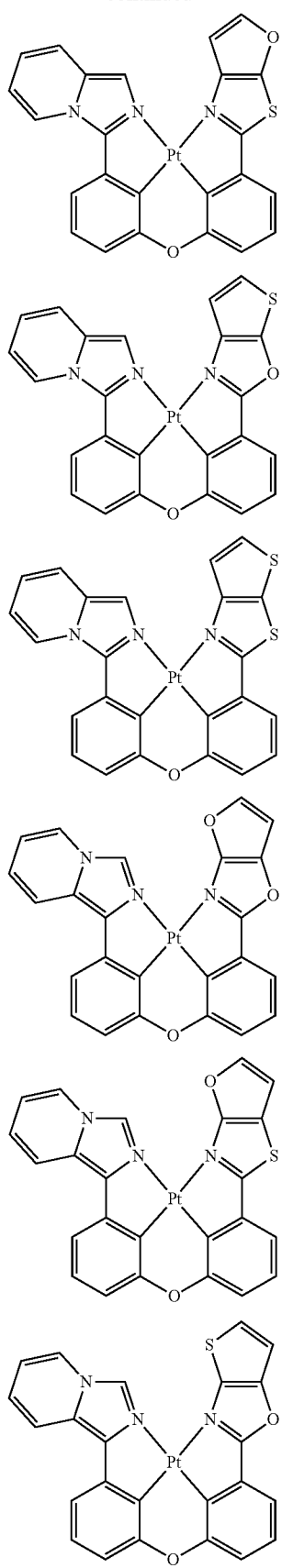

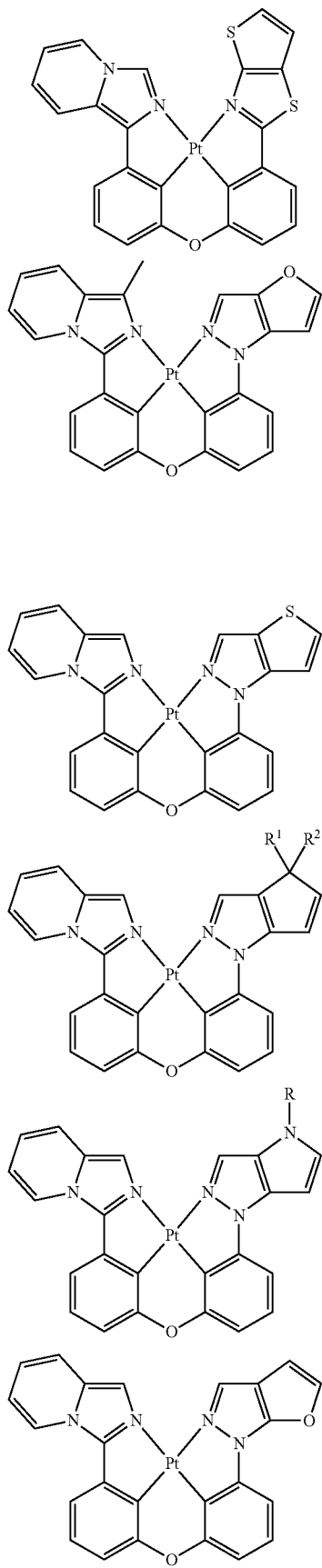
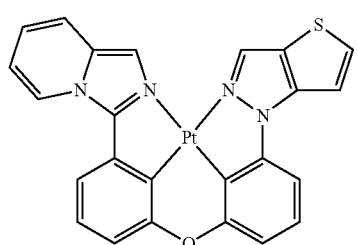
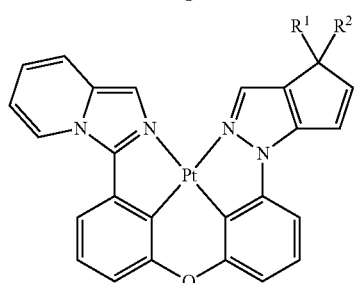
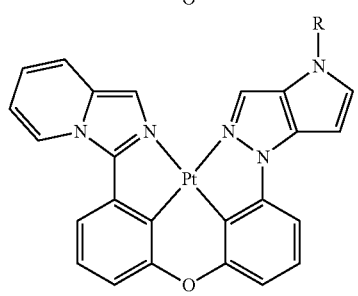
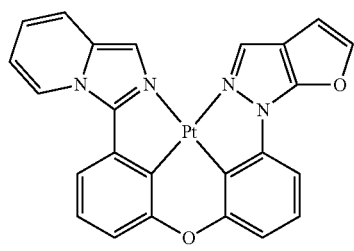
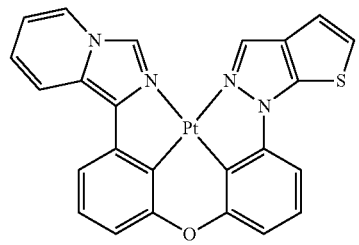
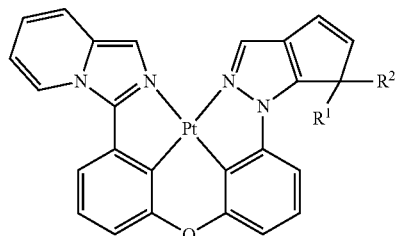
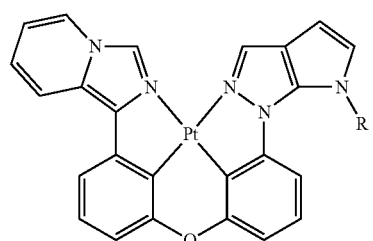
Structures 59
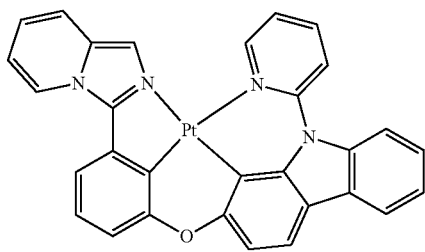
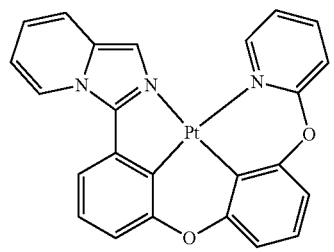
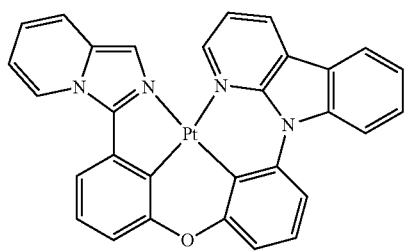

615
-continued
616
-continued
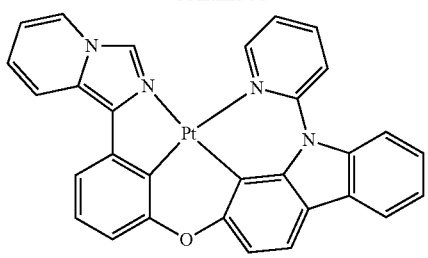
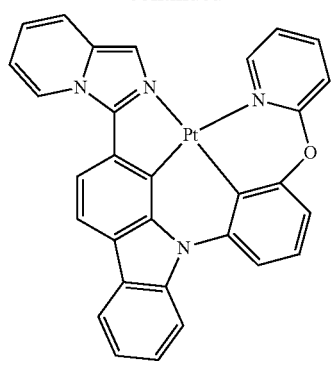
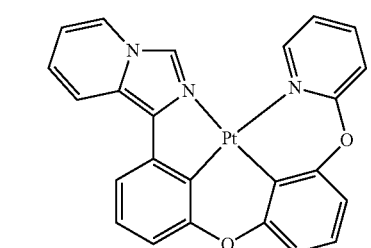
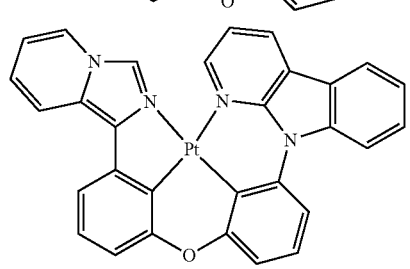
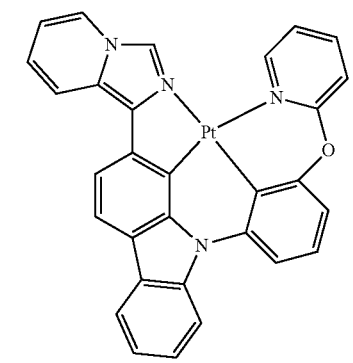
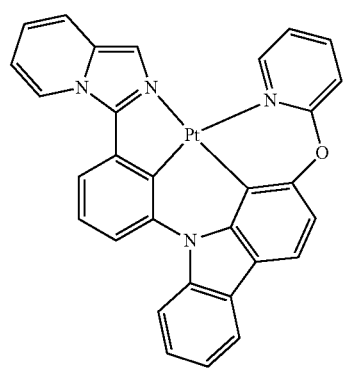
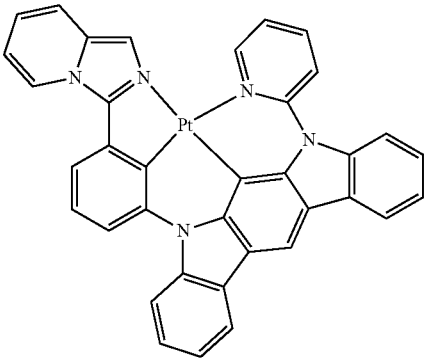
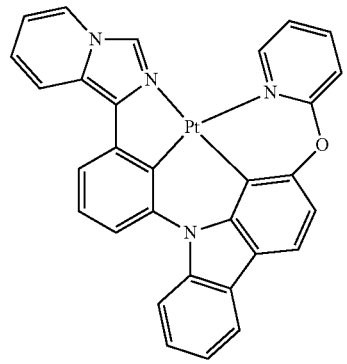
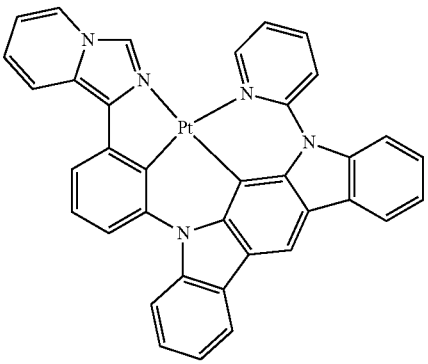

617
-continued
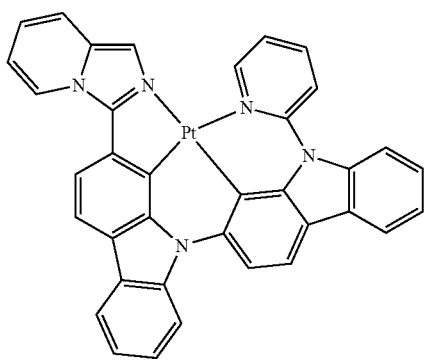
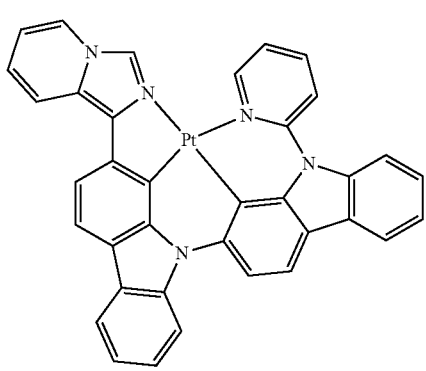
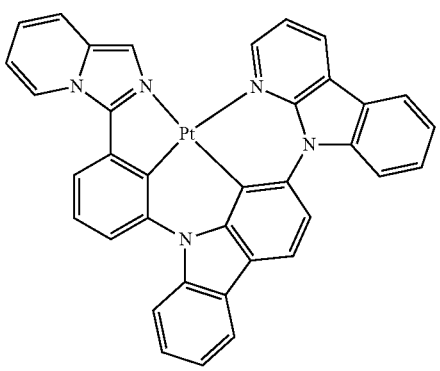
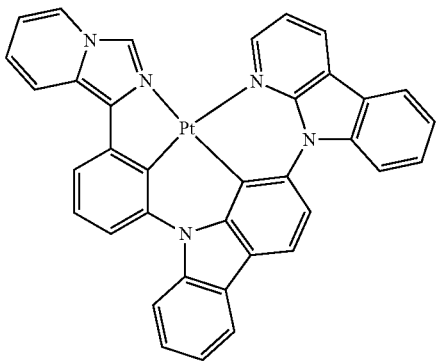
618
-continued
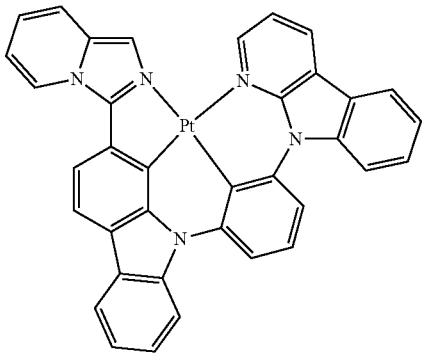
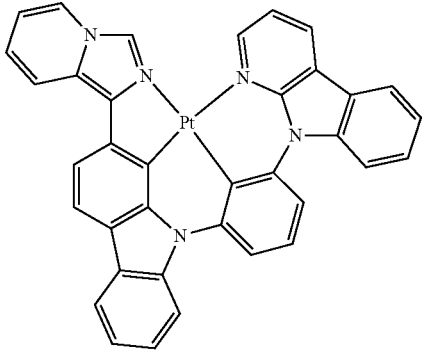
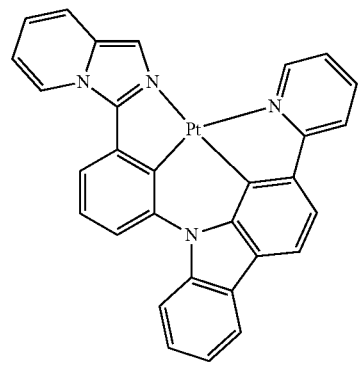
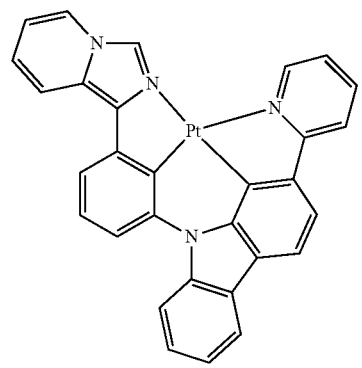

619
-continued
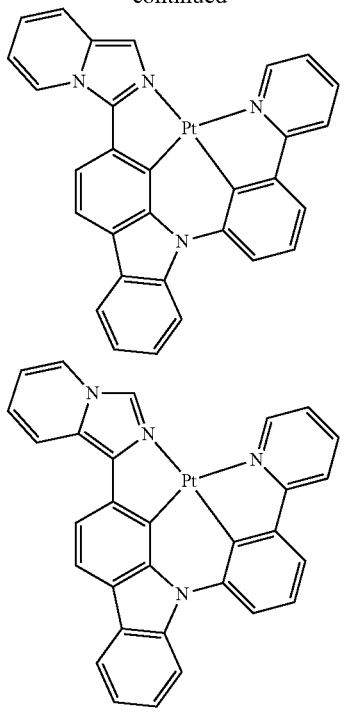
Structures
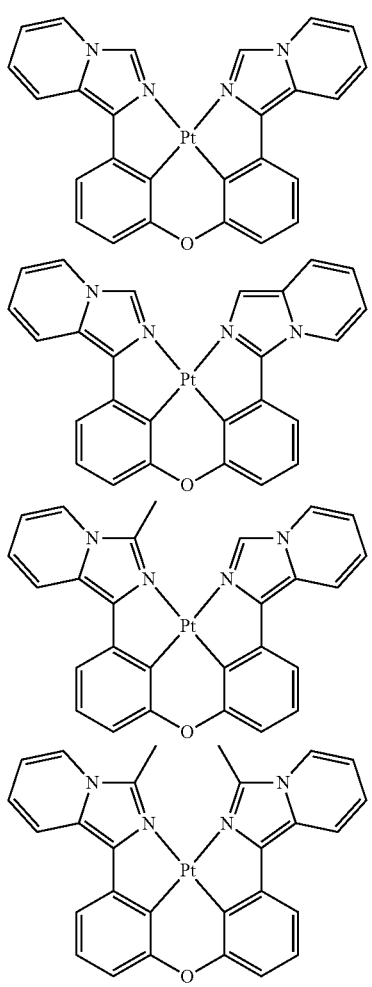
620
-continued
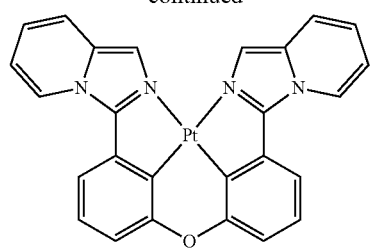
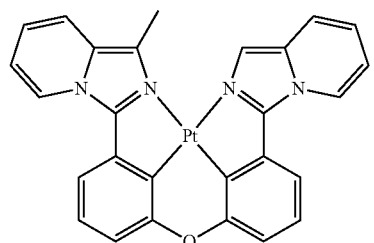
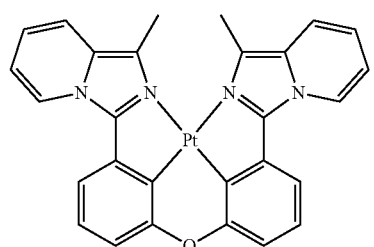
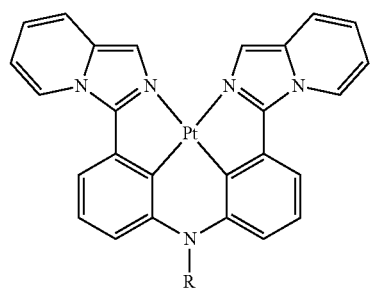
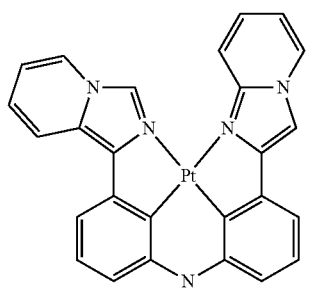
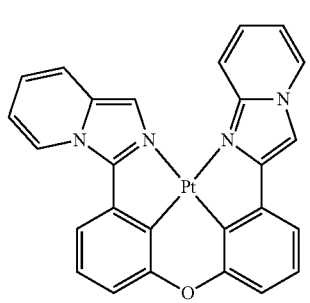

621
-continued
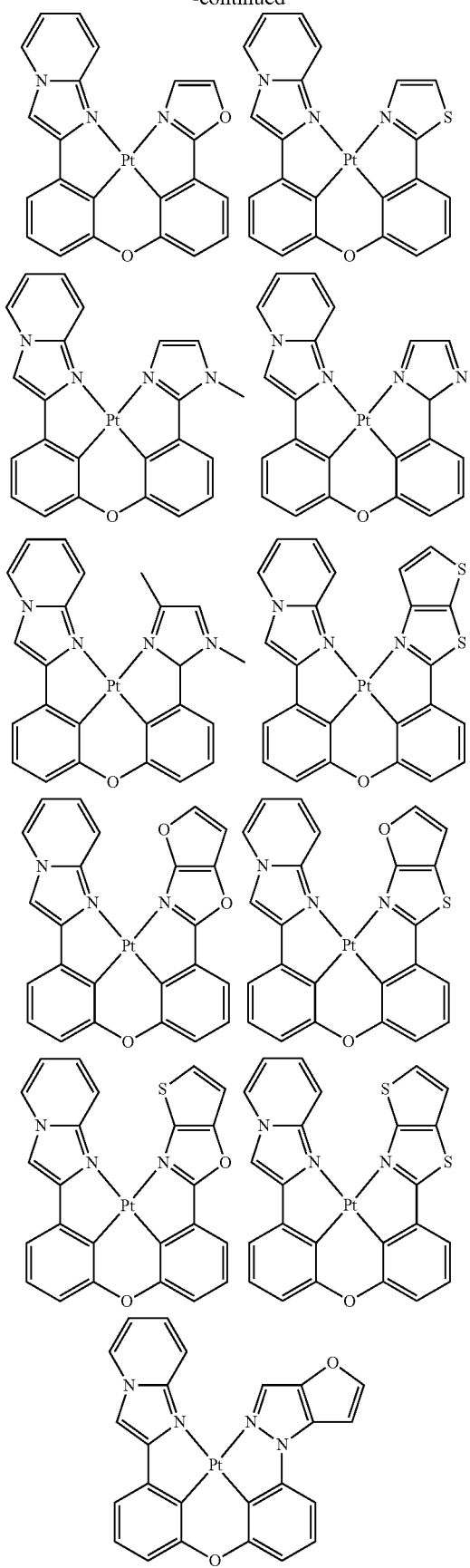
622
-continued
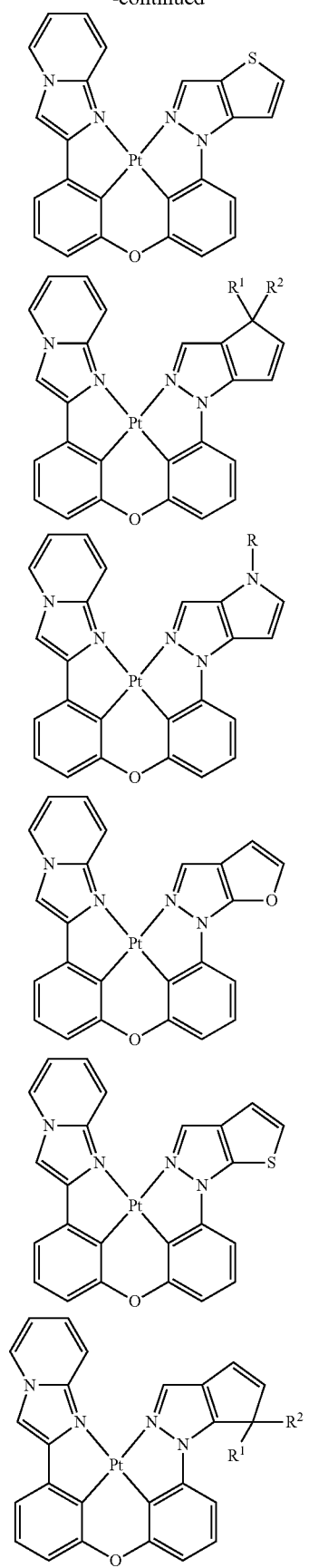

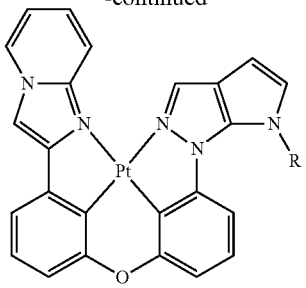

2. Compositions

Also disclosed herein are compositions comprising one or more of the compounds disclosed herein.

The compositions disclosed herein can further comprise host materials, hole blocking materials, electronic transfer materials, hole transfer materials, hole injection materials, or electronic injection materials.

The compositions disclosed herein are suited for use in a wide variety of optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

3. Devices

Also disclosed herein are devices comprising one or more compound and/or compositions disclosed herein.

In one aspect, the device is an electro-optical device. Electro-optical devices include, but are not limited to, photo-absorbing devices such as solar- and photo-sensitive devices, organic light emitting diodes (OLEDs), photo-emitting devices, or devices capable of both photo-absorption and emission and as markers for bio-applications. For example, the device can be an OLED.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art. Such devices are disclosed herein which comprise one or more of the compounds or compositions disclosed herein.

OLEDs can be produced by methods known to those skilled in the art. In general, the OLED is produced by successive vapor deposition of the individual layers onto a suitable substrate. Suitable substrates include, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods described herein are made and evaluated, and are intended to be purely exemplary of the disclosure and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the disclosed compounds described herein are recited in the examples. These methods are provided to illustrate various methods of preparation, but the present disclosure is not intended to be limited to any of the methods recited herein. Accordingly, one of skill in the art in possession of this disclosure could readily modify a recited method or utilize a different method to prepare one or more of the disclosed compounds. The following aspects are only exemplary and are not intended to limit the scope of the disclosure. Temperatures, catalysts, concentrations, reactant compositions, and other process conditions can vary, and one of skill in the art, in possession of this disclosure, could readily select appropriate reactants and conditions for a desired complex.

1. Example 1

Platinum complex PtON12 was prepared according to the following scheme:

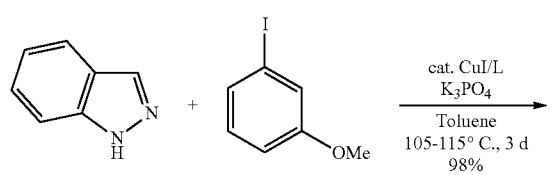

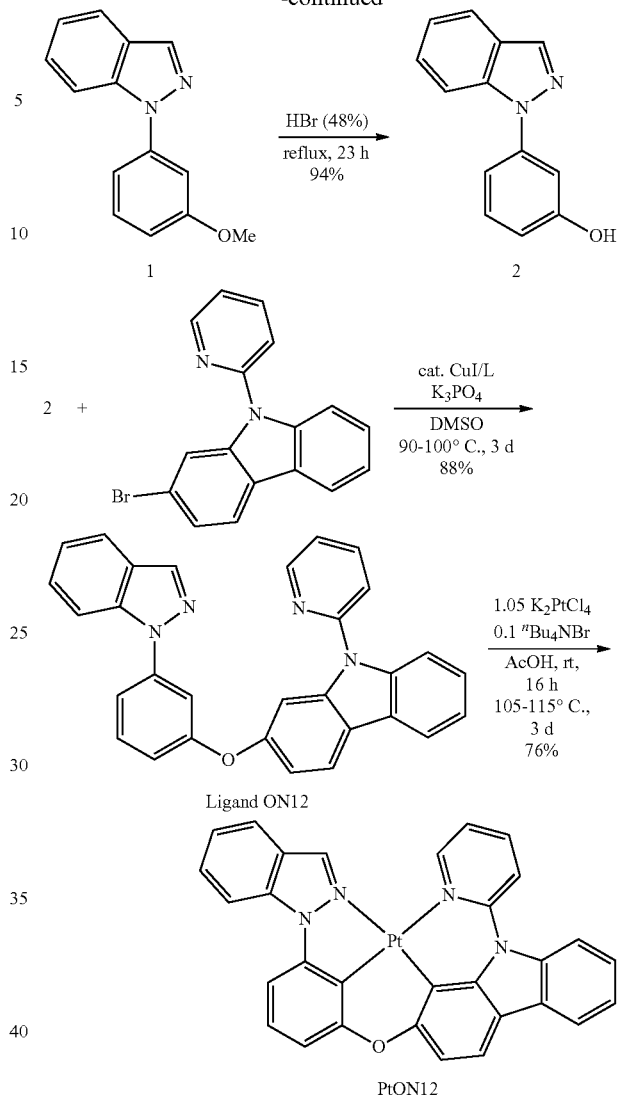

Synthesis of 1-(3-methoxyphenyl)-1H-indazole 1

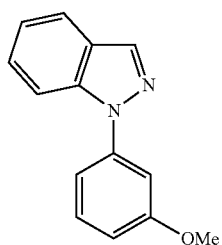 [SMILES: COc1cccc(-n2ncc3ccccc32)c1]

To a dry pressure tube equipped with a magnetic stir bar was added 1H-indazole (3.54 g, 30 mmol, 1.0 eq), 1-iodo-3-methoxybenzene (8.07 g, 36 mmol, 1.2 eq), CuI (0.29 g, 1.5 mmol, 0.05 eq), $K_2CO_3$ (13.37 g, 63 mmol, 2.1 eq) and trans-1,2-cyclohexanediamine (0.65 g, 6 mmol, 0.2 eq). Then the tube was taken into a glove box and solvent toluene (40 mL) was added. The mixture was bubbled with nitrogen for 5 minutes and then the tube was sealed. The tube was taken out of the glove box and the mixture was stirred in an oil bath at 105-115° C. for 3 days. The mixture was cooled down to ambient temperature, diluted with ethyl acetate, and then filtered and washed with ethyl acetate. The filtrate was concentrated and the residue was purified through column chromatography on silica gel using hexane and ethyl acetate (20:1-10:1) as eluent to obtain the desired product as a colorless liquid 6.62 g in 98% yield. $^1$H NMR (DMSO-$d_6$, 400 MHz): δ 3.85 (s, 3H), 6.98 (dd, J=8.0, 2.0 Hz, 1H), 7.25-7.30 (m, 2H), 7.35 (dd, J=8.0, 1.6 Hz, 1H), 7.49 (t, J=8.0 Hz, 2H), 7.86 (d, J=8.4 Hz, 1H), 7.89 (d, J=7.6 Hz, 1H), 8.37 (s, 1H). $^{13}$C NMR (DMSO-$d_6$, 100 MHz): δ 55.40, 107.75, 110.59, 112.42, 114.12, 121.49, 121.70, 125.10, 127.55, 130.48, 135.69, 138.13, 140.83, 160.13.

Synthesis of 3-(1H-indazol-1-yl)phenol 2

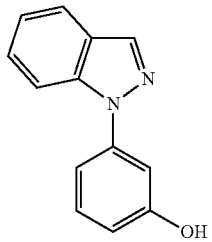 [SMILES: Oc1cccc(-n2ncc3ccccc32)c1]

A solution of 1-(3-methoxyphenyl)-1H-indazole 1 (6.50 g, 28.98 mmol) in hydrogen bromide acid (45 mL, 48%) was refluxed (110-120° C.) for 23 hours at an atmosphere of nitrogen. Then the mixture was cooled down to ambient temperature and neutralized with a solution of $K_2CO_3$ in water until there was no gas to generate. Then the precipitate was filtered off and washed with water several times. The collected solid was dried in air to afford the product as a brown solid 5.70 g in 94% yield. $^1$H NMR (DMSO-$d_6$, 400 MHz): δ 6.63 (dd, J=8.4, 2.0 Hz, 1H), 7.00-7.03 (m, 2H), 7.08 (t, J=7.6 Hz, 1H), 7.20 (t, J=7.6 Hz, 1H), 7.31 (d, J=7.6 Hz, 1H), 7.65 (d, J=7.2 Hz, 1H), 7.70 (d, J=8.0 Hz, 1H), 8.17 (s, 1H), 9.67 (bs, 1H). $^{13}$C NMR (DMSO-$d_6$, 100 MHz): δ 109.08, 110.54, 112.45, 113.63, 121.48, 121.61, 125.05, 127.42, 130.41, 135.48, 138.02, 140.72, 158.35.

Synthesis of 2-(3-(1H-indazol-1-yl)phenoxy)-9-(pyridin-2-yl)-9H-carbazole Ligand ON12

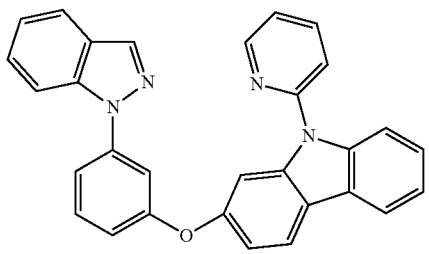 [SMILES: c1ccc(-n2c3ccccc3c3ccc(Oc4cccc(-n5ncc6ccccc65)c4)cc32)nc1]

To a dry Shlenck tube equipped with a magnetic stir bar was added 3-(1H-indazol-1-yl)phenol 2 (630 mg, 3.0 mmol, 1.0 eq), 2-bromo-9-(pyridin-2-yl)-9H-carbazole (1163 m g, 3.6 mmol, 1.2 eq), CuI (57 mg, 0.3 mmol, 0.1 eq), picolinic acid (74 mg, 0.6 mmol, 0.2 eq) and $K_3PO_4$ (1273 mg, 6.0 mmol, 2.0 eq). The tube was evacuated and backfilled with nitrogen. The evacuation and backfill procedure was repeated for another twice. Then solvent DMSO (9 mL) was added under the protection of nitrogen. The mixture was stirred in an oil bath at a temperature of 90-100° C. for 3 days and then cooled down to ambient temperature. Water was added to dissolve the solid. The mixture was extracted with ethyl acetate three times. The combined organic layer was washed with water three time, dried over sodium sulfate, and then filtered. The solvent was removed under reduced pressure, and the residue was purified through column chromatography on silica gel using hexane/ethyl acetate (10:1-5:1-3:1) as eluent to obtain the desired product Ligand ON12 as a colorless solid 1200 mg in 88% yield. $^1$H NMR (DMSO-$d_6$, 400 MHz): δ 7.05-7.08 (m, 1H), 7.15 (dd, J=8.4, 2.0 Hz, 1H), 7.24 (t, J=8.0 Hz, 1H), 7.32-7.36 (m, 2H), 7.42-7.47 (m, 3H), 7.52-7.59 (m, 2H), 7.61 (d, J=2.0 Hz, 1H), 7.77-7.83 (m, 3H), 7.86 (d, J=8.0 Hz, 1H), 8.07 (td, J=7.6, 2.0 Hz, 1H), 8.23 (d, J=7.6 Hz, 1H), 8.29 (d, J=7.6 Hz, 1H), 8.33 (s, 1H), 8.66 (dd, J=5.2, 1.6 Hz, 1H). $^{13}$C NMR (DMSO-$d_6$, 100 MHz): δ 102.73, 110.40, 111.12, 113.54, 115.66, 116.09, 119.05, 120.28, 120.22, 121.26, 121.56, 121.82, 122.12, 123.24, 125.16, 126.02, 127.64, 131.09, 136.02, 138.01, 139.35, 139.53, 139.94, 140.98, 149.52, 150.45, 154.58, 158.62.

Synthesis of Platinum Complex PtON12

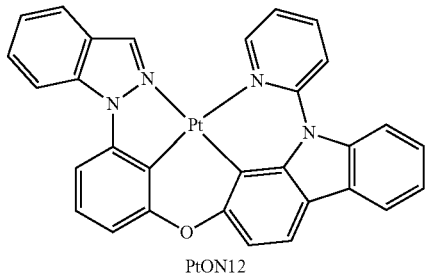

PtON12

To a dry pressure tube equipped with a magnetic stir bar was added Ligand ON12 (1080 mg, 2.39 mmol, 1.0 eq), $K_2PtCl_4$ (1040 mg, 2.51 mmol, 1.05 eq), "Bu$_4$NBr (77 mg, 0.24 mmol, 0.1 eq) and solvent acetic acid (143 mL). The mixture was bubbled with nitrogen for 30 minutes and then the tube was sealed. The mixture was stirred at room temperature for 16 hours and then in an oil bath at a temperature of 105-115° C. for another 3 days, and then cooled down to ambient temperature. Water (285 mL) was added, and the mixture was stirred at room temperature for 5 minutes. The precipitate was filtered off and washed with water three times. Then the solid was dried in air under reduced pressure. The collected solid was purified through flash column chromatography on silica gel using dichloromethane as eluent to obtain the desired product PtON12 as a brown yellow solid 1177 mg in 76% yield. The platinum complex 1170 mg was sublimated (275° C., 3.2×10$^{-6}$ torr) to give 600 mg of the compound as a yellow crystal. $^1$H NMR (DMSO-$d_6$, 400 MHz): δ 7.03 (d, J=8.4 Hz, 1H), 7.26 (d, J=8.4 Hz, 1H), 7.35 (t, J=8.4 Hz, 1H), 7.42 (d, J=7.6 Hz, 1H), 7.44-7.51 (m, 3H), 7.77 (t, J=8.0 Hz, 1H), 7.86 (d, J=8.0 Hz, 1H), 7.91 (d, J=8.4 Hz, 1H), 8.08 (d, J=7.6 Hz, 1H), 8.12 (d, J=8.0 Hz, 1H), 8.17 (d, J=7.2 Hz, 1H), 8.26 (d, J=8.4, 1.6 Hz, 1H), 8.33 (d, J=8.4 Hz, 1H), 8.49 (d, J=8.4 Hz, 1H), 8.92 (s, 1H), 9.41 (d, J=4.8 Hz, 1H). $^{13}$C NMR (DMSO-$d_6$, 100 MHz): δ 100.20, 106.12, 110.95, 111.18, 112.36, 112.41, 115.02, 115.70, 115.86, 116.14, 119.99, 120.52, 122.98, 123.04, 124.37, 124.55, 125.22, 127.92, 130.77, 136.07, 137.44, 137.97, 139.92, 141.84, 147.21, 147.65, 152.22, 152.25, 152.32.

Figure 2:
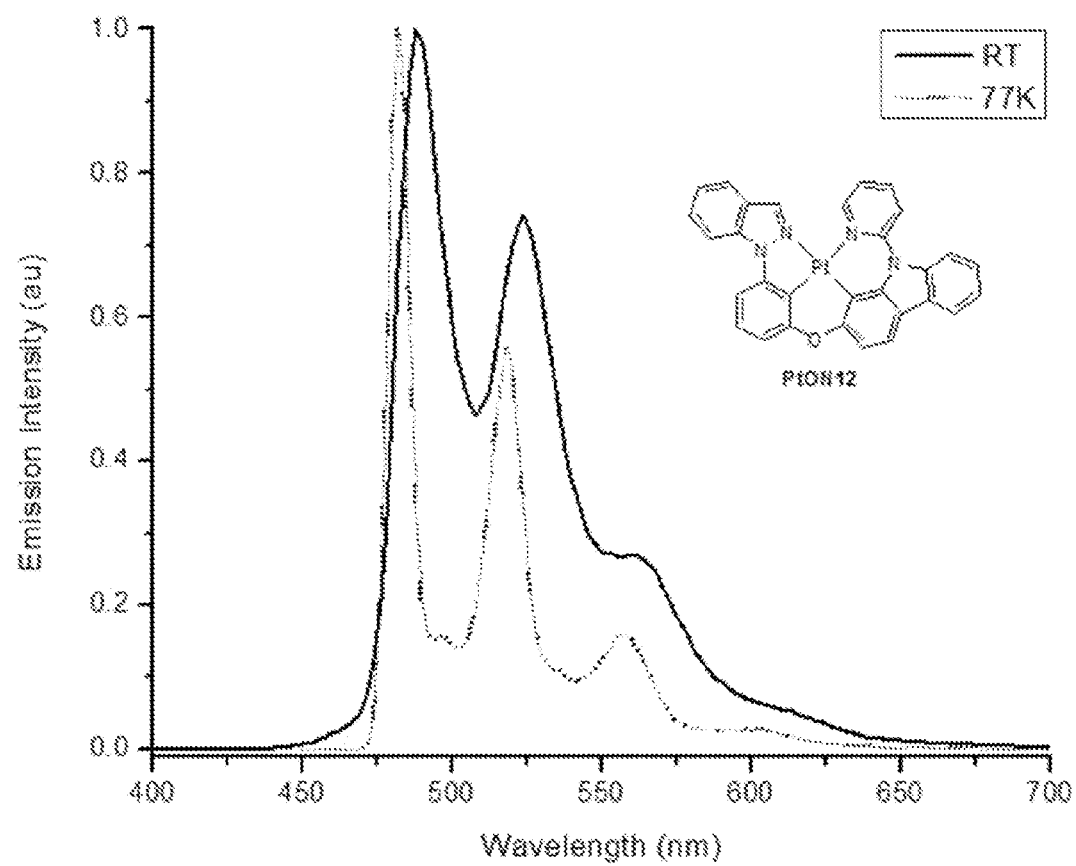
FIG. 2 illustrates emission spectra of PtON12 in $CH_2Cl_2$ at room temperature and in 2-methyltetrahydrofuran at 77K.

FIG. 2 illustrates emission spectra of PtON12 in CH$_2$Cl$_2$ at room temperature and in 2-methyltetrahydrofuran at 77K.

2. Example 2

Platinum complex PtON12-tBu was prepared according to the following scheme:

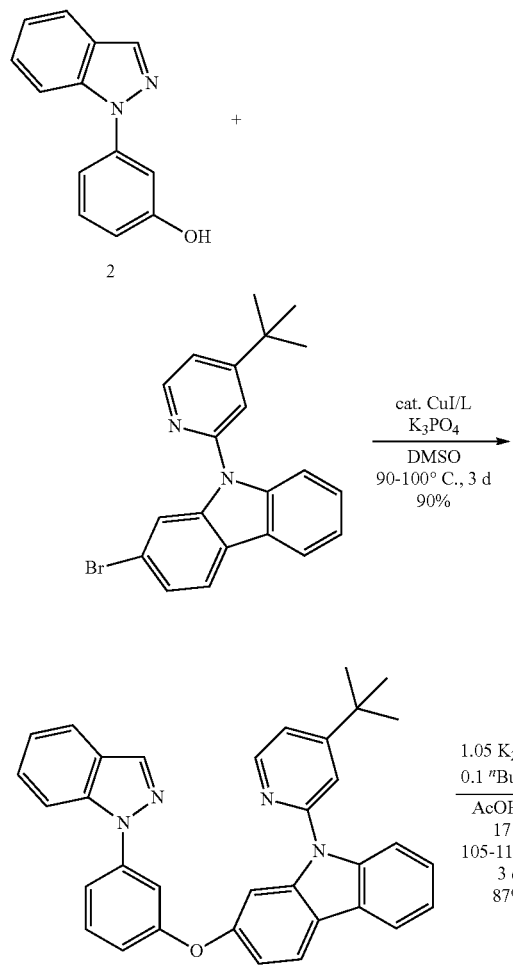

Synthesis of 2-(3-(1H-indazol-1-yl)phenoxy)-9-(4-tert-butylpyridin-2-yl)-9H-carbazole Ligand ON12-tBu:

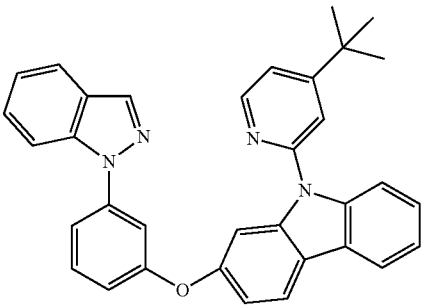 [SMILES: CC(C)(C)c1ccnc(-n2c3ccccc3c3ccc(Oc4cccc(-n5ncc6ccccc65)c4)cc32)c1]

To a dry Shlenck tube equipped with a magnetic stir bar was added 3-(1H-indazol-1-yl)phenol 2 (630 mg, 3.0 mmol, 1.0 eq), 9-(4-tert-butylpyridin-2-yl)-2-bromo-9H-carbazole (1365 m g, 3.6 mmol, 1.2 eq), CuI (57 mg, 0.3 mmol, 0.1 eq), picolinic acid (74 mg, 0.6 mmol, 0.2 eq) and K$_3$PO$_4$ (1273 mg, 6.0 mmol, 2.0 eq). The tube was evacuated and backfilled with nitrogen. The evacuation and backfill procedure was repeated another two times. Then solvent DMSO (9 mL) was added under the protection of nitrogen. The mixture was stirred in an oil bath at a temperature of 90-100° C. for 3 days and then cooled down to ambient temperature. Water was added to dissolve the solid. The mixture was extracted with ethyl acetate three times. The combined organic layer was washed with water three time, dried over sodium sulfate, and then filtered. The solvent was removed under reduced pressure, and the residue was purified through column chromatography on silica gel using hexane/ethyl acetate (10:1-5:1) as eluent to obtain the desired product Ligand ON12-tBu as a colorless solid 1378 mg in 90% yield. $^1$H NMR (DMSO-d$_6$, 400 MHz): δ 1.17 (s, 9H), 7.05-7.08 (m, 1H), 7.13 (dd, J=8.4, 2.0 Hz, 1H), 7.19 (t, J=7.6 Hz, 1H), 7.29 (t, J=7.6 Hz, 1H), 7.34 (dd, J=5.6, 1.2 Hz, 1H), 7.37-7.42 (m, 4H), 7.53-7.54 (m, 2H), 7.57 (s, 1H), 7.73 (d, J=8.0 Hz, 1H), 7.78 (d, J=8.8 Hz, 1H), 7.81 (d, J=8.4 Hz, 1H), 8.18 (d, J=7.6 Hz, 1H), 8.25 (d, J=8.8 Hz, 1H), 8.29 (s, 1H), 8.50 (d, J=4.8 Hz, 1H). $^{13}$C NMR (DMSO-d$_6$, 100 MHz): δ 29.93, 34.74, 101.50, 110.41, 111.15, 111.77, 113.13, 115.70, 116.34, 116.37, 119.21, 119.82, 120.12, 121.11, 121.53, 121.78, 121.84, 123.20, 125.19, 125.90, 127.58, 131.12, 136.01, 137.97, 139.42, 139.91, 141.08, 149.34, 150.61, 155.25, 158.09, 162.96.

Synthesis of Platinum Complex PtON12

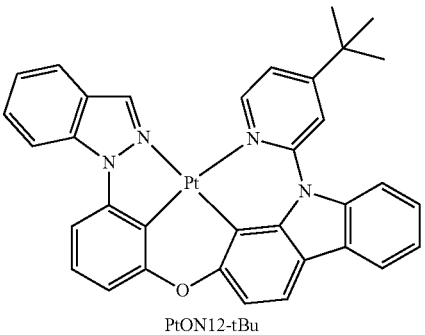

PtON12-tBu

To a dry pressure tube equipped with a magnetic stir bar was added Ligand ON12-tBu (1300 mg, 2.56 mmol, 1.0 eq), K₂PtCl₄ (1114 mg, 2.68 mmol, 1.05 eq), ⁿBu₄NBr (83 mg, 0.26 mmol, 0.1 eq) and solvent acetic acid (153 mL). The mixture was bubbled with nitrogen for 30 minutes and then the tube was sealed. The mixture was stirred at room temperature for 17 hours, then in an oil bath at a temperature of 105-115° C. for another 3 days, and then cooled down to ambient temperature. Water (306 mL) was added, and the mixture was stirred at room temperature for 5 minutes. The precipitate was filtered off and washed with water three times. Then the solid was dried in air under reduced pressure. The collected solid was purified through flash column chromatography on silica gel using dichloromethane as eluent to obtain the desired product PtON12-tBu as a yellow solid 1564 mg in 87% yield. ¹H NMR (DMSO-d₆, 400 MHz): δ 1.41 (s, 9H), 7.01 (d, J=8.8 Hz, 1H), 7.25 (d, J=8.4 Hz, 1H), 7.34 (t, J=7.6 Hz, 1H), 7.42 (t, J=7.6 Hz, 1H), 7.47 (t, J=7.6 Hz, 1H), 7.51-7.55 (m, 2H), 7.77 (t, J=8.0 Hz, 1H), 7.85 (d, J=7.6 Hz, 1H), 7.91 (d, J=8.4 Hz, 1H), 8.08 (d, J=7.6 Hz, 1H), 8.13 (d, J=7.6 Hz, 1H), 8.19 (d, J=8.4 Hz, 1H), 8.20 (s, 1H), 8.49 (d, J=8.8 Hz, 1H), 8.94 (s, 1H), 9.29 (d, J=6.4 Hz, 1H).

Figure 3:
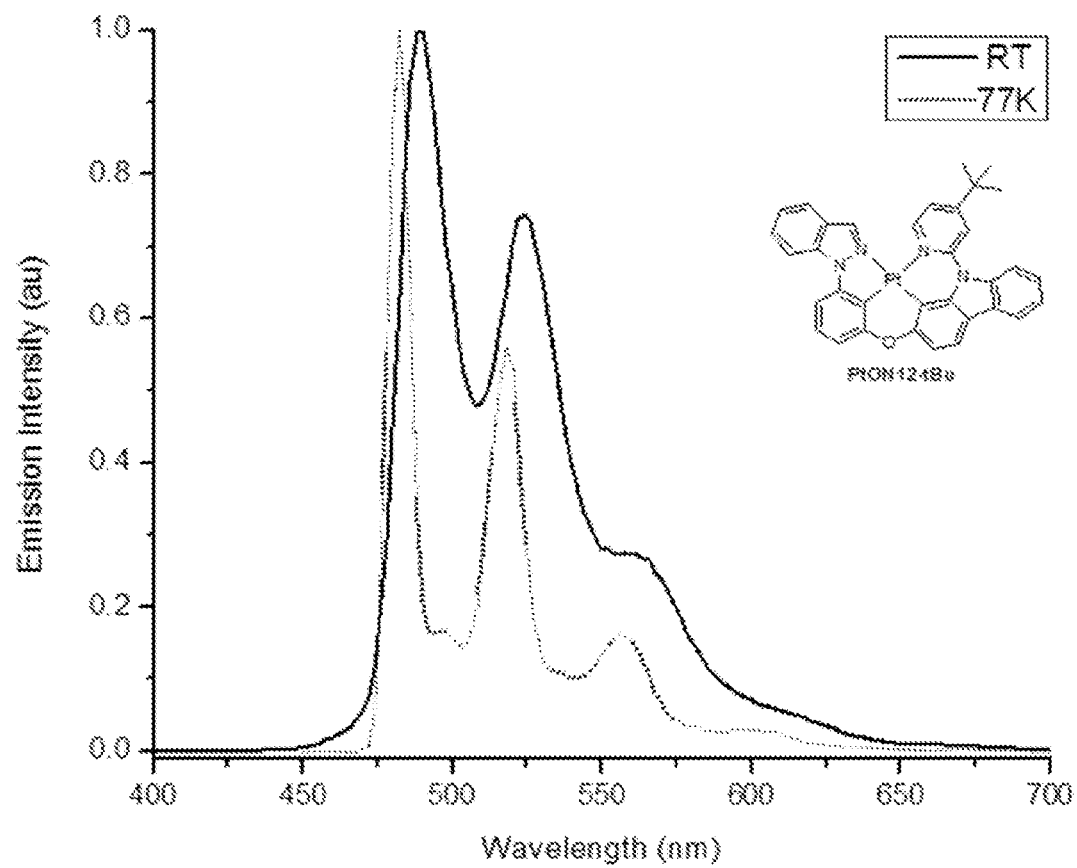
FIG. 3 illustrates emission spectra of PtON12-tBu in $CH_2Cl_2$ at room temperature and in 2-methyltetrahydrofuran at 77K.

FIG. 3 illustrates emission spectra of PtON12-tBu in CH₂Cl₂ at room temperature and in 2-methyltetrahydrofuran at 77K.

3. Example 3

Platinum complex PtON13 can be prepared according to the following scheme:

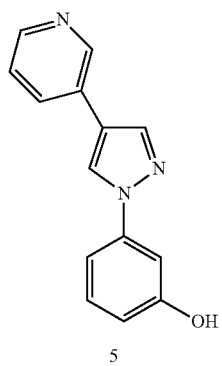

5

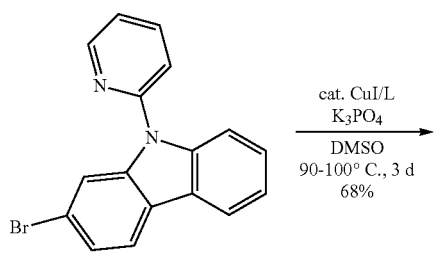

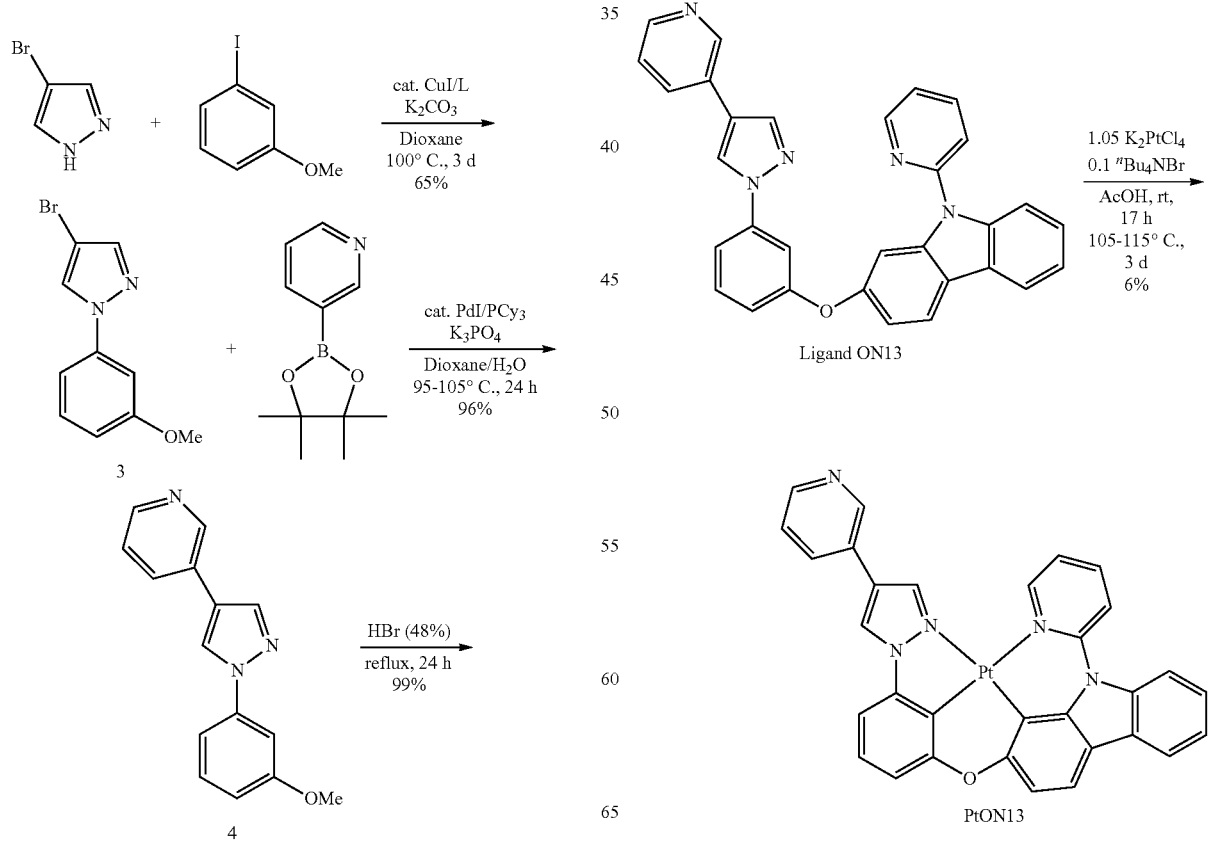

Synthesis of 4-bromo-1-(3-methoxyphenyl)-1H-pyrazole 3

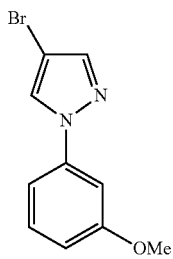 [SMILES: COc1cccc(-n2cc(Br)cn2)c1]

4-Bromo-1H-pyrazole (3674 mg, 25 mmol, 1.0 eq), CuI (95 mg, 0.5 mmol, 0.02 eq) and $K_2CO_3$ (7256 mg, 52.5 mmol, 2.1 eq) were added to a dry pressure tube equipped with a magnetic stir bar. Then trans-1,2-cyclohexanediamine (570 mg, 5 mmol, 0.2 eq), 1-iodo-3-methoxybenzene (3.57 mL, 30 mmol, 1.2 eq) and solvent dioxane (50 mL) were added in a nitrogen filled glove box. The mixture was bubbled with nitrogen for 5 minutes. The tube was sealed before being taken out of the glove box. The mixture was stirred in an oil bath at a temperature of 100° C. for two days. Then the mixture was cooled down to ambient temperature, filtered, and washed with ethyl acetate. The filtrate was concentrated and the residue was purified through column chromatography on silica gel using hexane and ethyl acetate (20:1-15:1) as eluent to obtain the desired product 4-bromo-1-(3-methoxyphenyl)-1H-pyrazole 3 as a colorless sticky liquid 4.09 g in 65% yield. $^1$H NMR (DMSO-$d_6$, 400 MHz): δ 3.82 (s, 3H), 6.89-6.92 (m, 1H), 7.39-7.41 (m, 3H), 7.86 (s, 1H), 8.81 (s, 1H). $^{13}$C NMR (DMSO-$d_6$, 100 MHz): δ 55.45, 94.92, 104.01, 110.35, 112.54, 128.30, 130.51, 140.26, 141.16, 160.15.

Synthesis of 3-(1-(3-methoxyphenyl)-1H-pyrazol-4-yl)pyridine 4

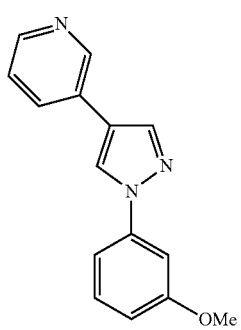 [SMILES: COc1cccc(-n2cc(-c3cccnc3)cn2)c1]

To a three-necked flask equipped with a magnetic stir bar and a condenser was added 3-(4,4,5,5-tetramethyl-1,3,2-dioxaborolan-2-yl)pyridine (1230 mg, 6.0 mmol, 1.2 eq), $Pd_2(dba)_3$ (183 mg, 0.2 mmol, 0.04 eq) and tricyclohexylphosphine $PCy_3$ (135 mg, 0.48 mmol, 0.096 eq). Then the flask was evacuated and backfilled with nitrogen. The evacuation and back fill procedure was repeated another two times. Then a solution of 4-bromo-1-(3-methoxyphenyl)-1H-pyrazole 3 (1266 mg, 5.0 mmol, 1.0 eq) in dioxane (25 mL) and a solution of $K_3PO_4$ (1804 mg, 8.5 mmol, 1.7 eq) in $H_2O$ (10 mL) were added by syringe independently under nitrogen. The mixture was stirred in an oil bath at a temperature of 95-105° C. for 24 hours, cooled down to ambient temperature, filtered and washed with ethyl acetate. The organic layer of the filtrate was separated, dried over sodium silphate, filtered, concentrated and the residue was purified through column chromatography on silica gel using hexane/ethyl acetate (10:1-5:1) first, then dichloromethane/methanol (10:1) as eluent to obtain the desired product 3-(1-(3-methoxyphenyl)-1H-pyrazol-4-yl)pyridine 4 as a brown solid 1.21 g in 96% yield. $^1$H NMR (DMSO-$d_6$, 400 MHz): δ 3.85 (s, 3H), 6.90-6.93 (m, 1H), 7.41-7.48 (m, 4H), 8.10 (dt, J=8.0, 2.0 Hz, 1H), 8.31 (s, 1H), 8.45 (dd, J=4.8, 1.6 Hz, 1H), 8.98 (d, J=1.2 Hz, 1H), 9.13 (s, 1H).

Synthesis of 3-(4-(pyridin-3-yl)-1H-pyrazol-1-yl)phenol 5

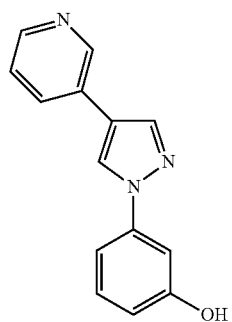 [SMILES: Oc1cccc(-n2cc(-c3cccnc3)cn2)c1]

A solution of 3-(1-(3-methoxyphenyl)-1H-pyrazol-4-yl)pyridine 4 (1.20 g, 4.77 mmol) in hydrogen bromide acid (15 mL, 48%) refluxed (110-120° C.) for 24 hours under an atmosphere of nitrogen. Then the mixture was cooled down to ambient temperature and neutralized with a solution of $K_2CO_3$ in water until there was no gas to generate. Then the precipitate was filtered off and washed with water several times. The collected solid was dried in air to afford the product as a brown solid 1.24 g in 99% yield. $^1$H NMR (DMSO-$d_6$, 400 MHz): δ 6.59 (dt, J=7.2, 2.0 Hz, 1H), 7.11-7.17 (m, 3H), 7.38 (dd, J=7.6, 1.6 Hz, 1H), 8.07 (dt, J=8.0, 2.0 Hz, 1H), 8.15 (s, 1H), 8.33-8.34 (m, 1H), 8.85 (d, J=1.6 Hz, 1H), 8.90 (s, 1H), 9.78 (bs, 1H).

Synthesis of 9-(pyridin-2-yl)-2-(3-(4-(pyridin-3-yl)-1H-pyrazol-1-yl)phenoxy)-9H-carbazole Ligand ON13

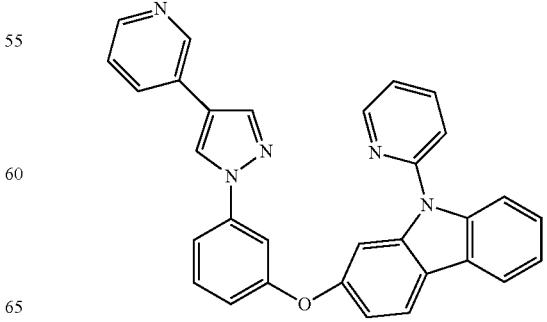

To a dry Shlenck tube equipped with a magnetic stir bar was added 3-(4-(pyridin-3-yl)-1H-pyrazol-1-yl)phenol (475 mg, 2.0 mmol, 1.0 eq), 2-bromo-9-(pyridin-2-yl)-9H-carbazole (776 m g, 2.4 mmol, 1.2 eq), CuI (38 mg, 0.2 mmol, 0.1 eq), picolinic acid (49 mg, 0.4 mmol, 0.2 eq) and $K_3PO_4$ (819 mg, 4.0 mmol, 2.0 eq). The tube was evacuated and backfilled with nitrogen. The evacuation and backfill procedure was repeated another two times. Then solvent DMSO (10 mL) was added under nitrogen. The mixture was stirred in an oil bath at a temperature of 90-100° C. for 3 days and then cooled down to ambient temperature. Water was added to dissolve solid. The mixture was extracted with ethyl acetate three times. The combined organic layer was washed with water three times, dried over sodium sulfate, and then filtered. The solvent was removed under reduced pressure, and the residue was purified through column chromatography on silica gel using dichloromethane/methanol (50:1) as eluent to obtain the desired product Ligand ON13 as a brown-red solid 656 mg in 68% yield. $^1$H NMR (DMSO-$d_6$, 400 MHz): δ 6.92 (dd, J=8.0, 2.4 Hz, 1H), 7.04 (dd, J=8.0, 1.6 Hz, 1H), 7.28 (t, J=7.6 Hz, 1H), 7.33-7.40 (m, 3H), 7.45 (t, J=8.0 Hz, 1H), 7.52 (d, J=2.0 Hz, 1H), 7.55 (t, J=2.0 Hz, 1H), 7.60 (dd, J=7.6, 1.6 Hz, 1H), 7.71 (s, 1H), 7.73 (s, 1H), 7.98-8.03 (m, 2H), 8.16 (d, J=7.6 Hz, 1H), 8.21 (d, J=7.2 Hz, 1H), 8.22 (s, 1H), 8.38 (dd, J=4.4, 1.6 Hz, 1H), 8.62 (dd, J=4.4, 1.6 Hz, 1H), 8.91 (d, J=2.4 Hz, 1H), 9.08 (s, 1H). $^{13}$C NMR (DMSO-$d_6$, 100 MHz): δ 102.54, 107.98, 111.12, 112.68, 113.27, 115.75, 119.02, 120.11, 120.19, 121.01, 121.27, 121.79, 122.11, 123.28, 123.87, 125.32, 125.99, 127.66, 131.06, 132.41, 138.90, 139.36, 139.49, 139.97, 140.78, 146.54, 147.62, 149.52, 150.48, 154.81, 158.56.

Synthesis of 9-(pyridin-2-yl)-2-(3-(4-(pyridin-3-yl)-1H-pyrazol-1-yl)phenoxy)-9H-carbazole platinum complex PtON13

PtON13

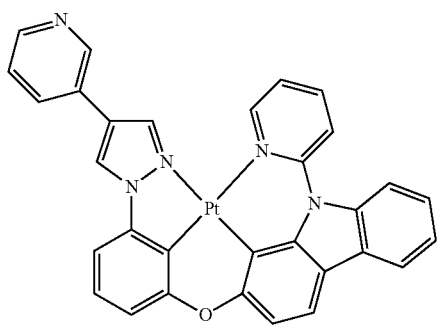

To a dry pressure tube equipped with a magnetic stir bar was added Ligand ON13 (600 mg, 1.25 mmol, 1.0 eq), $K_2PtCl_4$ (551 mg, 1.31 mmol, 1.05 eq), $^nBu_4NBr$ (40 mg, 0.125 mmol, 0.1 eq) and solvent acetic acid (75 mL). The mixture was bubbled with nitrogen for 30 minutes in a nitrogen filled glove box. The tube was sealed before being taken out of the glove box. The mixture was stirred at room temperature for 17 hours and then in an oil bath at a temperature of 105-115° C. for another 3 days, cooled down to ambient temperature and water (150 mL) was added. After stirring at room temperature for 5 minutes, the precipitate was filtered off and washed with water three times. Then the solid was dried in air under reduced pressure. The collected solid was purified through flash column chromatography on silica gel using dichloromethane/Et3N (100:1-50:1) as eluent to obtain the a yellow solid 233 mg, which was further purified by thermal sublimation to afford the desired product PtON13 as a yellow solid 50 mg in 6% total yield. $^1$H NMR (DMSO-$d_6$, 400 MHz): δ 7.01 (d, J=7.6 Hz, 1H), 7.22 (d, J=8.0 Hz, 1H), 7.28 (t, J=7.6 Hz, 1H), 7.41 (t, J=7.2 Hz, 1H), 7.44-7.54 (m, 4H), 7.89 (d, J=8.4 Hz, 1H), 8.09 (d, J=8.0 Hz, 1H), 8.16 (d, J=7.6 Hz, 1H), 8.23-8.30 (m, 3H), 8.55 (d, J=4.8 Hz, 1H), 8.76 (s, 1H), 9.15 (d, J=1.2 Hz, 1H), 9.35 (d, J=5.2 Hz, 1H). 9.51 (s, 1H). $^{13}$C NMR (DMSO-$d_6$, 100 MHz): δ 98.72, 106.08, 111.03, 112.54, 113.43, 114.95, 115.59, 115.79, 116.16, 119.99, 120.54, 120.62, 122.97, 123.96, 124.56, 124.86, 125.89, 126.90, 127.85, 132.85, 137.32, 137.98, 139.83, 141.80, 145.86, 146.88, 147.49, 148.24, 152.27, 152.46, 152.58.

Figure 4:
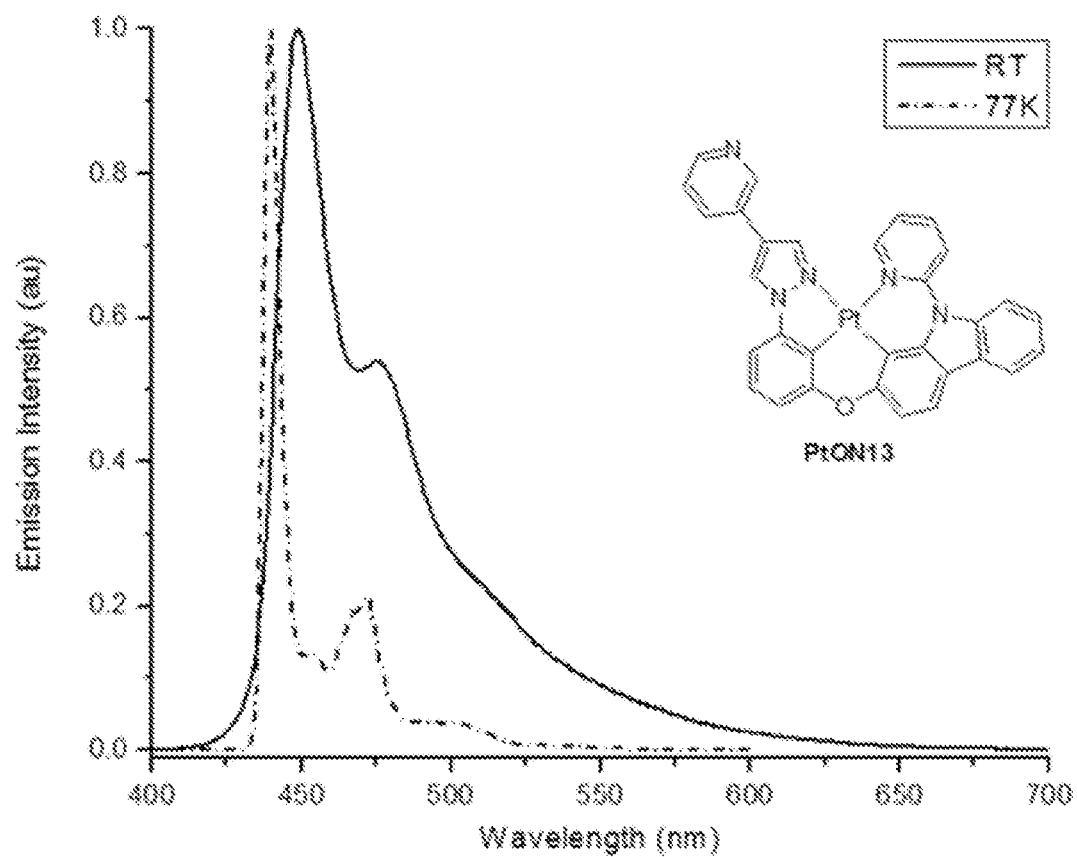
FIG. 4 illustrates emission spectra of PtON13 at room temperature in $CH_2Cl_2$ and at 77K in 2-methyltetrahydrofuran.

FIG. 4 illustrates emission spectra of PtON13 at room temperature in $CH_2Cl_2$ and at 77K in 2-methyltetrahydrofuran.

A number of embodiments have been described. Nevertheless, it will be understood that various modifications may be made without departing from the spirit and scope of the disclosure. Accordingly, other embodiments are within the scope of the following claims.

What is claimed is:
1. A compound of Formula II2:

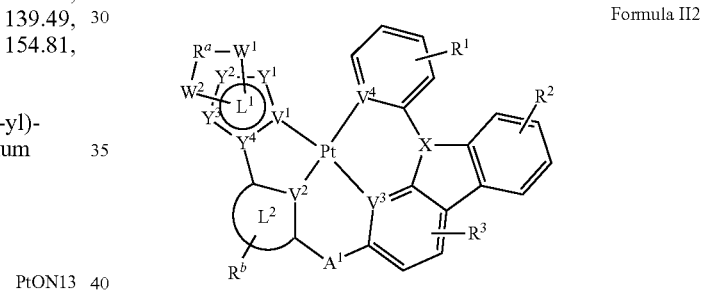

Formula II2 wherein:
$L^1$ is substituted or unsubstituted: five-membered heterocyclyl, heteroaryl, carbene, or N-heterocyclic carbene,
$L^2$ is phenyl,
$A^1$ is O, S, S=O, $SO_2$, Se, $NR^3$, $PR^3$, RP=O, $CR^1R^2$, C=O, $SiR^1R^2$, $GeR^1R^2$, BH, P(O)H, PH, NH, $CR^1H$, $CH_2$, $SiH_2$, $SiHR^1$, BH, or $BR^3$,
$V^1$ is C, $V^2$ is C, $V^3$ is C, and $V^4$ is N,
each of $Y^1$, $Y^2$, $Y^3$, and $Y^4$ is independently C, N, O, or S,
X is N,
each of $R^b$, $R^1$, $R^2$, and $R^3$ of Formula II2 is independently present or absent and if present, each of $R^b$, $R^1$, $R^2$, and $R^3$ present represents mono-, di-, or tri-substitutions, and each $R^b$, $R^1$, $R^2$, and $R^3$ present is independently substituted or unsubstituted and is selected from aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, and silyl, and wherein two or more of $R^b$ are optionally linked together, each of R, R$^1$, R$^2$, and R$^3$ of variable A$^1$ is independently substituted or unsubstituted and is selected from hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, and silyl, and wherein two or more of R, R$^1$, R$^2$, and R$^3$ are optionally linked together, each of

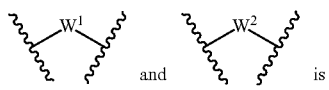

is independently:

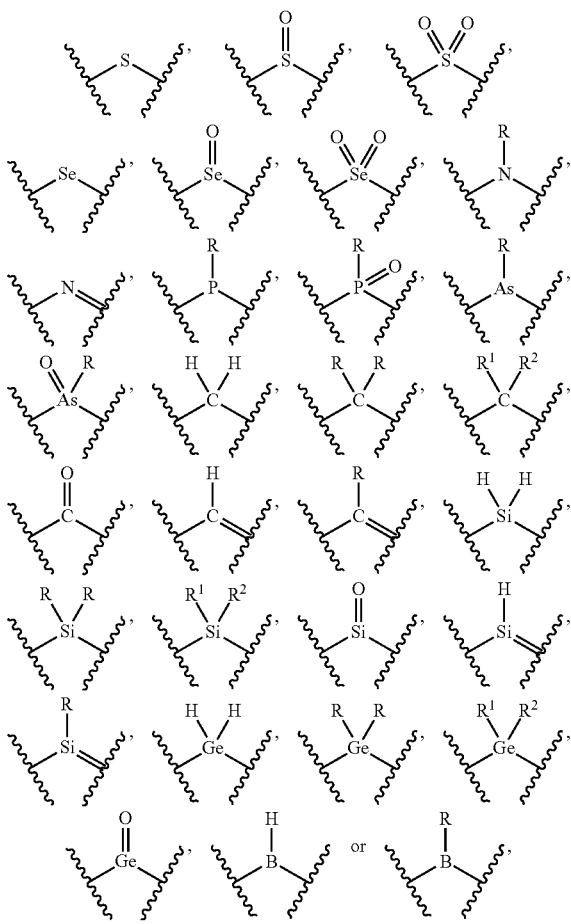

each

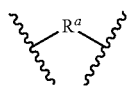

is independently:

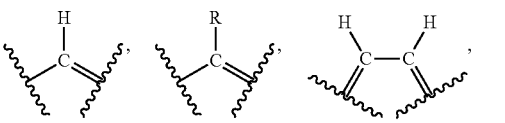

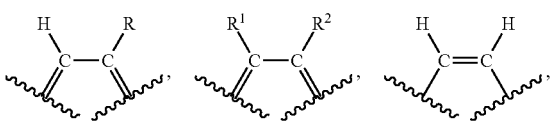

each of R, R$^1$, and R$^2$ of

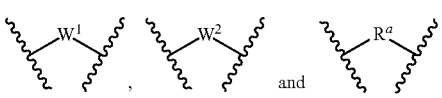

is independently substituted or unsubstituted and is selected from hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, and silyl, and wherein two or more of R, R$^1$, R$^2$, and R$^3$ are optionally linked together.

2. The compound of claim 1, wherein
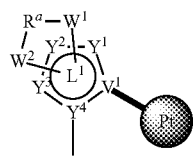
is one of the following:
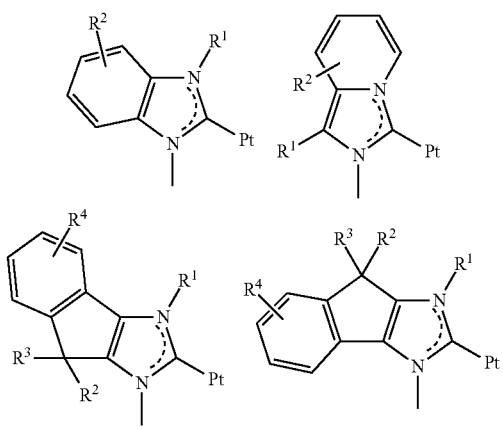
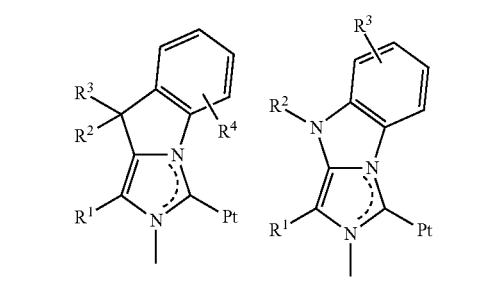
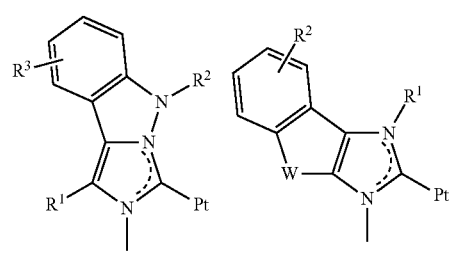
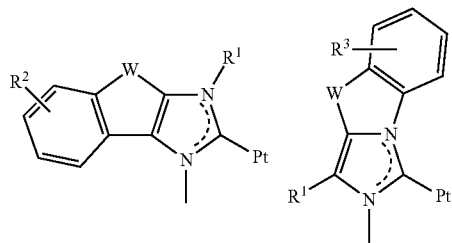
-continued
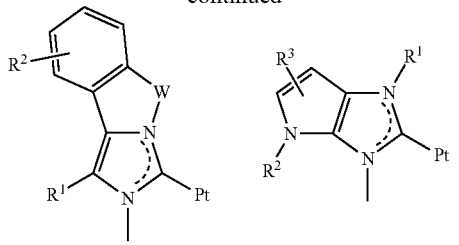
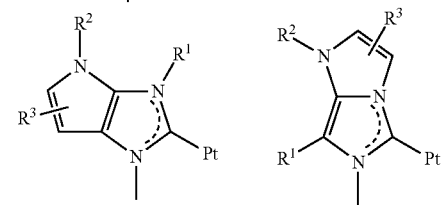
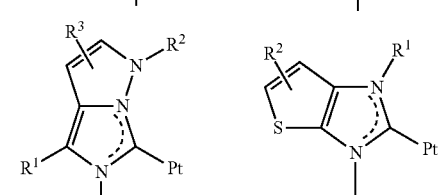
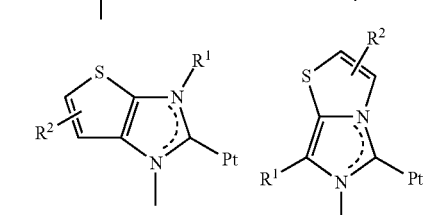
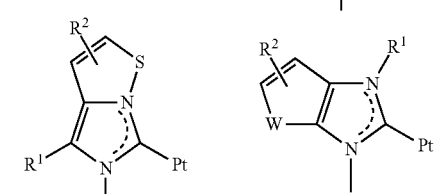
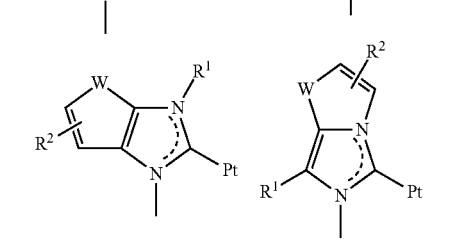
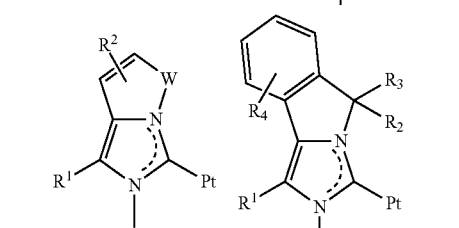

-continued

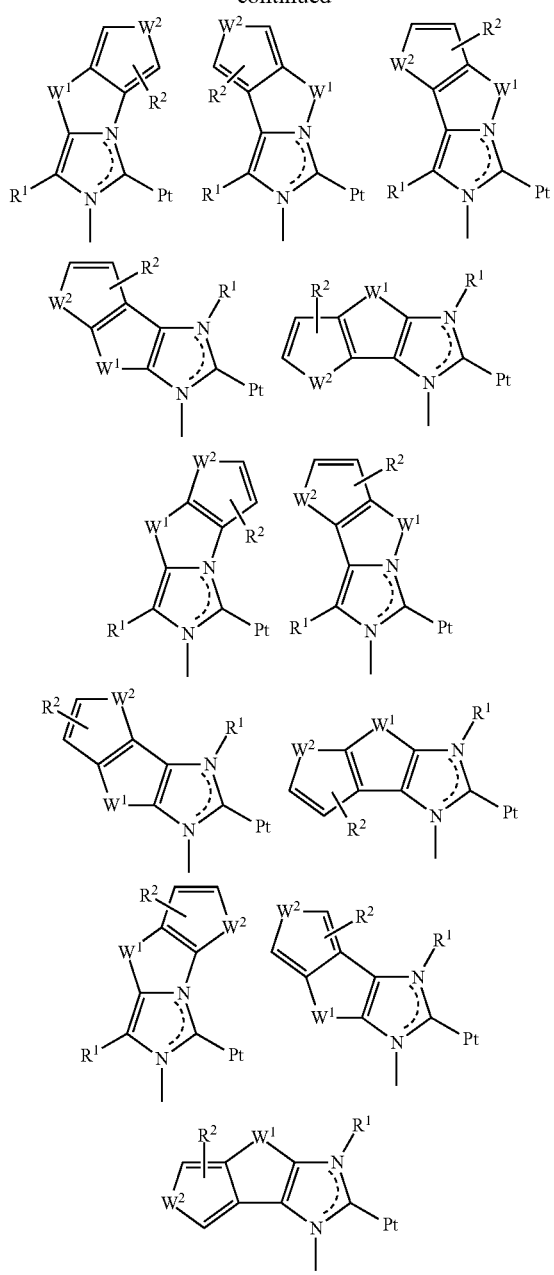

each of

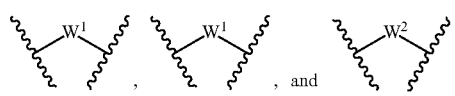

is independently:

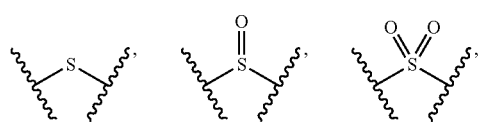

-continued

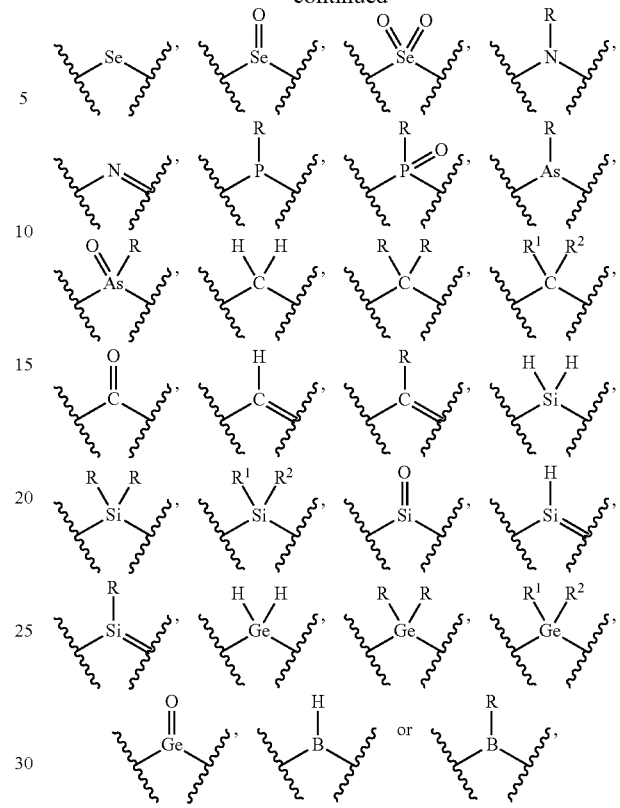

wherein each of R, $R^1$, $R^2$, $R^3$, and $R^4$ is independently a mono-, di-, tri, or tetra-substitution, wherein each of R, $R^1$, $R^2$, $R^3$, and $R^4$ independently is substituted or unsubstituted and is selected from hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, and silyl, and wherein two or more of R, $R^1$, $R^2$, $R^3$, and $R^4$ are optionally linked together.

3. A composition comprising one or more compounds of claim 1.

4. An emitter comprising one or more compounds of claim 1, wherein the emitter is a phosphorescent emitter, a delayed fluorescent emitter, or a combination thereof.

5. A device comprising one or more compounds of claim 1.

6. The device of claim 5, wherein the device comprises an organic light emitting diode.

7. The device of claim 5, wherein the device comprises a full color display.

8. The device of claim 5, wherein the device comprises a phosphorescent OLED device.

9. The device of claim 5, wherein the device comprises a fluorescent OLED device.

10. A photovoltaic device comprising one or more compounds of claim 1.

11. A luminescent display device comprising one or more compounds of claim 1.

12. A light emitting device comprising one or more compounds of claim 1.
13. A compound selected from:
Structures 13
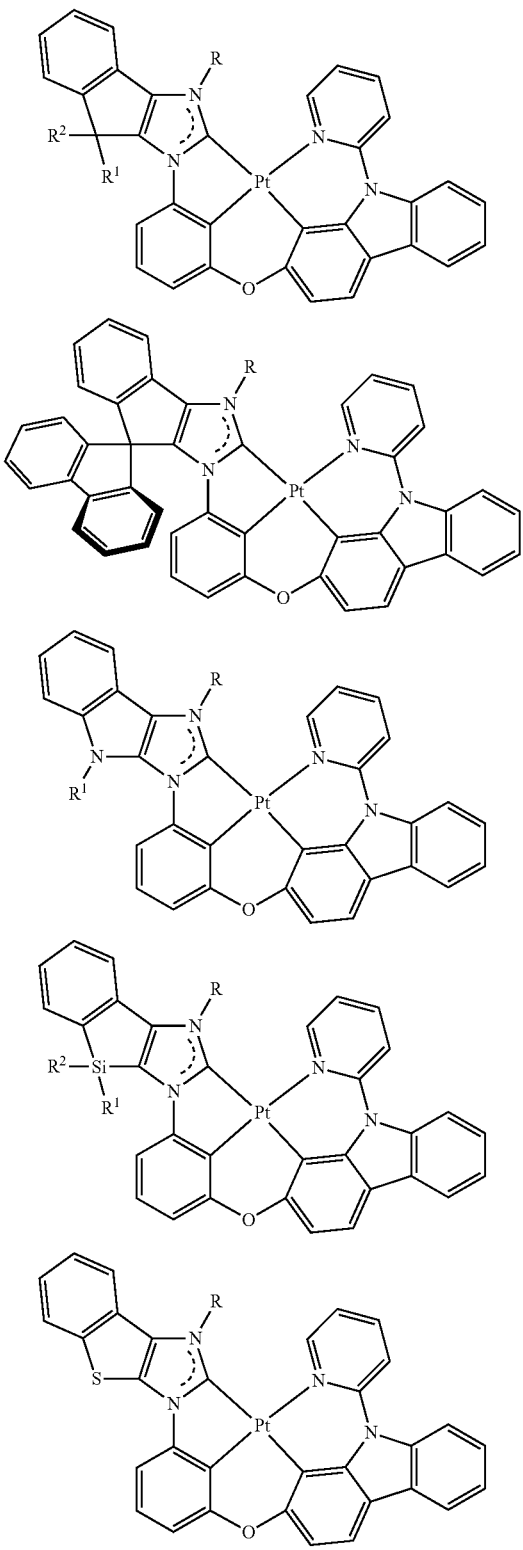
-continued
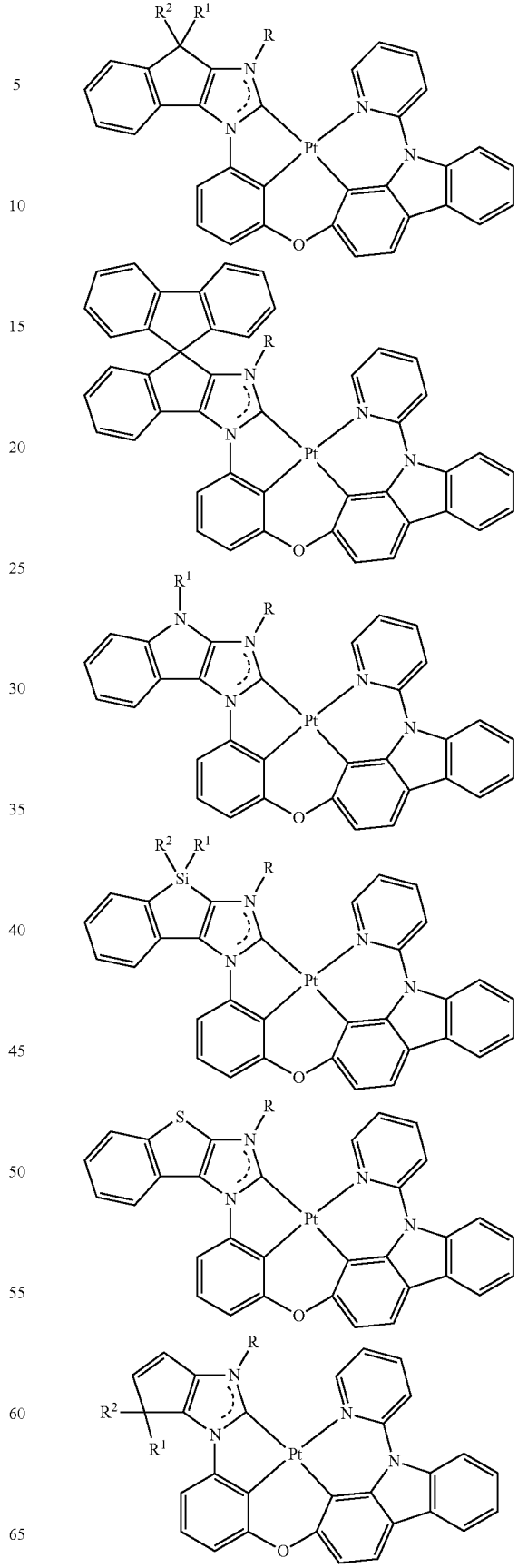

645
-continued
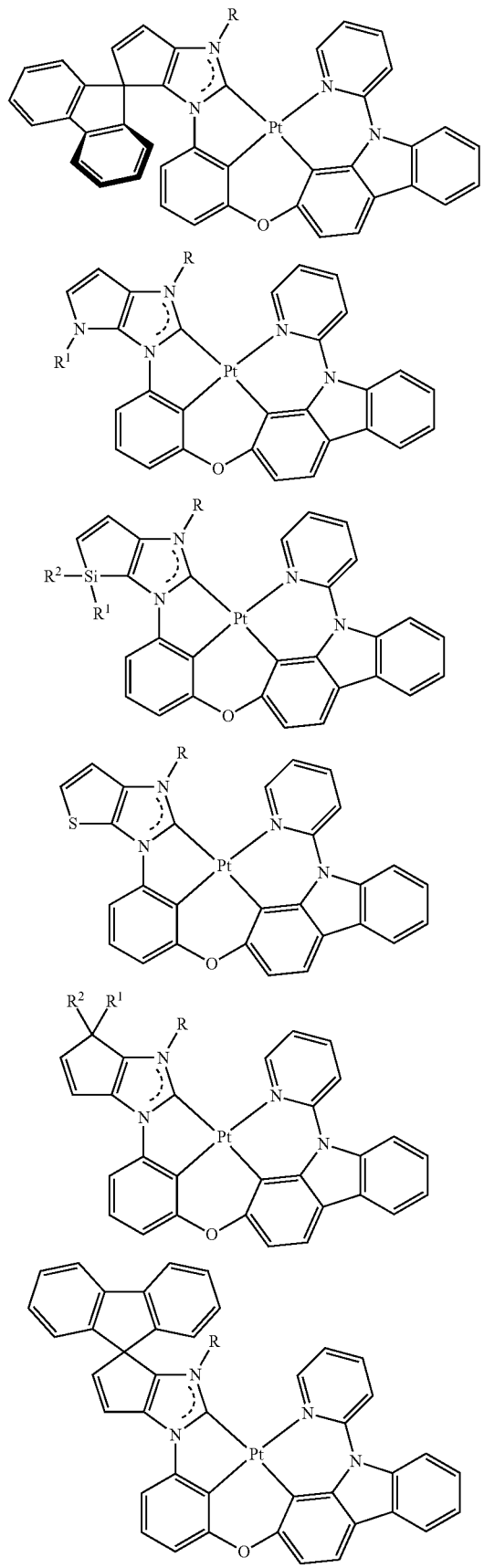
646
-continued
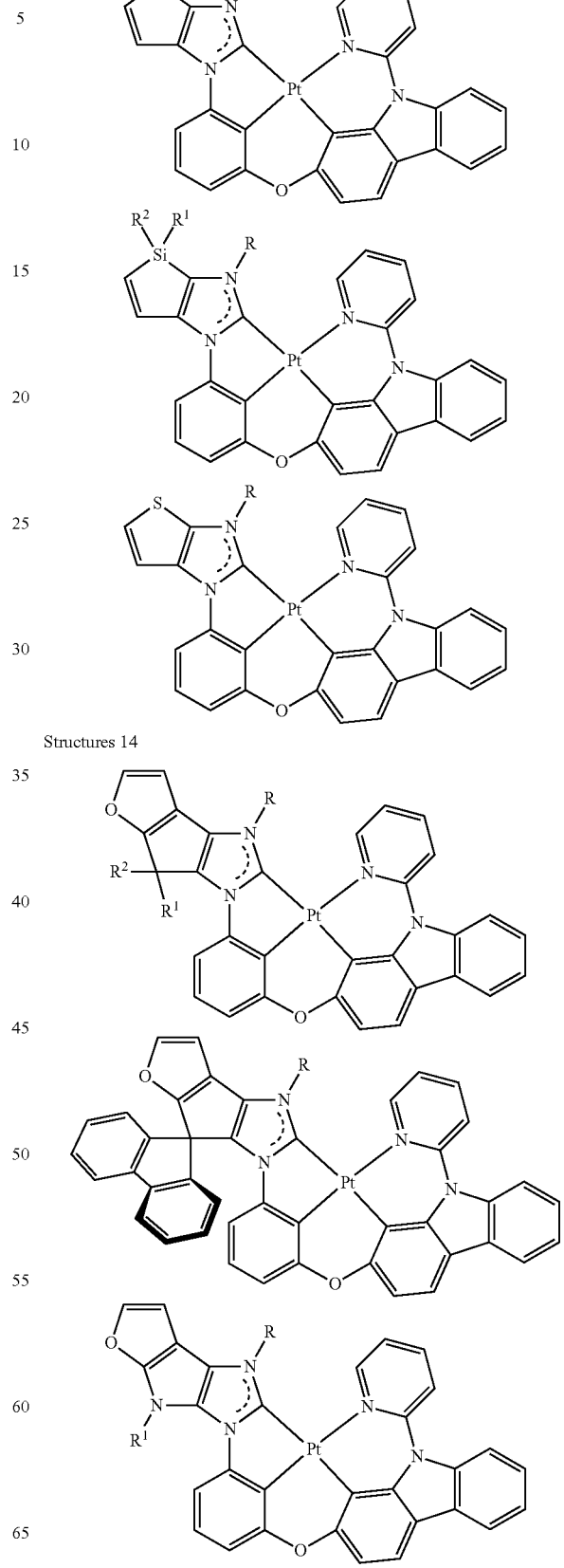
Structures 14

647
-continued
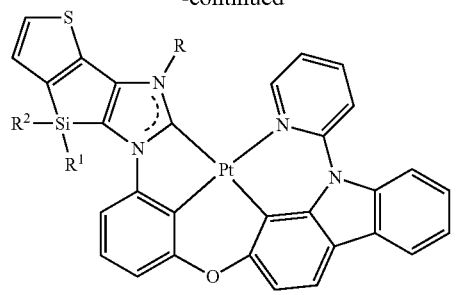
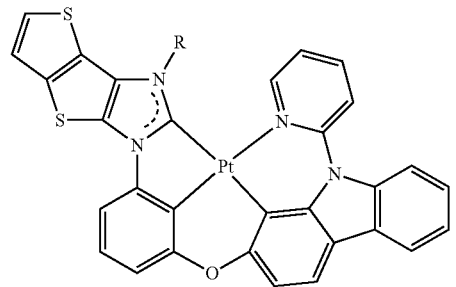
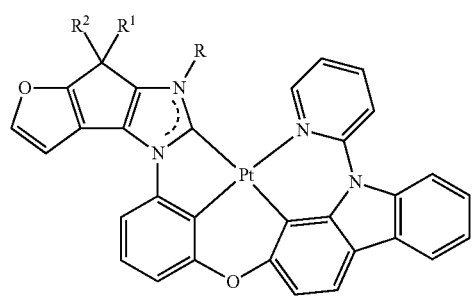
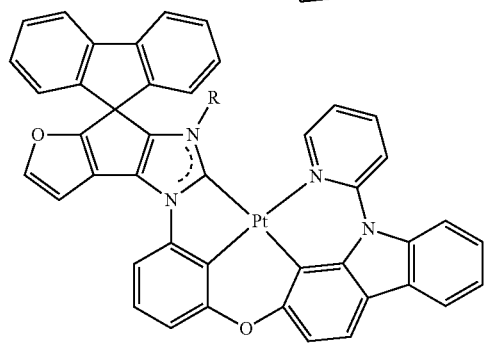
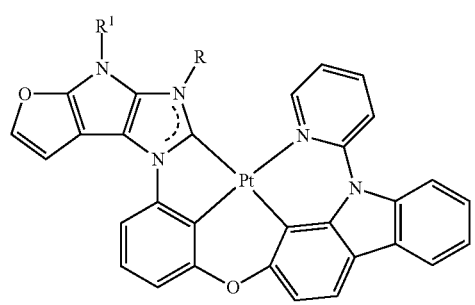
648
-continued
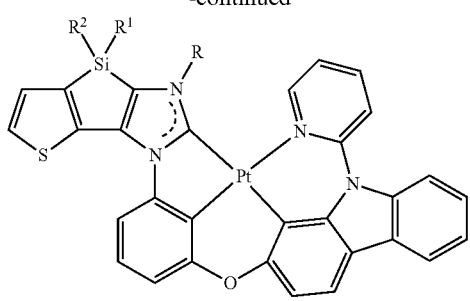
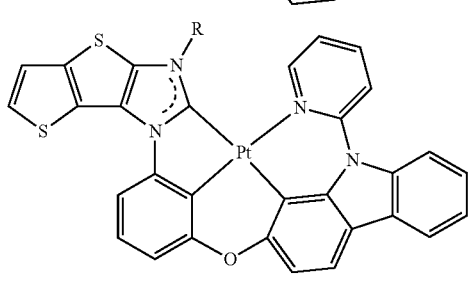
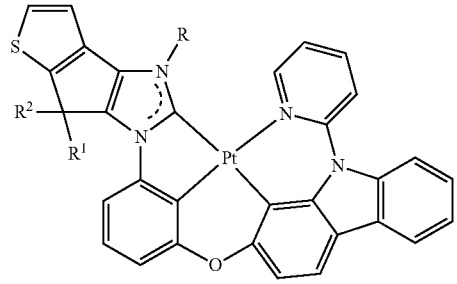
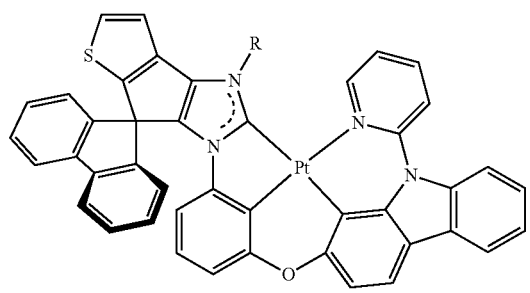
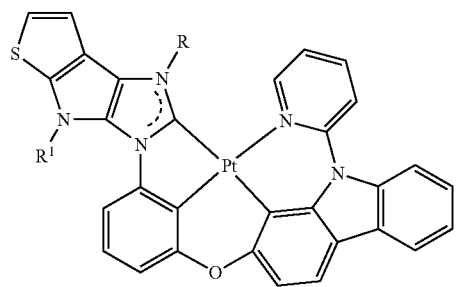
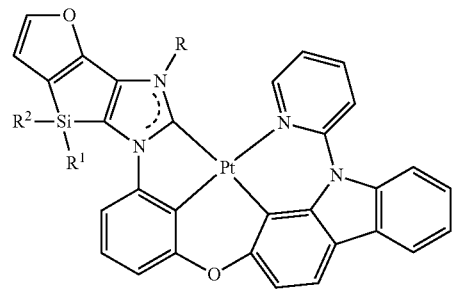

649
-continued

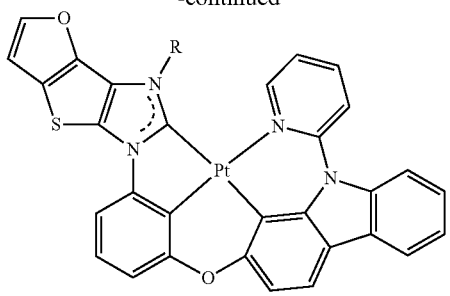

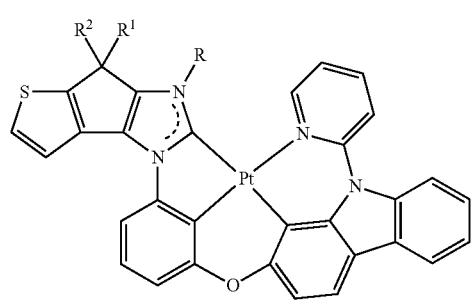

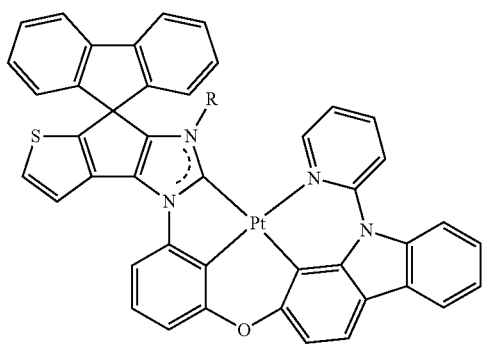

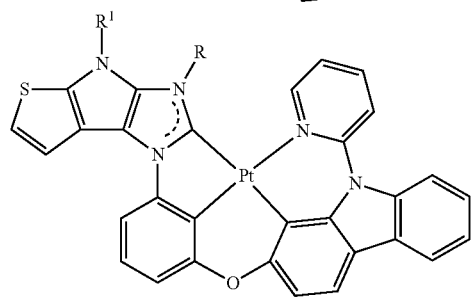

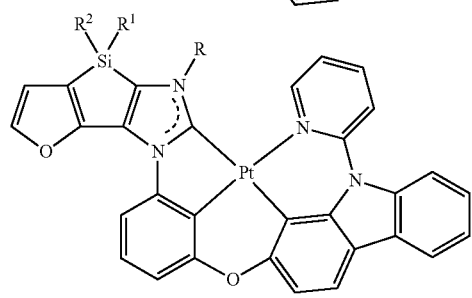

650
-continued

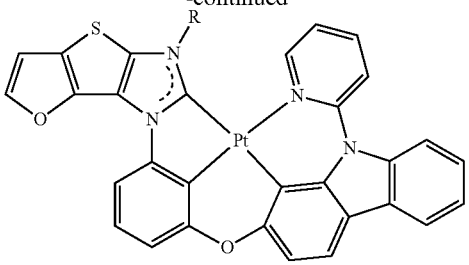

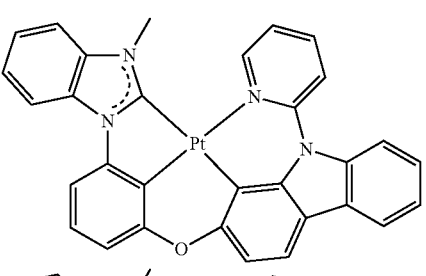

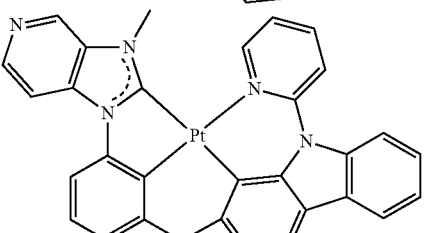

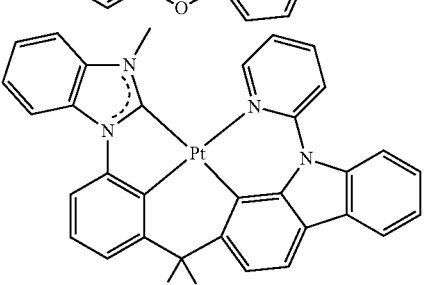

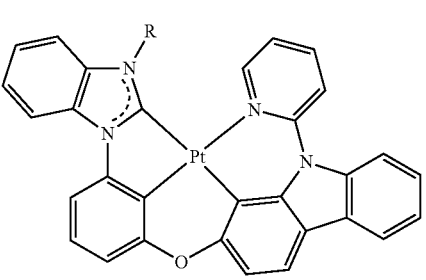

wherein each of R, $R^1$, and $R^2$ is independently substituted or unsubstituted and is selected from hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, mercapto, sulfo, carboxyl, hydrazino, and silyl, and wherein two or more of R, $R^1$, and $R^2$ are optionally linked together.

14. A composition comprising one or more compounds of claim 13.

15. An emitter comprising one or more compounds of claim 13, wherein the emitter is a phosphorescent emitter, a delayed fluorescent emitter, or a combination thereof.

16. A device comprising one or more compounds of claim 13.

17. The device of claim 16, wherein the device comprises an organic light emitting diode.

\* \* \* \* \*